(12) United States Patent
Barlaam et al.

(10) Patent No.: US 10,590,130 B2
(45) Date of Patent: *Mar. 17, 2020

(54) CHEMICAL COMPOUNDS

(71) Applicant: AstraZeneca AB, Sodertalje (SE)

(72) Inventors: Bernard Christophe Barlaam, Cambridge (GB); Daniel Hillebrand O'Donovan, Cambridge (GB); Samantha Jayne Hughes, Cambridge (GB); Thomas Andrew Moss, Cambridge (GB); Johannes Wilhelmus Maria Nissink, Cambridge (GB); James Stewart Scott, Cambridge (GB); Bin Yang, Waltham, MA (US)

(73) Assignee: AstraZeneca AB, Södertälje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/155,041

(22) Filed: Oct. 9, 2018

(65) Prior Publication Data
US 2019/0100520 A1 Apr. 4, 2019

Related U.S. Application Data

(63) Continuation of application No. 15/782,904, filed on Oct. 13, 2017, now Pat. No. 10,131,663.

(60) Provisional application No. 62/435,159, filed on Dec. 16, 2016, provisional application No. 62/411,799, filed on Oct. 24, 2016.

(51) Int. Cl.
| C07D 471/04 | (2006.01) |
| A61K 31/4745 | (2006.01) |
| A61K 31/497 | (2006.01) |
| A61K 45/06 | (2006.01) |

(52) U.S. Cl.
CPC ........ C07D 471/04 (2013.01); A61K 31/4745 (2013.01); A61K 31/497 (2013.01); A61K 45/06 (2013.01)

(58) Field of Classification Search
CPC .......................... C07D 471/12; A61K 31/437
See application file for complete search history.

(56) References Cited

U.S. PATENT DOCUMENTS

| 2012/0157402 A1 | 6/2012 | Cao et al. |
| 2018/0021316 A1 | 1/2018 | Scott et al. |

FOREIGN PATENT DOCUMENTS

| CN | 106518768 A | 3/2017 |
| CN | 107814798 A | 3/2018 |
| WO | 2010138695 A1 | 12/2010 |
| WO | 2010138758 A1 | 12/2010 |
| WO | 2011156518 A2 | 12/2011 |
| WO | 2011159769 A2 | 12/2011 |
| WO | 2013090829 A1 | 6/2013 |
| WO | 2013090836 A1 | 6/2013 |
| WO | 2014191726 A1 | 12/2014 |
| WO | 2014205136 A1 | 12/2014 |
| WO | 2014205138 A1 | 12/2014 |
| WO | 2015092634 A1 | 6/2015 |
| WO | 2016097071 A1 | 6/2016 |
| WO | 2016097072 A1 | 6/2016 |
| WO | 2016097073 A1 | 6/2016 |
| WO | 2016174551 A1 | 11/2016 |
| WO | 2016189011 A1 | 12/2016 |
| WO | 2016202161 A1 | 12/2016 |
| WO | 2017059139 A1 | 4/2017 |
| WO | 2017080338 A1 | 5/2017 |
| WO | 2017080966 A1 | 5/2017 |
| WO | 2017107754 A1 | 6/2017 |
| WO | 2017174757 A1 | 10/2017 |
| WO | 2017182493 A1 | 10/2017 |
| WO | 2017192991 A1 | 11/2017 |
| WO | 2018001232 A1 | 1/2018 |
| WO | 2018053354 A1 | 3/2018 |

OTHER PUBLICATIONS

Golub, Science, 1999, vol. 286, p. 531-537. (Year: 1999).*
Targeted Cancer Fact Sheet, retrieved from http://www.cancer.gov/about-cancer/treatment/types/targeted-therapies/targeted-therapies-fact-sheet, accessed Dec. 8, 2015 (Year: 2015).*
Cancer Prevention Overview, retrieved from https://www.cancer.gov/about-cancer/causes-prevention/patient-prevention-overview-pdq, Nov. 14, 2012 (Year: 2012).*
Chesworth et al., "Tetrahydroisoquinolines as subtype selective estrogen agonists/antagonists", Bioorg. and Med. Chem. Lett, 2004, 14(11), 2729-2733.
Golub, TR., "Molecular classification of cancer: class discovery and class prediction by gene expression monitoring." Science. Oct. 15, 1999;286(5439):531-7.
Targeted Cancer Therapies Fact Sheet-National Cancer Institute, "What are targeted cancer therapies?", Dec. 8, 2015.
Cancer Prevention Overview (PDQ)—National Cancer Institute, "What is prevention?", May 25, 2012.

* cited by examiner

*Primary Examiner* — Karen Cheng

(57) ABSTRACT

The specification relates to compounds of Formula (I):

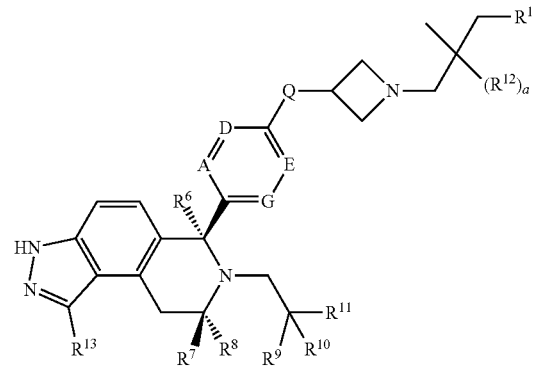

and to pharmaceutically acceptable salts thereof, to processes and intermediates used for their preparation, to pharmaceutical compositions containing them and to their use in the treatment of cell proliferative disorders.

9 Claims, 16 Drawing Sheets

Figure 1: X-Ray Powder Diffraction Pattern for Form A of N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine
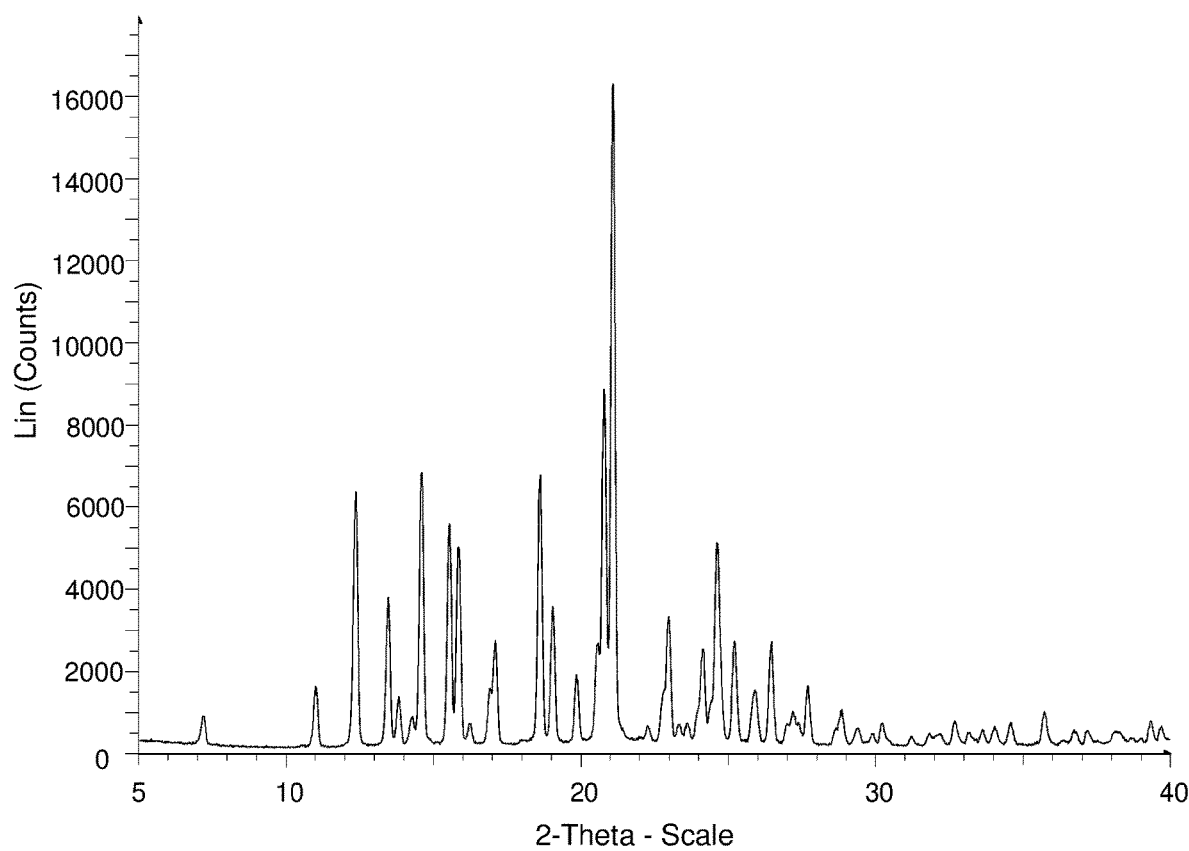

**Figure 2: DSC/TGA Thermogram for Form A of *N*-(1-(3-fluoropropyl)azetidin-3-yl)-6-((6*S*,8*R*)-8-methyl-7-(2,2,2-trifluoroethyl)-6,7,8,9-tetrahydro-3H-pyrazolo[4,3-f]isoquinolin-6-yl)pyridin-3-amine**
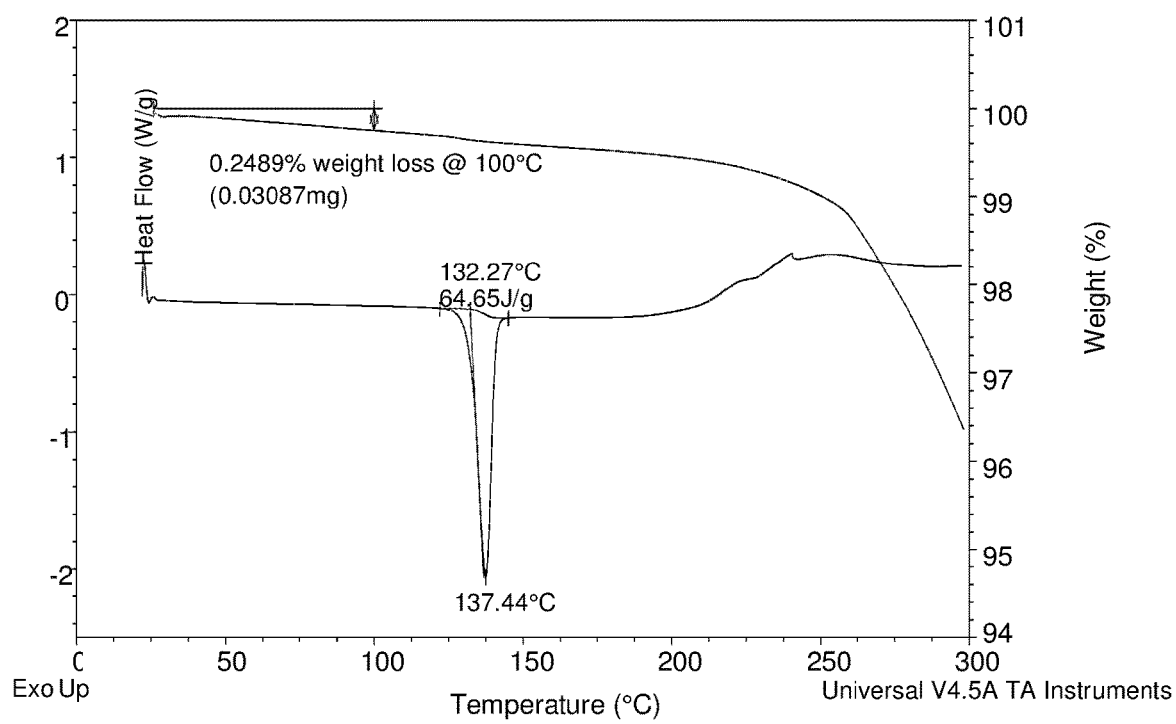

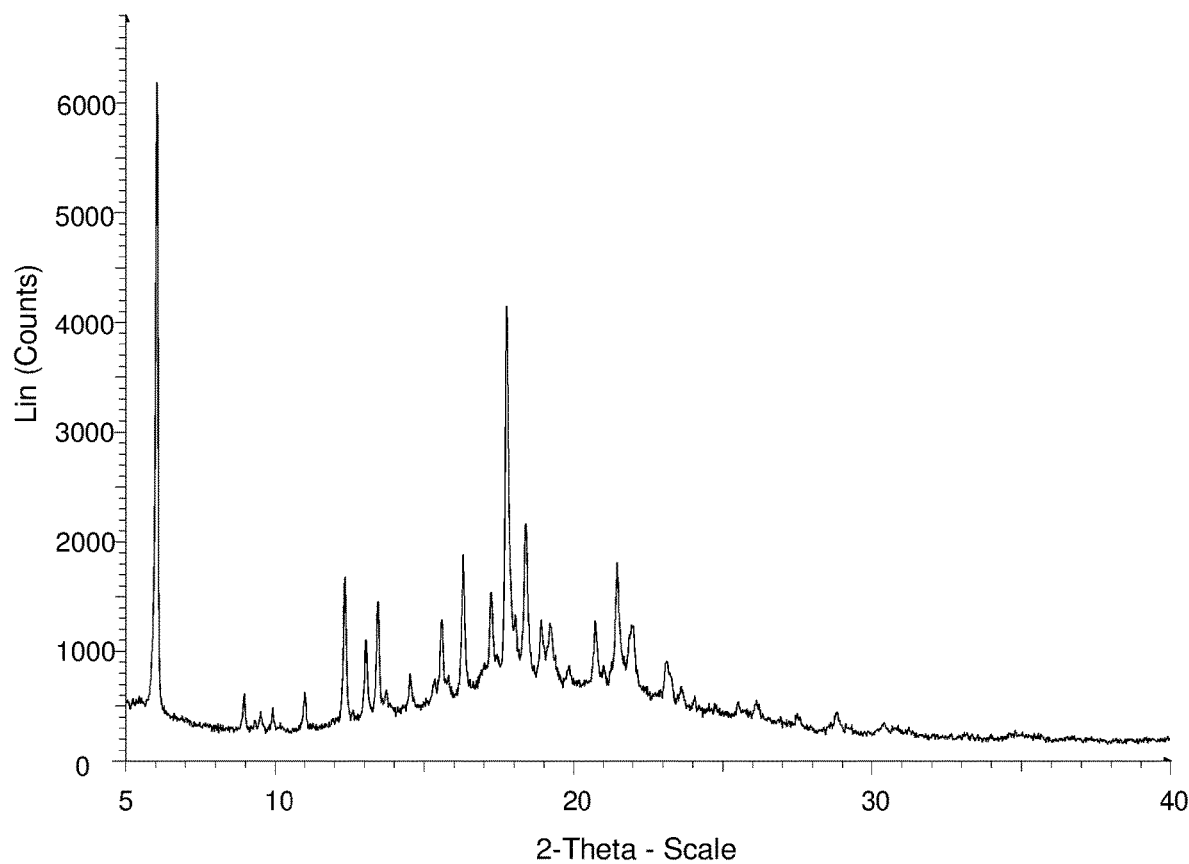
Figure 3: X-Ray Powder Diffraction Pattern for Form B of *N*-(1-(3-fluoropropyl)azetidin-3-yl)-6-((6*S*,8*R*)-8-methyl-7-(2,2,2-trifluoroethyl)-6,7,8,9-tetrahydro-3H-pyrazolo[4,3-f]isoquinolin-6-yl)pyridin-3-amine

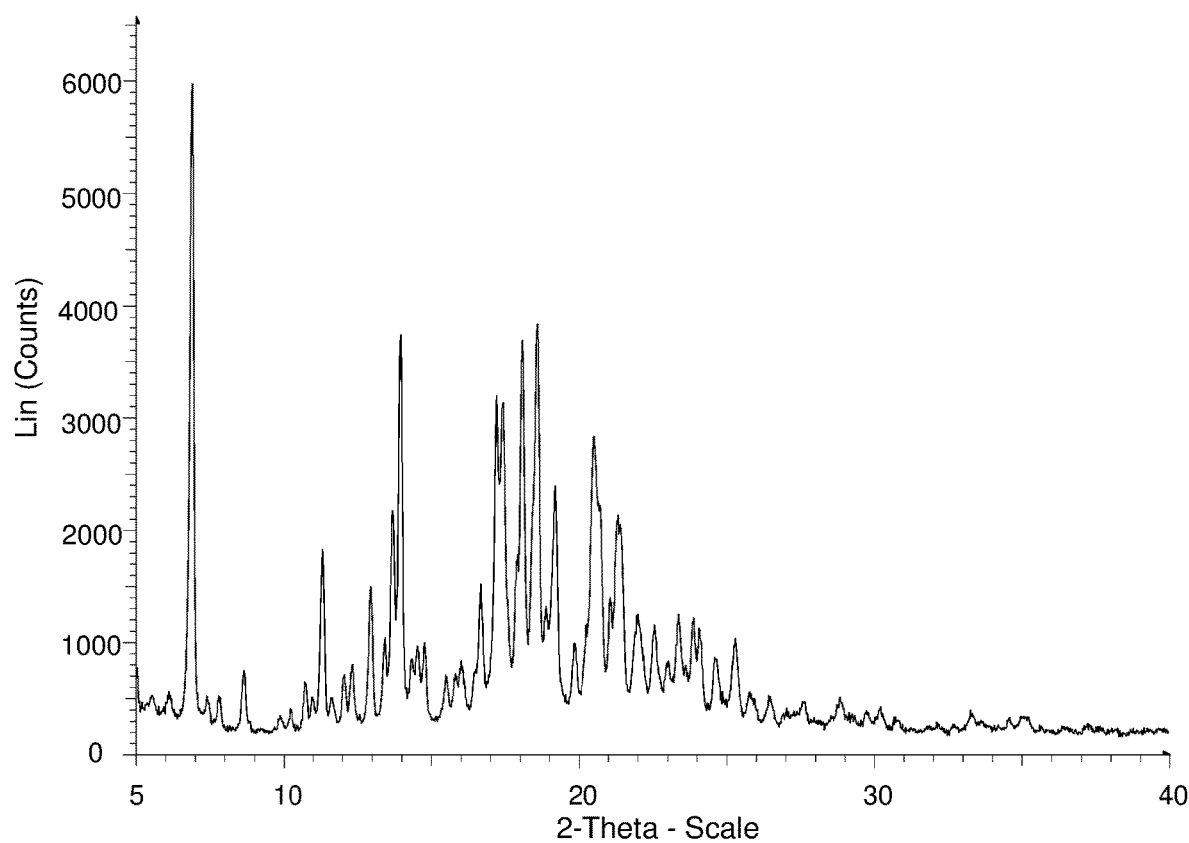
Figure 4: X-Ray Powder Diffraction Pattern for Form C of N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine Figure 5: DSC/TGA Thermogram for Form C of N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine
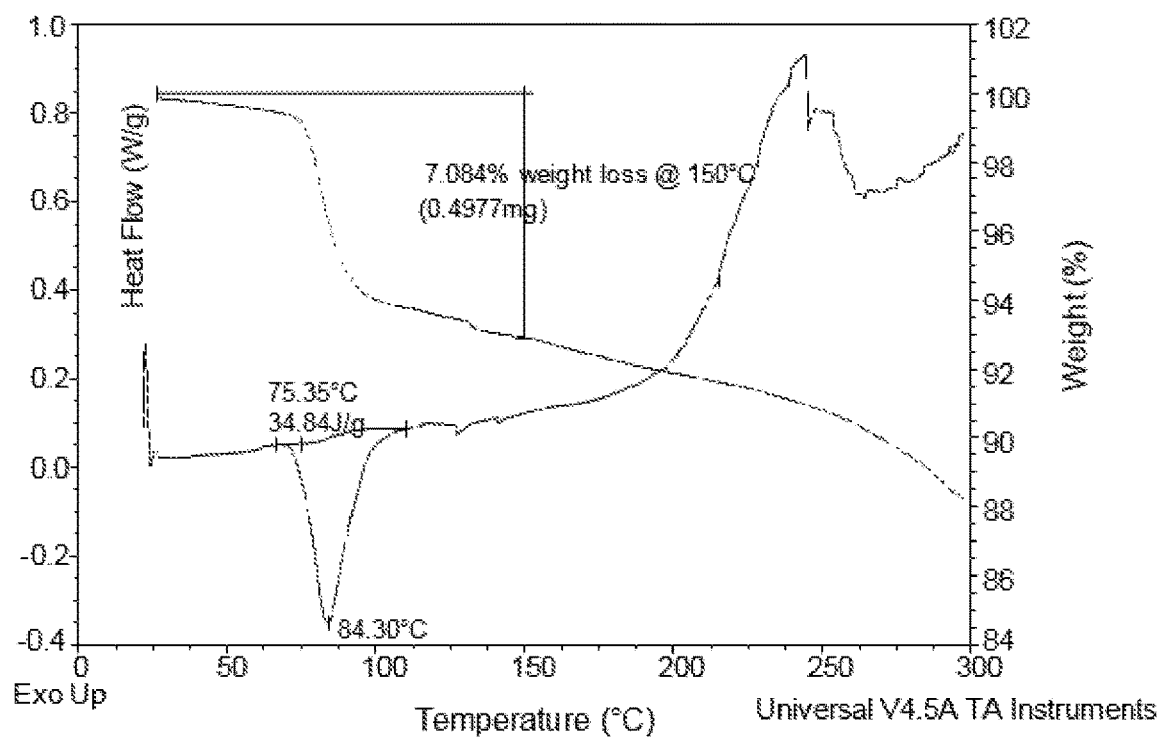

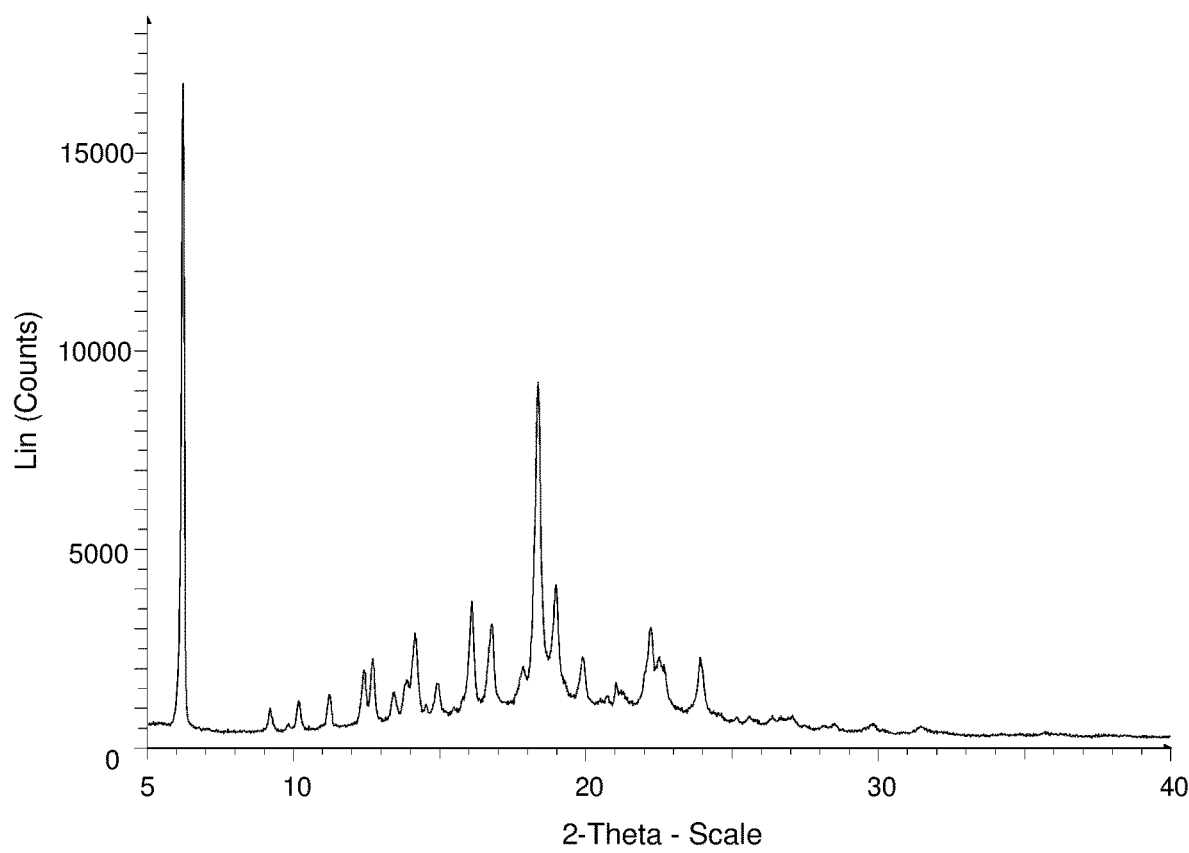
Figure 6: X-Ray Powder Diffraction Pattern for Form D of *N*-(1-(3-fluoropropyl)azetidin-3-yl)-6-((6*S*,8*R*)-8-methyl-7-(2,2,2-trifluoroethyl)-6,7,8,9-tetrahydro-3H-pyrazolo[4,3-f]isoquinolin-6-yl)pyridin-3-amine Figure 7: DSC/TGA Thermogram for Form D of *N*-(1-(3-fluoropropyl)azetidin-3-yl)-6-((6*S*,8*R*)-8-methyl-7-(2,2,2-trifluoroethyl)-6,7,8,9-tetrahydro-3H-pyrazolo[4,3-f]isoquinolin-6-yl)pyridin-3-amine
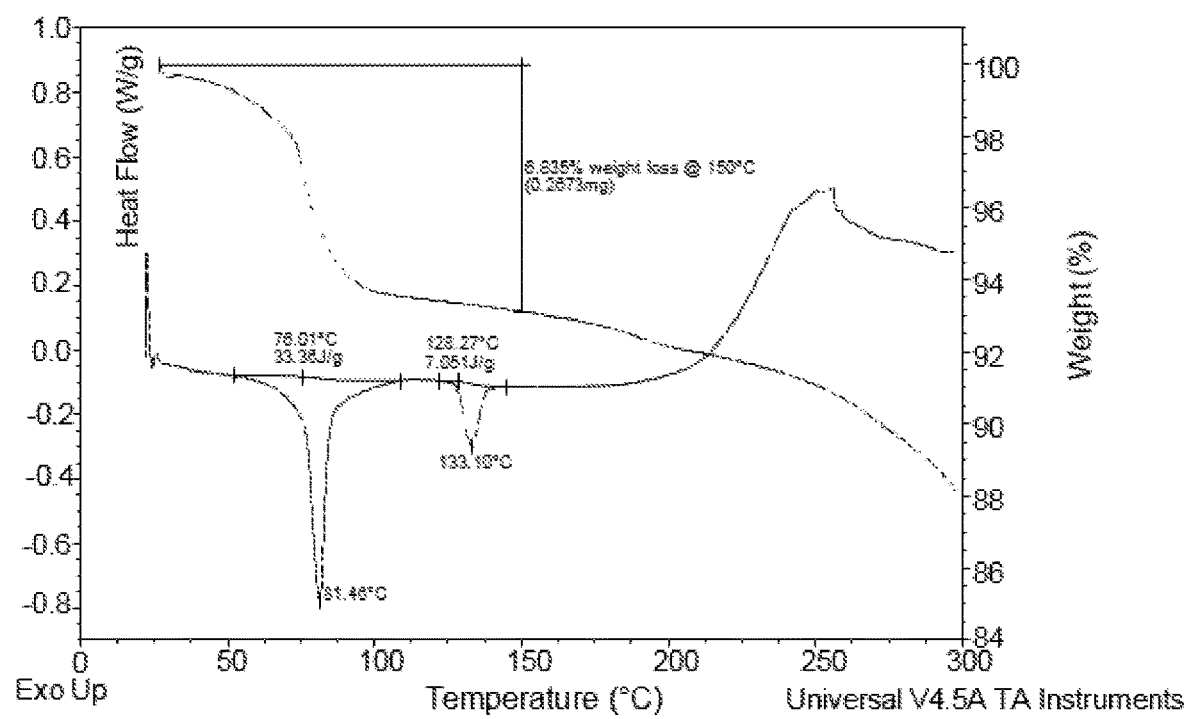

Figure 8: X-Ray Powder Diffraction Pattern for Form E of *N*-(1-(3-fluoropropyl)azetidin-3-yl)-6-((6*S*,8*R*)-8-methyl-7-(2,2,2-trifluoroethyl)-6,7,8,9-tetrahydro-3H-pyrazolo[4,3-f]isoquinolin-6-yl)pyridin-3-amine
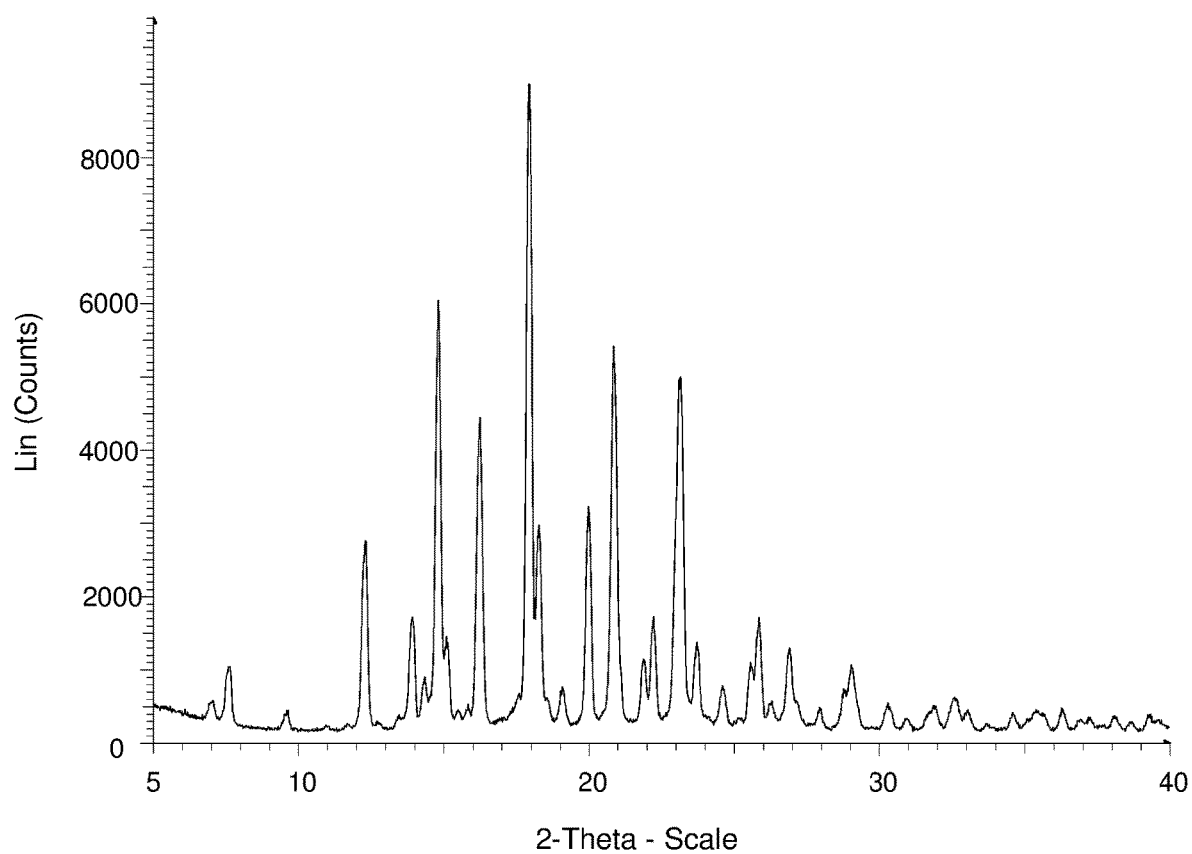

Figure 9: DSC/TGA Thermogram for Form E of *N*-(1-(3-fluoropropyl)azetidin-3-yl)-6-((6*S*,8*R*)-8-methyl-7-(2,2,2-trifluoroethyl)-6,7,8,9-tetrahydro-3H-pyrazolo[4,3-f]isoquinolin-6-yl)pyridin-3-amine
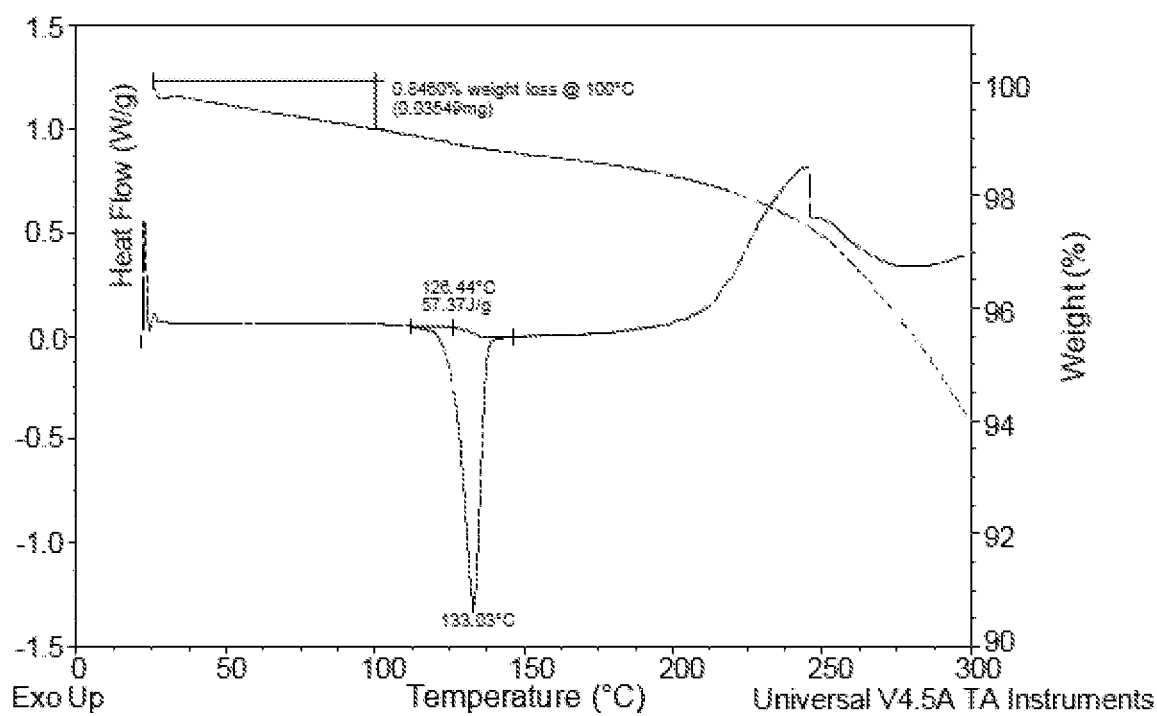

Figure 10: X-Ray Powder Diffraction Pattern for Form F of N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine
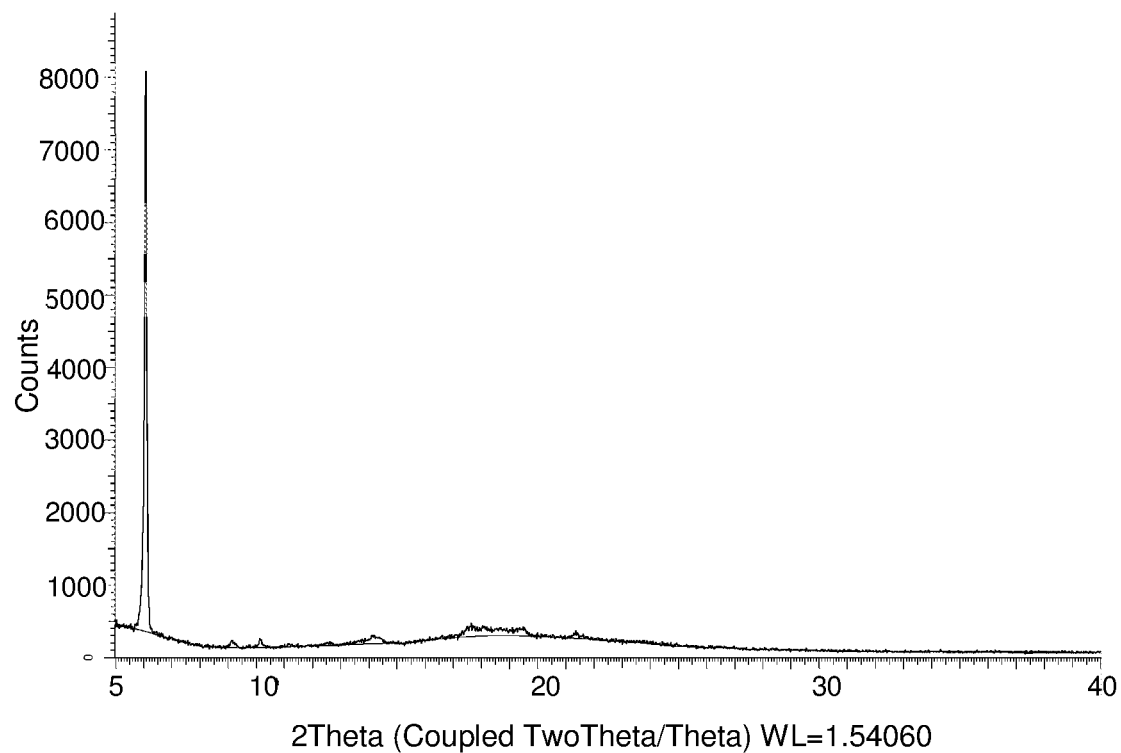

Figure 11: X-Ray Powder Diffraction Pattern for Form G of N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine
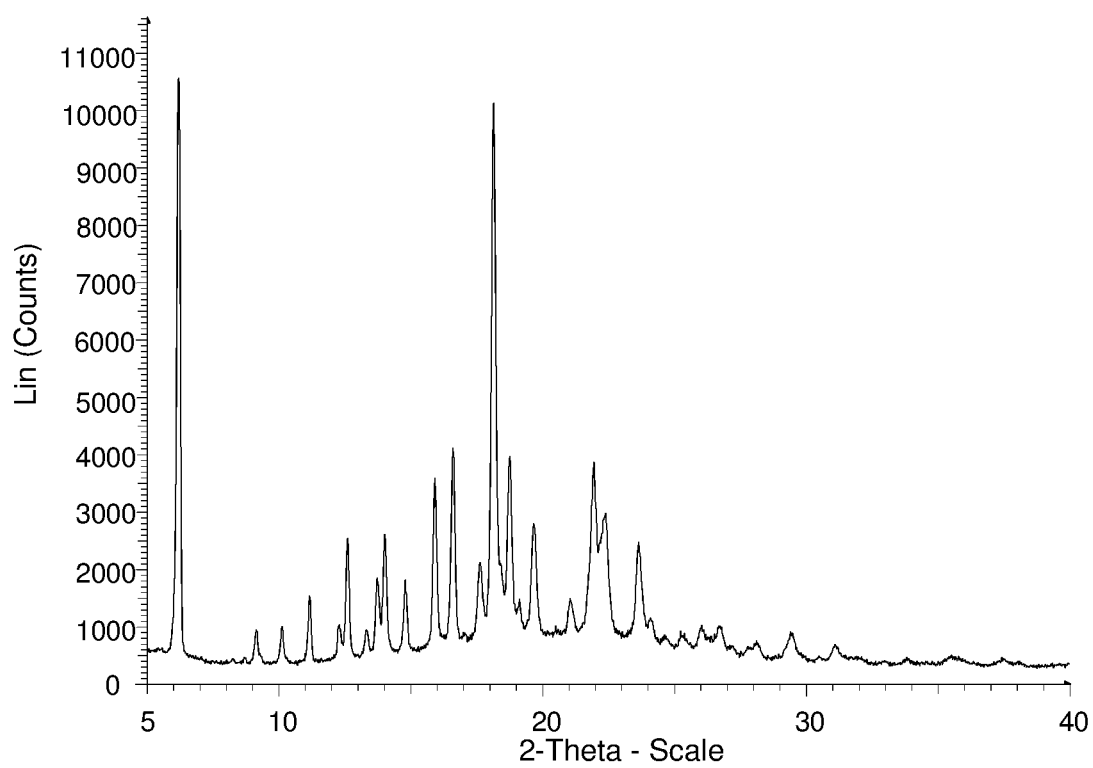

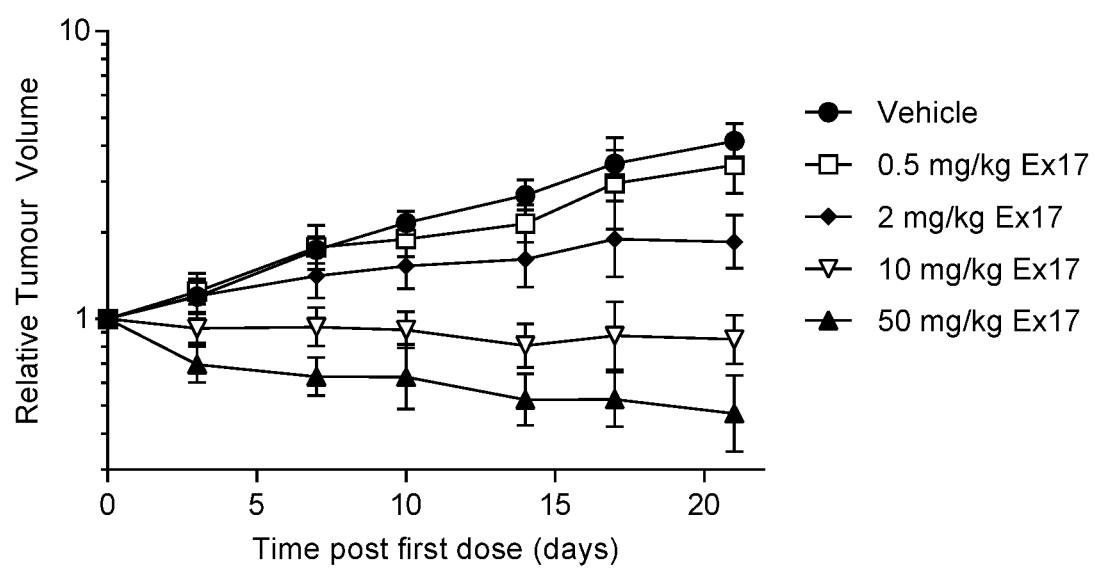
Figure 12: Human parental MCF7 xenograft anti-tumour efficacy study in mouse with
N-(1-(3-fluoropropyl)azetidin-3-yl)-6-((6S,8R)-8-methyl-7-(2,2,2-trifluoroethyl)-6,7,8,9-
tetrahydro-3H-pyrazolo[4,3-f]isoquinolin-6-yl)pyridin-3-amine Figure 13: Human Y537S ESR1 mutant MCF7 xenograft anti-tumour efficacy study in mouse with *N*-(1-(3-fluoropropyl)azetidin-3-yl)-6-((6*S*,8*R*)-8-methyl-7-(2,2,2-trifluoroethyl)-6,7,8,9-tetrahydro-3H-pyrazolo[4,3-f]isoquinolin-6-yl)pyridin-3-amine
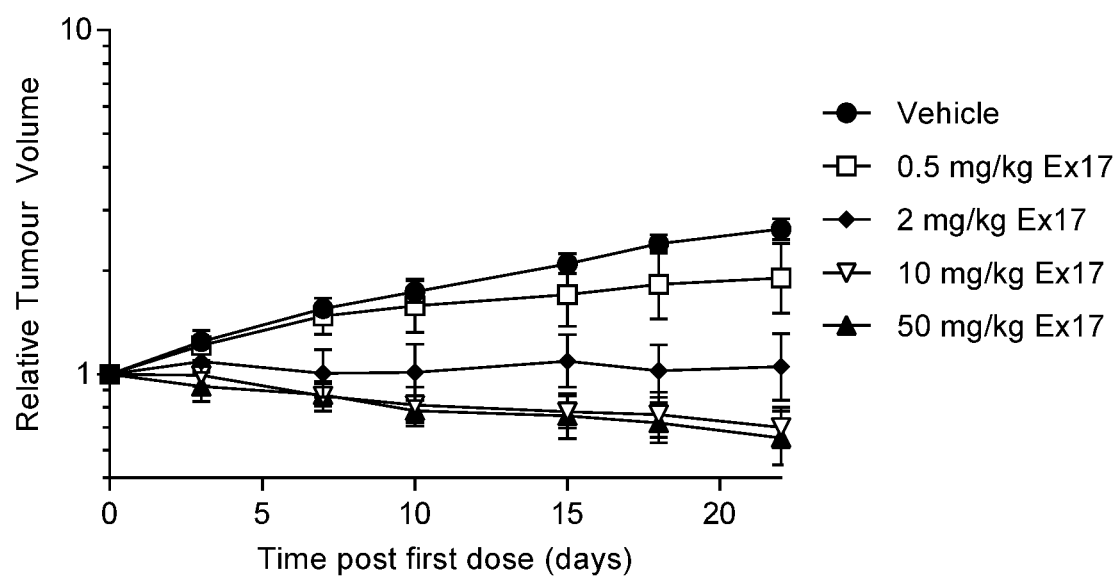

Figure 14: Human ESR1 mutant breast cancer patient derived xenograft CTC174 anti-tumour efficacy study in mouse with N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine
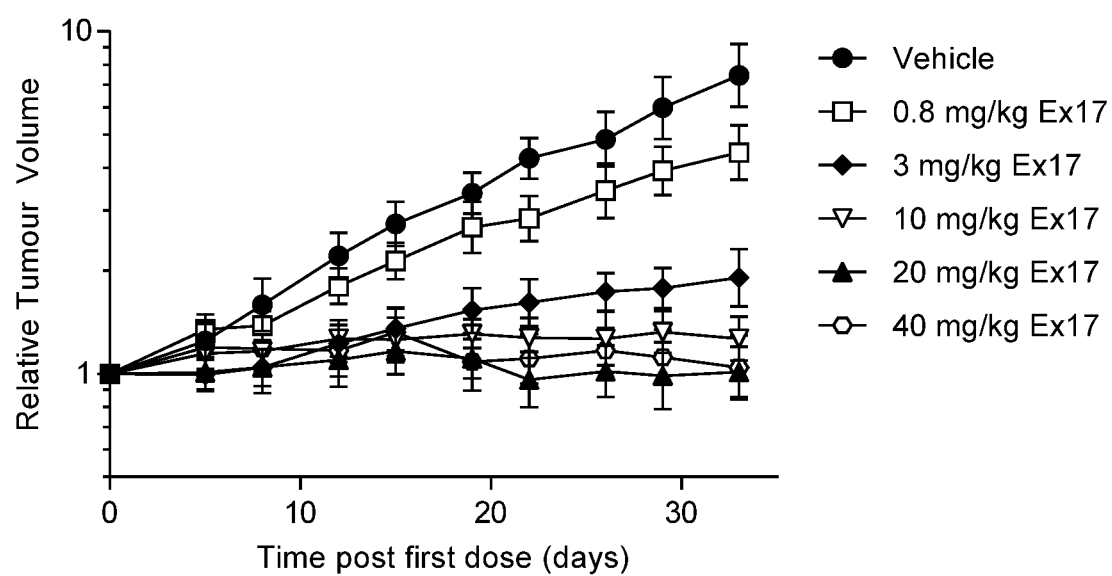

Figure 15: Human ESR1 mutant breast cancer patient derived xenograft CTC174 anti-tumour efficacy study in mouse with a combination of N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine and palbociclib
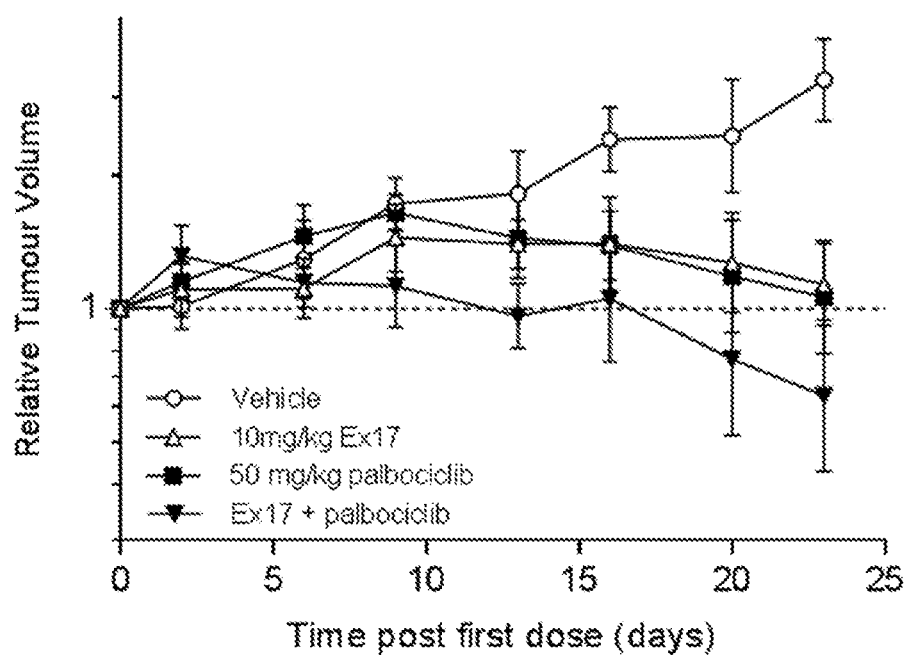

Figure 16: Human ESR1 mutant breast cancer patient derived xenograft CTC174 anti-tumour efficacy study in mouse with a combination of *N*-(1-(3-fluoropropyl)azetidin-3-yl)-6-((6*S*,8*R*)-8-methyl-7-(2,2,2-trifluoroethyl)-6,7,8,9-tetrahydro-3H-pyrazolo[4,3-f]isoquinolin-6-yl)pyridin-3-amine and vistusertib (AZD2014)
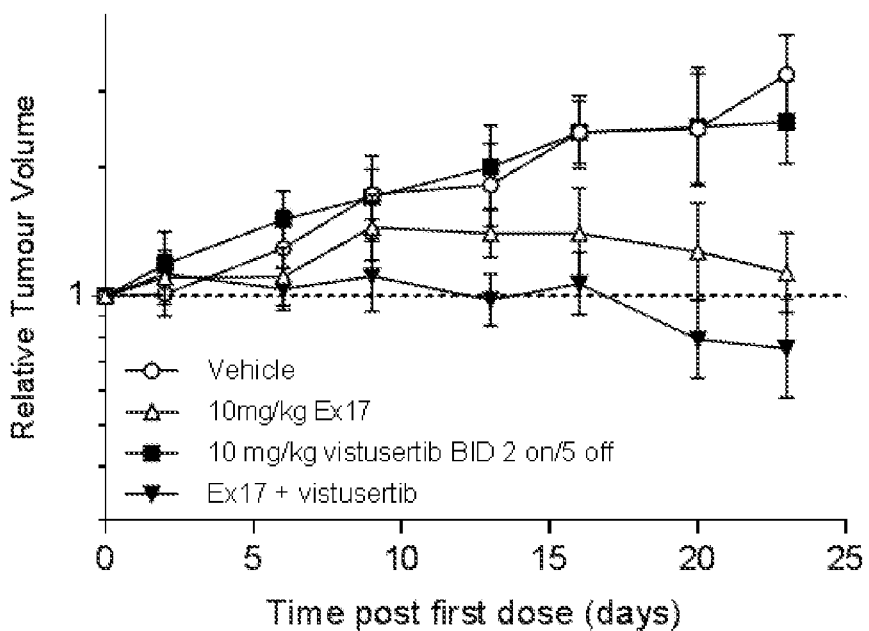

CHEMICAL COMPOUNDS

The specification relates to certain indazole compounds and pharmaceutically acceptable salts thereof that selectively down-regulate the estrogen receptor and possess anti-cancer activity. The specification also relates to use of said indazole compounds and pharmaceutically acceptable salts thereof in methods of treatment of the human or animal body, for example in prevention or treatment of cancer. The specification also relates to processes and intermediate compounds involved in the preparation of said indazole compounds and to pharmaceutical compositions containing them.

Estrogen receptor alpha (ERα, ESR1, NR3A) and estrogen receptor beta (ERβ, ESR2, NR3b) are steroid hormone receptors which are members of the large nuclear receptor family. Structured similarly to all nuclear receptors, ERα is composed of six functional domains (named A-F) (Dahlman-Wright, et al., *Pharmacol. Rev.*, 2006, 58:773-781) and is classified as a ligand-dependent transcription factor because after its association with the specific ligand, (the female sex steroid hormone 17b estradiol (E2)), the complex binds to genomic sequences, named Estrogen Receptor Elements (ERE) and interacts with co-regulators to modulate the transcription of target genes. The ERα gene is located on 6q25.1 and encodes a 595AA protein and multiple isoforms can be produced due to alternative splicing and translational start sites. In addition to the DNA binding domain (Domain C) and the ligand binding domain (Domain E) the receptor contains a N-terminal (A/B) domain, a hinge (D) domain that links the C and E domains and a C-terminal extension (F domain). While the C and E domains of ERα and ERβ are quite conserved (96% and 55% amino acid identity respectively) conservation of the A/B, D and F domains is poor (below 30% amino acid identity). Both receptors are involved in the regulation and development of the female reproductive tract and in addition play roles in the central nervous system, cardiovascular system and in bone metabolism. The genomic action of ERs occurs in the nucleus of the cell when the receptor binds EREs directly (direct activation or classical pathway) or indirectly (indirect activation or non-classical pathway). In the absence of ligand, ERs are associated with heat shock proteins, Hsp90 and Hsp70, and the associated chaperone machinery stabilizes the ligand binding domain (LBD) making it accessible to ligand. Liganded ER dissociates from the heat shock proteins leading to a conformational change in the receptor that allows dimerisation, DNA binding, interaction with co-activators or co-repressors and modulation of target gene expression. In the non-classical pathway, AP-1 and Sp-1 are alternative regulatory DNA sequences used by both isoforms of the receptor to modulate gene expression. In this example, ER does not interact directly with DNA but through associations with other DNA bound transcription factors e.g. c-Jun or c-Fos (Kushner et al., *Pure Applied Chemistry* 2003, 75:1757-1769). The precise mechanism whereby ER affects gene transcription is poorly understood but appears to be mediated by numerous nuclear factors that are recruited by the DNA bound receptor. The recruitment of co-regulators is primarily mediated by two protein surfaces, AF2 and AF1 which are located in E-domain and the A/B domain respectively. AF1 is regulated by growth factors and its activity depends on the cellular and promoter environment whereas AF2 is entirely dependent on ligand binding for activity. Although the two domains can act independently, maximal ER transcriptional activity is achieved through synergistic interactions via the two domains (Tzukerman, et al., *Mol. Endocrinology,* 1994, 8:21-30). Although ERs are considered transcription factors they can also act through non-genomic mechanisms as evidenced by rapid ER effects in tissues following E2 administration in a timescale that is considered too fast for a genomic action. It is still unclear if receptors responsible for the rapid actions of estrogen are the same nuclear ERs or distinct G-protein coupled steroid receptors (Warner, et al., *Steroids* 2006 71:91-95) but an increasing number of E2 induced pathways have been identified e.g. MAPK/ERK pathway and activation of endothelial nitric oxide synthase and PI3K/Akt pathway. In addition to ligand dependent pathways, ERα has been shown to have ligand independent activity through AF-1 which has been associated with stimulation of MAPK through growth factor signalling e.g. insulin like growth factor 1 (IGF-1) and epidermal growth factor (EGF). Activity of AF-1 is dependent on phosphorylation of Ser118 and an example of cross-talk between ER and growth factor signalling is the phosphorylation of Ser 118 by MAPK in response to growth factors such as IGF-1 and EGF (Kato, et al., *Science,* 1995, 270:1491-1494).

A large number of structurally distinct compounds have been shown to bind to ER. Some compounds such as endogenous ligand E2, act as receptor agonists whereas others competitively inhibit E2 binding and act as receptor antagonists. These compounds can be divided into 2 classes depending on their functional effects. Selective estrogen receptor modulators (SERMs) such as tamoxifen have the ability to act as both receptor agonists and antagonists depending on the cellular and promoter context as well as the ER isoform targeted. For example tamoxifen acts as an antagonist in breast but acts as a partial agonist in bone, the cardiovascular system and uterus. All SERMs appear to act as AF2 antagonists and derive their partial agonist characteristics through AF1. A second group, fulvestrant being an example, are classified as full antagonists and are capable of blocking estrogen activity via the complete inhibition of AF1 and AF2 domains through induction of a unique conformation change in the ligand binding domain (LBD) on compound binding which results in complete abrogation of the interaction between helix 12 and the remainder of the LBD, blocking co-factor recruitment (Wakeling, et al., *Cancer Res.,* 1991, 51:3867-3873; Pike, et al., *Structure,* 2001, 9:145-153).

Intracellular levels of ERα are down-regulated in the presence of E2 through the ubiquitin/proteosome (Ub/26S) pathway. Polyubiquitinylation of liganded ERα is catalysed by at least three enzymes; the ubiquitin-activating enzyme E1 activated ubiquitin is conjugated by E2 with lysine residues through an isopeptide bond by E3 ubiquitin ligase and polyubiquitinated ERα is then directed to the proteosome for degradation. Although ER-dependent transcription regulation and proteosome-mediated degradation of ER are linked (Lonard, et al., *Mol. Cell,* 2000 5:939-948), transcription in itself is not required for ERα degradation and assembly of the transcription initiation complex is sufficient to target ERα for nuclear proteosomal degradation. This E2 induced degradation process is believed to necessary for its ability to rapidly activate transcription in response to requirements for cell proliferation, differentiation and metabolism (Stenoien, et al., *Mol. Cell Biol.,* 2001, 21:4404-4412). Fulvestrant is also classified as a selective estrogen receptor down-regulator (SERD), a subset of antagonists that can also induce rapid down-regulation of ERα via the 26S proteosomal pathway. In contrast a SERM such as tamoxifen can increase ERα levels although the effect on transcription is similar to that seen for a SERD.

Approximately 70% of breast cancers express ER and/or progesterone receptors implying the hormone dependence of these tumour cells for growth. Other cancers such as ovarian and endometrial are also thought to be dependent on ERα signalling for growth. Therapies for such patients can inhibit ER signalling either by antagonising ligand binding to ER e.g. tamoxifen which is used to treat early and advanced ER positive breast cancer in both pre and post menopausal setting; antagonising and down-regulating ERα e.g. fulvestrant which is used to treat breast cancer in women which have progressed despite therapy with tamoxifen or aromatase inhibitors; or blocking estrogen synthesis e.g. aromatase inhibitors which are used to treat early and advanced ER positive breast cancer. Although these therapies have had an enormously positive impact on breast cancer treatment, a considerable number of patients whose tumours express ER display de novo resistance to existing ER therapies or develop resistance to these therapies over time. Several distinct mechanisms have been described to explain resistance to first-time tamoxifen therapy which mainly involve the switch from tamoxifen acting as an antagonist to an agonist, either through the lower affinity of certain co-factors binding to the tamoxifen-ERα complex being off-set by over-expression of these co-factors, or through the formation of secondary sites that facilitate the interaction of the tamoxifen-ERα complex with co-factors that normally do not bind to the complex. Resistance could therefore arise as a result of the outgrowth of cells expressing specific co-factors that drive the tamoxifen-ERα activity. There is also the possibility that other growth factor signalling pathways directly activate the ER receptor or co-activators to drive cell proliferation independently of ligand signalling.

More recently, mutations in ESR1 have been identified as a possible resistance mechanism in metastatic ER-positive patient derived tumour samples and patient-derived xenograft models (PDX) at frequencies varying from 17-25%. These mutations are predominantly, but not exclusively, in the ligand-binding domain leading to mutated functional proteins; examples of the amino acid changes include Ser463Pro, Val543Glu, Leu536Arg, Tyr537Ser, Tyr537Asn and Asp538Gly, with changes at amino acid 537 and 538 constituting the majority of the changes currently described. These mutations have been undetected previously in the genomes from primary breast samples characterised in the Cancer Genome Atlas database. Of 390 primary breast cancer samples positive for ER expression not a single mutation was detected in ESR1 (Cancer Genome Atlas Network, 2012 *Nature* 490: 61-70). The ligand binding domain mutations are thought to have developed as a resistance response to aromatase inhibitor endocrine therapies as these mutant receptors show basal transcriptional activity in the absence of estradiol. The crystal structure of ER, mutated at amino acids 537 and 538, showed that both mutants favoured the agonist conformation of ER by shifting the position of helix 12 to allow co-activator recruitment and thereby mimicking agonist activated wild type ER. Published data has shown that endocrine therapies such as tamoxifen and fulvestrant can still bind to ER mutant and inhibit transcriptional activation to some extent and that fulvestrant is capable of degrading Try537Ser but that higher doses may be needed for full receptor inhibition (Toy et al., *Nat. Genetics* 2013, 45: 1439-1445; Robinson et al., *Nat. Genetics* 2013, 45: 144601451; Li, S. et al. *Cell Rep.* 4, 1116-1130 (2013). It is therefore feasible that certain compounds of the Formula (I) or pharmaceutically acceptable salts thereof (as described hereinafter) will be capable of down-regulating and antagonising mutant ER although it is not known at this stage whether ESR1 mutations are associated with an altered clinical outcome.

Regardless of which resistance mechanism or combination of mechanisms takes place, many are still reliant on ER-dependent activities and removal of the receptor through a SERD mechanism offers the best way of removing the ERα receptor from the cell. Fulvestrant is currently the only SERD approved for clinical use, yet despite its mechanistic properties, the pharmacological properties of the drug have limited its efficacy due to the current limitation of a 500 mg monthly dose which results in less than 50% turnover of the receptor in patient samples compared to the complete down-regulation of the receptor seen in in vitro breast cell line experiments (Wardell, et al., *Biochem. Pharm.*, 2011, 82:122-130). Hence there is a need for new ER targeting agents that have the required pharmaceutical properties and SERD mechanism to provide enhanced benefit in the early, metastatic and acquired resistance setting.

The compounds of the specification have been found to possess potent anti-tumour activity, being useful in inhibiting the uncontrolled cellular proliferation which arises from malignant disease. The compounds of the specification provide an anti-tumour effect by, as a minimum, acting as SERDs. For example, the compounds of the specification may exhibit anti-tumour activity via the ability to down-regulate the estrogen receptor in a number of different breast cancer cell-lines, for example against the MCF-7, CAMA-1, BT474 and/or MDA-MB-134 breast cancer cell-lines. Such compounds may be expected to be more suitable as therapeutic agents, particularly for the treatment of cancer.

The compounds of the specification may also exhibit advantageous physical properties (for example, lower lipophilicity, higher aqueous solubility, higher permeability, lower plasma protein binding, and/or greater chemical stability), and/or favourable toxicity profiles (for example a decreased activity at hERG), and/or favourable metabolic or pharmacokinetic profiles, in comparison with other known SERDs. Such compounds may therefore be especially suitable as therapeutic agents, particularly for the treatment of cancer.

According to one aspect of the specification there is provided a compound of Formula (I):

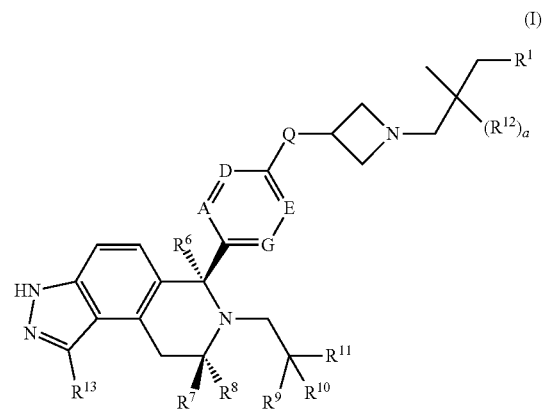

wherein:
A is $CR^2$ or N;
G is $CR^3$ or N;
D is $CR^4$ or N;
E is $CR^5$ or N;
Q is O, NH or NMe;

$R^1$ is $CH_2F$, $CHF_2$ or $CF_3$;
$R^2$ is H, F, Cl, Me, CN, OMe or OEt;
$R^3$ is H or F;
$R^4$ is H, F, CN or OMe;
$R^5$ is H or F;
$R^6$ is H, Me, $CH_2F$, $CHF_2$ or $CF_3$;
$R^7$ is H or Me;
$R^8$ is $C_{1-3}$ alkyl, $CH_2F$, $CHF_2$, $CF_3$ or $C_{3-4}$ cycloalkyl;
$R^9$ is Me, F or $CH_2F$;
$R^{10}$ is Me, F, $CH_2F$, $CHF_2$, $CF_3$, $CH_2OMe$ or $CH_2OH$;
$R^{11}$ is H or F; or
$R^{10}$ and $R^{11}$ taken together with the carbon atom to which they are attached form a cyclopropyl ring or an oxetane ring;
$R^{12}$ is independently selected from F or Me;
$R^{13}$ is H or F; and
a is 0, 1 or 2;
or a pharmaceutically acceptable salt thereof.

This specification also describes pharmaceutical compositions which comprise a compound of Formula (I), or a pharmaceutically acceptable salt thereof, in association with a pharmaceutically acceptable excipient.

This specification also describes a compound of Formula (I), or a pharmaceutically acceptable salt thereof, for use as a medicament.

This specification also describes a compound of Formula (I), or a pharmaceutically acceptable salt thereof, for use in the treatment of cancer.

This specification also describes combinations of a compound of Formula (I), or a pharmaceutically acceptable salt thereof, with another anti-tumour agent, for use in the treatment of cancer.

Further aspects of the specification will be apparent to one skilled in the art from reading this specification.

The $C_{1-3}$ alkyl group may be branched or unbranched. Examples of suitable $C_{1-3}$ alkyl groups are methyl (Me), ethyl (Et), n-propyl (n-Pr) or i-propyl (i-Pr).

The $C_{3-4}$ cycloalkyl group is an unsubstituted, monocyclic, unsaturated carbocyclic ring. Examples of suitable $C_{3-4}$ cycloalkyl groups are cyclopropyl and cyclobutyl.

In one embodiment there is provided a compound of Formula (I) as defined above.

In one embodiment there is provided a pharmaceutically acceptable salt of a compound of Formula (I).

In one embodiment A is $CR^2$.
In one embodiment G is $CR^3$.
In one embodiment A is $CR^2$ and G is $CR^3$.
In one embodiment A is $CR^2$ and G is N.
In one embodiment A is N and G is $CR^3$.
In one embodiment $R^2$ is H, F, Cl, Me, CN or OMe.
In one embodiment $R^2$ is H, F or OMe.
In one embodiment $R^2$ is H or F.
In one embodiment $R^2$ is H.
In one embodiment $R^2$ is F.
In one embodiment A is $CR^2$ and $R^2$ is H, F or OMe.
In one embodiment G is $CR^3$ and $R^3$ is H, F or OMe.
In one embodiment A is CH and G is CH.
In one embodiment A is C—F and G is C—F.
In one embodiment A is C—F and G is CH.
In one embodiment A is C—OMe and G is CH.
In one embodiment A is C—OMe and G is C—F.
In one embodiment one of A or G is CH and the other of A or G is N.
In one embodiment D is $CR^4$.
In one embodiment E is $CR^5$.
In one embodiment both D and E are CH.
In one embodiment both D and E are N.
In one embodiment one of D or E is CH and the other of D or E is N.
In one embodiment one of D or E is C—F and the other of D or E is CH.
In one embodiment one of D or E is C—OMe and the other of D or E is CH.
In one embodiment Q is O or NH.
In one embodiment Q is O.
In one embodiment Q is NH.
In one embodiment Q is NMe.
In one embodiment $R^1$ is $CH_2F$ or $CHF_2$.
In one embodiment $R^1$ is $CH_2F$.
In one embodiment $R^1$ is $CHF_2$.
In one embodiment $R^1$ is $CF_3$.
In one embodiment $R^6$ is H or Me.
In one embodiment $R^6$ is H.
In one embodiment $R^6$ is Me.
In one embodiment $R^7$ is H.
In one embodiment $R^7$ is Me.
In one embodiment $R^8$ is $C_{1-3}$ alkyl, $CHF_2$ or cyclopropyl.
In one embodiment $R^8$ is $C_{1-3}$ alkyl or $CHF_2$.
In one embodiment $R^8$ is $C_{1-3}$ alkyl.
In one embodiment $R^8$ is methyl.
In one embodiment $R^8$ is $CHF_2$.
In one embodiment $R^9$ is Me or F.
In one embodiment $R^9$ is Me.
In one embodiment $R^9$ is F.
In one embodiment $R^{10}$ is Me, F, $CH_2F$, $CH_2OMe$ or $CH_2OH$.
In one embodiment $R^{10}$ is Me, F, $CH_2OMe$ or $CH_2OH$.
In one embodiment $R^{10}$ is F, $CH_2OMe$ or $CH_2OH$.
In one embodiment $R^{10}$ is $CH_2OMe$ or $CH_2OH$.
In one embodiment $R^{10}$ is F.
In one embodiment $R^1$ is F.
In one embodiment $R^{11}$ is H.
In one embodiment $R^{10}$ and $R^{11}$ taken together with the carbon atom to which they are attached form a cyclopropyl ring or an oxetane ring.
In one embodiment $R^{10}$ and $R^{11}$ taken together with the carbon atom to which they are attached form a cyclopropyl ring.
In one embodiment $R^{10}$ and $R^{11}$ taken together with the carbon atom to which they are attached form an oxetane ring.
In one embodiment $R^{10}$ is $CH_2OMe$ or $CH_2OH$ and $R^{11}$ is F.
In one embodiment $R^{10}$ is $CH_2OMe$ or $CH_2OH$ and $R^9$ is Me.
In one embodiment $R^{10}$ is F and $R^9$ is F.
In one embodiment $R^9$ is Me or F and $R^2$ is H, F, Cl, Me, CN or OMe.
In one embodiment $R^9$ is Me and $R^{11}$ is F.
In one embodiment $R^9$ is F and $R^{11}$ is Me.
In one embodiment $R^9$ is F and $R^{11}$ is F.
In one embodiment $R^9$ is F and $R^{10}$ and $R^{11}$ taken together with the carbon atom to which they are attached form a cyclopropyl ring or an oxetane ring.
In one embodiment $R^9$ is F and $R^{10}$ and $R^{11}$ taken together with the carbon atom to which they are attached form a cyclopropyl ring.
In one embodiment $R^9$ is F and $R^{10}$ and $R^{11}$ taken together with the carbon atom to which they are attached form an oxetane ring.
In one embodiment the group $-CH_2-C(R^9)(R^{10})(R^{11})$ in the compound of Formula (I) is selected from the group consisting of:

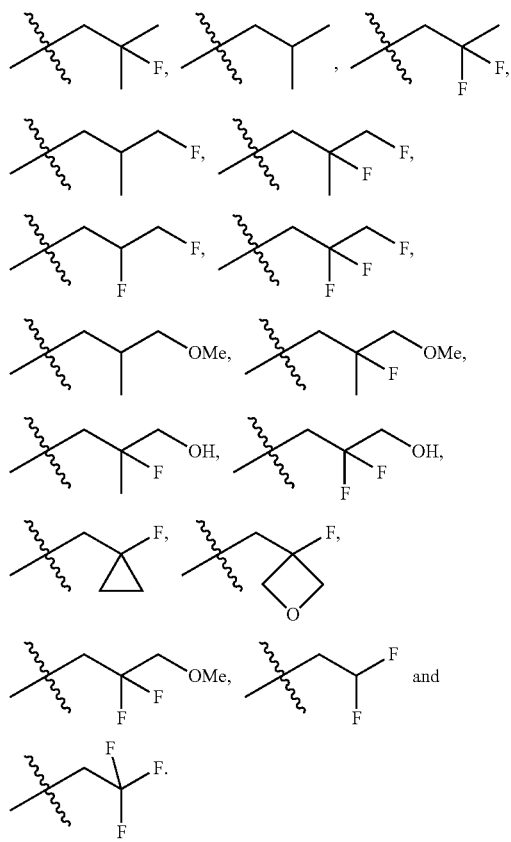

In one embodiment the group —CH$_2$—C(R$^9$)(R$^{10}$)(R$^{11}$) in the compound of Formula (I) is selected from the group consisting of:

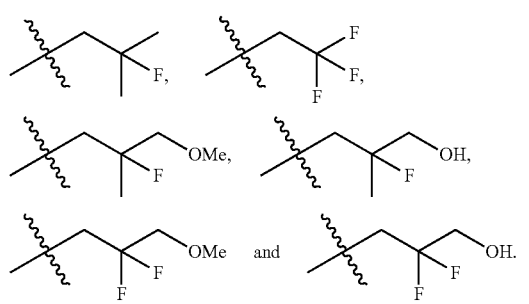

In one embodiment the group —CH$_2$—C(R$^9$)(R$^{10}$)(R$^{11}$) in the compound of Formula (I) is selected from the group consisting of:

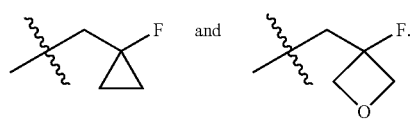 [SMILES: *CC1(F)CC1 ; "and" ; *CC1(F)COC1]

In one embodiment the group —CH$_2$—C(R$^9$)(R$^{10}$)(R$^{11}$) in the compound of Formula (I) is selected from the group consisting of:

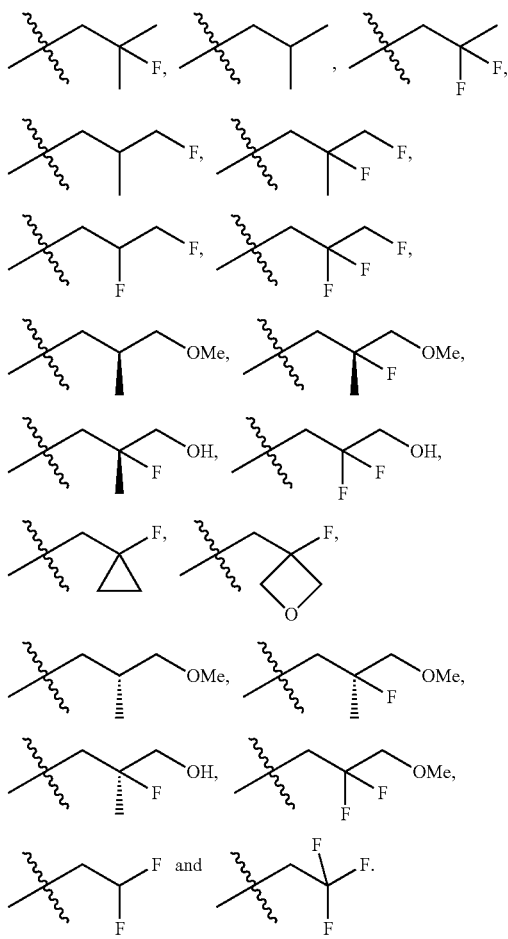

In one embodiment the group —CH$_2$—C(R$^9$)(R$^{10}$)(R$^{11}$) in the compound of Formula (I) is selected from the group consisting of:

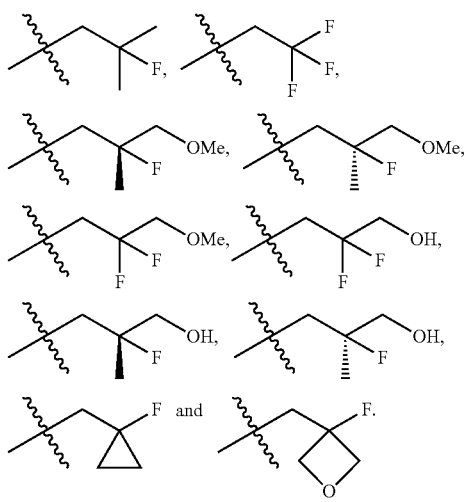

In one embodiment the group —CH$_2$—C(R$^9$)(R$^{10}$)(R$^{11}$) in the compound of Formula (I) is selected from the group consisting of:

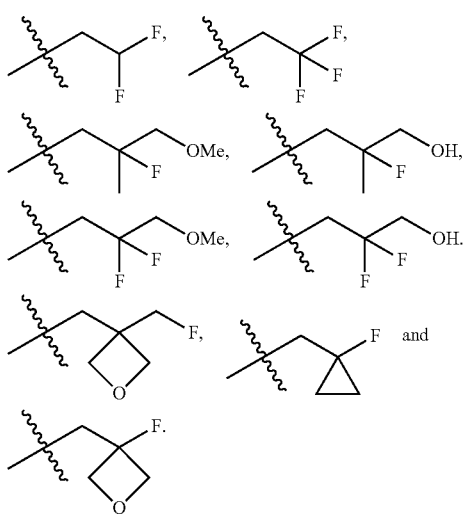

In one embodiment $R^{12}$ is Me.
In one embodiment $R^{12}$ is F.
In one embodiment $R^{13}$ is H.
In one embodiment $R^{13}$ is F.
In one embodiment a is 0 or 1.
In one embodiment a is 0.
In one embodiment a is 1.
In one embodiment a is 2.
In one embodiment there is provided a compound of Formula (IA):

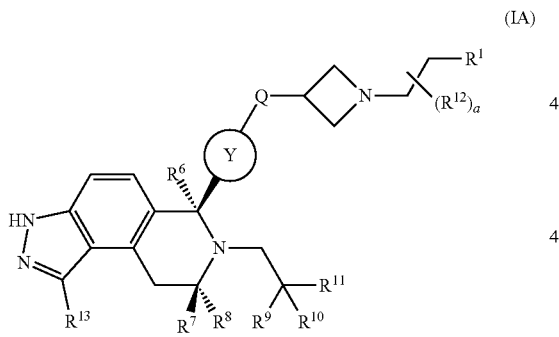

(IA)

wherein:
Q is O, NH or NMe;
$R^1$ is $CH_2F$, $CHF_2$ or $CF_3$;
$R^6$ is H or Me;
$R^7$ is H or Me;
$R^8$ is Me, $CHF_2$ or cyclopropyl;
$R^9$ is Me or F;
$R^{10}$ is Me, F, $CH_2F$, $CH_2OMe$ or $CH_2OH$;
$R^{11}$ is H or F; or
$R^{10}$ and $R^{11}$ taken together with the carbon atom to which they are attached form a cyclopropyl ring or an oxetane ring;
$R^{12}$ is independently selected from H or Me;
$R^{13}$ is H or F;
a is 0, 1 or 2; and Ring Y is selected from the group consisting of:

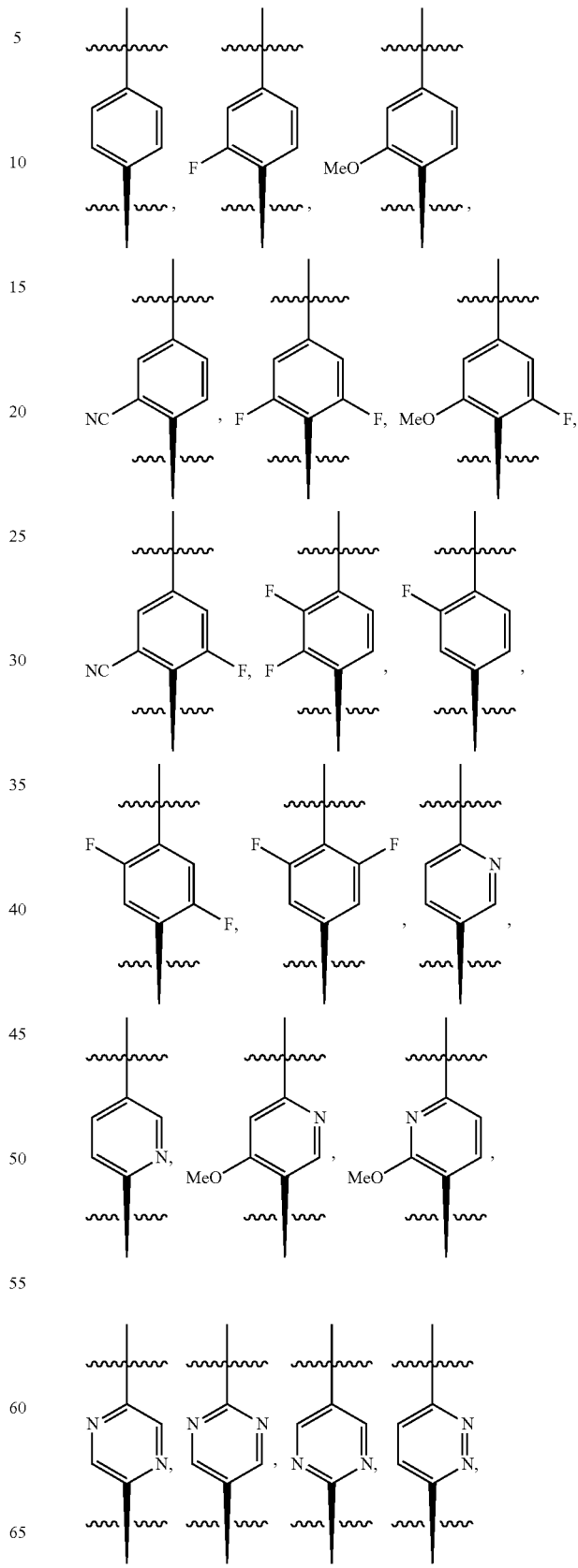

-continued

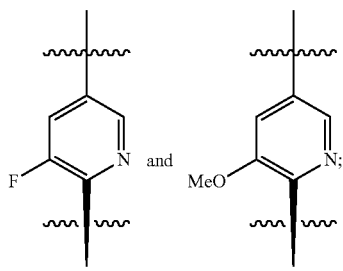 and 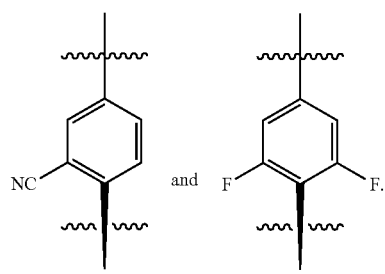

or a pharmaceutically acceptable salt thereof.

In one embodiment there is provided a compound of Formula (IA), or a pharmaceutically acceptable salt thereof, wherein Ring Y is selected from the group consisting of:

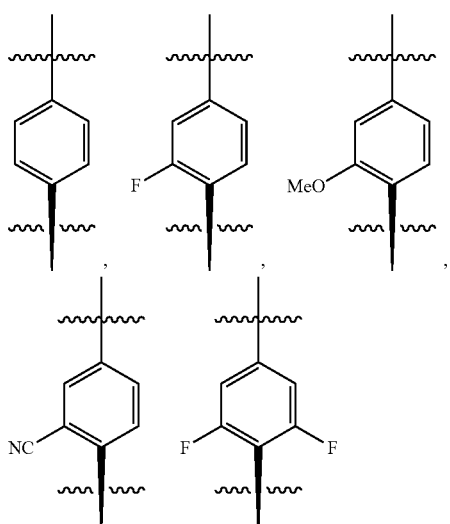

and .

In one embodiment there is provided a compound of Formula (IA), or a pharmaceutically acceptable salt thereof, wherein Ring Y is selected from the group consisting of:

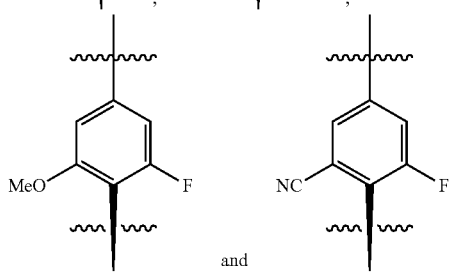

In one embodiment there is provided a compound of Formula (IA), or a pharmaceutically acceptable salt thereof, wherein Ring Y is selected from the group consisting of:

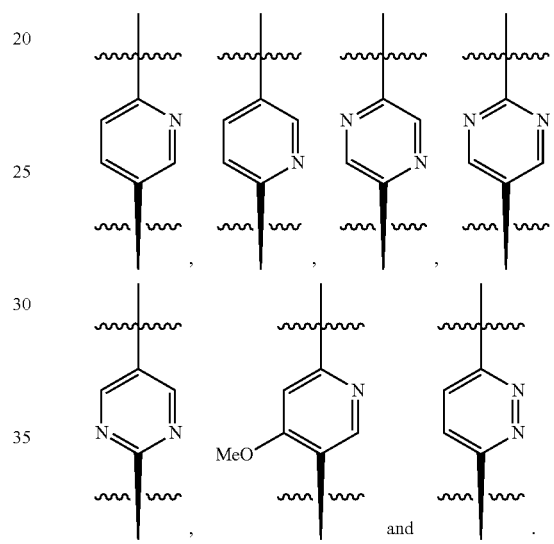

and .

In one embodiment there is provided a compound of Formula (IA), or a pharmaceutically acceptable salt thereof, wherein Ring Y is selected from the group consisting of:

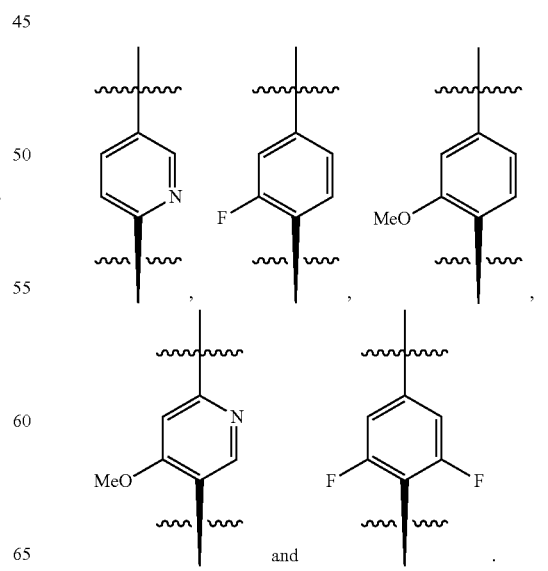

and .

In one embodiment there is provided a compound of Formula (IA), or a pharmaceutically acceptable salt thereof, wherein Ring Y is selected from the group consisting of:

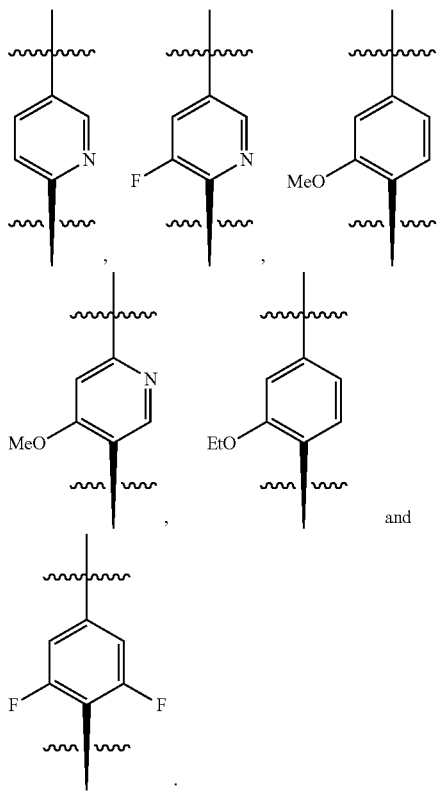

In one embodiment there is provided a compound of Formula (IA), or a pharmaceutically acceptable salt thereof, wherein Q is NH.

In one embodiment there is provided a compound of Formula (IA), or a pharmaceutically acceptable salt thereof, wherein Q is O.

In one embodiment there is provided a compound of Formula (IA), or a pharmaceutically acceptable salt thereof, wherein $R^1$ is $CH_2F$.

In one embodiment there is provided a compound of Formula (IA), or a pharmaceutically acceptable salt thereof, wherein $R^1$ is $CHF_2$.

In one embodiment there is provided a compound of Formula (IA), or a pharmaceutically acceptable salt thereof, wherein $R^6$ is H.

In one embodiment there is provided a compound of Formula (IA), or a pharmaceutically acceptable salt thereof, wherein $R^7$ is H.

In one embodiment there is provided a compound of Formula (IA), or a pharmaceutically acceptable salt thereof, wherein $R^8$ is Me.

In one embodiment there is provided a compound of Formula (IA), or a pharmaceutically acceptable salt thereof, wherein $R^{10}$ is F, $CH_2OMe$ or $CH_2OH$.

In one embodiment there is provided a compound of Formula (IA), or a pharmaceutically acceptable salt thereof, wherein $R^9$ is F and $R^{10}$ and $R^{11}$ taken together with the carbon atom to which they are attached form a cyclopropyl ring or an oxetane ring. In a further embodiment $R^{10}$ and $R^{11}$ taken together with the carbon atom to which they are attached form a cyclopropyl ring. In a further embodiment $R^{10}$ and $R^{11}$ taken together with the carbon atom to which they are attached form an oxetane ring.

In one embodiment there is provided a compound of Formula (IA), or a pharmaceutically acceptable salt thereof, wherein $R^8$ is Me.

In one embodiment the group $—CH_2—C(R^9)(R^{10})(R^{11})$ in the compound of Formula (IA) is selected from the group consisting of:

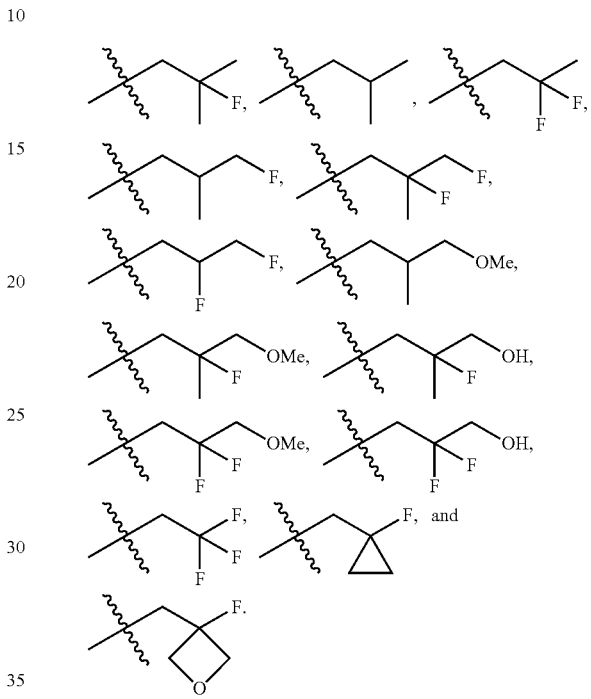

In one embodiment the group $—CH_2—C(R^9)(R^{10})(R^{11})$ in the compound of Formula (IA) is selected from the group consisting of:

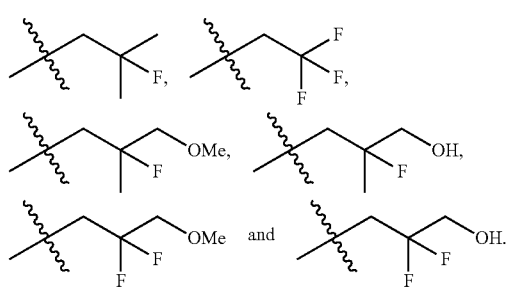

In one embodiment the group $—CH_2—C(R^9)(R^{10})(R^{11})$ in the compound of Formula (IA) is selected from the group consisting of:

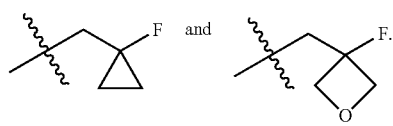 [SMILES: *CC1(F)CC1 ; *CC1(F)COC1]

In one embodiment the group $—CH_2—C(R^9)(R^{10})(R^{11})$ in the compound of Formula (IA) is selected from the group consisting of:

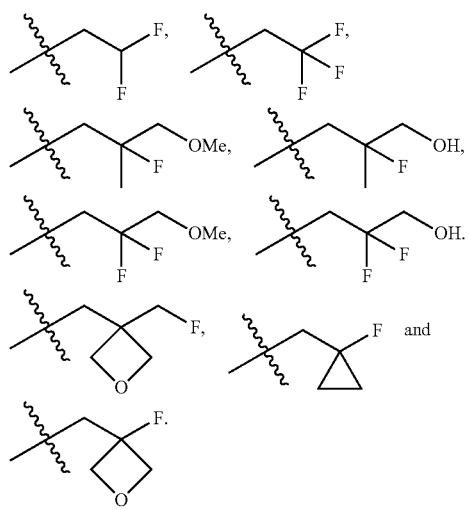

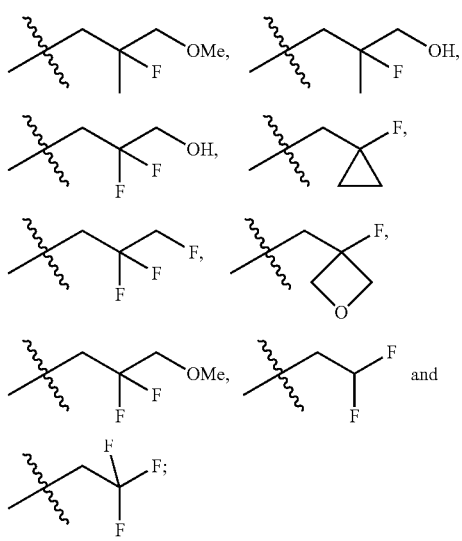

In one embodiment there is provided a compound of Formula (IA), or a pharmaceutically acceptable salt thereof, wherein $R^{13}$ is H.

In one embodiment there is provided a compound of Formula (IA), or a pharmaceutically acceptable salt thereof, wherein a is 0.

In one embodiment there is provided a compound of Formula (IB):

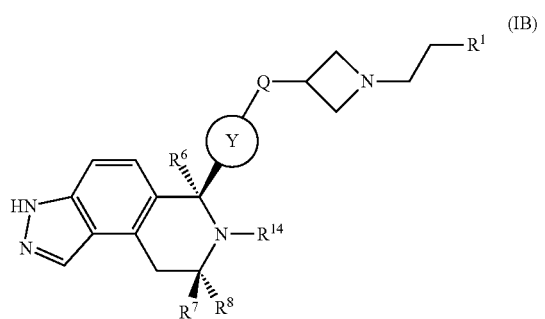

wherein:
Q is O, NH or NMe;
$R^1$ is $CH_2F$, $CHF_2$ or $CF_3$;
$R^6$ is H or Me;
$R^7$ is H or Me;
$R^8$ is Me, $CHF_2$ or cyclopropyl;
$R^{14}$ is selected from the group consisting of:

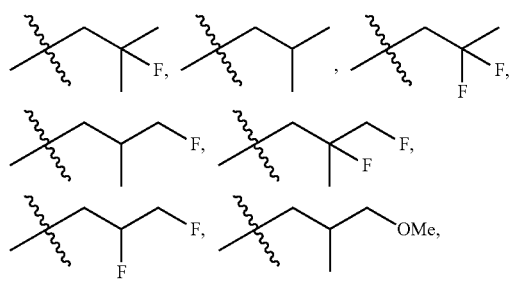

and Ring Y is selected from the group consisting of:

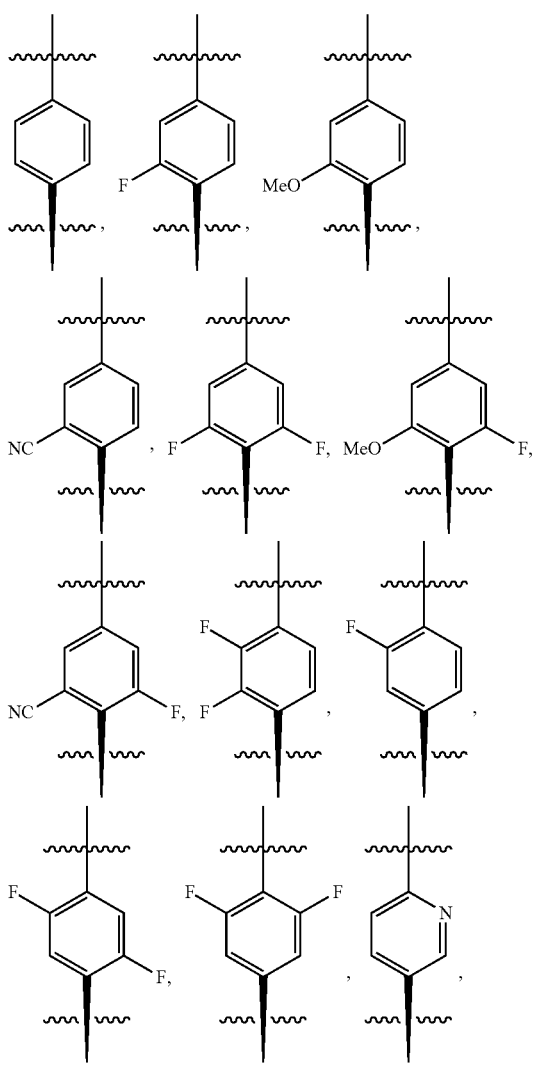

-continued

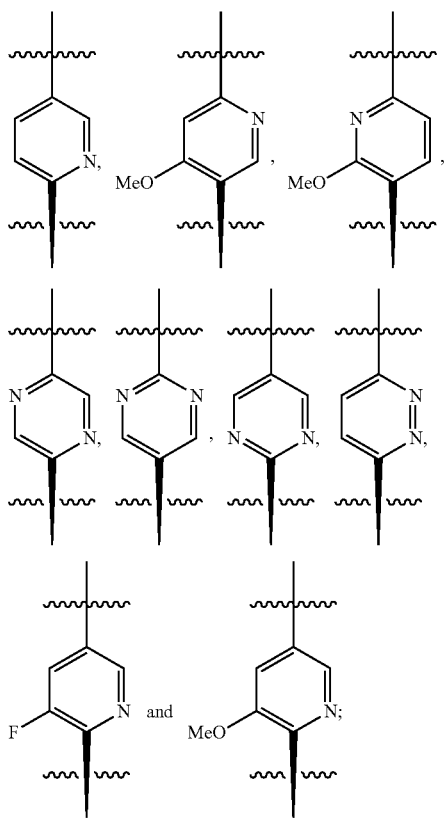

or a pharmaceutically acceptable salt thereof.

In one embodiment there is provided a compound of Formula (IB), or a pharmaceutically acceptable salt thereof, wherein Ring Y is selected from the group consisting of:

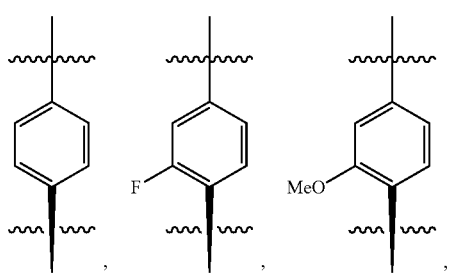

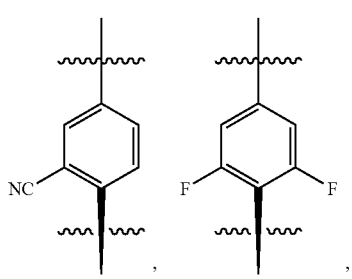

-continued

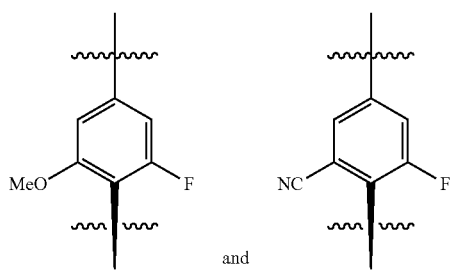

and

In one embodiment there is provided a compound of Formula (IB), or a pharmaceutically acceptable salt thereof, wherein Ring Y is selected from the group consisting of:

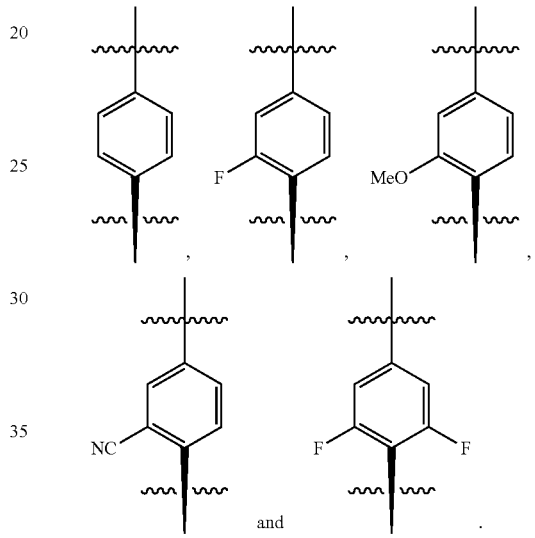

and

In one embodiment there is provided a compound of Formula (IB), or a pharmaceutically acceptable salt thereof, wherein Ring Y is selected from the group consisting of:

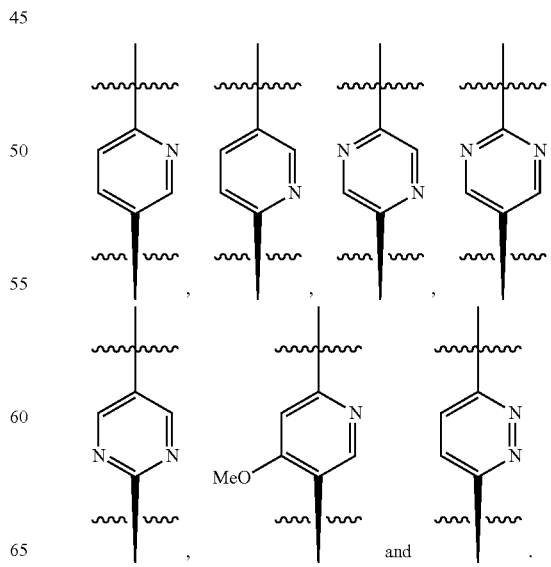

and

In one embodiment there is provided a compound of Formula (IB), or a pharmaceutically acceptable salt thereof, wherein Ring Y is selected from the group consisting of:

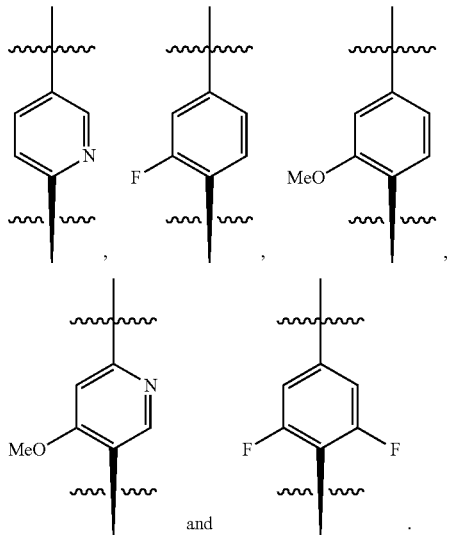

In one embodiment there is provided a compound of Formula (IB), or a pharmaceutically acceptable salt thereof, wherein Ring Y is selected from the group consisting of:

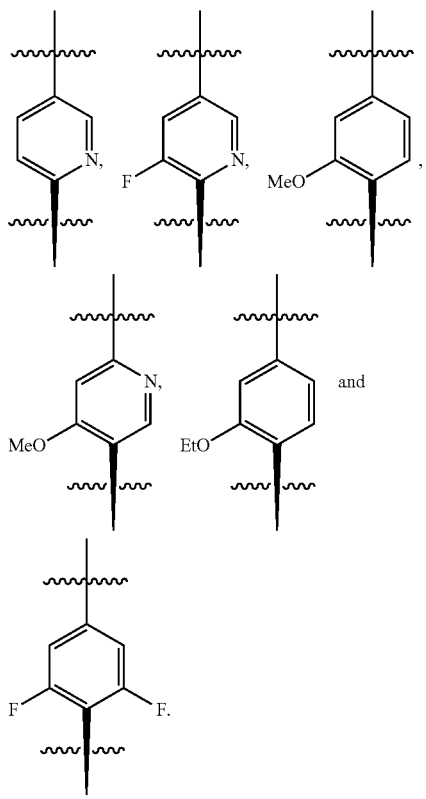

In one embodiment there is provided a compound of Formula (IB), or a pharmaceutically acceptable salt thereof, wherein Q is NH.

In one embodiment there is provided a compound of Formula (IB), or a pharmaceutically acceptable salt thereof, wherein Q is O.

In one embodiment there is provided a compound of Formula (IB), or a pharmaceutically acceptable salt thereof, wherein $R^1$ is $CH_2F$.

In one embodiment there is provided a compound of Formula (IB), or a pharmaceutically acceptable salt thereof, wherein $R^1$ is $CHF_2$.

In one embodiment there is provided a compound of Formula (IB), or a pharmaceutically acceptable salt thereof, wherein $R^6$ is H.

In one embodiment there is provided a compound of Formula (IB), or a pharmaceutically acceptable salt thereof, wherein $R^7$ is H.

In one embodiment there is provided a compound of Formula (IB), or a pharmaceutically acceptable salt thereof, wherein $R^8$ is Me.

In one embodiment the group $R^{14}$ in the compound of Formula (IB) is selected from the group consisting of:

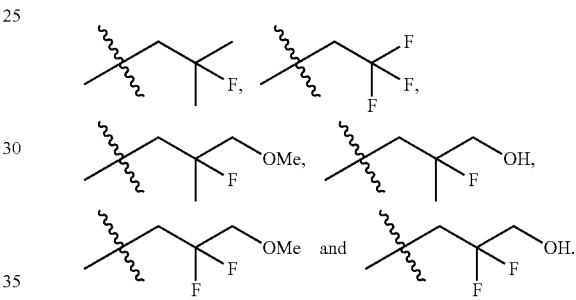

In one embodiment the group $R^{14}$ in the compound of Formula (IB) is selected from the group consisting of:

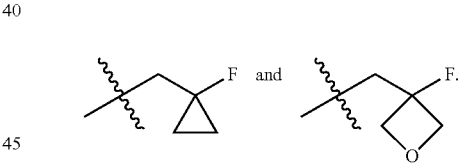

In one embodiment the group $R^{14}$ in the compound of Formula (IB) is selected from the group consisting of:

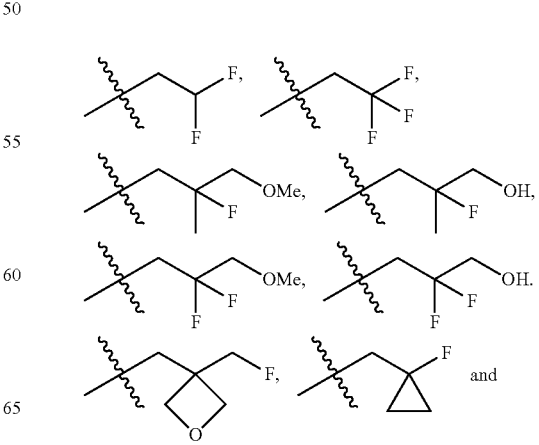

-continued

[structure: oxetane-CH2F fragment]

In a further aspect of the specification there is provided the compound of Formula (IC):

(IC)

[structure of Formula (IC)]

wherein:
A is $CR^2$ or N;
G is $CR^3$ or N;
D is $CR^4$ or N;
E is $CR^5$ or N;
Q is O, NH or NMe;
$R^1$ is $CH_2F$, $CHF_2$ or $CF_3$;
$R^2$ is H, F, Cl, Me, CN, OMe or OEt;
$R^3$ is H or F;
$R^4$ is H, F, CN or OMe;
$R^5$ is H or F;
$R^6$ is H, Me, $CH_2F$, $CHF_2$ or $CF_3$;
$R^7$ is H or Me;
$R^8$ is $C_{1-3}$ alkyl, $CH_2F$, $CHF_2$, $CF_3$ or $C_{3-4}$ cycloalkyl;
$R^9$ is Me, F or $CH_2F$;
$R^{10}$ is Me, F, $CH_2F$, $CHF_2$, $CF_3$, $CH_2OMe$ or $CH_2OH$;
$R^{11}$ is H or F; or
$R^{10}$ and $R^{11}$ taken together with the carbon atom to which they are attached form a cyclopropyl ring or an oxetane ring;
$R^{12}$ is independently selected from F or Me;
$R^{13}$ is H or F; and
a is 0, 1 or 2;
or a pharmaceutically acceptable salt thereof.

In one embodiment there is provided the compound of Formula (IC) or a pharmaceutically acceptable salt thereof wherein $R^2$ is H, F, Cl, Me, CN or OMe and $R^9$ is Me or F.

In a further embodiment there is provided the compound of Formula (IC) or a pharmaceutically acceptable salt thereof wherein the stereochemistry at the 6-position of the pyrazolo[4,3-f]isoquinoline ring is S.

In a further embodiment there is provided the compound of Formula (IC) or a pharmaceutically acceptable salt thereof wherein the stereochemistry at the 6-position of the pyrazolo[4,3-f]isoquinoline ring is R.

In a further embodiment there is provided the compound of Formula (IC) or a pharmaceutically acceptable salt thereof wherein the stereochemistry at the 8-position of the pyrazolo[4,3-f]isoquinoline ring is S.

In a further embodiment there is provided the compound of Formula (IC) or a pharmaceutically acceptable salt thereof wherein the stereochemistry at the 8-position of the pyrazolo[4,3-f]isoquinoline ring is R.

In one embodiment there is provided a compound of Formula (ID):

(ID)

[structure of Formula (ID)]

wherein:
Q is O or NH;
$R^1$ is $CH_2F$ or $CHF_2$;
$R^{14}$ is selected from the group consisting of:

[substituent structures]

and Ring Y is selected from the group consisting of:

[ring Y structures]

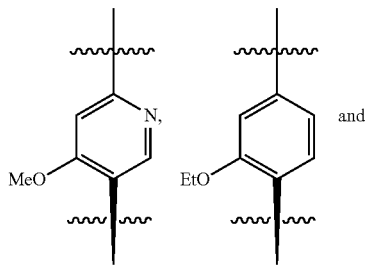 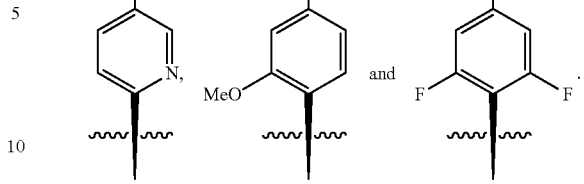

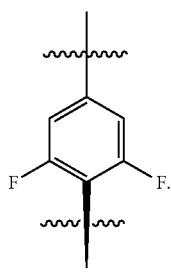

In one embodiment there is provided a compound of Formula (ID), or a pharmaceutically acceptable salt thereof, wherein Q is NH.

In one embodiment there is provided a compound of Formula (ID), or a pharmaceutically acceptable salt thereof, wherein Q is O.

In one embodiment there is provided a compound of Formula (ID), or a pharmaceutically acceptable salt thereof, wherein $R^1$ is $CH_2F$.

In one embodiment there is provided a compound of Formula (ID), or a pharmaceutically acceptable salt thereof, wherein Q is O and $R^1$ is $CH_2F$.

In one embodiment there is provided a compound of Formula (ID), or a pharmaceutically acceptable salt thereof, wherein Q is NH and $R^1$ is $CH_2F$.

In one embodiment there is provided a compound of Formula (ID), or a pharmaceutically acceptable salt thereof, wherein $R^{14}$ is selected from the group consisting of:

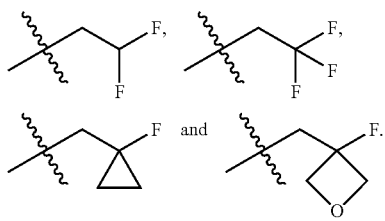

In one embodiment there is provided a compound of Formula (ID), or a pharmaceutically acceptable salt thereof, wherein Ring Y is selected from the group consisting of:

In one embodiment there is provided a compound of Formula (I), wherein the compound is selected from the group consisting of:
N-(4-((6S,8R)-7-(2,2-difluoro-3-methoxypropyl)-8-methyl-6,7,8,9-tetrahydro-3H-pyrazolo[4,3-f]isoquinolin-6-yl)-3-methoxyphenyl)-1-(3-fluoropropyl)azetidin-3-amine;
6-((6S,8R)-7-(2,2-difluoro-3-methoxypropyl)-8-methyl-6,7,8,9-tetrahydro-3H-pyrazolo[4,3-f]isoquinolin-6-yl)-N-(1-(3-fluoropropyl)azetidin-3-yl)pyridin-3-amine;
6-((6S,8R)-7-((1-fluorocyclopropyl)methyl)-8-methyl-6,7,8,9-tetrahydro-3H-pyrazolo[4,3-f]isoquinolin-6-yl)-N-(1-(3-fluoropropyl)azetidin-3-yl)pyridin-3-amine;
N-(4-((6S,8R)-7-(2-fluoro-3-methoxy-2-methylpropyl)-8-methyl-6,7,8,9-tetrahydro-3H-pyrazolo[4,3-f]isoquinolin-6-yl)-3-methoxyphenyl)-1-(3-fluoropropyl)azetidin-3-amine;
3-((6S,8R)-6-(2,6-difluoro-4-((1-(3-fluoropropyl)azetidin-3-yl)amino)phenyl)-8-methyl-3,6,8,9-tetrahydro-7H-pyrazolo[4,3-f]isoquinolin-7-yl)-2,2-difluoropropan-1-ol;
N-(4-((6S,8R)-7-((1-fluorocyclopropyl)methyl)-8-methyl-6,7,8,9-tetrahydro-3H-pyrazolo[4,3-f]isoquinolin-6-yl)-3-methoxyphenyl)-1-(3-fluoropropyl)azetidin-3-amine;
(6S,8R)-7-((1-fluorocyclopropyl)methyl)-6-(4-((1-(3-fluoropropyl)azetidin-3-yl)oxy)-2-methoxyphenyl)-8-methyl-6,7,8,9-tetrahydro-3H-pyrazolo[4,3-f]isoquinoline;
N-(3,5-difluoro-4-((6S,8R)-8-methyl-7-(2,2,2-trifluoroethyl)-6,7,8,9-tetrahydro-3H-pyrazolo[4,3-f]isoquinolin-6-yl)phenyl)-1-(3-fluoropropyl)azetidin-3-amine; and
5-((6S,8R)-7-((1-fluorocyclopropyl)methyl)-8-methyl-6,7,8,9-tetrahydro-3H-pyrazolo[4,3-f]isoquinolin-6-yl)-N-(1-(3-fluoropropyl)azetidin-3-yl)-4-methoxypyridin-2-amine;
or a pharmaceutically acceptable salt thereof.

In one embodiment there is provided a compound of Formula (I), wherein the compound is selected from the group consisting of:
N-(4-((6S,8R)-7-(2,2-difluoro-3-methoxypropyl)-8-methyl-6,7,8,9-tetrahydro-3H-pyrazolo[4,3-f]isoquinolin-6-yl)-3-methoxyphenyl)-1-(3-fluoropropyl)azetidin-3-amine;
6-((6S,8R)-7-(2,2-difluoro-3-methoxypropyl)-8-methyl-6,7,8,9-tetrahydro-3H-pyrazolo[4,3-f]isoquinolin-6-yl)-N-(1-(3-fluoropropyl)azetidin-3-yl)pyridin-3-amine;
6-((6S,8R)-7-((1-fluorocyclopropyl)methyl)-8-methyl-6,7,8,9-tetrahydro-3H-pyrazolo[4,3-f]isoquinolin-6-yl)-N-(1-(3-fluoropropyl)azetidin-3-yl)pyridin-3-amine;
N-(4-((6S,8R)-7-(2-fluoro-3-methoxy-2-methylpropyl)-8-methyl-6,7,8,9-tetrahydro-3H-pyrazolo[4,3-f]isoquinolin-6-yl)-3-methoxyphenyl)-1-(3-fluoropropyl)azetidin-3-amine;
3-((6S,8R)-6-(2,6-difluoro-4-((1-(3-fluoropropyl)azetidin-3-yl)amino)phenyl)-8-methyl-3,6,8,9-tetrahydro-7H-pyrazolo[4,3-f]isoquinolin-7-yl)-2,2-difluoropropan-1-ol;

N-(4-((6S,8R)-7-((1-fluorocyclopropyl)methyl)-8-methyl-6,7,8,9-tetrahydro-3H-pyrazolo[4,3-f]isoquinolin-6-yl)-3-methoxyphenyl)-1-(3-fluoropropyl)azetidin-3-amine;

(6S,8R)-7-((1-fluorocyclopropyl)methyl)-6-(4-((1-(3-fluoropropyl)azetidin-3-yl)oxy)-2-methoxyphenyl)-8-methyl-6,7,8,9-tetrahydro-3H-pyrazolo[4,3-f]isoquinoline;

N-(3,5-difluoro-4-((6S,8R)-8-methyl-7-(2,2,2-trifluoroethyl)-6,7,8,9-tetrahydro-3H-pyrazolo[4,3-f]isoquinolin-6-yl)phenyl)-1-(3-fluoropropyl)azetidin-3-amine;

5-((6S,8R)-7-((1-fluorocyclopropyl)methyl)-8-methyl-6,7,8,9-tetrahydro-3H-pyrazolo[4,3-f]isoquinolin-6-yl)-N-(1-(3-fluoropropyl)azetidin-3-yl)-4-methoxypyridin-2-amine;

N-(4-((6S,8R)-7-((3-(fluoromethyl)oxetan-3-yl)methyl)-8-methyl-6,7,8,9-tetrahydro-3H-pyrazolo[4,3-f]isoquinolin-6-yl)-3-methoxyphenyl)-1-(3-fluoropropyl)azetidin-3-amine;

N-(3,5-difluoro-4-((6S,8R)-7-((1-fluorocyclopropyl)methyl)-8-methyl-6,7,8,9-tetrahydro-3H-pyrazolo[4,3-f]isoquinolin-6-yl)phenyl)-1-(3-fluoropropyl)azetidin-3-amine;

(6S,8R)-7-(2-fluoro-3-methoxy-2-methylpropyl)-6-(4-(1-(3-fluoropropyl)azetidin-3-yloxy)-2-methoxyphenyl)-8-methyl-6,7,8,9-tetrahydro-3H-pyrazolo[4,3-f]isoquinoline;

N-(4-((6S,8R)-7-(2-fluoro-3-methoxy-2-methylpropyl)-8-methyl-6,7,8,9-tetrahydro-3H-pyrazolo[4,3-f]isoquinolin-6-yl)-3-methoxyphenyl)-1-(3-fluoropropyl)azetidin-3-amine;

2,2-difluoro-3-((6S,8R)-6-(5-((1-(3-fluoropropyl)azetidin-3-yl)amino)pyridin-2-yl)-8-methyl-3,6,8,9-tetrahydro-7H-pyrazolo[4,3-f]isoquinolin-7-yl)propan-1-ol;

N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine;

5-fluoro-6-((6S,8R)-7-((1-fluorocyclopropyl)methyl)-8-methyl-6,7,8,9-tetrahydro-3H-pyrazolo[4,3-f]isoquinolin-6-yl)-N-(1-(3-fluoropropyl)azetidin-3-yl)pyridin-3-amine;

N-(4-((6S,8R)-7-(2,2-difluoropropyl)-8-methyl-6,7,8,9-tetrahydro-3H-pyrazolo[4,3-f]isoquinolin-6-yl)-3-methoxyphenyl)-1-(3-fluoropropyl)azetidin-3-amine;

N-(3-ethoxy-4-((6S,8R)-7-((1-fluorocyclopropyl)methyl)-8-methyl-6,7,8,9-tetrahydro-3H-pyrazolo[4,3-f]isoquinolin-6-yl)phenyl)-1-(3-fluoropropyl)azetidin-3-amine;

N-(4-((6S,8R)-7-(2,2-difluoroethyl)-8-methyl-6,7,8,9-tetrahydro-3H-pyrazolo[4,3-f]isoquinolin-6-yl)-3-methoxyphenyl)-1-(3-fluoropropyl)azetidin-3-amine;

(6S,8R)-7-(2,2-difluoroethyl)-6-(4-((1-(3-fluoropropyl)azetidin-3-yl)oxy)-2-methoxyphenyl)-8-methyl-6,7,8,9-tetrahydro-3H-pyrazolo[4,3-f]isoquinoline;

3-((6S,8R)-6-(2,6-difluoro-4-(1-(3-fluoropropyl)azetidin-3-ylamino)phenyl)-8-methyl-8,9-dihydro-3H-pyrazolo[4,3-f]isoquinolin-7(6H)-yl)-2-fluoro-2-methylpropan-1-ol;

6-((6S,8R)-7-(2,2-difluoroethyl)-8-methyl-6,7,8,9-tetrahydro-3H-pyrazolo[4,3-f]isoquinolin-6-yl)-N-(1-(3-fluoropropyl)azetidin-3-yl)pyridin-3-amine; and (6S,8R)-7-(2,2-difluoroethyl)-6-(5-((1-(3-fluoropropyl)azetidin-3-yl)oxy)pyridin-2-yl)-8-methyl-6,7,8,9-tetrahydro-3H-pyrazolo[4,3-f]isoquinoline;

or a pharmaceutically acceptable salt thereof.

In one embodiment there is provided a compound of Formula (I), wherein the compound is selected from the group consisting of:

1-(3-fluoropropyl)-N-(4-((6R,8R)-8-methyl-7-(2,2,2-trifluoroethyl)-6,7,8,9-tetrahydro-3H-pyrazolo[4,3-f]isoquinolin-6-yl)phenyl)azetidin-3-amine;

1-(3-fluoropropyl)-N-(3-methoxy-4-((6S,8R)-8-methyl-7-(2,2,2-trifluoroethyl)-6,7,8,9-tetrahydro-3H-pyrazolo[4,3-f]isoquinolin-6-yl)phenyl)azetidin-3-amine;

2-fluoro-N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine;

5-fluoro-N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine;

2,2-difluoro-3-((6S,8R)-6-(3-fluoro-5-((1-(3-fluoropropyl)azetidin-3-yl)amino)pyridin-2-yl)-8-methyl-3,6,8,9-tetrahydro-7H-pyrazolo[4,3-f]isoquinolin-7-yl)propan-1-ol;

6-((6S,8R)-1-fluoro-8-methyl-7-(2,2,2-trifluoroethyl)-6,7,9,8-tetrahydro-3H-pyrazolo[4,3-f]isoquin-6-yl)-N-(3-fluoropropyl)azetidi-3-yl)pyridin-3-amine;

5-fluoro-6-((6S,8R)-1-fluoro-8-methyl-7-(2,2,2-trifluoroethyl)-6,7,8,9-tetrahydro-3H-pyrazolo[4,3-f]isoquinolin-6-yl)-N-(1-(3-fluoropropyl)azetidin-3-yl)pyridin-3-amine;

N-(1-(3-fluoropropyl)azetidin-3-yl)-N-methyl-6-((6S,8R)-8-methyl-7-(2,2,2-trifluoroethyl)-6,7,8,9-tetrahydro-3H-pyrazolo[4,3-f]isoquinolin-6-yl)pyridin-3-amine;

N-(1-(3-fluoropropyl)azetidin-3-yl)-6-((6S,8R)-6-deuterio-8-methyl-7-(2,2,2-trifluoroethyl)-6,7,8,9-tetrahydro-3H-pyrazolo[4,3-f]isoquinolin-6-yl)pyridin-3-amine;

N-(1-(3-fluoropropyl)azetidin-3-yl)-6-((6S,8R)-1-deuterio-8-methyl-7-(2,2,2-trifluoroethyl)-6,7,8,9-tetrahydro-3H-pyrazolo[4,3-f]isoquinolin-6-yl)pyridin-3-amine;

N-(1-(3-fluoropropyl)azetidin-3-yl)-5-methoxy-6-((6S,8R)-8-methyl-7-(2,2,2-trifluoroethyl)-6,7,8,9-tetrahydro-3H-pyrazolo[4,3-f]isoquinolin-6-yl)pyridin-3-amine;

5-((6S,8R)-1-fluoro-8-methyl-7-(2,2,2-trifluoroethyl)-6,7,8,9-tetrahydro-3H-pyrazolo[4,3-f]isoquinolin-6-yl)-N-(1-(3-fluoropropyl)azetidin-3-yl)pyrazin-2-amine;

2-fluoro-6-((6S,8R)-1-fluoro-8-methyl-7-(2,2,2-trifluoroethyl)-6,7,8,9-tetrahydro-3H-pyrazolo[4,3-f]isoquinolin-6-yl)-N-(1-(3-fluoropropyl)azetidin-3-yl)pyridin-3-amine;

6-fluoro-N-(1-(3-fluoropropyl)azetidin-3-yl)-5-((6S,8R)-8-methyl-7-(2,2,2-trifluoroethyl)-6,7,8,9-tetrahydro-3H-pyrazolo[4,3-f]isoquinolin-6-yl)pyridin-2-amine;

N-(2-fluoro-4-((6R,8R)-8-methyl-7-(2,2,2-trifluoroethyl)-6,7,8,9-tetrahydro-3H-pyrazolo[4,3-f]isoquinolin-6-yl)phenyl)-1-(3-fluoropropyl)azetidin-3-amine;

N-(1-(3-fluoropropyl)azetidin-3-yl)-5-((6S,8R)-8-methyl-7-(2,2,2-trifluoroethyl)-6,7,8,9-tetrahydro-3H-pyrazolo[4,3-f]isoquinolin-6-yl)pyrazin-2-amine;

6-((6S,8R)-7-(2,2-difluoroethyl)-8-methyl-6,7,8,9-tetrahydro-3H-pyrazolo[4,3-f]isoquinolin-6-yl)-N-(1-(3-fluoropropyl)azetidin-3-yl)-N-methylpyridin-3-amine;

6-((6S,8R)-7-(2,2-difluoroethyl)-6,8-dimethyl-6,7,8,9-tetrahydro-3H-pyrazolo[4,3-f]isoquinolin-6-yl)-N-(1-(3-fluoropropyl)azetidin-3-yl)pyridin-3-amine;

is N-(4-((6S,8R)-7-(2,2-difluoroethyl)-6,8-dimethyl-6,7,8,9-tetrahydro-3H-pyrazolo[4,3-f]isoquinolin-6-yl)-3-methoxyphenyl)-1-(3-fluoropropyl)azetidin-3-amine;

6-((6S,8R)-7-(2,2-difluoroethyl)-8-methyl-6,7,8,9-tetrahydro-3H-pyrazolo[4,3-f]isoquinolin-6-yl)-5-fluoro-N-(1-(3-fluoropropyl)azetidin-3-yl)pyridin-3-amine;

6-((6S,8R)-7-(2,2-difluoroethyl)-8-methyl-6,7,8,9-tetrahydro-3H-pyrazolo[4,3-f]isoquinolin-6-yl)-2-fluoro-N-(1-(3-fluoropropyl)azetidin-3-yl)pyridin-3-amine;

N-(4-((6R,8R)-7-(2,2-difluoroethyl)-8-methyl-6,7,8,9-tetrahydro-3H-pyrazolo[4,3-f]isoquinolin-6-yl)phenyl)-1-(3-fluoropropyl)azetidin-3-amine;

N-(4-((6S,8R)-7-(2,2-difluoroethyl)-8-methyl-6,7,8,9-tetrahydro-3H-pyrazolo[4,3-f]isoquinolin-6-yl)-3,5-difluorophenyl)-1-(3-fluoropropyl)azetidin-3-amine;

5-((6S,8R)-7-(2,2-difluoroethyl)-8-methyl-6,7,8,9-tetrahydro-3H-pyrazolo[4,3-f]isoquinolin-6-yl)-N-(1-(3-fluoropropyl)azetidin-3-yl)pyrazin-2-amine;

6-((6S,8S)-7-(2,2-difluoroethyl)-8-(difluoromethyl)-6,7,8,9-tetrahydro-3H-pyrazolo[4,3-f]isoquinolin-6-yl)-N-(1-(3-fluoropropyl)azetidin-3-yl)pyridin-3-amine;

N-(4-((6S,8R)-7-((1-fluorocyclopropyl)methyl)-8-methyl-6,7,8,9-tetrahydro-3H-pyrazolo[4,3-f]isoquinolin-6-yl)-3-methoxyphenyl)-1-(3-fluoropropyl)-N-methylazetidin-3-amine;

N-(2-fluoro-4-((6S,8R)-7-((1-fluorocyclopropyl)methyl)-8-methyl-6,7,8,9-tetrahydro-3H-pyrazolo[4,3-f]isoquinolin-6-yl)-5-methoxyphenyl)-1-(3-fluoropropyl)azetidin-3-amine;

5-((6S,8R)-7-((1-fluorocyclopropyl)methyl)-8-methyl-6,7,8,9-tetrahydro-3H-pyrazolo[4,3-f]isoquinolin-6-yl)-N-(1-(3-fluoropropyl)azetidin-3-yl)pyridin-2-amine;

5-((6S,8R)-7-((1-fluorocyclopropyl)methyl)-8-methyl-6,7,8,9-tetrahydro-3H-pyrazolo[4,3-f]isoquinolin-6-yl)-N-(1-(3-fluoropropyl)azetidin-3-yl)pyrazin-2-amine;

N-(4-((6S,8R)-7-((1-fluorocyclopropyl)methyl)-8-methyl-6,7,8,9-tetrahydro-3H-pyrazolo[4,3-f]isoquinolin-6-yl)-3-methoxyphenyl)-1-(3,3,3-trifluoropropyl)azetidin-3-amine;

6-((6S,8R)-7-((1-fluorocyclopropyl)methyl)-8-methyl-6,7,8,9-tetrahydro-3H-pyrazolo[4,3-f]isoquinolin-6-yl)-N-(1-(3-fluoropropyl)azetidin-3-yl)-N-methylpyridin-3-amine;

2,2-difluoro-3-((6S,8R)-6-(5-((1-(3-fluoropropyl)azetidin-3-yl)oxy)pyridin-2-yl)-8-methyl-3,6,8,9-tetrahydro-7H-pyrazolo[4,3-f]isoquinolin-7-yl)propan-1-ol;

2,2-difluoro-3-((6S,8R)-6-(3-fluoro-5-((1-(3-fluoropropyl)azetidin-3-yl)oxy)pyridin-2-yl)-8-methyl-3,6,8,9-tetrahydro-7H-pyrazolo[4,3-f]isoquinolin-7-yl)propan-1-ol;

2,2-difluoro-3-((6S,8R)-6-(4-((1-(3-fluoropropyl)azetidin-3-yl)amino)-2-methoxyphenyl)-8-methyl-3,6,8,9-tetrahydro-7H-pyrazolo[4,3-f]isoquinolin-7-yl)propan-1-ol;

2,2-difluoro-3-((6S,8R)-1-fluoro-6-(5-((1-(3-fluoropropyl)azetidin-3-yl)amino)pyridin-2-yl)-8-methyl-3,6,8,9-tetrahydro-7H-pyrazolo[4,3-f]isoquinolin-7-yl)propan-1-ol;

2,2-difluoro-3-((6S,8R)-1-fluoro-6-(6-fluoro-5-((1-(3-fluoropropyl)azetidin-3-yl)amino)pyridin-2-yl)-8-methyl-3,6,8,9-tetrahydro-7H-pyrazolo[4,3-f]isoquinolin-7-yl)propan-1-ol;

6-((6S,8R)-7-(2-fluoro-2-methylpropyl)-8-methyl-6,7,8,9-tetrahydro-3H-pyrazolo[4,3-f]isoquinolin-6-yl)-N-(1-(3-fluoropropyl)azetidin-3-yl)pyridin-3-amine;

N-(4-((6S,8R)-7-(2-fluoro-2-methylpropyl)-8-methyl-6,7,8,9-tetrahydro-3H-pyrazolo[4,3-f]isoquinolin-6-yl)-3-methoxyphenyl)-1-(3-fluoropropyl)azetidin-3-amine;

6-((6S,8R)-7-(2-fluoropropyl)-8-methyl-6,7,8,9-tetrahydro-3H-pyrazolo[4,3-f]isoquinolin-6-yl)-N-(1-(3-fluoropropyl)azetidin-3-yl)pyridin-3-amine;

6-((6S,8R)-7-(2-fluoropropyl)-8-methyl-6,7,8,9-tetrahydro-3H-pyrazolo[4,3-f]isoquinolin-6-yl)-N-(1-(3-fluoropropyl)azetidin-3-yl)pyridin-3-amine;

1-(3-fluoropropyl)-N-(4-((6S,8R)-7-(2-fluoropropyl)-8-methyl-6,7,8,9-tetrahydro-3H-pyrazolo[4,3-f]isoquinolin-6-yl)-3-methoxyphenyl)azetidin-3-amine;

1-(3-fluoropropyl)-N-(4-((6S,8R)-7-(2-fluoropropyl)-8-methyl-6,7,8,9-tetrahydro-3H-pyrazolo[4,3-f]isoquinolin-6-yl)-3-methoxyphenyl)azetidin-3-amine;

N-(1-(3-fluoropropyl)azetidin-3-yl)-6-((6S,8R)-7-isobutyl-8-methyl-6,7,8,9-tetrahydro-3H-pyrazolo[4,3-f]isoquinolin-6-yl)pyridin-3-amine;

6-((6S,8R)-7-(2,2-difluoropropyl)-8-methyl-6,7,8,9-tetrahydro-3H-pyrazolo[4,3-f]isoquinolin-6-yl)-N-(1-(3-fluoropropyl)azetidin-3-yl)pyridin-3-amine;

5-fluoro-N-(1-(3-fluoropropyl)azetidin-3-yl)-6-((6S,8R)-8-methyl-7-(2,2,3-trifluoropropyl)-6,7,8,9-tetrahydro-3H-pyrazolo[4,3-f]isoquinolin-6-yl)pyridin-3-amine;

(S)-6-(8,8-dimethyl-7-(2,2,2-trifluoroethyl)-6,7,8,9-tetrahydro-3H-pyrazolo[4,3-f]isoquinolin-6-yl)-N-(1-(3-fluoropropyl)azetidin-3-yl)pyridin-3-amine; and (S)-6-(7-(2,2-difluoroethyl)-8,8-dimethyl-6,7,8,9-tetrahydro-3H-pyrazolo[4,3-f]isoquinolin-6-yl)-N-(1-(3-fluoropropyl)azetidin-3-yl)pyridin-3-amine or a pharmaceutically acceptable salt thereof.

In one embodiment there is provided a compound of Formula (I) which is N-(1-(3-fluoropropyl)azetidin-3-yl)-6-(8-methyl-7-(2,2,2-trifluoroethyl)-6,7,8,9-tetrahydro-3H-pyrazolo[4,3-f]isoquinolin-6-yl)pyridin-3-amine, or a pharmaceutically acceptable salt thereof.

In one embodiment there is provided a compound of Formula (I) which is selected from the group consisting of:
N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine; and
N-(1-(3-fluoropropyl)azetidin-3-yl)-6-((6R,8R)-8-methyl-7-(2,2,2-trifluoroethyl)-6,7,8,9-tetrahydro-3H-pyrazolo[4,3-f]isoquinolin-6-yl)pyridin-3-amine;
or a pharmaceutically acceptable salt thereof.

In one embodiment there is provided a compound of Formula (I) which is N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine, or a pharmaceutically acceptable salt thereof.

In one embodiment there is provided a compound of Formula (I) which is N-(1-(3-fluoropropyl)azetidin-3-yl)-6-((6R,8R)-8-methyl-7-(2,2,2-trifluoroethyl)-6,7,8,9-tetrahydro-3H-pyrazolo[4,3-f]isoquinolin-6-yl)pyridin-3-amine, or a pharmaceutically acceptable salt thereof.

In one embodiment there is provided a compound of Formula (I), or a pharmaceutically acceptable salt thereof, wherein the compound is selected from any of the Examples in the specification. A further feature is any of the embodiments described in the specification with the proviso that any of the specific Examples are individually disclaimed. A further feature is any of the embodiments described in the specification with the proviso that any one or more of the compounds selected from the above list of examples of compounds of the specification are individually disclaimed.

For the avoidance of doubt, when a is 1, the $R^{12}$ substituent may be substituted on either carbon of the respective ethyl chain with which it is associated, and when a is 2, the $R^{12}$ substituent may be substituted at either a single carbon or at both carbons of the said ethyl chain. When a is 1 or 2, therefore, the following substitution patterns are possible, each of which represent a further embodiment:

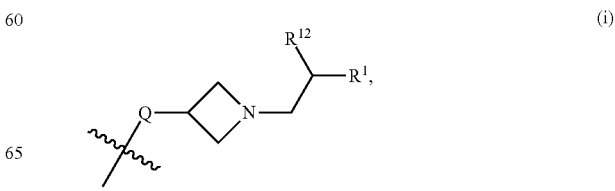

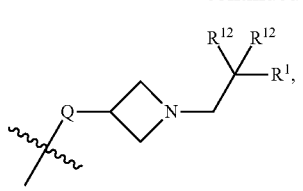
(ii)

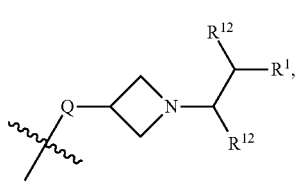
(iii)

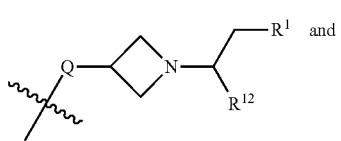
(iv)

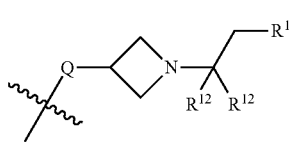
(v)

In a further embodiment, therefore, a is 1 or 2 and $R^{12}$ is attached to the remainder of the compound of Formula (I) as shown in (a) below:

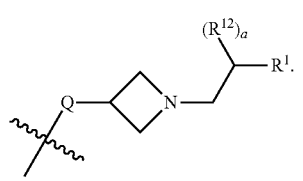
(a)

In a further embodiment, a is 1 or 2, $R^{12}$ is methyl, and $R^{12}$ is attached to the remainder of the compound of Formula (I) as shown in (b) below:

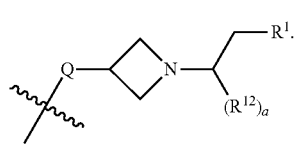
(b)

For the further avoidance of doubt, the use of "

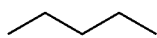

" in formulas of this specification denotes the point of attachment between different groups.

The compounds of Formula (I) have two or more chiral centres and it will be recognised that the compound of Formula (I) may be prepared, isolated and/or supplied with or without the presence, in addition, of one or more of the other possible enantiomeric and/or diastereomeric isomers of the compound of Formula (I) in any relative proportions. The preparation of enantioenriched/enantiopure and/or diastereoenriched/diastereopure compounds may be carried out by standard techniques of organic chemistry that are well known in the art, for example by synthesis from enantioenriched or enantiopure starting materials, use of an appropriate enantioenriched or enantiopure catalyst during synthesis, and/or by resolution of a racemic or partially enriched mixture of stereoisomers, for example via chiral chromatography.

For use in a pharmaceutical context it may be preferable to provide a compound of Formula (I) or a pharmaceutically acceptable salt thereof without large amounts of the other stereoisomeric forms being present.

Accordingly, in one embodiment there is provided a composition comprising a compound of Formula (I) or a pharmaceutically acceptable salt thereof, optionally together with one or more of the other stereoisomeric forms of the compound of Formula (I) or pharmaceutically acceptable salt thereof, wherein the compound of Formula (I) or pharmaceutically acceptable salt thereof is present within the composition with a diastereomeric excess (% de) of ≥90%.

In a further embodiment the % de in the above-mentioned composition is ≥95%.

In a further embodiment the % de in the above-mentioned composition is ≥98%.

In a further embodiment the % de in the above-mentioned composition is ≥99%.

In a further embodiment there is provided a composition comprising a compound of Formula (I) or a pharmaceutically acceptable salt thereof, optionally together with one or more of the other stereoisomeric forms of the compound of Formula (I) or pharmaceutically acceptable salt thereof, wherein the compound of Formula (I) or pharmaceutically acceptable salt thereof is present within the composition with an enantiomeric excess (% ee) of ≥90%.

In a further embodiment the % ee in the above-mentioned composition is ≥95%.

In a further embodiment the % ee in the above-mentioned composition is ≥98%.

In a further embodiment the % ee in the above-mentioned composition is ≥99%.

In a further embodiment there is provided a composition comprising a compound of Formula (I) or a pharmaceutically acceptable salt thereof, optionally together with one or more of the other stereoisomeric forms of the compound of Formula (I) or pharmaceutically acceptable salt thereof, wherein the compound of Formula (I) or pharmaceutically acceptable salt thereof is present within the composition with an enantiomeric excess (% ee) of ≥90% and a diastereomeric excess (% de) of ≥90%.

In further embodiments of the above-mentioned composition the % ee and % de may take any combination of values as listed below:

The % ee is ≤5% and the % de is ≥80%.
The % ee is ≤5% and the % de is ≥90%.
The % ee is ≤5% and the % de is ≥95%.
The % ee is ≤5% and the % de is ≥98%.
The % ee is ≥95% and the % de is ≥95%.
The % ee is ≥98% and the % de is ≥98%.
The % ee is ≥99% and the % de is ≥99%.

In a further embodiment there is provided a pharmaceutical composition which comprises a compound of the Formula (I) or a pharmaceutically acceptable salt thereof, in association with a pharmaceutically acceptable excipient.

In one embodiment there is provided a pharmaceutical composition which comprises a compound of the Formula (I) or a pharmaceutically acceptable salt thereof, in association with a pharmaceutically acceptable excipient, optionally further comprising one or more of the other stereoisomeric forms of the compound of Formula (I) or pharmaceutically acceptable salt thereof, wherein the compound of Formula (I) or pharmaceutically acceptable salt thereof is present within the composition with an enantiomeric excess (% ee) of ≥90%.

In a further embodiment the % ee in the above-mentioned composition is ≥95%.

In a further embodiment the % ee in the above-mentioned composition is ≥98%.

In a further embodiment the % ee in the above-mentioned composition is ≥99%.

In one embodiment there is provided a pharmaceutical composition which comprises a compound of the Formula (I) or a pharmaceutically acceptable salt thereof, in association with a pharmaceutically acceptable excipient, optionally further comprising one or more of the other stereoisomeric forms of the compound of Formula (I) or pharmaceutically acceptable salt thereof, wherein the compound of Formula (I) or pharmaceutically acceptable salt thereof is present within the composition with a diastereomeric excess (% de) of ≥90%.

In a further embodiment the % de in the above-mentioned composition is ≥95%.

In a further embodiment the % de in the above-mentioned composition is ≥98%.

In a further embodiment the % de in the above-mentioned composition is ≥99%.

In one embodiment there is provided a pharmaceutical composition which comprises a compound of the Formula (I) or a pharmaceutically acceptable salt thereof, in association with a pharmaceutically acceptable excipient, optionally further comprising one or more of the other stereoisomeric forms of the compound of Formula (I) or pharmaceutically acceptable salt thereof, wherein the compound of Formula (I) or pharmaceutically acceptable salt thereof is present within the composition with an enantiomeric excess (% ee) of ≥90% and a diastereomeric excess (% de) of ≥90%.

In further embodiments of the above-mentioned pharmaceutical composition the % ee and % de may take any combination of values as listed below:

The % ee is ≥95% and the % de is ≥95%.
The % ee is ≥98% and the % de is ≥98%.
The % ee is ≥99% and the % de is ≥99%.

The compounds of Formula (I) and pharmaceutically acceptable salts thereof may be prepared, used or supplied in amorphous form, crystalline form, or semicrystalline form and any given compound of Formula (I) or pharmaceutically acceptable salt thereof may be capable of being formed into more than one crystalline/polymorphic form, including hydrated (e.g. hemi-hydrate, a mono-hydrate, a di-hydrate, a tri-hydrate or other stoichiometry of hydrate) and/or solvated forms. It is to be understood that the present specification encompasses any and all such solid forms of the compound of Formula (I) and pharmaceutically acceptable salts thereof.

In further embodiments there is provided a compound of Formula (I), which is obtainable by the methods described in the 'Examples' section hereinafter.

The present specification is intended to include all isotopes of atoms occurring in the present compounds. Isotopes will be understood to include those atoms having the same atomic number but different mass numbers. For example, isotopes of hydrogen include tritium and deuterium. Isotopes of carbon include $^{13}C$ and $^{14}C$. Isotopes of nitrogen include $^{15}N$. In a particular embodiment there is provided a compound of Formula (I) wherein $R^6$ is deuterium.

A suitable pharmaceutically acceptable salt of a compound of the Formula (I) is, for example, an acid addition salt. A suitable pharmaceutically acceptable salt of a compound of Formula (I) may be, for example, an acid-addition salt of a compound of the Formula (I), for example an acid-addition salt with an inorganic or organic acid such as acetic acid, adipic acid, benzene sulfonic acid, benzoic acid, cinnamic acid, citric acid, D,L-lactic acid, ethane disulfonic acid, ethane sulfonic acid, fumaric acid, hydrochloric acid, L-tartaric acid, maleic acid, malic acid, malonic acid, methane sulfonic acid, napadisylic acid, phosphoric acid, saccharin, succinic acid, sulfuric acid, p-toluenesulfonic acid, toluene sulfonic acid or trifluoroacetic acid.

A further suitable pharmaceutically acceptable salt of a compound of the Formula (I) is, for example, a salt formed within the human or animal body after administration of a compound of the Formula (I) to said human or animal body.

The compound of Formula (I) or pharmaceutically acceptable salt thereof may be prepared as a co-crystal solid form. It is to be understood that a pharmaceutically acceptable co-crystal of a compound of the Formula (I) or pharmaceutically acceptable salts thereof, form an aspect of the present specification.

The specific solid forms described herein provide X-ray powder diffraction patterns substantially the same as the X-ray powder diffraction patterns shown in the Figures and have the various 2-theta values as shown in the Tables included herein. It will be understood that the 2-theta values of an X-ray powder diffraction pattern may vary slightly from one machine to another or from one sample to another, and so the values quoted are not to be construed as absolute.

It is known that an X-ray powder diffraction pattern may be obtained which has one or more measurement errors depending on measurement conditions (such as equipment or machine used). In particular, it is generally known that intensities in an X-ray powder diffraction pattern may fluctuate depending on measurement conditions. Therefore it should be understood that the solid forms of the present specification are not limited to the crystals that provide X-ray powder diffraction patterns that are identical to the X-ray powder diffraction pattern shown in the Figures, and any crystals providing X-ray powder diffraction patterns substantially the same as those shown in the Figures fall within the scope of the present specification. A person skilled in the art of X-ray powder diffraction is able to judge the substantial identity of X-ray powder diffraction patterns.

Persons skilled in the art of X-ray powder diffraction will realise that the relative intensity of peaks can be affected by, for example, grains above 30 μm in size and non-unitary aspect ratios, which may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values. (Jenkins, R & Snyder, R. L. 'Introduction to X-Ray Powder Diffractometry' John Wiley & Sons 1996; Bunn, C. W. (1948), Chemical Crystallography, Clarendon Press, London; Klug, H. P. & Alexander, L. E. (1974), X-Ray Diffraction Procedures).

Generally, a measurement error of a diffraction angle in an X-ray powder diffractogram is approximately plus or minus 0.2° 2-theta, and such degree of a measurement error should be taken into account when considering the X-ray powder diffraction pattern in the Figures and when reading data contained in the Tables included herein. Furthermore, it should be understood that intensities might fluctuate depending on experimental conditions and sample preparation (preferred orientation).

In this specification the form of the compound N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine (hereafter Compound X) was initially found to be an amorphous solid. Useful crystalline polymorphic forms of the compound have subsequently been produced using the conditions described in the experimental section.

Therefore in a further aspect of the specification there is provided polymorphic Form A of Compound X. This polymorphic form may be characterised in that it provides at least one of the following 2θ values measured using CuKa radiation: 15.5, 18.6 and 24.6°.

Polymorphic Form A of Compound X is characterised in providing an X-ray powder diffraction pattern, substantially as shown in FIG. 1.

Ten X-Ray powder diffraction peaks for this polymorphic form [Angle 2-theta (2θ), Intensity (%)] are: 21.1 (100%), 20.8 (54.3%), 14.6 (41.9%), 18.6 (41.6%), 12.3 (38.9%), 15.5 (34.1%), 24.6 (31.3%), 15.8 (30.6%), 13.4 (23.2%) and 19.0° (21.7%).

According to the present specification there is provided the polymorphic Form A of Compound X, which has an X-ray powder diffraction pattern with at least one specific peak at about 2-theta=15.5°.

According to the present specification there is provided the polymorphic Form A of Compound X, which has an X-ray powder diffraction pattern with at least one specific peak at about 2-theta=18.6°.

According to the present specification there is provided the polymorphic Form A of Compound X, which has an X-ray powder diffraction pattern with at least one specific peak at about 2-theta=24.6°.

According to the present specification there is provided the polymorphic Form A of Compound X, which has an X-ray powder diffraction pattern with at least two specific peaks at about 2-theta=15.5° and 18.6°.

According to the present specification there is provided the polymorphic Form A of Compound X, which has an X-ray powder diffraction pattern with specific peaks at about 2-theta=21.1, 20.8, 14.6, 18.6, 12.3, 15.5, 24.6, 15.8, 13.4 and 19.0°.

According to the present specification there is provided polymorphic Form A of Compound X which has an X-ray powder diffraction pattern substantially the same as the X-ray powder diffraction pattern shown in FIG. 1.

According to the present specification there is provided polymorphic Form A of Compound X, which has an X-ray powder diffraction pattern with at least one specific peak at 2-theta=15.5° plus or minus 0.2° 2-theta.

According to the present specification there is provided a polymorphic Form A of Compound X, which has an X-ray powder diffraction pattern with at least one specific peak at 2-theta=18.6° plus or minus 0.2° 2-theta.

According to the present specification there is provided the polymorphic Form A of Compound X, which has an X-ray powder diffraction pattern with at least two specific peaks at 2-theta=15.5° and 18.6° wherein said values may be plus or minus 0.2° 2-theta.

According to the present specification there is provided a polymorphic Form A of Compound X, which has an X-ray powder diffraction pattern with specific peaks at 2-theta=21.1, 20.8, 14.6, 18.6, 12.3, 15.5, 24.6, 15.8, 13.4 and 19.0° wherein said values may be plus or minus 0.2° 2-theta.

In a further aspect of the specification there is provided polymorphic Form E of Compound X. This polymorphic form may be characterised in that it provides at least one of the following 2θ values measured using CuKa radiation: 14.8, 16.2 and 17.9°.

Polymorphic Form E of Compound X is characterised in providing an X-ray powder diffraction pattern, substantially as shown in FIG. 8.

Ten X-Ray powder diffraction peaks for this polymorphic form [Angle 2-theta (2θ), Intensity (%)] are: 17.9 (100%), 14.8 (67.1%), 20.9 (60.1%), 23.1 (55.4%), 16.2 (49.3%), 20.0 (35.6%), 18.2 (32.9%), 12.3 (30.4%), 22.2 (19.0%) and 13.9° (18.9%).

According to the present specification there is provided the polymorphic Form E of Compound X, which has an X-ray powder diffraction pattern with at least one specific peak at about 2-theta=17.9°.

According to the present specification there is provided the polymorphic Form E of Compound X, which has an X-ray powder diffraction pattern with at least one specific peak at about 2-theta=14.8°.

According to the present specification there is provided the polymorphic Form E of Compound X, which has an X-ray powder diffraction pattern with at least one specific peak at about 2-theta=17.9°.

According to the present specification there is provided the polymorphic Form E of Compound X, which has an X-ray powder diffraction pattern with at least two specific peaks at about 2-theta=17.9° and 14.8°.

According to the present specification there is provided the polymorphic Form E of Compound X, which has an X-ray powder diffraction pattern with specific peaks at about 2-theta=17.9, 14.8, 20.9, 23.1, 16.2, 20.0, 18.2, 12.3, 22.2 and 13.9°.

According to the present specification there is provided polymorphic Form E of Compound X which has an X-ray powder diffraction pattern substantially the same as the X-ray powder diffraction pattern shown in FIG. 8.

According to the present specification there is provided polymorphic Form E of Compound X, which has an X-ray powder diffraction pattern with at least one specific peak at 2-theta=17.9° plus or minus 0.2° 2-theta.

According to the present specification there is provided a polymorphic Form E of Compound X, which has an X-ray powder diffraction pattern with at least one specific peak at 2-theta=14.8° plus or minus 0.2° 2-theta.

According to the present specification there is provided the polymorphic Form E of Compound X, which has an X-ray powder diffraction pattern with at least two specific peaks at 2-theta=17.9° and 14.8° wherein said values may be plus or minus 0.2° 2-theta.

According to the present specification there is provided a polymorphic Form E of Compound X, which has an X-ray powder diffraction pattern with specific peaks at 2-theta=17.9, 14.8, 20.9, 23.1, 16.2, 20.0, 18.2, 12.3, 22.2 and 13.9° wherein said values may be plus or minus 0.2° 2-theta.

It is to be understood that a suitable pharmaceutically acceptable pro-drug of a compound of the Formula (I) also forms an aspect of the present specification. Accordingly, the compounds of the specification may be administered in the form of a pro-drug, which is a compound that is broken down in the human or animal body to release a compound of the specification. A pro-drug may be used to alter the physical properties and/or the pharmacokinetic properties of a compound of the specification. A pro-drug can be formed when the compound of the specification contains a suitable group or substituent is to which a property-modifying group can be attached. Examples of pro-drugs include in-vivo cleavable ester or amide derivatives of the compound of the Formula (I).

Accordingly, one aspect of the present specification includes those compounds of Formula (I) as defined hereinbefore when made available by organic synthesis and when made available within the human or animal body by way of cleavage of a pro-drug thereof. Accordingly, the present specification includes those compounds of the Formula (I) that are produced by organic synthetic means and also such compounds that are produced in the human or animal body by way of metabolism of a precursor compound, that is a compound of the Formula (I) may be a synthetically-produced compound or a metabolically-produced compound.

A suitable pharmaceutically acceptable pro-drug of a compound of the Formula (I) is one that is based on reasonable medical judgement as being suitable for administration to the human or animal body without undesirable pharmacological activities and without undue toxicity.

Various forms of pro-drug have been described, for example in the following documents:— a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

The in-vivo effects of a compound of the Formula (I) may be exerted in part by one or more metabolites that are formed within the human or animal body after administration of a compound of the Formula (I). As stated hereinbefore, the in-vivo effects of a compound of the Formula (I) may also be exerted by way of metabolism of a precursor compound (a pro-drug).

For the avoidance of doubt it is to be understood that where in this specification a group is qualified by 'hereinbefore defined' or 'defined herein' the said group encompasses the first occurring and broadest definition as well as each and all of the alternative definitions for that group.

Another aspect of the present specification provides a process for preparing a compound of the Formula (I), or a pharmaceutically acceptable salt thereof. A suitable process is illustrated by the following representative process variants in which, unless otherwise stated, A, D, E, G, Q and $R^1$ to $R^{12}$ have any of the meanings defined hereinbefore. Necessary starting materials may be obtained by standard procedures of organic chemistry. The preparation of such starting materials is described in conjunction with the following representative process variants and within the accompanying Examples. Alternatively, necessary starting materials are obtainable by analogous procedures to those illustrated which are within the ordinary skill of an organic chemist.

Compounds of Formula (I) where $R^{13}$ is H may be made by, for example:

a) etherification of a suitable aryl or heteroaryl compound of Formula (II), where L is for example a halogen (such as iodine), or a trifluoromethanesulfonyl (triflate) group, or a boronic acid or ester, with an alcohol of Formula (III) using a suitable metal catalyst (for example RockPhos 3rd Generation Precatalyst) in a suitable solvent (such as toluene or DME) in the presence of a suitable base (such as cesium carbonate) and a suitable temperature (such as 90-120° C.); removal of the protecting group (PG) in Formula (II), such as THP, using acid conditions (such as anhydrous HCl in 1,4-dioxane) at suitable temperature (such as 10-30° C.).

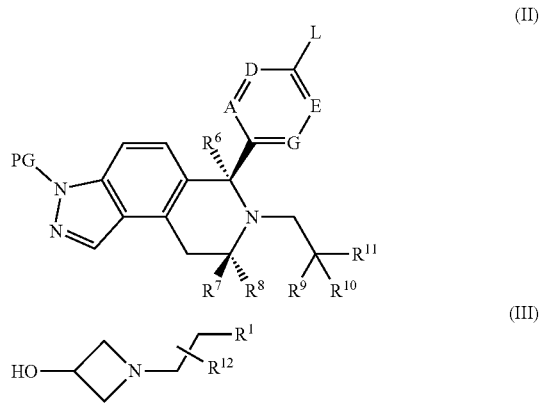

b) amination of a suitable aryl or heteroaryl compound of Formula (II), where L is for example a halogen (such as iodine), or a trifluoromethylsulfonyloxy (triflate) group, with an amine of Formula (IV) using a suitable metal catalyst (for example BrettPhos or RuPhos, and $Pd_2(dba)_3$) in a suitable solvent (for example 1,4-dioxane) in the presence of a suitable base (for example cesium carbonate, sodium tert-butoxide, or LiHMDS) at a suitable temperature (such as 90-130° C.); removal of the protecting group (PG), such as THP, using acid conditions (such as anhydrous HCl in 1,4-dioxane) at suitable temperature (such as 10-30° C.).

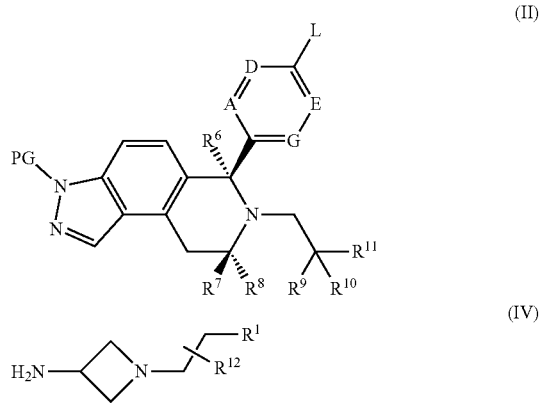

c) alkylation of a suitable phenol or hydroxyl heteroaryl compound of Formula (V) with an alcohol of Formula (III) via Mitsunobu reaction using appropriate reagents (such as triphenylphosphine and diisopropyl (E)-diazene-1,2-dicarboxylate) in a suitable solvent (such as THF); removal of the protecting group (PG), such as THP, in Formula (VII), using acid conditions (such as anhydrous HCl in 1,4-dioxane) at suitable temperature (such as 10-30° C.).

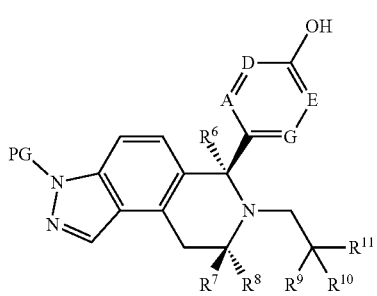
(V)

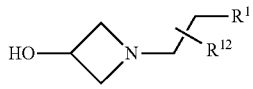
(III)

d) alkylation of a suitable aniline or heteroaryl amine or phenol or hydroxyl heteroaryl compound of Formula (VI) with a compound of Formula (VII) where LG is a leaving group (such as halide or mesylate), using mild bases (for example DIPEA) in a suitable solvent (such as DMF or MeCN); removal of the protecting group (PG), such as THP, using acid conditions (such as anhydrous HCl in 1,4-dioxane) at suitable temperature (such as 10-30° C.).

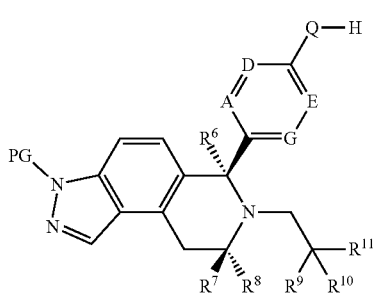
(VI)

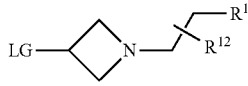
(VII)

e) Alkylation of amines of Formula (VIII) with a suitable alkylating group of Formula (IX) (wherein LG can be halide, as bromide, iodide or chloride, or may be some other suitable leaving group, such as mesylate) in a suitable solvent (such as DMF) in the presence of a suitable base (such as DIPEA) at a suitable temperature (such as 10-30° C.).

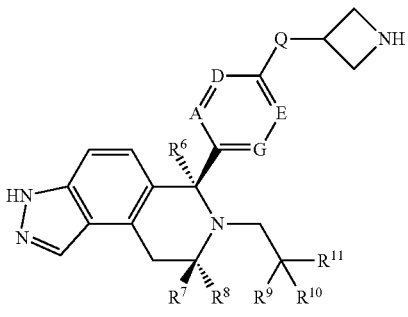
(VIII)

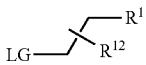
(IX)

Compounds of formula (II) where $R^6$ is not equal to hydrogen may be made, for example, from compounds of formula (X) by oxidation with a suitable reagent (for example bis(trifluoracetoxy)-iodobenzene) and treatment with an organometallic reagent (for example methyl magnesium bromide when $R^6$ is methyl) in a suitable solvent (for example THF) at low temperature (typically −80 to −60° C.).

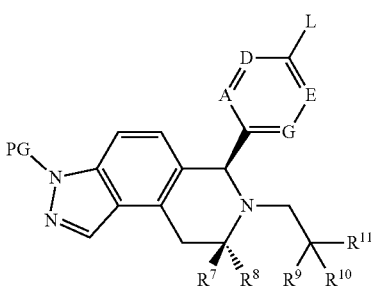
(X)

Compounds of formula (X) may be prepared by, for example, reaction of an aniline of Formula (XI) with suitable reagents to effect the construction of an indazole such as inorganic nitrite (such as sodium nitrite) in organic acid (such as propionic acid) at low temperature (typically −20 to 0° C.) or alternatively an acid anhydride (such as acetic anhydride) in the presence of a suitable base (such as potassium acetate) together with organic nitrite (such as isopentyl nitrite) optionally in the presence of a crown ether (such as 18-crown-6) in a suitable solvent (such as chloroform) at a suitable temperature (such as 70° C.).

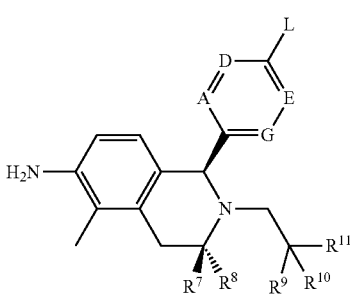
(XI)

Compounds of formula (XI) may be made by reaction of a compound of formula (XII) with a compound of formula (XIII) under conditions known in the art as suitable for Pictet-Spengler reactions, such as in the presence of acid (such as acetic acid) and in a suitable solvent (for example toluene or water) and a suitable temperature (such as 60-100° C.).

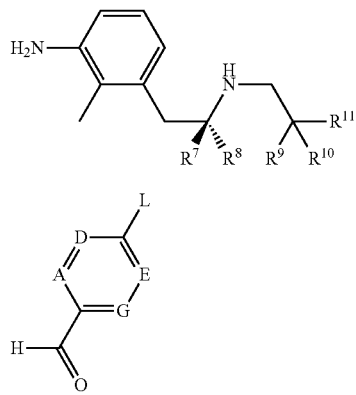

Compounds of formula (XII) may be prepared by functional group interconversions known to the art, for example aminations of halides of formula (XIV) from aryl halides (such as bromide) using a protected amine (such as diphenylmethanimine) in the presence of a suitable catalyst and ligand (such as bis(dibenzylideneacetone)palladium(0) and rac-2,2'-bis(diphenylphosphino)-1,1'-binaphthyl) in the presence of a suitable base (such as sodium tert-butoxide) in a suitable solvent (such as toluene) at a suitable temperature (such as 80-100° C.).

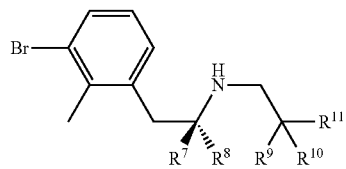

Compounds of Formula (XIV) may be prepared by:
a) reaction of a compound of formula (XV) with an aldehyde of formula (XVI), in a suitable solvent (for example THF) in the presence of a suitable reducing agent (such as sodium triacetoxyborohydride) and at a suitable temperature (such as 20-30° C.);
b) (i) reaction of a compound of formula (XV) with an acid of formula (XVII) under standard amide bond forming conditions (for example in the presence of an amide coupling reagent (such as HATU) and a suitable base (such as triethylamine) in a suitable solvent (such as DMF)), followed by (ii) reduction of the resultant amide bond using a suitable reducing agent (such as borane) in a suitable solvent (such as THF) at a suitable temperature (such as 60-70° C.);
c) reaction of a compound of formula (XV) with a compound of formula (XVIII), wherein LG is a suitable leaving group (for example a halogen atom (such as bromo or chloro) or triflate), in the presence of a suitable base (such as diisopropylethylamine) in a suitable solvent (for example DCM or dioxane) and at a suitable temperature (such as 20-85° C.).

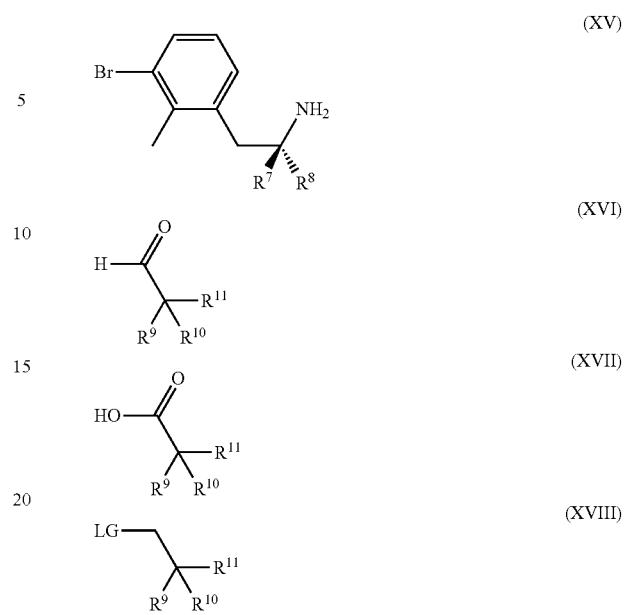

Compounds of formula (XV) may be prepared by a number of methods known to the art for the synthesis of chiral amines notably;
a) Ring opening of sulfamidates of Formula (XIX) according to the scheme shown below.

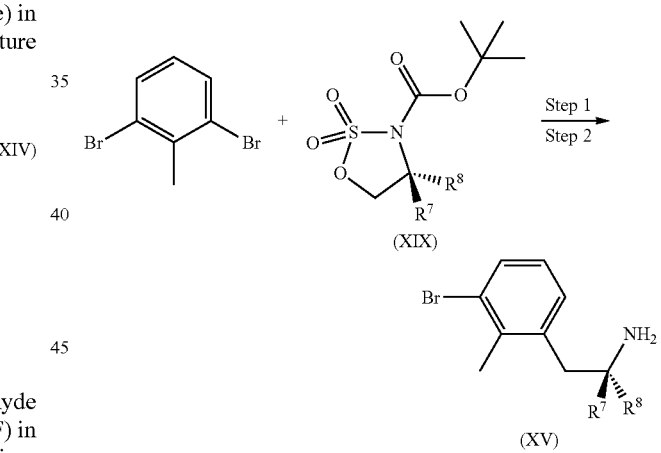

Step 1: Alkylation, e.g. n-butyllithium/THF/−78° C. to 0° C.
Step 2: Removal of protection groups, e.g. anhydrous HCl in MeOH/DCM, rt.
b) Phase transfer alklyation in the presence of a chiral catalyst (such as (1S,2S,4S,5R)-2-((R)-(allyloxy)(quinolin-4-yl)methyl)-1-(anthracen-9-ylmethyl)-5-vinylquinuclidin-1-ium bromide) followed by functional group manipulation.

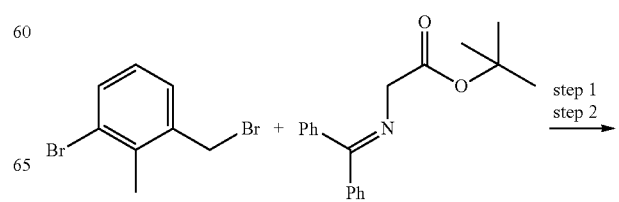

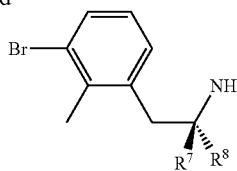

Step 1: Alkylation, e.g. Chiral catalyst, toluene/KOH, 0° C.
Step 2: Functional group interconversion.

Compounds of Formula (XII) may be directly prepared by:

a) reaction of a compound of formula (XX) with an aldehyde of formula (XVI), in a suitable solvent (for example THF) in the presence of a suitable reducing agent (such as sodium triacetoxyborohydride) and at a suitable temperature (such as 20-30° C.);

b) (i) reaction of a compound of formula (XX) with an acid of formula (XVII) under standard amide bond forming conditions (for example in the presence of an amide coupling reagent (such as HATU) and a suitable base (such as triethylamine) in a suitable solvent (such as DMF)), followed by (ii) reduction of the resultant amide bond using a suitable reducing agent (such as borane) in a suitable solvent (such as THF) at a suitable temperature (such as 60-70° C.);

c) reaction of a compound of formula (XX) with a compound of formula (XIII), wherein LG is a suitable leaving group (for example a halogen atom (such as bromo or chloro) or triflate), in the presence of a suitable base (such as diisopropylethylamine) in a suitable solvent (for example DCM or dioxane) and at a suitable temperature (such as 20-85° C.).

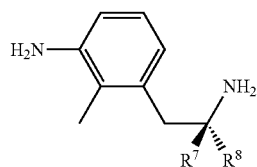
(XX)

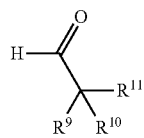
(XVI)

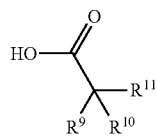
(XVII)

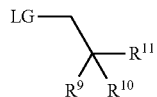
(XVIII)

Compounds of Formula (XX) may be prepared through a reaction sequence starting from a protected 3-bromo-2-methyl-aniline as shown below.

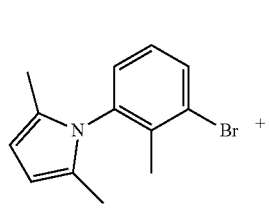

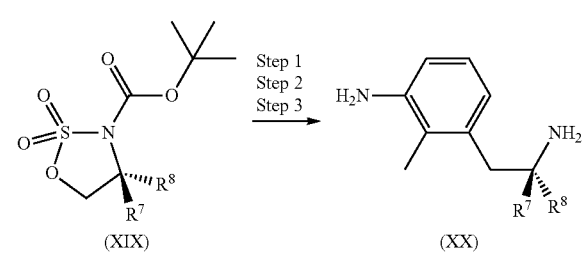

Step 1: Alkylation, e.g. n-butyllithium/THF/−78° C. to rt.
Step 2: Removal of amine protection groups, e.g. anhydrous HCl in MeOH/DCM, rt.
Step 3: Removal of aniline protection groups, e.g. refluxing in hydroxylamine.

Compounds of Formula (V) may be prepared through a sequence involving Pictet-Spengler cyclisation of a boronate ester-containing compound of Formula (XIII) as described above to give a compound of Formula (XXI). A compound of Formula (XXI) can be oxidized to a compound of Formula (V) using a suitable oxidant (such as hydrogen peroxide) in the presence of a suitable base (such as sodium hydroxide) in a suitable solvent (such as THF).

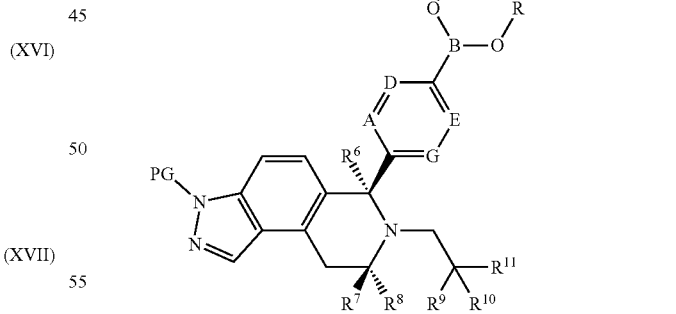
(XXI)

Compounds of Formula (VI, Q is NH) may be prepared through a sequence involving Pictet-Spengler cyclisation of a nitro containing compound of Formula (XIII) as described above to give a compound of Formula (XXII). A compound of Formula (XXII) can be reduced to a compound of Formula (VI) using suitable nitro reduction conditions (such as hydrogenation) in the presence of a suitable catalyst (such as platinum dioxide) in a suitable solvent (such as methanol).

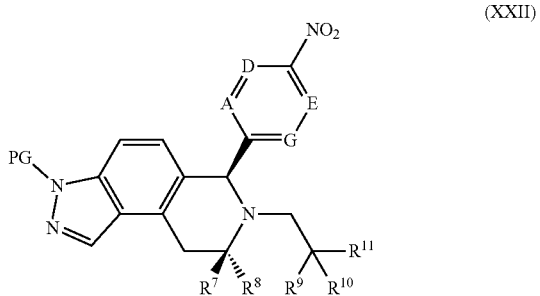

(XXII)

Compounds of Formula (VIII), where Q is O, may be prepared from aryl halides of Formula (II) and tert-butyl 3-hydroxyazetidine-1-carboxylate using a suitable metal catalyst (such as RockPhos 3rd Generation Precatalyst) in a suitable solvent (such as toluene or DME) in the presence of a suitable base (such as cesium carbonate) at a suitable temperature (such as 90-120° C.); the Boc protecting group may be subsequently removed under using an acid (such as trifluoroacetic acid) in a suitable solvent (such as DCM). Compounds of Formula (VIII) (Q is O) may also be prepared from a compound of Formula (V) under conditions known in the art as suitable for Mitsunobu reactions using appropriate reagents (such as triphenylphosphine and diisopropyl (E)-diazene-1,2-dicarboxylate) with tert-butyl 3-hydroxyazetidine-1-carboxylate in a suitable solvent (such as THF).

Compounds of Formula (VIII), where Q is NH, may be prepared from aryl halides of Formula (II) and tert-butyl 3-aminoazetidine-1-carboxylate using a suitable metal catalyst (for example for example RuPhos or BrettPhos and Pd$_2$(dba)$_3$) in a suitable solvent (for example 1,4-dioxane) in the presence of a suitable base (for example cesium carbonate, sodium tert-butoxide, or LiHMDS) at a suitable temperature (such as 90-130° C.); the Boc protecting group may be subsequently removed using an acid (such as trifluoroacetic acid) in a suitable solvent (such as DCM).

Compounds of Formula (III) may be prepared by:
a) Alkylation reaction between 3-hydroxyazetidine and compounds of Formula (IX) where LG for example a halogen or other leaving group (such as mesyl group) in the presence of a suitable base, such as cesium carbonate, in a suitable solvent, such as acetonitrile, at a suitable temperature, such as 120° C., and in a suitable container, such as a sealed tube.
b) Reductive amination reaction between 3-hydroxyazetidine and aldehyde or ketone compounds of Formula (XXIII) in the presence of a suitable reducing reagent, such as sodium triacetoxyborohydride, in a suitable solvent, such as DCM, in a suitable temperature, such as 10-30° C.

(XXIII)

Compounds of Formula (IV) may be prepared by:
a) (i) Alkylation reaction between compound of Formula (XXIV), where PG is a pretecting group for example Boc, and compounds of Formula (IX) where LG is for example a halogen or other leaving group, such as mesylate, in the presence of a suitable base, such as DIPEA, in a suitable solvent, such as 1,4-dioxane, at a suitable temperature, such as 10-30° C. (ii) Removal of the protection group under suitable conditions, such as acidic conditions for the removal of Boc.

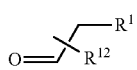

(XXIV)

b) (i) Reductive amination reaction between compounds of Formula (XXIV) and aldehyde or ketone compounds of Formula (XXIII) in the presence of a suitable reducing reagent, such as sodium triacetoxyborohydride, in a suitable solvent, such as DCM, in a suitable temperature, such as 10-30° C. (ii) Removal of the protection group under suitable conditions, such as acidic conditions for the removal of Boc.

It is to be understood that other permutations of the process steps in the process variants described above are also possible.

It will also be appreciated that, in some of the reactions mentioned hereinbefore, it may be necessary or desirable to protect any sensitive functionalities in the compounds. The instances where protection is necessary or desirable, and suitable methods for protection, are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy, it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an alkoxycarbonyl group such as a t-butoxycarbonyl group may be removed, for example, by treatment with a suitable acid as hydrochloric, sulphuric, formic, phosphoric or trifluoroacetic acid, and an arylmethoxycarbonyl group such as a benzyloxycarbonyl group may be removed, for example, by hydrogenation over a catalyst such as palladium-on-carbon, or by treatment with a Lewis acid, such as boron tris(trifluoroacetate). A suitable alternative protecting group for a primary amino group is, for example, a phthaloyl group, which may be removed by treatment with an alkylamine, for example dimethylaminopropylamine, or hydrazine.

A suitable protecting group for a hydroxy group is, for example, an acyl group, for example an alkanoyl group such as acetyl, an aroyl group, for example benzoyl, an arylmethyl group, for example benzyl, or a trialkyl or diarylalkyl silane, such as TBDMS or TBDPS. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

Certain of the intermediates defined herein are novel and these are provided as further features of the specification.

In one embodiment there is provided a compound of Formula (XXV), or a salt thereof:

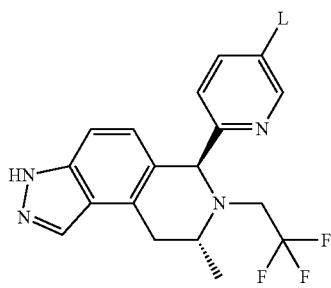

(XXV)

wherein L is bromo, chloro, iodo or trifluoromethanesulfonyl.

In a further embodiment L is bromo.

Biological Assays

The following assays were used to measure the effects of the compounds of the present specification.

ERα Binding Assay

The ability of compounds to bind to isolated Estrogen Receptor Alpha Ligand binding domain (ER alpha-LBD (GST)) was assessed in competition assays using a LanthaScreen™ Time-Resolved Fluorescence Resonance Energy Transfer (TR-FRET) detection end-point. For the LanthaScreen TR-FRET endpoint, a suitable fluorophore (Fluormone ES2, ThermoFisher, Product code P2645) and recombinant human Estrogen Receptor alpha ligand binding domain, residues 307-554 (expressed and purified in-house) were used to measure compound binding. The assay principle is that ER alpha-LBD (GST) is added to a fluorescent ligand to form a receptor/fluorophore complex. A terbium-labelled anti-GST antibody (Product code PV3551) is used to indirectly label the receptor by binding to its GST tag, and competitive binding is detected by a test compound's ability to displace the fluorescent ligand, resulting in a loss of TR-FRET signal between the Tb-anti-GST antibody and the tracer. The assay was performed as follows with all reagent additions carried out using the Beckman Coulter BioRAPTR FRD microfluidic workstation:

1. Acoustic dispense 120 nL of the test compound into a black low volume 384 well assay plates.
2. Prepare 1×ER alpha-LBD/Tb-antiGST Ab in ES2 screening buffer and incubate for 15 minutes.
3. Dispense 6 μL of the 1×AR-LBD/Tb-anti-GST Ab reagent into each well of the assay plate followed by 6 μL of Fluorophore reagent into each well of the assay plate
4. Cover the assay plate to protect the reagents from light and evaporation, and incubate at room temperature for 4 hours.
5. Excite at 337 nm and measure the fluorescent emission signal of each well at 490 nm and 520 nm using the BMG PheraSTAR.

Compounds were dosed directly from a compound source microplate containing serially diluted compound (4 wells containing 10 mM, 0.1 mM, 1 mM and 10 nM final compound respectively) to an assay microplate using the Labcyte Echo 550. The Echo 550 is a liquid handler that uses acoustic technology to perform direct microplate-to-microplate transfers of DMSO compound solutions and the system can be programmed to transfer multiple small nL volumes of compound from the different source plate wells to give the desired serial dilution of compound in the assay which is then back-filled to normalise the DMSO concentration across the dilution range.

In total 120 nL of compound plus DMSO were added to each well and compounds were tested in a 12-point concentration response format over a final compound concentration range of 10, 2.917, 1.042, 0.2083, 0.1, 0.0292, 0.0104, 0.002083, 0.001, 0.0002917, 0.0001042, and 0.00001 μM respectively. TR-FRET dose response data obtained with each compound was exported into a suitable software package (such as Origin or Genedata) to perform curve fitting analysis. Competitive ER alpha binding was expressed as an $IC_{50}$ value. This was determined by calculation of the concentration of compound that was required to give a 50% reduction in tracer compound binding to ER alpha-LBD.

MCF-7 ER Down-Regulation Assay

The ability of compounds to down-regulate Estrogen Receptor (ER) numbers was assessed in a cell based immuno-fluorescence assay using the MCF-7 human ductal carcinoma breast cell line. MCF-7 cells were revived directly from a cryovial (approx $5×10^6$ cells) in Assay Medium (phenol red free Dulbecco's Modified Eagle's medium (DMEM); Sigma D5921) containing 2 mM L-Glutamine and 5% (v/v) Charcoal/Dextran treated foetal calf serum. Cells were syringed once using a sterile 18 G×1.5 inch (1.2×40 mm) broad gauge needle and cell density was measured using a Coulter Counter (Beckman) Cells were further diluted in Assay Medium to a density of $3.75×10^4$ cells per mL and 40 μL per well added to transparent bottomed, black, tissue culture-treated 384 well plates (Costar, No. 3712) using a Thermo Scientific Matrix WellMate or Thermo Multidrop. Following cell seeding, plates were incubated overnight at 37° C., 5% $CO_2$ (Liconic carousel incubator). Test data was generated using the LabCyte Echo™ model 555 compound reformatter which is part of an automated workcell (Integrated Echo 2 workcell). Compound stock solutions (10 mM) of the test compounds were used to generate a 384 well compound dosing plate (Labcyte P-05525-CV1). 40 μL of each of the 10 mM compound stock solutions was dispensed into the first quadrant well and then 1:100 step-wise serial dilutions in DMSO were performed using a Hydra II (MATRIX UK) liquid handling unit to give 40 μL of diluted compound into quadrant wells 2 (0.1 mM), 3 (1 μM) and 4 (0.01 μM), respectively. 40 μL of DMSO added to wells in row P on the source plate allowed for DMSO normalisation across the dose range. To dose the control wells 40 µL of DMSO was added to row O1 and 40 µL of 100 µM fulvestrant in DMSO was added to row O3 on the compound source plate.

The Echo uses acoustic technology to perform direct microplate-to-microplate transfers of DMSO compound solutions to assay plates. The system can be programmed to transfer volumes as low as 2.5 nL in multiple increments between microplates and in so doing generates a serial dilution of compound in the assay plate which is then back-filled to normalise the DMSO concentration across the dilution range. Compounds were dispensed onto the cell plates with a compound source plate prepared as above producing a 12 point duplicate 3 µM to 3 µM dose range with 3-fold dilutions and one final 10-fold dilution using the Integrated Echo 2 workcell. The maximum signal control wells were dosed with DMSO to give a final concentration of 0.3%, and the minimum signal control wells were dosed with fulvestrant to give a final concentration of 100 nM accordingly. Plates were further incubated for 18-22 hours at 37° C., 5% $CO_2$ and then fixed by the addition of 20 µL of 11.1% (v/v) formaldehyde solution (in phosphate buffered saline (PBS)) giving a final formaldehyde concentration of 3.7% (v/v). Cells were fixed at room temperature for 20 mins before being washed two times with 250 µL PBS/Proclin (PBS with a Biocide preservative) using a BioTek plate-washer, 40 µL of PBS/Proclin was then added to all wells and the plates stored at 4° C. The fixing method described above was carried out on the Integrated Echo 2 workcell Immunostaining was performed using an automated AutoElisa workcell. The PBS/Proclin was aspirated from all wells and the cells permeabilised with 40 µL PBS containing 0.5% Tween™ 20 (v/v) for 1 hour at room temperature. The plates were washed three times in 250 µL of PBS/0.05% (v/v) Tween 20 with Proclin (PBST with a Biocide preservative) and then 20 µL of ERα (SP1) Rabbit monoclonal antibody (Thermofisher) 1:1000 in PBS/Tween™/3% (w/v) Bovine Serum Albumin was added. The plates were incubated overnight at 4° C. (Liconic carousel incubator) and then washed three times in 250 µL of PBS/0.05% (v/v) Tween™ 20 with Proclin (PBST). The plates were then incubated with 20 µL/well of a goat anti-rabbit IgG AlexaFluor 594 or goat anti-rabbit AlexaFluor 488 antibody (Molecular Probes) with Hoechst at 1:5000 in PBS/Tween™/3% (w/v) Bovine Serum Albumin for 1 hour at room temperature. The plates were then washed three times in 250 µL of PBS/0.05% (v/v) Tween™ 20 with Proclin (PB ST with a Biocide preservative). 20 µL of PBS was added to each well and the plates covered with a black plate seal and stored at 4° C. before being read. Plates were read using a Cellomics Arrayscan reading the 594 nm (24 hr time point) or 488 nm (5 hr timepoint) fluorescence to measure the ERα receptor level in each well. The mean total intensity was normalized for cell number giving the total intensity per cell. The data was exported into a suitable software package (such as Origin) to perform curve fitting analysis. Down-regulation of the ERα receptor was expressed as an $IC_{50}$ value and was determined by calculation of the concentration of compound that was required to give a 50% reduction of the average maximum Total Intensity signal.

The data shown in Table A were generated (the data below may be a result from a single experiment or an average of two or more experiments):

TABLE A

| Example | ER binding IC50 value (nM) | ER down regulation IC50 value (nM)[1] |
|---|---|---|
| 1 | 3.7 | 0.10 |
| 2 | 2.8 | 3.1 |
| 3 | 6.5 | 0.64 |
| 4 | 6.9 | 0.34 |
| 5 | 2.2 | 0.077 |
| 6 | 8.8 | 0.35 |
| 7 | 8.4 | 0.4 |
| 8 | 2.0 | 0.055 |
| 9 | 360 | >300 |
| 10 | 8 | 0.26 |
| 11 | 20 | 0.094 |
| 12 | 2.4 | 0.25 (83%) |
| 13 | 3.5 | 0.11 |
| 14 | 6.6 | >300 |
| 15 | 9.5 | 0.33 (84%) |
| 16 | 6.9 | 0.54 |
| 17 | 2.4 | 0.16 |
| 18 | 29 | 0.42 |
| 19 | 2.6 | 0.063 |
| 20 | 15 | 0.36 |
| 21 | 2.1 | 0.098 |
| 22 | 5.7 | 0.062 |
| 23 | 15 | 0.15 |
| 24 | 10 | 0.21 |
| 25 | 4.1 | 0.33 |
| 26 | 6.7 | 0.52 |
| 27 | 0.81 | 0.05 |
| 28 | 5.7 | 0.065 |
| 29 | 1.6 | 0.2 |
| 30 | 1.8 | 0.28 |
| 31 | 13 | 0.54 |
| 32 | 2.1 | 0.096 |
| 33 | 1.4 | 0.1 |
| 34 | 1.9 | 0.22 |
| 35 | 1.5 | 0.17 |
| 36 | 1.8 | 0.12 |
| 37 | 7.2 | 4.1 |
| 38 | 0.69 | 0.19 |
| 39 | 0.94 | 0.048 |
| 40 | 1.3 | 0.1 |
| 41 | 2.4 | 0.17 |
| 42 | 3.8 | 0.28 |
| 43 | 4.1 | 0.25 |
| 44 | 9.6 | 0.91 |
| 45 | 1.6 | 0.3 |
| 46 | 3.6 | 0.4 |
| 47 | 1.2 | 0.41 |
| 48 | 1.5 | 0.078 |
| 49 | 1.5 | 0.075 |
| 50 | 2.7 | 0.47 |
| 51 | 2.8 | 0.68 |
| 52 | 11 | 0.21 |
| 53 | 5.7 | 0.26 |
| 54 | 160 | >300 |
| 55 | 8.2 | 1.1 |
| 56 | 8.2 | 0.58 |
| 57 | 5 | 0.36 |
| 58 | 2.1 | 0.56 |
| 59 | 7.2 | 1.6 |
| 60 | 4.7 | 0.19 |
| 61 | 0.88 | 0.13 |
| 62 | 1 | 0.13 |
| 63 | 73 | 0.31 |
| 64 | 6.1 | 0.22 |
| 65 | 5.3 | 1 |
| 66 | 6.2 | 0.44 |
| 67 | 5 | 0.27 |
| 68 | 15 | 0.4 |
| 69 | 8.9 | 0.55 |
| 70 | 4.3 | 0.31 |
| 71 | 2 | 0.17 |
| 72 | 2.9 | 0.51 |
| 73 | 3.4 | 0.77 |

[1]Compounds which are active in the ER down-regulation assay show downregulation values >90% in the assay unless otherwise stated, in which case the % downregulation is shown in parentheses.

Western Blotting Assay

The ability of compounds to down-regulate estrogen receptor (ER) was assessed by western blotting using human breast cancer cell lines (MCF-7 and CAMA-1). Cells were plated into 12-well tissue culture-treated plates at $0.5 \times 10^6$/well in phenol red-free RPMI containing 2 mM L-glutamine and 5% (v/v) charcoal treated foetal calf serum (F6765, Sigma). Cells were incubated with compounds (100 nM) or vehicle control (0.1% DMSO) for 48 h at 37° C., 5% $CO_2$ before washing once with PBS and lysing with 80 µl lysis buffer (25 mM Tris/HCl, 3 mM EDTA, 3 mM EGTA, 50 mM NaF, 2 mM sodium orthovanadate, 0.27 M sucrose, 10 mM β-glycerophosphate, 5 mM sodium pyrophosphate, 0.5% TritonX-100, pH 6.8) on ice.

Cells were scraped, sonicated and centrifuged prior to performing a protein assay (DC Bio-Rad Protein kit, 500-0116) and making samples to a protein concentration of 1-2 mg/ml in lysis buffer containing 1×LDS Sample Buffer (NP0007, Invitrogen) and 1× NuPAGE sample reducing agent (NP0009, Invitrogen). Samples were boiled for 10 min at 95° C. and then frozen at −20° C. until ready for use.

10-20 µg protein was loaded onto 26-well Criterion gels (BioRad 345-0034). Gels were run at 125 V for 1 hr 25 min in running buffer (24 mM Tris Base Sigma, 192 mM Glycine, 3.5 mM SDS, made up in distilled water). Gels were then transferred at 30V for 2 hr in transfer buffer (25 mM Tris, 192 mM Glycine, 20% (v/v) methanol, pH 8.3, made up in distilled water) onto nitrocellulose membrane. The blot was stained with Ponceau S (P7170, Sigma) and cut according to appropriate molecular weight markers.

Membranes were blocked for 1 hour at room temp in 5% Marvel (w/v) in phosphate-buffered saline containing 0.05% Tween™ 20 (PBS/Tween). Blots were then incubated with anti-ERα (SP1) rabbit monoclonal antibody (Thermofisher) diluted 1:1000 at 4° C. overnight (with gentle shaking) followed by several washes with PBS/Tween. Secondary anti-rabbit HRP antibody (7074, CST) diluted 1:2000 dilution was incubated for 2 h at room temperature (with gentle shaking) followed by several washes with PBS/Tween. All antibodies were made up in 5% Marvel (w/v) in PBS/Tween.

The immunoblots were developed using Pierce WestDura chemiluminescent reagents (Thermo Scientific 34076) and developed/quantified on the G-box using Syngene software. Down-regulation of the ERα receptor was normalised to the vehicle control (0% down-regulation) and the 100 nM fulvestrant control (100% down-regulation) run within the same gel.

Table B shows the data generated for selected Examples (the data below may be a result from a single experiment or an average of two or more experiments):

TABLE B

| Example | CAMA1 Western % ER deg vs Fv | MCF7 Western % ER deg vs Fv |
| --- | --- | --- |
| 1 | 92 | 91 |
| 2 | 95 | 93 |
| 3 | 102 | 90 |
| 4 | 61 | 70 |
| 5 | 109 | 99 |
| 6 | 84 | 89 |
| 7 | 90 | 90 |
| 8 | 100 | 101 |
| 9 | 25 | −13 |
| 16 | 105 | 104 |
| 17 | 96 | 92 |
| 18 | 95 | 103 |
| 19 | 94 | 92 |
| 21 | 101 | 99 |
| 25 | 96 | 98 |
| 26 | 97 | 97 |
| 27 | 108 | 110 |
| 28 | 110 | 95 |
| 29 | 106 | 93 |
| 30 | 98 | 96 |
| 31 | 95 | 103 |
| 32 | 89 | 89 |
| 33 | 102 | 98 |
| 34 | 82 | 85 |
| 40 | 120 | 98 |
| 42 | 79 | 92 |
| 46 | 102 | 105 |
| 48 | 94 | 93 |
| 49 | 99 | 98 |
| 53 | 46 | 81 |
| 56 | 52 | 61 |
| 59 | 102 | 104 |
| 64 | 89 | 86 |
| 69 | 98 | 95 |
| 70 | 100 | 102 |

Human Hepatocyte Assay

The metabolic stability of compounds in human hepatocytes was assessed using the following protocol:

1. Prepare 10 mM stock solutions of compound and control compounds in appropriate solvent (DMSO). Place incubation medium (L-15 Medium) in a 37° C. water bath, and allow warming for at least 15 minutes prior to use.
2. Add 80 µL of acetonitrile to each well of the 96-well deep well plate (quenching plate).
3. In a new 96-well plate, dilute the 10 mM test compounds and the control compounds to 100 µM by combining 198 µL of acetonitrile and 2 µL of 10 mM stock.
4. Remove a vial of cryopreserved (less than −150° C.) human hepatocytes (LiverPool™ 10 Donor Human hepatocytes obtained from Celsis IVT. Chicago, Ill. (Product No. S01205)) from storage, ensuring that vials remain at cryogenic temperatures until thawing process ensues. As quickly as possible, thaw the cells by placing the vial in a 37° C. water bath and gently shaking the vials. Vials should remain in water bath until all ice crystals have dissolved and are no longer visible. After thawing is complete, spray vial with 70% ethanol, transfer the vial to a bio-safety cabinet.
5. Open the vial and pour the contents into the 50 mL conical tube containing thawing medium. Place the 50 mL conical tube into a centrifuge and spin at 100 g for 10 minutes. Upon completion of spin, aspirate thawing medium and resuspend hepatocytes in enough incubation medium to yield ~$1.5 \times 10^6$ cells/mL.
6. Using Cellometer® Vision, count cells and determine the viable cell density. Cells with poor viability (<80% viability) are not acceptable for use. Dilute cells with incubation medium to a working cell density of $1.0 \times 10^6$ viable cells/mL.
7. Transfer 247.5 µL of hepatocytes into each well of a 96-well cell culture plate. Place the plate on Eppendorf Thermomixer Comfort plate shaker to allow the hepatocytes to warm for 10 minutes.
8. Add 2.5 µL of 100 µM test compound or control compounds into an incubation well containing cells, mix to achieve a homogenous suspension at 0.5 min, which when achieved, will define the 0.5 min time point. At the 0.5 min time, transfer 20 μL of incubated mixture to wells in a "Quenching plate" followed by vortexing.

9. Incubate the plate at 37° C. at 900 rpm on an Eppendorf Thermomixer Comfort plate shaker. At 5, 15, 30, 45, 60, 80, 100 and 120 min, mix the incubation system and transfer samples of 20 μL incubated mixture at each time point to wells in a separate "Quenching plate" followed by vortexing.

10. Centrifuge the quenching plates for 20 minutes at 4,000 rpm. 4 different compounds are pooled into one cassette and used for LC/MS/MS analysis.

All calculations were carried out using Microsoft Excel. Peak areas were determined from extracted ion chromatograms. In vitro intrinsic clearance (in vitro $Cl_{int}$, in L/min/$10^6$ cells) of parent compound was determined by regression analysis of the Ln percent parent disappearance vs. time curve. The in vitro intrinsic clearance (in vitro $Cl_{int}$, in L/min/$10^6$ cells) was determined from the slope value using the following equation and is shown in Table C for selected examples:

in vitro $Cl_{int}$=kV/N

V=incubation volume (0.25 mL);

N=number of hepatocytes per well (0.25×$10^6$ cells).

TABLE C

| Example | $Cl_{int}$ (μL/min/$10^6$ cells) |
|---|---|
| 1 | 11 |
| 2 | 6 |
| 3 | 5 |
| 6 | 2 |
| 11 | 7 |
| 17 | 6 |
| 18 | 3 |
| 19 | 5 |
| 21 | 6 |
| 25 | 5 |
| 28 | 5 |
| 48 | 4 |

Physical Properties log D

The lipophilicity of a drug is an important physical property which may influence many biological and metabolic properties of a compound, for example the absorption, distribution, metabolism, excretion and toxicity profiles of a compound. The distribution coefficient between 1-octanol and aqueous buffer, Log DO/W, at pH 7.4, is the most commonly used measurement of the lipophilicity of a compound. The current method for measurement of Log DO/W is based on the traditional shake flask technique, but with the modification of measuring compounds in mixtures of ten at a time using UPLC with quantitative mass spectrometry (MS) as a method to measure the relative octanol and aqueous concentrations. The maximum capacity is 379 project compounds (48 pools with 10 compounds incl. three QC compounds) per experiment. 2 quality control (QC) samples, Cyclobenzaprine with moderate Log D and Nicardipine high Log D is used in all pools to ensure good quality. An additional QC sample Caffeine, with low Log D, are used and randomly placed in all runs. The method has been thoroughly validated against the previous shake flask methodologies.

Solubility

In order for an oral compound to reach the site of action, and in order for oral absorption from the gut to occur, that compound must be in solution, and therefore compounds which possess high intrinsic solubility may be more suitable for pharmaceutical use. The thermodynamic solubility of a research compound is measured under standard conditions. It is a shake-flask approach that uses 10 mM DMSO solutions which are supplied from the Compound Managements liquid store and is a high throughput method. The dried compounds are equilibrated in an aqueous phosphate buffer (pH 7.4) for 24 hours at 25° C., the portion with the dissolved compound is then separated from the remains. The solutions are analyzed and quantified using UPLC/MS/MS, QC-samples are incorporated in each assay-run to ensure the quality of the assay.

Human Plasma Protein Binding

Hunan plasma protein binding is a key factor in controlling the amount of free (unbound) drug available for binding to target and hence plays an important role in the observed efficacy of drugs in vivo. Therefore, compounds which possess high free fraction (low levels of plasma protein binding) may exhibit enhanced efficacy relative to a compound with similar potency and exposure levels. The automated equilibrium dialysis assay in human plasma uses the RED (Rapid Equilibrium Dialysis) Device and sample handling. The assay generally runs over two to three days including delivery of results. After dialysis for 18 hours, plasma and buffer samples are prepared for analysis by liquid chromatography and mass spectrometry. Samples are generally tested in singlicates and quantified by LC/MSMS by using a 7-point calibration curve in plasma. The compounds are pooled together in plasma pools up to 10 compounds. Three reference compounds are used in each run, Propranolol, Metoprolol and Warfarin. Warfarin is used as a control in each pool and Propranolol and Metoprolol are placed randomly in each run. An in-house Excel macro is used for preparation of files for the robot and the mass spectrometer and is also used for the calculations of fraction unbound (fu %) in plasma.

Table D shows the data for log D, solubility and plasma protein binding generated for selected Examples (the data below may be a result from a single experiment or an average of two or more experiments):

TABLE D

| Example | LogD pH 7.4 | Human plasma protein binding (% free) | Solubility (μM) |
|---|---|---|---|
| 1 | 3.4 | 8.3 | 379 |
| 2 | 2.6 | 28 | 217 |
| 3 | 2.5 | 26 | >941 |
| 4 | 2.7 | 21 | 991 |
| 5 | 3.3 | 8.6 | 297 |
| 6 | 2.4 | 34 | >947 |
| 7 | 3.5 | 11 | 470 |
| 8 | 4.4 | 0.99 | 90 |
| 9 | 1 | 21 | >1000 |
| 10 | 2.8 | 23 | 634 |
| 11 | 3.9 | 2 | 186 |
| 12 | 3.9 | 2.7 | 77 |
| 13 | 4 | 6.4 | 78 |
| 14 | 2.6 | 16 | 897 |
| 15 | 2.5 | 34 | 821 |
| 16 | 2 | 64 | 982 |
| 17 | 2.9 | 23 | 833 |
| 18 | 2.6 | 34 | 910 |
| 19 | 3.7 | 4.3 | 152 |
| 20 | 2.8 | 29 | 730 |
| 21 | 3.1 | 12 | 634 |

TABLE D-continued

| Example | LogD pH 7.4 | Human plasma protein binding (% free) | Solubility (μM) |
|---|---|---|---|
| 22 | 4 | 4.6 | 70 |
| 23 | 3.1 | 9.5 | 339 |
| 25 | 2.5 | 40 | 964 |
| 26 | 3 | 22 | 258 |
| 27 | 3.8 | 3.8 | 229 |
| 28 | 3.6 | 6 | 150 |
| 29 | 3 | 16 | 779 |
| 30 | 3 | 16 | 754 |
| 31 | 2 | 44 | >942 |
| 32 | 3.5 | 6.5 | 692 |
| 33 | 3.6 | 5.4 | 466 |
| 34 | 3.2 | 15 | 471 |
| 37 | 2.6 | 25 | 961 |
| 38 | 3.1 | 13 | 794 |
| 39 | 3.7 | 6.8 | 257 |
| 40 | 3.5 | 6.4 | 479 |
| 41 | 4.1 | 2.2 | 120 |
| 42 | 2.4 | NT | 712 |
| 44 | 3.2 | 10 | 998 |
| 45 | 3.9 | 6.2 | 172 |
| 46 | 2.5 | 31 | >1000 |
| 47 | 2.6 | NT | >1000 |
| 48 | 3.1 | 10 | 582 |
| 49 | 3.8 | NT | 163 |
| 50 | 2.1 | NT | 748 |
| 51 | 2.7 | 28 | >1000 |
| 52 | 3 | 19 | 864 |
| 53 | 3.2 | 11 | 691 |
| 54 | 1.4 | 57 | >1000 |
| 55 | 2.1 | NT | 987 |
| 56 | 3.6 | NT | 377 |
| 57 | 2.9 | NT | 615 |
| 58 | 2.4 | NT | 633 |
| 59 | 2.4 | 33 | 971 |
| 60 | 2.5 | 23 | 593 |
| 61 | 2.7 | 29 | 848 |
| 62 | 2.8 | 19 | 784 |
| 63 | 3.2 | 10 | 870 |
| 64 | 3.2 | 14 | 474 |
| 65 | 2.4 | NT | 790 |
| 66 | 2.3 | NT | 931 |
| 67 | 2.7 | 19 | 914 |
| 68 | 2.4 | 37 | 561 |
| 69 | 2.9 | 37 | >1000 |
| 70 | 2.9 | 24 | 857 |
| 71 | 3.2 | NT | 666 |
| 72 | 3.3 | 14 | 738 |
| 73 | 3 | 22 | 925 |

NT = not tested hERG Binding Assay hERG (human ether go go-related gene) potassium channels are essential for normal electrical activity in the heart. Arrhythmia can be induced by a blockage of hERG channels by a diverse group of drugs. This side effect is a common reason for drug failure in preclinical safety trials [Sanguinetti et al., Nature., 2006, 440, 463-469.] and therefore minimisation of hERG channel blocking activity may be a desirable property for drug candidates.

The purpose of the hERG binding assay is to evaluate the effects of test compounds on the voltage-dependent potassium channel encoded by the human ether go go-related gene (hERG) using a constitutively expressing CHO cell line on the Nanion Syncpatch 384PE automated patch clamp system.

The assay was conducted as follows with all reagents used at room temperature unless otherwise stated.

Reagent Preparations Include:
1. Internal "IC700" solution used to perfuse the underside of chip (in mM), KF 130, KCl 20, MgCl2 1, EGTA 10 and HEPES 10, (all Sigma-Aldrich; pH 7.2-7.3 using 10 M KOH, 320 mOsm) and supplemented with 25 □M escin.
2. External and cell buffer (in mM), NaCl 137, KCl 4, HEPES 10, D-glucose 10, CaCl2 2, MgCl2 1 (pH7.4, NaOH)
3. NMDG "reference" buffer used to establish a stable baseline prior to the addition of test compounds, NaCl 80, KCl 4, CaCl2 2, MgCl2 1, NMDG Cl 60, D-Glucose monohydrate 5, HEPES 10 (pH7.4 NaOH 298 mOsm)
4. Seal enhancer used to improve seal quality of cells, NaCl 80, KCl 3, CaCl2 10, HEPES 10, MgCl2 1 (pH7.4 NaOH)

Cell Preparations:
1. If using cell culture; cells to be incubated at 30° C. for approximately 4-6 days prior to being used. Day of assay lift cells using accutase and re-suspend in 20 ml cell buffer to a density of 0.8 to 1e6 cells/ml.
2. If using assay ready cryovials; rapidly thaw two cryovials at 37° C. and slowly pipette into 23 ml external solution
3. All cell preps to be incubated for 15 min on the shaking cell hotel set to 10° C. prior to starting assay Compound Preparations:
All compounds were acoustically dispensed in quadruplicate using a Labcyte Echo. A 10 mM stock solution is used to generate 6 compound source plates each at a different concentration to allow cumulative dosing onto cells (0.03167 mM, followed by 0.1 mM, then 0.3167 mM, 1 mM, 3.167 mM, 10 mM). 90 μl of reference buffer is added to each well of the source plates containing 600 nl of compound for a final compound concentration of 0.1 μM, 0.39 μM, 1.2 μM, 3.9 μM, 12.5 μM and 39.6 μM respectively. hERG assay (all dispense steps are performed using the liquid handling set up on the Nanion syncropatch)
1. Fill 384 well medium resistance 4 hole chips with 40 μl external buffer and perfuse internal buffer to the underside of plate.
2. Dispense 20 μl of cells into each well of the chip followed by 20 μl of seal enhancer.
3. Remove 40 μl of reagent from each well to the wash station, leaving a residual volume of 40 μl
4. Dispense 40 μl of reference buffer with a removal step of 40 μl after 3 min, repeat this step.
5. Dispense 40 μl of compound plate 1 (0.03167 mM), 'real time' recordings for 3 min exposure prior to removal of 40 μl. This step is repeated for 5 further subsequent compound plates in increasing concentrations to generate a cumulative concentration-effect curve in each well of the Syncropatch chip.

hERG-mediated currents were elicited using a voltage step protocol consisting of acontinuous holding voltage of −80 mV, with a 500 ms step to 60 mV followed by a 500 ms step to −40 mV every 15 seconds. hERG current magnitude was measured automatically from the leak-subtracted traces by the Nanion software by taking the peak of the hERG "tail" current at −40 mV every 15 seconds and taking the last three of these responses for each concentration to generate the concentration-effect curve.

Calculation of results is performed using APC package within Genedata. For the routine normalization of well data with Neutral and Inhibitor control well groups as reference, GeneData Assay Analyzer uses the following equation to normalize the signal values to the desired signal range:

$$N(x) = CR + \frac{x - <cr>}{<sr> - <cr>}(SR - CR)$$

x is the measured raw signal value of a well

<cr> is the median of the measured signal values for the Central Reference (Neutral) wells on a plate <sr> is the median of the measured signal values for the Scale Reference (Inhibitor) wells on a plate CR is the desired median normalized value for the Central Reference (Neutral)

SR is the desired median normalized value for the Scale Reference (Inhibitor)

Table E shows the hERG binding data for selected Examples (the data below may be a result from a single experiment or an average of two or more experiments):

TABLE E

| Example | hERG IC$_{50}$ (µM) |
|---|---|
| 1 | 10 |
| 2 | >40 |
| 3 | >36 |
| 4 | 17 |
| 5 | 13 |
| 6 | 9.1 |
| 16 | >40 |
| 17 | 22 |
| 18 | >38 |
| 19 | 5.4 |
| 21 | 5.3 |
| 25 | 28 |
| 27 | 7.9 |
| 28 | 7.8 |
| 29 | 27 |
| 30 | >33 |
| 31 | >40 |
| 32 | 14 |
| 33 | 14 |
| 34 | 7.7 |
| 37 | 20 |
| 38 | 18 |
| 39 | 14 |
| 40 | 4.5 |
| 41 | 6.5 |
| 42 | 7.9 |
| 45 | 4.2 |
| 46 | >40 |
| 49 | 8.2 |
| 50 | 13 |
| 51 | 9.1 |
| 52 | 2 |
| 55 | >40 |
| 57 | 16 |
| 58 | >40 |
| 59 | >40 |
| 60 | 11 |
| 61 | >40 |
| 62 | >40 |
| 63 | 13 |
| 64 | 13 |
| 65 | 31 |
| 66 | 26 |
| 67 | 14 |
| 68 | >40 |
| 69 | 24 |
| 70 | 24 |
| 73 | 12 |

Permeability

In order to maximize oral absorption, a drug must have sufficient transmembrane flux as well as avoid efflux by P-glycoprotein. The most widely used system for predicting oral absorption is by determination of the permeation rate of compounds through monolayers of a human colon adenocarcinoma cell line Caco-2.

Human Caco-2 Bidirectional Permeability A to B and B to A

An automated assay was used to determine the bidirectional permeability (efflux and uptake) of compounds in Caco-2 cells carried out over 2 hours at pH 7.4. Samples were analyzed through LC/MS/MS to estimate the apparent permeability coefficients (Papp) of compounds across Caco-2 cell monolayers and results are quoted in units of ×10$^{-6}$ cm/s.

The efflux ratio (ER) can be determined using the following equation:

$$ER = P_{app\ (B-A)} / P_{app\ (A-B)}$$

Where $P_{app\ (B-A)}$ indicates the apparent permeability coefficient in basolateral to apical direction, and $P_{app\ (A-B)}$ indicates the apparent permeability coefficient in apical to basolateral direction.

Human Caco-2 Passive Permeability A to B Papp

An automated assay was used to determine the passive permeability of compounds in Caco-2 cell monolayers carried out over 2 hours with an apical pH of 6.5 and basolateral pH of 7.4. The Caco-2 AB inhibition assay is carried out with chemical inhibition of the three major efflux transporters ABCB1 (P-gp), ABCG2 (BCRP) and ABCC2 (MRP2) in Caco-2 cells. Incubation of both apical and basolateral is carried out with a cocktail of inhibitors (50 µM quinidine, 20 µM sulfasalazine and 100 µM benzbromarone). Samples were analyzed through LC/MS/MS to estimate the apparent permeability coefficients (Papp) of compounds across Caco-2 cell monolayers and results are quoted in units of ×10$^{-6}$ cm/s.

Table F shows the data for permeability generated for selected Examples (the data below may be a result from a single experiment or an average of two or more experiments):

TABLE F

| Example | Bidirectional Caco-2 Papp (×10$^{-6}$ cm/s) | Bidirectional Caco-2 efflux ratio | Passive Caco-2 Papp (×10$^{-6}$ cm/s) |
|---|---|---|---|
| 1 | 0.9 | 9.4 | NT |
| 2 | 3.9 | 8.4 | NT |
| 3 | 2.3 | 9.2 | NT |
| 6 | 0.9 | 28 | 1.8 |
| 11 | 1.6 | 1.4 | NT |
| 16 | 1.6 | 9.7 | 1.7 |
| 17 | 4.7 | 5.5 | 13.3 |
| 19 | 4.2 | 2.6 | NT |
| 21 | 4.0 | 1.6 | 14.1 |
| 25 | 5.0 | 7.4 | 5.9 |
| 27 | 5.4 | 0.9 | NT |
| 28 | 1.2 | 3.8 | 24 |
| 29 | 12 | 0.9 | 24 |
| 30 | 2.7 | 7.8 | NT |
| 31 | 0.9 | 9.4 | NT |
| 32 | 3.4 | 1.5 | NT |
| 33 | 2.6 | 1.5 | NT |
| 47 | 18 | 1.1 | NT |
| 60 | 0.7 | 34 | NT |
| 64 | 2.0 | 5.6 | NT |

NT = not tested

Human Parental MCF7 Xenograft Anti-Tumour Efficacy in Mouse

To determine the effect of Example 17 on the growth of the MCF7 xenografts, the following study was performed. MCF7 cells (ATCC) were grown in vitro in exponential phase prior to implant. Briefly, male SCID mice weighing 18 g or more (Envigo UK) were implanted subcutaneously on the back with estrogen pellets (0.5 mg, 21 day release from Innovative Research of America) under recoverable anaesthetic. One day later mice were inoculated subcuaneously on the left flank with 5 million MCF7 cells, prepared as 0.1 ml cell suspension in 1:1 RPMI (Gibco, Life Technologies) and matrigel (Corning). When tumours reached ~250 mm$^3$ mice were randomised into groups of 9 mice (12 mice for vehicle control) and started receiving drug treatment. Compounds were prepared in vehicle (40% Tetraethylene Glycol (v/v), 7.5% Captisol (w/v) in water for injection) and given orally in a volume of 10 ml/kg once a day for 21 days at 0.5 mg/kg to 50 mg/kg. Tumours were measured twice a week and tumour volume calculated using the elliptical formula (pi/6×width×width×length). Data represent the geomean of tumour volume relative to the tumour volume on day of randomisation. Error bars are the 95% confidence interval (Graphpad Prism). This study demonstrated that doses of 10 mg/kg and above gave tumour regression (FIG. 12).

Human Y537S ESR1 Mutant MCF7 Xenograft Anti-Tumour Efficacy in Mouse

To determine the effect of Example 17 on the growth of the xenografts derived from MCF7 cells genetically engineered to express Y537S ESR1, the following study was performed. Y537S ESR1 MCF7 cells were created by genome editing and express only Y537S ESR1 (Ladd, et al., *Oncotarget*, 2016, 7:54120-54136). Briefly, male SCID mice weighing 18 g or more (Envigo UK) were inoculated subcuaneously on the left flank with 5 million Y537S ESR1 MCF7 cells, prepared as 0.1 ml cell suspension in 1:1 RPMI (Gibco, Life Technologies) and matrigel (Corning). When tumours reached ~250 mm$^3$ mice were randomised into groups of 9 mice (12 mice for vehicle control) and started receiving drug treatment. Compounds were prepared in vehicle (40% Tetraethylene Glycol (v/v), 7.5% Captisol (w/v) in water for injection) and given orally in a volume of 10 ml/kg once a day for 22 days at 0.5 mg/kg to 50 mg/kg. Tumours were measured twice a week and tumour volume calculated using the elliptical formula (pi/6×width×width×length). Data represent the geomean of tumour volume relative to the tumour volume on day of randomisation. Error bars are the 95% confidence interval (Graphpad Prism). This study demonstrated that doses of 10 mg/kg and above gave tumour regression (FIG. 13).

Human ESR1 Mutant Breast Cancer Patient Derived Xenograft CTC174 Anti-Tumour Efficacy in Mouse To determine the effect of Example 17 on the growth of the ESR1 mutant patient derived xenograft CTC174, female NSG mice were implanted with fragments of CTC174 in the mammary fat pad. CTC174 were derived from circulating tumour cells isolated from a patient with metastatic ER+ breast cancer and have been shown to carry a D538G mutation in ESR1 at a 0.33 allele frequency (Ladd, et al., *Oncotarget*, 2016, 7:54120-54136). Briefly, female ovariectomized NOD/SCID (Cg-Prkdcscid Il2rgtm1Wjl/SzJ) (NSG) mice (aged 6-7 weeks—The Jackson Laboratory) were implanted under recoverable anaesthetic with a ~50 mm$^3$ fragment of a CTC174 xenograft in the third mammary fat pad. When tumours reached ~200 mm$^3$ mice were randomised into groups of 10 mice and started receiving drug treatment. Compounds were prepared in vehicle (40% Tetraethylene Glycol (v/v), 7.5% Captisol (w/v) in water for injection) and given orally in a volume of 10 ml/kg once a day for 32 days at 0.8 mg/kg to 40 mg/kg. Tumours were measured twice a week and tumour volume calculated using the elliptical formula (pi/6×width×width×length). Data represent the geomean of tumour volume relative to the tumour volume on day of randomisation. Error bars are the 95% confidence interval (Graphpad Prism). This study demonstrated that doses of 10 mg/kg and above gave almost complete tumour growth inhibition (FIG. 14).

Human ESR1 Mutant Breast Cancer Patient Derived Xenograft CTC174 Anti-Tumour Drug Combination Efficacy in Mouse To determine the effect of Example 17 on the growth of the ESR1 mutant patient derived xenograft CTC174 in combination with the CDK4/6 inhibitor palbociclib or the mTORC1/2 inhibitor vistusertib (AZD2014), female NSG mice were implanted with fragments of CTC174 in the mammary fat pad. CTC174 were derived from circulating tumour cells isolated from a patient with metastatic ER+ breast cancer and have been shown to carry a D538G mutation in ESR1 at a 0.33 allele frequency (Ladd, et al., *Oncotarget*, 2016, 7:54120-54136). Briefly, female NOD/SCID (Cg-Prkdcscid Il2rgtm1Wjl/SzJ) (NSG) mice (aged 6-7 weeks—The Jackson Laboratory) were implanted under recoverable anaesthetic with a ~30 mm3 fragment of a CTC174 xenograft in the third mammary fat pad. When tumours reached ~500 mm3 mice were randomised into groups of 10 mice and started receiving drug treatment. Ex17 was prepared in vehicle (40% Tetraethylene Glycol (v/v), 7.5% Captisol (w/v) in water for injection) and given orally in a volume of 10 ml/kg once a day for 23 days at 10 mg/kg. Palbociclib and vistusertib were prepared in vehicle (1% polysorbate 80). Palbociclib was given orally in a volume of 10 ml/kg once a day for 23 days at 50 mg/kg. Vistusertib was given orally in a volume of 10 ml/kg twice a day in a 2 days on, 5 days off schedule for 23 days at 10 mg/kg. Vehicle treated group were dosed with 10 ml/kg 40% Tetraethylene Glycol (v/v), 7.5% Captisol (w/v) in water for injection orally once a day for 23 days. Tumours were measured twice a week and tumour volume calculated using the elliptical formula (pi/6×width×width×length). Data represent the geomean of tumour volume relative to the tumour volume on day of randomisation. Error bars are the 95% confidence interval (Graphpad Prism). This study demonstrated that Example 17 combined with either palbociclib (FIG. 15) or with vistusertib (AZD2014) (FIG. 16) gave a greater effect than either agent dosed alone.

According to a further aspect of the specification there is provided a pharmaceutical composition, which comprises a compound of the Formula (I), (IA), (IB), (IC) or (ID), or a pharmaceutically acceptable salt thereof, as defined hereinbefore in association with a pharmaceutically acceptable excipient.

Suitable pharmaceutically acceptable excipients for a tablet formulation include, for example, inert diluents, granulating and disintegrating agents, binding agents, lubricating agents, preservative agents and antioxidants. A further suitable pharmaceutically acceptable excipient may be a chelating agent. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may alternatively be in the form of hard gelatin capsules in which the active ingredient is mixed with an inert solid diluent, or as soft gelatin capsules in which the active ingredient is mixed with water or an oil.

Aqueous suspensions generally contain the active ingredient in finely powdered form together with one or more suspending agents, dispersing or wetting agents. The aqueous suspensions may also contain one or more preservatives, anti-oxidants, colouring agents, flavouring agents, and/or sweetening agents.

Oily suspensions may be formulated by suspending the active ingredient in a vegetable oil or in a mineral oil. The oily suspensions may also contain a thickening agent. Sweetening agents such as those set out above, and flavouring agents may be added to provide a palatable oral preparation. These compositions may be preserved by the addition of an anti-oxidant.

Dispersible powders and granules suitable for preparation of an aqueous suspension by the addition of water generally contain the active ingredient together with a dispersing or wetting agent, suspending agent and one or more preservatives. Additional excipients such as sweetening, flavouring and colouring agents, may also be present.

The pharmaceutical compositions of the specification may also be in the form of oil-in-water emulsions. The oily phase may be a vegetable oil or a mineral oil or a mixture of any of these. The emulsions may also contain sweetening, flavouring and preservative agents.

Syrups and elixirs may be formulated with sweetening agents, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent system.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient. Dry powder inhalers may also be suitable.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, oral administration to humans will generally require, for example, from 1 mg to 2 g of active agent (more suitably from 100 mg to 2 g, for example from 250 mg to 1.8 g, such as from 500 mg to 1.8 g, particularly from 500 mg to 1.5 g, conveniently from 500 mg to 1 g) to be administered compounded with an appropriate and convenient amount of excipients which may vary from about 3 to about 98 percent by weight of the total composition. It will be understood that, if a large dosage is required, multiple dosage forms may be required, for example two or more tablets or capsules, with the dose of active ingredient divided conveniently between them. Typically, unit dosage forms will contain about 10 mg to 0.5 g of a compound of this specification, although a unit dosage form may contain up to 1 g. Conveniently, a single solid dosage form may contain between 1 and 300 mg of active ingredient.

The size of the dose for therapeutic or prophylactic purposes of compounds of the present specification will naturally vary according to the nature and severity of the disease state, the age and sex of the animal or patient and the route of administration, according to well known principles of medicine.

In using compounds of the present specification for therapeutic or prophylactic purposes it will generally be administered so that a daily dose in the range, for example, 1 mg/kg to 100 mg/kg body weight is received, given if required in divided doses. In general, lower doses will be administered when a parenteral route is employed. Thus, for example, for intravenous administration, a dose in the range, for example, 1 mg/kg to 25 mg/kg body weight will generally be used. Similarly, for administration by inhalation, a dose in the range, for example, 1 mg/kg to 25 mg/kg body weight will be used. Oral administration is however preferred, particularly in tablet form.

In one aspect of the specification, compounds of the present specification or pharmaceutically acceptable salts thereof, are administered as tablets comprising 10 mg to 100 mg of the compound of the specification (or a pharmaceutically acceptable salt thereof), wherein one or more tablets are administered as required to achieve the desired dose.

As stated above, it is known that signalling through ERα causes tumourigenesis by one or more of the effects of mediating proliferation of cancer and other cells, mediating angiogenic events and mediating the motility, migration and invasiveness of cancer cells. We have found that the compounds of the present specification possess potent anti-tumour activity which it is believed is obtained by way of antagonism and down-regulation of ERα that is involved in the signal transduction steps which lead to the proliferation and survival of tumour cells and the invasiveness and migratory ability of metastasising tumour cells.

Accordingly, the compounds of the present specification may be of value as anti-tumour agents, in particular as selective inhibitors of the proliferation, survival, motility, dissemination and invasiveness of mammalian cancer cells leading to inhibition of tumour growth and survival and to inhibition of metastatic tumour growth. Particularly, the compounds of the present specification may be of value as anti-proliferative and anti-invasive agents in the containment and/or treatment of solid tumour disease. Particularly, the compounds of the present specification may be useful in the prevention or treatment of those tumours which are sensitive to inhibition of ERα and that are involved in the signal transduction steps which lead to the proliferation and survival of tumour cells and the migratory ability and invasiveness of metastasising tumour cells. Further, the compounds of the present specification may be useful in the prevention or treatment of those tumours which are mediated alone or in part by antagonism and down-regulation of ERα, i.e. the compounds may be used to produce an ERα inhibitory effect in a warm-blooded animal in need of such treatment.

According to a further aspect of the specification there is provided a compound of the Formula (I), (IA), (IB), (IC) or (ID), or a pharmaceutically acceptable salt thereof, as defined hereinbefore for use as a medicament in a warm-blooded animal such as man.

According to a further aspect of the specification, there is provided a compound of the Formula (I), (IA), (IB), (IC) or (ID), or a pharmaceutically acceptable salt thereof, as defined hereinbefore for use in the production of an anti-proliferative effect in a warm-blooded animal such as man.

According to a further aspect of the specification there is provided a compound of the Formula (I), (IA), (IB), (IC) or (ID), or a pharmaceutically acceptable salt thereof, as defined hereinbefore for use in a warm-blooded animal such as man as an anti-invasive agent in the containment and/or treatment of solid tumour disease.

According to a further aspect of the specification, there is provided the use of a compound of the Formula (I), (IA), (IB), (IC) or (ID), or a pharmaceutically acceptable salt thereof, as defined hereinbefore, for the production of an anti-proliferative effect in a warm-blooded animal such as man.

According to a further aspect of the specification there is provided the use of a compound of the Formula (I), (IA), (IB), (IC) or (ID), or a pharmaceutically acceptable salt thereof, as defined hereinbefore, in the manufacture of a medicament for use in the production of an anti-proliferative effect in a warm-blooded animal such as man.

According to a further aspect of the specification there is provided the use of a compound of the Formula (I), (IA), (IB), (IC) or (ID), or a pharmaceutically acceptable salt thereof, as defined hereinbefore, in the manufacture of a medicament for use in a warm-blooded animal such as man as an anti-invasive agent in the containment and/or treatment of solid tumour disease.

According to a further aspect of the specification there is provided a method for producing an anti-proliferative effect in a warm-blooded animal, such as man, in need of such treatment which comprises administering to said animal an effective amount of a compound of the Formula (I), (IA), (IB), (IC) or (ID), or a pharmaceutically acceptable salt thereof, as defined hereinbefore.

According to a further aspect of the specification there is provided a method for producing an anti-invasive effect by the containment and/or treatment of solid tumour disease in a warm-blooded animal, such as man, in need of such treatment which comprises administering to said animal an effective amount of a compound of the Formula (I), (IA), (IB), (IC) or (ID), or a pharmaceutically acceptable salt thereof, as defined hereinbefore.

According to a further aspect of the specification, there is provided a compound of the Formula (I), (IA), (IB), (IC) or (ID), or a pharmaceutically acceptable salt thereof, as defined hereinbefore, for use in the prevention or treatment of cancer in a warm-blooded animal such as man.

According to a further aspect of the specification there is provided the use of a compound of the Formula (I), (IA), (IB), (IC) or (ID), or a pharmaceutically acceptable salt thereof, as defined hereinbefore in the manufacture of a medicament for use in the prevention or treatment of cancer in a warm-blooded animal such as man.

According to a further aspect of the specification there is provided a method for the prevention or treatment of cancer in a warm-blooded animal, such as man, in need of such treatment which comprises administering to said animal an effective amount of a compound of the Formula (I), (IA), (IB), (IC) or (ID), or a pharmaceutically acceptable salt thereof, as defined hereinbefore.

According to a further aspect of the specification, there is provided a compound of the Formula (I), (IA), (IB), (IC) or (ID), or a pharmaceutically acceptable salt thereof, as defined hereinbefore for use in the prevention or treatment of solid tumour disease in a warm-blooded animal such as man.

According to a further aspect of the specification there is provided the use of a compound of the Formula (I), (IA), (IB), (IC) or (ID), or a pharmaceutically acceptable salt thereof, as defined hereinbefore, in the manufacture of a medicament for use in the prevention or treatment of solid tumour disease in a warm-blooded animal such as man.

According to a further aspect of the specification there is provided a method for the prevention or treatment of solid tumour disease in a warm-blooded animal, such as man, in need of such treatment which comprises administering to said animal an effective amount of a compound of the Formula (I), (IA), (IB), (IC) or (ID), or a pharmaceutically acceptable salt thereof, as defined hereinbefore.

According to a further aspect of the specification there is provided a compound of the Formula (I), (IA), (IB), (IC) or (ID), or a pharmaceutically acceptable salt thereof, as defined hereinbefore, for use in the prevention or treatment of those tumours which are sensitive to inhibition of ERα that are involved in the signal transduction steps which lead to the proliferation, survival, invasiveness and migratory ability of tumour cells.

According to a further aspect of the specification there is provided the use of a compound of the Formula (I), (IA), (IB), (IC) or (ID), or a pharmaceutically acceptable salt thereof, as defined hereinbefore, in the manufacture of a medicament for use in the prevention or treatment of those tumours which are sensitive to inhibition of ERα that are involved in the signal transduction steps which lead to the proliferation, survival, invasiveness and migratory ability of tumour cells.

According to a further aspect of the specification there is provided a method for the prevention or treatment of those tumours which are sensitive to inhibition of ERα that are involved in the signal transduction steps which lead to the proliferation, survival, invasiveness and migratory ability of tumour cells which comprises administering to said animal an effective amount of a compound of the Formula (I), (IA), (IB), (IC) or (ID), or a pharmaceutically acceptable salt thereof, as defined hereinbefore.

According to a further aspect of the specification there is provided a compound of the Formula (I), (IA), (IB), (IC) or (ID), or a pharmaceutically acceptable salt thereof, as defined hereinbefore for use in providing an inhibitory effect on ERα.

According to a further aspect of the specification there is provided the use of a compound of the Formula (I), (IA), (IB), (IC) or (ID), or a pharmaceutically acceptable salt thereof, as defined hereinbefore in the manufacture of a medicament for use in providing an inhibitory effect on ERα.

According to a further aspect of the specification there is also provided a method for providing an inhibitory effect on ERα which comprises administering an effective amount of a compound of the Formula (I), (IA), (IB), (IC) or (ID), or a pharmaceutically acceptable salt thereof, as defined hereinbefore.

According to a further aspect of the specification there is provided a compound of the Formula (I), (IA), (IB), (IC) or (ID), or a pharmaceutically acceptable salt thereof, as defined hereinbefore, for use in providing a selective inhibitory effect on ERα.

According to a further aspect of the specification there is provided the use of a compound of the Formula (I), (IA), (IB), (IC) or (ID), or a pharmaceutically acceptable salt thereof, as defined hereinbefore, in the manufacture of a medicament for use in providing a selective inhibitory effect on ERα.

According to a further aspect of the specification there is also provided a method for providing a selective inhibitory effect on ERα which comprises administering an effective amount of a compound of the Formula (I), (IA), (IB), (IC) or (ID), or a pharmaceutically acceptable salt thereof, as defined hereinbefore.

Described herein are compounds that can bind to ERα ligand binding domain and are selective estrogen receptor degraders. In biochemical and cell based assays the compounds of the present specification are shown to be potent estrogen receptor binders and reduce cellular levels of ERα and may therefore be useful in the treatment of estrogen sensitive diseases or conditions (including diseases that have developed resistance to endocrine therapies), i.e. for use in the treatment of cancer of the breast and gynaecological cancers (including endometrial, ovarian and cervical) and cancers expressing ERα mutated proteins which may be de novo mutations or have arisen as a result of treatment with a prior endocrine therapy such as an aromatase inhibitor.

According to a further aspect of the specification there is provided a compound of the Formula (I), (IA), (IB), (IC) or (ID), or a pharmaceutically acceptable salt thereof, as defined hereinbefore, for use in the treatment of breast or gynaecological cancers.

According to a further aspect of the specification there is provided a compound of the Formula (I), (IA), (IB), (IC) or (ID), or a pharmaceutically acceptable salt thereof, as defined hereinbefore, for use in the treatment of cancer of the breast, endometrium, ovary or cervix.

According to a further aspect of the specification there is provided a compound of the Formula (I), (IA), (IB), (IC) or (ID), or a pharmaceutically acceptable salt thereof, as defined hereinbefore, for use in the treatment of cancer of the breast.

According to a further aspect of the specification there is provided a compound of the Formula (I), (IA), (IB), (IC) or (ID), or a pharmaceutically acceptable salt thereof, as defined hereinbefore, for use in the treatment of cancer of the breast, wherein the cancer has developed resistance to one or more other endocrine therapies.

According to a further aspect of the specification there is provided a method for treating breast or gynaecological cancers, which comprises administering an effective amount of a compound of the Formula (I), (IA), (IB), (IC) or (ID), or a pharmaceutically acceptable salt thereof, as defined hereinbefore.

According to a further aspect of the specification there is provided a method for treating cancer of the breast, endometrium, ovary or cervix, which comprises administering an effective amount of a compound of the Formula (I), (IA), (IB), (IC) or (ID), or a pharmaceutically acceptable salt thereof, as defined hereinbefore.

According to a further aspect of the specification there is provided a method for treating breast cancer, which comprises administering an effective amount of a compound of the Formula (I), (IA), (IB), (IC) or (ID), or a pharmaceutically acceptable salt thereof, as defined hereinbefore.

According to a further aspect of the specification there is provided a method for treating breast cancer, wherein the cancer has developed resistance to one or more other endocrine therapies, which comprises administering an effective amount of a compound of the Formula (I), (IA), (IB), (IC) or (ID), or a pharmaceutically acceptable salt thereof, as defined hereinbefore.

According to a further aspect of the specification there is provided the use of a compound of the Formula (I), (IA), (IB), (IC) or (ID), or a pharmaceutically acceptable salt thereof, as defined hereinbefore, in the manufacture of a medicament for use in the treatment of breast or gynaecological cancers.

According to a further aspect of the specification there is provided the use of a compound of the Formula (I), (IA), (IB), (IC) or (ID), or a pharmaceutically acceptable salt thereof, as defined hereinbefore, in the manufacture of a medicament for use in the treatment of cancer of the breast, endometrium, ovary or cervix.

According to a further aspect of the specification there is provided the use of a compound of the Formula (I), (IA), (IB), (IC) or (ID), or a pharmaceutically acceptable salt thereof, as defined hereinbefore, in the manufacture of a medicament for use in the treatment of breast cancer.

According to a further aspect of the specification there is provided the use of a compound of the Formula (I), (IA), (IB), (IC) or (ID), or a pharmaceutically acceptable salt thereof, as defined hereinbefore, in the manufacture of a medicament for use in the treatment of breast cancer, wherein the cancer has developed resistance to one or more other endocrine therapies.

In one feature of the specification, the cancer to be treated is breast cancer. In a further aspect of this feature, the breast cancer is Estrogen Receptor+ve (ER+ve). In one embodiment of this aspect, the compound of Formula (I), (IA), (IB), (IC) or (ID), is dosed in combination with another anticancer agent, such as an anti-hormonal agent as defined herein.

According to a further aspect of the specification there is provided a compound of the Formula (I), (IA), (IB), (IC) or (ID), or a pharmaceutically acceptable salt thereof, as defined hereinbefore, for use in the treatment of ER+ve breast cancer.

According to a further aspect of the specification there is provided a method for treating ER+ve breast cancer, which comprises administering an effective amount of a compound of the Formula (I), (IA), (IB), (IC) or (ID), or a pharmaceutically acceptable salt thereof, as defined hereinbefore.

According to a further aspect of the specification there is provided the use of a compound of the Formula (I), (IA), (IB), (IC) or (ID), or a pharmaceutically acceptable salt thereof, as defined herein before in the manufacture of a medicament for use in the treatment of ER+ve breast cancer.

As stated hereinbefore, the in-vivo effects of a compound of the Formula (I), (IA), (IB), (IC) or (ID) may be exerted in part by one or more metabolites that are formed within the human or animal body after administration of a compound of the Formula (I), (IA), (IB), (IC) or (ID).

The present specification therefore also contemplates a method for inhibiting ER-α in a patient, comprising administering to a patient an amount of a compound of Formula (I), (IA), (IB), (IC) or (ID), or a pharmaceutically acceptable salt thereof, effective in inhibiting ER-α in the patient.

The present specification therefore also contemplates a method for inhibiting ER-α in a patient, comprising administering to a patient an amount of a compound of Formula (I), (IA), (IB), (IC) or (ID), or a pharmaceutically acceptable salt thereof, effective in inhibiting ER-α in the patient.

The anti-cancer treatment defined herein may be applied as a sole therapy or may involve, in addition to the compounds of the specification, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) antihormonal agents such as antioestrogens (for example tamoxifen, fulvestrant, toremifene, raloxifene, droloxifene and iodoxyfene), progestogens (for example megestrol acetate), aromatase inhibitors (for example as anastrozole, letrozole, vorazole and exemestane);

(iii) inhibitors of growth factor function and their downstream signalling pathways: included are Ab modulators of any growth factor or growth factor receptor targets, reviewed by Stern et al. *Critical Reviews in Oncology/Haematology*, 2005, 54, pp 11-29); also included are small molecule inhibitors of such targets, for example kinase inhibitors—examples include the anti-erbB2 antibody trastuzumab [Herceptin™], the anti-EGFR antibody panitumumab, the anti-EGFR antibody cetuximab [Erbitux, C225] and tyrosine kinase inhibitors including inhibitors of the erbB receptor family, such as epidermal growth factor family receptor (EGFR/erbB1) tyrosine kinase inhibitors such as gefitinib or erlotinib, erbB2 tyrosine kinase inhibitors such as lapatinib, and mixed erb1/2 inhibitors such as afatanib; similar strategies are available for other classes of growth factors and their receptors, for example inhibitors of the hepatocyte growth factor family or their receptors including c-met and ron; inhibitors of the insulin and insulin growth factor family or their receptors (IGFR, IR) inhibitors of the platelet-derived growth factor family or their receptors (PDGFR), and inhibitors of signalling mediated by other receptor tyrosine kinases such as c-kit, AnLK, and CSF-1R; also included are modulators which target signalling proteins in the PI3-kinase signalling pathway, for example, inhibitors of PI3-kinase isoforms such as PI3K-α/β/γ and ser/thr kinases such as AKT, mTOR (such as AZD2014), PDK, SGK, PI4K or PIP5K; also included are inhibitors of serine/threonine kinases not listed above, for example raf inhibitors such as vemurafenib, MEK inhibitors such as selumetinib (AZD6244), Abl inhibitors such as imatinib or nilotinib, Btk inhibitors such as ibrutinib, Syk inhibitors such as fostamatinib, aurora kinase inhibitors (for example AZD1152), inhibitors of other ser/thr kinases such as JAKs, STATs and IRAK4, and cyclin dependent kinase inhibitors for example inhibitors of CDK1, CDK7, CDK9 and CDK4/6 such as palbociclib;

iv) modulators of DNA damage signalling pathways, for example PARP inhibitors (e.g. Olaparib), ATR inhibitors or ATM inhibitors;

v) modulators of apoptotic and cell death pathways such as Bcl family modulators (e.g. ABT-263/Navitoclax, ABT-199);

(vi) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as sorafenib, axitinib, pazopanib, sunitinib and vandetanib (and compounds that work by other mechanisms (for example linomide, inhibitors of integrin αvβ3 function and angiostatin)];

(vii) vascular damaging agents, such as Combretastatin A4;

(viii) anti-invasion agents, for example c-Src kinase family inhibitors like (dasatinib, *J. Med. Chem.*, 2004, 47, 6658-6661) and bosutinib (SKI-606), and metalloproteinase inhibitors like marimastat, inhibitors of urokinase plasminogen activator receptor function or antibodies to Heparanase];

(ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies. Specific examples include monoclonal antibodies targeting PD-1 (e.g. BMS-936558) or CTLA4 (e.g. ipilimumab and tremelimumab);

(x) Antisense or RNAi based therapies, for example those which are directed to the targets listed.

(xi) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy.

Accordingly, in one embodiment there is provided a compound of Formula (I), (IA), (IB), (IC) or (ID), or a pharmaceutically acceptable salt thereof, and an additional anti-tumour substance for the conjoint treatment of cancer.

According to this aspect of the specification there is provided a combination suitable for use in the treatment of cancer comprising a compound of the Formula (I), (IA), (IB), (IC) or (ID), or a pharmaceutically acceptable salt thereof and another anti-tumour agent, in particular any one of the anti tumour agents listed under (i)-(xi) above. In particular, the anti-tumour agent listed under (i)-(xi) above is the standard of care for the specific cancer to be treated; the person skilled in the art will understand the meaning of "standard of care".

Therefore in a further aspect of the specification there is provided a compound of the Formula (I), (IA), (IB), (IC) or (ID), or a pharmaceutically acceptable salt thereof, in combination with another anti-tumour agent, in particular an anti-tumour agent selected from one listed under (i)-(xi) herein above.

In a further aspect of the specification there is provided a compound of the Formula (I), (IA), (IB), (IC) or (ID), or a pharmaceutically acceptable salt thereof, in combination with another anti-tumour agent, in particular an anti-tumour agent selected from one listed under (i) above.

In a further aspect of the specification there is provided a compound of the Formula (I), (IA), (IB), (IC) or (ID), or a pharmaceutically acceptable salt thereof, and any one of the anti-tumour agents listed under (i) above.

In a further aspect of the specification there is provided a combination suitable for use in the treatment of cancer comprising a compound of the Formula (I), (IA), (IB), (IC) or (ID), or a pharmaceutically acceptable salt thereof, and a taxoid, such as for example taxol or taxotere, conveniently taxotere.

In a further aspect of the specification there is provided a compound of the Formula (I), (IA), (IB), (IC) or (ID), or a pharmaceutically acceptable salt thereof, in combination with another anti-tumour agent, in particular an anti-tumour agent selected from one listed under (ii) herein above.

In a further aspect of the specification there is provided a combination suitable for use in the treatment of cancer comprising a compound of the Formula (I), (IA), (IB), (IC) or (ID), or a pharmaceutically acceptable salt thereof, and any one of the antihormonal agents listed under (ii) above, for example any one of the anti-oestrogens listed in (ii) above, or for example an aromatase inhibitor listed in (ii) above.

In a further aspect of the specification there is provided a combination suitable for use in the treatment of cancer comprising a compound of the Formula (I), (IA), (IB), (IC) or (ID), or a pharmaceutically acceptable salt thereof, and an mTOR inhibitor, such as AZD2014.

In a further aspect of the specification there is provided a combination suitable for use in the treatment of cancer comprising a compound of the Formula (I), (IA), (IB), (IC) or (ID), or a pharmaceutically acceptable salt thereof, and a PI3Kα-inhibitor, such as the compound 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one, or a pharmaceutically-acceptable salt thereof.

In a further aspect of the specification there is provided a combination suitable for use in the treatment of cancer comprising a compound of the Formula (I), (IA), (IB), (IC) or (ID), or a pharmaceutically acceptable salt thereof, and a CDK4/6 inhibitor, such as palbociclib.

In one aspect the above combination of a compound of the Formula (I), (IA), (IB), (IC) or (ID), or a pharmaceutically acceptable salt thereof, with an anti-tumour agent listed in (ii) above, or an mTOR inhibitor (such as AZD2014), or a PI3K-α inhibitor (such as the compound 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one) or a CDK4/6 inhibitor (such as palbociclib), is suitable for use in the treatment of breast or gynaecological cancers, such as cancer of the breast, endometrium, ovary or cervix, particularly breast cancer, such as ER+ve breast cancer.

Herein, where the term "combination" is used it is to be understood that this refers to simultaneous, separate or sequential administration. In one aspect of the specification "combination" refers to simultaneous administration. In another aspect of the specification "combination" refers to separate administration. In a further aspect of the specification "combination" refers to sequential administration. Where the administration is sequential or separate, the delay in administering the second component should not be such as to lose the beneficial effect of the combination. Where a combination of two or more components is administered separately or sequential, it will be understood that the dosage regime for each component may be different to and independent of the other components. Conveniently, the compounds of the present specification are dosed once daily.

According to a further aspect of the specification there is provided a pharmaceutical composition which comprises a compound of Formula (I), (IA), (IB), (IC) or (ID), or a pharmaceutically acceptable salt thereof in combination with an anti-tumour agent selected from one listed under (i)-(xi) herein above, in association with a pharmaceutically acceptable excipient.

According to a further aspect of the specification there is provided a pharmaceutical composition which comprises a compound of Formula (I), (IA), (IB), (IC) or (ID), or a pharmaceutically acceptable salt thereof in combination with any one of antihormonal agents listed under (ii) above, for example any one of the anti-oestrogens listed in (ii) above, or for example an aromatase inhibitor listed in (ii) above in association with a pharmaceutically acceptable excipient.

In a further aspect of the specification there is provided a pharmaceutical composition comprising a compound of the Formula (I), (IA), (IB), (IC) or (ID), or a pharmaceutically acceptable salt thereof, and an mTOR inhibitor, such as AZD2014, in association with a pharmaceutically acceptable excipient.

In a further aspect of the specification there is provided a pharmaceutical composition comprising a compound of the Formula (I), (IA), (IB), (IC) or (ID), or a pharmaceutically acceptable salt thereof, and a PI3Kα-inhibitor, such as the compound 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one, in association with a pharmaceutically acceptable excipient.

In a further aspect of the specification there is provided a pharmaceutical composition comprising a compound of the Formula (I), (IA), (IB), (IC) or (ID), or a pharmaceutically acceptable salt thereof, and a CDK4/6 inhibitor (such as palbociclib) in association with a pharmaceutically acceptable excipient.

According to a further aspect of the specification there is provided a pharmaceutical composition which comprises a compound of the Formula (I), (IA), (IB), (IC) or (ID), or a pharmaceutically acceptable salt thereof, in combination with an anti-tumour agent selected from one listed under (i)-(xi) herein above, in association with a pharmaceutically acceptable excipient for use in treating cancer.

According to a further aspect of the specification there is provided a pharmaceutical composition which comprises a compound of the Formula (I), (IA), (IB), (IC) or (ID), or a pharmaceutically acceptable salt thereof, in combination with any one of antihormonal agents listed under (ii) above, for example any one of the anti-oestrogens listed in (ii) above, or for example an aromatase inhibitor listed in (ii) above in association with a pharmaceutically acceptable excipient for use in treating cancer.

In a further aspect of the specification there is provided a pharmaceutical composition comprising a compound of the Formula (I), (IA), (IB), (IC) or (ID), or a pharmaceutically acceptable salt thereof, and an mTOR inhibitor, such as AZD2014, in association with a pharmaceutically acceptable excipient for use in treating cancer.

In a further aspect of the specification there is provided a pharmaceutical composition comprising a compound of the Formula (I), (IA), (IB), (IC) or (ID), or a pharmaceutically acceptable salt thereof, and a PI3Kα-inhibitor, such as the compound 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one, in association with a pharmaceutically acceptable excipient for use in treating cancer.

In a further aspect of the specification there is provided a pharmaceutical composition comprising a compound of the Formula (I), (IA), (IB), (IC) or (ID), or a pharmaceutically acceptable salt thereof, and a CDK4/6 inhibitor (such as palbociclib) in association with a pharmaceutically acceptable excipient for use in treating cancer.

In one aspect the above pharmaceutical compositions of a compound of the Formula (I), (IA), (IB), (IC) or (ID), or a pharmaceutically acceptable salt thereof, with an anti-tumour agent listed in (ii) above, or an mTOR inhibitor (such as AZD2014), or a PI3K-α inhibitor (such as the compound 1-(4-(5-(5-amino-6-(5-tert-butyl-1,3,4-oxadiazol-2-yl) pyrazin-2-yl)-1-ethyl-1H-1,2,4-triazol-3-yl)piperidin-1-yl)-3-hydroxypropan-1-one) or a CDK4/6 inhibitor (such as palbociclib), is suitable for use in the treatment of breast or gynaecological cancers, such as cancer of the breast, endometrium, ovary or cervix, particularly breast cancer, such as ER+ve breast cancer.

According to another feature of the specification there is provided the use of a compound of the Formula (I), (IA), (IB), (IC) or (ID), or a pharmaceutically acceptable salt thereof in combination with an anti-tumour agent selected from one listed under (i)-(xi) herein above, in the manufacture of a medicament for use in the treatment of cancer in a warm-blooded animal, such as man.

According to a further aspect of the specification there is provided the use of a compound of Formula (I), (IA), (IB), (IC) or (ID), or a pharmaceutically acceptable salt thereof in combination with any one of antihormonal agents listed under (ii) above, for example any one of the anti-oestrogens listed in (ii) above, or for example an aromatase inhibitor listed in (ii) above in the manufacture of a medicament for use in the treatment of cancer in a warm-blooded animal, such as man.

In a further aspect of the specification there is provided the use of a compound of the Formula (I), (IA), (IB), (IC) or (ID), or a pharmaceutically acceptable salt thereof, in combination with an mTOR inhibitor, such as AZD2014, in the manufacture of a medicament for use in the treatment of cancer in a warm-blooded animal, such as man.

In a further aspect of the specification there is provided the use of a compound of the Formula (I), (IA), (IB), (IC) or (ID), or a pharmaceutically acceptable salt thereof, in combination with a PI3Kα-inhibitor, such as the compound 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one, in the manufacture of a medicament for use in the treatment of cancer in a warm-blooded animal, such as man.

In a further aspect of the specification there is provided the use a compound of the Formula (I), (IA), (IB), (IC) or (ID), or a pharmaceutically acceptable salt thereof, in combination with a CDK4/6 inhibitor (such as palbociclib) in the manufacture of a medicament for use in the treatment of cancer in a warm-blooded animal, such as man.

In one aspect the above uses of a compound of the Formula (I), (IA), (IB), (IC) or (ID), or a pharmaceutically acceptable salt thereof, in combination with an anti-tumour agent listed in (ii) above, or an mTOR inhibitor (such as AZD2014), or a PI3K-α inhibitor (such as the compound 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one) or a CDK4/6 inhibitor (such as palbociclib), is suitable for use in the manufacture of a medicament for the treatment of breast or gynaecological cancers, such as cancer of the breast, endometrium, ovary or cervix, particularly breast cancer, such as ER+ve breast cancer.

Therefore in an additional feature of the specification, there is provided a method of treating cancer in a warm-blooded animal, such as man, in need of such treatment which comprises administering to said animal an effective amount of a compound of the Formula (I), or a pharmaceutically acceptable salt thereof, in combination with an anti-tumour agent selected from one listed under (i)-(xi) herein above.

According to a further aspect of the specification there is provided a method of treating cancer in a warm-blooded animal, such as man, in need of such treatment which comprises administering to said animal an effective amount of a compound of Formula (I), (IA), (IB), (IC) or (ID), or a pharmaceutically acceptable salt thereof in combination with any one of antihormonal agents listed under (ii) above, for example any one of the anti-oestrogens listed in (ii) above, or for example an aromatase inhibitor listed in (ii) above.

In a further aspect of the specification there is provided a method of treating cancer in a warm-blooded animal, such as man, in need of such treatment which comprises administering to said animal an effective amount of a compound of the Formula (I), (IA), (IB), (IC) or (ID), or a pharmaceutically acceptable salt thereof, in combination with an mTOR inhibitor, such as AZD2014.

In a further aspect of the specification there provided a method of treating cancer in a warm-blooded animal, such as man, in need of such treatment which comprises administering to said animal an effective amount of a compound of the Formula (I), (IA), (IB), (IC) or (ID), or a pharmaceutically acceptable salt thereof, in combination with a PI3Kα-inhibitor, such as the compound 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one.

In a further aspect of the specification there is provided a method of treating cancer in a warm-blooded animal, such as man, in need of such treatment which comprises administering to said animal an effective amount of a compound of the Formula (I), (IA), (IB), (IC) or (ID), or a pharmaceutically acceptable salt thereof, in combination with a CDK4/6 inhibitor (such as palbociclib).

In one aspect the above combinations, pharmaceutical compositions, uses and methods of treating cancer, are methods for the treatment of breast or gynaecological cancers, such as cancer of the breast, endometrium, ovary or cervix, particularly breast cancer, such as ER+ve breast cancer.

According to a further aspect of the present specification there is provided a kit comprising a compound of Formula (I), (IA), (IB), (IC) or (ID), or a pharmaceutically acceptable salt thereof in combination with an anti-tumour agent selected from one listed under (i)-(xi) herein above.

According to a further aspect of the present specification there is provided a kit comprising a compound of Formula (I), (IA), (IB), (IC) or (ID), or a pharmaceutically acceptable salt thereof in combination with an anti-tumour agent selected from one listed under (i) or (ii) herein above.

According to a further aspect of the present specification there is provided a kit comprising:
a) a compound of Formula (I), (IA), (IB), (IC) or (ID), or a pharmaceutically acceptable salt thereof in a first unit dosage form;
b) an anti-tumour agent selected from one listed under (i)-(xi) herein above in a second unit dosage form; and
c) container means for containing said first and second dosage forms.

According to a further aspect of the present specification there is provided a kit comprising:
a) a compound of Formula (I), (IA), (IB), (IC) or (ID), or a pharmaceutically acceptable salt thereof in a first unit dosage form;
b) an anti-tumour agent selected from one listed under (i)-(ii) herein above in a second unit dosage form; and
c) container means for containing said first and second dosage forms.

According to a further aspect of the present specification there is provided a kit comprising:
a) a compound of the Formula (I), (IA), (IB), (IC) or (ID), or a pharmaceutically acceptable salt thereof, in a first unit dosage form;
b) an anti-tumour agent selected from an anti-tumour agent listed in (ii) above, an mTOR inhibitor (such as AZD2014), a PI3Kα-inhibitor, such as the compound 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one, and a CDK4/6 inhibitor, such as palbociclib, in a second unit dosage form; and c) container means for containing said first and second dosage forms.

Combination therapy as described above may be added on top of standard of care therapy typically carried out according to its usual prescribing schedule.

Although the compounds of the Formula (I), (IA), (IB), (IC) or (ID), are primarily of value as therapeutic agents for use in warm-blooded animals (including man), they are also useful whenever it is required to inhibit ER-α. Thus, they are useful as pharmacological standards for use in the development of new biological tests and in the search for new pharmacological agents.

Personalised Healthcare

Another aspect of the present specification is based on identifying a link between the status of the gene encoding ERα and potential susceptibility to treatment with a compound of Formula (I), (IA), (IB), (IC) or (ID). In particular, ERα gene status may indicate that a patient is less likely to respond to exisiting hormone therapy (such as aromatase inhibitors), in part at least because some ERα mutations are though to arise as resistance mechanisms to existing treatments. A SERD, particularly a SERD which can be administered orally in potentially larger doses without excessive inconvenince, may then advantageously be used to treat patients with ERα mutations who may be resistant to other therapies. This therefore provides opportunities, methods and tools for selecting patients for treatment with a compound of Formula (I), (IA), (IB), (IC) or (ID), particularly cancer patients. The present specification relates to patient selection tools and methods (including personalised medicine). The selection is based on whether the tumour cells to be treated possess wild-type or mutant ERα gene. The ERα gene status could therefore be used as a biomarker to indicate that selecting treatment with a SERD may be advantageous. For the avoidance of doubt, compounds of the Formula (I), (IA), (IB), (IC) or (ID), as described herein, are thought to be similarly active against wild-type and mutant ERα genes, at least those mutations in ERα gene identified at the date of filing this application.

There is a clear need for biomarkers that will enrich for or select patients whose tumours will respond to treatment with a SERD, such as a compound of Formula (I), (IA), (IB), (IC) or (ID). Patient selection biomarkers that identify the patients most likely to respond to one agent over another are ideal in the treatment of cancer, since they reduce the unnecessary treatment of patients with non-responding tumours to the potential side effects of such agents.

A biomarker can be described as "a characteristic that is objectively measured and evaluated as an indicator of normal biologic processes, pathogenic processes, or pharmacologic responses to a therapeutic intervention". A biomarker is any identifiable and measurable indicator associated with a particular condition or disease where there is a correlation between the presence or level of the biomarker and some aspect of the condition or disease (including the presence of, the level or changing level of, the type of, the stage of, the susceptibility to the condition or disease, or the responsiveness to a drug used for treating the condition or disease). The correlation may be qualitative, quantitative, or both qualitative and quantitative. Typically a biomarker is a compound, compound fragment or group of compounds. Such compounds may be any compounds found in or produced by an organism, including proteins (and peptides), nucleic acids and other compounds.

Biomarkers may have a predictive power, and as such may be used to predict or detect the presence, level, type or stage of particular conditions or diseases (including the presence or level of particular microorganisms or toxins), the susceptibility (including genetic susceptibility) to particular conditions or diseases, or the response to particular treatments (including drug treatments). It is thought that biomarkers will play an increasingly important role in the future of drug discovery and development, by improving the efficiency of research and development programs. Biomarkers can be used as diagnostic agents, monitors of disease progression, monitors of treatment and predictors of clinical outcome. For example, various biomarker research projects are attempting to identify markers of specific cancers and of specific cardiovascular and immunological diseases. It is believed that the development of new validated biomarkers will lead both to significant reductions in healthcare and drug development costs and to significant improvements in treatment for a wide variety of diseases and conditions.

In order to optimally design clinical trials and to gain the most information from these trials, a biomarker may be required. The marker may be measurable in surrogate and tumour tissues. Ideally these markers will also correlate with efficacy and thus could ultimately be used for patient selection.

Thus, the technical problem underlying this aspect of the present specification is the identification of means for stratification of patients for treatment with a compound of Formula (I). The technical problem is solved by provision of the embodiments characterized in the claims and/or description herein.

Tumours which contain wild type ERα are believed to be susceptible to treatment with a compound of Formula (I), (IA), (IB), (IC) or (ID), for example as a first-line treatment. Tumours may also respond to treatment with a compound of Formula (I), (IA), (IB), (IC) or (ID) as a second-line, third-line or subsequent therapy and this may be useful, in particular, where the tumours contain mutant ERα and may thus be resistant to existing therapies such as AIs. A higher dosage of a compound of Formula (I), (IA), (IB), (IC) or (ID) may be required in the resistant setting than in wild type tumours).

The specification provides a method of determining sensitivity of cells to a compound of Formula (I), (IA), (IB), (IC) or (ID). The method comprises determining the status of ERα gene in said cells. A cell is defined as sensitive to a compound of Formula (I), (IA), (IB), (IC) or (ID) if it inhibits the increase in cell number in a cell growth assay (either through inhibition of cell proliferation and/or through increased cell death). Methods of the specification are useful for predicting which cells are more likely to respond to a compound of Formula (I), (IA), (IB), (IC) or (ID) by growth inhibition.

A sample "representative of the tumour" can be the actual tumour sample isolated, or may be a sample that has been further processed, e.g. a sample of PCR amplified nucleic acid from the tumour sample.

Definitions

In this Personalised Healthcare section:

"Allele" refers to a particular form of a genetic locus, distinguished from other forms by its particular nucleotide or amino acid sequence.

"Amplification reactions" are nucleic acid reactions which result in specific amplification of target nucleic acids over non-target nucleic acids. The polymerase chain reaction (PCR) is a well known amplification reaction.

"Cancer" is used herein to refer to neoplastic growth arising from cellular transformation to a neoplastic phenotype. Such cellular transformation often involves genetic mutation.

"Gene" is a segment of DNA that contains all the information for the regulated biosynthesis of an RNA product, including a promoter, exons, introns, and other sequence elements which may be located within 5' or 3' flanking regions (not within the transcribed portions of the gene) that control expression.

"Gene status" refers to whether the gene is wild type or not (i.e. mutant).

"Label" refers to a composition capable of producing a detectable signal indicative of the presence of the target polynucleotide in an assay sample. Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means.

"Non-synonymous variation" refers to a variation (variance) in or overlapping the coding sequence of a gene that result in the production of a distinct (altered) polypeptide sequence. These variations may or may not affect protein function and include missense variants (resulting in substitution of one amino acid for another), nonsense variants (resulting in a truncated polypeptide due to generation of a premature stop codon) and insertion/deletion variants.

"Synonymous variation" refers to a variation (variance) in the coding sequence of a gene that does not affect sequence of the encoded polypeptide. These variations may affect protein function indirectly (for example by altering expression of the gene), but, in the absence of evidence to the contrary, are generally assumed to be innocuous.

"Nucleic acid" refers to single stranded or double stranded DNA and RNA molecules including natural nucleic acids found in nature and/or modified, artificial nucleic acids having modified backbones or bases, as are known in the art.

"Primer" refers to a single stranded DNA oligonucleotide sequence capable of acting as a point of initiation for synthesis of a primer extension product which is complementary to the nucleic acid strand to be copied. The length and sequence of the primer must be such that they are able to prime the synthesis of extension products. A typical primer contains at least about 7 nucleotides in length of a sequence substantially complementary to the target sequence, but somewhat longer primers are preferred. Usually primers contain about 15-26 nucleotides, but longer or shorter primers may also be employed.

"Polymorphic site" is a position within a locus at which at least two alternative sequences are found in a population.

"Polymorphism" refers to the sequence variation observed in an individual at a polymorphic site. Polymorphisms include nucleotide substitutions, insertions, deletions and microsatellites and may, but need not, result in detectable differences in gene expression or protein function. In the absence of evidence of an effect on expression or protein function, common polymorphisms, including non-synonymous variants, are generally considered to be included in the definition of wild-type gene sequence. A catalog of human polymorphisms and associated annotation, including validation, observed frequencies, and disease association, is maintained by NCBI (dbSNP: http://www.ncbi.nlm.nih.gov/projects/SNP/). Please note that the term "polymorphism" when used in the context of gene sequences should not be confused with the term "polymorphism" when used in the context of solid state form of a compound that is the crystalline or amorphous nature of a compound. The skilled person will understand the intended meaning by its context.

"Probe" refers to single stranded sequence-specific oligonucleotides which have a sequence that is exactly complementary to the target sequence of the allele to be detected.

"Response" is defined by measurements taken according to Response Evaluation Criteria in Solid Tumours (RECIST) involving the classification of patients into two main groups: those that show a partial response or stable disease and those that show signs of progressive disease.

"Stringent hybridisation conditions" refers to an overnight incubation at 42° C. in a solution comprising 50% formamide, 5×SSC (750 mM NaCl, 75 mM trisodium citrate), 50 mM sodium phosphate (pH 7.6), 5×Denhardt's solution, 10% dextran sulphate, and 20 pg/ml denatured, sheared salmon sperm DNA, followed by washing the filters in 0.1×SSC at about 65° C.

"Survival" encompasses a patients' overall survival and progression-free survival.

"Overall survival" (OS) is defined as the time from the initiation of drug administration to death from any cause. "Progression-free survival" (PFS) is defined as the time from the initiation of drug administration to first appearance of progressive disease or death from any cause.

According to one aspect of the specification there is provided a method for selecting a patient for treatment with a compound of Formula (I), (IA), (IB), (IC) or (ID), the method comprising providing a tumour cell containing sample from a patient;

determining whether the ERα gene in the patient's tumour cell containing sample is wild type or mutant; and selecting a patient for treatment with a compound of Formula (I), (IA), (IB), (IC) or (ID) based thereon.

The method may include or exclude the actual patient sample isolation step. Thus, according to one aspect of the specification there is provided a method for selecting a patient for treatment with a compound of Formula (I), (IA), (IB), (IC) or (ID), the method comprising determining whether the ERα gene in a tumour cell containing sample previously isolated from the patient is wild type or mutant; and selecting a patient for treatment with a compound of Formula (I), (IA), (IB), (IC) or (ID) based thereon.

In one embodiment, the patient is selected for treatment with a compound of Formula (I) if the tumour cell DNA has a mutant ERα gene. In other embodiments, a patient whose tumour cell DNA possesses a wild type ERα gene is selected for treatment with a compound of Formula (I), (IA), (IB), (IC) or (ID).

For the purpose of this specification, a gene status of wild-type is meant to indicate normal or appropriate expression of the gene and normal function of the encoded protein.

In contrast, mutant status is meant to indicate expression of a protein with altered function, consistent with the known roles of mutant ERα genes in cancer (as described herein). Any number of genetic or epigenetic alterations, including but not limited to mutation, amplification, deletion, genomic rearrangement, or changes in methylation profile, may result in a mutant status. However, if such alterations nevertheless result in appropriate expression of the normal protein, or a functionally equivalent variant, then the gene status is regarded as wild-type. Examples of variants that typically would not result in a functional mutant gene status include synonymous coding variants and common polymorphisms (synonymous or non-synonymous). As discussed below, gene status can be assessed by a functional assay, or it may be inferred from the nature of detected deviations from a reference sequence.

In certain embodiments the wild-type or mutant status of the ERα gene is determined by the presence or absence of non-synonymous nucleic acid variations in the genes. Observed non-synonymous variations corresponding to known common polymorphisms with no annotated functional effects do not contribute to a gene status of mutant.

Other variations in the ERα gene that signify mutant status include splice site variations that decrease recognition of an intron/exon junction during processing of pre-mRNA to mRNA. This can result in exon skipping or the inclusion of normally intronic sequence in spliced mRNA (intron retention or utilization of cryptic splice junctions). This can, in turn, result in the production of aberrant protein with insertions and/or deletions relative to the normal protein. Thus, in other embodiments, the gene has a mutant status if there is a variant that alters splice site recognition sequence at an intron/exon junction.

For ESR1, reference sequences are available for the gene (GenBank accession number: NG_008493), mRNA (GenBank accession number: NM_000125), and protein (GenBank accession number: NP_000116 or Swiss-Prot accession: P03372). A person of skill in the art will be able to determine the ESR1 gene status, i.e. whether a particular ESR1 gene is wild type or mutant, based on comparison of DNA or protein sequence with wild type.

It will be apparent that the gene and mRNA sequences disclosed for ERα gene are representative sequences. In normal individuals there are two copies of each gene, a maternal and paternal copy, which will likely have some sequence differences, moreover within a population there will exist numerous allelic variants of the gene sequence. Other sequences regarded as wild type include those that possess one or more synonymous changes to the nucleic acid sequence (which changes do not alter the encoded protein sequence), non-synonymous common polymorphisms (e.g. germ-line polymorphisms) which alter the protein sequence but do not affect protein function, and intronic non-splice-site sequence changes.

There are numerous techniques available to the person skilled in the art to determine the gene status of ERα. The gene status can be determined by determination of the nucleic acid sequence. This could be via direct sequencing of the full-length gene or analysis of specific sites within the gene, e.g. commonly mutated sites.

Samples

The patient's sample to be tested for the gene status can be any tumour tissue or tumour-cell containing sample obtained or obtainable from the individual. The test sample is conveniently a sample of blood, mouth swab, biopsy, or other body fluid or tissue obtained from an individual. Particular examples include: circulating tumour cells, circulating DNA in the plasma or serum, cells isolated from the ascites fluid of ovarian cancer patients, lung sputum for patients with tumours within the lung, a fine needle aspirate from a breast cancer patient, urine, peripheral blood, a cell scraping, a hair follicle, a skin punch or a buccal sample.

It will be appreciated that the test sample may equally be a nucleic acid sequence corresponding to the sequence in the test sample, that is to say that all or a part of the region in the sample nucleic acid may firstly be amplified using any convenient technique e.g. polymerase chain reaction (PCR), before analysis. The nucleic acid may be genomic DNA or fractionated or whole cell RNA. In particular embodiments the RNA is whole cell RNA and is used directly as the template for labelling a first strand cDNA using random primers or poly A primers. The nucleic acid or protein in the test sample may be extracted from the sample according to standard methodologies (see Green & Sambrook, Eds., Molecular Cloning: A Laboratory Manual, (2012, 4th edition, Vol. 1-3, ISBN 9781936113422), Cold Spring Harbor Laboratory Press, Cold Spring Harbor, N.Y.)

The diagnostic methods of the specification can be undertaken using a sample previously taken from the individual or patient. Such samples may be preserved by freezing or fixed and embedded in formalin-paraffin or other media. Alternatively, a fresh tumour cell containing sample may be obtained and used.

The methods of the specification can be applied using cells from any tumour. Suitable tumours for treatment with a compound of Formula (I) have been described hereinbefore.

Methods for Detection of Nucleic Acids

The detection of mutant ERα nucleic acids can be employed, in the context of the present specification, to select drug treatment. Since mutations in these genes occur at the DNA level, the methods of the specification can be based on detection of mutations or variances in genomic DNA, as well as transcripts and proteins themselves. It can be desirable to confirm mutations in genomic DNA by analysis of transcripts and/or polypeptides, in order to ensure that the detected mutation is indeed expressed in the subject.

It will be apparent to the person skilled in the art that there are a large number of analytical procedures which may be used to detect the presence or absence of variant nucleotides at one or more positions in a gene. In general, the detection of allelic variation requires a mutation discrimination technique, optionally an amplification reaction (such as one based on polymerase chain reaction) and optionally a signal generation system. There are a multitude of mutation detection techniques available in the art and these may be used in combination with a signal generation system, of which there are numerous available in the art. Many methods for the detection of allelic variation are reviewed by Nollau et al., *Clin. Chem.*, 1997, 43, 1114-1120; Anderson S M. *Expert Rev Mol Diagn.*, 2011, 11, 635-642; Meyerson M. et al., *Nat Rev Genet.*, 2010, 11, 685-696; and in standard textbooks, for example "*Laboratory Protocols for Mutation Detection*", Ed. by U. Landegren, Oxford University Press, 1996 and "PCR", $2^{nd}$ Edition by Newton & Graham, BIOS Scientific Publishers Limited, 1997.

As noted above, determining the presence or absence of a particular variance or plurality of variances in the ERα gene in a patient with cancer can be performed in a variety of ways. Such tests are commonly performed using DNA or RNA collected from biological samples, e.g., tissue biopsies, urine, stool, sputum, blood, cells, tissue scrapings, breast aspirates or other cellular materials, and can be performed by a variety of methods including, but not limited to, PCR, hybridization with allele-specific probes, enzymatic mutation detection, chemical cleavage of mismatches, mass spectrometry or DNA sequencing, including minisequencing.

Suitable mutation detection techniques include amplification refractory mutation system (ARMS™), amplification refractory mutation system linear extension (ALEX™), competitive oligonucleotide priming system (COPS), Taqman, Molecular Beacons, restriction fragment length polymorphism (RFLP), and restriction site based PCR and fluorescence resonance energy transfer (FRET) techniques.

In particular embodiments the method employed for determining the nucleotide(s) within a biomarker gene is selected from: allele-specific amplification (allele specific PCR)—such as amplification refractory mutation system (ARMS), sequencing, allelic discrimination assay, hybridisation, restriction fragment length polymorphism (RFLP) or oligonucleotide ligation assay (OLA).

In particular embodiments, hybridization with allele specific probes can be conducted by: (1) allele specific oligonucleotides bound to a solid phase (e.g. glass, silicon, nylon membranes) with the labelled sample in solution, for example as in many DNA chip applications; or, (2) bound sample (often cloned DNA or PCR amplified DNA) and labelled oligonucleotides in solution (either allele specific or short so as to allow sequencing by hybridization). Diagnostic tests may involve a panel of variances, often on a solid support, which enables the simultaneous determination of more than one variance. Such hybridization probes are well known in the art (see, e.g., Green & Sambrook, Eds., Molecular Cloning: A Laboratory Manual, (2012, 4th edition, Vol. 1-3, ISBN 9781936113422), Cold Spring Harbor Laboratory Press, Cold Spring Harbor, N.Y.) and may span two or more variance sites.

Thus, in one embodiment, the detection of the presence or absence of at least one mutation provides for contacting ERα nucleic acid containing a putative mutation site with at least one nucleic acid probe. The probe preferentially hybridizes with a nucleic acid sequence including a variance site and containing complementary nucleotide bases at the variance site under selective hybridization conditions. Hybridization can be detected with a detectable label using labels known to one skilled in the art. Such labels include, but are not limited to radioactive, fluorescent, dye, and enzymatic labels.

In another embodiment, the detection of the presence or absence of at least one mutation provides for contacting ERα nucleic acid containing a putative mutation site with at least one nucleic acid primer. The primer preferentially hybridizes with a nucleic acid sequence including a variance site and containing complementary nucleotide bases at the variance site under selective hybridization conditions.

Oligonucleotides used as primers for specific amplification may carry the complementary nucleotide base to the mutation of interest in the centre of the molecule (so that amplification depends on differential hybridization; see, e.g., Gibbs, et al., 1989. *Nucl. Acids Res.*, 17, 2437-248) or at the extreme 3'-terminus of one primer where, under appropriate conditions, mismatch can prevent, or reduce polymerase extension (see, e.g., Prossner, 1993, *Tibtech,* 11 238).

In yet another embodiment, the detection of the presence or absence of at least one mutation comprises sequencing at least one nucleic acid sequence and comparing the obtained sequence with the known wild type nucleic acid sequence.

Alternatively, the presence or absence of at least one mutation comprises mass spectrometric determination of at least one nucleic acid sequence.

In one embodiment, the detection of the presence or absence of at least one nucleic acid variance comprises performing a polymerase chain reaction (PCR). The target nucleic acid sequence containing the hypothetical variance is amplified and the nucleotide sequence of the amplified nucleic acid is determined. Determining the nucleotide sequence of the amplified nucleic acid comprises sequencing at least one nucleic acid segment. Alternatively, amplification products can be analysed using any method capable of separating the amplification products according to their size, including automated and manual gel electrophoresis, and the like.

Mutations in genomic nucleic acid are advantageously detected by techniques based on mobility shift in amplified nucleic acid fragments. For instance, Chen et al., *Anal Biochem* 1996, 239, 61-9, describe the detection of single-base mutations by a competitive mobility shift assay. Moreover, assays based on the technique of Marcelino et al., *BioTechniques* 1999, 26, 1134-1148 are available commercially.

In a particular example, capillary heteroduplex analysis may be used to detect the presence of mutations based on mobility shift of duplex nucleic acids in capillary systems as a result of the presence of mismatches.

Generation of nucleic acids for analysis from samples generally requires nucleic acid amplification. Many amplification methods rely on an enzymatic chain reaction (such as a polymerase chain reaction, a ligase chain reaction, or a self-sustained sequence replication) or from the replication of all or part of the vector into which it has been cloned. Preferably, the amplification according to the specification is an exponential amplification, as exhibited by for example the polymerase chain reaction.

Many target and signal amplification methods have been described in the literature, for example, general reviews of these methods in Landegren, U., et al., *Science,* 1988 242, 229-237 and Lewis, R., *Genetic Engineering News* 1990, 10, 54-55. These amplification methods can be used in the methods of our specification, and include polymerase chain reaction (PCR), PCR in situ, ligase amplification reaction (LAR), ligase hybridisation, Qβ bacteriophage replicase, transcription-based amplification system (TAS), genomic amplification with transcript sequencing (GAWTS), nucleic acid sequence-based amplification (NASBA) and in situ hybridisation. Primers suitable for use in various amplification techniques can be prepared according to methods known in the art.

Polymerase Chain Reaction (PCR) PCR is a nucleic acid amplification method described inter alia in U.S. Pat. Nos. 4,683,195 and 4,683,202. PCR consists of repeated cycles of DNA polymerase generated primer extension reactions. The target DNA is heat denatured and two oligonucleotides, which bracket the target sequence on opposite strands of the DNA to be amplified, are hybridised. These oligonucleotides become primers for use with DNA polymerase. The DNA is copied by primer extension to make a second copy of both strands. By repeating the cycle of heat denaturation, primer hybridisation and extension, the target DNA can be amplified a million fold or more in about two to four hours. PCR is a molecular biology tool, which must be used in conjunction with a detection technique to determine the results of amplification. An advantage of PCR is that it increases sensitivity by amplifying the amount of target DNA by 1 million to 1 billion fold in approximately 4 hours. PCR can be used to amplify any known nucleic acid in a diagnostic context (Mok et al., *Gynaecologic Oncology,* 1994, 52: 247-252).

An allele specific amplification technique such as Amplification Refractory Mutation System (ARMS™) (Newton et al., *Nucleic Acids Res.,* 1989, 17, 2503-2516) can also be used to detect single base mutations. Under the appropriate PCR amplification conditions a single base mismatch located at the 3'-end of the primer is sufficient for preferential amplification of the perfectly matched allele (Newton et al., 1989, supra), allowing the discrimination of closely related species. The basis of an amplification system using the primers described above is that oligonucleotides with a mismatched 3′-residue will not function as primers in the PCR under appropriate conditions. This amplification system allows genotyping solely by inspection of reaction mixtures after agarose gel electrophoresis.

Analysis of amplification products can be performed using any method capable of separating the amplification products according to their size, including automated and manual gel electrophoresis, mass spectrometry, and the like.

The methods of nucleic acid isolation, amplification and analysis are routine for one skilled in the art and examples of protocols can be found, for example, Green & Sambrook, Eds., Molecular Cloning: A Laboratory Manual, (2012, 4th edition, Vol. 1-3, ISBN 9781936113422), Cold Spring Harbor Laboratory Press, Cold Spring Harbor, N.Y.) Particularly useful protocol source for methods used in PCR amplification is *PCR (Basics: From Background to Bench)* by M. J. McPherson, S. G. Mailer, R. Beynon, C. Howe, Springer Verlag; 1st edition (Oct. 15, 2000), ISBN: 0387916008.

The present specification also provides predictive and diagnostic kits comprising degenerate primers to amplify a target nucleic acid in the ERα gene and instructions comprising; amplification protocol and analysis of the results. The kit may alternatively also comprise buffers, enzymes, and containers for performing the amplification and analysis of the amplification products. The kit may also be a component of a screening, or diagnostic kit comprising other tools such as DNA microarrays, or other supports. Preferably, the kit also provides one or more control templates, such as nucleic acids isolated from normal tissue sample, and/or a series of samples representing different variances in the reference genes.

In one embodiment, the kit provides two or more primer pairs, each pair capable of amplifying a different region of the reference (ERα) gene (each region a site of potential variance) thereby providing a kit for analysis of expression of several gene variances in a biological sample in one reaction or several parallel reactions.

Primers in the kits may be labelled, for example fluorescently labelled, to facilitate detection of the amplification products and consequent analysis of the nucleic acid variances. The kit may also allow for more than one variance to be detected in one analysis. A combination kit will therefore comprise of primers capable of amplifying different segments of the reference gene. The primers may be differentially labelled, for example using different fluorescent labels, so as to differentiate between the variances.

In another aspect, the specification provides a method of treating a patient suffering from cancer comprising: determining the mutant or wild type status of the ERα gene in the patient's tumour cells and if the ERα gene is mutant, administering to the patient an effective amount of a compound of Formula (I), (IA), (IB), (IC) or (ID).

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. "Less effective" means that the treatment results in a therapeutically significant lower level of pharmacological effectiveness and/or a therapeutically greater level of adverse physiological effects.

According to another aspect of the specification there is provided the use of a compound of Formula (I), (IA), (IB), (IC) or (ID), or a pharmaceutically acceptable salt thereof to treat a cancer patient whose tumour cells have been identified as possessing a mutant ERα gene.

According to another aspect of the specification there is provided a compound of Formula (I), (IA), (IB), (IC) or (ID), or a pharmaceutically acceptable salt thereof for treating cancers with tumour cells identified as harbouring mutant ERα gene.

According to another aspect of the specification there is provided a method of treating cancers with tumour cells identified as harbouring mutant ERα gene comprising administering an effective amount of a compound of Formula (I), (IA), (IB), (IC) or (ID), or a pharmaceutically acceptable salt thereof.

In still further embodiments, the specification relates to a pharmaceutical composition comprising a compound of Formula (I), (IA), (IB), (IC) or (ID), for use in the prevention and treatment of cancer with tumour cells identified as harbouring a mutant ERα gene.

For all the aspects above, mutant forms of ERα determined/identified are at all positions across the gene.

For all the aspects above, using tumours such as breast cancer as an example, particular mutant forms of ERα determined/identified are those at positions Ser463Pro, Val543Glu, Leu536Arg, Tyr537Ser, Tyr537Asn and Asp538Gly.

DESCRIPTION OF DRAWINGS

FIG. 1 shows the X-Ray Powder Diffraction Pattern for Form A of N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine.

FIG. 2 shows the DSC/TGA Thermogram for Form A of N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine.

FIG. 3 shows the X-Ray Powder Diffraction Pattern for Form B of N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine.

FIG. 4 shows the X-Ray Powder Diffraction Pattern for Form C of N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine.

FIG. 5 shows the DSC/TGA Thermogram for Form C of N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine.

FIG. 6 shows the X-Ray Powder Diffraction Pattern for Form D of N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine.

FIG. 7 shows the DSC/TGA Thermogram for Form D of N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine.

FIG. 8 shows the X-Ray Powder Diffraction Pattern for Form E of N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine.

FIG. 9 shows the DSC/TGA Thermogram for Form E of N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine.

FIG. 10 shows the X-Ray Powder Diffraction Pattern for Form F of N-(1-(3-fluoropropyl)azetidin-3-yl)-6-((6S,8R)-

8-methyl-7-(2,2,2-trifluoroethyl)-6,7,8,9-tetrahydro-3H-pyrazolo[4,3-f]isoquinolin-6-yl)pyridin-3-amine.

FIG. 11 shows the X-Ray Powder Diffraction Pattern for Form G of N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine.

FIG. 12 shows the results of a human parental MCF7 xenograft anti-tumour efficacy study in mouse with N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine.

FIG. 13 shows the results of a human Y537S ESR1 mutant MCF7 xenograft anti-tumour efficacy study in mouse with N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine.

FIG. 14 shows the results of a human ESR1 mutant breast cancer patient derived xenograft CTC174 anti-tumour efficacy study in mouse with N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine.

FIG. 15 shows the results of a human ESR1 mutant breast cancer patient derived xenograft CTC174 anti-tumour efficacy study in mouse with a combination of N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine and palbociclib.

FIG. 16 shows the results of a human ESR1 mutant breast cancer patient derived xenograft CTC174 anti-tumour efficacy study in mouse with a combination of N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine and vistusertib (AZD2014).

EXAMPLES

The compounds described in this specification are further illustrated in the following Examples. These Examples are given by way of illustration only and are non-limiting. In general:

(i) operations were carried out at ambient temperature, i.e. in the range 17 to 25° C. and under an atmosphere of an inert gas such as nitrogen unless otherwise stated;

(ii) evaporations were carried out by rotary evaporation or utilising Genevac equipment or Biotage v10 evaporator in vacuo and work-up procedures were carried out after removal of residual solids by filtration;

(iii) flash chromatography purifications were performed on an automated Teledyne Isco CombiFlash® Rf or Teledyne Isco CombiFlash® Companion® using prepacked RediSep Rf Gold™ Silica Columns (20-40 μm, spherical particles), GraceResolv™ Cartridges (Davisil® silica) or Silicycle cartridges (40-63 μm).

(iv) preparative chromatography was performed on a Gilson prep HPLC instrument with UV collection or via supercritical fluid chromatography performed on a Waters Prep 100 SFC-MS instrument with MS- and UV-triggered collection or a Thar MultiGram III SFC instrument with UV collection;

(v) chiral preparative chromatography was performed on a Gilson instrument with UV collection (233 injector/fraction collector, 333 & 334 pumps, 155 UV detector) or a Varian Prep Star instrument (2×SD1 pumps, 325 UV detector, 701 fraction collector) pump running with Gilson 305 injection;

(vi) yields, where present, are not necessarily the maximum attainable;

(vii) in general, the structures of end-products of the Formula I were confirmed by nuclear magnetic resonance (NMR) spectroscopy; NMR chemical shift values were measured on the delta scale [proton magnetic resonance spectra were determined using a Bruker Avance 500 (500 MHz) or Bruker Avance 400 (400 MHz) instrument]; measurements were taken at ambient temperature unless otherwise specified; the following abbreviations have been used: s, singlet; d, doublet; t, triplet; q, quartet; m, multiplet; dd, doublet of doublets; ddd, doublet of doublet of doublet; dt, doublet of triplets; bs, broad signal (viii) in general, end-products of the Formula I were also characterised by mass spectroscopy following liquid chromatography (LCMS or UPLC); UPLC was carried out using a Waters UPLC fitted with Waters SQ mass spectrometer (Column temp 40, UV=220-300 nm, Mass Spec=ESI with positive/negative switching) at a flow rate of 1 ml/min using a solvent system of 97% A+3% B to 3% A to 97% B over 1.50 mins (total runtime with equilibration back to starting conditions etc 1.70 min), where A=0.1% formic acid in water (for acid work) or 0.1% ammonia in water (for base work) B=acetonitrile. For acid analysis the column used was Waters Acquity HSS T3 1.8 μm 2.1×50 mm, for base analysis the column used was Waters Acquity BEH 1.7 μm 2.1×50 mm; LCMS was carried out using a Waters Alliance HT (2795) fitted with a Waters ZQ ESCi mass spectrometer and a Phenomenex Gemini-NX (50×2.1 mm 5 μm) column at a flow rate of 1.1 ml/min 95% A to 95% B over 4 min with a 0.5 min hold. The modifier is kept at a constant 5% C (50:50 acetonitrile:water 0.1% formic acid) or D (50:50 acetonitrile:water 0.1% ammonium hydroxide (0.88 SG) depending on whether it is an acidic or basic method.

(ix) ion exchange purification was generally performed using a SCX-2 (Biotage, Propylsulfonic acid functionalized silica. Manufactured using a trifunctional silane. Non end-capped) cartridge.

(x) intermediate purity was assessed by thin layer chromatographic, mass spectral, HPLC (high performance liquid chromatography) and/or NMR analysis;

(xi) the following abbreviations have been used:—
AcOH acetic acid
aq. Aqueous
Boc tert-butoxycarbonyl
n-BuLi n-butyl lithium
tBuOH tert-butanol
Brettphos 2-(dicyclohexylphosphino)3,6-dimethoxy-2',4',6'-triisopropyl-1,1'-biphenyl
CDCl$_3$ deutero-chloroform
CHCl$_3$ chloroform
Conc. concentrated
DCM dichloromethane
DIPEA diisopropylethylamine
DMAP dimethylaminopyridine
DMSO dimethyl sulphoxide
EtOH ethanol
EtOAc ethyl acetate
HATU 1-[bis(dimethylamino)methylene]-1H-1,2,3-triazolo[4,5-b]pyridinium 3-oxid hexafluorophosphate
HCl hydrochloric acid
HPLC high performance liquid chromatography
K$_2$CO$_3$ potassium carbonate
MeOH methanol
MgSO$_4$ magnesium sulfate
NaH sodium hydride
NaHCO$_3$ sodium bicarbonate Na₂SO₄ sodium sulfate
Pd₂(dba)₃ tris(dibenzylideneacetone)dipalladium(0)
Rac-BINAP (±)-2,2'-Bis(diphenylphosphino)-1,1'-binaphthalene
rt/RT room temperature
RockPhos 3^rd generation [(2-Di-tert-butylphosphino-3-methoxy-6-precatalyst methyl-2',4',6'-triisopropyl-1,1'-biphenyl)-2-(2-aminobiphenyl)]palladium(II) methanesulfonate
Ruphos 2-Dicyclohexylphosphino-2',6'-diisopropoxy-1,1'-biphenyl
sat. saturated
SFC supercritical fluid chromatography
sol. solution
TBAF tetra-n-butylammonium fluoride
TEA triethylamine
THF tetrahydrofuran
THP tetrahydropyran
TFA trifluoroacetic acid
Xantphos 4,5-bis(diphenylphosphino)-9,9-dimethyl xanthene Example 1

N-(4-((6S,8R)-7-(2,2-difluoro-3-methoxypropyl)-8-methyl-6,7,8,9-tetrahydro-3H-pyrazolo[4,3-f]isoquinolin-6-yl)-3-methoxyphenyl)-1-(3-fluoropropyl)azetidin-3-amine

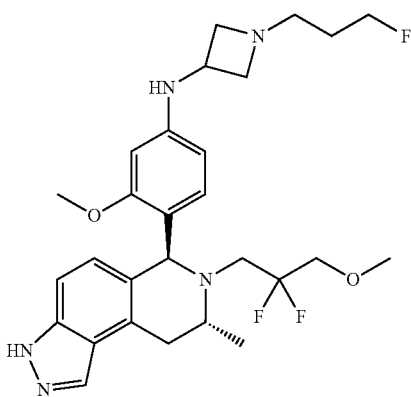 [SMILES: COCC(F)(F)CN1[C@H](c2ccc(NC3CN(CCCF)C3)cc2OC)c2ccc3[nH]ncc3c2C[C@H]1C]

[(2-Di-cyclohexylphosphino-3,6-dimethoxy-2',4',6'-triisopropyl-1,1'-biphenyl)-2-(2'-amino-1,1'-biphenyl)]palladium(II) methanesulfonate (BrettPhos Pd G3) (6.80 mg, 7.50 μmol) was added to a suspension of (6S,8R)-6-(4-bromo-2-methoxyphenyl)-7-(2,2-difluoro-3-methoxypropyl)-8-methyl-3-(tetrahydro-2H-pyran-2-yl)-6,7,8,9-tetrahydro-3H-pyrazolo[4,3-f]isoquinoline (85 mg, 0.15 mmol), 1-(3-fluoropropyl)azetidin-3-amine (29.7 mg, 0.23 mmol) and sodium tert-butoxide (28.8 mg, 0.30 mmol) in degassed 1,4-dioxane (1.5 mL) and the reaction was heated to 90° C. for 3 hours. After cooling, the reaction was diluted with DCM and washed with water. The aqueous was extracted with DCM, then the combined organics were dried and evaporated. The crude residue was dissolved in DCM (2 mL) and TFA (0.7 mL) was added. The reaction was stirred at room temperature for 1 hour, then it was diluted with DCM and basified by addition of saturated NaHCO₃ solution. The layers were separated and the aqueous was extracted with DCM. The combined organics were dried and evaporated, then the crude product was purified by flash silica chromatography, elution gradient 0 to 20% MeOH in EtOAc. Pure fractions were evaporated to dryness to afford N-(4-((6S,8R)-7-(2,2-difluoro-3-methoxypropyl)-8-methyl-6,7,8,9-tetrahydro-3H-pyrazolo[4,3-f]isoquinolin-6-yl)-3-methoxyphenyl)-1-(3-fluoropropyl)azetidin-3-amine (39.0 mg, 49%) as a beige solid. ¹H NMR (500 MHz, CDCl₃, 27° C.) 1.09 (3H, d), 1.83 (2H, ddd), 2.65-2.86 (4H, m), 2.96-3.08 (1H, m), 3.11 (1H, dd), 3.22 (2H, d), 3.38 (3H, s), 3.51-3.63 (2H, m), 3.73-3.82 (1H, m), 3.82 (3H, s), 3.86 (2H, q), 4.15-4.28 (1H, m), 4.43 (1H, t), 4.53 (1H, t), 5.37 (1H, s), 5.88 (1H, dd), 6.14 (1H, d), 6.46 (1H, d), 6.80 (1H, d), 7.13 (1H, d), 8.04 (1H, d). m/z: ES+ [M+H]+ 532.

The (6S,8R)-6-(4-bromo-2-methoxyphenyl)-7-(2,2-difluoro-3-methoxypropyl)-8-methyl-3-(tetrahydro-2H-pyran-2-yl)-6,7,8,9-tetrahydro-3H-pyrazolo[4,3-f]isoquinoline was prepared as follows:

Preparation of 2,2-difluoro-3-(trityloxy)propan-1-ol

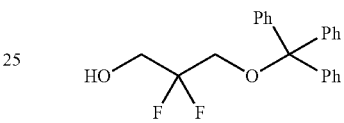

2,2-Difluoropropane-1,3-diol (2.50 g, 22.3 mmol) was dissolved in DCM (61.7 mL) and THF (15.4 mL). DIPEA (3.93 mL, 22.3 mmol) was added, followed by (chloromethanetriyl)tribenzene (6.22 g, 22.3 mmol) and finally DMAP (0.288 g, 2.23 mmol). The reaction was heated to 40° C. for 2 hours. After cooling, the reaction was washed with 1N HCl solution, then dried and evaporated. The crude product was purified by flash silica chromatography, elution gradient 0 to 25% EtOAc in heptane. Pure fractions were evaporated to dryness to afford 2,2-difluoro-3-(trityloxy)propan-1-ol (4.43 g, 56%) as a colourless solid. ¹H NMR (500 MHz, CDCl₃) 3.42 (2H, t), 3.92 (2H, t), 7.23-7.3 (4H, m), 7.3-7.39 (6H, m), 7.39-7.49 (6H, m).

Preparation of ((2,2-difluoro-3-methoxypropoxy)methanetriyl)tribenzene

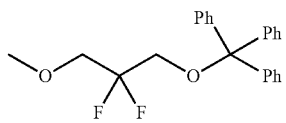 [SMILES: COCC(F)(F)COC(c1ccccc1)(c1ccccc1)c1ccccc1]

Sodium hydride (0.562 g, 14.0 mmol) was added to a solution of 2,2-difluoro-3-(trityloxy)propan-1-ol (4.15 g, 11.7 mmol) in THF (46 mL) and the reaction was stirred for 1 hour, then iodomethane (0.802 mL, 12.9 mmol) was added in THF (5 mL). The reaction was stirred for a further 1 hour. The reaction was quenched with water and brine, then extracted with EtOAc. The organic layer was dried and evaporated to afford ((2,2-difluoro-3-methoxypropoxy)methanetriyl)tribenzene (4.18 g, 97%) as a pale yellow oil. ¹H NMR (500 MHz, CDCl₃) 3.36 (2H, t), 3.40 (3H, s), 3.77 (2H, t), 7.15-7.28 (3H, m), 7.28-7.38 (6H, m), 7.39-7.47 (6H, m).

Preparation of 2,2-difluoro-3-methoxypropyl trifluoromethanesulfonate

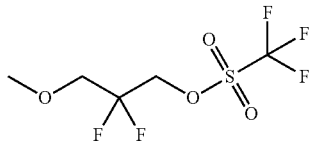

Trifluoromethanesulfonic anhydride (1.918 mL, 11.40 mmol) was added to a solution of ((2,2-difluoro-3-methoxypropoxy)methanetriyl)tribenzene (4.00 g, 10.9 mmol) in DCM (39.6 mL). The reaction was stirred for 30 minutes, then triethylsilane (1.934 mL, 11.94 mmol) was added and the reaction was stirred for a further 30 minutes. The reaction was evaporated, and the triflate, was used directly in the next stage.

Preparation of (R)-1-(3-bromo-2-methylphenyl)propan-2-amine

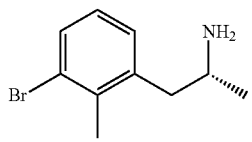

n-BuLi (26.1 mL, 41.8 mmol) was added dropwise to a solution of 1,3-dibromo-2-methylbenzene (9.95 g, 39.8 mmol) in THF (100 mL) at −78° C. After stirring for 30 minutes, (R)-tert-butyl 4-methyl-1,2,3-oxathiazolidine-3-carboxylate 2,2-dioxide (10.39 g, 43.8 mmol) was added in portions and the reaction was stirred for a further 30 minutes before being allowed to warm to 0° C. over 30 minutes. 1N citric acid was added and the mixture was stirred for 5 minutes before it was extracted with EtOAc (×2). The combined organic phases were evaporated. The residue was stirred in 4M HCl in dioxane (69.7 mL, 278.7 mmol) at room temperature for 1 hour, then the volatiles were evaporated. The residue was suspended in diethyl ether, and extracted with water (×2). The combined aqueous phases were basified by addition of 2N Na$_2$CO$_3$, then extracted with DCM (×3). The combined organics phases were dried over MgSO$_4$ and concentrated to afford (R)-1-(3-bromo-2-methylphenyl)propan-2-amine (7.55 g, 83%) as a yellow oil. $^1$H NMR (400 MHz, CDCl$_3$, 27° C.) 1.13 (3H, d), 1.43 (2H, s), 2.40 (3H, s), 2.61 (1H, dd), 2.77 (1H, dd), 3.14 (1H, dq), 6.97 (1H, t), 7.08 (1H, d), 7.43 (1H, d). m/z (ES+), [M+H]+=228.

Preparation of (R)-N-(1-(3-bromo-2-methylphenyl)propan-2-yl)-2,2-difluoro-3-methoxypropan-1-amine

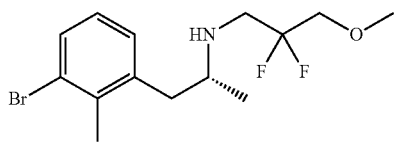 [SMILES: COCC(F)(F)CN[C@H](C)Cc1cccc(Br)c1C]

2,2-Difluoro-3-methoxypropyl trifluoromethanesulfonate (3.03 g, 11.73 mmol) (crude from the previous step) was added to a solution of (R)-1-(3-bromo-2-methylphenyl)propan-2-amine (2.327 g, 10.2 mmol) and DIPEA (2.82 mL, 16.32 mmol) in 1,4-dioxane (34.3 mL) and the reaction was heated to 80° C. overnight. After cooling, the volatiles were evaporated, then the residue was dissolved in DCM and washed with brine. The organic phase was dried and evaporated, then the crude product was purified by flash silica chromatography, elution gradient 0 to 100% EtOAc in heptane. Pure fractions were evaporated to dryness to afford (R)-N-(1-(3-bromo-2-methylphenyl)propan-2-yl)-2,2-difluoro-3-methoxypropan-1-amine (2.330 g, 68%) as a pale yellow oil. $^1$H NMR (500 MHz, CDCl$_3$) 1.06 (3H, d), 2.40 (3H, s), 2.63 (1H, dd), 2.82 (1H, dd), 2.86-2.94 (1H, m), 2.95-3.11 (2H, m), 3.38 (3H, s), 3.51-3.63 (2H, m), 6.94-7 (1H, m), 7.07 (1H, dd), 7.4-7.51 (1H, m). m/z: ES+ [M+H]+ 336.

Preparation of (R)-3-(2-((2,2-difluoro-3-methoxypropyl)amino)propyl)-2-methylaniline

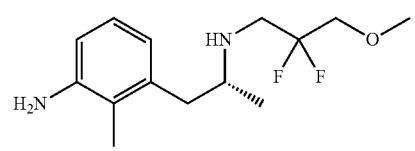 [SMILES: COCC(F)(F)CN[C@H](C)Cc1cccc(N)c1C]

Pd$_2$(dba)$_3$ (0.184 g, 0.20 mmol) and Rac-BINAP (0.250 g, 0.40 mmol) were added to a suspension of (R)-N-(1-(3-bromo-2-methylphenyl)propan-2-yl)-2,2-difluoro-3-methoxypropan-1-amine (2.25 g, 6.69 mmol), benzophenone imine (1.334 g, 7.36 mmol) and sodium tert-butoxide (0.965 g, 10.0 mmol) in degassed toluene (28.5 mL) and the reaction was heated to 90° C. for 3 hours. After cooling, the toluene was largely evaporated, then the residue was dissolved in DCM and washed with water. The aqueous phase was extracted with DCM, then the organics were evaporated to ~50 mL volume. 2N HCl solution (50 mL) was added and the biphasic mixture was stirred vigorously for 30 minutes. The layers were separated, then the aqueous was extracted with DCM. The organic phase was back extracted with 1N HCl. The combined aqueous phases were basified by addition of solid K$_2$CO$_3$ then extracted with DCM (×3), and the combined DCM extracts were dried and evaporated to afford (R)-3-(2-((2,2-difluoro-3-methoxypropyl)amino)propyl)-2-methylaniline (1.780 g, 98%) as a light brown oil. $^1$H NMR (500 MHz, CDCl$_3$) 1.06 (3H, d), 2.11 (3H, s), 2.59 (1H, dd), 2.75 (1H, dd), 2.86-2.94 (1H, m), 2.94-3.12 (2H, m), 3.38 (3H, s), 3.53-3.63 (4H, m), 6.5-6.68 (2H, m), 6.86-7.01 (1H, m). m/z: ES+ [M+H]+ 273.

Preparation of (1S,3R)-1-(4-bromo-2-methoxyphenyl)-2-(2,2-difluoro-3-methoxypropyl)-3,5-dimethyl-1,2,3,4-tetrahydroisoquinolin-6-amine

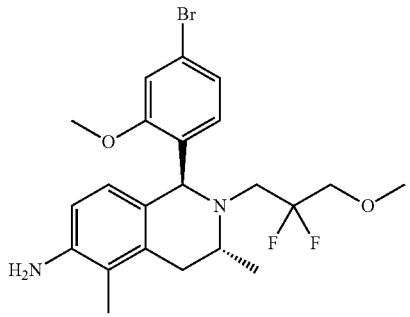 [SMILES: COCC(F)(F)CN1[C@H](c2ccc(Br)cc2OC)c2ccc(N)c(C)c2C[C@H]1C]

(R)-3-(2-((2,2-Difluoro-3-methoxypropyl)amino)propyl)-2-methylaniline (490 mg, 1.80 mmol) and 4-bromo-2-methoxybenzaldehyde (813 mg, 3.78 mmol) were heated in acetic acid (8.8 mL) and water (0.162 mL, 9.00 mmol) to 75° C. overnight. After cooling, the acetic acid was evaporated under vacuum, then the residue was dissolved in EtOAc (20 mL) and 2N HCl solution (20 mL) was added. The biphasic mixture was stirred for 30 minutes, then the layers were separated. The organic phase was extracted with water, then the aqueous phase was basified by addition of 2N NaOH solution and extracted with DCM (×2). The combined DCM layers were dried and evaporated, then the crude product was purified by flash silica chromatography, elution gradient 0 to 50% EtOAc in heptane. Pure fractions were evaporated to dryness to afford (1S,3R)-1-(4-bromo-2-methoxyphenyl)-2-(2,2-difluoro-3-methoxypropyl)-3,5-dimethyl-1,2,3,4-tetrahydroisoquinolin-6-amine (384 mg, 46%) as a beige solid. $^1$H NMR (500 MHz, CDCl$_3$, 27° C.) 1.03 (3H, d), 2.07 (3H, s), 2.42 (1H, dd), 2.60-2.76 (2H, m), 2.99 (1H, ddd), 3.34 (1H, d), 3.36 (3H, s), 3.52 (2H, s), 3.54-3.66 (1H, m), 3.76 (1H, ddd), 3.87 (3H, s), 5.28 (1H, s), 6.47 (2H, s), 6.59 (1H, d), 6.88 (1H, dd), 7.01 (1H, d). m/z: ES+ [M+H]+ 469.

Preparation of (6S,8R)-6-(4-bromo-2-methoxyphenyl)-7-(2,2-difluoro-3-methoxypropyl)-8-methyl-6,7,8,9-tetrahydro-3H-pyrazolo[4,3-f]isoquinoline

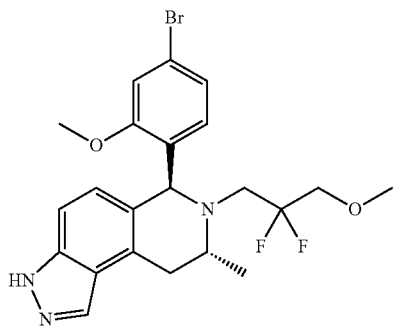 [SMILES: COCC(F)(F)CN1[C@H](c2ccc(Br)cc2OC)c2ccc3[nH]ncc3c2C[C@H]1C]

Sodium nitrite (59.8 mg, 0.87 mmol) was added in water (0.2 mL) to a cooled solution of (1S,3R)-1-(4-bromo-2-methoxyphenyl)-2-(2,2-difluoro-3-methoxypropyl)-3,5-dimethyl-1,2,3,4-tetrahydroisoquinolin-6-amine (370 mg, 0.79 mmol) in propionic acid (2628 µL)/water (526 µL) at −10° C. The reaction was stirred for 1 hour, then ice-cold EtOAc (20 mL) was added. The reaction was quenched by addition of cold saturated NaHCO$_3$ solution and stirred for 15 minutes, before being allowed to warm to room temperature. The layers were separated and the aqueous was extracted with EtOAc. The combined organics were dried and evaporated, then the crude product was purified by flash silica chromatography, elution gradient 0 to 50% EtOAc in heptane. Pure fractions were evaporated to dryness to afford (6S,8R)-6-(4-bromo-2-methoxyphenyl)-7-(2,2-difluoro-3-methoxypropyl)-8-methyl-6,7,8,9-tetrahydro-3H-pyrazolo[4,3-f]isoquinoline (252 mg, 67%) as a beige solid. $^1$H NMR (500 MHz, CDCl$_3$, 27° C.) 1.10 (3H, d), 2.72 (1H, td), 2.85 (1H, dd), 3.08 (1H, ddd), 3.16 (1H, dd), 3.36 (3H, s), 3.48-3.66 (2H, m), 3.65-3.81 (1H, m), 3.90 (3H, s), 5.44 (1H, s), 6.59 (1H, d), 6.77 (1H, d), 6.89 (1H, dd), 7.05 (1H, d), 7.19 (1H, dd), 8.07 (1H, d). m/z: ES+ [M+H]+ 480.

Preparation of (6S,8R)-6-(4-bromo-2-methoxyphenyl)-7-(2,2-difluoro-3-methoxypropyl)-8-methyl-3-(tetrahydro-2H-pyran-2-yl)-6,7,8,9-tetrahydro-3H-pyrazolo[4,3-f]isoquinoline

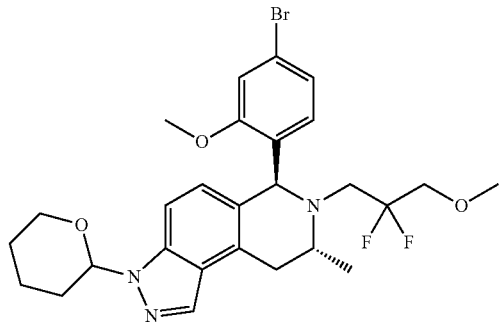 [SMILES: COCC(F)(F)CN1[C@H](c2ccc(Br)cc2OC)c2ccc3c(cnn3C3CCCCO3)c2C[C@H]1C]

3,4-Dihydro-2H-pyran (0.064 mL, 0.70 mmol) was added to a solution of (6S,8R)-6-(4-bromo-2-methoxyphenyl)-7-(2,2-difluoro-3-methoxypropyl)-8-methyl-6,7,8,9-tetrahydro-3H-pyrazolo[4,3-f]isoquinoline (240 mg, 0.50 mmol) and p-toluenesulfonic acid hydrate (9.51 mg, 0.05 mmol) in DCM (2.5 mL) and the reaction was heated to 40° C. for 1 hour. After cooling, the reaction was diluted with DCM and washed with saturated NaHCO$_3$ solution. The organic phase was dried and evaporated. The crude residue was passed through a plug of silica gel (EtOAc/heptane, 1:1 as eluent) and the filtrate was evaporated to afford (6S,8R)-6-(4-bromo-2-methoxyphenyl)-7-(2,2-difluoro-3-methoxypropyl)-8-methyl-3-(tetrahydro-2H-pyran-2-yl)-6,7,8,9-tetrahydro-3H-pyrazolo[4,3-f]isoquinoline (262 mg, 93%) as a pale yellow solid as a 5:1 ratio of THP regioisomers (each THP regioisomer is a diastereosiomeric mixture). m/z: ES+ [M+H]+ 564.

Preparation of tert-butyl (1-(3-fluoropropyl)azetidin-3-yl)carbamate

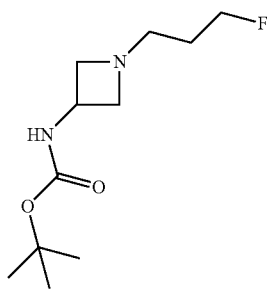 [SMILES: CC(C)(C)OC(=O)NC1CN(CCCF)C1]

Potassium carbonate (1.605 g, 11.61 mmol), tert-butyl azetidin-3-ylcarbamate (1.0 g, 5.81 mmol) and 1-fluoro-3-iodopropane (1.146 g, 6.10 mmol) were suspended in acetonitrile (11.61 mL) and sealed into a microwave tube. The reaction was heated to 95° C. for 15 minutes in the microwave reactor. Reaction was cooled to room temperature, diluted with EtOAc (100 mL) and extracted from saturated NaHCO$_3$ (50 mL). The organic phase was dried over MgSO$_4$, filtered and evaporated to afford tert-butyl (1-(3-fluoropropyl)azetidin-3-yl)carbamate (1.248 g, 93%) as a yellow solid. $^1$H NMR (500 MHz, CDCl$_3$, 22° C.) 1.44 (9H, s), 1.68-1.80 (2H, m), 2.56 (2H, t), 2.88 (2H, s), 3.66 (2H, t), 4.31 (1H, d), 4.43 (1H, t), 4.53 (1H, t), 4.90 (1H, s).

Preparation of 1-(3-fluoropropyl)azetidin-3-amine

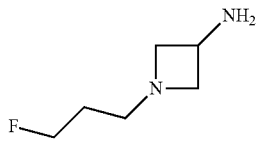

TFA (2.69 ml) was added to a solution of tert-butyl (1-(3-fluoropropyl)azetidin-3-yl)carbamate (1.248 g, 5.37 mmol) in DCM (8.06 mL) and the reaction was stirred at room temperature for 1 hour. The volatiles were evaporated and purified by ion exchange chromatography, using an SCX column. The desired product was eluted from the column using 1M NH$_3$/MeOH and pure fractions were evaporated to dryness to afford 1-(3-fluoropropyl)azetidin-3-amine (0.697 g, 98%) as a colourless oil. $^1$H NMR (500 MHz, CDCl$_3$, 27° C.) 1.66-1.83 (2H, m), 1.96 (3H, s), 2.54 (2H, t), 2.67 (2H, td), 3.58-3.70 (2H, m), 4.43 (1H, t), 4.52 (1H, t).

Example 2

6-((6S,8R)-7-(2,2-difluoro-3-methoxypropyl)-8-methyl-6,7,8,9-tetrahydro-3H-pyrazolo[4,3-f]isoquinolin-6-yl)-N-(1-(3-fluoropropyl)azetidin-3-yl)pyridin-3-amine

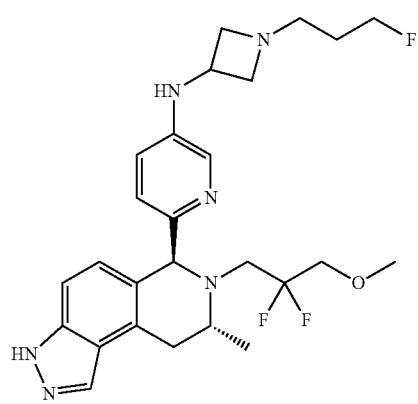 [SMILES: COCC(F)(F)CN1[C@H](c2ccc(NC3CN(CCCF)C3)cn2)c2ccc3[nH]ncc3c2C[C@H]1C]

[(2-Di-cyclohexylphosphino-3,6-dimethoxy-2',4',6'-triisopropyl-1,1'-biphenyl)-2-(2'-amino-1,1'-biphenyl)]palladium(II) methanesulfonate (BrettPhos Pd G3) (6.83 mg, 8.00 μmol) and sodium tert-butoxide (48.0 mg, 0.50 mmol) were added to a degassed solution of (6S,8R)-6-(5-bromopyridin-2-yl)-7-(2,2-difluoro-3-methoxypropyl)-8-methyl-3-(tetrahydro-2H-pyran-2-yl)-6,7,8,9-tetrahydro-3H-pyrazolo[4,3-f]isoquinoline (107 mg, 0.20 mmol) and 1-(3-fluoropropyl)azetidin-3-amine (52.9 mg, 0.40 mmol) in 1,4-dioxane (1.6 mL) and the reaction was heated to 90° C. for 5 hours. After cooling, the reaction was diluted with DCM and washed with water. The organic phase was evaporated, then dissolved in DCM (2 mL), before TFA (1 mL) was added. The mixture was stirred at room temperature for 1 hour, then was diluted with DCM and washed with saturated NaHCO$_3$ solution. The layers were separated and the aqueous was extracted with DCM. The combined organics were dried and evaporated, then the crude product was purified by flash silica chromatography, elution gradient 0 to 20% MeOH in EtOAc. Pure fractions were evaporated to dryness to afford 6-((6S,8R)-7-(2,2-difluoro-3-methoxypropyl)-8-methyl-6,7,8,9-tetrahydro-3H-pyrazolo[4,3-f]isoquinolin-6-yl)-N-(1-(3-fluoropropyl)azetidin-3-yl)pyridin-3-amine (83 mg, 83%) as a beige solid. $^1$H NMR (500 MHz, CDCl$_3$) 1.12 (3H, d), 1.79 (2H, ddd), 2.71 (2H, t), 2.75-2.90 (2H, m), 3.06-3.23 (3H, m), 3.39 (3H, s), 3.51-3.66 (2H, m), 3.66-3.76 (1H, m), 3.76-3.84 (2H, m), 4.14 (1H, s), 4.44 (2H, t), 4.53 (1H, t), 5.06 (1H, s), 6.80 (1H, dd), 6.88 (1H, d), 7.13 (2H, dd), 7.84 (1H, d), 7.99 (1H, d). m/z: ES+ [M+H]+ 503.

The (6S,8R)-6-(5-bromopyridin-2-yl)-7-(2,2-difluoro-3-methoxypropyl)-8-methyl-3-(tetrahydro-2H-pyran-2-yl)-6,7,8,9-tetrahydro-3H-pyrazolo[4,3-f]isoquinoline was prepared as follows:

Preparation of (1S,3R)-1-(5-bromopyridin-2-yl)-2-(2,2-difluoro-3-methoxypropyl)-3,5-dimethyl-1,2,3,4-tetrahydroisoquinolin-6-amine

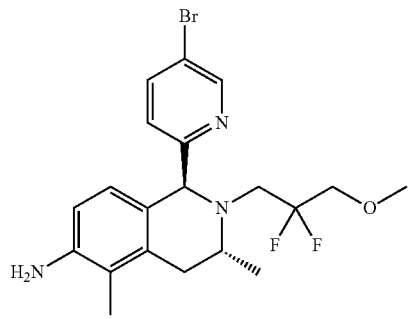 [SMILES: COCC(F)(F)CN1[C@H](c2ccc(Br)cn2)c2ccc(N)c(C)c2C[C@H]1C]

5-Bromopicolinaldehyde (1172 mg, 6.30 mmol) was added to a solution of (R)-3-(2-((2,2-difluoro-3-methoxypropyl)amino)propyl)-2-methylaniline (817 mg, 3.00 mmol) in acetic acid (14.7 mL) and water (270 µL, 15.0 mmol) and the reaction was heated to 80° C. for 2 hours. After cooling, the volatiles were evaporated under vacuum. The residue was dissolved in DCM and washed with saturated NaHCO$_3$ solution. The organic was evaporated to a volume ~20 mL and 2N HCl solution (20 mL) was added. The biphasic mixture was stirred for 15 minutes, then separated. The organic was extracted with water, then the aqueous phase was back-extracted with DCM. The aqueous phase was then basified by addition of solid K$_2$CO$_3$, then extracted with DCM. The organic extracts were dried and evaporated. The crude product was purified by flash silica chromatography, elution gradient 0 to 50% EtOAc in heptane. Pure fractions were evaporated to dryness to afford (1S,3R)-1-(5-bromopyridin-2-yl)-2-(2,2-difluoro-3-methoxypropyl)-3,5-dimethyl-1,2,3,4-tetrahydroisoquinolin-6-amine (810 mg, 61%) as a beige solid. $^1$H NMR (500 MHz, CDCl$_3$) 1.07 (3H, d), 2.05 (3H, s), 2.49 (1H, d), 2.75 (2H, dd), 3.04-3.17 (1H, m), 3.30-3.36 (1H, m), 3.37 (3H, s), 3.58-3.74 (2H, m), 4.96 (1H, s), 6.51 (1H, d), 6.60 (1H, d), 7.22 (1H, d), 7.68 (1H, dd), 8.55 (1H, dd). m/z: ES+ [M+H]+ 440.

Preparation of (6S,8R)-6-(5-bromopyridin-2-yl)-7-(2,2-difluoro-3-methoxypropyl)-8-methyl-6,7,8,9-tetrahydro-3H-pyrazolo[4,3-f]isoquinoline

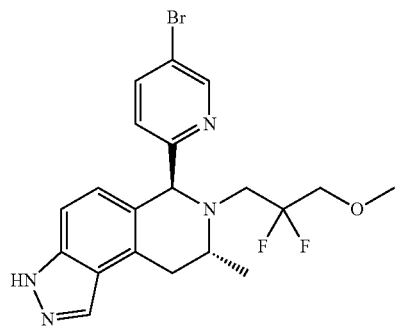 [SMILES: COCC(F)(F)CN1[C@H](c2ccc(Br)cn2)c2ccc3[nH]ncc3c2C[C@H]1C]

Sodium nitrite (133 mg, 1.93 mmol) was added in water (0.5 mL) to a cooled solution of (1S,3R)-1-(5-bromopyridin-2-yl)-2-(2,2-difluoro-3-methoxypropyl)-3,5-dimethyl-1,2,3,4-tetrahydroisoquinolin-6-amine (771 mg, 1.75 mmol) in propionic acid (5833 µL)/water (1167 µL) at −15° C. The reaction was stirred for 30 minutes, then EtOAc (50 mL), which had been cooled in dry-ice was added. The reaction was quenched by addition of 2N Na$_2$CO$_3$ until bubbling ceased, then the layers were separated. The aqueous was extracted with EtOAc, then the organic was dried and evaporated. The crude product was purified by flash silica chromatography, elution gradient 0 to 50% EtOAc in heptane. Pure fractions were evaporated to dryness to afford (6S,8R)-6-(5-bromopyridin-2-yl)-7-(2,2-difluoro-3-methoxypropyl)-8-methyl-6,7,8,9-tetrahydro-3H-pyrazolo[4,3-f]isoquinoline (460 mg, 58%) as a pale yellow solid. $^1$H NMR (500 MHz, CDCl$_3$) 1.14 (3H, d), 2.81 (1H, dd), 2.88 (1H, dd), 3.10-3.26 (2H, m), 3.38 (3H, s), 3.46-3.55 (1H, m), 3.58-3.76 (2H, m), 5.13 (1H, s), 6.94 (1H, d), 7.23 (1H, dd), 7.29 (1H, d), 7.72 (1H, dd), 8.05 (1H, d), 8.57 (1H, dd). m/z: ES+ [M+H]+ 451.

Preparation of (6S,8R)-6-(5-bromopyridin-2-yl)-7-(2,2-difluoro-3-methoxypropyl)-8-methyl-3-(tetrahydro-2H-pyran-2-yl)-6,7,8,9-tetrahydro-3H-pyrazolo[4,3-f]isoquinoline

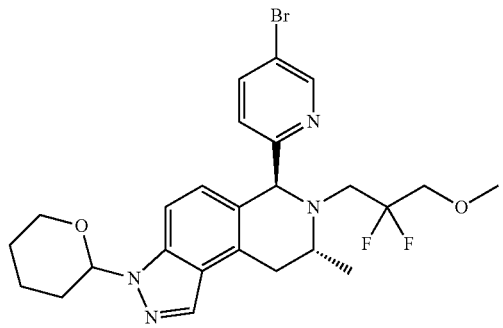 [SMILES: COCC(F)(F)CN1[C@H](c2ccc(Br)cn2)c2ccc3c(cnn3C3CCCCO3)c2C[C@H]1C]

3,4-Dihydro-2H-pyran (0.114 mL, 1.25 mmol) was added to a solution of (6S,8R)-6-(5-bromopyridin-2-yl)-7-(2,2-difluoro-3-methoxypropyl)-8-methyl-6,7,8,9-tetrahydro-3H-pyrazolo[4,3-f]isoquinoline (450 mg, 1.00 mmol) and PTSA hydrate (37.9 mg, 0.20 mmol) in DCM (5 mL) and the reaction was heated to 45° C. for 3 hours. After cooling, the reaction was diluted with DCM and washed with saturated NaHCO$_3$ solution. The organic phase was dried and evaporated, then the crude was passed through a plug of silica (1:1 EtOAc/heptane). The filtrate was evaporated to afford (6S,8R)-6-(5-bromopyridin-2-yl)-7-(2,2-difluoro-3-methoxypropyl)-8-methyl-3-(tetrahydro-2H-pyran-2-yl)-6,7,8,9-tetrahydro-3H-pyrazolo[4,3-f]isoquinoline (510 mg, 9%) as an orange solid (~6.5:1 ratio of THP regioisomers). m/z: ES+ [M+H]+ 535.

Example 3

6-((6S,8R)-7-((1-fluorocyclopropyl)methyl)-8-methyl-6,7,8,9-tetrahydro-3H-pyrazolo[4,3-f]isoquinolin-6-yl)-N-(1-(3-fluoropropyl)azetidin-3-yl)pyridin-3-amine

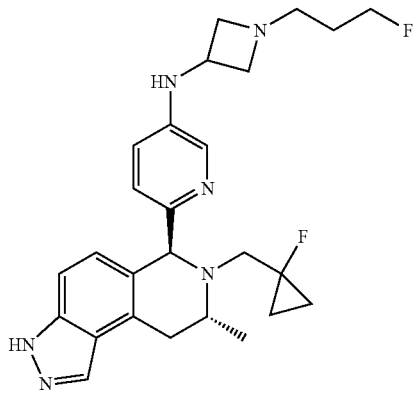 [SMILES: C[C@@H]1Cc2c(ccc3[nH]ncc23)[C@@H](c2ccc(NC3CN(CCCF)C3)cn2)N1CC1(F)CC1]

[(2-Di-cyclohexylphosphino-3,6-dimethoxy-2',4',6'-triisopropyl-1,1'-biphenyl)-2-(2'-amino-1,1'-biphenyl)]palladium(II) methanesulfonate (BrettPhos Pd G3) (12.11 mg, 0.01 mmol) and sodium tert-butoxide (85 mg, 0.89 mmol) were added to a degassed solution of (6S,8R)-6-(5-bromopyridin-2-yl)-7-((1-fluorocyclopropyl)methyl)-8-methyl-3-(tetrahydro-2H-pyran-2-yl)-6,7,8,9-tetrahydro-3H-pyrazolo[4,3-f]isoquinoline (177 mg, 0.35 mmol) and 1-(3-fluoropropyl)azetidin-3-amine (94 mg, 0.71 mmol) in 1,4-dioxane (2835 µL) and the reaction was heated to 90° C. for 5 hours. After cooling, the reaction was diluted with DCM and washed with water. The organic phase was evaporated, then dissolved in DCM (2 mL), before TFA (1 mL) was added. The mixture was stirred at room temperature for 1 hour, then was diluted with DCM and washed with saturated NaHCO₃ solution. The layers were separated and the aqueous phase was extracted with DCM. The combined organics were dried and evaporated to give the crude product. The crude product was purified by preparative LCMS (Waters SunFire column, 5µ silica, 19 mm diameter, 100 mm length), using decreasingly polar mixtures of water (containing 1% NH₃) and MeCN as eluents.

Fractions containing the desired compounds were evaporated to dryness to give 6-((6S,8R)-7-((1-fluorocyclopropyl)methyl)-8-methyl-6,7,8,9-tetrahydro-3H-pyrazolo[4,3-f]isoquinolin-6-yl)-N-(1-(3-fluoropropyl)azetidin-3-yl)pyridin-3-amine (17.0 mg, 10%) as a beige solid. ¹H NMR (500 MHz, CDCl₃, 27° C.) 0.36-0.46 (1H, m), 0.49-0.59 (1H, m), 0.88-1.07 (2H, m), 1.09 (3H, d), 1.69-1.75 (1H, m), 1.75-1.81 (1H, m), 2.59 (2H, t), 2.70 (1H, dd), 2.86-2.96 (3H, m), 3.01-3.11 (1H, m), 3.37-3.44 (1H, m), 3.72 (2H, q), 3.78-3.88 (1H, m), 3.95 (1H, d), 4.04-4.13 (1H, m), 4.44 (1H, t), 4.53 (1H, t), 4.95 (1H, s), 6.75 (1H, dd), 6.91 (1H, d), 7.12-7.17 (2H, m), 7.86 (1H, d), 8.05 (1H, d), 10.04 (1H, s). m/z: ES+ [M+H]+ 467.

The (6S,8R)-6-(5-bromopyridin-2-yl)-7-((1-fluorocyclopropyl)methyl)-8-methyl-3-(tetrahydro-2H-pyran-2-yl)-6,7,8,9-tetrahydro-3H-pyrazolo[4,3-f]isoquinoline was prepared as follows:

Preparation of 1-(3-bromo-2-methylphenyl)-2,5-dimethyl-1H-pyrrole

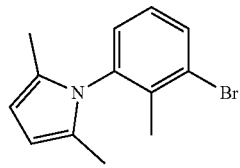

A mixture of 3-bromo-2-methylaniline (40 g, 215 mmol), hexane-2,5-dione (25.3 mL, 215 mmol) and p-toluenesulfonic acid monohydrate (0.409 g, 2.15 mmol) in toluene (300 mL) was heated at reflux conditions for 2 hours in a flask equipped with a condenser and Dean-Stark trap. The mixture was then cooled to room temperature and washed sequentially with saturated aqueous sodium bicarbonate, aqueous HCl (1N), and saturated aqueous sodium chloride. The organic layer was dried over sodium sulfate, filtered and concentrated under reduced pressure to give crude 1-(3-bromo-2-methylphenyl)-2,5-dimethyl-1H-pyrrole (57.9 g, 102%) as a pale yellow oil. ¹H NMR (300 MHz, DMSO-d₆, 27° C.) 1.8 (6H, s), 1.9 (3H, s), 5.8 (2H, s), 7.2-7.4 (2H, m), 7.7 (1H, dd). m/z: ES+ [M+H]+ 264.

Preparation of tert-butyl (R)-(1-(3-(2,5-dimethyl-1H-pyrrol-1-yl)-2-methylphenyl)propan-2-yl)carbamate

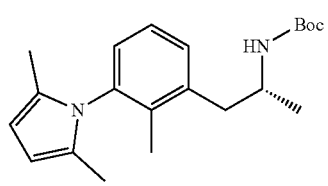 [SMILES: Cc1c(C[C@@H](C)NC(=O)OC(C)(C)C)cccc1-n1c(C)ccc1C]

n-Butyllithium in hexane (2.5M; 89 mL, 221 mmol) was added over 15 minutes to a solution of crude 1-(3-bromo-2-methylphenyl)-2,5-dimethyl-1H-pyrrole (55.7 g, 211 mmol) in THF (400 mL) at −78° C. After 30 minutes, tert-butyl (R)-4-methyl-1,2,3-oxathiazolidine-3-carboxylate 2,2-dioxide (50 g, 211 mmol) was added. The resulting mixture was stirred at −78° C. for 15 minutes and allowed to warm to room temperature over 2 hours. Aqueous citric acid (1N; 250 mL) was added, and stirring was continued for 30 minutes. The mixture was extracted with hexanes, and the combined organic layers were washed with saturated aqueous sodium carbonate, dried over sodium sulfate, filtered, and concentrated under reduced pressure. The resulting brown solid, crude tert-butyl (R)-(1-(3-(2,5-dimethyl-1H-pyrrol-1-yl)-2-methylphenyl)propan-2-yl)carbamate was used in the next step without further purification. m/z: ES+ [M+H]+ 343.

Preparation of (R)-1-(3-(2,5-dimethyl-1H-pyrrol-1-yl)-2-methylphenyl)propan-2-amine

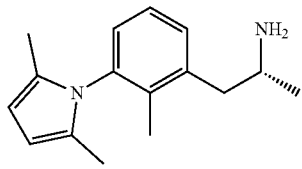 [SMILES: Cc1c(C[C@@H](C)N)cccc1-n1c(C)ccc1C]

Hydrochloric acid in dioxane (4 M; 100 mL, 400 mmol) was added to a suspension of crude tert-butyl (R)-(1-(3-(2,5-dimethyl-1H-pyrrol-1-yl)-2-methylphenyl)propan-2-yl)carbamate in MeOH (200 mL) and DCM (50 mL). The resulting red solution was stirred at room temperature for 4 hours and then concentrated under reduced pressure. The resulting brown solid was used in the next step without further purification. m/z: ES+ [M+H]+ 243.

Preparation of (R)-3-(2-aminopropyl)-2-methylaniline

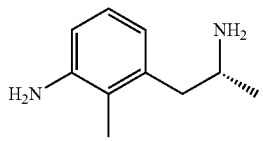

A mixture of crude (R)-1-(3-(2,5-dimethyl-1H-pyrrol-1-yl)-2-methylphenyl)propan-2-amine dihydrochloride, aqueous hydroxylamine (50 wt %; 107 mL, 1.74 mol), and hydroxylamine hydrochloride (97 g, 1.39 mol) in ethanol (400 mL) was warmed to reflux conditions. After 18 hours, the reaction was cooled to 0° C., basified with aqueous sodium hydroxide (50 wt %; 153 g, 1.92 mol) and extracted with DCM. The organic layer was dried over sodium sulfate, filtered and concentrated under reduced pressure. The resulting residue was purified by SFC (Princeton Chromatography DEAP column, 100 mm length, 30 mm diameter, 5 μm, 40° C. column temperature, 100 bar column pressure, 100 mg/mL flow rate), eluting with 25% methanol containing 0.2% NH$_4$OH in CO$_2$, to afford (R)-3-(2-aminopropyl)-2-methylaniline (24 g, 84%) as a light amber solid. $^1$H NMR (500 MHz, DMSO, 27° C.) 1.05 (3H, d), 1.99 (3H, s), 2.55 (1H, dd), 2.93 (1H, dd), 3.11-3.25 (1H, m), 4.77 (2H, s), 6.35 (1H, dd), 6.52 (1H, dd), 6.81 (1H, t). Alkyl NH$_2$ protons not observed. m/z: ES+ [M+H]+ 165.

Preparation of (R)-N-(1-(3-amino-2-methylphenyl)propan-2-yl)-1-fluorocyclopropane-1-carboxamide

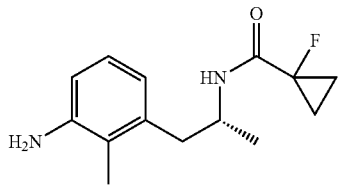 [SMILES: Cc1c(N)cccc1C[C@@H](C)NC(=O)C1(F)CC1]

(R)-3-(2-aminopropyl)-2-methylaniline (1.70 g, 10.4 mmol) was dissolved in DMF (29.9 mL) and treated with 1-fluorocyclopropane-1-carboxylic acid (1.00 g, 9.61 mmol), HATU (4.02 g, 10.6 mmol), and TEA (2.68 mL, 19.22 mmol). The reaction was stirred at room temperature for 3 hours and then quenched with water and extracted with EtOAc. The organic layer was washed with saturated aqueous sodium chloride, dried over sodium sulfate, and filtered. The filtrate was concentrated under reduced pressure, and the resulting residue was dried under vacuum overnight to remove residual DMF. The residue was then adsorbed onto silica and purified by flash column silica chromatography, elution gradient 0 to 80% ethyl acetate in hexanes to afford (R)-N-(1-(3-amino-2-methylphenyl)propan-2-yl)-1-fluorocyclopropane-1-carboxamide (1.47 g, 61.1%) as a light yellow solid. $^1$H NMR (300 MHz, DMSO-d$_6$, 27° C.) 1.01-1.28 (7H, m), 2.02 (3H, s), 2.54-2.62 (1H, m), 2.83 (1H, dd), 3.89-4.16 (1H, m), 4.68 (2H, s), 6.38 (1H, d), 6.49 (1H, d), 6.78 (1H, t), 8.14 (1H, d) m/z: ES+ [M+H]+251.

Preparation of (R)-3-(2-(((1-fluorocyclopropyl)methyl)amino)propyl)-2-methylaniline

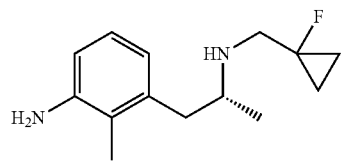 [SMILES: Cc1c(N)cccc1C[C@@H](C)NCC1(F)CC1]

Borane tetrahydrofuran complex in THF (1 M; 35.2 ml, 35.2 mmol) was added to a solution of (R)-N-(1-(3-amino-2-methylphenyl)propan-2-yl)-1-fluorocyclopropane-1-carboxamide (1.47 g, 5.87 mmol) in THF (13.7 mL) at room temperature under nitrogen. The reaction was then heated at 65° C. for 6 hrs. The reaction was cooled to 0° C. and quenched cautiously with MeOH (gas evolution). The solution was then concentrated under reduced pressure and stored in the freezer for 18 hours. The residue was dissolved in MeOH (6 mL) and heated at 65° C. for 3 hrs. The solution was cooled to room temperature and then concentrated under reduced pressure. The residue obtained was purified by flash silica chromatography, elution gradient 0 to 16% methanol in DCM, to afford (R)-3-(2-(((1-fluorocyclopropyl)methyl)amino)propyl)-2-methylaniline (1.14 g, 82%) as colorless oil. $^1$H NMR (300 MHz, DMSO-d$_6$, 27° C.) 0.54-0.70 (2H, m), 0.79-1.02 (5H, m), 1.64 (1H, br. s.), 1.99 (3H, s), 2.36 (1H, dd), 2.69-2.97 (4H, m), 4.68 (2H, s), 6.36 (1H, d), 6.49 (1H, d), 6.79 (1H, t). m/z: ES+ [M+H]+237.

Preparation of (1S,3R)-1-(5-bromopyridin-2-yl)-2-((1-fluorocyclopropyl)methyl)-3,5-dimethyl-1,2,3,4-tetrahydroisoquinolin-6-amine

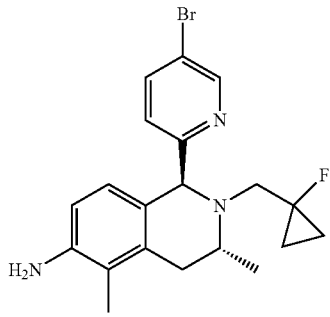 [SMILES: Cc1c(N)ccc2c1C[C@@H](C)N(CC1(F)CC1)[C@@H]2c1ccc(Br)cn1]

5-Bromopicolinaldehyde (507 mg, 2.72 mmol) was added to a stirred solution of (R)-3-(2-(((1-fluorocyclopropyl)methyl)amino)propyl)-2-methylaniline (322 mg, 1.36 mmol) in acetic acid (7028 μL) and water (143 μL). The resulting mixture was heated to 90° C. and stirred at this temperature for 5 hours. The mixture was concentrated and dissolved in EtOAC (50 mL) and saturated NaHCO$_3$ (25 mL). The aqueous layer was extracted with EtOAc (2×50 mL). The combined organics were concentrated under reduced pressure. The residue was dissolved in DCM (20 mL) and 1M HCl (20 mL). The mixture was stirred vigorously for 30 minutes. The layers were separated and the the aqueous layer was washed with DCM (20 mL). The aqueous layer was basified to >pH 10 with solid NaOH. The solution was extracted with DCM (3×25 mL). The combined organics were dried (phase separator cartridge) and concentrated to give the crude product. The crude product was purified by flash silica chromatography, elution gradient 0 to 60% EtOAc in heptane. Pure fractions were evaporated to dryness to afford (1S,3R)-1-(5-bromopyridin-2-yl)-2-((1-fluorocyclopropyl)methyl)-3,5-dimethyl-1,2,3,4-tetrahydroisoquinolin-6-amine (217 mg, 39%) as a yellow gum. $^1$H NMR (500 MHz, CDCl$_3$, 27° C.) 0.33-0.47 (1H, m), 0.49-0.6 (1H, m), 0.89-1.01 (2H, m), 1.04 (3H, d), 2.06 (3H, s), 2.55-2.64 (2H, m), 2.92-3.04 (2H, m), 3.51 (2H, s), 3.65-3.72 (1H, m), 4.88 (1H, s), 6.45 (1H, d), 6.58 (1H, d), 7.31 (1H, dd), 7.66 (1H, dd), 8.54 (1H, dd). m/z: ES+ [M+H]+ 404.

Preparation of (6S,8R)-6-(5-bromopyridin-2-yl)-7-((1-fluorocyclopropyl)methyl)-8-methyl-6,7,8,9-tetrahydro-3H-pyrazolo[4,3-f]isoquinoline

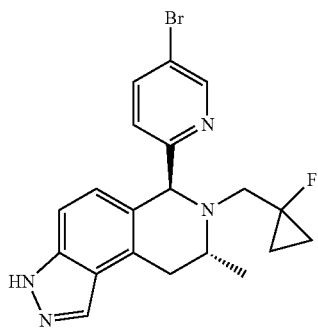 [SMILES: C[C@@H]1Cc2c(ccc3[nH]ncc23)[C@@H](c2ccc(Br)cn2)N1CC1(F)CC1]

(1S,3R)-1-(5-Bromopyridin-2-yl)-2-((1-fluorocyclopropyl)methyl)-3,5-dimethyl-1,2,3,4-tetrahydroisoquinolin-6-amine (295 mg, 0.73 mmol) in propionic acid (8291 μL) was cooled to −20° C. Sodium nitrite (50.3 mg, 0.73 mmol) in water (829 μL) was added dropwise over 2-3 minutes. The reaction mixture was stirred at −20° C. for 45 minutes. The reaction mixture was diluted with ice-cold EtOAc (30 mL). The reaction mixture was poured into saturated NaHCO$_3$ (40 mL). The mixture was stirred vigorously for 5 minutes. The layers were separated and the organic layer was washed with saturated NaHCO$_3$ (2×30 mL). The combined aqueous layers were back extracted with EtOAc (2×30 mL). The combined organic phases were dried (Na$_2$SO$_4$) and concentrated to give the crude product as brown oil. The crude material was purified by flash silica column chromatography eluting with 0-45% EtOAc in heptane to afford (6S,8R)-6-(5-bromopyridin-2-yl)-7-((1-fluorocyclopropyl)methyl)-8-methyl-6,7,8,9-tetrahydro-3H-pyrazolo[4,3-f]isoquinoline (107 mg, 35%) as an orange solid. $^1$H NMR (500 MHz, CDCl$_3$, 27° C.) 0.35-0.44 (1H, m), 0.51-0.63 (1H, m), 0.92-1.07 (2H, m), 1.09 (2H, d), 2.69 (1H, dd), 2.96 (1H, dd), 3.01-3.10 (1H, m), 3.33-3.49 (2H, m), 3.78-3.89 (1H, m), 5.03 (1H, s), 6.95 (1H, d), 7.19 (1H, d), 7.34-7.39 (1H, m), 7.68 (1H, dd), 8.07 (1H, d), 8.58 (1H, dd). m/z: ES+ [M+H]+ 415 and 417.

Preparation of (6S,8R)-6-(5-bromopyridin-2-yl)-7-((1-fluorocyclopropyl)methyl)-8-methyl-3-(tetrahydro-2H-pyran-2-yl)-6,7,8,9-tetrahydro-3H-pyrazolo[4,3-f]isoquinoline

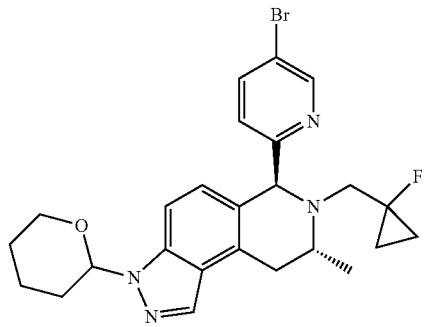 [SMILES: C[C@@H]1Cc2c(ccc3c2cnn3C2CCCCO2)[C@@H](c2ccc(Br)cn2)N1CC1(F)CC1]

3,4-Dihydro-2H-pyran (0.029 mL, 0.32 mmol) was added to a solution of (6S,8R)-6-(5-bromopyridin-2-yl)-7-((1-fluorocyclopropyl)methyl)-8-methyl-6,7,8,9-tetrahydro-3H-pyrazolo[4,3-f]isoquinoline (107 mg, 0.26 mmol) and 4-methylbenzenesulfonic acid hydrate (9.80 mg, 0.05 mmol) in DCM (2 mL) and the reaction was heated to 45° C. for 3 hours. Further 3,4-dihydro-2H-pyran (0.235 mL, 2.58 mmol) and 4-methylbenzenesulfonic acid hydrate (49.0 mg, 0.26 mmol) were added and the mixture was heated at 45° C. for 16 hours. The reaction was diluted with DCM and washed with saturated NaHCO$_3$ solution. The organic phase was dried and evaporated, then the crude was passed through a plug of silica (1:1 EtOAc/heptane). The filtrate was evaporated to afford (6S,8R)-6-(5-bromopyridin-2-yl)-7-((1-fluorocyclopropyl)methyl)-8-methyl-3-(tetrahydro-2H-pyran-2-yl)-6,7,8,9-tetrahydro-3H-pyrazolo[4,3-f]isoquinoline as a brown oil that was used without further purification. m/z: ES+ [M+H]+ 499.

Example 4

N-(4-((6S,8R)-7-(2-fluoro-3-methoxy-2-methylpropyl)-8-methyl-6,7,8,9-tetrahydro-3H-pyrazolo[4,3-f]isoquinolin-6-yl)-3-methoxyphenyl)-1-(3-fluoropropyl)azetidin-3-amine (Diastereoisomeric Mixture)

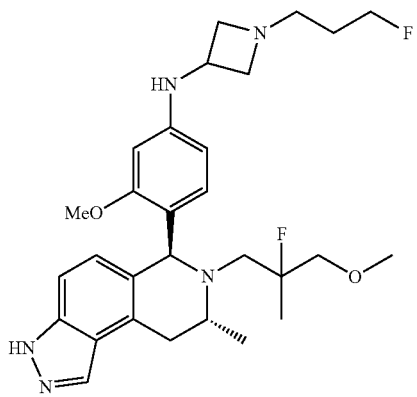 [SMILES: COCC(C)(F)CN1[C@H](c2ccc(NC3CN(CCCF)C3)cc2OC)c2ccc3[nH]ncc3c2C[C@H]1C]

1-(3-Fluoropropyl)azetidin-3-amine (50 mg, 0.37 mmol), a mixture of (6S,8R)-6-(4-bromo-2-methoxyphenyl)-7-(2-fluoro-3-methoxy-2-methylpropyl)-8-methyl-3-(tetrahydro-2H-pyran-2-yl)-6,7,8,9-tetrahydro-3H-pyrazolo[4,3-f]isoquinoline and (6S,8R)-6-(4-bromo-2-methoxyphenyl)-7-(2-fluoro-3-methoxy-2-methylpropyl)-8-methyl-2-(tetrahydro-2H-pyran-2-yl)-6,7,8,9-tetrahydro-2H-pyrazolo[4,3-f]isoquinoline (140 mg, 0.25 mmol), cesium carbonate (163 mg, 0.50 mmol) and [(2-di-cyclohexylphosphino-3,6-dimethoxy-2',4',6'-triisopropyl-1,1'-biphenyl)-2-(2'-amino-1,1'-biphenyl)]palladium(II) methanesulfonate (BrettPhos Pd G3) (23 mg, 0.02 mmol) were suspended in 1,4-dioxane (2 mL) and sealed into a microwave tube. The reaction was heated to 100° C. for 4 hours under microwave irradiation. The reaction mixture was diluted with DCM (25 mL) and washed with water (25 mL). The organic layer was evaporated. The residue was dissolved in DCM (3 mL) and TFA (1 mL). The reaction mixture was stirred at room temperature for 1 hour and then partitioned between DCM and 2M NaOH (20 mL each). The organic phase was evaporated and the crude product purified by preparative HPLC (Waters CSH C18 OBD column, 5µ silica, 30 mm diameter, 100 mm length), using decreasingly polar mixtures of water (containing 1% NH₃) and MeCN as eluents to afford N-(4-((6S,8R)-7-(2-fluoro-3-methoxy-2-methylpropyl)-8-methyl-6,7,8,9-tetrahydro-3H-pyrazolo[4,3-f]isoquinolin-6-yl)-3-methoxyphenyl)-1-(3-fluoropropyl)azetidin-3-amine (26.0 mg, 20%) as a gum as a mixture of diastereoisomers. $^1$H NMR (500 MHz, DMSO-$d_6$, 27° C.) 0.94-0.99 (3H, m), 1.16-1.24 (3H, m), 1.64 (2H, dq), 2.39-2.47 (3H, m), 2.70 (2H, t), 2.74-2.84 (2H, m), 3.03-3.21 (2H, m), 3.24 (3H, d), 3.48 (2H, dd), 3.58-3.64 (2H, m), 3.79 (3H, d), 3.88-3.94 (1H, m), 4.44 (2H, dt), 5.17 (1H, d), 5.88 (1H, td), 5.97 (1H, dd), 6.16 (1H, d), 6.32-6.38 (1H, m), 6.63 (1H, t), 7.16 (1H, dd), 8.02 (1H, s), 12.91 (1H, s). $^{19}$F NMR (471 MHz, DMSO-$d_6$, 27° C.) −218.19, −149.21, −148.22. m/z: ES+ [M+H]+ 528.

The mixture of (6S,8R)-6-(4-bromo-2-methoxyphenyl)-7-(2-fluoro-3-methoxy-2-methylpropyl)-8-methyl-3-(tetrahydro-2H-pyran-2-yl)-6,7,8,9-tetrahydro-3H-pyrazolo[4,3-f]isoquinoline and (6S,8R)-6-(4-bromo-2-methoxyphenyl)-7-(2-fluoro-3-methoxy-2-methylpropyl)-8-methyl-2-(tetrahydro-2H-pyran-2-yl)-6,7,8,9-tetrahydro-2H-pyrazolo[4,3-f]isoquinoline were prepared as follows;

Preparation of a diastereoisomeric mixture of N—((R)-1-(3-bromo-2-methylphenyl)propan-2-yl)-2-fluoro-3-methoxy-2-methylpropan-1-amine

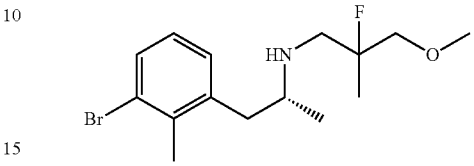

Trifluoromethanesulfonic anhydride (2.148 ml, 12.79 mmol) was added to ((2-fluoro-3-methoxy-2-methylpropoxy)methanetriyl)tribenzene (4.44 g, 12.18 mmol) dissolved in dichloromethane (50 mL) and the reaction mixture stirred at room temperature for 30 minutes. Triethylsilane (2.140 ml, 13.40 mmol) was then added and the mixture was stirred for a further 30 minutes. The reaction was concentrated to afford crude racemic 2-fluoro-3-methoxy-2-methylpropyl trifluoromethanesulfonate that was used directly in the next step without further purification.

DIPEA (5.36 mL, 30.68 mmol) was added to (R)-1-(3-bromo-2-methylphenyl)propan-2-amine (2.80 g, 12.3 mmol) and 2-fluoro-3-methoxy-2-methylpropyl trifluoromethanesulfonate (3.12 g, 12.3 mmol) in 1,4-dioxane (60 mL) at room temperature under nitrogen [exotherm]. The resulting mixture was stirred at 85° C. for 24 hours. The reaction mixture was allowed to cool and the reaction mixture evaporated. The crude product was purified by flash silica chromatography, elution gradient 0 to 60% EtOAc in heptane to afford N—((R)-1-(3-bromo-2-methylphenyl)propan-2-yl)-2-fluoro-3-methoxy-2-methylpropan-1-amine (2.480 g, 73%) as an oil as a mixture of diastereoisomers. $^1$H NMR (500 MHz, CDCl₃, 27° C.) 1.02-1.07 (3H, m), 1.31 (1.5H, d), 1.32 (1.5H, d), 2.41 (3H, s), 2.57-2.66 (1H, m), 2.68-2.90 (4H, m), 3.34 (1.5H, d), 3.35 (1.5H, d), 3.38-3.46 (2H, m), 6.96 (1H, t), 7.07 (1H, d), 7.42 (1H, d). NH not seen. $^{19}$F NMR (471 MHz, CDCl₃, 27° C.) −157.94, −157.53. m/z: ES+ [M+H]+ 332/334.

Preparation of a diastereoisomeric mixture of 3-((R)-2-((2-fluoro-3-methoxy-2-methylpropyl)amino)propyl)-2-methylaniline

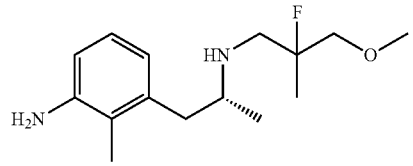 [SMILES: COCC(C)(F)CN[C@H](C)Cc1cccc(N)c1C]

Tris(dibenzylideneacetone)dipalladium(0) (0.205 g, 0.22 mmol) and (±)-2,2'-bis(diphenylphosphino)-1,1'-binaphthalene (0.279 g, 0.45 mmol) were added to a suspension of a diastereoisomeric mixture of N—((R)-1-(3-bromo-2-methylphenyl)propan-2-yl)-2-fluoro-3-methoxy-2-methylpropan-1-amine (2.48 g, 7.46 mmol), benzophenone imine (1.487 g, 8.21 mmol) and sodium tert-butoxide (1.076 g, 11.20 mmol) in degassed toluene (30 mL) and the reaction was heated to 90° C. for 3 hours. After cooling, the toluene was evaporated. The residue was dissolved in DCM (250 mL) and washed with water (250 mL). The aqueous was extracted with DCM (100 mL) and the combined organics were concentrated to approximately 50 mL. 2 M HCl solution (50 mL) was added and the biphasic mixture was stirred vigorously for 30 minutes. The layers were separated and the aqueous phase was extracted with DCM. The aqueous phase was basified with 2 M aqueous NaOH. This was extracted with DCM (2×250 mL) and the combined DCM extracts were evaporated to give 3-((R)-2-((2-fluoro-3-methoxy-2-methylpropyl)amino)propyl)-2-methylaniline (2.00 g, 100%) as an oil as mixture of diastereoisomers. $^1$H NMR (500 MHz, CDCl$_3$, 27° C.) 1.04 (3H, d), 1.31 (1.5H, d), 1.32 (1.5H, d), 2.11 (3H, s), 2.53-2.60 (1H, m), 2.70-2.89 (4H, m), 3.35 (2H, d), 3.36 (1.5H, d), 3.43 (1.5H, dd), 3.58 (2H, s), 6.57 (1H, d), 6.61 (1H, d), 6.94 (1H, t), 7.58 (1H, s). $^{19}$F NMR (471 MHz, CDCl$_3$, 27° C.) −157.61, −157.30. m/z: ES+ [M+H]+ 269.

Preparation of a diastereoisomeric mixture of (1S, 3R)-1-(4-bromo-2-methoxyphenyl)-2-(2-fluoro-3-methoxy-2-methylpropyl)-3,5-dimethyl-1,2,3,4-tetrahydroisoquinolin-6-amine

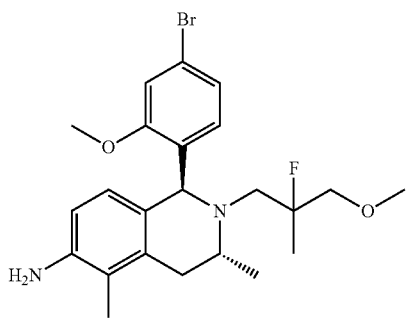 [SMILES: COCC(C)(F)CN1[C@H](c2ccc(Br)cc2OC)c2ccc(N)c(C)c2C[C@H]1C]

A diastereoisomeric mixture of 3-((2R)-2-((2-Fluoro-3-methoxy-2-methylpropyl)amino)propyl)-2-methylaniline (2.00 g, 7.45 mmol) and 4-bromo-2-methoxybenzaldehyde (3.37 g, 15.6 mmol) were heated in acetic acid (30 mL) and water (0.671 mL, 37.3 mmol) to 70° C. overnight. After cooling, the acetic acid was evaporated. The residue was dissolved in EtOAc (40 mL) and 2N HCl solution (40 mL) was added. The biphasic mixture was stirred for 30 minutes, then the layers were separated. The organic phase was extracted with water, then the combined aqueous phases were basified by addition of 2N NaOH solution and extracted with DCM (2×200 mL). The combined DCM layers were evaporated and the crude product was purified by flash silica chromatography, elution gradient 0 to 50% EtOAc in heptane to afford first (1S,3R)-1-(4-bromo-2-methoxyphenyl)-2-(2-fluoro-3-methoxy-2-methylpropyl)-3,5-dimethyl-1,2,3,4-tetrahydroisoquinolin-6-amine (0.354 g, 10%) as a single diastereoisomer. $^1$H NMR (500 MHz, DMSO-d$_6$, 27° C.) 0.91 (3H, d), 1.22 (3H, d), 1.94 (3H, s), 2.26-2.40 (2H, m), 2.65-2.78 (2H, m), 3.16-3.25 (4H, m), 3.42 (1H, dd), 3.85 (3H, s), 4.61 (2H, s), 5.10 (1H, s), 6.24 (1H, d), 6.37 (1H, d), 6.61 (1H, d), 6.95 (1H, dd), 7.15 (1H, d). One proton partially obscured by water. $^{19}$F NMR (471 MHz, DMSO-d$_6$, 27° C.) −149.65. m/z: ES+ [M+H]+ 465/467. Followed by fractions containing a mixture of diastereoisomers of (1S,3R)-1-(4-bromo-2-methoxyphenyl)-2-(2-fluoro-3-methoxy-2-methylpropyl)-3,5-dimethyl-1,2,3,4-tetrahydroisoquinolin-6-amine (1.700 g, 49%) $^{19}$F NMR (471 MHz, DMSO-d$_6$, 27° C.) −149.65, −148.78. m/z: ES+ [M+H]+ 465/467. Followed by fractions containing the second diastereoisomer of (1S,3R)-1-(4-bromo-2-methoxyphenyl)-2-(2-fluoro-3-methoxy-2-methylpropyl)-3,5-dimethyl-1,2,3,4-tetrahydroisoquinolin-6-amine (0.274 g, 8%) as a single diastereoisomer. $^1$H NMR (500 MHz, DMSO-d$_6$, 27° C.) 0.91 (3H, d), 1.16 (3H, d), 1.93 (3H, s), 2.26-2.4 (2H, m), 2.63-2.74 (2H, m), 3.23 (3H, s), 3.35 (1H, dd), 3.47 (1H, dd), 3.85 (3H, s), 4.60 (2H, s), 5.09 (1H, s), 6.24 (1H, d), 6.37 (1H, d), 6.61 (1H, d), 6.93 (1H, dd), 7.15 (1H, d). One proton obscured by water. $^{19}$F NMR (471 MHz, DMSO-d$_6$, 27° C.) −148.78. m/z: ES+ [M+H]+ 465/467. All as gums.

Preparation of a diastereoisomeric mixture of (6S, 8R)-6-(4-bromo-2-methoxyphenyl)-7-(2-fluoro-3-methoxy-2-methylpropyl)-8-methyl-6,7,8,9-tetrahydro-3H-pyrazolo[4,3-f]isoquinoline

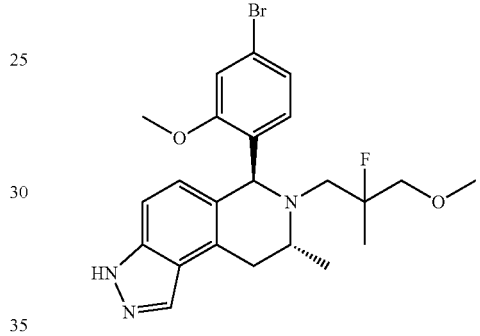

A solution of sodium nitrite (0.277 g, 4.02 mmol) in water (1.0 mL) was added to a solution of a diastereoisomeric mixture of (1S,3R)-1-(4-bromo-2-methoxyphenyl)-2-(2-fluoro-3-methoxy-2-methylpropyl)-3,5-dimethyl-1,2,3,4-tetrahydroisoquinolin-6-amine (1.70 g, 3.65 mmol) in propionic acid (15 mL) at −10° C. The reaction was stirred for 1 hour, then ice-cold EtOAc (20 mL) was added. The reaction was quenched by addition of aqueous NaHCO$_3$ solution (30 mL) and stirred for 15 minutes, before being allowed to warm to room temperature. The organic phase was washed with aqueous NaHCO$_3$ solution (30 mL) and brine (20 mL), dried (Na$_2$SO$_4$), filtered and evaporated. The crude product was purified by flash silica chromatography, elution gradient 0 to 50% EtOAc in heptane to afford (6S,8R)-6-(4-bromo-2-methoxyphenyl)-7-(2-fluoro-3-methoxy-2-methylpropyl)-8-methyl-6,7,8,9-tetrahydro-3H-pyrazolo[4,3-f]isoquinoline (0.950 g, 55%) as a brown solid as a mixture of diastereoisomers. $^1$H NMR (500 MHz, DMSO-d$_6$, 27° C.) 0.95-0.97 (3H, m), 1.14-1.23 (3H, m), 2.31-2.40 (1H, m), 2.78-2.88 (2H, m), 3.11-3.21 (2.5H, s), 3.23 (1.5H, s), 3.32-3.38 (1H, m), 3.40-3.52 (2H, m), 3.88 (1.5H, s), 3.89 (1.5H, s), 5.28 (1H, s), 6.59-6.69 (2H, m), 6.92-6.96 (1H, m), 7.16-7.22 (2H, m), 8.05 (1H, s), 12.96 (1H, s). $^{19}$F NMR (471 MHz, DMSO-d$_6$, 27° C.) −149.65, −148.68. m/z: ES+ [M+H]+ 476/478.

Preparation of a mixture of (6S,8R)-6-(4-bromo-2-methoxyphenyl)-7-(2-fluoro-3-methoxy-2-methylpropyl)-8-methyl-3-(tetrahydro-2H-pyran-2-yl)-6,7,8,9-tetrahydro-3H-pyrazolo[4,3-f]isoquinoline and (6S,8R)-6-(4-bromo-2-methoxyphenyl)-7-(2-fluoro-3-methoxy-2-methylpropyl)-8-methyl-2-(tetrahydro-2H-pyran-2-yl)-6,7,8,9-tetrahydro-2H-pyrazolo[4,3-f]isoquinoline

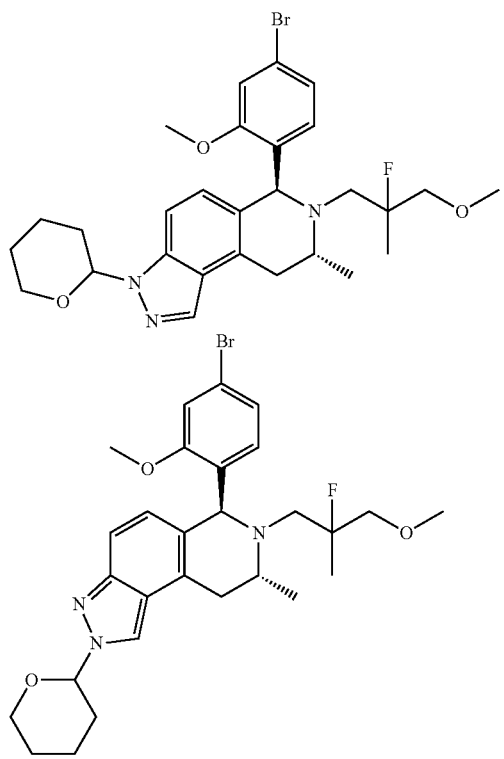

4-Methylbenzenesulfonic acid hydrate (0.038 g, 0.20 mmol) was added to a solution of a diastereoisomeric mixture of (6S,8R)-6-(4-bromo-2-methoxyphenyl)-7-(2-fluoro-3-methoxy-2-methylpropyl)-8-methyl-6,7,8,9-tetrahydro-3H-pyrazolo[4,3-f]isoquinoline (0.950 g, 1.99 mmol) and 3,4-dihydro-2H-pyran (0.546 mL, 5.98 mmol) in DCM (30 mL) and the mixture was heated at 40° C. overnight. More 3,4-dihydro-2H-pyran (0.546 mL, 5.98 mmol) and 4-methylbenzenesulfonic acid hydrate (0.038 g, 0.20 mmol) were added. Heating continued for 7 hours. Further portions of 3,4-dihydro-2H-pyran (0.546 mL, 5.98 mmol) and 4-methylbenzenesulfonic acid hydrate (0.038 g, 0.20 mmol) were added and the reaction heated overnight. The reaction mixture was diluted with DCM (50 mL) and washed with saturated aqueous NaHCO₃ (50 mL). The organic phase was evaporated to a dark brown oil and the crude product was purified by flash silica chromatography, elution gradient 0 to 35% EtOAc in heptane to afford a mixture of (6S,8R)-6-(4-bromo-2-methoxyphenyl)-7-(2-fluoro-3-methoxy-2-methylpropyl)-8-methyl-3-(tetrahydro-2H-pyran-2-yl)-6,7,8,9-tetrahydro-3H-pyrazolo[4,3-f]isoquinoline and (6S,8R)-6-(4-bromo-2-methoxyphenyl)-7-(2-fluoro-3-methoxy-2-methylpropyl)-8-methyl-2-(tetrahydro-2H-pyran-2-yl)-6,7,8,9-tetrahydro-2H-pyrazolo[4,3-f]isoquinoline (0.960 g, 86%) as a foam, as a mixture of diastereoisomers. $^1$H NMR (471 MHz, DMSO-d₆, 27° C.) −149.79, −149.74, −149.69, −149.65, −148.77, −148.73, −148.69, −148.66. m/z: ES+ [M+H]+ 560/562.

Example 5

3-((6S,8R)-6-(2,6-difluoro-4-((1-(3-fluoropropyl)azetidin-3-yl)amino)phenyl)-8-methyl-3,6,8,9-tetrahydro-7H-pyrazolo[4,3-f]isoquinolin-7-yl)-2,2-difluoropropan-1-ol TBAF in THF (1 M; 160 µL, 0.16 mmol) was added to a solution of N-(4-((6S,8R)-7-(3-((tert-butyldiphenylsilyl)oxy)-2,2-difluoropropyl)-8-methyl-6,7,8,9-tetrahydro-3H-pyrazolo[4,3-f]isoquinolin-6-yl)-3,5-difluorophenyl)-1-(3-fluoropropyl)azetidin-3-amine (80 mg, 0.10 mmol) in THF (0.5 mL) at room temperature. After 4 hours, the reaction was concentrated under reduced pressure, and the resulting residue was purified by flash silica chromatography, elution gradient 30 to 90% (10% MeOH in DCM containing 1% NH₄OH) in DCM. Product fractions were concentrated under reduced pressure, and the resulting residue was repurified using the same conditions. Product fractions were again concentrated under reduced pressure, and the resulting residue was purified by preparative HPLC (Waters XBridge Prep C18 OBD column, 5µ silica, 19 mm diameter, 100 mm length) using decreasingly polar mixtures of water (containing 0.2% ammonium hydroxide) and MeCN as eluents (40 to 70% over 7 min) to afford 3-((6S,8R)-6-(2,6-difluoro-4-((1-(3-fluoropropyl)azetidin-3-yl)amino)phenyl)-8-methyl-3,6,8,9-tetrahydro-7H-pyrazolo[4,3-f]isoquinolin-7-yl)-2,2-difluoropropan-1-ol (17 mg, 31%) as white solid. $^1$H NMR (500 MHz, DMSO-d₆, 27° C.) 1.02 (3H, d), 1.59-1.69 (2H, m), 2.44 (2H, t), 2.56-2.67 (1H, m), 2.72 (2H, t), 2.88 (1H, dd), 3.02-3.13 (1H, m), 3.17 (1H, dd), 3.49-3.56 (1H, m), 3.57-3.69 (3H, m), 3.91 (1H, tdt), 4.44 (2H, dt), 5.08 (1H, s), 5.25 (1H, br. s), 6.07 (2H, d), 6.64 (1H, d), 6.69 (1H, d), 7.20 (1H, d), 8.04 (1H, s), 12.95 (1H, br. s). One H not observed. m/z: ES+ [M+H]+ 524.

The N-(4-((6S,8R)-7-(3-((tert-butyldiphenylsilyl)oxy)-2,2-difluoropropyl)-8-methyl-6,7,8,9-tetrahydro-3H-pyrazolo[4,3-f]isoquinolin-6-yl)-3,5-difluorophenyl)-1-(3-fluoropropyl)azetidin-3-amine was prepared as follows:

Preparation 3-((tert-butyldiphenylsilyl)oxy)-2,2-difluoropropan-1-ol

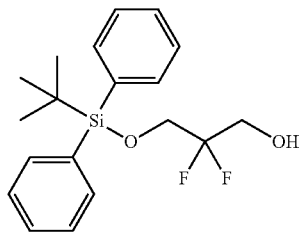 [SMILES: CC(C)(C)[Si](OCC(F)(F)CO)(c1ccccc1)c1ccccc1]

NaH in mineral oil (60 wt %; 343 mg, 8.58 mmol) was added in one portion to a stirred solution of 2,2-difluoropropane-1,3-diol (874 mg, 7.80 mmol) in THF (32 mL) at 0° C. The reaction was allowed to warm to room temperature, and was stirred at room temperature for 2 h. The reaction mixture was again cooled to 0° C., and tert-butyldiphenylchlorosilane (2.0 mL, 7.8 mmol) was added dropwise via syringe. The reaction mixture was allowed to warm to room temperature over 1 hour and was then quenched with water and extracted with EtOAc. The organic layer was dried with $Na_2SO_4$, filtered, and the filtrate was concentrated under reduced pressure. The resulting residue was purified by flash silica chromatography, eluting with isocratic 5% ethyl acetate in hexanes, to afford 3-((tert-butyldiphenylsilyl)oxy)-2,2-difluoropropan-1-ol (1.94, 71%) as a colorless oil. $^1$H NMR (300 MHz, CHLOROFORM-d, 27° C.) δ ppm 1.03-1.14 (9H, s), 3.87-3.93 (4H, m), 7.37-7.44 (6H, m), 7.64-7.66 (4H, m).

Preparation of 3-((tert-butyldiphenylsilyl)oxy)-2,2-difluoropropyl trifluoromethane sulfonate

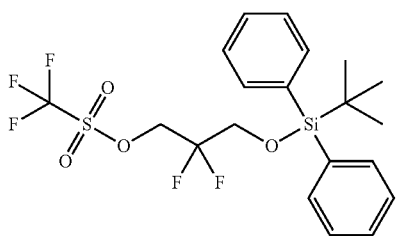 [SMILES: CC(C)(C)[Si](OCC(F)(F)COS(=O)(=O)C(F)(F)F)(c1ccccc1)c1ccccc1]

A solution of 3-((tert-butyldiphenylsilyl)oxy)-2,2-difluoropropan-1-ol (1.94 g, 5.55 mmol) and 2,6-dimethylpyridine (1.94 ml, 16.6 mmol) in DCM (18 ml) was cooled to −10° C. (salt/ice bath). Trifluoromethanesulfonic anhydride (1.88 ml, 11.1 mmol) was added slowly dropwise over 10 minutes. The reaction was maintained under these conditions for 2 hours. The reaction was then washed with water, aqueous HCl (1N; 100 mL), and saturated aqueous sodium bicarbonate. The organic layer was dried over $MgSO_4$, filtered, and concentrated under reduced pressure to afford 3-((tert-butyldiphenylsilyl)oxy)-2,2-difluoropropyl trifluoromethanesulfonate (2.68 g, 100%) as a red oil. $^1$H NMR (300 MHz, CHLOROFORM-d, 27° C.) 1.03-1.14 (9H, s), 3.90 (2H, t), 4.76 (2H, t), 7.39-7.56 (6H, m), 7.59-7.75 (4H, m).

Preparation of 3-((tert-butyldiphenylsilyl)oxy)-2,2-difluoropropyl trifluoromethane sulfonate

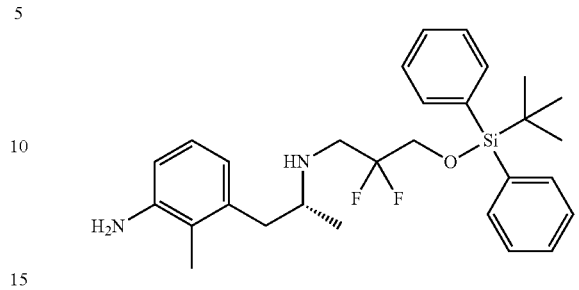

3-((Tert-butyldiphenylsilyl)oxy)-2,2-difluoropropyl trifluoromethanesulfonate (1.92 g, 3.98 mmol) was added to a solution of (R)-3-(2-aminopropyl)-2-methylaniline (0.784 g, 4.77 mmol) and DIPEA (1.031 ml, 5.97 mmol) in 1,4-dioxane (15 ml). The reaction was heated at 85° C. for 18 hours. After cooling, the reaction was diluted with DCM and washed with water. The aqueous layer was extracted with DCM, and the combined organic layers were dried over magnesium sulfate, filtered, and concentrated under reduced pressure. The resulting residue was purified by flash silica chromatography, elution gradient 0 to 4% methanolic ammonia in DCM. Pure fractions were concentrated to dryness to afford (R)-3-(2-((3-((tert-butyldiphenylsilyl)oxy)-2,2-difluoropropyl)amino)propyl)-2-methylaniline (1.97 g, 100%) as a yellow oil. $^1$H NMR (300 MHz, METHANOL-$d_4$, 27° C.) δ ppm 0.97-1.12 (12H, m), 2.10 (3H, s), 2.53-2.63 (1H, m), 2.74-2.84 (1H, m), 2.86-2.99 (1H, m), 3.00-3.19 (2H, m), 3.80 (2H, td), 6.53 (1H, d), 6.63 (1H, d), 6.86 (1H, t), 7.38-7.50 (6H, m), 7.64-7.72 (4H, m). m/z: ES+ [M+H]+ 497.

Preparation (1S,3R)-1-(4-bromo-2,6-difluorophenyl)-2-(3-((tert-butyldiphenylsilyl)oxy)-2,2-difluoropropyl)-3,5-dimethyl-1,2,3,4-tetrahydroisoquinolin-6-amine

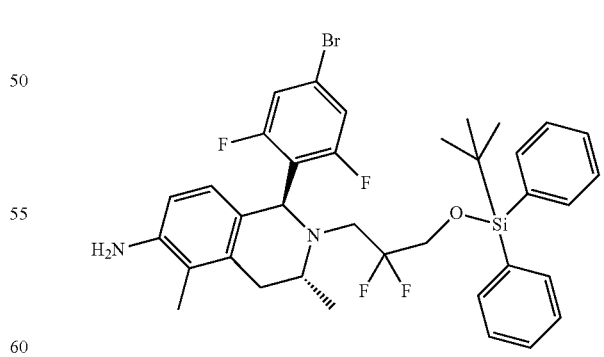

4-Bromo-2,6-difluorobenzaldehyde (1.55 g, 7.02 mmol) was added to a solution of (R)-3-(2-((3-((tert-butyldiphenylsilyl)oxy)-2,2-difluoropropyl)amino)propyl)-2-methylaniline (1.74 g, 3.51 mmol) in acetic acid (17 mL) and water (0.32 mL, 18 mmol), and the reaction was heated at 80° C.

overnight. The reaction was concentrated under reduced pressure, and the residue was partitioned between EtOAc and saturated aqueous NaHCO$_3$. The organic layer was concentrated under reduced pressure and purified by flash silica chromatography, elution gradient 20 to 80% ethyl acetate in hexanes, to afford (1S,3R)-1-(4-bromo-2,6-difluorophenyl)-2-(3-((tert-butyldiphenylsilyl)oxy)-2,2-difluoropropyl)-3,5-dimethyl-1,2,3,4-tetrahydroisoquinolin-6-amine (1.33 g, 54.5%) as a solid.

$^1$H NMR (300 MHz, CHLOROFORM-d, 27° C.) δ ppm 1.04-1.11 (12H, m), 2.25-2.38 (3H, m), 2.53-2.65 (1H, m), 2.73 (1H, q), 2.86-3.03 (1H, m), 3.15-3.38 (1H, m), 3.52-3.71 (2H, m), 3.85-4.01 (1H, m), 5.31 (1H, d), 6.58-6.64 (1H, m), 6.67-6.73 (1H, m), 6.88-6.95 (2H, m), 7.18-7.24 (2H, m), 7.37-7.50 (6H, m), 7.60-7.70 (4H, m). m/z: ES+ [M+H]+ 699.

Preparation of (6S,8R)-6-(4-bromo-2,6-difluorophenyl)-7-(3-((tert-butyldiphenylsilyl)oxy)-2,2-difluoropropyl)-8-methyl-6,7,8,9-tetrahydro-3H-pyrazolo[4,3-f]isoquinoline

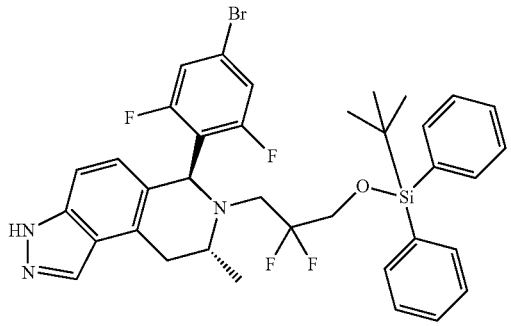 [SMILES: C[C@@H]1Cc2c(ccc3[nH]ncc23)[C@@H](c2c(F)cc(Br)cc2F)N1CC(F)(F)CO[Si](c1ccccc1)(c1ccccc1)C(C)(C)C]

Sodium nitrite (0.130 g, 1.89 mmol) in water (0.900 mL) was added dropwise to a solution of (1S,3R)-1-(4-bromo-2,6-difluorophenyl)-2-(3-((tert-butyldiphenylsilyl)oxy)-2,2-difluoropropyl)-3,5-dimethyl-1,2,3,4-tetrahydroisoquinolin-6-amine (1.32 g, 1.89 mmol) in propionic acid (9 mL) at −8° C. (salt/ice bath) and stirred under these conditions for 20 minutes. The reaction was diluted with ethyl acetate (20 mL, precooled to −10° C.) and quenched with slow addition of saturated aqueous NaHCO$_3$ (30 mL, precooled to −10° C.) over 15 min at 0° C. The mixture was allowed to warm to room temperature and maintained under these conditions for 18 hours. The organic layer was separated, and the aqueous layer was extracted with EtOAc. The combined organic layers were washed with saturated aqueous NaHCO$_3$ and water, dried over sodium sulfate, filtered, and concentrated under reduced pressure. The resulting residue was purified by flash silica chromatography, elution gradient 15 to 50% ethyl acetate in hexanes, to afford (6S,8R)-6-(4-bromo-2,6-difluorophenyl)-7-(3-((tert-butyldiphenylsilyl)oxy)-2,2-difluoropropyl)-8-methyl-6,7,8,9-tetrahydro-3H-pyrazolo[4,3-f]isoquinoline (0.520 g, 38.8%) as light brown solid. $^1$H NMR (300 MHz, CHLOROFORM-d, 27° C.) δ ppm 1.07 (9H, s), 1.12 (3H, d), 2.72-2.92 (2H, m), 3.21-3.39 (2H, m), 3.51-3.66 (1H, m), 3.67-3.79 (1H, m), 3.86-4.00 (1H, m), 5.37 (1H, s), 6.81 (1H, d), 6.87-6.98 (2H, m), 7.25-7.29 (1H, m), 7.35-7.50 (6H, m), 7.59-7.70 (4H, m), 8.14 (1H, s). Indole NH not observed. m/z: ES+ [M+H]+ 710.

Preparation of (6S,8R)-6-(4-bromo-2,6-difluorophenyl)-7-(3-((tert-butyldiphenylsilyl)oxy)-2,2-difluoropropyl)-8-methyl-3-(tetrahydro-2H-pyran-2-yl)-6,7,8,9-tetrahydro-3H-pyrazolo[4,3-f]isoquinoline

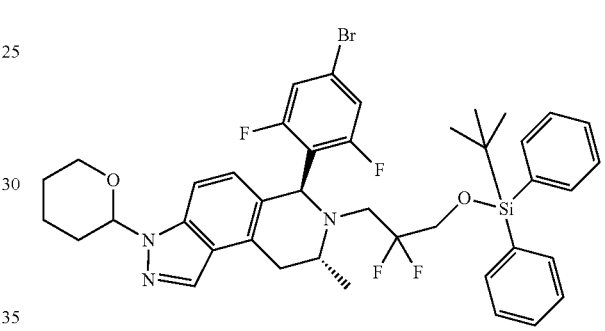

3,4-Dihydro-2H-pyran (95 μL, 1.04 mmol) was added to a solution of (6S,8R)-6-(4-bromo-2,6-difluorophenyl)-7-(3-((tert-butyldiphenylsilyl)oxy)-2,2-difluoropropyl)-8-methyl-6,7,8,9-tetrahydro-3H-pyrazolo[4,3-f]isoquinoline (492 mg, 0.69 mmol) and para-toluenesulfonic acid monohydrate (13 mg, 0.07 mmol) in DCM (3.5 mL), and the reaction was heated under reflux conditions for 6 hours. After cooling, the reaction was washed with saturated aqueous NaHCO$_3$, dried over Na$_2$SO$_4$, filtered, and concentrated under reduced pressure. The residue was purified by flash silica chromatography, elution gradient 10 to 30% ethyl acetate in hexanes, to afford (6S,8R)-6-(4-bromo-2,6-difluorophenyl)-7-(3-((tert-butyldiphenylsilyl)oxy)-2,2-difluoropropyl)-8-methyl-3-(tetrahydro-2H-pyran-2-yl)-6,7,8,9-tetrahydro-3H-pyrazolo[4,3-f]isoquinoline (474 mg, 86%) as a light brown gummy solid. $^1$H NMR (300 MHz, CHLOROFORM-d, 27° C.) 1.06 (9H, s), 1.19-1.25 (3H, m), 1.74-1.84 (3H, m), 2.09-2.20 (2H, m), 2.49-2.67 (1H, m), 2.84-2.96 (2H, m), 3.27-3.45 (2H, m), 3.61-3.87 (3H, m), 4.04 (2H, d), 5.52 (1H, s), 5.66-5.72 (1H, m), 6.78 (1H, d), 6.94 (2H, d), 7.32 (1H, d), 7.36-7.50 (6H, m), 7.60-7.68 (4H, m), 8.04 (1H, s).

Preparation of tert-butyl 3-((4-((6S,8R)-7-(3-((tert-butyldiphenylsilyl)oxy)-2,2-difluoropropyl)-8-methyl-3-(tetrahydro-2H-pyran-2-yl)-6,7,8,9-tetrahydro-3H-pyrazolo[4,3-f]isoquinolin-6-yl)-3,5-difluorophenyl)amino)azetidine-1-carboxylate

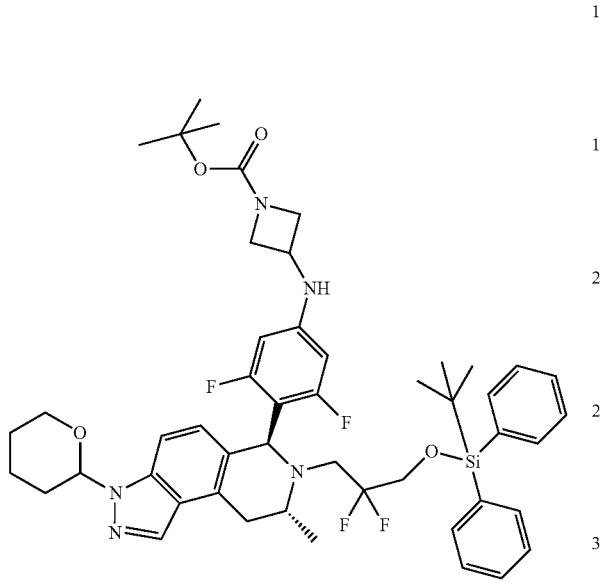

A degassed mixture of (6S,8R)-6-(4-bromo-2,6-difluorophenyl)-7-(3-((tert-butyldiphenylsilyl)oxy)-2,2-difluoropropyl)-8-methyl-3-(tetrahydro-2H-pyran-2-yl)-6,7,8,9-tetrahydro-3H-pyrazolo[4,3-f]isoquinoline (0.474 g, 0.600 mmol), tert-butyl 3-aminoazetidine-1-carboxylate (0.15 g, 0.89 mmol), Xantphos (0.069 g, 0.12 mmol), Pd$_2$(dba)$_3$ (0.06 g, 0.06 mmol), and cesium carbonate (0.389 g, 1.19 mmol) in dioxane (3 mL) was heated at 115° C. for 4 hours. The reaction was then concentrated under reduced pressure, and the resulting residue was adsorbed onto silica gel and purified by flash silica chromatography, elution gradient 5 to 50% ethyl acetate in hexanes, to afford tert-butyl 3-((4-((6S,8R)-7-(3-((tert-butyldiphenylsilyl)oxy)-2,2-difluoropropyl)-8-methyl-3-(tetrahydro-2H-pyran-2-yl)-6,7,8,9-tetrahydro-3H-pyrazolo[4,3-f]isoquinolin-6-yl)-3,5-difluorophenyl)amino)azetidine-1-carboxylate (0.377 g, 71.3%) as a solid. $^1$H NMR (300 MHz, CHLOROFORM-d, 27° C.) 1.06 (9H, s), 1.12 (3H, d), 1.46 (9H, s), 1.65-1.84 (3H, m), 2.07-2.23 (2H, m), 2.58 (1H, d), 2.75-2.91 (2H, m), 3.16-3.34 (2H, m), 3.52-3.78 (5H, m), 3.91-4.07 (3H, m), 4.19-4.29 (2H, m), 5.23-5.34 (1H, m), 5.67 (1H, dd), 5.81 (2H, d), 6.81 (1H, d), 7.25-7.29 (1H, m), 7.35-7.48 (6H, m), 7.65 (4H, ddd), 8.02 (1H, s). Aniline NH not observed. m/z: ES+ [M+H]+ 886.

Preparation of N-(4-((6S,8R)-7-(3-((tert-butyldiphenylsilyl)oxy)-2,2-difluoropropyl)-8-methyl-6,7,8,9-tetrahydro-3H-pyrazolo[4,3-f]isoquinolin-6-yl)-3,5-difluorophenyl)azetidin-3-amine

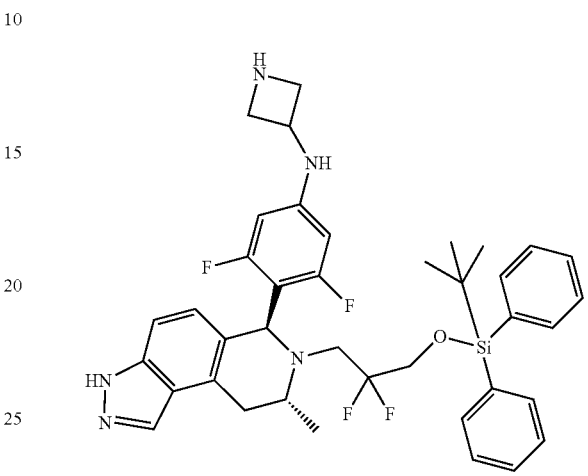

TFA (328 µL, 4.25 mmol) was added slowly to a solution of tert-butyl 3-((4-((6S,8R)-7-(3-((tert-butyldiphenylsilyl)oxy)-2,2-difluoropropyl)-8-methyl-3-(tetrahydro-2H-pyran-2-yl)-6,7,8,9-tetrahydro-3H-pyrazolo[4,3-f]isoquinolin 6 yl) 3,5-difluorophenyl)amino)azetidine-1-carboxylate (377 mg, 0.43 mmol) in DCM (2 mL) at 0° C. The reaction was allowed to warm to room temperature and was stirred under these conditions for 1 hour. The reaction was then concentrated under reduced pressure, and the resulting residue was partitioned between ethyl acetate and saturated aqueous NaHCO$_3$. The organic layer was dried over MgSO$_4$, filtered, and concentrated under reduced pressure. The resulting residue was purified by flash silica chromatography, elution gradient 30 to 70% (10% methanol in DCM containing 1% ammonium hydroxide) in DCM to afford N-(4-((6S,8R)-7-(3-((tert-butyldiphenylsilyl)oxy)-2,2-difluoropropyl)-8-methyl-6,7,8,9-tetrahydro-3H-pyrazolo[4,3-f]isoquinolin-6-yl)-3,5-difluorophenyl)azetidin-3-amine (166 mg, 55.6%) as pale solid. $^1$H NMR (300 MHz, CHLOROFORM-d, 27° C.) 0.96-1.20 (12H, m), 2.62-3.03 (2H, m), 3.10-3.42 (2H, m), 3.42-3.63 (3H, m), 3.63-3.80 (2H, m), 3.81-4.08 (3H, m), 4.15-4.28 (1H, m), 4.38 (1H, d), 5.23 (1H, s), 5.83 (2H, m), 6.80 (1H, m), 7.15 (1H, d), 7.32-7.53 (6H, m), 7.61-7.81 (4H, m), 8.06 (1H, s). Indazole NH not observed. m/z: ES+ [M+H]+ 702.

Preparation of N-(4-((6S,8R)-7-(3-((tert-butyldiphenylsilyl)oxy)-2,2-difluoropropyl)-8-methyl-6,7,8,9-tetrahydro-3H-pyrazolo[4,3-f]isoquinolin-6-yl)-3,5-difluorophenyl)-1-(3-fluoropropyl)azetidin-3-amine Example 6

N-(4-((6S,8R)-7-((1-fluorocyclopropyl)methyl)-8-methyl-6,7,8,9-tetrahydro-3H-pyrazolo[4,3-f]isoquinolin-6-yl)-3-methoxyphenyl)-1-(3-fluoropropyl)azetidin-3-amine

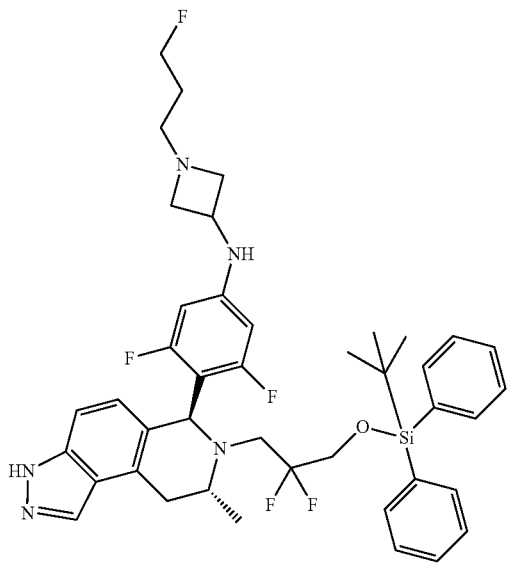 [SMILES: C[C@@H]1Cc2c(ccc3[nH]ncc23)[C@@H](c2c(F)cc(NC3CN(CCCF)C3)cc2F)N1CC(F)(F)CO[Si](c1ccccc1)(c1ccccc1)C(C)(C)C]

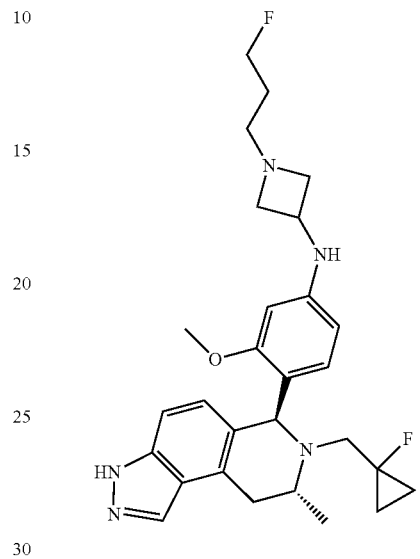

1-Fluoro-3-iodopropane (40.9 µL, 0.39 mmol) was added to a solution of N-(4-((6S,8R)-7-((1-fluorocyclopropyl)methyl)-8-methyl-6,7,8,9-tetrahydro-3H-pyrazolo[4,3-f]isoquinolin-6-yl)-3-methoxyphenyl)azetidin-3-amine (169 mg, 0.39 mmol) and DIPEA (203 µL, 1.16 mmol) in NMP (1.7 mL) at room temperature. After 18 hours, the reaction was concentrated under reduced pressure. The resulting residue was purified by reverse phase flash chromatography (C18), eluting with decreasingly polar mixtures of water (containing 0.2% ammonium hydroxide) and MeCN as eluents. Product fractions were combined and lyopholized to afford N-(4-((6S,8R)-7-((1-fluorocyclopropyl)methyl)-8-methyl-6,7,8,9-tetrahydro-3H-pyrazolo[4,3-f]isoquinolin-6-yl)-3-methoxyphenyl)-1-(3-fluoropropyl)azetidin-3-amine (75 mg, 39%) as clear residue. $^1$H NMR (500 MHz, DMSO-d$_6$, 27° C.) 0.39-0.46 (1H, m), 0.47-0.54 (1H, m), 0.77-0.85 (2H, m), 0.91 (3H, d), 1.51-1.64 (2H, m), 2.38 (2H, t), 2.54 (1H, dd), 2.63 (2H, q), 2.75-2.90 (2H, m), 3.14 (1H, dd), 3.52-3.64 (3H, m), 3.73 (3H, s), 3.79-3.88 (1H, m), 4.38 (2H, dt), 5.10 (1H, s), 5.82-5.87 (1H, m), 5.91 (1H, d), 6.09 (1H, d), 6.49 (1H, d), 6.57 (1H, d), 7.07 (1H, d), 7.94 (1H, s), 12.83 (1H, s). m/z: ES+ [M+H]+ 496.

1-Fluoro-3-iodopropane (40 mg, 0.21 mmol) was added to a solution of N-(4-((6S,8R)-7-(3-((tert-butyldiphenylsilyl)oxy)-2,2-difluoropropyl)-8-methyl-6,7,8,9-tetrahydro-3H-pyrazolo[4,3-f]isoquinolin-6-yl)-3,5-difluorophenyl)azetidin-3-amine (144 mg, 0.21 mmol) and DIPEA (107 µL, 0.62 mmol) in DMF (1 mL) at ambient temperature. The reaction was stirred at room temperature fo 3 hours and then diluted with EtOAc (40 mL) and washed with saturated aqueous sodium chloride (3×20 mL). The organic layers were dried over MgSO$_4$, filtered, and concentrated under reduced pressure. The resulting residue was purified by flash silica chromatography, elution gradient 15 to 30% (10% methanol in DCM containing 1% ammonium hydroxide) in DCM, to afford N-(4-((6S,8R)-7-(3-((tert-butyldiphenylsilyl)oxy)-2,2-difluoropropyl)-8-methyl-6,7,8,9-tetrahydro-3H-pyrazolo[4,3-f]isoquinolin-6-yl)-3,5-difluorophenyl)-1-(3-fluoropropyl)azetidin-3-amine (87 mg, 56%) as yellow solid. m/z: ES+ [M+H]+ 762.

The N-(4-((6S,8R)-7-((1-fluorocyclopropyl)methyl)-8-methyl-6,7,8,9-tetrahydro-3H-pyrazolo[4,3-f]isoquinolin-6-yl)-3-methoxyphenyl)azetidin-3-amine was prepared as follows.

Preparation of (1S,3R)-1-(4-bromo-2-methoxyphenyl)-2-((1-fluorocyclopropyl)methyl)-3,5-dimethyl-1,2,3,4-tetrahydroisoquinolin-6-amine

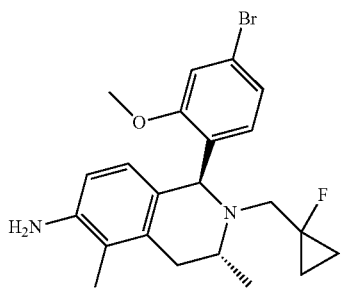 [SMILES: COc1cc(Br)ccc1[C@@H]1c2ccc(N)c(C)c2C[C@@H](C)N1CC1(F)CC1]

(R)-3-(2-(((1-Fluorocyclopropyl)methyl)amino)propyl)-2-methylaniline (451 mg, 1.91 mmol) and 4-bromo-2-methoxybenzaldehyde (410 mg, 1.91 mmol) in a mixture of water (172 mg, 9.54 mmol) and acetic acid (7.5 mL) were heated at 80° C. for 6 hours. The reaction was concentrated under reduced pressure, and the resulting residue was treated with aqueous HCl (1N; 18 mL). The mixture was stirred at 80° C. for 18 hours. The reaction was then cooled and saturated aqueous NaHCO₃ was added. The mixture was extracted with DCM, and the organic layer was concentrated under reduced pressure. The resulting residue was purified flash silica chromatography, elution gradient 5 to 35% ethyl acetate in hexanes, to afford (1S,3R)-1-(4-bromo-2-methoxyphenyl)-2-((1-fluorocyclopropyl)methyl)-3,5-dimethyl-1,2,3,4-tetrahydroisoquinolin-6-amine (591 mg, 71.5%) as a gummy film. ¹H NMR (300 MHz, DMSO-d₆, 27° C.) 0.42-0.61 (2H, m), 0.81-0.91 (2H, m), 0.93 (3H, d), 1.93 (3H, s), 2.43-2.48 (2H, m), 2.72-2.89 (2H, m), 3.48-3.57 (1H, m), 3.87 (3H, s), 4.57 (2H, s), 5.12 (1H, s), 6.24 (1H, d), 6.35 (1H, d), 6.82 (1H, d), 6.96 (1H, d), 7.16 (1H, d). m/z: ES+ [M+H]+ 433.

Preparation of (6S,8R)-6-(4-bromo-2-methoxyphenyl)-7-((1-fluorocyclopropyl)methyl)-8-methyl-6,7,8,9-tetrahydro-3H-pyrazolo[4,3-f]isoquinoline

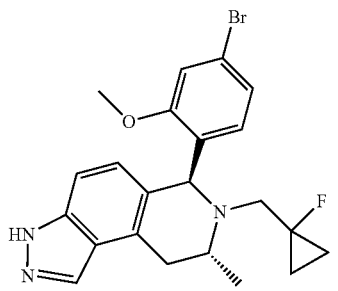 [SMILES: COc1cc(Br)ccc1[C@@H]1c2ccc3[nH]ncc3c2C[C@@H](C)N1CC1(F)CC1]

Acetic acid (0.392 ml, 6.84 mmol) was added to (1S,3R)-1-(4-bromo-2-methoxyphenyl)-2-((1-fluorocyclopropyl)methyl)-3,5-dimethyl-1,2,3,4-tetrahydroisoquinolin-6-amine (0.593 g, 1.37 mmol) in CHCl₃ (5 mL), and the resulting solution was cooled to 0° C. Isopentyl nitrite (0.321 g, 2.74 mmol) in CHCl₃ (1 mL) was added to the reaction dropwise, and the reaction was stirred at 0° C. for another 2 hours. Then saturated aqueous NaHCO₃ (1 g in 20 mL of water) was added slowly. The reaction was stirred at 0° C. for 10 minutes, and then the layers were separated. The organic layer was purified by flash column chromatography, elutiong gradient 5 to 35% ethyl acetate in hexanes, to afford (6S,8R)-6-(4-bromo-2-methoxyphenyl)-7-((1-fluorocyclopropyl)methyl)-8-methyl-6,7,8,9-tetrahydro-3H-pyrazolo[4,3-f]isoquinoline (0.299 g, 49.2%) as light brown solid. ¹H NMR (300 MHz, DMSO-d₆, 27° C.) δ ppm 0.39-0.65 (2H, m), 0.77-0.96 (2H, m), 1.00 (3H, d), 2.52-2.63 (1H, m), 2.87-3.03 (2H, m), 3.21-3.28 (1H, m), 3.71 (1H, d), 3.92 (3H, s), 5.31 (1H, s), 6.65 (1H, d), 6.86-6.92 (1H, m), 6.97 (1H, m), 7.18 (1H, d), 7.23 (1H, d), 8.05 (1H, s), 12.94 (1H, s). m/z: ES+ [M+H]+ 444.

Preparation of (6S,8R)-6-(4-bromo-2-methoxyphenyl)-7-((1-fluorocyclopropyl)methyl)-8-methyl-3-(tetrahydro-2H-pyran-2-yl)-6,7,8,9-tetrahydro-3H-pyrazolo[4,3-f]isoquinoline

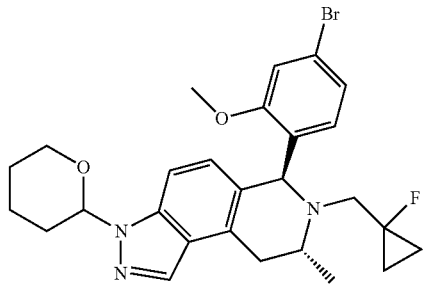 [SMILES: COc1cc(Br)ccc1[C@@H]1c2ccc3c(cnn3C3CCCCO3)c2C[C@@H](C)N1CC1(F)CC1]

3,4-Dihydro-2H-pyran (176 μL, 1.93 mmol) was added to a solution of (6S,8R)-6-(4-bromo-2-methoxyphenyl)-7-((1-fluorocyclopropyl)methyl)-8-methyl-6,7,8,9-tetrahydro-3H-pyrazolo[4,3-f]isoquinoline (286 mg, 0.64 mmol) and para-toluenesulfonic acid monohydrate (12 mg, 0.060 mmol) in DCM (2.5 ml). The reaction was subjected to microwave conditions (100° C., 300 W) for 6 hours. Upon cooling, the reaction was washed with saturated aqueous NaHCO₃, dried over Na₂SO₄, filtered, and concentrated under reduced pressure. The resulting residue was purified by flash silica chromatography, elution gradient 10 to 30% ethyl acetate in hexanes, to afford (6S,8R)-6-(4-bromo-2-methoxyphenyl)-7-((1-fluorocyclopropyl)methyl)-8-methyl-3-(tetrahydro-2H-pyran-2-yl)-6,7,8,9-tetrahydro-3H-pyrazolo[4,3-f]isoquinoline (299 mg, 88%) as a light brown gummy solid. m/z: ES+ [M+H]+528.

Preparation of tert-butyl 3-((4-((6S,8R)-7-((1-fluorocyclopropyl)methyl)-8-methyl-3-(tetrahydro-2H-pyran-2-yl)-6,7,8,9-tetrahydro-3H-pyrazolo[4,3-f]isoquinolin-6-yl)-3-methoxyphenyl)amino)azetidine-1-carboxylate

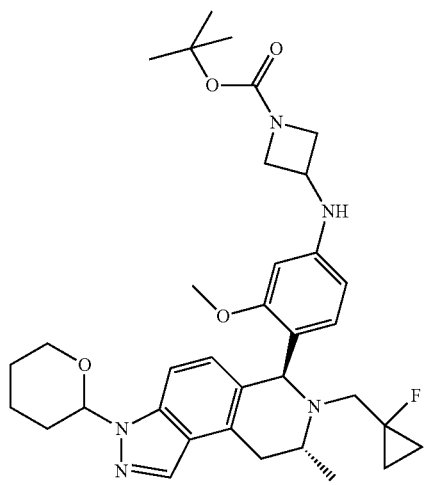 [SMILES: COc1cc(NC2CN(C(=O)OC(C)(C)C)C2)ccc1[C@@H]1c2ccc3c(cnn3C3CCCCO3)c2C[C@@H](C)N1CC1(F)CC1]

(6S,8R)-6-(4-bromo-2-methoxyphenyl)-7-((1-fluorocyclopropyl)methyl)-8-methyl-3-(tetrahydro-2H-pyran-2-yl)-6,7,8,9-tetrahydro-3H-pyrazolo[4,3-f]isoquinoline (278 mg, 0.53 mmol), tert-butyl 3-aminoazetidine-1-carboxylate (136 mg, 0.79 mmol), cesium carbonate (343 mg, 1.05 mmol), and BrettPhos 3rd Generation Precatalyst (24 mg, 0.030 mmol) in dioxane (2.5 mL) were subjected to microwave conditions (100° C., 300 W) for 6 hours. The reaction was then concentrated under reduced pressure, and the resulting residue was adsorbed onto silica gel before purification via flash silica chromatography, elution gradient 20 to 60% ethyl acetate in hexanes, to afford tert-butyl 3-((4-((6S,8R)-7-((1-fluorocyclopropyl)methyl)-8-methyl-3-(tetrahydro-2H-pyran-2-yl)-6,7,8,9-tetrahydro-3H-pyrazolo[4,3-f]isoquinolin-6-yl)-3-methoxyphenyl)amino)azetidine-1-carboxylate (296 mg, 91%). m/z: ES+ [M+H]+ 620.

Preparation of N-(4-((6S,8R)-7-((1-fluorocyclopropyl)methyl)-8-methyl-6,7,8,9-tetrahydro-3H-pyrazolo[4,3-f]isoquinolin-6-yl)-3-methoxyphenyl)azetidin-3-amine

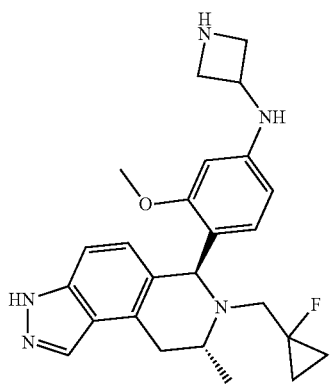 [SMILES: COc1cc(NC2CNC2)ccc1[C@@H]1c2ccc3[nH]ncc3c2C[C@@H](C)N1CC1(F)CC1]

HCl in dioxane (4 M; 1.2 mL, 4.78 mmol) was added dropwise to a solution of tert-butyl 3-((4-((6S,8R)-7-((1-fluorocyclopropyl)methyl)-8-methyl-3-(tetrahydro-2H-pyran-2-yl)-6,7,8,9-tetrahydro-3H-pyrazolo[4,3-f]isoquinolin-6-yl)-3-methoxyphenyl)amino)azetidine-1-carboxylate (296 mg, 0.48 mmol) in MeOH (3.5 ml). After stirring at room temperature overnight, the reaction was concentrated under reduced pressure, and the resulting residue was dissolved in MeOH (2 mL). This solution was then loaded onto an SCX-2 ion-exchange cartridge that had been pretreated with methanol. The cartridge was washed with methanol and then 7N ammonia in methanol. Product fractions were concentrated under reduced pressure to afford N-(4-((6S,8R)-7-((1-fluorocyclopropyl)methyl)-8-methyl-6,7,8,9-tetrahydro-3H-pyrazolo[4,3-f]isoquinolin-6-yl)-3-methoxyphenyl)azetidin-3-amine (181 mg, 87%) as a pale solid. m/z: ES+ [M+H]+ 436.

Example 7

(6S,8R)-7-((1-fluorocyclopropyl)methyl)-6-(4-((1-(3-fluoropropyl)azetidin-3-yl)oxy)-2-methoxyphenyl)-8-methyl-6,7,8,9-tetrahydro-3H-pyrazolo[4,3-f]isoquinoline

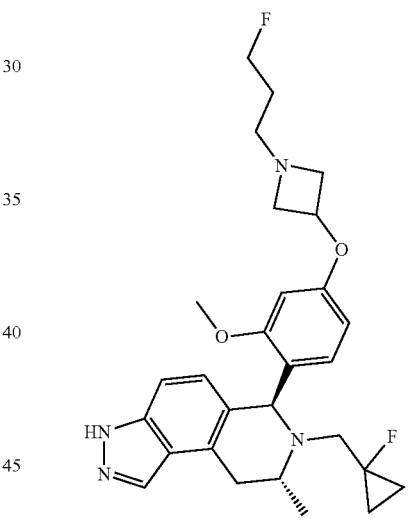

1-Fluoro-3-iodopropane (5.79 µL, 0.05 mmol) was added to a solution of (6S,8R)-6-(4-(azetidin-3-yloxy)-2-methoxyphenyl)-7-((1-fluorocyclopropyl)methyl)-8-methyl-6,7,8,9-tetrahydro-3H-pyrazolo[4,3-f]isoquinoline trifluoroacetic acid salt (0.030 g, 0.050 mmol) and DIPEA (0.029 mL, 0.16 mmol) in NMP (0.52 ml) at room temperature. After 3 hours, the reaction was diluted with EtOAc (40 mL) and washed with saturated aqueous sodium chloride (3×20 mL). The organic layer was dried over MgSO$_4$, filtered and concentrated under reduced pressure. The resulting residue was purified by flash silica chromatography, elution gradient 15 to 30% (MeOH in DCM containing 1% ammonium hydroxide) in DCM to afford (6S,8R)-7-((1-fluorocyclopropyl)methyl)-6-(4-((1-(3-fluoropropyl)azetidin-3-yl)oxy)-2-methoxyphenyl)-8-methyl-6,7,8,9-tetrahydro-3H-pyrazolo[4,3-f]isoquinoline (5 mg, 18%) as white solid. $^1$H NMR (500 MHz, Methanol-d$_4$, 26° C.) 0.45-0.56 (2H, m), 0.85-1.03 (2H, m), 1.12 (3H, d), 1.67-1.81 (2H, m), 2.50-2.62 (1H, m), 2.61-2.68 (2H, m), 2.92 (1H, dd), 3.08-3.21 (3H, m), 3.25-3.28 (1H, m), 3.70-3.84 (3H, m), 3.86-3.91 (3H, m), 4.45 (2H, dt), 4.73-4.82 (1H, m), 5.49 (1H, br. s), 6.19 (1H, d), 6.50 (1H, br. s.), 6.72 (1H, d), 6.79 (1H, d), 7.18 (1H, d), 8.05 (1H, s). Indazole NH not observed. m/z: ES+ [M+H]+ 497.

The N-(4-((6S,8R)-7-((1-fluorocyclopropyl)methyl)-8-methyl-6,7,8,9-tetrahydro-3H-pyrazolo[4,3-f]isoquinolin-6-yl)-3-methoxyphenyl)azetidin-3-amine trifluoroacetic acid salt was prepared as follows:

Preparation of (6S,8R)-7-((1-fluorocyclopropyl)methyl)-6-(2-methoxy-4-(4,4,5,5-tetramethyl-1,3,2-dioxaborolan-2-yl)phenyl)-8-methyl-3-(tetrahydro-2H-pyran-2-yl)-6,7,8,9-tetrahydro-3H-pyrazolo[4,3-f]isoquinoline

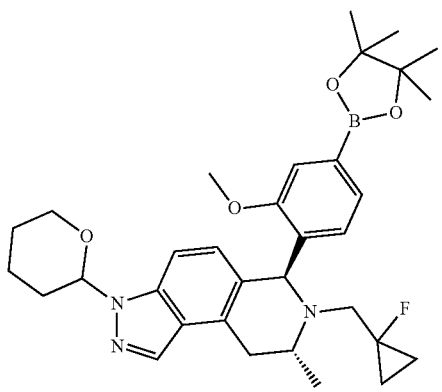 [SMILES: COc1cc(B2OC(C)(C)C(C)(C)O2)ccc1[C@@H]1c2ccc3c(cnn3C3CCCCO3)c2C[C@@H](C)N1CC1(F)CC1]

A mixture of (6S,8R)-6-(4-bromo-2-methoxyphenyl)-7-((1-fluorocyclopropyl)methyl)-8-methyl-3-(tetrahydro-2H-pyran-2-yl)-6,7,8,9-tetrahydro-3H-pyrazolo[4,3-f]isoquinoline (369 mg, 0.70 mmol; prepared according to Example 6), bis(pinacolato)diboron (266 mg, 1.05 mmol), [1,1'-bis(diphenylphosphino)ferrocene]dichloropalladium(II) (51 mg, 0.070 mmol) and potassium acetate (233 mg, 2.37 mmol) in dioxane (3.50 mL) was degassed and purged with nitrogen. The reaction mixture was then warmed to 80° C. After stirring under these conditions for 18 hours, the reaction mixture was cooled to room temperature, filtered through a pad of Celite®, and washed with EtOAc (100 mL). The filtrate was washed with water (100 mL), the aqueous layer was extracted with EtOAc (2×70 mL), and the combined organic layers were washed with water (3×70 mL) and saturated aqueous sodium chloride (50 mL) before being dried over MgSO₄, filtered, and concentrated under reduced pressure. The resulting residue was purified by flash silica chromatography, elution gradient 0 to 25% ethyl acetate in hexane to (6S,8R)-7-((1-fluorocyclopropyl)methyl)-6-(2-methoxy-4-(4,4,5,5-tetramethyl-1,3,2-dioxaborolan-2-yl)phenyl)-8-methyl-3-(tetrahydro-2H-pyran-2-yl)-6,7,8,9-tetrahydro-3H-pyrazolo[4,3-f]isoquinoline (186 mg, 46.3%) as a yellow solid. m/z: ES+ [M+H]+576.

Preparation of 4-((6S,8R)-7-((1-fluorocyclopropyl)methyl)-8-methyl-3-(tetrahydro-2H-pyran-2-yl)-6,7,8,9-tetrahydro-3H-pyrazolo[4,3-f]isoquinolin-6-yl)-3-methoxyphenol

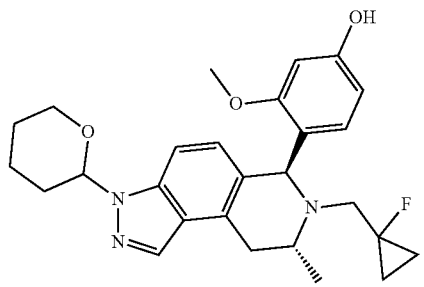 [SMILES: COc1cc(O)ccc1[C@@H]1c2ccc3c(cnn3C3CCCCO3)c2C[C@@H](C)N1CC1(F)CC1]

Aqueous hydrogen peroxide (33%; 75 μL, 0.74 mmol) was added dropwise to a stirred solution of (6S,8R)-7-((1-fluorocyclopropyl)methyl)-6-(2-methoxy-4-(4,4,5,5-tetramethyl-1,3,2-dioxaborolan-2-yl)phenyl)-8-methyl-3-(tetrahydro-2H-pyran-2-yl)-6,7,8,9-tetrahydro-3H-pyrazolo[4,3-f]isoquinoline (186 mg, 0.32 mmol) and aqueous sodium hydroxide (1 M; 350 μL, 0.32 mmol) in THF (2.5 mL) at 5° C. under air. The resulting mixture was stirred at 5° C. for 5 minutes. The reaction was then diluted with water (50 mL) and DCM (100 mL). The layers were separated, and the aqueous layer was extracted with DCM (2×50 mL). The combined organic layers were dried over sodium sulfate, filtered, and concentrated under reduced pressure. The resulting residue was purified by flash silica chromatography, elution gradient 20 to 50% ethyl acetate in hexanes, to afford 4-((6S,8R)-7-((1-fluorocyclopropyl)methyl)-8-methyl-3-(tetrahydro-2H-pyran-2-yl)-6,7,8,9-tetrahydro-3H-pyrazolo[4,3-j]isoquinolin-6-yl)-3-methoxyphenol (94 mg, 62.5%) as a yellow solid. m/z: ES+ [M+H]+ 466.

Preparation of tert-butyl 3-(4-((6S,8R)-7-((1-fluorocyclopropyl)methyl)-8-methyl-3-(tetrahydro-2H-pyran-2-yl)-6,7,8,9-tetrahydro-3H-pyrazolo[4,3-f]isoquinolin-6-yl)-3-methoxyphenoxy)azetidine-1-carboxylate

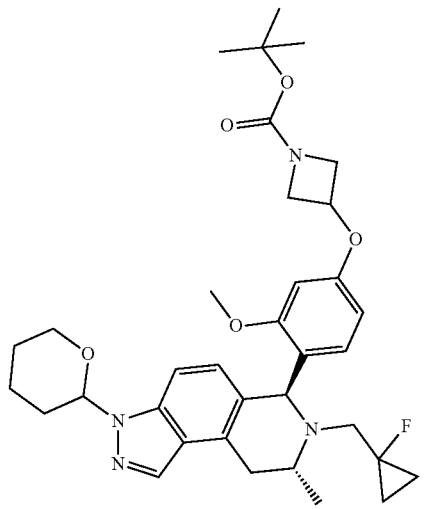 [SMILES: COc1cc(OC2CN(C(=O)OC(C)(C)C)C2)ccc1[C@@H]1c2ccc3c(cnn3C3CCCCO3)c2C[C@@H](C)N1CC1(F)CC1]

Diethyl (E)-diazene-1,2-dicarboxylate (88 mg, 0.20 mmol) was added to a solution of 4-((6S,8R)-7-((1-fluorocyclopropyl)methyl)-8-methyl-3-(tetrahydro-2H-pyran-2-yl)-6,7,8,9-tetrahydro-3H-pyrazolo[4,3-f]isoquinolin-6-yl)-3-methoxyphenol (94 mg, 0.20 mmol), tert-butyl 3-hydroxyazetidine-1-carboxylate (35 mg, 0.20 mmol), triphenylphosphine (53 mg, 0.20 mmol) and toluene (2.03 mL). The reaction was then warmed to 110° C. After 15 hours, the reaction was cooled, concentrated under reduced pressure, and purified by flash silica chromatography, elution gradient 0 to 30% ethyl acetate in hexanes, to afford tert-butyl 3-(4-((6S,8R)-7-((1-fluorocyclopropyl)methyl)-8-methyl-3-(tetrahydro-2H-pyran-2-yl)-6,7,8,9-tetrahydro-3H-pyrazolo[4,3-f]isoquinolin-6-yl)-3-methoxyphenoxy)azetidine-1-carboxylate (95 mg, 75%). m/z: ES+ [M+H]+ 621.

Preparation of tert-butyl 3-(4-((6S,8R)-7-((1-fluorocyclopropyl)methyl)-8-methyl-3-(tetrahydro-2H-pyran-2-yl)-6,7,8,9-tetrahydro-3H-pyrazolo[4,3-f]isoquinolin-6-yl)-3-methoxyphenoxy)azetidine-1-carboxylate trifluoroacetic acid salt

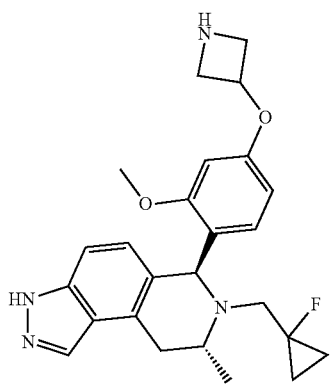 [SMILES: COc1cc(OC2CNC2)ccc1[C@@H]1c2ccc3[nH]ncc3c2C[C@@H](C)N1CC1(F)CC1]

HCl in dioxane (4N; 383 µL, 1.53 mmol) was added dropwise to a solution of tert-butyl 3-(4-((6S,8R)-7-((1-fluorocyclopropyl)methyl)-8-methyl-3-(tetrahydro-2H-pyran-2-yl)-6,7,8,9-tetrahydro-3H-pyrazolo[4,3-f]isoquinolin-6-yl)-3-methoxyphenoxy)azetidine-1-carboxylate (95 mg, 0.15 mmol) in MeOH (1 mL), and the reaction was stirred at room temperature for 18 hours. The reaction was concentrated under reduced pressure, and the resulting residue was purified by reverse phase flash chromatography, using decreasingly polar mixtures of water (containing 0.01% TFA) and MeCN as eluents (20 to 80%) to afford (6S,8R)-6-(4-(azetidin-3-yloxy)-2-methoxyphenyl)-7-((1-fluorocyclopropyl)methyl)-8-methyl-6,7,8,9-tetrahydro-3H-pyrazolo[4,3-f]isoquinoline (30 mg, 36%) as a TFA salt. $^1$H NMR (300 MHz, METHANOL-d$_4$, 27° C.) 0.86-1.09 (2H, m), 1.26-1.52 (3H, m), 1.59 (3H, d), 3.22-3.31 (1H, m), 3.36-3.47 (1H, m), 3.66 (1H, dd), 4.03 (3H, s), 4.07-4.27 (4H, m), 4.52-4.62 (2H, m), 5.14-5.27 (1H, m), 6.33 (1H, dd), 6.57-6.63 (1H, m), 6.68 (1H, d), 6.75 (1H, s), 6.93 (1H, d), 7.50 (1H, d), 8.23 (1H, s). Indazole NH and addition H not observed. m/z: ES+ [M+H]+ 437.

Example 8

N-(3,5-difluoro-4-((6S,8R)-8-methyl-7-(2,2,2-trifluoroethyl)-6,7,8,9-tetrahydro-3H-pyrazolo[4,3-f]isoquinolin-6-yl)phenyl)-1-(3-fluoropropyl)azetidin-3-amine

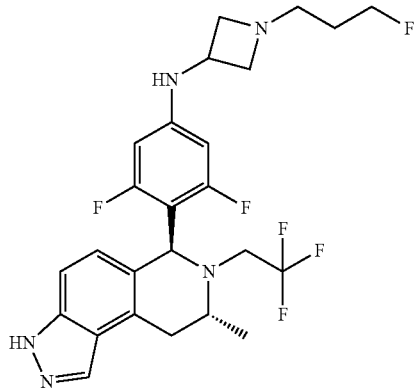 [SMILES: C[C@@H]1Cc2c(ccc3[nH]ncc23)[C@@H](c2c(F)cc(NC3CN(CCCF)C3)cc2F)N1CC(F)(F)F]

1-Fluoro-3-iodopropane (5.4 µl, 0.050 mmol) and diisopropylethylamine (0.013 mL, 0.070 mmol) were added to a stirred solution of N-(3,5-difluoro-4-((6S,8R)-8-methyl-7-(2,2,2-trifluoroethyl)-6,7,8,9-tetrahydro-3H-pyrazolo[4,3-f]isoquinolin-6-yl)phenyl)azetidin-3-amine (22 mg, 0.050 mmol) in NMP (0.4 mL) at ambient temperature. After 16 hours the crude reaction was purified directly by reverse phase preparative HPLC (Waters XBridge C18 column, 19 mm diameter, 100 mm length, 5 µm silica), elution gradient 40 to 70% MeCN in water containing 0.2% ammonium hydroxide as a modifier. Product fractions were concentrated to dryness to afford N-(3,5-difluoro-4-((6S,8R)-8-methyl-7-(2,2,2-trifluoroethyl)-6,7,8,9-tetrahydro-3H-pyrazolo[4,3-f]isoquinolin-6-yl)phenyl)-1-(3-fluoropropyl)azetidin-3-amine (9 mg, 36%) as a pale yellow solid. $^1$H NMR (500 MHz, CD$_2$Cl$_2$, 27° C.) 1.11 (3H, d), 1.69-1.78 (3H, m), 2.51-2.59 (2H, m), 2.81-2.94 (3H, m), 2.95-3.03 (1H, m), 3.16-3.30 (1H, m), 3.59-3.70 (3H, m), 3.94-4.05 (1H, m), 4.41 (1H, t), 4.45 (1H, d), 4.51 (1H, t), 5.27 (1H, s), 6.02 (2H, d), 6.83 (1H, d), 7.21 (1H, d), 8.03 (1H, s), 10.47 (1H, br. s). m/z: ES+ [M+H]+ 512.

The N-(3,5-difluoro-4-((6S,8R)-8-methyl-7-(2,2,2-trifluoroethyl)-6,7,8,9-tetrahydro-3H-pyrazolo[4,3-f]isoquinolin-6-yl)phenyl)azetidin-3-amine was prepared as follows;

Preparation of of 2,2,2-trifluoroethyl trifluoromethanesulfonate

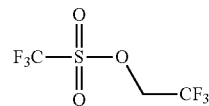

Trifluoromethanesulfonic anhydride (3.14 mL, 18.6 mmol) was added dropwise via syringe over 5 minutes to a stirred solution of 2,2,2-trifluoroethan-1-ol (1.23 mL, 16.9 mmol) and 2,6-dimethylpyridine (2.36 mL, 20.3 mmol) in DCM (50 mL) at −10° C. After 2 hours the reaction was washed successively with aqueous HCl (1N; 2×30 mL) and saturated aqueous NaHCO₃ (20 mL). The organic layer was then dried over MgSO₄, filtered, and concentrated under reduced pressure to give 2,2,2-trifluoroethyl trifluoromethanesulfonate (0.92 g, 23%) as a red oil. ¹H NMR (300 MHz, CDCl₃, 27° C.) 4.69 (2H, q).

Preparation of (R)-2-methyl-3-(2-((2,2,2-trifluoroethyl)amino)propyl)aniline

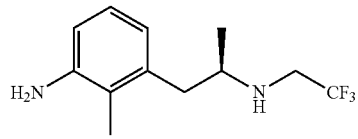 [SMILES: Cc1c(N)cccc1C[C@@H](C)NCC(F)(F)F]

2,2,2-Trifluoroethyl trifluoromethanesulfonate (1.3 g, 2.8 mmol) was added to a stirred solution of (R)-3-(2-aminopropyl)-2-methylaniline (0.460 g, 2.80 mmol; prepared according to Example 3) and diisopropylethylamine (0.636 mL, 3.64 mmol) in 1,4-dioxane (10 mL). The reaction was heated at 65° C. for 15 hours and then cooled and concentrated under reduced pressure. The resulting residue was dissolved in EtOAc (50 mL) and washed with a mixture of saturated aqueous NaHCO₃ and saturated aqueous sodium chloride. The aqueous layer was extracted with EtOAc (20 mL), and the combined organic layers were dried over MgSO₄, filtered, and concentrated under reduced pressure. The resulting residue was dissolved in MeOH, adsorbed onto diatomaceous earth under reduced pressure, and purified by flash silica chromatography, elution gradient 1 to 6% MeOH in DCM. Product fractions were concentrated to dryness to afford (R)-2-methyl-3-(2-((2,2,2-trifluoroethyl)amino)propyl)aniline (0.30 g, 44%) as a pale orange gum. ¹H NMR (300 MHz, CDCl₃, 27° C.) 1.07 (3H, d), 2.09 (3H, s), 2.63 (1H, dd), 2.76 (1H, dd), 2.92-3.05 (1H, m), 3.15 (2H, q), 6.58 (2H, d), 6.85-7.00 (1H, m). Signals for three NH's not observed. m/z: ES+ [M+H]+ 247.

Preparation of (1S,3R)-1-(4-bromo-2,6-difluorophenyl)-3,5-dimethyl-2-(2,2,2-trifluoroethyl)-1,2,3,4-tetrahydroisoquinolin-6-amine

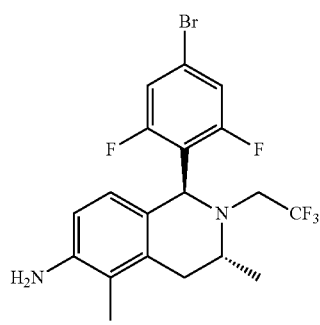 [SMILES: Cc1c(N)ccc2c1C[C@@H](C)N(CC(F)(F)F)[C@@H]2c1c(F)cc(Br)cc1F]

(R)-2-methyl-3-(2-((2,2,2-trifluoroethyl)amino)propyl) aniline (303 mg, 1.23 mmol) and 4-bromo-2,6-difluorobenzaldehyde (544 mg, 2.46 mmol) were heated in a mixture of acetic acid (5 mL) and water (0.111 mL) at 90° C. for 2 hours. The reaction was allowed to slowly cool to ambient temperature and stirred overnight. The reaction was then concentrated under reduced pressure, and the resulting residue was dissolved in EtOAc (30 mL) and washed with saturated aqueous NaHCO₃ (2×20 mL). The combined aqueous layers were extracted with EtOAc (2×20 mL), and the combined organic layers were washed with saturated aqueous sodium chloride and concentrated to minimal volume (~20 mL). Aqueous HCl (1N; 20 mL) was added, and the biphasic mixture was stirred vigorously for 2 hours. The layers were separated, and the aqueous layer was extracted with EtOAc (20 mL). The aqueous layer was basified by the addition of solid sodium carbonate (until pH~8 as measured using a pH strip) and then extracted with DCM (3×20 mL). The combined DCM extracts were dried over MgSO₄, filtered, and concentrated under reduced pressure to afford 40 mg of crude product. Meanwhile, the combined EtOAc extracts were washed with saturated aqueous sodium chloride and concentrated to dryness. The resultant residue was dissolved in THF (10 mL) and stirred with polystyrene-bound tosylhydrazide (1.03 g, 2.76 mmol) for 14 hours. The mixture was filtered, and the resin was washed successively with THF (10 mL) and MeOH (3×10 mL). The filtrate was combined with the previously obtained ca. 40 mg of crude product and concentrated under reduced pressure. This final residue was purified by flash silica chromatography, elution gradient 0 to 30% EtOAc in hexanes. Product fractions were concentrated to dryness to afford (1S,3R)-1-(4-bromo-2,6-difluorophenyl)-3,5-dimethyl-2-(2,2,2-trifluoroethyl)-1,2,3,4-tetrahydroisoquinolin-6-amine (230 mg, 41%) as a pale yellow solid. ¹H NMR (300 MHz, CDCl₃, 27° C.) 1.04 (3H, d), 2.42 (3H, s), 2.58 (1H, dd), 2.74-2.87 (1H, m), 3.02-3.28 (2H, m), 3.46-3.59 (1H, m), 5.27 (1H, s), 6.66 (1H, d), 7.02 (2H, d), 7.32 (1H, d), 9.95-10.73 (2H, br. s). m/z: ES+ [M+H]+ 449.

Preparation of (6S,8R)-6-(4-bromo-2,6-difluorophenyl)-8-methyl-7-(2,2,2-trifluoroethyl)-6,7,8,9-tetrahydro-3H-pyrazolo[4,3-f]isoquinoline

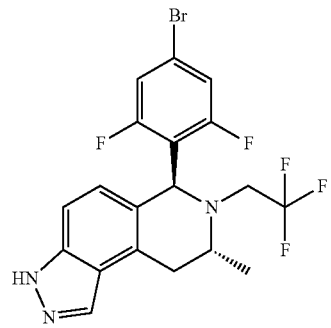 [SMILES: C[C@@H]1Cc2c(ccc3[nH]ncc23)[C@@H](c2c(F)cc(Br)cc2F)N1CC(F)(F)F]

A solution of sodium nitrite (35 mg, 0.51 mmol) in water (0.20 mL) was added dropwise over 1 minute to a stirred solution of (1S,3R)-1-(4-bromo-2,6-difluorophenyl)-3,5-dimethyl-2-(2,2,2-trifluoroethyl)-1,2,3,4-tetrahydroisoquinolin-6-amine (230 mg, 0.51 mmol) in propionic acid (2 mL) at approximately −20° C. (ice-NaCl bath). After 15 minutes the reaction was diluted with ice-cold EtOAc (15 mL). The biphasic mixture was stirred vigorously under these conditions and neutralized by the slow addition of solid Na₂CO₃ (until basic as measured using a pH strip). The cooling bath was removed. The phases were separated, and the organic layer washed with saturated aqueous NaHCO₃ (2×15 mL), saturated aqueous sodium chloride (15 mL), dried over MgSO₄, filtered, and concentrated under reduced pressure. The resulting residue was purified by flash silica chromatography, elution gradient 5 to 35% EtOAc in hexanes. Product fractions were concentrated to dryness to afford (6S,8R)-6-(4-bromo-2,6-difluorophenyl)-8-methyl-7-(2,2,2-trifluoroethyl)-6,7,8,9-tetrahydro-3H-pyrazolo[4,3-f]isoquinoline (104 mg, 45%) as a pale orange film. ¹H NMR (300 MHz, CDCl₃, 27° C.) 1.15 (3H, d), 2.89-3.04 (2H, m), 3.20-3.36 (1H, m), 3.50 (1H, dd), 3.61-3.75 (1H, m), 5.41 (1H, s), 6.80 (1H, d), 7.01-7.11 (2H, m), 7.23 (1H, d), 8.10 (1H, s), 10.24 (1H, br. s). m/z: ES+ [M+H]+ 460.

Preparation of (6S,8R)-6-(4-bromo-2,6-difluorophenyl)-8-methyl-3-(tetrahydro-2H-pyran-2-yl)-7-(2,2,2-trifluoroethyl)-6,7,8,9-tetrahydro-3H-pyrazolo[4,3-f]isoquinoline

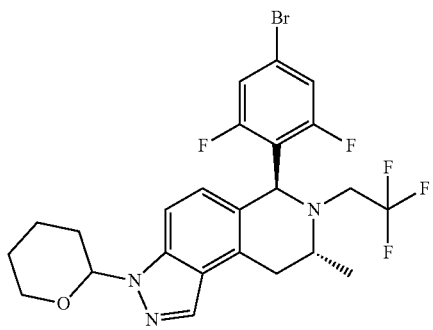 [SMILES: C[C@@H]1Cc2c(ccc3c2cnn3C2CCCCO2)[C@@H](c2c(F)cc(Br)cc2F)N1CC(F)(F)F]

3,4-Dihydro-2H-pyran (0.103 mL, 1.13 mmol) and p-toluenesulfonic acid monohydrate (2 mg, 0.01 mmol) were added to a stirred solution of (6S,8R)-6-(4-bromo-2,6-difluorophenyl)-8-methyl-7-(2,2,2-trifluoroethyl)-6,7,8,9-tetrahydro-3H-pyrazolo[4,3-f]isoquinoline (104 mg, 0.23 mmol) in DCM (1.5 mL). The reaction was maintained under reflux conditions for 1 hour. After cooling, the reaction was diluted with DCM, washed with saturated aqueous NaHCO₃, dried over MgSO₄, filtered, and concentrated under reduced pressure. The resulting residue was purified by flash silica chromatography, elution gradient 0 to 30% EtOAc in hexanes. Product fractions were concentrated to dryness to afford (6S,8R)-6-(4-bromo-2,6-difluorophenyl)-8-methyl-3-(tetrahydro-2H-pyran-2-yl)-7-(2,2,2-trifluoroethyl)-6,7,8,9-tetrahydro-3H-pyrazolo[4,3-f]isoquinoline (117 mg, 95%) as pale yellow solid. m/z: ES+ [M+H]+ 544.

Preparation of tert-butyl 3-((3,5-difluoro-4-((6S,8R)-8-methyl-3-(tetrahydro-2H-pyran-2-yl)-7-(2,2,2-trifluoroethyl)-6,7,8,9-tetrahydro-3H-pyrazolo[4,3-f]isoquinolin-6-yl)phenyl)amino)azetidine-1-carboxylate

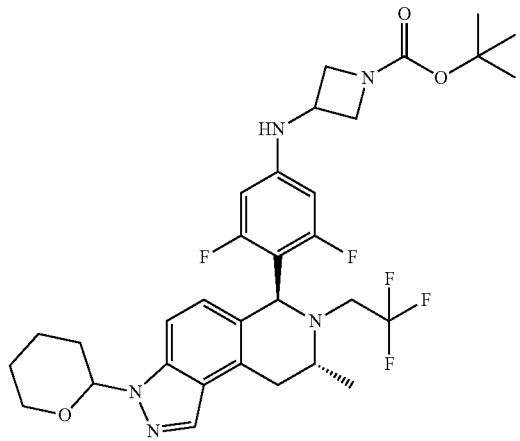 [SMILES: C[C@@H]1Cc2c(ccc3c2cnn3C2CCCCO2)[C@@H](c2c(F)cc(NC3CN(C(=O)OC(C)(C)C)C3)cc2F)N1CC(F)(F)F]

A vial was charged with a stir bar, (6S,8R)-6-(4-bromo-2,6-difluorophenyl)-8-methyl-3-(tetrahydro-2H-pyran-2-yl)-7-(2,2,2-trifluoroethyl)-6,7,8,9-tetrahydro-3H-pyrazolo[4,3-f]isoquinoline (55 mg, 0.10 mmol), tert-butyl 3-aminoazetidine-1-carboxylate (26 mg, 0.15 mmol), Pd₂dba₃ (9 mg, 0.01 mmol), Xantphos (12 mg, 0.02 mmol), and cesium carbonate (99 mg, 0.30 mmol). The vial was sealed and evacuated/backfilled with nitrogen (3×) prior to the addition of degassed 1,4-dioxane (1 mL) via syringe. The mixture was stirred at ambient temperature for 2 minutes then placed in a heating block at that had been preheated to 90° C. After 22 hours, the mixture was allowed to cool to room temperature and then diluted with EtOAc. The mixture was filtered through diatomaceous earth, and the filtrate was concentrated under reduced pressure. The resulting residue was purified by flash silica chromatography, elution gradient 0 to 45% EtOAc in hexanes. Product fractions were concentrated to dryness to afford tert-butyl 3-((3,5-difluoro-4-((6S,8R)-8-methyl-3-(tetrahydro-2H-pyran-2-yl)-7-(2,2,2-trifluoroethyl)-6,7,8,9-tetrahydro-3H-pyrazolo[4,3-f]isoquinolin-6-yl)phenyl)amino)azetidine-1-carboxylate (46 mg, 72%) as a pale yellow solid. ¹H NMR (300 MHz, CDCl₃, 27° C.) 1.08 (3H, d), 1.42 (9H, s), 1.55-1.81 (4H, m), 1.97-2.23 (2H, m), 2.45-2.63 (1H, m), 2.80-3.02 (2H, m), 3.09-3.27 (1H, m), 3.34-3.47 (1H, m), 3.53-3.65 (1H, m), 3.66-3.75 (3H, m), 3.92-4.02 (1H, m), 4.19-4.32 (3H, m), 5.25 (1H, s), 5.58-5.67 (1H, m), 5.93 (2H, dd), 6.81 (1H, d), 7.22-7.27 (1H, m), 7.98 (1H, s). Partial overlap of the multiplet at 7.22 to 7.27 ppm with chloroform. m/z: ES+ [M+H]+ 636.

Preparation of N-(3,5-difluoro-4-((6S,8R)-8-methyl-7-(2,2,2-trifluoroethyl)-6,7,8,9-tetrahydro-3H-pyrazolo[4,3-f]isoquinolin-6-yl)phenyl)azetidin-3-amine

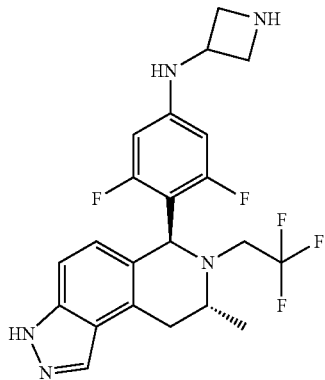 [SMILES: C[C@@H]1Cc2c(ccc3[nH]ncc23)[C@@H](c2c(F)cc(NC3CNC3)cc2F)N1CC(F)(F)F]

The tert-butyl 3-((3,5-difluoro-4-((6S,8R)-8-methyl-3-(tetrahydro-2H-pyran-2-yl)-7-(2,2,2-trifluoroethyl)-6,7,8,9-tetrahydro-3H-pyrazolo[4,3-f]isoquinolin-6-yl)phenyl)amino)azetidine-1-carboxylate (46 mg, 0.08 mmol) was dissolved in formic acid (0.50 mL, 13 mmol), and the stirred solution warmed to 30° C. After 27 hours the reaction was concentrated under reduced pressure. The resulting residue was dissolved in 5% IPA/DCM and neutralized with saturated aqueous NaHCO₃. The phases were separated, and the aqueous layer was extracted with 5% IPA/DCM (2×4 mL). The combined organic layers were dried over MgSO₄, filtered, and concentrated under reduced pressure to afford crude N-(3,5-difluoro-4-((6S,8R)-8-methyl-7-(2,2,2-trifluoroethyl)-6,7,8,9-tetrahydro-3H-pyrazolo[4,3-f]isoquinolin-6-yl)phenyl)azetidin-3-amine (38 mg, 111%) contaminated with a small amount of partially deprotected starting material as a pale yellow film. m/z: ES+ [M+H]+ 452.

Example 9

5-((6S,8R)-7-((1-fluorocyclopropyl)methyl)-8-methyl-6,7,8,9-tetrahydro-3H-pyrazolo[4,3-f]isoquinolin-6-yl)-N-(1-(3-fluoropropyl)azetidin-3-yl)-4-methoxypyridin-2-amine

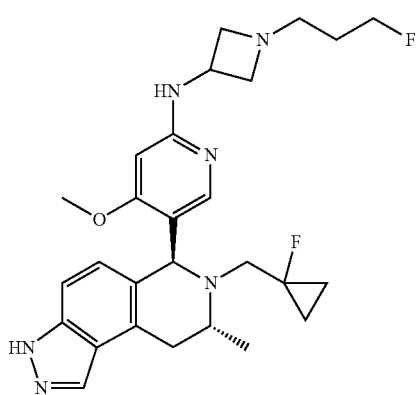 [SMILES: COc1cc(NC2CN(CCCF)C2)ncc1[C@@H]1c2ccc3[nH]ncc3c2C[C@@H](C)N1CC1(F)CC1]

DMF (1 mL) and DIPEA (0.022 ml, 0.13 mmol) were added sequentially to a flask charged with N-(azetidin-3-yl)-5-((6S,8R)-7-((1-fluorocyclopropyl)methyl)-8-methyl-6,7,8,9-tetrahydro-3H-pyrazolo[4,3-j]isoquinolin-6-yl)-4-methoxypyridin-2-amine (22 mg, 0.050 mmol). 1-Fluoro-3-iodopropane (9 mg, 0.05 mmol) in DMF (0.1 mL) was then added. After 2 hours, the reaction was diluted with saturated aqueous sodium chloride, and the mixture was extracted in EtOAC (3×). The combined organic layers were washed with water and dried over sodium sulfate, filtered and concentrated under reduced pressure. The resulting crude film was purified by flash silica chromatography, elution gradient 2 to 10% MeOH in DCM, to give 5-((6S,8R)-7-((1-fluorocyclopropyl)methyl)-8-methyl-6,7,8,9-tetrahydro-3H-pyrazolo[4,3-f]isoquinolin-6-yl)-N-(1-(3-fluoropropyl)azetidin-3-yl)-4-methoxypyridin-2-amine (9.0 mg, 36%) as a dry film. ¹H NMR (500 MHz, CHLOROFORM-d, 27° C.) δ ppm 0.46-0.66 (2H, m), 0.85-1.05 (2H, m), 1.09 (3H, d), 1.64-1.78 (2H, m), 2.50-2.61 (3H, m), 2.83 (1H, dd), 2.87-2.96 (2H, m), 3.04-3.21 (2H, m), 3.56-3.69 (2H, m), 3.70-3.76 (1H, m), 3.85 (3H, s), 4.30-4.37 (1H, m), 4.45 (2H, dt), 4.93 (1H, br d), 5.32 (1H, s), 5.82 (1H, s), 6.76 (1H, d), 7.00 (1H, d), 7.32 (1H, s), 7.99 (1H, s), 11.00 (1H, br s). m/z: ES+ [M+H]+ 497

The N-(azetidin-3-yl)-5-((6S,8R)-7-((1-fluorocyclopropyl)methyl)-8-methyl-6,7,8,9-tetrahydro-3H-pyrazolo[4,3-f]isoquinolin-6-yl)-4-methoxypyridin-2-amine was prepared as described below Preparation of (1S,3R)-1-(6-bromo-4-methoxypyridin-3-yl)-2-((1-fluorocyclopropyl)methyl)-3,5-dimethyl-1,2,3,4-tetrahydroisoquinolin-6-amine

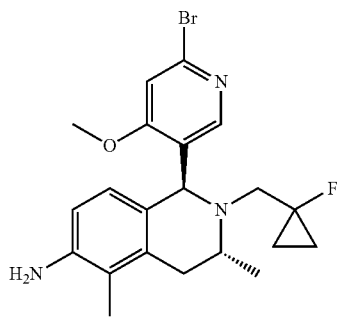 [SMILES: COc1cc(Br)ncc1[C@@H]1c2ccc(N)c(C)c2C[C@@H](C)N1CC1(F)CC1]

6-Bromo-4-methoxynicotinaldehyde (1.46 g, 6.77 mmol) was added to a solution of (R)-3-(2-(((1-fluorocyclopropyl)methyl)amino)propyl)-2-methylaniline (0.800 g, 3.39 mmol) in AcOH (27 ml) and water (0.305 g, 16.9 mmol), and the reaction was heated at 85° C. for 18 hours. After cooling, the reaction was concentrated under reduced pressure, and the resulting residue was diluted with ethyl acetate and basified with saturated aqueous sodium hydrogencarbonate. The organic layer was combined with aqueous HCl (1N), and the biphasic mixture was stirred at room temperature for 30 minutes. The organic layer was washed with aqueous HCl (1N), then the combined aqueous layers were extracted with ethyl acetate. The aqueous layer was then basified by addition of solid K₂CO₃ and extracted with ethyl acetate (2×). The combined ethyl acetate extracts from the basified aqueous layer were dried over sodium sulfate, filtered, and concentrated under reduced pressure. The resulting residue was purified by silica flash chromatography elution gradient 10 to 100% ethyl acetate in hexanes to afford (1S,3R)-1-(6-bromo-4-methoxypyridin-3-yl)-2-((1-fluorocyclopropyl)methyl)-3,5-dimethyl-1,2,3,4-tetrahydroisoquinolin-6-amine (0.450 g, 30.6%) as a gum. ¹H NMR (400 MHz, DMSO-d$_6$, 27° C.) δ ppm 0.47-0.64 (2H, m), 0.87-0.98 (5H, m), 1.95 (3H, s), 2.42-2.48 (1H, m), 2.79 (1H, dd), 2.87-2.99 (1H, m), 3.41-3.50 (H, m), 3.92-3.97 (3H, m), 4.66 (2H, s), 5.11 (1H, s), 6.30 (1H, d), 6.39 (1H, d), 7.26 (1H, s), 7.64 (1H, s). One hydrogen obscured by DMSO. m/z: ES+ [M+H]+ 434.

Preparation of (6S,8R)-6-(6-bromo-4-methoxypyridin-3-yl)-7-((1-fluorocyclopropyl)methyl)-8-methyl-6,7,8,9-tetrahydro-3H-pyrazolo[4,3-f]isoquinoline

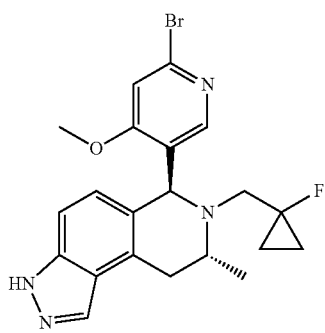

A solution of sodium nitrite (0.045 g, 0.65 mmol) in water (0.75 mL) was added dropwise to a solution of (1S,3R)-1-(6-bromo-4-methoxypyridin-3-yl)-2-((1-fluorocyclopropyl)methyl)-3,5-dimethyl-1,2,3,4-tetrahydroisoquinolin-6-amine (0.270 g, 0.62 mmol) in propionic acid (3.0 mL) at −15° C. (salt/ice bath), and the reaction was stirred under these conditions 1 hour. Ice-cold EtOAc (10 mL) was added followed by saturated aqueous NaHCO$_3$ (15 mL) portionwise. The layers were separated, and the organic layer was washed with saturated aqueous NaHCO$_3$ (2×). The combined aqueous layers (pH=8) were extracted with EtOAc, and then all combined organic layers were dried over sodium sulfate, filtered, and concentrated under reduced pressure. The resulting residue was purified by silica flash chromatography, elution gradient 20 to 60% ethyl acetate in hexanes to give (6S,8R)-6-(6-bromo-4-methoxypyridin-3-yl)-7-((1-fluorocyclopropyl)methyl)-8-methyl-6,7,8,9-tetrahydro-3H-pyrazolo[4,3-f]isoquinoline (0.11 g, 41%) as a gum. ¹H NMR (400 MHz, DMSO-d$_6$, 27° C.) 0.47-0.64 (2H, m), 0.87-0.97 (2H, m), 0.97-1.01 (3H, m), 2.51-2.63 (1H, m), 2.89 (1H, dd), 2.94-3.06 (1H, m), 3.23 (1H, br dd), 3.54-3.67 (1H, m), 3.97 (3H, s), 5.28 (1H, s), 6.68 (1H, d), 7.21 (1H, d), 7.30 (1H, s), 7.68 (1H, s), 8.06 (1H, s), 12.98 (1H, br s). m/z: ES+ [M+H]+ 445.

Preparation of (6S,8R)-6-(6-bromo-4-methoxy-3-pyridyl)-7-[(1-fluorocyclopropyl)methyl]-8-methyl-3-[(2R)-tetrahydropyran-2-yl]-8,9-dihydro-6H-pyrazolo[4,3-f]isoquinoline and (6S,8R)-6-(6-bromo-4-methoxypyridin-3-yl)-7-((1-fluorocyclopropyl)methyl)-8-methyl-2-(tetrahydro-2H-pyran-2-yl)-6,7,8,9-tetrahydro-2H-pyrazolo[4,3-f]isoquinoline

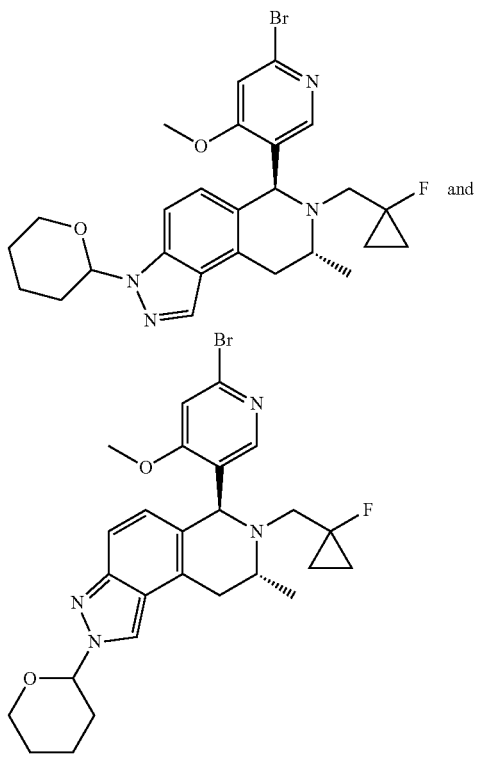

DCM (4 mL) was added to a flask charged with (6S,8R)-6-(6-bromo-4-methoxypyridin-3-yl)-7-((1-fluorocyclopropyl)methyl)-8-methyl-6,7,8,9-tetrahydro-3H-pyrazolo[4,3-f]isoquinoline (150 mg, 0.34 mmol) and 4-methylbenzenesulfonic acid hydrate (71 mg, 0.37 mmol). 3,4-Dihydro-2H-pyran (43 mg, 0.51 mmol) was added to the stirred reaction, and the reaction was stirred at RT overnight. The reaction was washed with saturated aqueous sodium hydrogencarboante, and the organic layer was dried over sodium sulfate, filtered, and concentrated under reduced pressure to give crude brow gum. This was purified by flash chromatography, elution gradient 5 to 40% EtOAc in hexanes to give a mixture of (6S,8R)-6-(6-bromo-4-methoxy-3-pyridyl)-7-[(1-fluorocyclopropyl)methyl]-8-methyl-3-[(2R)-tetrahydropyran-2-yl]-8,9-dihydro-6H-pyrazolo[4,3-f]isoquinoline and (6S,8R)-6-(6-bromo-4-methoxypyridin-3-yl)-7-((1-fluorocyclopropyl)methyl)-8-methyl-2-(tetrahydro-2H-pyran-2-yl)-6,7,8,9-tetrahydro-2H-pyrazolo[4,3-f]isoquinoline (151 mg, 85%) as a gum. ¹H NMR (400 MHz, CHLOROFORM-d, 27° C.) 0.45-0.61 (2H, m), 0.96-1.06 (2H, m), 1.09 (3H, d), 1.46-1.91 (3H, m), 2.03-2.20 (2H, m), 2.47-2.63 (2H, m), 2.88 (1H, ddd), 3.14 (1H, dd), 3.20-3.31 (1H, m), 3.64-3.79 (2H, m), 3.96 (3H, d), 3.98-4.06 (1H, m), 5.40 (1H, d), 5.64-5.71 (1H, m), 6.78 (1H, d), 6.99 (1H, d), 7.25-7.33 (1H, m), 7.76 (1H, d), 8.02 (1H, d).

Preparation of tert-butyl 3-((5-(((6S,8R)-7-((1-fluorocyclopropyl)methyl)-8-methyl-3-(tetrahydro-2H-pyran-2-yl)-6,7,8,9-tetrahydro-3H-pyrazolo[4,3-f]isoquinolin-6-yl)-4-methoxypyridin-2-yl)amino)azetidine-1-carboxylate and tert-butyl 3-(5-((6S,8R)-7-((1-fluorocyclopropyl)methyl)-8-methyl-2-(tetrahydro-2H-pyran-2-yl)-6,7,8,9-tetrahydro-2H-pyrazolo[4,3-f]isoquinolin-6-yl)-4-methoxypyridin-2-ylamino)azetidine-1-carboxylate

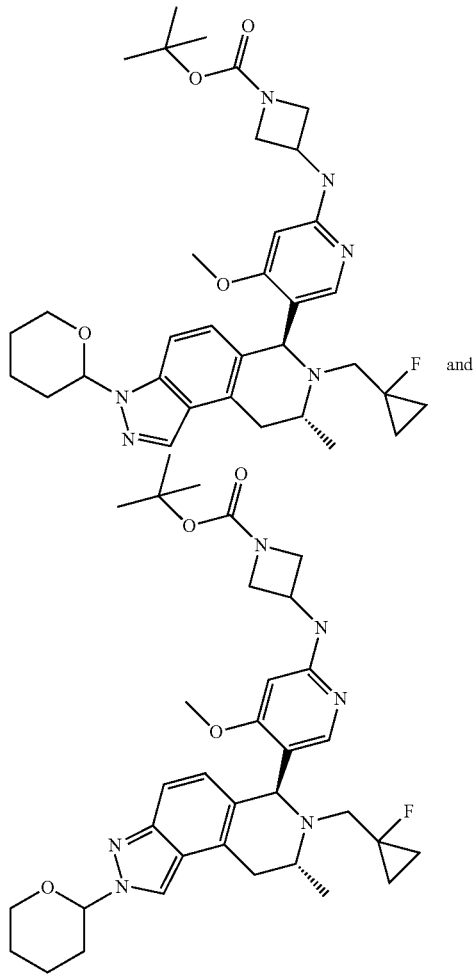

Dioxane (2.7 mL) was added to a flask charged with a mixture of (6S,8R)-6-(6-bromo-4-methoxypyridin-3-yl)-7-((1-fluorocyclopropyl)methyl)-8-methyl-3-(tetrahydro-2H-pyran-2-yl)-6,7,8,9-tetrahydro-3H-pyrazolo[4,3-f]isoquinoline and (6S,8R)-6-(6-bromo-4-methoxypyridin-3-yl)-7-((1-fluorocyclopropyl)methyl)-8-methyl-2-(tetrahydro-2H-pyran-2-yl)-6,7,8,9-tetrahydro-2H-pyrazolo[4,3-f]isoquinoline (140 mg, 0.26 mmol), cesium carbonate (172 mg, 0.53 mmol) and tert-butyl 3-aminoazetidine-1-carboxylate (68 mg, 0.40 mmol), and the reaction flask was evacuated and back-filled with nitrogen (3×). BrettPhos 3rd Generation Precatalyst (24 mg, 0.030 mmol) was added, and the flask was again evacuated and back-filled with nitrogen (3×). The reaction was heated at 110° C. for 4 hours. The reaction was cooled to room temperature, filtered, and concentrated under reduced pressure. The resulting um was purified by flash silica chromatography, elution gradient 30 to 100% ethyl acetate in hexanes to give a mixture of tert-butyl 3-((5-((6S,8R)-7-((1-fluorocyclopropyl)methyl)-8-methyl-3-(tetrahydro-2H-pyran-2-yl)-6,7,8,9-tetrahydro-3H-pyrazolo[4,3-f]isoquinolin-6-yl)-4-methoxypyridin-2-yl)amino)azetidine-1-carboxylate and tert-butyl 3-(5-((6S,8R)-7-((1-fluorocyclopropyl)methyl)-8-methyl-2-(tetrahydro-2H-pyran-2-yl)-6,7,8,9-tetrahydro-2H-pyrazolo[4,3-f]isoquinolin-6-yl)-4-methoxypyridin-2-ylamino)azetidine-1-carboxylate (53 mg, 32%) as a dry film. $^1$H NMR (400 MHz, CHLOROFORM-d, 27° C.) 0.50-0.68 (2H, m), 0.96-1.09 (2H, m), 1.12 (3H, d), 1.42-1.47 (9H, m), 1.60-1.88 (3H, m), 2.07-2.21 (2H, m), 2.50-2.67 (2H, m), 2.85 (1H, ddd), 3.10-3.23 (2H, m), 3.63-3.79 (4H, m), 3.87-3.91 (3H, m), 3.99-4.07 (1H, m), 4.24-4.33 (2H, m), 4.42-4.52 (1H, m), 5.36 (1H, d), 5.64-5.73 (1H, m), 5.83 (1H, d), 6.85 (1H, d), 7.26-7.32 (2H, m), 7.40 (1H, d), 8.00-8.03 (1H, m). m/z: ES+ [M+H]+ 621.

Preparation of N-(azetidin-3-yl)-5-((6S,8R)-7-((1-fluorocyclopropyl)methyl)-8-methyl-6,7,8,9-tetrahydro-3H-pyrazolo[4,3-f]isoquinolin-6-yl)-4-methoxypyridin-2-amine

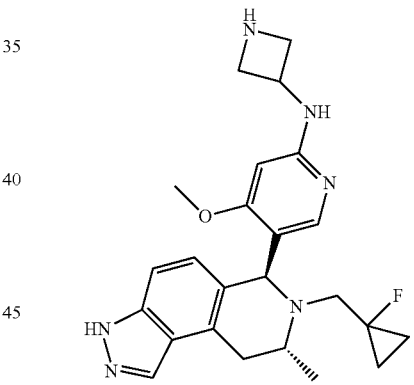

Methanol (0.5 mL) was added to a flask charged with tert-butyl 3-((5-((6S,8R)-7-((1-fluorocyclopropyl)methyl)-8-methyl-3-(tetrahydro-2H-pyran-2-yl)-6,7,8,9-tetrahydro-3H-pyrazolo[4,3-f]isoquinolin-6-yl)-4-methoxypyridin-2-yl)amino)azetidine-1-carboxylate (0.047 g, 0.080 mmol). HCl in dioxane (4 M; 0.5 mL, 2 mmol) was added, and stirring continued for 2 hours. The reaction was then concentrated under reduced pressure, and the resulting residue was purified using an SCX-2 cartage, eluting with 3N ammonia in methanol, to give crude N-(azetidin-3-yl)-5-((6S,8R)-7-((1-fluorocyclopropyl)methyl)-8-methyl-6,7,8,9-tetrahydro-3H-pyrazolo[4,3-f]isoquinolin-6-yl)-4-methoxypyridin-2-amine (25 mg, 76%) as a gum. The product was used in the next step without further purification. m/z: ES+ [M+H]+ 437.

Example 10

N-(4-((6S,8R)-7-((3-(fluoromethyl)oxetan-3-yl)methyl)-8-methyl-6,7,8,9-tetrahydro-3H-pyrazolo[4,3-f]isoquinolin-6-yl)-3-methoxyphenyl)-1-(3-fluoropropyl)azetidin-3-amine

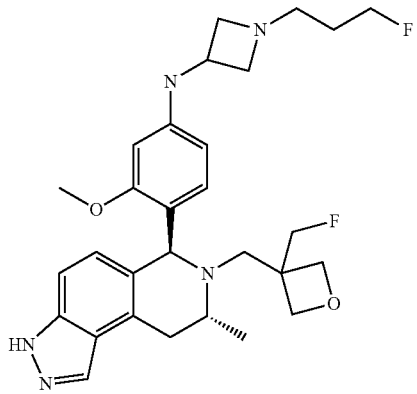 [SMILES: COc1cc(NC2CN(CCCF)C2)ccc1[C@@H]1c2ccc3[nH]ncc3c2C[C@@H](C)N1CC1(CF)COC1]

1-(3-Fluoropropyl)azetidin-3-amine (47.3 mg, 0.36 mmol) was added in 1,4-dioxane (1.4 mL) to a sealed microwave vial containing (6S,8R)-6-(4-bromo-2-methoxyphenyl)-7-((3-(fluoromethyl)oxetan-3-yl)methyl)-8-methyl-3-(tetrahydro-2H-pyran-2-yl)-6,7,8,9-tetrahydro-3H-pyrazolo[4,3-f]isoquinoline (100 mg, 0.18 mmol), sodium tert-butoxide (34.4 mg, 0.36 mmol) and [(2-dicyclohexylphosphino-3,6-dimethoxy-2',4',6'-triisopropyl-1,1'-biphenyl)-2-(2'-amino-1,1'-biphenyl)]palladium(II) methanesulfonate (BrettPhos Pd G3) (8.10 mg, 8.95 µmol). The vial was degassed with bubbling nitrogen for 10 min, then was heated to 90° C. for 1 hour. After cooling, the reaction was diluted with EtOAc and washed with water. The aqueous phase was extracted with EtOAc, then the combined organics were evaporated. The crude residue was dissolved in DCM (2 mL) and TFA (1 mL) was added. The mixture was stirred for 1 hour, then evaporated. The residue was dissolved in DCM and washed with saturated aqueous NaHCO$_3$ solution. The aqueous layer was extracted with DCM, then the combined organics were dried over Na$_2$SO$_4$ and evaporated. The crude product was purified by preparative HPLC (Waters XBridge Prep C18 OBD column, 5µ silica, 19 mm diameter, 100 mm length), using decreasingly polar mixtures of water (containing 0.1% NH$_3$) and MeCN as eluents. Fractions containing the desired compound were evaporated to dryness to afford N-(4-((6S,8R)-7-((3-(fluoromethyl)oxetan-3-yl)methyl)-8-methyl-6,7,8,9-tetrahydro-3H-pyrazolo[4,3-f]isoquinolin-6-yl)-3-methoxyphenyl)-1-(3-fluoropropyl)azetidin-3-amine (59.0 mg, 63%) as a beige solid. $^1$H NMR (500 MHz, CDCl$_3$, 27° C.) 1.07 (3H, d), 1.68-1.87 (2H, m), 2.62 (2H, t), 2.75 (1H, d), 2.83 (1H, dd), 2.87-2.96 (3H, m), 3.10 (1H, dd), 3.27 (1H, dt), 3.74 (2H, q), 3.84 (3H, s), 4.04-4.14 (2H, m), 4.43 (4H, td), 4.53 (1H, t), 4.58 (1H, d), 4.78 (2H, td), 5.11 (1H, s), 5.90 (1H, dd), 6.12 (1H, d), 6.48 (1H, d), 6.80 (1H, d), 7.15 (1H, d), 8.05 (1H, d); m/z: ES+ [M+H]+526.

The N-(4-((6S,8R)-7-((3-(fluoromethyl)oxetan-3-yl)methyl)-8-methyl-6,7,8,9-tetrahydro-3H-pyrazolo[4,3-f]isoquinolin-6-yl)-3-methoxyphenyl)-1-(3-fluoropropyl)azetidin-3-amine was prepared as follows:

Preparation of (3-(fluoromethyl)oxetan-3-yl)methanol

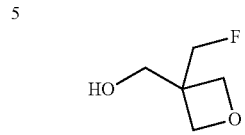

Cesium fluoride (5.03 g, 33.14 mmol) was added to a flask containing (3-(bromomethyl)oxetan-3-yl)methanol (2.00 g, 11.05 mmol) in ethylene glycol (6 mL) and the reaction was heated to 150° C. for 2 hours. After cooling, the reaction was diluted with EtOAc (30 mL) and water (30 mL). The aqueous was extracted with diethyl ether (3×30 mL) and ethyl acetate (3×30 mL). The combined organics were dried over MgSO$_4$, filtered and evaporated, then the crude product was purified by flash silica chromatography, elution gradient 0 to 100% EtOAc in heptane. Product containing fractions were evaporated to dryness to afford (3-(fluoromethyl)oxetan-3-yl)methanol (0.734 g, 55%) as a colourless liquid. $^1$H NMR (500 MHz, CDCl$_3$, 27° C.) 3.92 (2H, s), 4.52 (4H, t), 4.59-4.89 (2H, m).

Preparation of (3-(fluoromethyl)oxetan-3-yl)methyl trifluoromethanesulfonate

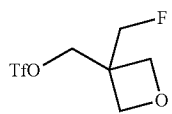

Trifluoromethanesulfonic anhydride (1.47 ml, 8.74 mmol), followed by 2,6-dimethylpyridine (1.12 ml, 9.57 mmol) were added to a solution of (3-(fluoromethyl)oxetan-3-yl)methanol (1.00 g, 8.32 mmol) in DCM (30.7 mL) and the reaction was stirred at 0° C. for 1 hour. The reaction was washed with water and 1N citric acid solution, then dried over Na$_2$SO$_4$, filtered and evaporated to afford (3-(fluoromethyl)oxetan-3-yl)methyl trifluoromethanesulfonate (1.98 g, 94%) as a red oil, which was used directly without further purification. $^1$H NMR (500 MHz, CDCl$_3$, 27° C.) 4.40-4.75 (8H, m).

Preparation of (R)-3-(2-(((3-(fluoromethyl)oxetan-3-yl)methyl)amino)propyl)-2-methylaniline

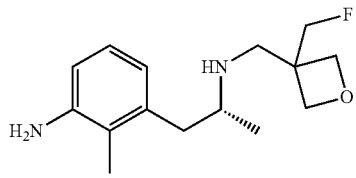 [SMILES: Cc1c(N)cccc1C[C@@H](C)NCC1(CF)COC1]

(3-(Fluoromethyl)oxetan-3-yl)methyl trifluoromethanesulfonate (1.92 g, 7.61 mmol) was added to a solution of (R)-3-(2-aminopropyl)-2-methylaniline (1.00 g, 6.09 mmol) and DIPEA (1.58 ml, 9.13 mmol) in 1,4-dioxane (18.7 mL) and the reaction was heated to 70° C. for 5 hours. After cooling, the reaction was diluted with EtOAc and washed with water. The aqueous phase was extracted with EtOAc, then the combined organics were dried over Na₂SO₄, filtered and evaporated. The crude product was purified by flash silica chromatography, elution gradient 0 to 10% MeOH in EtOAc. Pure fractions were evaporated to dryness to afford (R)-3-(2-(((3-(fluoromethyl)oxetan-3-yl)methyl)amino)propyl)-2-methylaniline (0.673 g, 42%) as a pale yellow gum. ¹H NMR (500 MHz, CDCl₃, 27° C.) 1.11 (3H, d), 2.04 (3H, s), 2.59-2.71 (1H, m), 2.76-3.10 (4H, m), 4.34-4.52 (4H, m), 4.53-4.68 (2H, m), 6.58 (1H, d), 6.60 (1H, d), 6.95 (1H, t). m/z: ES+ [M+H]+ 267.

Preparation of (1S,3R)-1-(4-bromo-2-methoxyphenyl)-2-((3-(fluoromethyl)oxetan-3-yl)methyl)-3,5-dimethyl-1,2,3,4-tetrahydroisoquinolin-6-amine

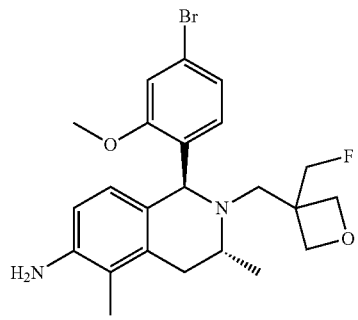 [SMILES: COc1cc(Br)ccc1[C@@H]1c2ccc(N)c(C)c2C[C@@H](C)N1CC1(CF)COC1]

4-Bromo-2-methoxybenzaldehyde (645 mg, 3.00 mmol) was added to a solution of (R)-3-(2-(((3-(fluoromethyl)oxetan-3-yl)methyl)amino)propyl)-2-methylaniline (400 mg, 1.5 mmol) in acetic acid (7.4 mL) and water (135 µl, 7.50 mmol). The reaction was heated to 80° C. for 4 hours. After cooling, the acetic acid was evaporated, then the residue was dissolved in DCM and washed with saturated aqueous NaHCO₃. The organic layer was dried over Na₂SO₄, filtered and evaporated. The residue was dissolved in methanol (5 mL), then hydroxylamine hydrochloride (313 mg, 4.50 mmol) and potassium acetate (588 mg, 6.00 mmol) were added and the reaction was stirred at room temperature for 30 minutes. The volatiles were evaporated, then the residue was dissolved in DCM and water. The layers were separated, then the aqueous was extracted with DCM. The combined organics were dried over Na₂SO₄, filtered and evaporated, then the crude product was purified by flash silica chromatography, elution gradient 0 to 50% EtOAc in heptane. Product containing fractions were evaporated to dryness to afford (1S,3R)-1-(4-bromo-2-methoxyphenyl)-2-((3-(fluoromethyl)oxetan-3-yl)methyl)-3,5-dimethyl-1,2,3,4-tetrahydroisoquinolin-6-amine (302 mg, 43%) as a beige solid. ¹H NMR (500 MHz, CDCl₃, 27° C.) 1.01 (3H, d), 2.07 (3H, s), 2.45 (1H, dd), 2.61-2.73 (1H, m), 2.86 (1H, d), 3.01-3.14 (1H, m), 3.54 (2H, s), 3.87 (3H, s), 4.41-4.48 (2H, m), 4.51 (1H, d), 4.53-4.60 (2H, m), 4.67 (1H, d), 4.73-4.81 (1H, m), 5.00 (1H, s), 6.47 (1H, s), 6.47 (1H, s), 6.61 (1H, d), 6.88 (1H, dd), 7.01 (1H, d). m/z: ES+ [M+H]+ 463.

Preparation of (6S,8R)-6-(4-bromo-2-methoxyphenyl)-7-((3-(fluoromethyl)oxetan-3-yl)methyl)-8-methyl-6,7,8,9-tetrahydro-3H-pyrazolo[4,3-f]isoquinoline

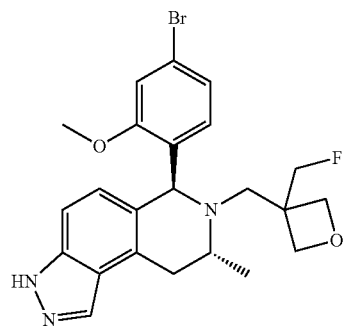 [SMILES: COc1cc(Br)ccc1[C@@H]1c2ccc3[nH]ncc3c2C[C@@H](C)N1CC1(CF)COC1]

Sodium nitrite (39.1 mg, 0.57 mmol) was added in water (0.5 mL) to a cooled solution of (1S,3R)-1-(4-bromo-2-methoxyphenyl)-2-((3-(fluoromethyl)oxetan-3-yl)methyl)-3,5-dimethyl-1,2,3,4-tetrahydroisoquinolin-6-amine (250 mg, 0.54 mmol) in propionic acid (2.2 mL) at −15° C. (dry-ice/acetone bath). After stirring for 30 mins, ice-cold toluene (15 mL) was added and the reaction was stirred at 0° C. for 15 min and then warmed to room temperature for 1 hour. Water (15 mL) was added and the layers were separated. The aqueous layer was extracted with EtOAc (2×15 mL), then the combined organics were washed with saturated aqueous sodium chloride, dried over Na₂SO₄, filtered and evaporated. The crude product was purified by flash silica chromatography, elution gradient 0 to 50% EtOAc in heptane. Product containing fractions were evaporated to dryness to afford (6S,8R)-6-(4-bromo-2-methoxyphenyl)-7-((3-(fluoromethyl)oxetan-3-yl)methyl)-8-methyl-6,7,8,9-tetrahydro-3H-pyrazolo[4,3-f]isoquinoline (188 mg, 74%) as a beige solid. ¹H NMR (500 MHz, CDCl₃, 27° C.) 1.07 (3H, d), 2.70 (1H, d), 2.87 (1H, dd), 2.97 (1H, d), 3.11-3.18 (1H, m), 3.18-3.27 (1H, m), 3.90 (3H, s), 4.42-4.52 (3H, m), 4.59 (1H, d), 4.63-4.87 (2H, m), 5.19 (1H, s), 6.63 (1H, d), 6.76 (1H, d), 6.88 (1H, dd), 7.05 (1H, d), 7.19 (1H, d), 8.09 (1H, d). m/z: ES+ [M+H]+ 474.

Preparation of (6S,8R)-6-(4-bromo-2-methoxyphenyl)-7-((3-(fluoromethyl)oxetan-3-yl)methyl)-8-methyl-3-(tetrahydro-2H-pyran-2-yl)-6,7,8,9-tetrahydro-3H-pyrazolo[4,3-f]isoquinoline

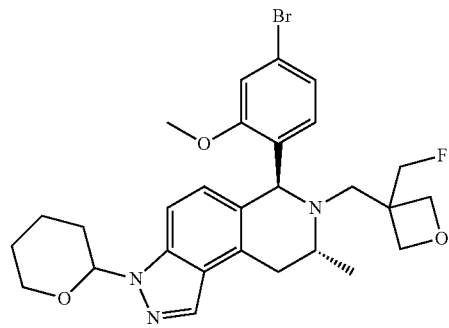 [SMILES: COc1cc(Br)ccc1[C@@H]1c2ccc3c(cnn3C3CCCCO3)c2C[C@@H](C)N1CC1(CF)COC1]

3,4-Dihydro-2H-pyran (67.3 µl, 0.74 mmol) was added to a solution of (6S,8R)-6-(4-bromo-2-methoxyphenyl)-7-((3-(fluoromethyl)oxetan-3-yl)methyl)-8-methyl-6,7,8,9-tetrahydro-3H-pyrazolo[4,3-f]isoquinoline (175 mg, 0.37 mmol) and 4-methylbenzenesulfonic acid hydrate (14.0 mg, 0.07 mmol) in DCM (3.6 mL) and the reaction was stirred at 40° C. for 2 hours. After cooling, the reaction was diluted with DCM and washed with saturated aqueous NaHCO$_3$, dried over Na$_2$SO$_4$, filtered and evaporated. The residue was passed through a silica plug, eluting with EtOAc/heptane (1:1). The filtrate was evaporated to afford (6S,8R)-6-(4-bromo-2-methoxyphenyl)-7-((3-(fluoromethyl)oxetan-3-yl)methyl)-8-methyl-3-(tetrahydro-2H-pyran-2-yl)-6,7,8,9-tetrahydro-3H-pyrazolo[4,3-f]isoquinoline (196 mg, 95%) as a beige solid, which was used directly in the next stage. m/z: ES+ [M+H]+ 558.

Example 11

N-(3,5-difluoro-4-((6S,8R)-7-((1-fluorocyclopropyl)methyl)-8-methyl-6,7,8,9-tetrahydro-3H-pyrazolo[4,3-f]isoquinolin-6-yl)phenyl)-1-(3-fluoropropyl)azetidin-3-amine

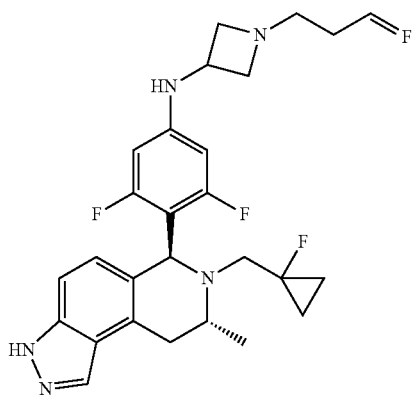

4N HCl in dioxane (0.25 mL, 0.99 mmol) was added to a solution of N-(3,5-difluoro-4-((6S,8R)-7-((1-fluorocyclopropyl)methyl)-8-methyl-3-(tetrahydro-2H-pyran-2-yl)-6,7,8,9-tetrahydro-3H-pyrazolo[4,3-f]isoquinolin-6-yl)phenyl)-1-(3-fluoropropyl)azetidin-3-amine (58 mg, 0.10 mmol) in methanol (0.30 mL) and the reaction was stirred at room temperature for 2 hours. The volatiles were evaporated and the residue was suspended in saturated aqueous NaHCO$_3$ (30 mL) and extracted with DCM (×2). The organic phase was dried over MgSO$_4$, filtered and evaporated. The crude residue was puried by silica gel chromatography and eluted using a gradient of 0 to 10% 1M NH$_3$/MeOH in DCM. Product containing fractions were evaporated to dryness to afford N-(3,5-difluoro-4-((6S,8R)-7-((1-fluorocyclopropyl)methyl)-8-methyl-6,7,8,9-tetrahydro-3H-pyrazolo[4,3-f]isoquinolin-6-yl)phenyl)-1-(3-fluoropropyl)azetidin-3-amine (45.4 mg, 91%) as a white solid. $^1$H NMR (500 MHz, CDCl$_3$, 27° C.) 0.47 (2H, dtd), 0.95 (2H, dt), 1.08 (3H, d), 1.68-1.85 (2H, m), 2.59 (2H, s), 2.69 (1H, dd), 2.91 (3H, dq), 3.14 (1H, dd), 3.43 (1H, dd), 3.69 (2H, q), 3.81 (1H, dd), 4.01 (1H, q), 4.28 (1H, d), 4.43 (1H, t), 4.53 (1H, t), 5.19 (1H, s), 5.96 (2H, d), 6.82 (1H, d), 7.15 (1H, d), 8.06 (1H, d), 10.36 (1H, s). m/z (ES+), [M+H]+=502.

The N-(3,5-difluoro-4-((6S,8R)-7-((1-fluorocyclopropyl)methyl)-8-methyl-6,7,8,9-tetrahydro-3H-pyrazolo[4,3-f]isoquinolin-6-yl)phenyl)-1-(3-fluoropropyl)azetidin-3-amine was prepared as follows:

Preparation of (1S,3R)-1-(4-bromo-2,6-difluorophenyl)-2-((1-fluorocyclopropyl)methyl)-3,5-dimethyl-1,2,3,4-tetrahydroisoquinolin-6-amine

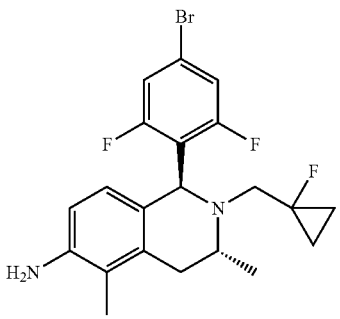 [SMILES: Cc1c(N)ccc2c1C[C@@H](C)N(CC1(F)CC1)[C@@H]2c1c(F)cc(Br)cc1F]

(R)-3-(2-(((1-Fluorocyclopropyl)methyl)amino)propyl)-2-methylaniline (0.35 g, 1.48 mmol) and 4-bromo-2,6-difluorobenzaldehyde (0.33 g, 1.48 mmol) in a mixture of H$_2$O (0.13 mL, 7.40 mmol) and acetic acid (5.79 mL) were heated at 80° C. for 7 hours. The solvent was evaporated and the residue was treated with HCl (1N, 10 mL) and was stirred at room temperature for 1 hour. To the reaction was added solid Na$_2$CO$_3$ until the reaction pH was >8. The mixture was diluted with H$_2$O (40 mL) and extracted twice with EtOAc (2×50 mL). The organic phase was dried over MgSO$_4$, filtered, concentrated and was purified by silica chromatography (10 to 70% EtOAc in heptanes) to afford (1S,3R)-1-(4-bromo-2,6-difluorophenyl)-2-((1-fluorocyclopropyl)methyl)-3,5-dimethyl-1,2,3,4-tetrahydroisoquinolin-6-amine (0.285 g, 44%) as a pale yellow gum. $^1$H NMR (500 MHz, CDCl$_3$, 27° C.) 0.44 (2H, dq), 0.91-0.95 (1H, m), 0.95-0.99 (1H, m), 1.02 (3H, d), 2.06 (3H, s), 2.50-2.65 (2H, m), 3.00-3.15 (2H, m), 3.50 (2H, s), 3.69 (1H, d), 5.17 (1H, s), 6.42 (2H, s), 6.97 (1H, d), 6.99 (1H, d). m/z (ES+), [M+H]+=439.

Preparation of (6S,8R)-6-(4-bromo-2,6-difluorophenyl)-7-((1-fluorocyclopropyl)methyl)-8-methyl-6,7,8,9-tetrahydro-3H-pyrazolo[4,3-f]isoquinoline

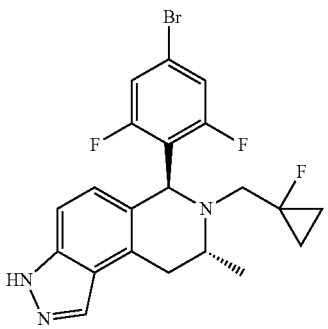 [SMILES: C[C@@H]1Cc2c(ccc3[nH]ncc23)[C@@H](c2c(F)cc(Br)cc2F)N1CC1(F)CC1]

(1S,3R)-1-(4-Bromo-2,6-difluorophenyl)-2-((1-fluorocyclopropyl)methyl)-3,5-dimethyl-1,2,3,4-tetrahydroisoquinolin-6-amine (0.280 g, 0.64 mmol) in propionic acid (2.66 mL) was cooled to −17° C. (dry ice/acetone bath). Sodium nitrite (0.044 g, 0.64 mmol) in water (0.53 mL) was added dropwise and the reaction mixture was stirred at −17° C. for 30 minutes. The reaction mixture was diluted with ice-cold toluene (15 mL) and stirred at 4° C. for 15 minutes. The mixture was then stirred and warmed to room temperature for 45 minutes. The reaction mixture was washed with water (2×15 mL), the combined aqueous phases were washed with EtOAc (2×10 mL), the combined organics washed with saturated aqueous sodium chloride (1×20 mL), dried (MgSO₄), filtered and the filtrate evaporated to an orange-brown oil. The crude material was purified by flash silica chromatography, elution gradient 0-40% EtOAc in heptane to afford (6S,8R)-6-(4-bromo-2,6-difluorophenyl)-7-((1-fluorocyclopropyl)methyl)-8-methyl-6,7,8,9-tetrahydro-3H-pyrazolo[4,3-f]isoquinoline (0.216 g, 75%) as an off-white solid. ¹H NMR (500 MHz, CDCl₃, 27° C.) 0.46 (2H, dddd), 0.91-1.04 (2H, m), 1.07 (3H, d), 2.66 (1H, dd), 2.95 (1H, dd), 3.15 (1H, dd), 3.46 (1H, dd), 3.83 (1H, dd), 5.32 (1H, s), 6.76 (1H, d), 7.00 (2H, d), 7.18 (1H, d), 8.09 (1H, d), 10.52 (1H, s). m/z (ES+), [M+H]+=450.

Preparation of (6S,8R)-6-(4-bromo-2,6-difluorophenyl)-7-((1-fluorocyclopropyl)methyl)-8-methyl-3-(tetrahydro-2H-pyran-2-yl)-6,7,8,9-tetrahydro-3H-pyrazolo[4,3-f]isoquinoline and (6S,8R)-6-(4-bromo-2,6-difluorophenyl)-7-((1-fluorocyclopropyl)methyl)-8-methyl-2-(tetrahydro-2H-pyran-2-yl)-6,7,8,9-tetrahydro-3H-pyrazolo[4,3-f]isoquinoline

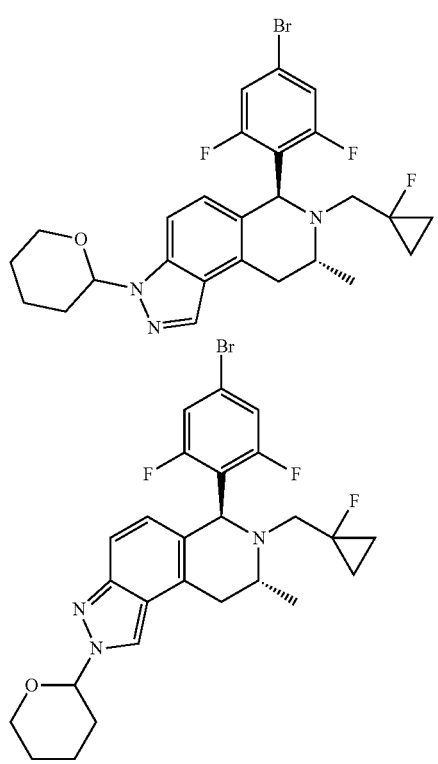

A microwave vial was charged with (6S,8R)-6-(4-bromo-2,6-difluorophenyl)-7-((1-fluorocyclopropyl)methyl)-8-methyl-6,7,8,9-tetrahydro-3H-pyrazolo[4,3-f]isoquinoline (216 mg, 0.48 mmol), 4-methylbenzenesulfonic acid hydrate (9.1 mg, 0.05 mmol), 3,4-dihydro-2H-pyran (0.07 mL, 0.72 mmol) and DCM (2 mL). The mixture was heated in a microwave at 80° C. for 20 minutes. A further (0.035 mL, 0.36 mmol) of 3,4-dihydro-2H-pyran was added and the reaction was heated to 85° C. for a further 15 minutes. The reaction was diluted with DCM and washed with saturated aqueous NaHCO₃, then the organic layer was dried over Na₂SO₄, filtered and concentrated. The crude product was purified by flash silica chromatography, elution gradient 0 to 50% EtOAc in heptane. Product containing fractions were evaporated to dryness to afford two regioisomeric THP-protected products (6S,8R)-6-(4-bromo-2,6-difluorophenyl)-7-((1-fluorocyclopropyl)methyl)-8-methyl-3-(tetrahydro-2H-pyran-2-yl)-6,7,8,9-tetrahydro-3H-pyrazolo[4,3-f]isoquinoline and (6S,8R)-6-(4-bromo-2,6-difluorophenyl)-7-((1-fluorocyclopropyl)methyl)-8-methyl-2-(tetrahydro-2H-pyran-2-yl)-6,7,8,9-tetrahydro-3H-pyrazolo[4,3-f]isoquinoline (237 mg, 92%) as a pale yellow gum (data for major isomer given). ¹H NMR (500 MHz, CDCl₃, 27° C.) 0.35-0.55 (2H, m), 0.96 (2H, ddd), 1.05 (3H, dd), 1.58-1.84 (3H, m), 1.97-2.32 (3H, m), 2.64 (1H, dd), 2.77 (1H, dd), 3.14 (1H, ddd), 3.29-3.54 (1H, m), 3.62-3.91 (2H, m), 3.96-4.25 (1H, m), 5.26 (1H, d), 5.65 (1H, ddd), 6.64 (1H, d), 7.00 (2H, d), 7.26-7.45 (1H, m), 8.13 (1H, dd). m/z (ES+), [M+H]+=534.

Preparation of N-(3,5-difluoro-4-((6S,8R)-7-((1-fluorocyclopropyl)methyl)-8-methyl-2-(tetrahydro-2H-pyran-2-yl)-6,7,8,9-tetrahydro-3H-pyrazolo[4,3-f]isoquinolin-6-yl)phenyl)-1-(3-fluoropropyl)azetidin-3-amine

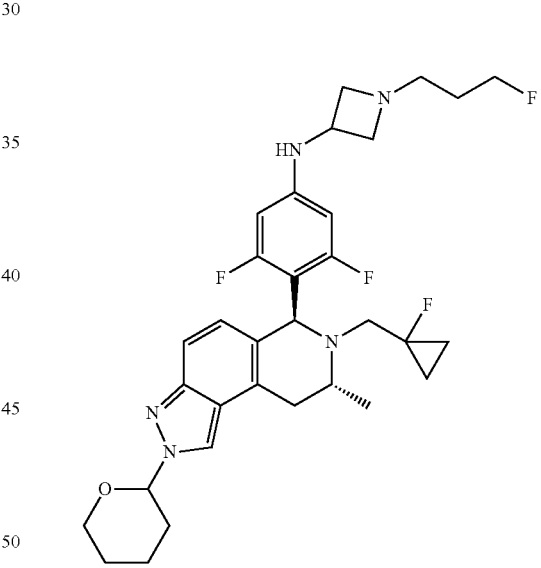

[(2-Di-cyclohexylphosphino-3,6-dimethoxy-2′,4′,6′-tri-isopropyl-1,1′-biphenyl)-2-(2′-amino-1,1′-biphenyl)]palladium(II) methanesulfonate (BrettPhos Pd G3) (5.0 mg, 5.54 μmol) was added to a suspension of (6S,8R)-6-(4-bromo-2,6-difluorophenyl)-7-((1-fluorocyclopropyl)methyl)-8-methyl-3-(tetrahydro-2H-pyran-2-yl)-6,7,8,9-tetrahydro-3H-pyrazolo[4,3-f]isoquinoline and (6S,8R)-6-(4-bromo-2,6-difluorophenyl)-7-((1-fluorocyclopropyl)methyl)-8-methyl-2-(tetrahydro-2H-pyran-2-yl)-6,7,8,9-tetrahydro-3H-pyrazolo[4,3-f]isoquinoline (37 mg, 0.07 mmol), 1-(3-fluoropropyl)azetidin-3-amine (22.9 mg, 0.17 mmol) and sodium tert-butoxide (13.3 mg, 0.14 mmol) in degassed 1,4-dioxane (0.58 mL) and the reaction was heated to 95° C. for 1.5 hours in the microwave. The reaction mixture was diluted with EtOAc, filtered through celite and evaporated to dryness. The crude product was purified by flash silica chromatography, elution gradient 0 to 10% 1M NH$_3$/MeOH in DCM. Pure fractions were evaporated to dryness to afford N-(3,5-difluoro-4-((6S,8R)-7-((1-fluorocyclopropyl)methyl)-8-methyl-2-(tetrahydro-2H-pyran-2-yl)-6,7,8,9-tetrahydro-3H-pyrazolo[4,3-f]isoquinolin-6-yl)phenyl)-1-(3-fluoropropyl)azetidin-3-amine (18.0 mg, 44%) as a colourless dry film. $^1$H NMR (500 MHz, CDCl$_3$, 27° C.) 0.38-0.54 (2H, m), 0.94 (2H, ddd), 1.06 (3H, dd), 1.67-1.82 (4H, m), 2.04-2.25 (4H, m), 2.59 (2H, t), 2.63-2.77 (2H, m), 2.89 (2H, dd), 3.14 (1H, s), 3.29-3.37 (1H, m), 3.70 (2H, q), 3.75-3.81 (2H, m), 4.00 (1H, q), 4.12-4.17 (1H, m), 4.22 (1H, d), 4.43 (1H, t), 4.52 (1H, t), 5.10 (1H, s), 5.55-5.74 (1H, m), 5.96 (2H, d), 6.71 (1H, d), 7.28-7.44 (1H, m), 8.10 (1H, dd). m/z (ES+), [M+H]+=586.

Examples 12 & 13

Preparation of individual diastereoisomers of (6S,8R)-7-(2-fluoro-3-methoxy-2-methylpropyl)-6-(4-(1-(3-fluoropropyl)azetidin-3-yloxy)-2-methoxyphenyl)-8-methyl-6,7,8,9-tetrahydro-3H-pyrazolo[4,3-f]isoquinoline

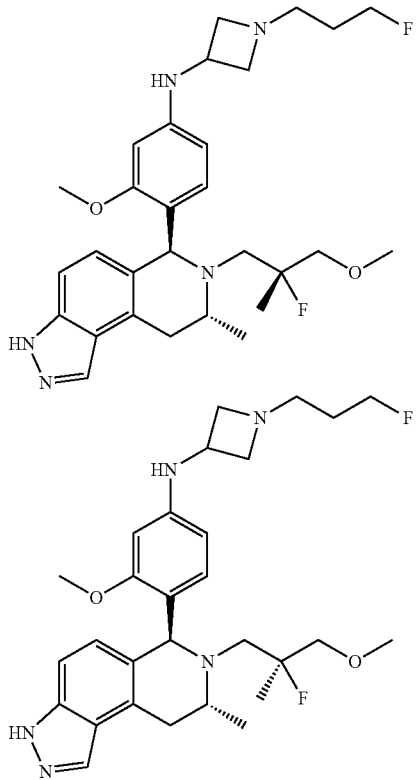 [SMILES: COC[C@](C)(F)CN1[C@H](c2ccc(NC3CN(CCCF)C3)cc2OC)c2ccc3[nH]ncc3c2C[C@H]1C ; COC[C@@](C)(F)CN1[C@H](c2ccc(NC3CN(CCCF)C3)cc2OC)c2ccc3[nH]ncc3c2C[C@H]1C]

DMF (0.66 mL) followed by DIPEA (23.9 µl, 0.14 mmol) were added to a flask charged with (6S,8R)-6-(4-(azetidin-3-yloxy)-2-methoxyphenyl)-7-(2-fluoro-3-methoxy-2-methylpropyl)-8-methyl-6,7,8,9-tetrahydro-3H-pyrazolo[4,3-f]isoquinoline (32 mg, 0.07 mmol). Into the stirred reaction was injected dropwise 1-fluoro-3-iodopropane (13.5 mg, 0.07 mmol) and the reaction was stirred at room temperature overnight. The reaction was evaporated to dryness and the residue was purified by flash silica chromatography, elution gradient 0 to 10% 1M NH$_3$/MeOH in DCM. Product containing fractions were evaporated to dryness to afford the product as a diastereoisomeric mixture. The diastereoisomers were separated by chiral preparative SFC (Phenomonex Lux C4 column, 5µ silica, 30 mm diameter, 250 mm length), using decreasingly isocratic 40% MeOH+ 0.1% NH$_3$ in CO$_2$ as eluent to afford the first eluting isomer (8.0 mg, 22%) and the second eluting isomer (8.0 mg, 22%) as pale yellow dry films.

Isomer 1: $^1$H NMR (500 MHz, CDCl$_3$, 27° C.) 1.06 (3H, d), 1.28 (3H, d), 1.72-1.83 (2H, m), 2.47 (1H, dd), 2.63 (2H, t), 2.8-2.95 (2H, m), 3.03-3.11 (2H, m), 3.19 (2H, s), 3.33 (3H, s), 3.56 (1H, dd), 3.67 (1H, d), 3.79 (2H, q), 3.86 (3H, s), 4.44 (1H, t), 4.53 (1H, t), 4.74 (1H, t), 5.32 (1H, s), 6.10 (1H, d), 6.41 (1H, d), 6.69 (1H, d), 6.76 (1H, d), 7.13 (1H, d), 8.05 (1H, d), 10.20 (1H, s). m/z (ES+), [M+H]+=529;

Isomer 2: $^1$H NMR (500 MHz, CDCl$_3$, 27° C.) 1.06 (3H, d), 1.25 (3H, d), 1.70-1.82 (2H, m), 2.45-2.56 (1H, m), 2.63 (2H, t), 2.78-2.91 (2H, m), 3.02-3.11 (2H, m), 3.18 (1H, d), 3.36 (3H, s), 3.42 (1H, dd), 3.47-3.55 (1H, m), 3.62 (1H, d), 3.74-3.82 (2H, m), 3.86 (3H, s), 4.43 (1H, t), 4.53 (1H, t), 4.73 (1H, t), 5.36 (1H, s), 6.08 (1H, dd), 6.41 (1H, d), 6.67 (1H, d), 6.79 (1H, d), 7.15 (1H, d), 8.06 (1H, d), 10.20 (1H, s). m/z (ES+), [M+H]+=529.

The (6S,8R)-6-(4-(azetidin-3-yloxy)-2-methoxyphenyl)-7-(2-fluoro-3-methoxy-2-methylpropyl)-8-methyl-6,7,8,9-tetrahydro-3H-pyrazolo[4,3-f]isoquinoline was prepared as follows:

Preparation of a diastereoisomeric mixture of (6S,8R)-6-(4-(azetidin-3-yloxy)-2-methoxyphenyl)-7-(2-fluoro-3-methoxy-2-methylpropyl)-8-methyl-6,7,8,9-tetrahydro-3H-pyrazolo[4,3-f]isoquinoline

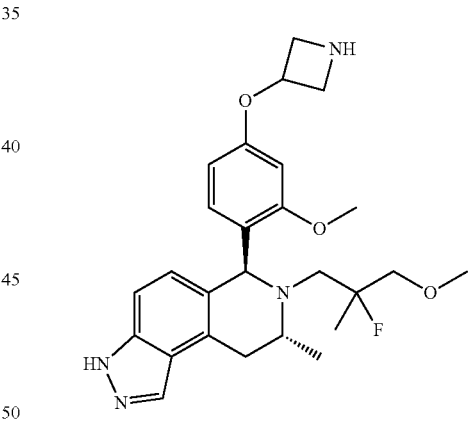

Tert-butyl 3-hydroxyazetidine-1-carboxylate (102 mg, 0.59 mmol), (6S,8R)-6-(4-bromo-2-methoxyphenyl)-7-(2-fluoro-3-methoxy-2-methylpropyl)-8-methyl-3-(tetrahydro-2H-pyran-2-yl)-6,7,8,9-tetrahydro-3H-pyrazolo[4,3-f]isoquinoline (110 mg, 0.20 mmol), tert-butyl 3-hydroxyazetidine-1-carboxylate (102 mg, 0.59 mmol), Pd RockPhos 3rd generation (16.6 mg, 0.02 mmol) and cesium carbonate (128 mg, 0.39 mmol) were suspended in toluene (1.26 mL) and sealed into a microwave tube. The reaction was heated to 95° C. for 20 hours. The reaction mixture was diluted with EtOAc (25 mL) and filtered through celite. The crude product was purified by flash silica chromatography, elution gradient 0 to 100% EtOAc in heptane. The fractions containing the impure product were evaporated to dryness and dissolved in DCM (1.3 mL) to which TFA (378 µl, 4.91 mmol) was added dropwise. The reaction was stirred at room temperature for 2 hours, then volatiles were removed in vacuo. The residue was washed with saturated aqueous NaHCO$_3$ (30 mL) and extracted with DCM (2×30 mL). The combined organic phase was dried over MgSO$_4$, filtered and evaporated. The crude product was purified by flash silica chromatography, elution gradient 0 to 40% 1M NH$_3$/MeOH in DCM. Pure fractions were evaporated to dryness to afford (6S,8R)-6-(4-(azetidin-3-yloxy)-2-methoxyphenyl)-7-(2-fluoro-3-methoxy-2-methylpropyl)-8-methyl-6,7,8,9-tetrahydro-3H-pyrazolo[4,3-f]isoquinoline (35.0 mg, 38%) as a white solid. $^1$H NMR (500 MHz, CDCl$_3$, 27° C.) 1.06 (3H, dd), 1.24-1.35 (3H, m), 2.49 (1H, dt), 2.76-2.96 (2H, m), 3.08-3.27 (2H, m), 3.34 (3H, d), 3.41 (1H, s), 3.53-3.69 (2H, m), 3.69-3.93 (7H, m), 4.81-5.08 (1H, m), 5.34 (1H, d), 6.02-6.12 (1H, m), 6.40 (1H, t), 6.68 (1H, s), 6.77 (1H, dd), 7.13 (1H, d), 8.05 (1H, t). m/z (ES+), [M+H]+=469.

Examples 14 & 15

Preparation of individual diastereoisomers of N-(4-((6S,8R)-7-(2-fluoro-3-methoxy-2-methylpropyl)-8-methyl-6,7,8,9-tetrahydro-3H-pyrazolo[4,3-f]isoquinolin-6-yl)-3-methoxyphenyl)-1-(3-fluoropropyl)azetidin-3-amine

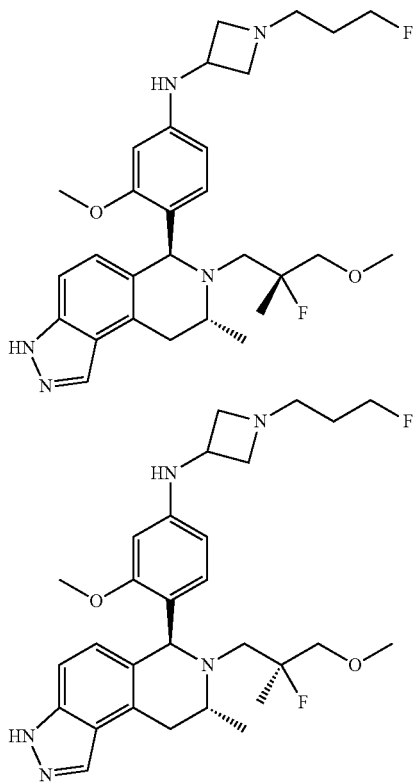 [SMILES: COC[C@](C)(F)CN1[C@H](c2ccc(NC3CN(CCCF)C3)cc2OC)c2ccc3[nH]ncc3c2C[C@H]1C ; COC[C@@](C)(F)CN1[C@H](c2ccc(NC3CN(CCCF)C3)cc2OC)c2ccc3[nH]ncc3c2C[C@H]1C]

1-(3-Fluoropropyl)azetidin-3-amine (175 mg, 1.32 mmol), (6S,8R)-6-(4-bromo-2-methoxyphenyl)-7-(2-fluoro-3-methoxy-2-methylpropyl)-8-methyl-3-(tetrahydro-2H-pyran-2-yl)-6,7,8,9-tetrahydro-3H-pyrazolo[4,3-f]isoquinoline (370 mg, 0.66 mmol) and sodium tert-butoxide (127 mg, 1.32 mmol) were suspended in 1,4-dioxane (8 mL). The mixture was degassed and [(2-di-cyclohexylphosphino-3,6-dimethoxy-2',4',6'-triisopropyl-1,1'-biphenyl)-2-(2'-amino-1,1'-biphenyl)]palladium(II) methanesulfonate (Brett Phos G3) (60 mg, 0.07 mmol) was added. The reaction was heated to 100° C. for 3 hours. The reaction mixture was diluted with DCM (100 mL) and washed with water (100 mL). The organic layer was evaporated. This process was repeated using 114 mg (0.3 mmol) of the aryl bromide. The combined crude products from these reactions was suspended in hydrochloric acid (2M, 5 mL) and stirred at room temperature for 2 hours. The reaction mixture was diluted with water (10 mL) and washed with EtOAc (10 mL). The aqueous phase was basified with 2M aqueous sodium hydroxide and extracted with DCM (2×15 mL). The combined organics were evaporated and the crude product was purified by flash silica chromatography, elution gradient 0 to 20% MeOH in DCM. Fractions were evaporated to dryness to afford the crude product as a mixture of diastereoisomers which were separated by chiral preparative SFC (Phenomonex Lux C4 column, 5µ silica, 30 mm diameter, 250 mm length), using decreasingly isocratic 40% MeOH+0.1% NH$_3$ in CO$_2$ as eluent to afford the first eluting isomer (42 mg, 19%) and the second eluting isomer (29 mg, 13%)

Isomer 1: $^1$H NMR (500 MHz, DMSO, 27° C.) 0.96 (3H, d), 1.20 (3H, d), 2.36-2.44 (1H, m), 2.65-2.85 (3H, m), 2.92 (4H, q), 3.05-3.22 (3H, m), 3.23 (3H, s), 3.24-3.27 (2H, m), 3.46-3.59 (2H, m), 3.78 (3H, s), 4.49 (2H, dd), 5.16 (1H, s), 5.35 (1H, t), 5.95 (1H, dd), 6.23 (1H, d), 6.36 (1H, d), 6.63 (1H, d), 7.16 (1H, d), 8.02 (1H, s), 12.90 (1H, s); $^{19}$F NMR (471 MHz, DMSO, 27° C.) −219.77, −149.11, m/z: ES+ [M+H]+ 528.

Isomer 2: $^1$H NMR (500 MHz, DMSO, 27° C.) 0.97 (3H, d), 1.19 (3H, d), 2.68-2.81 (3H, m), 2.88-2.95 (3H, m), 3.05-3.11 (1H, m), 3.21-3.28 (5H, m), 3.32-3.39 (1H, m), 3.43-3.56 (2H, m), 3.79 (3H, s), 4.49 (2H, dd), 5.17 (1H, s), 5.34 (1H, t), 5.93 (1H, dd), 6.23 (1H, d), 6.35 (1H, d), 6.64 (1H, d), 7.16 (1H, d), 8.02 (1H, s), 12.90 (1H, s); $^{19}$F NMR (471 MHz, DMSO, 27° C.) −219.76, −148.20; m/z: ES+ [M+H]+ 528.

Example 16

Preparation of 2,2-difluoro-3-((6S,8R)-6-(5-((1-(3-fluoropropyl)azetidin-3-yl)amino)pyridin-2-yl)-8-methyl-3,6,8,9-tetrahydro-7H-pyrazolo[4,3-f]isoquinolin-7-yl)propan-1-ol

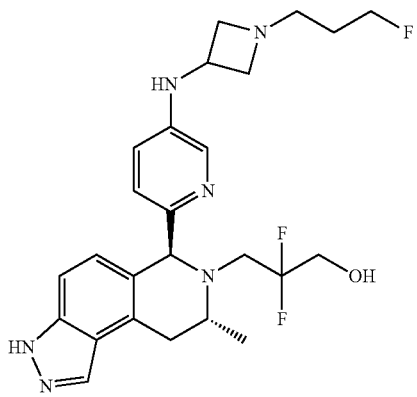 [SMILES: C[C@@H]1Cc2c(ccc3[nH]ncc23)[C@@H](c2ccc(NC3CN(CCCF)C3)cn2)N1CC(F)(F)CO]

Hydrochloric acid (2.0 M, 0.5 mL) was added to 2,2-difluoro-3-((6S,8R)-6-(5-((1-(3-fluoropropyl)azetidin-3-yl)amino)pyridin-2-yl)-8-methyl-3-(tetrahydro-2H-pyran-2-yl)-3,6,8,9-tetrahydro-7H-pyrazolo[4,3-f]isoquinolin-7-yl)

propan-1-ol (0.132 g, 0.23 mmol) and the solution was stirred at room temperature for 3 hours. The reaction mixture was purified by ion exchange chromatography, using an SCX column. The desired product was eluted from the column using 1M NH$_3$/MeOH to afford 2,2-difluoro-3-((6S,8R)-6-(5-((1-(3-fluoropropyl)azetidin-3-yl)amino)pyridin-2-yl)-8-methyl-3,6,8,9-tetrahydro-7H-pyrazolo[4,3-f]isoquinolin-7-yl)propan-1-ol (0.084 g, 75%) as a white solid. $^1$H NMR (500 MHz, DMSO, 27° C.) 1.04 (3H, d), 1.20-1.28 (2H, m) 1.59-1.71 (2H, m), 2.60-2.70 (1H, m), 2.73-2.84 (3H, m), 2.99 (1H, dd), 3.08-3.18 (1H, m), 3.41 (1H, d), 3.61-3.72 (4H, m), 3.93 (1H, d), 4.44 (2H, dt), 4.94 (1H, s), 5.42 (1H, t), 6.21 (1H, d), 6.78-6.82 (2H, m), 6.90 (1H, d), 7.21 (1H, d), 7.74 (1H, d), 8.03 (1H, s), 12.94 (1H, s); $^1$H NMR (471 MHz, DMSO, 27° C.) −218.24, −108.31; m/z: ES+ [M+H]+ 489.

The 2,2-difluoro-3-((6S,8R)-6-(5-((1-(3-fluoropropyl)azetidin-3-yl)amino)pyridin-2-yl)-8-methyl-3-(tetrahydro-2H-pyran-2-yl)-3,6,8,9-tetrahydro-7H-pyrazolo[4,3-f]isoquinolin-7-yl)propan-1-ol was prepared as follows:

Preparation of (1S,3R)-1-(5-bromopyridin-2-yl)-2-(3-((tert-butyldiphenylsilyl)oxy)-2,2-difluoropropyl)-3,5-dimethyl-1,2,3,4-tetrahydroisoquinolin-6-amine

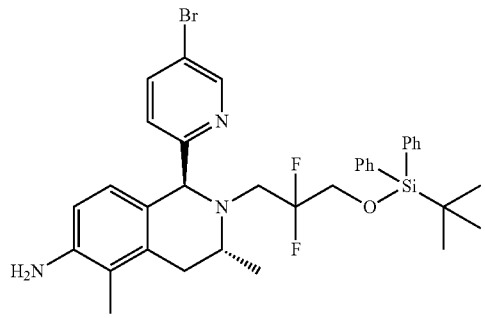 [SMILES: Cc1c(N)ccc2c1C[C@@H](C)N(CC(F)(F)CO[Si](c1ccccc1)(c1ccccc1)C(C)(C)C)[C@@H]2c1ccc(Br)cn1]

(R)-3-(2-((3-((Tert-butyldiphenylsilyl)oxy)-2,2-difluoropropyl)amino)propyl)-2-methylaniline (1.20 g, 2.42 mmol) and 5-bromopicolinaldehyde (0.944 g, 5.07 mmol) were heated in acetic acid (12 mL) and water (0.22 mL, 12.08 mmol) to 70° C. for 30 minutes. The reaction mixture was evaporated and the residue was redissolved in ethanol (10 mL). Potassium acetate (0.594 g, 6.05 mmol) and hydroxylamine hydrochloride (0.252 g, 3.63 mmol) were added. The reaction mixture was stirred at room temperature for 30 minutes then evaporated and the residue partitioned between DCM (30 mL) and saturated aqueous sodium bicarbonate (30 mL). The organic phase was evaporated and the crude product was purified by flash silica chromatography, elution gradient 0 to 50% EtOAc in heptane to afford (1S,3R)-1-(5-bromopyridin-2-yl)-2-(3-((tert-butyldiphenylsilyl)oxy)-2,2-difluoropropyl)-3,5-dimethyl-1,2,3,4-tetrahydroisoquinolin-6-amine (1.090 g, 68%) as a colourless gum. $^1$H NMR (500 MHz, DMSO, 27° C.) 0.96 (9H, s), 0.98 (3H, d), 1.94 (3H, s), 2.40 (1H, dd), 2.57 (1H, dd), 2.66-2.78 (1H, m), 3.11-3.22 (2H, m), 3.84-3.93 (1H, m), 3.95-4.05 (1H, m), 4.69 (2H, s), 4.91 (1H, s), 6.39 (1H, d), 6.42 (1H, d), 6.99 (1H, d), 7.39-7.48 (6H, m), 7.59 (4H, ddd), 7.80 (1H, dd), 8.51 (1H, dd); $^1$H NMR (471 MHz, DMSO, 27° C.) −109.84 (d), −108.39 (d); m/z: ES+ [M+H]+ 664/666.

Preparation of (6S,8R)-6-(5-bromopyridin-2-yl)-7-(3-((tert-butyldiphenylsilyl)oxy)-2,2-difluoropropyl)-8-methyl-6,7,8,9-tetrahydro-3H-pyrazolo[4,3-f]isoquinoline

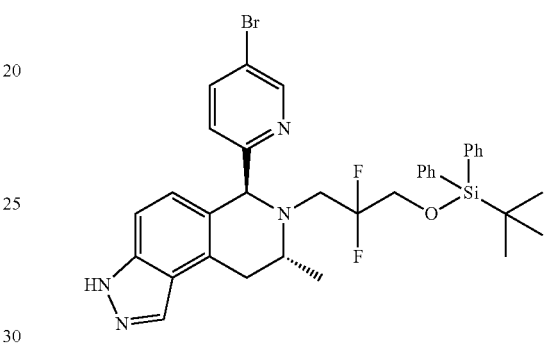

Sodium nitrite (119 mg, 1.72 mmol) in water (1.0 mL) was added to an ice cooled solution of (1S,3R)-1-(5-bromopyridin-2-yl)-2-(3-((tert-butyldiphenylsilyl)oxy)-2,2-difluoropropyl)-3,5-dimethyl-1,2,3,4-tetrahydroisoquinolin-6-amine (1.09 g, 1.64 mmol) and para-toluenesulfonic acid hydrate (0.94 g, 4.92 mmol) in acetonitrile (6 mL). The reaction was stirred for 15 minutes and then warmed to room temperature for 45 minutes. After cooling back to 4° C., tetrabutylammonium acetate (2.54 g, 8.20 mmol) in ice-cold MeCN (40 mL) was added and the reaction was stirred for 15 minutes before warming to room temperature for a further 30 minutes, EtOAc (120 mL) was added followed by 2 M NaOH (100 mL). The organic phase was washed with saturated aqueous sodium chloride, dried (Na$_2$SO$_4$) and evaporated. The crude product was purified by flash silica chromatography, elution gradient 0 to 50% EtOAc in heptane to afford (6S,8R)-6-(5-bromopyridin-2-yl)-7-(3-((tert-butyldiphenylsilyl)oxy)-2,2-difluoropropyl)-8-methyl-6,7,8,9-tetrahydro-3H-pyrazolo[4,3-f]isoquinoline (0.330 g, 30%) as a light brown foam.

$^1$H NMR (500 MHz, DMSO, 27° C.) 0.97 (9H, s), 1.06 (3H, d), 2.75-2.91 (2H, m), 2.99-3.06 (1H, m), 3.34-3.41 (2H, m), 3.88-4.01 (2H, m), 5.12 (1H, s), 6.83 (1H, d), 7.12 (1H, d), 7.26 (1H, d), 7.39-7.45 (4H, m), 7.46-7.50 (2H, m), 7.56-7.62 (4H, m), 7.85 (1H, dd), 8.07-8.09 (1H, m), 8.54 (1H, dd), 13.02 (1H, s); $^{19}$F NMR (471 MHz, DMSO, 27° C.) −110.01 (d), −108.72 (d); m/z: ES+ [M+H]+ 675/677.

Preparation of a diastereoisomeric mixture of (6S,8R)-6-(5-bromopyridin-2-yl)-7-(3-((tert-butyldiphenylsilyl)oxy)-2,2-difluoropropyl)-8-methyl-3-(tetrahydro-2H-pyran-2-yl)-6,7,8,9-tetrahydro-3H-pyrazolo[4,3-f]isoquinoline

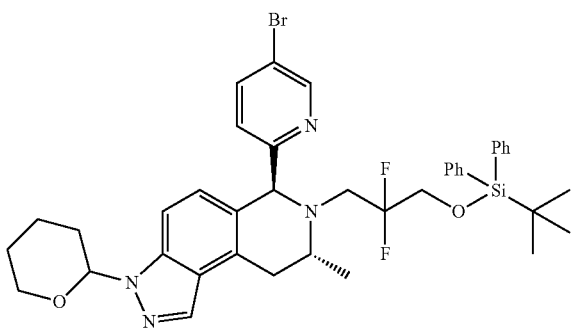 [SMILES: C[C@@H]1Cc2c(ccc3c2cnn3C2CCCCO2)[C@@H](c2ccc(Br)cn2)N1CC(F)(F)CO[Si](c1ccccc1)(c1ccccc1)C(C)(C)C]

To a solution of (6S,8R)-6-(5-bromopyridin-2-yl)-7-(3-((tert-butyldiphenylsilyl)oxy)-2,2-difluoropropyl)-8-methyl-6,7,8,9-tetrahydro-3H-pyrazolo[4,3-f]isoquinoline (0.330 g, 0.49 mmol) and 3,4-dihydro-2H-pyran (0.13 mL, 1.47 mmol) in DCM (5 mL) was added para toluenesulfonic acid hydrate (93 mg, 0.49 mmol) and the reaction heated at 40° C. for 1 hour. The reaction mixture was diluted with DCM (20 mL) and washed with saturated aqueous sodium bicarbonate (20 mL). The organic phase was evaporated to a dark brown oil and the crude product was purified by flash silica chromatography, elution gradient 0 to 50% EtOAc in heptane to afford (6S,8R)-6-(5-bromopyridin-2-yl)-7-(3-((tert-butyldiphenylsilyl)oxy)-2,2-difluoropropyl)-8-methyl-3-((S)-tetrahydro-2H-pyran-2-yl)-6,7,8,9-tetrahydro-3H-pyrazolo[4,3-f]isoquinoline (0.330 g, 89%) as a gum. $^{19}$F NMR (471 MHz, DMSO, 27° C.) −110.03 (d), −108.83 (d), −108.79 (d); m/z: ES+ [M+H]+ 759/761.

Preparation of a diastereoisomeric mixture of 6-((6S,8R)-7-(3-((tert-butyldiphenylsilyl)oxy)-2,2-difluoropropyl)-8-methyl-3-(tetrahydro-2H-pyran-2-yl)-6,7,8,9-tetrahydro-3H-pyrazolo[4,3-f]isoquinolin-6-yl)-N-(1-(3-fluoropropyl)azetidin-3-yl)pyridin-3-amine

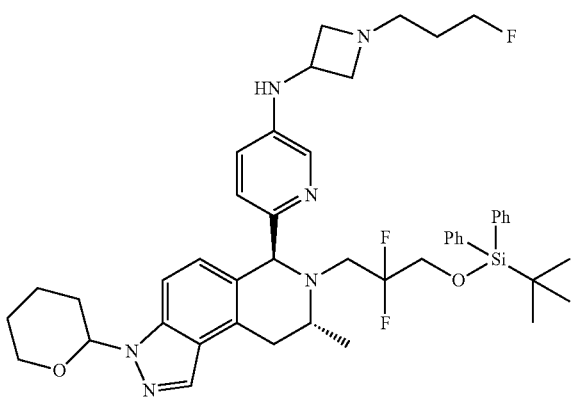 [SMILES: C[C@@H]1Cc2c(ccc3c2cnn3C2CCCCO2)[C@@H](c2ccc(NC3CN(CCCF)C3)cn2)N1CC(F)(F)CO[Si](c1ccccc1)(c1ccccc1)C(C)(C)C]

1-(3-Fluoropropyl)azetidin-3-amine (0.115 g, 0.87 mmol), (6S,8R)-6-(5-bromopyridin-2-yl)-7-(3-((tert-butyldiphenylsilyl)oxy)-2,2-difluoropropyl)-8-methyl-3-(tetrahydro-2H-pyran-2-yl)-6,7,8,9-tetrahydro-3H-pyrazolo[4,3-f]isoquinoline (0.330 g, 0.43 mmol), dicyclohexyl(2',4',6'-triisopropyl-3,6-dimethoxy-[1,1'-biphenyl]-2-yl)phosphane (0.023 g, 0.04 mmol) and sodium tert-butoxide (0.125 g, 1.30 mmol) were suspended in 1,4-dioxane (4 mL). The mixture was degassed and [(2-di-cyclohexylphosphino-3,6-dimethoxy-2',4',6'-triisopropyl-1,1'-biphenyl)-2-(2'-amino-1,1'-biphenyl)]palladium(II) methanesulfonate methanesulfonate (BrettPhos G3) (0.039 g, 0.04 mmol) was added. The reaction was heated to 100° C. for 3 hours. The reaction mixture was diluted with DCM (50 mL) and washed with water (50 mL). The organic layer was evaporated and the crude product was purified by flash silica chromatography, elution gradient 0 to 20% MeOH in DCM to afford 6-((6S,8R)-7-(3-((tert-butyldiphenylsilyl)oxy)-2,2-difluoropropyl)-8-methyl-3-(tetrahydro-2H-pyran-2-yl)-6,7,8,9-tetrahydro-3H-pyrazolo[4,3-f]isoquinolin-6-yl)-N-(1-(3-fluoropropyl)azetidin-3-yl)pyridin-3-amine (0.264 g, 75%) as a yellow gum as a mixture of diastereoisomers. $^{19}$F NMR (471 MHz, DMSO, 27° C.) −218.19, −110.13, −109.44, −108.6, −107.8; m/z: ES+ [M+H]+ 811.

Preparation of a diastereoisomeric mixture of 2,2-difluoro-3-((6S,8R)-6-(5-((1-(3-fluoropropyl)azetidin-3-yl)amino)pyridin-2-yl)-8-methyl-3,6,8,9-tetrahydro-7H-pyrazolo[4,3-f]isoquinolin-7-yl)propan-1-ol

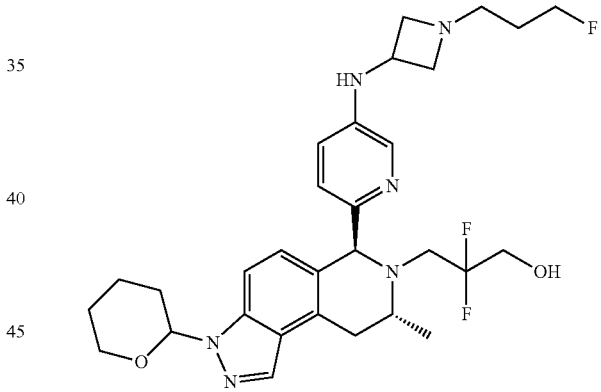

Tetrabutylammonium fluoride (1.0 M in THF, 0.5 mL, 0.50 mmol) was added to solution of 6-((6S,8R)-7-(3-((tert-butyldiphenylsilyl)oxy)-2,2-difluoropropyl)-8-methyl-3-(tetrahydro-2H-pyran-2-yl)-6,7,8,9-tetrahydro-3H-pyrazolo[4,3-f]isoquinolin-6-yl)-N-(1-(3-fluoropropyl)azetidin-3-yl)pyridin-3-amine (0.264 g, 0.33 mmol) in THF (2 mL). The reaction mixture was stirred at room temperature for 4 hours and the reaction mixture was evaporated and the residue partitioned between DCM (20 mL) and water (20 mL). The organic phase was evaporated and the crude product was purified by flash silica chromatography, elution gradient 0 to 20% MeOH in DCM to afford 2,2-difluoro-3-((6S,8R)-6-(5-((1-(3-fluoropropyl)azetidin-3-yl)amino)pyridin-2-yl)-8-methyl-3-(tetrahydro-2H-pyran-2-yl)-3,6,8,9-tetrahydro-7H-pyrazolo[4,3-f]isoquinolin-7-yl)propan-1-ol (0.132 g, 71%) as a colourless dry film as a mixture of diastereoisomers. $^{19}$F NMR (471 MHz, DMSO, 27° C.) −218.19, −108.42, −108.39; m/z: ES+ [M+H]+ 573.

Example 17

Preparation of N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine

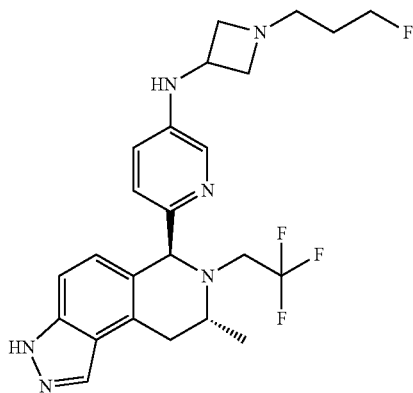 [SMILES: C[C@@H]1Cc2c(ccc3[nH]ncc23)[C@@H](c2ccc(NC3CN(CCCF)C3)cn2)N1CC(F)(F)F]

1-(3-Fluoropropyl)azetidin-3-amine (50 mg, 0.38 mmol), (6S,8R)-6-(5-bromopyridin-2-yl)-8-methyl-3-(tetrahydro-2H-pyran-2-yl)-7-(2,2,2-trifluoroethyl)-6,7,8,9-tetrahydro-3H-pyrazolo[4,3-f]isoquinoline (0.100 g, 0.20 mmol), cesium carbonate (128 mg, 0.39 mmol) and [(2-di-cyclohexylphosphino-3,6-dimethoxy-2',4',6'-triisopropyl-1,1'-biphenyl)-2-(2'-amino-1,1'-biphenyl)]palladium(II) methanesulfonate methanesulfonate (Brett Phos G3) (23 mg, 0.02 mmol) were suspended in 1,4-dioxane (2 mL) and sealed into a microwave tube. The reaction was heated to 100° C. for 4 hours under microwave irradiation. The reaction mixture was diluted with DCM (20 mL) and washed with water (20 mL). The organic layer was evaporated and the crude product was dissolved in DCM (3 mL) and TFA (0.3 mL). The reaction was stirred at room temperature for 1 hour then the reaction mixture was partitioned between DCM (20 mL) and 2M NaOH (20 mL). The organic phase was evaporated and the crude product was purified by flash silica chromatography, elution gradient 0 to 20% MeOH in DCM. Product containing fractions were evaporated to dryness to afford N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine (9.0 mg, 10%) as a colourless dry film. $^{1}$H NMR (500 MHz, CDCl$_3$, 27° C.) 1.14 (3H, d), 1.70-1.82 (2H, m), 2.62 (2H, t), 2.85 (1H, dd), 2.93-3.06 (3H, m), 3.20-3.31 (2H, m), 3.59 (1H, td), 3.73 (2H, dt), 4.10 (2H, dd), 4.48 (2H, dt), 5.03 (1H, s), 6.80 (1H, dd), 6.89 (1H, d), 7.15 (1H, d), 7.21 (1H, d), 7.84 (1H, dd), 8.01 (1H, d); $^{19}$F NMR (471 MHz, DMSO, 27° C.) −224.69, −75.55; m/z: ES+ [M+H]+ 477.

The (6S,8R)-6-(5-bromopyridin-2-yl)-8-methyl-3-(tetrahydro-2H-pyran-2-yl)-7-(2,2,2-trifluoroethyl)-6,7,8,9-tetrahydro-3H-pyrazolo[4,3-f]isoquinoline was prepared as follows.

Preparation of (1S,3R)-1-(5-bromopyridin-2-yl)-3,5-dimethyl-2-(2,2,2-trifluoroethyl)-1,2,3,4-tetrahydroisoquinolin-6-amine

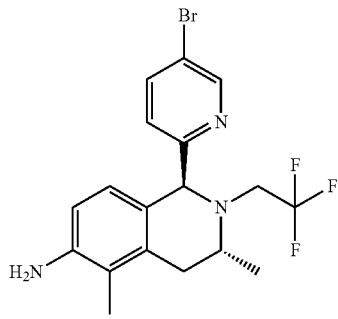 [SMILES: Cc1c(N)ccc2c1C[C@@H](C)N(CC(F)(F)F)[C@@H]2c1ccc(Br)cn1]

(R)-2-Methyl-3-(2-((2,2,2-trifluoroethyl)amino)propyl)aniline (0.290 g, 1.18 mmol) and 5-bromopicolinaldehyde (0.460 g, 2.47 mmol) were heated in acetic acid (6 mL) and water (0.1 mL) to 70° C. for 30 minutes. The reaction mixture was evaporated and the residue dissolved in ethanol (10 mL). Potassium acetate (0.290 g, 2.95 mmol) and hydroxylamine hydrochloride (0.123 g, 1.77 mmol) were added and the reaction mixture was stirred at room temperature for 30 minutes. The reaction mixture was evaporated and the residue was partitioned between DCM (30 mL) and saturated aqueous sodium bicarbonate (30 mL). The organic phase was evaporated and the crude product was purified by flash silica chromatography, elution gradient 0 to 50% EtOAc in heptane to afford (1S,3R)-1-(5-bromopyridin-2-yl)-3,5-dimethyl-2-(2,2,2-trifluoroethyl)-1,2,3,4-tetrahydroisoquinolin-6-amine (0.264 g, 54%) as a colourless dry film. $^{1}$H NMR (500 MHz, DMSO, 27° C.) 1.03 (3H, d), 1.94 (3H, s), 2.45 (1H, dd), 2.67 (1H, dd), 2.90 (1H, dd), 3.22-3.29 (1H, m), 3.49 (1H, dd), 4.69 (2H, s), 4.85 (1H, s), 6.40-6.46 (2H, m), 7.21 (1H, d), 7.95 (1H, dd), 8.56 (1H, dd); $^{19}$F NMR (471 MHz, DMSO, 27° C.) −69.83; m/z: ES+ [M+H]+ 414/416.

Preparation of (6S,8R)-6-(5-bromopyridin-2-yl)-8-methyl-3-(tetrahydro-2H-pyran-2-yl)-7-(2,2,2-trifluoroethyl)-6,7,8,9-tetrahydro-3H-pyrazolo[4,3-f]isoquinoline

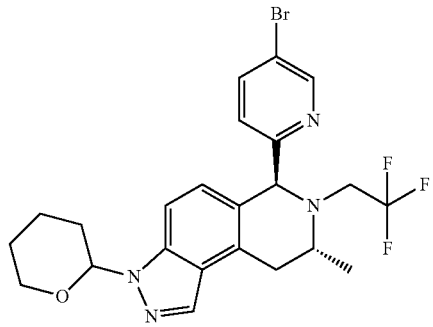 [SMILES: C[C@@H]1Cc2c(ccc3c2cnn3C2CCCCO2)[C@@H](c2ccc(Br)cn2)N1CC(F)(F)F]

Sodium nitrite (0.048 g, 0.70 mmol) was added in water (0.2 mL) to a cooled solution of (1S,3R)-1-(5-bromopyridin-2-yl)-3,5-dimethyl-2-(2,2,2-trifluoroethyl)-1,2,3,4-tetrahydroisoquinolin-6-amine (0.264 g, 0.64 mmol) in propionic acid (2.5 mL) at −10° C. The reaction was stirred for 1 h, then ice-cold EtOAc (10 mL) was added. The reaction was quenched by addition of aqueous saturated sodium bicarbonate (15 mL) and stirred for 15 minutes before being allowed to warm to room temperature. The organic phase was dried (Na₂SO₄) and evaporated to give crude (6S,8R)-6-(5-bromopyridin-2-yl)-8-methyl-7-(2,2,2-trifluoroethyl)-6,7,8,9-tetrahydro-3H-pyrazolo[4,3-f]isoquinoline (0.272 g, 0.64 mmol) as a brown gum. The material was dissolved in DCM (10 mL) and para toluenesulfonic acid hydrate (0.012 g, 0.06 mmol) was added and the mixture heated at 40° C. for 2 hours. The reaction mixture was diluted with DCM (20 mL) and washed with aqueous NaOH (2M, 30 mL). The organic phase was evaporated to a dark brown oil and the crude product was purified by flash silica chromatography, elution gradient 0 to 40% EtOAc in heptane to afford (6S,8R)-6-(5-bromopyridin-2-yl)-8-methyl-3-(tetrahydro-2H-pyran-2-yl)-7-(2,2,2-trifluoroethyl)-6,7,8,9-tetrahydro-3H-pyrazolo[4,3-f]isoquinoline (0.142 g, 44%). m/z: ES+ [M+H]+ 509/511.

Alternative Route #1 to Example 17:

Preparation of N-[1-(3-fluoropropyl)azetidin-3-yl]-6-[(6S,8R)-8-methyl-7-(2,2,2-trifluoroethyl)-3,6,8,9-tetrahydropyrazolo[4,3-f]isoquinolin-6-yl]pyridin-3-amine

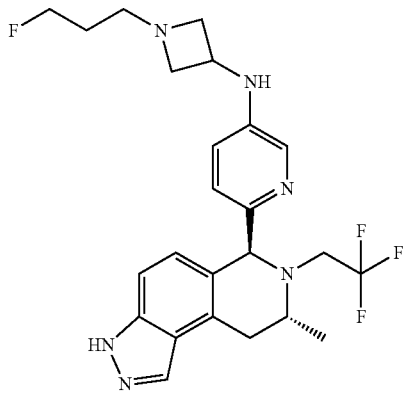 [SMILES: C[C@@H]1Cc2c(ccc3[nH]ncc23)[C@@H](c2ccc(NC3CN(CCCF)C3)cn2)N1CC(F)(F)F]

Trifluoro acetic acid (1.30 L, 17.04 mol) was added to a stirred solution of tert-butyl (1-(3-fluoropropyl)azetidin-3-yl)carbamate (0.50 Kg, 2.04 mol) in DCM (1.50 L) at 0° C. over 0.5 hours. The mixture was allowed to warm to 20° C. and stirred at 20° C. for 2.5 hours. The mixture was heated to 30° C. and stirring was continued for 1 hour. The mixture was concentrated under reduced pressure and the residue was concentrated under reduced pressure from toluene (3×3.00 L). The resulting residue was dissolved in 1,4-dioxane (3.00 L) and treated with 30% sodium 2-methylbutan-2-olate solution in Me-THF (5.50 L, 13.63 mol) over 45 minutes, ensuring the temperature did not exceed 29° C. A solution of 90% w/w (6S,8R)-6-(5-bromopyridin-2-yl)-8-methyl-7-(2,2,2-trifluoroethyl)-6,7,8,9-tetrahydro-3H-pyrazolo[4,3-f]isoquinoline (0.81 Kg, 1.70 mol) in 1,4-dioxane (1.50 L) and BrettPhos Pd G3 (0.077 Kg, 0.085 mol) were added and the atmosphere was replaced with nitrogen using cycles of vacuum and nitrogen (3×). The mixture was heated to 55° C. and stirred at 55° C. for 2.5 hours. The mixture was cooled to 21° C. and an 8% NaHCO₃ solution in water (7.16 L, 6.82 mol) was added, followed by isopropyl acetate (4.50 L). The mixture was stirred for 2-3 minutes and the layers were separated. The organic layer was washed with 8% NaHCO₃ solution in water (7.16 L, 6.82 mol), stirring the mixture for 5 minutes and then the layers were separated. The combined aqueous layers were extracted with isopropyl acetate (4.50 L). The combined organic layers were treated with Silicycle (SiliaMetS-Thiol, 400 g, 1.26 mmol/g, 6 eq vs. Pd) and the mixture was stirred for 16 hours. The solids were removed by filtration through celite, washing the filter-cake with isopropyl acetate. The filtrate was concentrated under reduced pressure (bath temperature 40° C.). The residue was dissolved in ispropyl acetate (5.00 L) and treated with further Silicycle (SiliaMetS-Thiol, 250 g, 1.26 mmol/g, 3.7 eq vs. Pd). The resulting mixture was stirred at 21° C. for 16 hours. The solids were removed by filtration through celite, washing the filter-cake with isopropyl acetate (2.50 L). The filtrate was concentrated under reduced pressure (bath temperature 40° C.) to give a brown foam. The crude product was purified by preparative SFC (Lux C4 column, 50 mm diameter, 250 mm length), using a gradient elution of a EtOH/DEA 100/0.5 in CO₂, 140 bar mobile phase at a flow rate of 400 mL/minute at 40° C.) to give a light brown solid foam. EtOAc (2.00 L) was added and the solution was concentrated under reduced pressure. EtOAc (1.90 L) and heptane (1.90 L) were added and the mixture was seeded at 25° C. The mixture was kept at 25° C. for 1 hour. Heptane (6.50 L) was added over 2 hours to the stirring mixture. The resulting mixture was stirred at 22° C. for 18 hours. The resulting solid was collected by filtration, washing the filter-cake with 1:5 EtOAc/heptane (2.50 L). The solid was sucked dry under a nitrogen blanket for 30 minutes, then dried under vacuum at 40° C. for 9 days to give N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine (626 g, 77%) as an off-white solid. ¹H NMR (600 MHz, DMSO-d₆, 27° C.) 1.07 (3H d) 1.63 (2H, dquin), 2.45 (2H, t), 2.72 (2H, br t), 2.83 (1H, br dd), 2.91-3.00 (1H, m), 3.06 (1H, br dd) 3.42-3.55 (2H, m), 3.58-3.65 (2H, m), 3.92 (1H, dquin) 4.43 (2H, dt) 4.92 (1H, s), 6.22 (1H, d), 6.79 (1H, d) 6.82 (1H, dd), 6.96 (1H, d), 7.21 (1H, d), 7.73 (1H, d), 8.04 (1H, s), 12.96 (1H, s). m/z: ES+ [M+H]+ 477.

Procedures used to prepare the starting materials tert-butyl (1-(3-fluoropropyl)azetidin-3-yl)carbamate and (6S, 8R)-6-(5-bromopyridin-2-yl)-8-methyl-7-(2,2,2-trifluoroethyl)-6,7,8,9-tetrahydro-3H-pyrazolo[4,3-f]isoquinoline are described below.

Preparation of tert-butyl (1-(3-fluoropropyl)azetidin-3-yl)carbamate

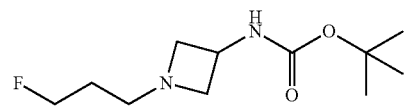 [SMILES: CC(C)(C)OC(=O)NC1CN(CCCF)C1]

Reaction was performed in duplicate and combined for workup: 1-Fluoro-3-iodo-propane (189 g, 1.00 mol) was added to a stirred mixture of tert-butyl N-(azetidin-3-yl)carbamate;hydrochloride (200 g, 0.96 mol) and K₂CO₃ (331 g, 2.40 mol) in THF (1.40 L) and water (0.50 mol) at 20° C. The reaction mixture was heated to 70° C. and stirred at 70° C. for 1.5 hours. The two reaction mixtures combined and added to water (2.5 L) and EtOAc (2.0 L). The mixture was stirred at 21° C. for 3 minutes. The layers were separated and the organic layer was washed with water (2×2.0 L) and saturated ammonium chloride solution (2.0 L). The organic layer was concentrated under reduced pressure to give the crude product. Toluene (400 mL) was added and the mixture was heated to 60° C. Heptane (1.6 L) was added and the mixture was allowed to cool to 21° C. and stirred for 15 minutes. The solid was collected by filtration and sucked dry to give tert-butyl (1-(3-fluoropropyl)azetidin-3-yl)carbamate (230 g, 52%) as a white solid. $^1$H NMR (500 MHz, CDCl$_3$, 27° C.) 1.44 (9H, s), 1.68-1.80 (2H, m), 2.56 (2H, t), 2.87 (2H, s), 3.66 (2H, t), 4.29 (1H, s), 4.43 (1H, t), 4.52 (1H, t), 4.86 (1H, s).

Preparation of 4-bromo-1-tetrahydropyran-2-yl-indazole

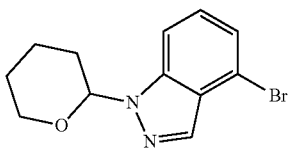 [SMILES: Brc1cccc2c1cnn2C1CCCCO1]

To a slurry of 4-bromo-1H-indazole (1.50 Kg, 7.60 mol) and 3,4-dihydro-2H-pyran (0.96 Kg, 11.40 mol) in DCM (2.40 L) was added 4-methylbenzenesulfonic acid hydrate (11.60 g, 0.06 mol) at 20° C. under nitrogen. The resulting slurry was stirred at between 20° C. and 29° C. (small exotherm) for 110 minutes. The resulting solution was washed with saturated aqueous NaHCO$_3$, (2.00 L), and the organic layer was evaporated under reduced pressure. Hot (70° C.) heptane (2.50 L) was added and the mixture was evaporated under reduced pressure to give a crystalline solid. Purification by recrystallisation from hot (70° C.) heptane (7.00 L) was carried out allowing the solution to cool slowly to 34° C. The resulting solid was collected by filtration and washed with cold heptane to give 4-bromo-1-tetrahydropyran-2-yl-indazole (1.87 Kg, 87%) as a crystalline solid. $^1$H NMR (300 MHz, DMSO-d$_6$, 27° C.) 1.54-1.66 (2H, m), 1.67-1.85 (1H, m), 1.94-2.09 (2H, m), 2.31-2.45 (1H, m), 3.70-3.81 (1H, m), 3.83-3.97 (1H, m), 5.88 (1H, dd), 7.32-7.39 (1H, m), 7.40-7.44 (1H, m), 7.79 (1H, dt), 8.09 (1H, d) m/z: ES– [M–H]$^-$ 282.

Preparation of tert-butyl N-[(1R)-1-methyl-2-(1-tetrahydropyran-2-ylindazol-4-yl)ethyl]carbamate

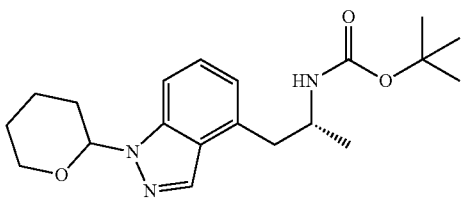 [SMILES: C[C@H](Cc1cccc2c1cnn2C1CCCCO1)NC(=O)OC(C)(C)C]

A solution of 4-bromo-1-(tetrahydro-2H-pyran-2-yl)-1H-indazole (0.70 Kg, 2.49 mol) in THF (3.50 L) was gradually cooled in 10° C. increments to −70° C. 2.5 M Butyllithium in hexanes (1.10 L, 2.74 mol) was added over 70 minutes, keeping the internal temperature below −60° C. The resulting mixture was stirred at −72° C. for 1 hour. 2.3 M hexyllithium in hexanes (0.054 L, 0.12 mol) was added, followed by a solution of tert-butyl (R)-4-methyl-1,2,3-oxathiazolidine-3-carboxylate 2,2-dioxide (652 g, 2.74 mol) in THF (2.80 L) over 2 hours, ensuring the internal temperature did not exceed −58° C. The resulting mixture was stirred at −60° C. for 16 hours. The mixture was slowly warmed to −10° C. over 1.5 hours. Water (2.10 L) was carefully added. The layers were separated and the organic layer was washed with saturated brine (1.40 L) and the organic layer was concentrated under reduced pressure to give an oil. IPA (1.50 L) was added and the mixture was concentrated under reduced pressure to give tert-butyl ((2R)-1-(1-(tetrahydro-2H-pyran-2-yl)-1H-indazol-4-yl)propan-2-yl)carbamate (1.27 Kg, >100%) as a brown oil. This was taken on without further purification. $^1$H NMR (500 MHz, CDCl$_3$, 27° C.) 1.08 (3H, dd), 1.43 (9H, s), 1.63-1.69 (1H, m), 1.73-1.82 (2H, m), 2.07 (1H, dd), 2.17 (1H, dd), 2.53-2.64 (1H, m), 2.95 (1H, s), 3.21 (1H, dt), 3.70-3.80 (1H, m), 3.97-4.12 (2H, m), 4.33-4.49 (1H, m), 5.71 (1H, ddd), 6.96 (1H, dd), 7.31 (1H, ddd), 7.46 (1H, d), 8.13 (1H, s). m/z: ES+ [M.+] 359

Preparation of (2R)-1-(1H-indazol-4-yl)propan-2-amine.dihydrochloride

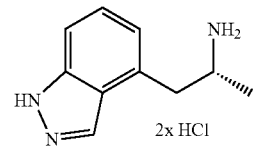

12 M HCl (1.00 L, 12.0 mol) was added over 20 minutes to a stirred solution of tert-butyl((2R)-1-(1-(tetrahydro-2H-pyran-2-yl)-1H-indazol-4-yl)propan-2-yl)carbamate (1.27 Kg, 1.76 mol) in IPA (1.50 L), keeping the internal temperature below 30° C. The resulting mixture was heated to 40° C. and stirred at 40° C. for 16 hours. The temperature was increased to 55° C. and a further portion of 12 M HCl (0.20 L, 2.40 mol) was added and stirring was continued for 7 hours. MTBE (2.50 L) was added and the mixture was allowed to stir at 25° C. for 16 hours. The resulting solid was collected by filtration and the filter-cake was washed with 10% IPA in MTBE (2.00 L). The resulting solid was dried under reduced pressure at 40° C. for 72 hours to give (2R)-1-(1H-indazol-4-yl)propan-2-amine;dihydrochloride (0.39 Kg, 89%) as an off-white solid.

$^1$H NMR (500 MHz, DMSO, 27° C.) 1.12 (3H, d), 2.96 (1H, dd), 3.39 (1H, dd), 3.45-3.55 (1H, m), 6.94 (1H, d), 7.28 (1H, dd), 7.43 (1H, d), 8.23 (3H, s), 8.28 (1H, d). m/z: ES+ [M.+] 175.

Preparation of (2R)-1-(1H-indazol-4-yl)-N-(2,2,2-trifluoroethyl)propan-2-amine

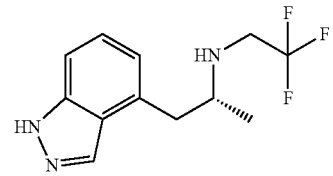 [SMILES: C[C@H](Cc1cccc2[nH]ncc12)NCC(F)(F)F]

A solution of 2,2,2-trifluoroethyl trifluoromethanesulfonate (0.73 Kg, 2.94 mol) in MeCN (2.00 L) was added to a stirred mixture of (R)-1-(1H-indazol-4-yl)propan-2-amine dihydrochloride (0.77 Kg, 2.94 mol) and K$_2$CO$_3$ (1.26 Kg, 9.13 mol) in MeCN (8.00 L) at 25° C. under nitrogen. The resulting mixture was heated to 60° C. and stirred at 60° C. for 18 hours. MeCN (5.00 L) was added and the solids were removed by filtration. The filtrate was concentrated under reduced pressure and the resulting solid was dissolved in EtOAc (10.00 L), washed with water (4.0 L) and dilute saturated aqueous sodium chloride (4.8 L). The organic layer was concentrated under reduced pressure to give (2R)-1-(1H-indazol-4-yl)-N-(2,2,2-trifluoroethyl)propan-2-amine (0.73 Kg, 96%). $^1$H NMR (500 MHz, CDCl$_3$, 27° C.) 1.12 (3H, d), 2.96 (1H, dd), 3.08 (1H, dd), 3.14-3.33 (3H, m), 6.98 (1H, d), 7.32 (1H, dd), 7.37-7.41 (1H, m), 8.13 (1H, d), 10.86 (1H, s). m/z: ES+ [M+H]+ 257.

Preparation of (6S,8R)-6-(5-bromo-2-pyridyl)-8-methyl-7-(2,2,2-trifluoroethyl)-3,6,8,9-tetrahydropyrazolo[4,3-f]isoquinoline

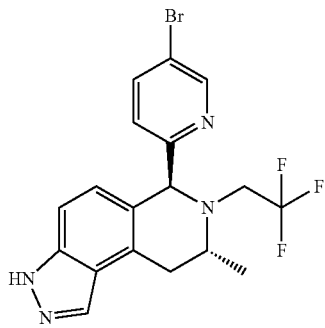 [SMILES: C[C@@H]1Cc2c(ccc3[nH]ncc23)[C@@H](c2ccc(Br)cn2)N1CC(F)(F)F]

Trifluoroacetic acid (0.66 L, 8.66 mol) was slowly added to a stirred mixture of 5-bromopicolinaldehyde (0.55 Kg, 2.89 mol) and (R)-1-(1H-indazol-4-yl)-N-(2,2,2-trifluoroethyl)propan-2-amine (0.83 Kg, 2.89 mol) in toluene (7.30 L) at 21° C. The resulting solution was heated to 80° C. and stirred at 80° C. for 18 hours. The temperature was increased to 90° C. and heating continued for 4 hours. The mixture was allowed to cool to 80° C. and a further portion of 5-bromopicolinaldehyde (0.015 Kg, 0.081 mol) was added and the solution was stirred at 80° C. for 16 hours. The mixture was allowed to cool to 21° C. and saturated aqueous NaHCO$_3$ (6.60 L) was added over 20 minutes. EtOAc (5.00 L) was added and the layers were separated. The organic layer was washed with saturated aqueous NaHCO$_3$ (3.30 L) and concentrated under reduced pressure. Ethanol was added and the mixture was concentrated under reduced pressure to give the crude product as a crispy solid. The cis isomer was removed by preparative SFC (SuperSep 1™ column (filled with CelluCoat™ 10 µm), 50 mm diameter, 250 mm length), eluting 28% EtOH in CO$_2$, 140 bar mobile phase at a flow rate of 450 mL/minute at 30° C.) to give to give (6S,8R)-6-(5-bromo-2-pyridyl)-8-methyl-7-(2,2,2-trifluoroethyl)-3,6,8,9-tetrahydropyrazolo[4,3-f]isoquinoline (0.94 Kg, 77%) as a pale yellow solid. $^1$H NMR (500 MHz, CDCl$_3$, 27° C.) 1.16 (3H, d), 2.89 (1H, dd), 2.99 (1H, dq), 3.25-3.34 (2H, m), 3.55 (1H, td), 5.10 (1H, s), 6.93 (1H, d), 7.22 (1H, d), 7.40 (1H, d), 7.75 (1H, dd), 8.05 (1H, d), 8.56 (1H, dd), 10.24 (1H, s). m/z: ES+ [M+H]+ 427.

Alternative Route #2 to Example 17

Preparation of N-[1-(3-fluoropropyl)azetidin-3-yl]-6-[(6S,8R)-8-methyl-7-(2,2,2-trifluoroethyl)-3,6,8,9-tetrahydropyrazolo[4,3-f]isoquinolin-6-yl]pyridin-3-amine

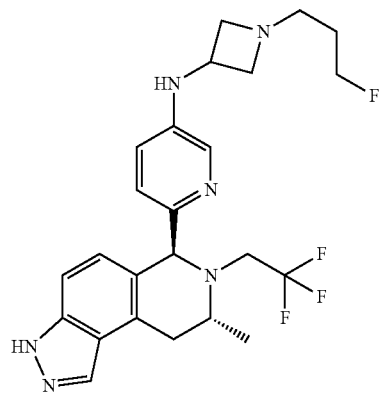 [SMILES: C[C@@H]1Cc2c(ccc3[nH]ncc23)[C@@H](c2ccc(NC3CN(CCCF)C3)cn2)N1CC(F)(F)F]

1-(3-Fluoropropyl)azetidin-3-amine (6.31 g, 37.98 mmol) was added to a solution of (6S,8R)-6-(5-bromopyridin-2-yl)-8-methyl-7-(2,2,2-tri fluoroethyl)-6,7,8,9-tetrahydro-3H-pyrazolo[4,3-f]isoquinoline (15.47 g, 34.92 mmol) in 1,4-dioxane (175 mL). The resulting solution was degassed under vacuum for 5 minutes, then backfilled with nitrogen (×2).

Sodium tert-butoxide (13.43 g, 139.69 mmol) was added, followed by BrettPhos 3rd Generation Precatalyst (0.95 g, 1.05 mmol). The resulting mixture was heated at 55° C. for 18 hours. The mixture was poured into EtOAc and water. Saturated brine was added, and the layers were separated. The organic layer was washed with saturated aqueous sodium chloride (×3), and the combined aqueous layers were extracted with EtOAc. The combined organic layers were dried over Na$_2$SO$_4$, filtered and concentrated under reduced pressure. The resulting residue was purified by flash silica chromatography, elution gradient 0 to 50% methanol in ethyl acetate. Fractions containing the desired product were combined, concentrated under reduced pressure, and then repurified by flash silica chromatography, elution gradient 0 to 40% EtOAc in hexanes, to afford a red-orange solid. This solid was dissolved in 10% MeOH in DCM, filtered, washing the filtercake with DCM. The combined filtrates were concentrated under reduced pressure to give N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine (15.28 g, 92%) as a light orange foam solid. The trans and cis isomers were separated by preparative SFC ((S,S) Whelk-01 column, 30 mm diameter, 250 mm length), eluting with 30% (0.2% NH$_4$OH in MeOH) in CO$_2$, 100 bar mobile phase at a flow rate of 20 mL/minute at 40° C.). The fractions containing the trans isomer were concentrated under reduced pressure. The resulting residue was further purified by flash silica chromatography, elution gradient 0 to 30% MeOH in EtOAc. Fractions containing the desired product were concentrated under reduced pressure, then concentrated from MeCN (×2) to give N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine (10.76 g, 74%) as a pale yellow foam/ solid. $^1$H NMR (600 MHz, DMSO-d$_6$, 27° C.) 1.07 (3H d) 1.63 (2H, dquin), 2.45 (2H, t), 2.72 (2H, br t), 2.83 (1H, br dd), 2.91-3.00 (1H, m), 3.06 (1H, br dd) 3.42-3.55 (2H, m), 3.58-3.65 (2H, m), 3.92 (1H, dquin) 4.43 (2H, dt) 4.92 (1H, s), 6.22 (1H, d), 6.79 (1H, d) 6.82 (1H, dd), 6.96 (1H, d), 7.21 (1H, d), 7.73 (1H, d), 8.04 (1H, s), 12.96 (1H, s). m/z: ES+(M+H)+477.

Fractions from the SFC containing the cis isomer was concentrated under reduced pressure and the resulting residue was further purified by flash silica chromatography, elution gradient 0 to 30% MeOH in EtOAc. Fractions containing the desired product were concentrated under reduced pressure, and the resulting residue was filtered to afford N-(1-(3-fluoropropyl)azetidin-3-yl)-6-((6R,8R)-8-methyl-7-(2,2,2-trifluoroethyl)-6,7,8,9-tetrahydro-3H-pyrazolo[4,3-f]isoquinolin-6-yl)pyridin-3-amine (1.13 g, 8%) as a light yellow foam solid. $^1$H NMR (300 MHz, DMSO-d$_6$, 27° C.) 1.28 (3H, d), 1.55-1.75 (2H, m), 2.42-2.49 (2H, m), 2.76 (2H, br t), 2.80-2.92 (1H, m), 3.07-3.18 (1H, m), 3.18-3.28 (1H, m), 3.38-3.54 (2H, m), 3.59-3.70 (2H, m), 3.95 (1H, sxt), 4.45 (2H, dt), 5.11 (1H, s), 6.21 (1H, d), 6.72 (1H, d), 6.82 (1H, dd), 7.02 (1H, d), 7.19 (1H, d), 7.78 (1H, d), 8.06 (1H, s), 12.94 (1H, s). m/z: ES+(M+H)+477.

Procedures used to prepare the starting material (6S,8R)-6-(5-bromopyridin-2-yl)-8-methyl-7-(2,2,2-trifluoroethyl)-6,7,8,9-tetrahydro-3H-pyrazolo[4,3-f]isoquinoline are described below.

Preparation of 2,2,2-trifluoro-N-[(1R)-2-(1H-indazol-4-yl)-1-methyl-ethyl]acetamide

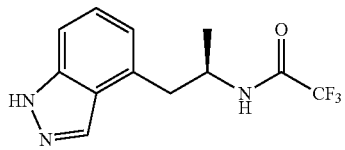 [SMILES: C[C@H](Cc1cccc2[nH]ncc12)NC(=O)C(F)(F)F]

TEA (26.0 mL, 186.5 mmol) was added via syringe to a stirred slurry of (R)-1-(1H-indazol-4-yl)propan-2-amine dihydrochloride (15.29 g, 61.61 mmol) and ethyl 2,2,2-trifluoroacetate (8.09 mL, 67.8 mmol) in MeOH (150 mL) at room temperature. The resulting solution was stirred at room temperature for 18 hours then concentrated under reduced pressure. The resulting solid was then dissolved in DCM (40 mL) and the residual triethylamine hydrochloride was precipitated out by the addition Et$_2$O (300 mL). The slurry was stirred for 5 minutes then filtered and the filtrate was concentrated under reduced pressure to give a solid. The solid was dissolved in EtOAc and saturated aqueous sodium chloride. The layers were separated and the organic layer was washed with saturated saturated aqueous sodium chloride, dried over MgSO$_4$, filtered and concentrated to afford the (R)-N-(1-(1H-indazol-4-yl)propan-2-yl)-2,2,2-trifluoroacetamide (16.51 g, 99%) as an off white solid. $^1$H NMR (300 MHz, DMSO-d$_6$, 27° C.) 1.19 (3H, d), 3.03 (1H, dd), 3.13 (1H, dd), 4.13-4.30 (1H, m), 6.89 (1H, d), 7.25 (1H, dd), 7.38 (1H, d), 8.18 (1H, t), 9.35 (1H, br d), 13.01 (1H, s). m/z: ES+ [M+H]+ 272.

Preparation of (2R)-1-(1H-indazol-4-yl)-N-(2,2,2-trifluoroethyl)propan-2-amine

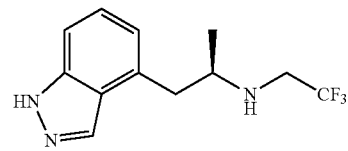 [SMILES: C[C@H](Cc1cccc2[nH]ncc12)NCC(F)(F)F]

1M Borane THF complex in THF (365 mL, 365.0 mmol) was added rapidly dropwise via cannula to a stirred solution of (R)-N-(1-(1H-indazol-4-yl)propan-2-yl)-2,2,2-trifluoroacetamide (16.5 g, 60.8 mmol) in THF (100 mL) at room temperature (gas evolution; small exotherm observed during course of addition). The reaction was then heated at 60° C. for 15.5 hours then allowed to cool to room temperature. The reaction was placed in an ambient temperature water bath and MeOH (80 mL) was slowly added drop-wise. The reaction mixture was concentrated under reduced pressure, and the resulting residue was dissolved in MeOH (80 mL) and concentrated under reduced pressure. The resulting residue was dissolved in MeOH (250 mL) and placed in an ambient temperature water bath. A slurry of 10% palladium on carbon (6.47 g, 6.08 mmol) in MeOH (90 mL) was added, rinsing down the flask with MeOH (10 mL) (some gas evolution was noted). The mixture was stirred at room temperature for approximately 3 minutes then heated at 65° C. for 2 hours, After cooling to room temperature, the mixture was filtered through celite and concentrated under reduced pressure. The pale yellow residue was dissolved in DCM and filtered and the filtrate was concentrated under reduced pressure. The resulting residue was purified by flash silica chromatography, elution gradient 10 to 60% EtOAc in hexanes. Fractions containing the desired product were concentrated under reduced pressure to afford (R)-1-(1H-indazol-4-yl)-N-(2,2,2-trifluoroethyl)propan-2-amine (14.21 g, 86%) as a pale yellow oil. $^1$H NMR (300 MHz, DMSO-d$_6$, 27° C.) 0.91 (3H, d), 2.17-2.30 (1H, m), 2.71 (1H, dd), 2.98-3.17 (2H, m), 3.22-3.38 (2H, m), 6.89 (1H, d), 7.24 (1H, dd), 7.35 (1H, d), 8.12 (1H, t), 12.97 (1H, br s). m/z: ES+ [M+H]+ 258.

Preparation of (6S,8R)-6-(5-bromo-2-pyridyl)-8-methyl-7-(2,2,2-trifluoroethyl)-3,6,8,9-tetrahydropyrazolo[4,3-f]isoquinoline

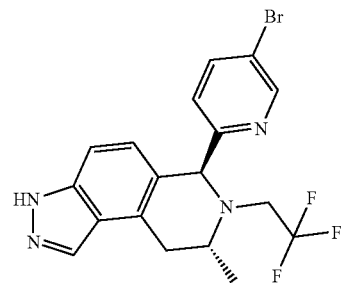 [SMILES: C[C@@H]1Cc2c(ccc3[nH]ncc23)[C@@H](c2ccc(Br)cn2)N1CC(F)(F)F]

5-Bromopicolinaldehyde (9.80 g, 52.7 mmol) was added to a stirred solution of (R)-1-(1H-indazol-4-yl)-N-(2,2,2-trifluoroethyl)propan-2-amine (14.05 g, 51.66 mmol) in toluene (246 mL) under nitrogen. Trifluoroacetic acid (12.30 mL) was then added and the reaction was heated at 90° C. for 4.5 hours. The mixture was allowed to cool to room temperature and EtOAc (200 mL) was added. The mixture was cooled to 5° C. and the mixture was basified by slow addition of saturated aqueous NaHCO₃. The resulting layers were separated and the aqueous layer was extracted with EtOAc (2×80 mL). The combined organic extracts were washed with saturated aqueous NaHCO₃, saturated aqueous sodium chloride, dried over MgSO₄, filtered and concentrated under reduced pressure. The resulting residue was purified by flash silica chromatography, elution gradient 5 to 60% EtOAc in hexanes. Fractions containing the desired product were concentrated under reduced pressure, then dried in vacuo at 50° C. for 3 hours to afford (6S,8R)-6-(5-bromopyridin-2-yl)-8-methyl-7-(2,2,2-trifluoroethyl)-6,7,8,9-tetrahydro-3H-pyrazolo[4,3-f]isoquinoline (19.29 g, 88%) as a pale orange solid. 1H NMR analysis revealed a 10:1 trans/cis isomers. ¹H NMR (300 MHz, DMSO-d₆, 27° C.) 1.10 (3H, d), 2.83-2.94 (1H, m), 2.95-3.14 (2H, m), 3.34-3.47 (1H, m), 3.49-3.72 (1H, m), 5.10 (1H, s), 6.88 (1H, d), 7.25 (1H, d), 7.33 (1H, d), 7.99 (1H, dd), 8.06 (1H, d), 8.56 (1H, d), 13.00 (1H, s) m/z: ES+ [M+H]+ 425.

Alternative routes to intermediates used in the synthesis of Example 17:

Preparation of N-[(1R)-2-(3-amino-2-methyl-phenyl)-1-methyl-ethyl]-2,2,2-trifluoro-acetamide

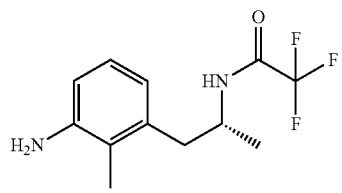 [SMILES: Cc1c(N)cccc1C[C@@H](C)NC(=O)C(F)(F)F]

A solution of (R)-3-(2-aminopropyl)-2-methylaniline (0.51 g, 3.13 mmol), DIPEA (0.55 mL, 3.13 mmol), and ethyl 2,2,2-trifluoroacetate (0.47 mL, 3.91 mmol) in MeOH (9.5 mL) was stirred at room temperature under nitrogen for 16 hours. The reaction mixture was concentrated under reduced pressure. DCM and water were added and the layers were separated. The aqueous layer was extracted with DCM (3×50 mL), and the combined organic layers were dried (Na₂SO₄) and filtered. The crude product was purified by flash silica chromatography, elution gradient 0 to 100% EtOAc in hexane. Pure fractions were evaporated to dryness to afford N-[(1R)-2-(3-amino-2-methyl-phenyl)-1-methyl-ethyl]-2,2,2-trifluoro-acetamide (680 mg, 83%). ¹H NMR (300 MHz, DMSO-d₆, 27° C.) 1.06-1.14 (m, 3H), 2.01 (s, 3H), 2.54-2.71 (m, 1H), 2.72-2.84 (m, 1H), 4.04-4.12 (m, 1H), 4.60-4.77 (m, 2H), 6.24-6.37 (m, 1H), 6.43-6.52 (m, 1H), 6.72-6.84 (m, 1H), 9.19-9.32 (m, 1H). m/z: ES+ [M+H]+ 261.

Preparation of 2-methyl-3-[(2R)-2-(2,2,2-trifluoroethylamino)propyl]aniline

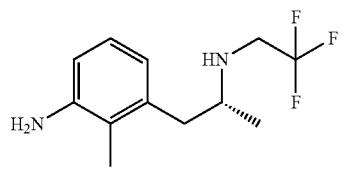 [SMILES: Cc1c(N)cccc1C[C@@H](C)NCC(F)(F)F]

1.0M borane in THF, in THF (19.4 mL, 19.37 mmol) was added to a stirred solution of (R)-N-(1-(3-amino-2-methylphenyl)propan-2-yl)-2,2,2-trifluoroacetamide (840 mg, 3.23 mmol) in THF (10 mL). The reaction mixture was heated at 65° C. under nitrogen for 6 hours. The mixture was allowed to cool to room temperature and MeOH was carefully added. The resulting mixture was stirred at room temperature for 30 minutes and then concentrated under reduced pressure. The resulting residue was dissolved in MeOH and heated to 65° C. for 6 hours. The mixture was allowed to cool to room temperature and then concentrated under reduced pressure to give the crude product which was purified by flash silica chromatography, elution gradient 0 to 100% EtOAc in hexane. Product containing fractions were evaporated to dryness to afford 2-methyl-3-[(2R)-2-(2,2,2-trifluoroethylamino)propyl]aniline (665 mg, 84%). ¹H NMR (300 MHz, DMSO-d₆, 27° C.) 0.89 (s, 3H), 1.98 (s, 3H), 2.08-2.22 (m, 1H), 2.25-2.42 (m, 1H), 2.69-2.87 (m, 2H), 3.15-3.29 (m, 2H), 4.61-4.75 (m, 2H), 6.30-6.40 (m, 1H), 6.43-6.54 (m, 1H), 6.71-6.83 (m, 1H). m/z: ES+ [M+H]+ 247.

Preparation of (2R)-1-(3-bromo-2-methyl-phenyl)-N-(2,2,2-trifluoroethyl)propan-2-amine

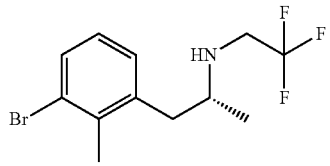 [SMILES: Cc1c(Br)cccc1C[C@@H](C)NCC(F)(F)F]

DIPEA (2.99 mL, 17.10 mmol) was added to (R)-1-(3-bromo-2-methylphenyl)propan-2-amine (1.30 g, 5.70 mmol), and 2,2,2-trifluoroethyl trifluoromethanesulfonate (0.23 M in DCM, 29.7 mL, 6.84 mmol) in 1,4-dioxane (25 mL) at room temperature under nitrogen. The resulting mixture was stirred at 85° C. for 16 hours. The reaction mixture was concentrated under reduced pressure and the crude product was purified by flash silica chromatography, elution gradient 0 to 50% EtOAc in heptane. Product containing fractions were concentrated under reduced pressure to afford (R)-1-(3-bromo-2-methylphenyl)-N-(2,2,2-trifluoroethyl)propan-2-amine (0.56 g, 32%) as an oil. ¹H NMR (500 MHz, DMSO, 27° C.) 0.91 (3H, d), 2.26 (1H, q), 2.34 (3H, s), 2.78-2.86 (1H, m), 2.89 (1H, dd), 3.19-3.28 (2H, m), 7.01-7.06 (1H, m), 7.15 (1H, dd), 7.43 (1H, dd). m/z: ES+ [M+H]+ 310/312.

Preparation of 2-methyl-3-[(2R)-2-(2,2,2-trifluoroethylamino)propyl]aniline

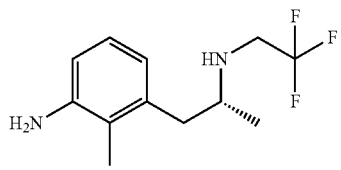 [SMILES: Cc1c(N)cccc1C[C@@H](C)NCC(F)(F)F]

Tris(dibenzylideneacetone)dipalladium(0) (0.050 g, 0.05 mmol) and (±)-2,2'-Bis(diphenylphosphino)-1,1'-binaphthalene (0.067 g, 0.11 mmol) were added to a suspension of (R)-1-(3-bromo-2-methylphenyl)-N-(2,2,2-trifluoroethyl)

propan-2-amine (0.56 g, 1.81 mmol), benzophenone imine (0.33 mL, 1.99 mmol) and sodium tert-butoxide (0.26 g, 2.71 mmol) in degassed toluene (7 mL) and the reaction was heated to 90° C. for 16 hours. After cooling to room temperature, the mixture was concentrated under reduced pressure. The residue was dissolved in DCM (50 mL) and washed with water (50 mL). The aqueous was extracted with DCM (25 mL) and the combined organics were concentrated to ~25 mL. 2 M HCl solution (50 mL) was added and the biphasic mixture was stirred vigorously for 30 min. The layers were separated and the aqueous layer was washed with DCM. The aqueous phase was basified by addition of 2 M aqueous NaOH. The resulting mixture was extracted with DCM (2×100 mL) and the combined organic extracts were concentrated under reduced pressure to give (R)-2-methyl-3-(2-((2,2,2-trifluoroethyl)amino)propyl)aniline (0.31 g, 70%) as an oil. $^1$H NMR (500 MHz, DMSO, 27° C.) 0.90 (3H, d), 1.98 (3H, s), 2.12-2.18 (1H, m), 2.30-2.36 (1H, m), 2.74-2.82 (2H, m), 3.17-3.29 (2H, m), 4.69 (2H, s), 6.35 (1H, dd), 6.48 (1H, dd), 6.78 (1H, t). ES+ [M+H]+247.

Preparation of (1S,3R)-1-(5-bromo-2-pyridyl)-3,5-dimethyl-2-(2,2,2-trifluoroethyl)-3,4-dihydro-1H-isoquinolin-6-amine

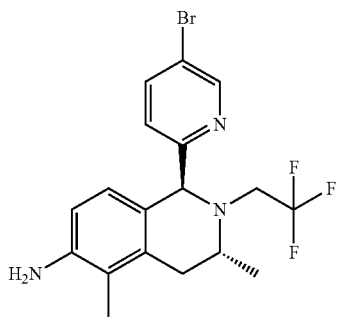 [SMILES: Cc1c(N)ccc2c1C[C@@H](C)N(CC(F)(F)F)[C@@H]2c1ccc(Br)cn1]

Trifluoromethanesulfonic acid ytterbium(III) salt (0.17 g, 0.27 mmol) was added to a stirred solution of (R)-2-methyl-3-(2-((2,2,2-trifluoroethyl)amino)propyl)aniline (1.35 g, 5.49 mmol), 5-bromopicolinaldehyde (1.02 g, 5.49 mmol) and water (0.49 mL, 27.43 mmol) in MeCN (21.5 mL). The resulting solution was stirred at 80° C. for 1 hour. The mixture was concentrated under reduced pressure and the residue was dry-loaded onto silica gel and was purified by flash silica chromatography, elution gradient 10 to 30% EtOAc in hexane. Fractions containing the desired product were concentrated to dryness to afford (1S,3R)-1-(5-bromopyridin-2-yl)-3,5-dimethyl-2-(2,2,2-trifluoroethyl)-1,2,3,4-tetrahydroisoquinolin-6-amine (2.22 g, 98%) as a yellowish gum. $^1$H NMR (300 MHz, DMSO-d$_6$, 27° C.) 0.88 (3H, d), 1.91 (3H, s), 2.37-2.46 (1H, m), 2.60-2.76 (1H, m), 2.76-3.00 (1H, m), 3.15-3.28 (1H, m), 3.34-3.63 (1H, m), 4.65 (2H, s), 4.85 (1H, s), 6.19-6.52 (2H, m), 7.10-7.31 (1H, m), 7.97 (1H, dd), 8.62 (1H, d). m/z: ES+ [M+H]+ 414.

Preparation of (6S,8R)-6-(5-bromo-2-pyridyl)-8-methyl-7-(2,2,2-trifluoroethyl)-3,6,8,9-tetrahydropyrazolo[4,3-f]isoquinoline

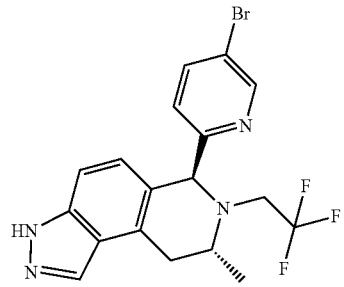 [SMILES: C[C@@H]1Cc2c(ccc3[nH]ncc23)[C@@H](c2ccc(Br)cn2)N1CC(F)(F)F]

(1S,3R)-1-(5-bromopyridin-2-yl)-3,5-dimethyl-2-(2,2,2-trifluoroethyl)-1,2,3,4-tetrahydroisoquinolin-6-amine (2.21 g, 5.33 mmol) in propionic acid (14.0 mL) was cooled to −20° C. A solution of sodium nitrite (0.40 g, 5.86 mmol) in water (2.8 mL) was added dropwise over 5 minutes, keeping the bath temperature between −20° C. and −15° C. The resulting mixture was stirred at −20° C. for 45 minutes. Toluene (80 mL), cooled to −15° C., was poured into the reaction, and the reaction was stirred for 15 minutes. A solution of sodium carbonate (12.0 g, 113 mmol) in water (125 mL) was slowly added and the mixture was allowed to warm to room temperature. EtOAc (100 mL) was added and the layers were separated. The aqueous layer was extracted with CHCl$_3$/IPA (3:1) (100 mL). The combined organic layers were dried over MgSO$_4$, filtered, and concentrated under reduced pressure to give the crude product which was purified by flash silica chromatography, elution gradient 15 to 50% EtOAc in hexane. Product containing fractions were evaporated to dryness to afford (6S,8R)-6-(5-bromopyridin-2-yl)-8-methyl-7-(2,2,2-trifluoroethyl)-6,7,8,9-tetrahydro-3H-pyrazolo[4,3-f]isoquinoline (1.63 g, 72%) as a brown solid. $^1$H NMR (300 MHz, DMSO-d$_6$, 27° C.) 1.10 (3H, d), 2.83-2.96 (1H, m), 2.96-3.14 (2H, m), 3.35-3.48 (1H, m), 3.49-3.73 (1H, m), 5.11 (1H, s), 6.87 (1H, d), 7.27 (1H, d), 7.35 (1H, d), 7.99 (1H, dd), 8.09 (1H, s), 8.53-8.63 (1H, m), 12.96 (1H, s). m/z: ES+ [M+H]+ 425.

Preparation of tert-butyl (1-Q-fluoropropyl)azetidin-3-yl)carbamate

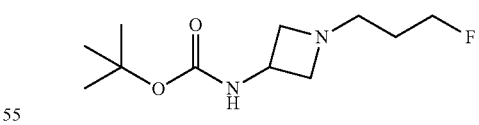

A suspension of tert-butyl azetidin-3-ylcarbamate (10.00 g, 58.06 mmol), 1-fluoro-3-iodopropane (11.13 g, 59.22 mmol) and potassium carbonate (16.05 g, 116.13 mmol) in MeCN (200 mL) were stirred at room temperature for 2 days. The solids were removed by filtration and the filtrate was concentrated under reduced pressure. The residue was treated with water and extracted with DCM. The combined organic extracts were dried over Na$_2$SO$_4$, filtered and concentrated under reduced pressure to give tert-butyl (1-(3-fluoropropyl)azetidin-3-yl)carbamate (13.40 g, 99%) as a pale yellow solid. $^1$H NMR (300 MHz, CDCl$_3$, 27° C.) 1.45

(9H, s), 1.61-1.92 (2H, m), 2.51-2.67 (2H, m), 2.85 (2H, br s), 3.57-3.72 (2H, m), 4.30 (1H, br d), 4.36-4.63 (2H, m), 4.89 (1H, br d).

Alternative Preparation of tert-butyl (1-(3-fluoropropyl)azetidin-3-yl)carbamate

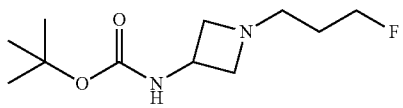 [SMILES: CC(C)(C)OC(=O)NC1CN(CCCF)C1]

Trifluoromethanesulfonic anhydride (2.31 mL, 13.75 mmol), followed by 2,6-dimethylpyridine (1.74 mL, 15.00 mmol) were added to a solution of 3-fluoropropan-1-ol (0.94 mL, 12.5 mmol) in DCM (47 mL) at 0° C. and the reaction was stirred at 0° C. for 1 hour. The reaction mixture was washed with 1N HCl, then the organic layer was dried and carefully evaporated. The residue was then added to a separate flask containing a suspension of tert-butyl azetidin-3-ylcarbamate (1.94 g, 11.25 mmol) and DIPEA (3.24 ml, 18.75 mmol) in dioxane/DCM (1:1, 40 mL) and the reaction was stirred at room temperature (exothermic on addition of triflate). The reaction mixture was diluted with DCM and washed with NH$_4$Cl solution. The organic layer was dried and evaporated under reduced pressure to give the crude product. The crude product was purified by flash silica chromatography, elution gradient 0 to 10% 1M NH$_3$/MeOH in DCM. Pure fractions were evaporated to dryness to afford tert-butyl (1-(3-fluoropropyl)azetidin-3-yl)carbamate (2.82 g, 97%) as a mauve oil $^1$H NMR as above.

Preparation of 1-(3-fluoropropyl)azetidin-3-amine

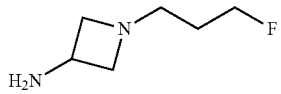

Trifluroacetic acid (39.8 mL, 517 mmol) was added dropwise over 30 minutes to a solution of tert-butyl (1-(3-fluoropropyl)azetidin-3-yl)carbamate (20.0 g, 86 mmol) in DCM (67.8 mL) that had been immersed in a water bath. After 18 hours, the reaction was concentrated under reduced pressure to an orange oil. This oil was dissolved in 10% methanol in DCM (125 mL) and potassium carbonate (71.4 g, 517 mmol) was added with vigorous stirring. After 15 min, another 30 g of potassium carbonate were added. Stirring became sluggish, and Celite was added (~15 g). Stirring was continued for another 15 minutes, and the mixture was filtered with a 10% methanol in DCM wash. The filtrate was concentrated under reduced pressure on a rotary evaporator (pressure: 100 mbar, water bath temperature: 30° C.), and the resulting orange oil was purified by flash silica chromatography (λ detection=210 nm), elution gradient 0 to 15% (2 M ammonia in methanol) in DCM to afford 1-(3-fluoropropyl)azetidin-3-amine (12.8 g) contaminated with 28 wt % methanol based on NMR integration as a yellow oil. This material could be used directly, stored in the freezer for later use, or further purified by vacuum distillation as according to the following example: 1-(3-fluoropropyl)azetidin-3-amine (14.8 g) as a light yellow oil was distilled using a short path distillation apparatus with jacketed water cooling under vacuum (vacuum pump) conditions. The flask containing the amine was immersed in an oil bath, and the bath temperature was gradually increased to 140° C. over a period of 30 minutes. Distillation occurred with a bath temperature of 110-135° C. and an approximate head temperature of 70° C. to afford 1-(3-fluoropropyl) azetidin-3-amine (12.4 g, 84%) as a clear colorless oil. This oil was stored in the freezer before use. $^1$H NMR (300 MHz, DMSO-d$_6$, 27° C.) 1.52-1.70 (2H, m), 1.75 (2H, br s), 2.38 (2H, t), 2.43-2.48 (2H, m), 3.27-3.39 (1H, m), 3.42-3.48 (2H, m), 4.43 (2H, dt). m/z: ES+ [M+H]+ 133.

Example 17A: Preparation of N-(1-(3-fluoropropyl) azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine Form A (Anhydrous Form)

Method 1

4.0 mg of amorphous N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine was dissolved in 100 ul of EtOAc to form a clear solution. About 200 ul of heptane was added slowly to the solution, a cloudy suspension was formed. The slurry was stirred at the ambient condition for 3 days. Crystalline material of Form A was obtained.

Method 2

1.60 g of amorphous N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine was suspended in 15 ml of acetone/H$_2$O (10:1) mixture. A slurry was formed, and then a gel was formed. 10 mg of N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f] isoquinolin-6-yl)pyridin-3-amine Form A seed was added after 2 hours, and the suspension was stirred at the ambient temperature for 1 day whereupon the gel became solid cakes. The solid cakes on the wall and bottom were manually removed into the solution, and a homogenous slurry was obtained after stirring for 1 hour. The solid was collected by filtration and washed with 5.0 ml of acetone/H$_2$O (1:10) twice, followed with H$_2$O several times. 1.45 g of white powder was obtained (90% yield) as Form A after drying in vacuum for 4 hours.

Method 3

501 mg of amorphous material of N-(1-(3-fluoropropyl) azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine was dissolved in 1.0 ml of EtOAc to form a brown solution. To the solution, 1.0 ml of heptane was added slowly. At the end of the addition, solid started to form but then dissolved. 2-5 mg of N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine-Form A was added to the clear brown solution, whereupon solid started to precipitate. The suspension was stirred at the ambient temperature for 1 day. The solid was collected by filtration and dried in air. 345 mg of off-white powder was obtained (yield: ~69%) as Form A.

Form A from method 2 was analyzed by XRPD and the results are tabulated below (Table 1) and shown in FIG. 1.

TABLE 1

XRPD Peaks for Form A

| Angle (2θ ± 0.2°) | Intensity (%) |
|---|---|
| 21.1 | 100.0 |
| 20.8 | 54.3 |
| 14.6 | 41.9 |
| 18.6 | 41.6 |
| 12.3 | 38.9 |
| 15.5 | 34.1 |
| 24.6 | 31.3 |
| 15.8 | 30.6 |
| 13.4 | 23.2 |
| 19.0 | 21.7 |

Form A was analyzed by thermal techniques. DSC analysis indicated that Form A has a melting point with an onset at 132° C. and a peak at 137° C. TGA indicated that Form A exhibits a mass loss of about 0.2% upon heating from about 25° C. to about 100° C. A representative DSC/TGA thermogram of Form A is shown in FIG. 2.

Example 17B: Preparation of N-(1-(3-fluoropropyl) azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine Form B (TBME Solvate)

100 mg of N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine (amorphous material) was partially dissolved in 1.0 ml of TBME. The suspension was stirred under ambient conditions, whereupon more solid precipitated out in the suspension. The slurry was stirred for 2 hours. N-(1-(3-fluoropropyl) azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine-Form B was identified when the slurry was directly amounted in the sample holder for the XRPD characterization. Form B converted to Form C after the solid was filtered and dried in the ambient condition.

Form B was analyzed by XRPD and the results are tabulated below (Table 2) and shown in FIG. 3.

TABLE 2

XRPD Peaks for Form B

| Angle (2θ ± 0.2°) | Intensity (%) |
|---|---|
| 6.0 | 100.0 |
| 17.8 | 67.0 |
| 18.4 | 34.9 |
| 16.3 | 30.3 |
| 21.5 | 29.2 |
| 12.3 | 27.0 |
| 17.2 | 24.8 |
| 13.4 | 23.3 |
| 18.1 | 21.6 |
| 15.6 | 20.6 |

Example 17C: Preparation of N-(1-(3-fluoropropyl) azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine Form C (TBME Solvate)

200 mg of N-(1-(3-fluoropropyl) azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine amorphous material was almost dissolved in 1 ml of TBME. The suspension was stirred under ambient conditions, whereupon more solid precipitated out after 10 minutes. The slurry was stirred for 2 hours and then evaporated under ambient conditions. Form C was obtained after the resulting solid was dried under ambient conditions.

Form C was analyzed by XRPD and the results are tabulated below (Table 3) and shown in FIG. 4.

TABLE 3

XRPD Peaks for Form C

| Angle (2θ ± 0.2°) | Intensity (%) |
|---|---|
| 6.8 | 100.0 |
| 18.6 | 64.1 |
| 13.9 | 62.5 |
| 18.0 | 61.6 |
| 17.2 | 53.4 |
| 17.4 | 52.4 |
| 20.5 | 47.3 |
| 19.2 | 40.0 |
| 20.7 | 37.4 |
| 13.7 | 36.3 |

Form C was analyzed by thermal techniques. DSC analysis indicated that Form C has an endotherm event of desolvation with an onset at 75° C. and a peak at 84° C. TGA indicated that Form C exhibits a mass loss of about 7.1% upon heating from about 25° C. to about 150° C. A representative DSC/TGA thermogram of Form C is shown in FIG. 5.

Example 17D: Preparation of N-(1-(3-fluoropropyl) azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine Form D (CPME Solvate)

150 mg of N-(1-(3-fluoropropyl) azetidin-3-yl)-6-((6S, 8R)-8-methyl-7-(2,2,2-trifluoroethyl)-6,7,8,9-tetrahydro-3H-pyrazolo[4,3-f]isoquinolin-6-yl)pyridin-3-amine amorphous material was stirred in 2.0 ml of CPME (cyclopentyl methyl ether). After stirring for 1 day, the solid was isolated by filtration and dried in air. ~50 mg of white powder of Form D was obtained.

Form D was analyzed by XRPD and the results are tabulated below (Table 4) and shown in FIG. 6.

TABLE 4

XRPD Peaks for Form D

| Angle (2θ ± 0.2°) | Intensity (%) |
|---|---|
| 6.2 | 100.0 |
| 18.3 | 55.0 |
| 18.9 | 24.3 |
| 16.1 | 21.8 |
| 16.8 | 18.4 |
| 22.2 | 17.9 |
| 14.1 | 17.1 |
| 19.9 | 13.5 |
| 22.5 | 13.5 |
| 23.9 | 13.4 |

Form D was analyzed by thermal techniques. DSC analysis indicated that Form D has an endotherm event of desolvation with an onset at 76° C. and a peak at 81° C., followed by another endotherm event with an onset at 128° C. and a peak at 133° C. TGA indicated that Form D exhibits a mass loss of about 6.8% upon heating from about 25° C. to about 150° C. A representative DSC/TGA thermogram of Form D is shown in FIG. 7.

Example 17E: Preparation of N-(1-(3-fluoropropyl) azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine Form E (Anhydrous Form)

Method 1

100 mg of amorphous N-(1-(3-fluoropropyl) azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine was added into 2.0 ml of heptane to form a slurry. 0.40 ml of EtOAc was added. After stirring for 2 hours, extra 0.10 ml of EtOAc was added to the slurry and the slurry was stirred under ambient conditions for 18 hours, whereupon a new crystalline form, Form E, was identified by XRPD. 75 mg of white solid of Form E was obtained after the solid was isolated and dried at the ambient condition (yield: 75%).

Method 2

1.002 g of amorphous N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine was dissolved in 5.0 ml of EtOAc to obtain a clear light brown solution. 5.0 ml of heptane was added and the solution remained clear. 10 mg of N-(1-(3-fluoropropyl) azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine-Form E seeds were added, and the suspension was stirred at ambient temperature. The solid started to precipitate under ambient conditions, and a wet cake was formed after 1 hour. 5.0 ml of EtOAc was added slowly to the slurry and the resulting slurry was stirred at ambient temperature for 1 hour. Another 10 ml of heptane was added, more solid started to precipitate. After stirring under ambient conditions for 2 hours, the slurry was heated to 60° C. and stirred at 60° C. for 2 hours. The slurry was cooled down to ambient temperature and stirred for 18 hours. The off-white solid of Form E was isolated by filtration and washed with 1:4 EtOAc/heptane mixed solvent for 3 times. 0.875 g of pale white powder was collected after air-dried (yield: 87%).

Form E from method 1 was analyzed by XRPD and the results are tabulated below (Table 5) and shown in FIG. 8.

TABLE 5

XRPD Peaks for Form E

| Angle (2θ ± 0.2°) | Intensity (%) |
|---|---|
| 17.9 | 100.0 |
| 14.8 | 67.1 |
| 20.9 | 60.1 |
| 23.1 | 55.4 |
| 16.2 | 49.3 |
| 20.0 | 35.6 |
| 18.2 | 32.9 |
| 12.3 | 30.4 |
| 22.2 | 19.0 |
| 13.9 | 18.9 |

Form E was analyzed by thermal techniques. DSC analysis indicated that Form E has a melting point with an onset at 126° C. and a peak at 133° C. TGA indicated that Form E exhibits a mass loss of about 0.8% upon heating from about 25° C. to about 100° C. A representative DSC/TGA thermogram of Form E is shown in FIG. 9.

Example 17F: Preparation of N-(1-(3-fluoropropyl) azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine Form F (Heptane Solvate)

20 mg of amorphous N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine was dissolved in 200 ul of acetone. 1.0 ml of heptane was added slowly to the solution. The solution started to become cloudy and then formed a slurry. The slurry was stirred at the ambient temperature after 1.0 ml of heptane was added. Needle-like particles was observed in the slurry. The slurry was heated to 60° C. and stirred for 2 hours and then cooled down to the ambient temperature. Needle particles were formed.

The slurry of resulting Form F was analyzed by XRPD and the results are shown in FIG. 10. Crystallinity of Form F was decreasing during XRPD characterization, and the second run of the XRPD indicated an amorphous material was obtained after drying in the sample holder.

Example 17F: Preparation of N-(1-(3-fluoropropyl) azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine Form G (Methylpentanone Solvate)

100 mg of amorphous N-(1-(3-fluoropropyl) azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine was suspended in 200 ul of methylpentanone, and 2-5 mg of N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine-Form A was added, whereupon a cake was formed after stirring under ambient conditions for 10 minutes. 200 ul of methylpentanone was added and a slurry was formed. The slurry was stirred at the ambient condition for 18 hours. XRPD showed that a crystalline form, N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine-Form G was formed. Form G converted to partially amorphous material after isolation and drying under ambient conditions.

Form G was analyzed by XRPD and the results are tabulated below (Table 6) and shown in FIG. 10.

TABLE 6

XRPD Peaks for Form G

| Angle (2θ ± 0.2°) | Intensity (%) |
|---|---|
| 6.2 | 100.0 |
| 18.1 | 95.9 |
| 16.6 | 38.8 |
| 18.7 | 37.5 |
| 21.9 | 36.5 |
| 15.9 | 33.9 |
| 22.4 | 28.1 |
| 19.7 | 26.4 |

TABLE 6-continued

XRPD Peaks for Form G

| Angle (2θ ± 0.2°) | Intensity (%) |
|---|---|
| 14.0 | 24.6 |
| 12.6 | 23.9 |

Example 18

5-fluoro-6-((6S,8R)-7-((1-fluorocyclopropyl)methyl)-8-methyl-6,7,8,9-tetrahydro-3H-pyrazolo[4,3-f]isoquinolin-6-yl)-N-(1-(3-fluoropropyl)azetidin-3-yl)pyridin-3-amine

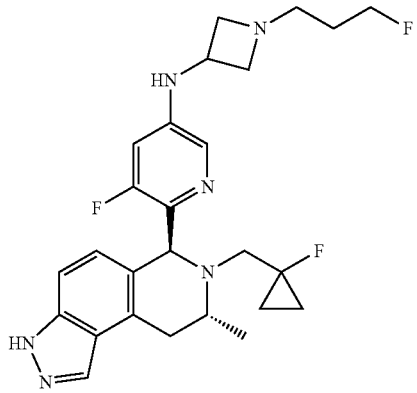 [SMILES: C[C@@H]1Cc2c(ccc3[nH]ncc23)[C@@H](c2ncc(NC3CN(CCCF)C3)cc2F)N1CC1(F)CC1]

[(2-Di-cyclohexylphosphino-3,6-dimethoxy-2',4',6'-triisopropyl-1,1'-biphenyl)-2-(2'-amino-1,1'-biphenyl)]palladium(II) methanesulfonate methanesulfonate (Brett Phos G3) (48.6 mg, 0.05 mmol) was added to degassed solution of 1-(3-fluoropropyl)azetidin-3-amine (95 mg, 0.72 mmol), (6S,8R)-6-(5-bromo-3-fluoropyridin-2-yl)-7-((1-fluorocyclopropyl)methyl)-8-methyl-6,7,8,9-tetrahydro-3H-pyrazolo[4,3-f]isoquinoline (155 mg, 0.36 mmol) and sodium tert-butoxide (206 mg, 2.15 mmol) in 1,4-dioxane (3 mL) under nitrogen. The resulting solution was stirred at 90° C. for 2 hours. The reaction mixture was diluted with EtOAc (50 mL), and washed sequentially with water (50 mL) and saturated aqueous sodium chloride (50 mL). The organic layer was dried with MgSO₄, filtered and evaporated to afford crude product which was purified by preparative HPLC (Waters XBridge Prep C18 OBD column, 5µ silica, 50 mm diameter, 100 mm length), using decreasingly polar mixtures of water (containing 0.1% NH₃) and MeCN as eluents. Fractions containing the desired compound were evaporated to dryness to afford 5-fluoro-6-((6S,8R)-7-((1-fluorocyclopropyl)methyl)-8-methyl-6,7,8,9-tetrahydro-3H-pyrazolo[4,3-f]isoquinolin-6-yl)-N-(1-(3-fluoropropyl)azetidin-3-yl)pyridin-3-amine (39.0 mg, 22%) as a white solid. ¹H NMR (500 MHz, CDCl₃, 27° C.) 0.48-0.61 (2H, m), 0.92-1.09 (2H, m), 1.13 (3H, d), 1.68-1.83 (2H, m), 2.56-2.62 (2H, m), 2.67 (1H, dd), 2.86 (1H, dd), 2.90-2.95 (2H, m), 3.17 (1H, dd), 3.27 (1H, dd), 3.70 (2H, q), 3.87 (1H, td), 4.04 (1H, q), 4.21 (1H, d), 4.43 (1H, t), 4.53 (1H, t), 5.39 (1H, s), 6.50 (1H, dd), 6.79 (1H, d), 7.12 (1H, d), 7.68 (1H, d), 8.03 (1H, s); m/z: ES+ [M+H]+ 485.

The 5-fluoro-6-((6S,8R)-7-((1-fluorocyclopropyl)methyl)-8-methyl-6,7,8,9-tetrahydro-3H-pyrazolo[4,3-f]isoquinolin-6-yl)-N-(1-(3-fluoropropyl)azetidin-3-yl)pyridin-3-amine was prepared as follows:

Preparation of 1-(5-bromo-3-fluoropyridin-2-yl)-N-((1S,3R)-1-(5-bromo-3-fluoropyridin-2-yl)-2-((1-fluorocyclopropyl)methyl)-3,5-dimethyl-1,2,3,4-tetrahydroisoquinolin-6-yl)methanimine

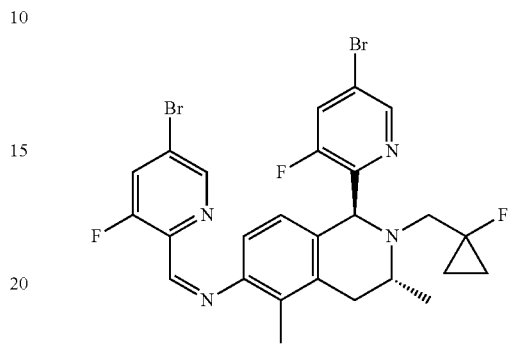

5-Bromo-3-fluoropicolinaldehyde (1.09 g, 5.33 mmol) was added to (R)-3-(2-(((1-fluorocyclopropyl)methyl)amino)propyl)-2-methylaniline (630 mg, 2.67 mmol) and water (0.240 mL, 13.33 mmol) in acetic acid (12 mL). The resulting solution was stirred at 70° C. for 2 hours. The reaction mixture was concentrated and diluted with EtOAc (50 mL) and washed sequentially with saturated aqueous NaHCO₃ (50 mL). The organic layer was dried with MgSO₄, filtered and evaporated to afford 1-(5-bromo-3-fluoropyridin-2-yl)-N-((1S,3R)-1-(5-bromo-3-fluoropyridin-2-yl)-2-((1-fluorocyclopropyl)methyl)-3,5-dimethyl-1,2,3,4-tetrahydroisoquinolin-6-yl)methanimine as a crude product (1.53 g, 2.51 mmol). m/z: ES+ [M+H]+ 607.

Preparation of (1S,3R)-1-(5-bromo-3-fluoropyridin-2-yl)-2-((1-fluorocyclopropyl)methyl)-3,5-dimethyl-1,2,3,4-tetrahydroisoquinolin-6-amine

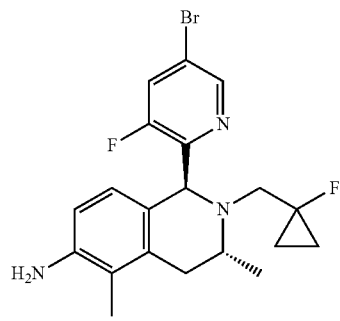 [SMILES: Cc1c(N)ccc2c1C[C@@H](C)N(CC1(F)CC1)[C@@H]2c1ncc(Br)cc1F]

Hydroxylamine hydrochloride (0.174 g, 2.51 mmol) was added to 1-(5-bromo-3-fluoropyridin-2-yl)-N-((1S,3R)-1-(5-bromo-3-fluoropyridin-2-yl)-2-((1-fluorocyclopropyl)methyl)-3,5-dimethyl-1,2,3,4-tetrahydroisoquinolin-6-yl)methanimine (1.53 g, 2.51 mmol) and potassium acetate (0.62 g, 6.27 mmol) in MeOH (12 mL). The resulting solution was stirred at 20° C. for 5 hours. The reaction mixture was concentrated and diluted with DCM (75 mL) and washed sequentially with NaOH (2M, 75 mL) and saturated aqueous sodium chloride (50 mL). The organic layer was dried with MgSO₄, filtered and evaporated to afford crude product which was purified by flash silica chromatography, elution gradient 0 to 20% EtOAc in heptane. Product containing fractions were evaporated to dryness to afford (1S,3R)-1-(5-bromo-3-fluoropyridin-2-yl)-2-((1-fluorocyclopropyl)methyl)-3,5-dimethyl-1,2,3,4-tetrahydroisoquinolin-6-amine (0.672 g, 63%) as a colourless gum. ¹H NMR (500 MHz, CDCl₃, 27° C.) 0.45-0.61 (2H, m), 0.92-1.06 (2H, m), 1.07 (3H, d), 2.07 (3H, s), 2.51 (1H, dd), 2.59 (1H, dd), 2.85 (1H, dd), 3.13 (1H, dd), 3.52 (2H, s), 3.64-3.75 (1H, m), 5.35 (1H, s), 6.48 (2H, s), 7.52 (1H, dd), 8.36 (1H, dd); m/z: ES+ [M+H]+ 422/424.

Preparation of (6S,8R)-6-(5-bromo-3-fluoropyridin-2-yl)-7-((1-fluorocyclopropyl)methyl)-8-methyl-6,7,8,9-tetrahydro-3H-pyrazolo[4,3-f]isoquinoline

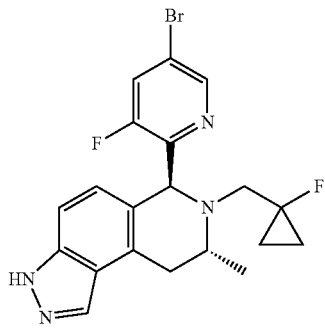 [SMILES: C[C@@H]1Cc2c(ccc3[nH]ncc23)[C@@H](c2ncc(Br)cc2F)N1CC1(F)CC1]

(1S,3R)-1-(5-Bromo-3-fluoropyridin-2-yl)-2-((1-fluorocyclopropyl)methyl)-3,5-dimethyl-1,2,3,4-tetrahydroisoquinolin-6-amine (0.672 g, 1.59 mmol) in propionic acid (6.63 mL) was cooled to −17° C. (dry ice/acetone). Sodium nitrite (0.110 g, 1.59 mmol) in water (1.33 mL) was added dropwise and the reaction mixture stirred at −17° C. for 30 minutes. The reaction mixture was diluted with ice-cold toluene (30 mL), stirred at 0° C. for 15 minutes then at room temperature for 45 minutes. The reaction mixture was washed with water (2×25 mL), the combined aqueous phases washed with EtOAc (25 mL), the combined organics were washed with saturated aqueous sodium chloride (50 mL), dried (MgSO₄), filtered and the filtrate evaporated to an orange-brown oil. The crude material was purified by flash silica chromatography, elution gradient 0-50% EtOAc in heptane to afford (6S,8R)-6-(5-bromo-3-fluoropyridin-2-yl)-7-((1-fluorocyclopropyl)methyl)-8-methyl-6,7,8,9-tetrahydro-3H-pyrazolo[4,3-f]isoquinoline (0.310 g, 45%) as an orange solid. ¹H NMR (500 MHz, CDCl₃, 27° C.) 0.50-0.59 (2H, m), 1.03 (2H, dd), 1.13 (3H, d), 2.72 (1H, dd), 2.91 (1H, dd), 3.16 (1H, dd), 3.27 (1H, dd), 3.77-3.90 (1H, m), 5.50 (1H, s), 6.80 (1H, d), 7.20 (1H, dd), 7.56 (1H, dd), 8.07 (1H, d), 8.36 (1H, dd); m/z: ES+ [M+H]+ 433.

Example 19

Preparation of N-(4-((6S,8R)-7-(2,2-difluoropropyl)-8-methyl-6,7,8,9-tetrahydro-3H-pyrazolo[4,3-f]isoquinolin-6-yl)-3-methoxyphenyl)-1-(3-fluoropropyl)azetidin-3-amine

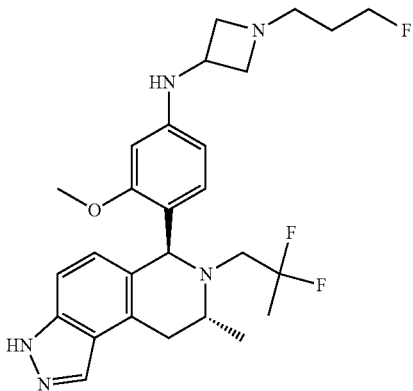 [SMILES: COc1cc(NC2CN(CCCF)C2)ccc1[C@@H]1c2ccc3[nH]ncc3c2C[C@@H](C)N1CC(C)(F)F]

DMF (2 mL) and DIPEA (0.074 mL, 0.42 mmol) were added sequentially to a flask charged with N-(4-((6S,8R)-7-(2,2-difluoropropyl)-8-methyl-6,7,8,9-tetrahydro-3H-pyrazolo[4,3-f]isoquinolin-6-yl)-3-methoxyphenyl)azetidin-3-amine (75 mg, 0.17 mmol). 1-Fluoro-3-iodopropane (31.9 mg, 0.17 mmol) in DMF (0.1 mL) was then added, and stirring was continued for 2 hours. The reaction was stopped, diluted with saturated aqueous sodium chloride and the compound was extracted in EtOAC (×3). The combined extracts were washed with water and dried over sodium sulfate, filtered and concentrated under reduced pressure to afford a film. This material was purified by flash silica chromatography, eluting with 2 to 10% (methanol containing 1% ammonium hydroxide) in DCM to afford N-(4-((6S,8R)-7-(2,2-difluoropropyl)-8-methyl-6,7,8,9-tetrahydro-3H-pyrazolo[4,3-f]isoquinolin-6-yl)-3-methoxyphenyl)-1-(3-fluoropropyl)azetidin-3-amine (43 mg, 51%). ¹H NMR (400 MHz, DMSO-d₆, 27° C.) 1.00 (3H, d), 1.45-1.70 (5H, m), 2.44 (2H, t), 2.55-2.66 (1H, m), 2.66-2.72 (2H, m), 2.79 (1H, dd), 2.87-3.01 (1H, m), 3.10 (1H, br dd), 3.38-3.53 (1H, m), 3.56-3.67 (2H, m), 3.77 (3H, s), 3.85-3.97 (1H, m), 4.43 (2H, dt), 5.21 (1H, s), 5.88 (1H, dd), 6.00 (1H, d), 6.16 (1H, d), 6.35 (1H, d), 6.64 (1H, d), 7.17 (1H, d), 8.02 (1H, s), 12.92 (1H, d). m/z: (ES+), [M+H]+=502.

The starting material N-(4-((6S,8R)-7-(2,2-difluoropropyl)-8-methyl-6,7,8,9-tetrahydro-3H-pyrazolo[4,3-f]isoquinolin-6-yl)-3-methoxyphenyl)azetidin-3-amine was prepared according to the procedures below.

Preparation of 2,2-difluoropropyl trifluoromethanesulfonate

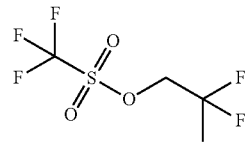

Trifluoromethanesulfonic anhydride (3.29 ml, 19.5 mmol) was added dropwise to a solution of 2,2-difluoropropan-1-ol (1.7 g, 18 mmol) in DCM (40 mL) at −10° C. (salt/ice bath). 2,6-Dimethylpyridine (2.5 mL, 21 mmol) was then added, and the reaction was stirred for 1 hour under these conditions. The reaction was then washed with water (×2), and the organic layer was dried over $Na_2SO_4$, filtered and concentrated under reduced pressure (vacuum ~200 mbars) to afford 2,2-difluoropropyl trifluoromethanesulfonate (2.1 g, 52%) as a red oil. $^1$H NMR (400 MHz, CHLOROFORM-d, 27° C.) 4.48 (2H, t), 1.73 (3H, t).

Preparation of (R)-3-(2-((2,2-difluoropropyl)amino)propyl)-2-methylaniline

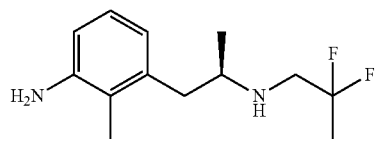 [SMILES: Cc1c(N)cccc1C[C@@H](C)NCC(C)(F)F]

2,2-Difluoropropyl trifluoromethanesulfonate (1.68 g, 7.37 mmol) was added to a stirred solution of (R)-3-(2-aminopropyl)-2-methylaniline (1.1 g, 6.7 mmol) and DIPEA (1.52 ml, 8.71 mmol) in 1,4-dioxane (20 mL). The reaction was heated at 65° C. for 3 hours before being cooled to room temperature and then concentrated under reduced pressure. The resulting residue was dissolved in EtOAc (30 mL) and washed with saturated aqueous $NaHCO_3$. The aqueous layer was extracted with EtOAc (20 mL) and the combined organic layers were dried over $Na_2SO_4$, filtered and concentrated under reduced pressure. The resulting red oil was purified by flash silica chromatography, elution gradient 30 to 90% ethyl acetate in hexanes, to afford (R)-3-(2-((2,2-difluoropropyl)amino)propyl)-2-methylaniline (1.02 g, 63%) as a gum. $^1$H NMR (500 MHz, DMSO-$d_6$, 27° C.) 0.90 (3H, d), 1.55 (3H, t), 1.75 (1H, br s), 1.97 (3H, s), 2.29-2.38 (1H, m), 2.69-2.76 (2H, m), 2.86 (2H, br t), 4.69 (2H, s), 6.34 (1H, d), 6.47 (1H, d), 6.77 (1H, t). m/z: (ES+), [M+H]+=439.

Preparation of (1S,3R)-1-(4-bromo-2-methoxyphenyl)-2-(2,2-difluoropropyl)-3,5-dimethyl-1,2,3,4-tetrahydroisoquinolin-6-amine

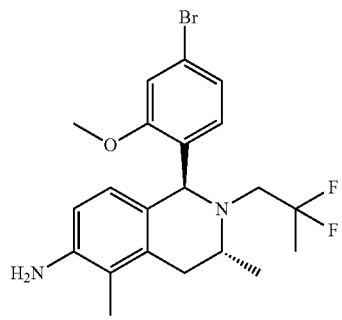 [SMILES: COc1cc(Br)ccc1[C@@H]1c2ccc(N)c(C)c2C[C@@H](C)N1CC(C)(F)F]

4-Bromo-2-methoxybenzaldehyde (1.07 g, 4.95 mmol) was added to a solution of (R)-3-(2-((2,2-difluoropropyl)amino)propyl)-2-methylaniline (0.600 g, 2.48 mmol) in AcOH (12 mL) and water (0.223 g, 12.4 mmol), and the reaction was heated at 80° C. for 18 hours. After cooling, the volatiles were concentrated under reduced pressure, and the resulting residue was dissolved in EtOAc. The solution was neutralized by washing with saturated aqueous $NaHCO_3$. The organic layer was combined with aqueous HCl (1N), and the biphasic mixture was stirred at room temperature for 30 minutes. The layers were then separated, and the organic layer was washed with aqueous HCl (1N). The combined aqueous layers were extracted with EtOAc and then basified by addition of solid $K_2CO_3$. The organic layer was then extracted with EtOAc (×2), and the combined organic layers were dried over sodium sulfate, filtered, and concentrated under reduced pressure. The resulting residue was purified by flash silica chromatography, elution gradient 10 to 60% ethyl acetate in hexanes, to afford (1S,3R)-1-(4-bromo-2-methoxyphenyl)-2-(2,2-difluoropropyl)-3,5-dimethyl-1,2,3,4-tetrahydroisoquinolin-6-amine (0.576 g, 53%) as a gum. $^1$H NMR (400 MHz, DMSO-$d_6$, 27° C.) 0.95 (3H, d), 1.54 (3H, t), 1.93 (3H, s), 2.27-2.43 (2H, m), 2.57-2.74 (1H, m), 2.76-2.98 (1H, m), 3.19-3.26 (1H, m), 3.84 (3H, s), 4.63 (2H, s), 5.12 (1H, s), 6.26 (1H, d), 6.38 (1H, d), 6.58 (1H, d), 6.94 (1H, dd), 7.16 (1H, d). m/z: (ES+), [M+H]+=439.

Also isolated was N-((1S,3R)-1-(4-bromo-2-methoxyphenyl)-2-(2,2-difluoropropyl)-3,5-dimethyl-1,2,3,4-tetrahydroisoquinolin-6-yl)acetamide (0.081 g, 7%) as a gum.

Preparation of (6S,8R)-6-(4-bromo-2-methoxyphenyl)-7-(2,2-difluoropropyl)-8-methyl-6,7,8,9-tetrahydro-3H-pyrazolo[4,3-f]isoquinoline

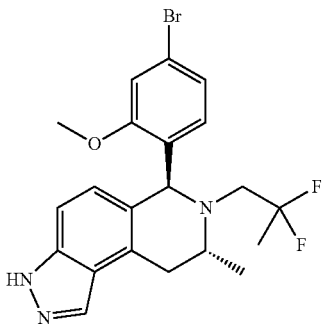 [SMILES: COc1cc(Br)ccc1[C@@H]1c2ccc3[nH]ncc3c2C[C@@H](C)N1CC(C)(F)F]

Sodium nitrite (0.049 g, 0.72 mmol) as a solution in water (0.750 mL) was added dropwise to a cooled solution of (1S,3R)-1-(4-bromo-2-methoxyphenyl)-2-(2,2-difluoropropyl)-3,5-dimethyl-1,2,3,4-tetrahydroisoquinolin-6-amine (0.30 g, 0.68 mmol) in propionic acid (2.5 mL) at −15° C., and the reaction was stirred for 1 hour under these conditions. Ice-cold EtOAc (10 mL) was added followed by saturated aqueous $NaHCO_3$ (10 mL) in portions. The layers were separated, and the the organic layer was washed with saturated aqueous $NaHCO_3$. The combined aqueous layers were extracted with EtOAc, and all organic layers were combined, dried over $Na_2SO_4$, filtered and concentrated under reduced pressure. The resulting residue was purified by flash silica chromatography, elution gradient 20 to 70% ethyl acetate in hexanes, to afford (6S,8R)-6-(4-bromo-2-methoxyphenyl)-7-(2,2-difluoropropyl)-8-methyl-6,7,8,9-tetrahydro-3H-pyrazolo[4,3-f]isoquinoline (0.23 g, 75%) as a gum. $^1$H NMR (500 MHz, DMSO-$d_6$, 27° C.) 1.01 (3H, d), 1.53 (3H, t), 2.84 (1H, dd), 2.96-3.09 (1H, m), 3.14 (1H, br dd), 3.36-3.48 (1H, m), 3.89 (3H, s), 5.32 (1H, s), 6.64 (2H, app t), 6.94 (1H, dd), 7.16-7.27 (2H, m), 8.06 (1H, s), 12.99 (1H, br s). 1H obscured by DMSO. m/z: (ES+), [M+H]+=450.

Preparation of (6S,8R)-6-(4-bromo-2-methoxyphenyl)-7-(2,2-difluoropropyl)-8-methyl-3-(tetrahydro-2H-pyran-2-yl)-6,7,8,9-tetrahydro-3H-pyrazolo[4,3-f]isoquinoline and (6S,8R)-6-(4-bromo-2-methoxyphenyl)-7-(2,2-difluoropropyl)-8-methyl-2-(tetrahydro-2H-pyran-2-yl)-6,7,8,9-tetrahydro-2H-pyrazolo[4,3-f]isoquinoline

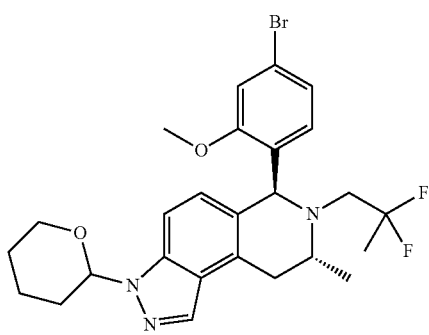

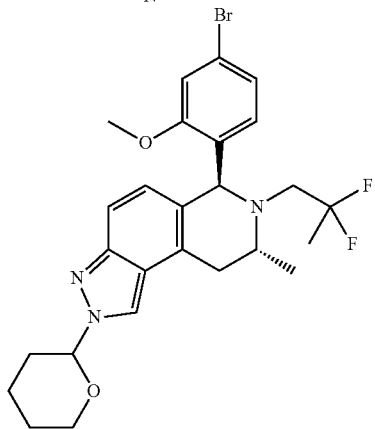

DCM (7 mL) was added to a flask charged with (6S,8R)-6-(4-bromo-2-methoxyphenyl)-7-(2,2-difluoropropyl)-8-methyl-6,7,8,9-tetrahydro-3H-pyrazolo[4,3-f]isoquinoline (0.3 g, 0.67 mmol) and 4-methylbenzenesulfonic acid hydrate (0.025 g, 0.13 mmol). 3,4-Dihydro-2H-pyran (0.084 g, 1.0 mmol) was added, and the reaction was stirred at room temperature for 18 hours. The reaction was washed with saturated aqueous sodium hydrogencarbonate, and the organic layer was dried over Na₂SO₄, filtered, and concentrated under reduced pressure. The resulting residue was purified by flash chromatography, eluting with 5 to 40% ethyl acetate in hexanes, to afford (6S,8R)-6-(4-bromo-2-methoxyphenyl)-7-(2,2-difluoropropyl)-8-methyl-3-(tetrahydro-2H-pyran-2-yl)-6,7,8,9-tetrahydro-3H-pyrazolo[4,3-f]isoquinoline (175 mg, 49%) as a gum. ¹H NMR (400 MHz, CHLOROFORM-d, 27° C.) 0.99-1.13 (3H, br s), 1.48-1.88 (6H, m), 2.01-2.08 (1H, m), 2.08-2.18 (1H, m), 2.48-2.70 (2H, m), 2.82 (1H, dt), 2.88-3.04 (1H, m), 3.20 (1H, br d), 3.55-3.67 (1H, m), 3.63-3.73 (1H, m), 3.88 (3H, s), 3.94-3.98 (1H, m), 5.42 (1H, br s), 5.63 (1H, dt), 6.64 (1H, dd), 6.73 (1H, dd), 6.86 (1H, dd), 7.03 (1H, t), 7.25-7.29 (1H, m), 7.98 (1H, d). m/z: (ES+), [M+H]+=534.

Also isolated was (6S,8R)-6-(4-bromo-2-methoxyphenyl)-7-(2,2-difluoropropyl)-8-methyl-2-(tetrahydro-2H-pyran-2-yl)-6,7,8,9-tetrahydro-2H-pyrazolo[4,3-f]isoquinoline (68 mg, 19%) as a gum. ¹H NMR (400 MHz, CHLOROFORM-d, 27° C.) 1.02-1.07 (3H, m), 1.42-1.53 (3H, m), 1.59-1.81 (3H, m), 2.03-2.09 (1H, m), 2.18-2.25 (2H, m), 2.59 (1H, qd), 2.69 (1H, dd), 2.86-2.98 (1H, m), 3.02-3.14 (1H, m), 3.46-3.57 (1H, m), 3.72-3.82 (1H, m), 3.87-3.90 (3H, m), 4.11-4.16 (1H, m), 5.31 (1H, s), 5.61-5.68 (1H, m), 6.60 (1H, dd), 6.72 (1H, dd), 6.88 (1H, dt), 7.01-7.05 (1H, m), 7.36 (1H, d), 8.09 (1H, s). m/z: (ES+), [M+H]+=534.

Preparation of tert-butyl 3-((4-((6S,8R)-7-(2,2-difluoropropyl)-8-methyl-3-(tetrahydro-2H-pyran-2-yl)-6,7,8,9-tetrahydro-3H-pyrazolo[4,3-f]isoquinolin-6-yl)-3-methoxyphenyl)amino)azetidine-1-carboxylate

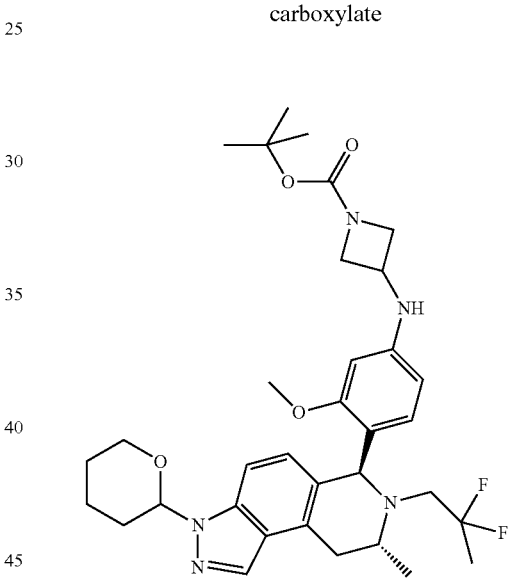

Dioxane (3.5 mL) was added to a flask charged with Cs₂CO₃ (213 mg, 0.65 mmol), tert-butyl 3-aminoazetidine-1-carboxylate (85 mg, 0.49 mmol), and (6S,8R)-6-(4-bromo-2-methoxyphenyl)-7-(2,2-difluoropropyl)-8-methyl-3-(tetrahydro-2H-pyran-2-yl)-6,7,8,9-tetrahydro-3H-pyrazolo[4,3-f]isoquinoline (175 mg, 0.33 mmol). The reaction flask was evacuated and back filled with nitrogen (×3). BrettPhos 3rd Generation Precatalyst (30 mg, 0.03 mmol) was added, and the flask was again evacuated and back-filled with nitrogen (×3). The reaction was heated at 100° C. for 4 hours. The reaction was cooled to room temperature, filtered, and concentrated under reduced pressure. The resulting crude gum was purified by flash silica chromatography, eluting with 15 to 70% ethyl acetate in hexanes, to afford tert-butyl 3-((4-((6S,8R)-7-(2,2-difluoropropyl)-8-methyl-3-(tetrahydro-2H-pyran-2-yl)-6,7,8,9-tetrahydro-3H-pyrazolo[4,3-f]isoquinolin-6-yl)-3-methoxyphenyl)amino)azetidine-1-carboxylate (152 mg, 74%) as a film. ¹H NMR (400 MHz, CHLOROFORM-d, 27° C.) 1.05 (3H, d), 1.42 (9H, s), 1.44-1.57 (3H, m), 1.57-1.63 (1H, m), 1.66-1.77 (2H, m), 2.04-2.08 (1H, m), 2.09-2.18 (1H, m), 2.47-2.69 (2H, m), 2.79 (1H, dt), 2.84-2.99 (1H, m), 3.16 (1H, br dd), 3.48-3.61 (1H, m), 3.69 (3H, dt), 3.83 (3H, s), 3.94-4.04 (2H, m), 4.15 (1H, br s), 4.20-4.29 (2H, m), 5.32 (1H, s), 5.63 (1H, dt), 5.86 (1H, dd), 6.07 (1H, t), 6.55 (1H, dd), 6.78 (1H, dd), 7.20-7.23 (1H, m), 7.98 (1H, d). m/z: (ES+), [M+H]+=626.

Preparation of N-(4-((6S,8R)-7-(2,2-difluoropropyl)-8-methyl-6,7,8,9-tetrahydro-3H-pyrazolo[4,3-f]isoquinolin-6-yl)-3-methoxyphenyl)azetidin-3-amine

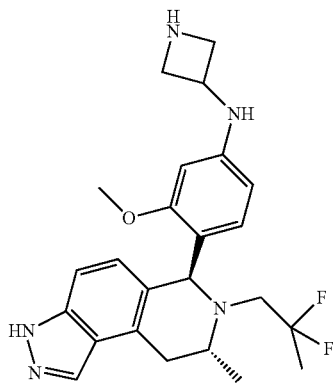 [SMILES: COc1cc(NC2CNC2)ccc1[C@@H]1c2ccc3[nH]ncc3c2C[C@@H](C)N1CC(C)(F)F]

Methanol (1 mL) and then HCl in dioxane (4 M; 1 mL, 4 mmol) were added sequentially to a flask charged with tert-butyl 3-((4-((6S,8R)-7-(2,2-difluoropropyl)-8-methyl-3-(tetrahydro-2H-pyran-2-yl)-6,7,8,9-tetrahydro-3H-pyrazolo[4,3-f]isoquinolin-6-yl)-3-methoxyphenyl)amino)azetidine-1-carboxylate (140 mg, 0.22 mmol). After 2 hours, the reaction was concentrated under reduced pressure and the resulting residue was purified using an SCX-2 cartage that had been pre-treated with methanol. The compound was eluted first with methanol and then ammonia in methanol (3N). Product fractions were concentrated under reduced pressure to afford N-(4-((6S,8R)-7-(2,2-difluoropropyl)-8-methyl-6,7,8,9-tetrahydro-3H-pyrazolo[4,3-f]isoquinolin-6-yl)-3-methoxyphenyl)azetidin-3-amine (91 mg, 92%) as a gum. The product was used in the next step without further purification. ¹H NMR (400 MHz, DMSO-d₆, 27° C.) 1.00 (3H, d), 1.52 (3H, t), 2.55-2.59 (1H, m), 2.78 (1H, dd), 2.85-2.99 (1H, m), 3.09 (1H, dd), 3.39-3.50 (1H, m), 3.55-3.66 (2H, m), 3.77 (3H, s), 4.03-4.14 (1H, m), 5.21 (1H, s), 5.85 (1H, dd), 6.05 (1H, br d), 6.14 (1H, d), 6.34 (1H, d), 6.63 (1H, d), 7.17 (1H, d), 8.02 (1H, s), 12.93 (1H, br s). 3H not observed. m/z: (ES+), [M+H]+=442.

Example 20

Preparation of N-(3-ethoxy-4-((6S,8R)-7-((1-fluorocyclopropyl)methyl)-8-methyl-6,7,8,9-tetrahydro-3H-pyrazolo[4,3-f]isoquinolin-6-yl)phenyl)-1-(3-fluoropropyl)azetidin-3-amine

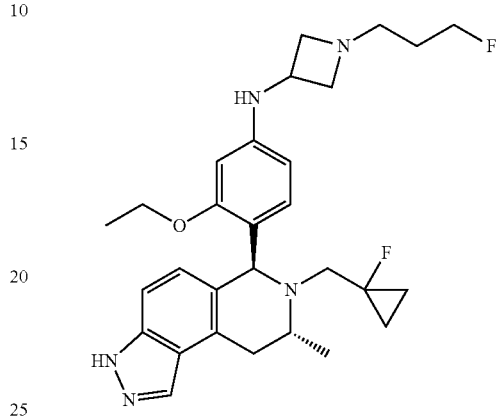

DMF (2 mL) and DIPEA (0.050 mL, 0.28 mmol) were added sequentially to a flask charged with N-(3-ethoxy-4-((6S,8R)-7-((1-fluorocyclopropyl)methyl)-8-methyl-6,7,8,9-tetrahydro-3H-pyrazolo[4,3-f]isoquinolin-6-yl)phenyl)azetidin-3-amine (0.051 g, 0.11 mmol). 1-Fluoro-3-iodopropane (0.021 g, 0.11 mmol) was added as a solution in DMF (0.2 mL), and after 2 hours, the reaction was diluted with saturated aqueous sodium hydrogencarbonate. The mixture was extracted with ethyl acetate (×3), and the combined organic layers were washed with water, dried over sodium sulfate, filtered, and concentrated under reduced pressure. The resulting residue was purified by flash silica chromatography, elution gradient 2 to 10% (methanol containing 1% ammonium hydroxide) in DCM. Product fractions were combined, concentrated under reduced pressure, and the resulting residue was purified by flash silica chromatography using the above conditions to afford N-(3-ethoxy-4-((6S,8R)-7-((1-fluorocyclopropyl)methyl)-8-methyl-6,7,8,9-tetrahydro-3H-pyrazolo[4,3-f]isoquinolin-6-yl)phenyl)-1-(3-fluoropropyl)azetidin-3-amine (0.023 g, 40%). ¹H NMR (CHLOROFORM-d, 27° C.) 0.50 (2H, br d), 0.88-1.05 (2H, m), 1.12 (3H, br d), 1.45 (3H, t), 1.75-1.87 (2H, m), 2.59-2.73 (3H, m), 2.87-3.04 (3H, m), 3.04-3.15 (1H, m), 3.41 (1H, br dd), 3.73-3.90 (3H, m), 3.93-4.18 (4H, m), 4.52 (2H, dt), 5.37 (1H, br s), 5.99 (1H, dd), 6.13 (1H, br d), 6.80-6.89 (2H, m), 7.14 (1H, d), 8.06-8.08 (1H, m), 10.02 (1H, br s). m/z: (ES+), [M+H]+=510.

Procedures used to prepare N-(3-ethoxy-4-((6S,8R)-7-((1-fluorocyclopropyl)methyl)-8-methyl-6,7,8,9-tetrahydro-3H-pyrazolo[4,3-f]isoquinolin-6-yl)phenyl)azetidin-3-amine are described below.

Preparation of (1S,3R)-1-(4-bromo-2-ethoxyphenyl)-2-((1-fluorocyclopropyl)methyl)-3,5-dimethyl-1,2,3,4-tetrahydroisoquinolin-6-amine

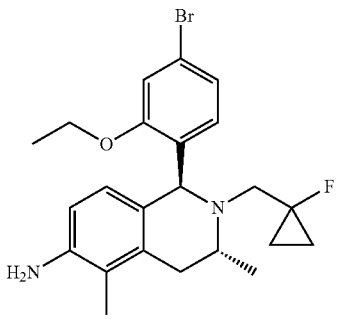 [SMILES: CCOc1cc(Br)ccc1[C@@H]1c2ccc(N)c(C)c2C[C@@H](C)N1CC1(F)CC1]

4-Bromo-2-ethoxybenzaldehyde (0.775 g, 3.39 mmol) was added to a solution of (R)-3-(2-(((1-fluorocyclopropyl)methyl)amino)propyl)-2-methylaniline (0.400 g, 1.69 mmol) in AcOH (9 mL) and water (0.152 g, 8.46 mmol). The reaction was heated at 80° C. for 18 hours. After cooling, the reaction was concentrated under reduced pressure, and then the residue was dissolved in EtOAc and washed with saturated aqueous NaHCO$_3$. The layers were separated, and the organic phase was combined with aqueous hydrochloric acid (1N). After stirring the biphasic mixture for 30 minutes, the layers were separated. The organic layer was washed with aqueous HCl (1N), and the combined aqueous layers were extracted with EtOAc (×2). The combined aqueous layers were then basified by addition of solid K$_2$CO$_3$ and extracted with EtOAc (×2). The organic extracts were combined, dried over sodium sulfate, filtered, and concentrated under reduced pressure. The resulting residue was purified by flash silica chromatography, elution gradient 10 to 60% ethyl acetate in hexanes to afford (1S,3R)-1-(4-bromo-2-ethoxyphenyl)-2-((1-fluorocyclopropyl)methyl)-3,5-dimethyl-1,2,3,4-tetrahydroisoquinolin-6-amine (0.48 g, 63%) as a solid. 1H NMR (400 MHz, DMSO-d$_6$, 27° C.) 0.40-0.59 (2H, m), 0.83-0.93 (2H, m), 0.94 (3H, d), 1.35 (3H, t), 1.93-1.96 (3H, m), 2.45-2.53 (2H, m), 2.80-2.93 (2H, m), 3.57 (1H, br d), 4.14 (2H, q), 4.58 (2H, s), 5.15 (1H, s), 6.26 (1H, d), 6.35 (1H, d), 6.86 (1H, d), 6.95 (1H, dd), 7.15 (1H, d). m/z: (ES+), [M+H]+=447.

Preparation of (6S,8R)-6-(4-bromo-2-ethoxyphenyl)-7-((1-fluorocyclopropyl)methyl)-8-methyl-6,7,8,9-tetrahydro-3H-pyrazolo[4,3-f]isoquinoline

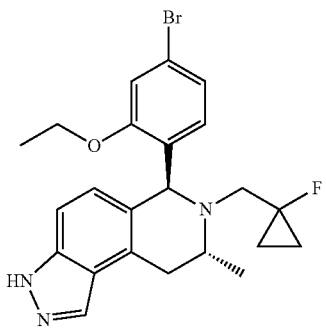 [SMILES: CCOc1cc(Br)ccc1[C@@H]1c2ccc3[nH]ncc3c2C[C@@H](C)N1CC1(F)CC1]

Sodium nitrite (0.039 g, 0.56 mmol) as a solution in water (0.750 mL) was added dropwise to a cooled solution of (1S,3R)-1-(4-bromo-2-ethoxyphenyl)-2-((1-fluorocyclopropyl)methyl)-3,5-dimethyl-1,2,3,4-tetrahydroisoquinolin-6-amine (0.240 g, 0.54 mmol) in propionic acid (3.0 mL) at −15° C., and the reaction was maintained under these conditions for 1 hour. Then ice-cold EtOAc (10 mL) was added, followed by saturated aqueous NaHCO$_3$ (15 mL) in portions. Once addition was complete and gas evolution ceased, the layers were separated. The organic layer was washed with saturated aqueous NaHCO$_3$ (×2), and the combined aqueous layers were extracted with EtOAc (×2). The combined organic layers were dried over sodium sulfate, filtered and concentrated under reduced pressure. The resulting residue was purified by flash chromatography, elution gradient 20 to 60% ethyl acetate in hexanes, to afford (6S,8R)-6-(4-bromo-2-ethoxyphenyl)-7-((1-fluorocyclopropyl)methyl)-8-methyl-6,7,8,9-tetrahydro-3H-pyrazolo[4,3-f]isoquinoline (0.145 g, 59%) as a gum. $^1$H NMR (500 MHz, DMSO-d$_6$, 27° C.) 0.45 (1H, br s), 0.57 (1H, br s), 0.83-0.98 (2H, m), 1.00 (3H, d), 1.37 (3H, t), 2.54-2.63 (1H, m), 2.87-3.00 (2H, m), 3.27-3.32 (1H, m), 3.74 (1H, br d), 4.13-4.23 (2H, m), 5.32 (1H, s), 6.67 (1H, d), 6.94 (1H, s), 6.96-6.99 (1H, m), 7.19 (1H, d), 7.22 (1H, d), 8.06 (1H, s), 12.96 (1H, s). m/z: (ES+), [M+H]+=458.

Preparation of (6S,8R)-6-(4-bromo-2-ethoxyphenyl)-7-((1-fluorocyclopropyl)methyl)-8-methyl-3-(tetrahydro-2H-pyran-2-yl)-6,7,8,9-tetrahydro-3H-pyrazolo[4,3-f]isoquinoline

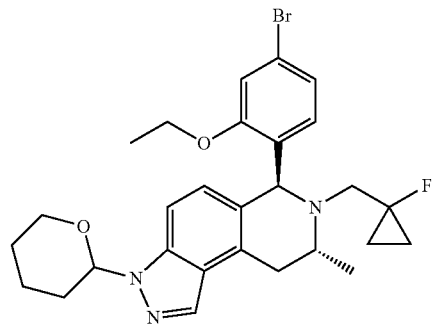 [SMILES: CCOc1cc(Br)ccc1[C@@H]1c2ccc3c(cnn3C3CCCCO3)c2C[C@@H](C)N1CC1(F)CC1]

DCM (3 mL) and 3,4-dihydro-2H-pyran (35.8 mg, 0.43 mmol) were added to a flask charged with (6S,8R)-6-(4-bromo-2-ethoxyphenyl)-7-((1-fluorocyclopropyl)methyl)-8-methyl-6,7,8,9-tetrahydro-3H-pyrazolo[4,3-f]isoquinoline (130 mg, 0.28 mmol) and 4-methylbenzenesulfonic acid hydrate (10.79 mg, 0.06 mmol). The reaction was stirred at room temperature for 18 hours. The reaction was washed with saturated aqueous sodium hydrogen carbonate, and the organic layer was dried over sodium sulfate, filtered, and concentrated under reduced pressure. The resulting brown gum was purified by flash silica chromatography, elution gradient 5 to 40% ethyl acetate in hexanes, to afford (6S,8R)-6-(4-bromo-2-ethoxyphenyl)-7-((1-fluorocyclopropyl)

methyl)-8-methyl-3-(tetrahydro-2H-pyran-2-yl)-6,7,8,9-tetrahydro-3H-pyrazolo[4,3-f]isoquinoline (147 mg, 96%) as a dry film. $^1$H NMR (500 MHz, CHLOROFORM-d, 27° C.) 0.42-0.51 (2H, m), 0.94-1.03 (2H, m), 1.07-1.12 (3H, m), 1.49 (3H, t), 1.61-1.68 (1H, m), 1.73-1.79 (2H, m), 2.02-2.10 (1H, m), 2.12-2.20 (1H, m), 2.53-2.63 (2H, m), 2.93 (1H, dt), 3.10 (1H, ddd), 3.38-3.46 (1H, m), 3.65-3.77 (1H, m), 3.83-3.92 (1H, m), 4.00-4.07 (1H, m), 4.12-4.19 (2H, m), 5.43 (1H, s), 5.66 (1H, ddd), 6.81 (1H, d), 6.89-6.93 (1H, m), 6.95-7.00 (1H, m), 7.03-7.06 (1H, m), 7.25 (1H, dd), 8.03 (1H, s). m/z: (ES+), [M+H]+=542.

Preparation of tert-butyl 3-((3-ethoxy-4-((6S,8R)-7-((1-fluorocyclopropyl)methyl)-8-methyl-3-(tetrahydro-2H-pyran-2-yl)-6,7,8,9-tetrahydro-3H-pyrazolo[4,3-f]isoquinolin-6-yl)phenyl)amino)azetidine-1-carboxylate

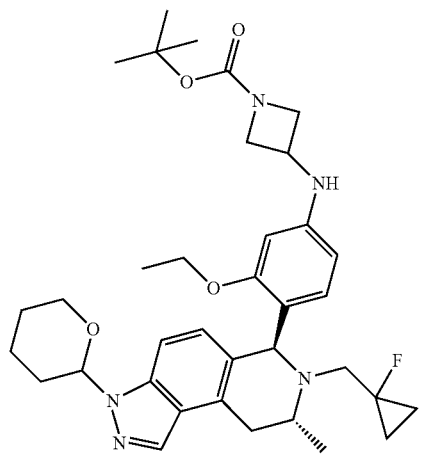 [SMILES: CCOc1cc(NC2CN(C(=O)OC(C)(C)C)C2)ccc1[C@@H]1c2ccc3c(cnn3C3CCCCO3)c2C[C@@H](C)N1CC1(F)CC1]

Dioxane (2.7 mL) was added to a flask charged with (6S,8R)-6-(4-bromo-2-ethoxyphenyl)-7-((1-fluorocyclopropyl)methyl)-8-methyl-3-(tetrahydro-2H-pyran-2-yl)-6,7,8,9-tetrahydro-3H-pyrazolo[4,3-f]isoquinoline (140 mg, 0.26 mmol), Cs$_2$CO$_3$ (168 mg, 0.52 mmol) and tert-butyl 3-aminoazetidine-1-carboxylate (67 mg, 0.39 mmol). The reaction flask was evacuated and filled with N$_2$ (×3). BrettPhos 3$^{rd}$ Generation Precatalyst (23 mg, 0.030 mmol) was added, and the flask was evacuated and filled with nitrogen (×3). The reaction was heated at 90° C. for 1 hour and then at 90° C. for 44 hours. The reaction was cooled to room temperature, filtered, and concentrated under reduced pressure. The resulting gum was purified by flash chromatography, elution gradient 30 to 100% ethyl acetate in hexanes, to afford tert-butyl 3-((3-ethoxy-4-((6S,8R)-7-((1-fluorocyclopropyl)methyl)-8-methyl-3-(tetrahydro-2H-pyran-2-yl)-6,7,8,9-tetrahydro-3H-pyrazolo[4,3-f]isoquinolin-6-yl)phenyl)amino)azetidine-1-carboxylate (86 mg, 53%) as a gum. $^1$H NMR (500 MHz, CHLOROFORM-d, 27° C.) 0.39-0.49 (2H, m), 0.87-0.95 (2H, m), 1.06 (3H, d), 1.38-1.45 (12H, m), 1.57-1.62 (1H, m), 1.68-1.74 (2H, m), 1.98-2.06 (1H, m), 2.07-2.15 (1H, m), 2.49-2.63 (2H, m), 2.85 (1H, dt), 3.05 (1H, br t), 3.29-3.35 (1H, m), 3.63-3.73 (3H, m), 3.75-3.83 (1H, m), 3.92 (1H, br d), 3.99 (1H, br d), 4.05 (2H, q), 4.14 (1H, br dd), 4.18-4.26 (2H, m), 5.33 (1H, s), 5.58-5.63 (1H, m), 5.90 (1H, br d), 6.02-6.06 (1H, m), 6.76 (1H, dd), 6.80 (1H, d), 7.19 (1H, d), 7.97 (1H, s). m/z: (ES+), [M+H]+=634.

Preparation of N-(3-ethoxy-4-((6S,8R)-7-((1-fluorocyclopropyl)methyl)-8-methyl-6,7,8,9-tetrahydro-3H-pyrazolo[4,3-f]isoquinolin-6-yl)phenyl)azetidin-3-amine

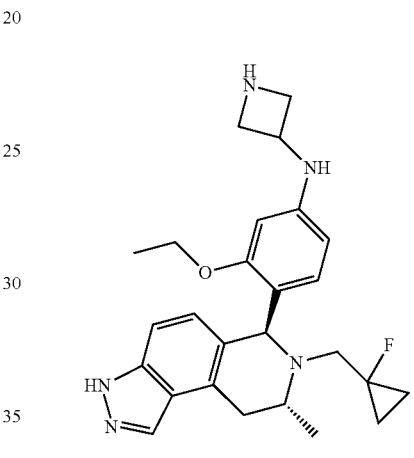

Methanol (0.5 mL) was added to a flask charged with tert-butyl 3-((3-ethoxy-4-((6S,8R)-7-((1-fluorocyclopropyl)methyl)-8-methyl-3-(tetrahydro-2H-pyran-2-yl)-6,7,8,9-tetrahydro-3H-pyrazolo[4,3-f]isoquinolin-6-yl)phenyl)amino)azetidine-1-carboxylate (0.080 g, 0.13 mmol). Hydrochloric acid in dioxane (4 M; 0.5 mL, 2 mmol) was added, and stirring was continued for 2 hours. The reaction was then concentrated under reduced pressure, and the resulting residue was purified using an SCX-2 cartridge that had been pre-treated with methanol, eluting first with methanol and then with ammonia in methanol (3N), to afford N-(3-ethoxy-4-((6S,8R)-7-((1-fluorocyclopropyl)methyl)-8-methyl-6,7,8,9-tetrahydro-3H-pyrazolo[4,3-f]isoquinolin-6-yl)phenyl)azetidin-3-amine (0.057 g, 99%) as a solid. $^1$H NMR (500 MHz, CHLOROFORM-d, 27° C.) 0.44-0.55 (2H, m), 0.90-1.00 (2H, m), 1.12 (3H, d), 1.45 (3H, t), 2.61-2.71 (1H, m), 2.92 (1H, br dd), 3.10 (1H, br dd), 3.40 (1H, br dd), 3.51-3.58 (2H, m), 3.83-3.90 (1H, m), 3.91-4.02 (2H, m), 4.03-4.16 (3H, m), 4.36 (1H, sxt), 5.38 (1H, s), 5.98 (1H, dd), 6.12 (1H, br d), 6.77-6.89 (2H, m), 7.13 (1H, d), 8.07 (1H, s), 10.09 (1H, br s). One H not observed and likely obscured by water peak. m/z (ES+), [M+H]+=450.

Example 21

Preparation of N-(4-((6S,8R)-7-(2,2-difluoroethyl)-8-methyl-6,7,8,9-tetrahydro-3H-pyrazolo[4,3-f]isoquinolin-6-yl)-3-methoxyphenyl)-1-(3-fluoropropyl)azetidin-3-amine

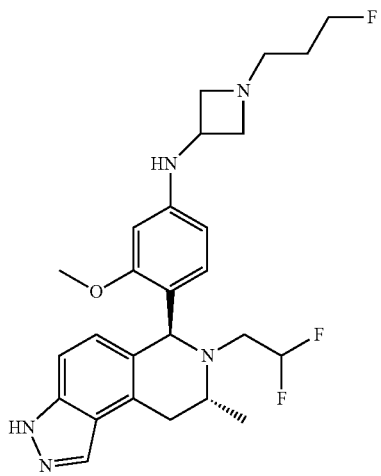 [SMILES: COc1cc(NC2CN(CCCF)C2)ccc1[C@@H]1c2ccc3[nH]ncc3c2C[C@@H](C)N1CC(F)F]

Hydrochloric acid in dioxane (4 M; 1.23 mL, 5.2 mmol) was added dropwisely to a stirred solution of tert-butyl 3-(4-((6S,8R)-7-(2,2-difluoroethyl)-8-methyl-2-(tetrahydro-2H-pyran-2-yl)-6,7,8,9-tetrahydro-2H-pyrazolo[4,3-f]isoquinolin-6-yl)-3-methoxyphenylamino)azetidine-1-carboxylate (316 mg, 0.52 mmol) in MeOH (5 mL). The mixture was stirred at room temperature for 18 hours. The reaction was concentrated under reduced pressure, and the resulting residue was dissolved in MeOH. Excess tetraalkylammonium carbonate macroporous resin (Aldrich; 18-50 mesh; 2.5-3.5 mmol/g N loading) was added, and the mixture was stirred at room temperature for 5 minutes. The mixture was filtered, and the filtrate was dried over sodium sulfate, filtered, and concentrated under reduced pressure to afford crude N-(4-((6S,8R)-7-(2,2-difluoroethyl)-8-methyl-6,7,8,9-tetrahydro-3H-pyrazolo[4,3-f]isoquinolin-6-yl)-3-methoxyphenyl)azetidin-3-amine as a gum (220 mg). This material was directly used in next step without further purification. m/z: (ES+), [M+H]+=428.

A mixture of N-(4-((6S,8R)-7-(2,2-difluoroethyl)-8-methyl-6,7,8,9-tetrahydro-3H-pyrazolo[4,3-f]isoquinolin-6-yl)-3-methoxyphenyl)azetidin-3-amine (220 mg, 0.51 mmol), 1-fluoro-3-iodopropane (106 mg, 0.57 mmol), and DIPEA (0.270 mL, 1.54 mmol) in DMF (5 mL) was stirred at room temperature for 18 hours. The reaction was diluted with DCM and washed with saturated aqueous ammonium chloride. The aqueous layer was extracted with DCM, and the combined organic layers were dried over sodium sulfate, filtered, and concentrated under reduced pressure. The resulting residue was purified by preparative HPLC (Xbridge C18 column, 19 mm×150 mm; 5 µm; flow rate: 20 mL/min), eluting with 40 to 80% acetonitrile in water containing 0.2% ammonium hydroxide. Product fractions were concentrated under reduced pressure, and the resulting residue was purified by preparative SFC (2-ethylpyridine column, 19 mm×150 mm, 5 µm; flow rate: 75 mL/min; column temperature: 40° C.; outlet pressure: 100 bar), eluting with 15% methanol containing 0.2% ammonium hydroxide in carbon dioxide, to afford N-(4-((6S,8R)-7-(2,2-difluoroethyl)-8-methyl-6,7,8,9-tetrahydro-3H-pyrazolo[4,3-f]isoquinolin-6-yl)-3-methoxyphenyl)-1-(3-fluoropropyl)azetidin-3-amine (82 mg, 33% two steps) as a white solid. $^1$H NMR (300 MHz, DMSO-d$_6$, 27° C.) 1.03 (3H, d), 1.55-1.74 (2H, m), 2.41-2.47 (2H, m), 2.53-2.83 (4H, m), 2.86-3.04 (1H, m), 3.10 (1H, br dd), 3.32-3.43 (1H, m), 3.58-3.66 (2H, m), 3.82 (3H, s), 3.86-3.98 (1H, m), 4.45 (2H, dt), 5.21 (1H, s), 5.89 (1H, t), 5.90 (1H, dd), 6.01 (1H, d), 6.19 (1H, d), 6.35 (1H, d), 6.67 (1H, d), 7.19 (1H, d), 8.03 (1H, s), 12.92-12.96 (1H, m). m/z: ES+ [M+H]+ 488.

The starting material tert-butyl 3-((4-((6S,8R)-7-(2,2-difluoroethyl)-8-methyl-2-(tetrahydro-2H-pyran-2-yl)-6,7,8,9-tetrahydro-3H-pyrazolo[4,3-f]isoquinolin-6-yl)-3-methoxyphenyl)amino)azetidine-1-carboxylate was prepared according to the following procedures.

Preparation of (6S,8R)-6-(4-bromo-2-methoxyphenyl)-7-(2,2-difluoroethyl)-8-methyl-3-(tetrahydro-2H-pyran-2-yl)-6,7,8,9-tetrahydro-3H-pyrazolo[4,3-f]isoquinoline and (6S,8R)-6-(4-bromo-2-methoxyphenyl)-7-(2,2-difluoroethyl)-8-methyl-2-(tetrahydro-2H-pyran-2-yl)-6,7,8,9-tetrahydro-2H-pyrazolo[4,3-f]isoquinoline

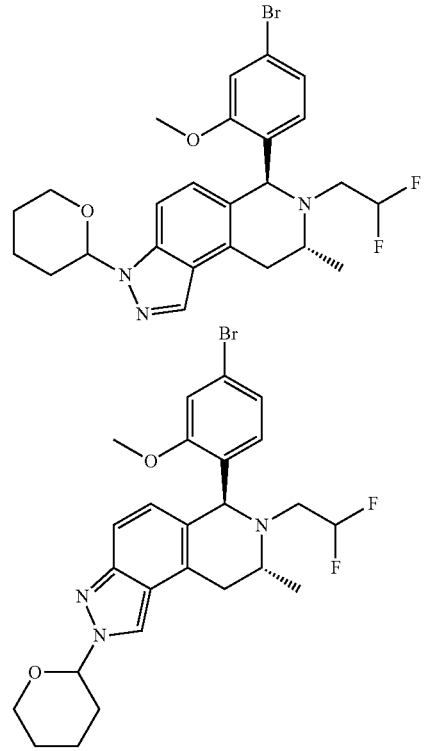

A microwave vial was charged with (6S,8R)-6-(4-bromo-2-methoxyphenyl)-7-(2,2-difluoroethyl)-8-methyl-6,7,8,9-tetrahydro-3H-pyrazolo[4,3-f]isoquinoline (986 mg, 2.26 mmol), 4-methylbenzenesulfonic acid hydrate (43 mg, 0.23 mmol), 3,4-dihydro-2H-pyran (0.31 mL, 3.4 mmol) and DCM. The reaction was heated at 80° C. under microwave conditions (300 W) for 20 minutes. The reaction was then cooled and diluted with DCM before being washed with saturated aqueous sodium hydrogencarbonate. The layers were separated, and the organic layer was dried over sodium sulfate, filtered, and concentrated under reduced pressure.

The resulting residue was purified by flash silica chromatography, elution gradient 0 to 70% EtOAc in hexanes, to afford faster eluting (6S,8R)-6-(4-bromo-2-methoxyphenyl)-7-(2,2-difluoroethyl)-8-methyl-3-(tetrahydro-2H-pyran-2-yl)-6,7,8,9-tetrahydro-3H-pyrazolo[4,3-f]isoquinoline (457 mg, 39%) as an orange solid. $^1$H NMR (300 MHz, CHLOROFORM-d, 27° C.) 1.04-1.22 (3H, m), 1.59-1.86 (3H, m), 2.04-2.23 (2H, m), 2.53-3.31 (5H, m), 3.40-3.57 (1H, m), 3.68-3.79 (1H, m), 3.97 (3H, s), 4.00-4.09 (1H, m), 5.41 (1H, br s), 5.69 (1H, br s), 5.66-5.73 (1H, m), 6.67 (1H, dd), 6.80 (1H, dd), 6.92 (1H, dd), 7.06-7.12 (1H, m), 7.29-7.37 (1H, m), 8.03 (1H, s). m/z: ES+ [M+H]+ 612. Also isolated was slower eluting (6S,8R)-6-(4-bromo-2-methoxyphenyl)-7-(2,2-difluoroethyl)-8-methyl-2-(tetrahydro-2H-pyran-2-yl)-6,7,8,9-tetrahydro-2H-pyrazolo[4,3-f]isoquinoline (627 mg, 57%) as a beige powder. $^1$H NMR (300 MHz, CHLOROFORM-d, 27° C.) 1.12 (3H, br d), 1.64-1.87 (3H, m), 2.03-2.17 (1H, m), 2.18-2.29 (2H, m), 2.61-2.83 (2H, m), 2.89-3.15 (2H, m), 3.43 (1H, br s), 3.75-3.86 (1H, m), 3.95 (3H, s), 4.13-4.20 (1H, m), 5.32 (1H, s), 5.79 (1H, br t), 5.66-5.73 (1H, m), 6.63-6.77 (2H, m), 6.93 (1H, d), 7.09 (1H, d), 7.43 (1H, d), 8.14 (1H, s). m/z: ES+ [M+H]+ 612.

Preparation of tert-butyl 3-(4-(((6S,8R)-7-(2,2-difluoroethyl)-8-methyl-2-(tetrahydro-2H-pyran-2-yl)-6,7,8,9-tetrahydro-2H-pyrazolo[4,3-f]isoquinolin-6-yl)-3-methoxyphenylamino)azetidine-1-carboxylate

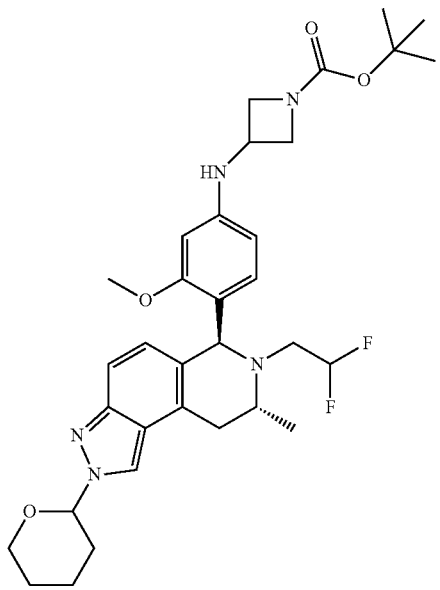 [SMILES: COc1cc(NC2CN(C(=O)OC(C)(C)C)C2)ccc1[C@@H]1c2ccc3nn(C4CCCCO4)cc3c2C[C@@H](C)N1CC(F)F]

A microwave vial was charged with (6S,8R)-6-(4-bromo-2-methoxyphenyl)-7-(2,2-difluoroethyl)-8-methyl-2-(tetrahydro-2H-pyran-2-yl)-6,7,8,9-tetrahydro-2H-pyrazolo[4,3-f]isoquinoline (310 mg, 0.60 mmol), tert-butyl 3-aminoazetidine-1-carboxylate (154 mg, 0.89 mmol), Cs$_2$CO$_3$ (388 mg, 1.19 mmol), and BrettPhos 3$^{rd}$ Generation Precatalyst (54.0 mg, 0.06 mmol). The vial was degassed and filled with nitrogen (×2). The vial was degassed again and re-filled with 1,4-dioxane (6 mL) and nitrogen. The vial was degassed again and re-filled with nitrogen. The mixture was heated under microwave conditions (300 W, 110° C.) for 3.5 hours. The reaction was diluted with DCM and washed with saturated aqueous sodium hydrogencarboante.

The organic layer was dried over sodium sulfate, filtered, and concentrated under reduced pressure. The resulting residue was purified by flash silica chromatography, elution gradient 20 to 60% EtOAc in hexanes, to afford tert-butyl 3-(4-(((6S,8R)-7-(2,2-difluoroethyl)-8-methyl-2-(tetrahydro-2H-pyran-2-yl)-6,7,8,9-tetrahydro-2H-pyrazolo[4,3-f]isoquinolin-6-yl)-3-methoxyphenylamino)azetidine-1-carboxylate (322 mg, 88%) as an off-white solid. $^1$H NMR (300 MHz, CHLOROFORM-d, 27° C.) 1.08 (3H, br d), 1.39-1.43 (9H, m), 1.58-1.81 (3H, m), 2.06 (1H, br dd), 2.13-2.25 (2H, m), 2.58-2.71 (1H, m), 2.82-3.11 (2H, m), 3.34-3.50 (1H, m), 3.66-3.81 (3H, m), 3.86 (3H, s), 3.90-4.01 (1H, m), 4.08-4.20 (3H, m), 4.19-4.29 (2H, m), 5.22 (1H, s), 5.76 (1H, t), 5.64 (1H, t), 5.88 (1H, br d), 6.09 (1H, d), 6.59 (1H, br t), 6.67 (1H, d), 7.37 (1H, br d), 8.08 (1H, s). m/z: ES+ [M+H]+ 612.

Example 22

Preparation of (6S,8R)-7-(2,2-difluoroethyl)-6-(4-((1-(3-fluoropropyl)azetidin-3-yl)oxy)-2-methoxyphenyl)-8-methyl-6,7,8,9-tetrahydro-3H-pyrazolo[4,3-f]isoquinoline

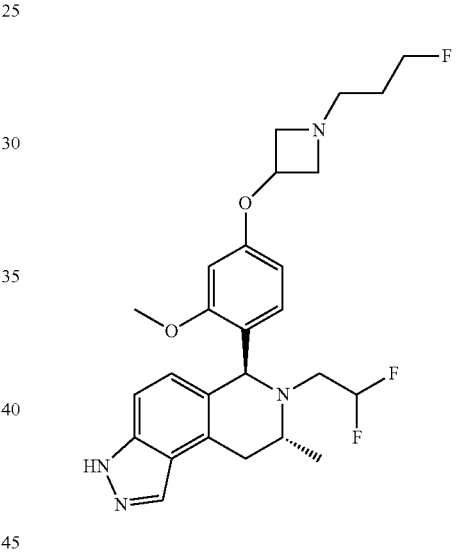

HCl in dioxane (4 M; 1.02 mL, 4.08 mmol) was added dropwisely to a stirred solution of tert-butyl 3-(4-(((6S,8R)-7-(2,2-difluoroethyl)-8-methyl-3-(tetrahydro-2H-pyran-2-yl)-6,7,8,9-tetrahydro-2H-pyrazolo[4,3-f]isoquinolin-6-yl)-3-methoxyphenoxy)azetidine-1-carboxylate (250 mg, 0.41 mmol) in MeOH (4 mL). The mixture was stirred at room temperature for 18 hours. The reaction was then concentrated under reduced pressure, and the resulting residue was dissolved with MeOH. Excess tetraalkylammonium carbonate macroporous resin (Aldrich; 18-50 mesh; 2.5-3.5 mmol/g N loading) was added, and the mixture was stirred at room temperature for 5 minutes before being dried over sodium sulfate, filtered, and concentrated under reduced pressure to afford crude (6S,8R)-6-(4-(azetidin-3-yloxy)-2-methoxyphenyl)-7-(2,2-difluoroethyl)-8-methyl-6,7,8,9-tetrahydro-3H-pyrazolo[4,3-f]isoquinoline (179 mg), which was directly used in next step without further purification. m/z: ES+ [M+H]+ 429.

A mixture of (6S,8R)-6-(4-(azetidin-3-yloxy)-2-methoxyphenyl)-7-(2,2-difluoroethyl)-8-methyl-6,7,8,9-tetrahydro-3H-pyrazolo[4,3-f]isoquinoline (178 mg, 0.42 mmol), 1-fluoro-3-iodopropane (94 mg, 0.50 mmol), and DIPEA (0.218 mL, 1.25 mmol) in DMF (4 mL) was stirred at room temperature for 18 hours. The reaction was then diluted with DCM and washed with saturated aqueous ammonium chloride. The layers were separated, and the aqueous layer was extracted with DCM. The combined organic layers were dried over sodium sulfate, filtered, and concentrated under reduced pressure. The resulting residue was purified by preparative SFC (2-ethylpyridine column; 19 mm×150 mm; 5 μm; flow rate: 75 mL/min; column temperature: 40° C.; outlet pressure: 100 bar), eluting with 15% (methanol containing 0.2% ammonium hydroxide) in carbon dioxide to afford (6S,8R)-7-(2,2-difluoroethyl)-6-(4-((1-(3-fluoropropyl)azetidin-3-yl)oxy)-2-methoxyphenyl)-8-methyl-6,7,8,9-tetrahydro-3H-pyrazolo[4,3-f]isoquinoline (70 mg, 35% over two steps) as a white solid. $^1$H NMR (300 MHz, DMSO-$d_6$, 27° C.) 1.02 (3H, d), 1.61-1.84 (2H, m), 2.55-2.84 (3H, m), 2.90-3.13 (2H, m), 3.18-3.43 (4H, m), 3.87 (3H, s), 3.89-4.00 (2H, m), 4.45 (2H, dt), 4.81 (1H, quin), 5.28 (1H, s), 5.74-6.16 (1H, m), 6.19 (1H, dd), 6.49-6.54 (2H, m), 6.66 (1H, d), 7.21 (1H, d), 8.04 (1H, s), 12.98 (1H, s). m/z: ES+ [M+H]+ 489.

Procedures used to prepare the starting material tert-butyl 3-(4-((6S,8R)-7-(2,2-difluoroethyl)-8-methyl-3-(tetrahydro-2H-pyran-2-yl)-6,7,8,9-tetrahydro-3H-pyrazolo[4,3-f]isoquinolin-6-yl)-3-methoxyphenoxy)azetidine-1-carboxylate are described below.

Preparation of tert-butyl 3-(4-((6S,8R)-7-(2,2-difluoroethyl)-8-methyl-3-(tetrahydro-2H-pyran-2-yl)-6,7,8,9-tetrahydro-3H-pyrazolo[4,3-f]isoquinolin-6-yl)-3-methoxyphenoxy)azetidine-1-carboxylate

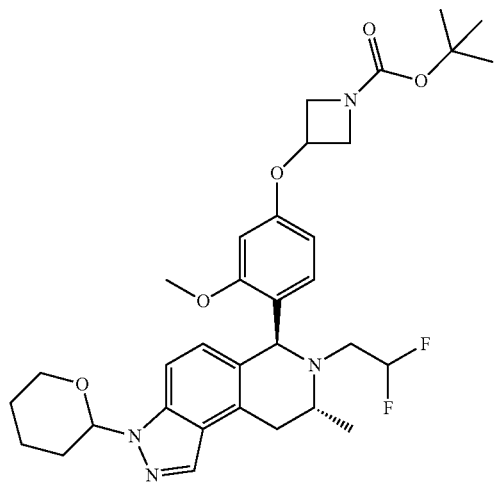 [SMILES: COc1cc(OC2CN(C(=O)OC(C)(C)C)C2)ccc1[C@@H]1c2ccc3c(cnn3C3CCCCO3)c2C[C@@H](C)N1CC(F)F]

A microwave vial was charged with (6S,8R)-6-(4-bromo-2-methoxyphenyl)-7-(2,2-difluoroethyl)-8-methyl-3-(tetrahydro-2H-pyran-2-yl)-6,7,8,9-tetrahydro-3H-pyrazolo[4,3-f]isoquinoline (259 mg, 0.50 mmol), tert-butyl 3-hydroxyazetidine-1-carboxylate (259 mg, 1.49 mmol), cesium carbonate (324 mg, 1.00 mmol), and RockPhos 3rd Generation Precatalyst (42 mg, 0.050 mmol). The vial was evacuated and re-filled with nitrogen (×2). Then the vial was evacuated and re-filled with toluene (3 mL). The vial was evacuated and re-filled with nitrogen. The mixture was heated at 110° C. for 4 hours. The reaction was diluted with DCM and washed with saturated aqueous sodium hydrogencarbonate. The organic layer was dried over sodium sulfate, filtered, and concentrated under reduced pressure. The resulting residue was purified by flash silica chromatography, elution gradient 0 to 60% EtOAc in hexanes to afford tert-butyl 3-(4-((6S,8R)-7-(2,2-difluoroethyl)-8-methyl-3-(tetrahydro-2H-pyran-2-yl)-6,7,8,9-tetrahydro-3H-pyrazolo[4,3-f]isoquinolin-6-yl)-3-methoxyphenoxy) azetidine-1-carboxylate (220 mg, 72%) as a white foam solid. $^1$H NMR (400 MHz, DMSO-$d_6$, 100° C.) 1.03-1.09 (3H, m), 1.40 (9H, s), 1.56-1.64 (2H, m), 1.67-1.84 (1H, m), 1.93-2.01 (1H, m), 2.02-2.12 (1H, m), 2.34-2.46 (1H, m), 2.59-2.74 (1H, m), 2.84 (1H, dt), 2.93-3.06 (1H, m), 3.13-3.23 (1H, m), 3.40-3.50 (1H, m), 3.65-3.74 (1H, m), 3.76-3.84 (2H, m), 3.84-3.91 (4H, m), 4.21-4.28 (2H, m), 4.97 (1H, tt), 5.33 (1H, s), 5.67-6.00 (1H, m), 5.74 (1H, dd), 6.23 (1H, ddd), 6.54 (1H, d), 6.66 (1H, t), 6.73 (1H, d), 7.35 (1H, d), 8.04 (1H, s). m/z: ES+ [M+H]+ 613.

Examples 23 and 24

Preparation of of individual diastereoisomers of 3-((6S,8R)-6-(2,6-difluoro-4-(1-(3-fluoropropyl)azetidin-3-ylamino)phenyl)-8-methyl-8,9-dihydro-3H-pyrazolo[4,3-f]isoquinolin-7(6H)-yl)-2-fluoro-2-methylpropan-1-ol

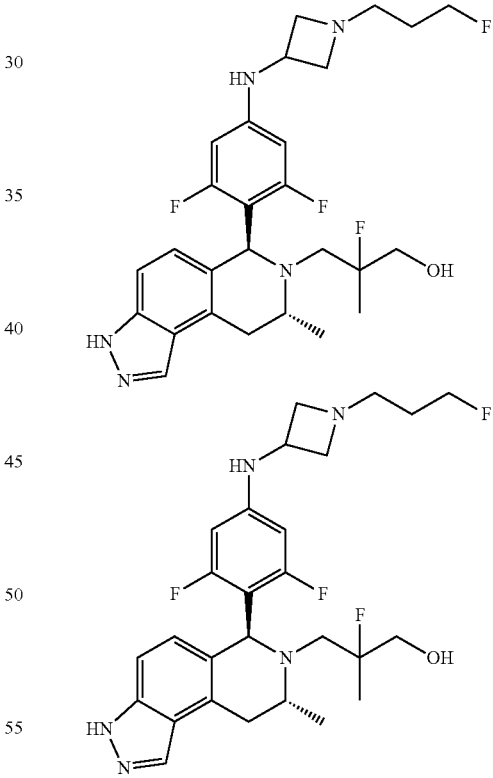

Tetrabutylammonium fluoride in THF (1 M; 0.114 mL, 0.11 mmol) was added dropwise via syringe to a stirred solution of N-(4-((6S,8R)-7-(3-((tert-butyldiphenylsilyl)oxy)-2-fluoro-2-methylpropyl)-8-methyl-6,7,8,9-tetrahydro-3H-pyrazolo[4,3-f]isoquinolin-6-yl)-3,5-difluorophenyl)-1-(3-fluoropropyl)azetidin-3-amine (82 mg, 0.08 mmol) in THF (0.75 mL). After 2.5 hours additional tetrabutylammonium fluoride in THF (1 M; 0.08 mL, 0.08 mmol) was added and the reaction was stirred for a further 18 hours.

The reaction was diluted with DCM and washed successively with saturated aqueous NaHCO₃ and saturated aqueous sodium chloride, dried over MgSO₄, filtered and concentrated under reduced pressure. The resulting residue was purified by flash silica chromatography, elution gradient 0.5 to 10% MeOH in DCM. Product fractions were concentrated under reduced pressure and the resulting residue was further purified by preparative HPLC (Waters XBridge Prep C18 OBD column, 5 μm silica, 19 mm diameter, 150 mm length), using an elution gradient of 45 to 85% acetonitrile in (water containing 0.2% NH₄OH). Product fractions were concentrated under reduced pressure to afford first eluting isomer 1 (2.7 mg, 7%) and second eluting isomer (2.1 mg, 5%) of 3-((6S,8R)-6-(2,6-difluoro-4-(1-(3-fluoropropyl)azetidin-3-ylamino)phenyl)-8-methyl-8,9-dihydro-3H-pyrazolo[4,3-f]isoquinolin-7(6H)-yl)-2-fluoro-2-methylpropan-1-ol as pale yellow films.

Isomer 1: ¹H NMR (500 MHz, CD₂Cl₂, 27° C.) 1.13 (3H, d), 1.17 (3H, d), 1.66-1.78 (3H, m), 2.54 (2H, t), 2.69 (1H, dd), 2.81-2.94 (3H, m), 3.00 (1H, dd), 3.31 (1H, dd), 3.51-3.59 (1H, m), 3.60-3.71 (4H, m), 3.95-4.03 (1H, m), 4.38 (1H, br s), 4.46 (2H, dt), 5.26 (1H, s), 6.01 (2H, br d), 6.84 (1H, d), 7.21 (1H, d), 8.03 (1H, s), 10.19 (1H, br s). m/z: ES+ [M+H]+ 520.

Isomer 2: ¹H NMR (500 MHz, CD₂Cl₂, 27° C.) 1.05 (3H, d), 1.09 (3H, d), 1.65-1.80 (2H, m), 2.54 (2H, t), 2.62 (1H, dd), 2.83-2.88 (2H, m), 2.91-3.00 (1H, m), 3.13-3.24 (1H, m), 3.33-3.46 (2H, m), 3.48-3.58 (1H, m), 3.66 (2H, q), 3.96-4.04 (2H, m), 4.40 (1H, dt), 4.41-4.53 (2H, m), 4.64 (1H, br d), 5.03 (1H, s), 6.06 (2H, br d), 6.76 (1H, d), 7.19 (1H, d), 8.03 (1H, s), 10.19 (1H, br s). m/z: ES+ [M+H]+ 520.

Procedures used to prepare the starting material N-(4-((6S,8R)-7-(3-((tert-butyldiphenylsilyl)oxy)-2-fluoro-2-methylpropyl)-8-methyl-6,7,8,9-tetrahydro-3H-pyrazolo[4,3-f]isoquinolin-6-yl)-3,5-difluorophenyl)-1-(3-fluoropropyl)azetidin-3-amine are described below.

Preparation of dimethyl 2-fluoro-2-methyl-propanedioate

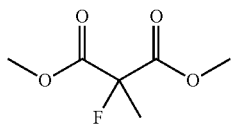

Sodium hydride (60% dispersion in mineral oil; 2.93 g, 73.3 mmol) was added to a solution of dimethyl 2-fluoromalonate (10.0 g, 66.6 mmol) in THF (218 mL) with vigorous stirring. After 30 minutes iodomethane (4.56 mL, 73.3 mmol) was added. The reaction was stirred for a further 3 hours. The reaction was quenched with water and then extracted with EtOAc (4×100 mL). The combined organic layers were dried over Na₂SO₄, filtered, and concentrated under reduced pressure to afford dimethyl 2-fluoro-2-methyl-propanedioate (8.4 g, 77%) as an orange oil. ¹H NMR (300 MHz, DMSO-d₆, 27° C.) 1.72 (3H, d), 3.77 (6H, s).

Preparation of 2-fluoro-2-methylpropane-1,3-diol

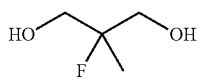

Lithium aluminium hydride (4.50 g, 112.6 mmol) was added portion-wise to a stirred solution of dimethyl 2-fluoro-2-methyl-propanedioate (8.40 g, 51.2 mmol) in THF (205 mL) at 0° C. The reaction was warmed to room temperature and stirred under these conditions for 1 hour. The reaction mixture was then cooled to 0° C. and cautiously quenched by sequential dropwise addition of water (5.85 mL), 15 wt % aqueous NaOH (5.85 mL), and water (18 mL). The resulting gelatinous suspension was stirred rapidly for 1 hour. The precipitate was removed by filtration, and the filtrate was concentrated under reduced pressure. The resulting residue was dissolved in a mixture of CHCl₃/IPA (3:1), dried over Na₂SO₄, filtered, and concentrated under reduced pressure to afford 2-fluoro-2-methylpropane-1,3-diol (3.28 g, 46%) as an orange oil. This oil was used in the next step without further purification. ¹H NMR (300 MHz, DMSO-d₆, 27° C.) 1.18 (3H, d), 3.42 (4H, dd), 4.80 (2H, t).

Preparation of 3-((tert-butyldiphenylsilyl)oxy)-2-fluoro-2-methylpropan-1-ol

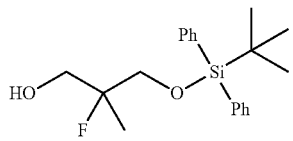 [SMILES: CC(F)(CO)CO[Si](c1ccccc1)(c1ccccc1)C(C)(C)C]

Sodium hydride (60% dispersion in mineral oil; 1.1 g, 27.5 mmol) was added to a stirred solution of 2-fluoro-2-methylpropane-1,3-diol (2.7 g, 25 mmol) in THF (93 mL) at 0° C. and the reaction was stirred for 1 hour. Tert-butylchlorodiphenylsilane (6.5 mL, 25 mmol) was added, and the reaction was stirred for an additional 1 hour. The reaction was quenched with water, the layers were separated, and the aqueous layer was extracted with EtOAc (2×100 mL). The combined organic layers were dried over Na₂SO₄, filtered, and adsorbed onto silica gel under reduced pressure. Purification by flash silica chromatography, elution gradient 0 to 50% EtOAc in hexanes, afforded 3-((tert-butyldiphenylsilyl)oxy)-2-fluoro-2-methylpropan-1-ol (4.4 g, 51%) as a clear gum. ¹H NMR (300 MHz, DMSO-d₆, 27° C.) 1.00 (9H, s), 1.27 (3H, d), 3.48 (1H, dd), 3.53 (1H, dd), 3.66 (1H, d), 3.73 (1H, br s), 4.93 (1H, t), 7.40-7.48 (6H, m), 7.59-7.66 (4H, m). m/z: ES+ [M+H]+347.

Preparation of 3-((tert-butyldiphenylsilyl)oxy)-2-fluoro-2-methylpropyl trifluoromethanesulfonate

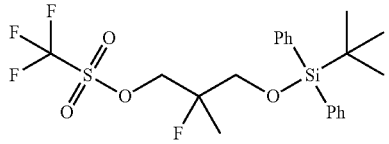 [SMILES: CC(F)(CO[Si](c1ccccc1)(c1ccccc1)C(C)(C)C)COS(=O)(=O)C(F)(F)F]

Trifluoromethanesulfonic anhydride (1.3 mL, 7.6 mmol) was added dropwise to a stirred solution of 3-((tert-butyldiphenylsilyl)oxy)-2-fluoro-2-methylpropan-1-ol (2.2 g, 6.35 mmol) and 2,6-dimethylpyridine (1.28 mL, 7.6 mmol) in DCM (22 mL) at −10° C. (salt/ice bath). The reaction was maintained under these conditions for 1.5 hours. The reaction was then diluted with DCM (100 mL) and washed successively with aqueous HCl (1N), saturated aqueous NaHCO₃, and saturated aqueous NaCl. The organic layer was dried over Na₂SO₄, filtered, and concentrated under reduced pressure to afford 3-((tert-butyldiphenylsilyl)oxy)-2-fluoro-2-methylpropyl trifluoromethanesulfonate (3.2 g) as a red oil. This oil was used in the next step without further purification.

Preparation of a diastereoisomeric mixture of 3-((2R)-2-((3-((tert-butyldiphenylsilyl)oxy)-2-fluoro-2-methylpropyl)amino)propyl)-2-methylaniline

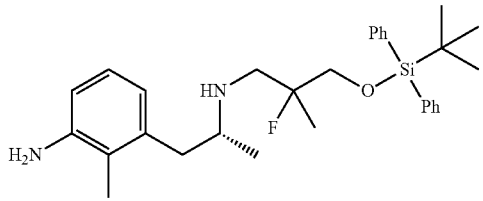 [SMILES: Cc1c(N)cccc1C[C@@H](C)NCC(C)(F)CO[Si](c1ccccc1)(c1ccccc1)C(C)(C)C]

3-((Tert-butyldiphenylsilyl)oxy)-2-fluoro-2-methylpropyl trifluoromethanesulfonate (3.04 g, 6.35 mmol) was added to a solution of (R)-3-(2-aminopropyl)-2-methylaniline (1.04 g, 6.35 mmol) and diisopropylethylamine (1.65 mL, 9.53 mmol) in 1,4-dioxane (24 mL). The reaction was heated at 85° C. for 18 hours. After cooling, the reaction was diluted with DCM (250 mL) and washed with water. The aqueous layer was extracted with DCM (2×100 mL), and the combined organics were dried over Na₂SO₄, filtered, and concentrated under reduced pressure. The resulting residue was purified by flash silica chromatography, elution gradient 0 to 25% MeOH in DCM. Product fractions were concentrated under reduced pressure to afford 3-((2R)-2-((3-((tert-butyldiphenylsilyl)oxy)-2-fluoro-2-methylpropyl)amino)propyl)-2-methylaniline (2.10 g, 95%) as a gum. ¹H NMR (300 MHz, DMSO-d₆, 27° C.) 0.90 (3H, dd), 1.01 (9H, d), 1.29 (3H, dd), 1.41 (1H, br s), 1.97 (3H, d), 2.29-2.43 (1H, m), 2.65-2.91 (4H, m), 3.62-3.82 (2H, m), 4.67 (2H, s), 6.28-6.36 (1H, m), 6.47 (1H, dd), 6.69-6.81 (1H, m), 7.40-7.52 (6H, m), 7.61-7.69 (4H, m). m/z: ES+ [M+H]+ 494.

Preparation of a diastereoisomeric mixture of (1S, 3R)-1-(4-bromo-2,6-difluorophenyl)-2-(3-((tert-butyldiphenylsilyl)oxy)-2-fluoro-2-methylpropyl)-3,5-dimethyl-1,2,3,4-tetrahydroisoquinolin-6-amine

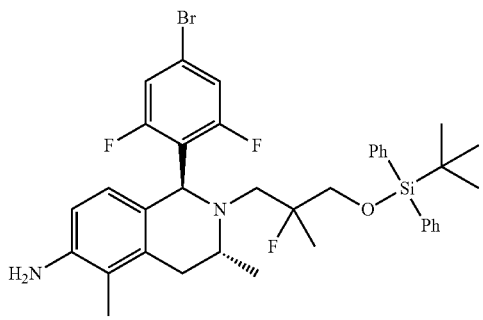 [SMILES: Cc1c(N)ccc2c1C[C@@H](C)N(CC(C)(F)CO[Si](c1ccccc1)(c1ccccc1)C(C)(C)C)[C@@H]2c1c(F)cc(Br)cc1F]

4-bromo-2,6-difluorobenzaldehyde (628 mg, 2.84 mmol) was added to a stirred solution of 3-((2R)-2-((3-((tert-butyldiphenylsilyl)oxy)-2-fluoro-2-methylpropyl)amino)propyl)-2-methylaniline (700 mg, 1.42 mmol) and water (0.128 mL, 7.10 mmol) in a mixture of acetic acid (10 mL) and toluene (4 mL). The reaction was heated at 90° C. for 18 hours before being heated at reflux conditions for another 4 hours. The reaction was allowed to cool and was concentrated under reduced pressure. The resulting residue was dissolved in DCM and washed with saturated aqueous NaHCO₃. The aqueous phase was extracted with DCM (20 mL) and the combined organic layers were concentrated under reduced pressure. The residue was dissolved in a mixture of MeOH/DCM (5:1, 18 mL) and then hydroxylamine hydrochloride (148 mg, 2.13 mmol) and sodium acetate (233 mg, 2.84 mmol) were added. The mixture was stirred at 35° C. for 5 minutes and then concentrated under reduced pressure. The resulting residue was dissolved in EtOAc and washed sequentially with saturated aqueous NaHCO₃ and saturated aqueous NaCl before being dried over MgSO₄, filtered and concentrated under reduced pressure. The resulting residue was purified by flash silica chromatography, elution gradient 0 to 35% EtOAc in hexanes to afford (1S,3R)-1-(4-bromo-2,6-difluorophenyl)-2-(3-((tert-butyldiphenylsilyl)oxy)-2-fluoro-2-methylpropyl)-3,5-dimethyl-1,2,3,4-tetrahydroisoquinolin-6-amine (339 mg, 34%) as a pale yellow film. ¹H NMR (500 MHz, CDCl₃, 27° C.) 1.05 (9H, d), 1.19 (3H, dd), 2.08 (3H, s), 2.35 (1H, dd), 2.47-2.67 (2H, m), 2.84-3.01 (1H, m), 3.02-3.14 (1H, m), 3.22 (1H, dd), 3.40-3.63 (3H, m), 3.66-3.79 (1H, m), 3.92 (1H, dd), 5.15 (1H, d), 6.38-6.47 (2H, m), 6.83 (1H, d), 6.93-7.00 (1H, m), 7.38-7.49 (6H, m), 7.59-7.71 (4H, m), 8.69 (1H, s). m/z: ES+ [M+H]+ 695.

Preparation of a diastereoisomeric mixture of (6S, 8R)-6-(4-bromo-2,6-difluorophenyl)-7-(3-((tert-butyldiphenylsilyl)oxy)-2-fluoro-2-methylpropyl)-8-methyl-6,7,8,9-tetrahydro-3H-pyrazolo[4,3-f]isoquinoline

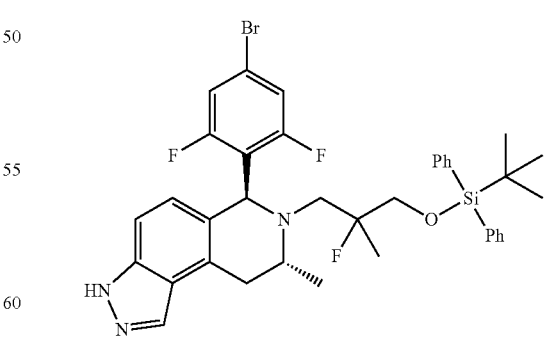

Sodium nitrite (33.6 mg, 0.49 mmol) as a solution in water (0.400 mL) was added dropwise to a cooled solution of (1S,3R)-1-(4-bromo-2,6-difluorophenyl)-2-(3-((tert-butyldiphenylsilyl)oxy)-2-fluoro-2-methylpropyl)-3,5-dimethyl-1,2,3,4-tetrahydroisoquinolin-6-amine (339 mg, 0.49 mmol) in propionic acid (4 mL) at −20° C., and the reaction was stirred for 30 minutes under these conditions. Ice-cold EtOAc (20 mL) was added followed by portion-wise addition of saturated aqueous NaHCO₃ (5 mL).

The biphasic mixture was stirred vigorously and neutralized by slow addition of solid Na₂CO₃. The phases were separated, and the organic layers were washed with saturated aqueous NaHCO₃ (2×30 mL) and saturated aqueous NaCl (30 mL) before being dried over MgSO₄, filtered, and concentrated under reduced pressure. The resulting residue was purified by flash silica chromatography, elution gradient 0 to 40% EtOAc in hexanes, to afford (6S,8R)-6-(4-bromo-2,6-difluorophenyl)-7-(3-((tert-butyldiphenylsilyl)oxy)-2-fluoro-2-methylpropyl)-8-methyl-6,7,8,9-tetrahydro-3H-pyrazolo[4,3-f]isoquinoline (206 mg, 60%) as a pale yellow solid. $^1$H NMR (500 MHz, CDCl₃, 27° C.) 0.98 (4.5H, s), 1.00 (1.5H, d), 1.02 (1.5H, d), 1.04 (4.5H, s), 1.15 (1.5H, d), 1.23 (1.5H, d), 2.30-2.47 (0.5H, m), 2.60 (0.5H, dd), 2.81 (0.5H, dd), 2.89 (0.5H, dd), 3.02 (0.5H, dd), 3.06-3.21 (1H, m), 3.22-3.33 (0.5H, m), 3.37-3.51 (1H, m), 3.51-3.60 (0.5H, m), 3.61-3.72 (0.5H, m), 3.73-3.83 (0.5H, m), 3.89 (0.5H, dd), 5.22 (0.5H, s), 5.27 (0.5H, s), 6.70 (1H, dd), 6.81 (1H, br d), 6.91-7.00 (1H, m), 7.14 (1H, t), 7.33-7.47 (6H, m), 7.55-7.67 (4H, m), 8.07 (1H, br d). Indazole NH not observed. m/z: ES+ [M+H]+ 706.

Preparation of a diastereoisomeric mixture of (6S, 8R)-6-(4-bromo-2,6-difluorophenyl)-7-(3-((tert-butyldiphenylsilyl)oxy)-2-fluoro-2-methylpropyl)-8-methyl-3-(tetrahydro-2H-pyran-2-yl)-6,7,8,9-tetrahydro-3H-pyrazolo[4,3-f]isoquinoline

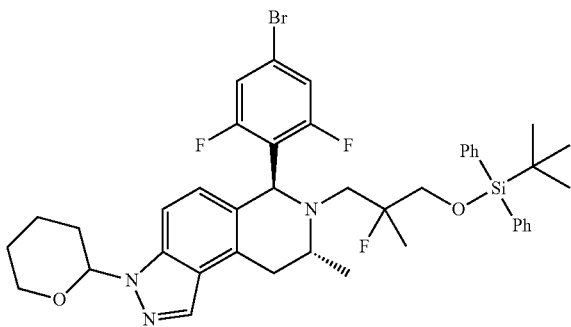 [SMILES: C[C@@H]1Cc2c(ccc3c2cnn3C2CCCCO2)[C@@H](c2c(F)cc(Br)cc2F)N1CC(C)(F)CO[Si](c1ccccc1)(c1ccccc1)C(C)(C)C]

3,4-Dihydro-2H-pyran (0.129 mL, 1.41 mmol) and para-toluenesulfonic acid monohydrate (2.7 mg, 0.01 mmol) were added to a stirred solution of (6S,8R)-6-(4-bromo-2,6-difluorophenyl)-7-(3-((tert-butyldiphenylsilyl)oxy)-2-fluoro-2-methylpropyl)-8-methyl-6,7,8,9-tetrahydro-3H-pyrazolo[4,3-f]isoquinoline (200 mg, 0.28 mmol) in DCM (2 mL). The reaction was heated at 45° C. for 21 hours. The reaction was allowed to cool and then diluted with DCM, washed with saturated aqueous NaHCO₃, dried over MgSO₄, filtered, and concentrated under reduced pressure. The resulting residue was purified by flash silica chromatography, elution gradient 5 to 30% EtOAc in hexanes, to afford (6S,8R)-6-(4-bromo-2,6-difluorophenyl)-7-(3-((tert-butyldiphenylsilyl)oxy)-2-fluoro-2-methylpropyl)-8-methyl-3-(tetrahydro-2H-pyran-2-yl)-6,7,8,9-tetrahydro-3H-pyrazolo[4,3-f]isoquinoline (176 mg, 79%) as a colorless film. m/z: ES+ [M+H]+ 790.

Preparation of a diastereoisomeric mixture of tert-butyl 3-((4-((6S,8R)-7-(3-((tert-butyldiphenylsilyl)oxy)-2-fluoro-2-methylpropyl)-8-methyl-3-(tetrahydro-2H-pyran-2-yl)-6,7,8,9-tetrahydro-3H-pyrazolo[4,3-f]isoquinolin-6-yl)-3,5-difluorophenyl)amino)azetidine-1-carboxylate

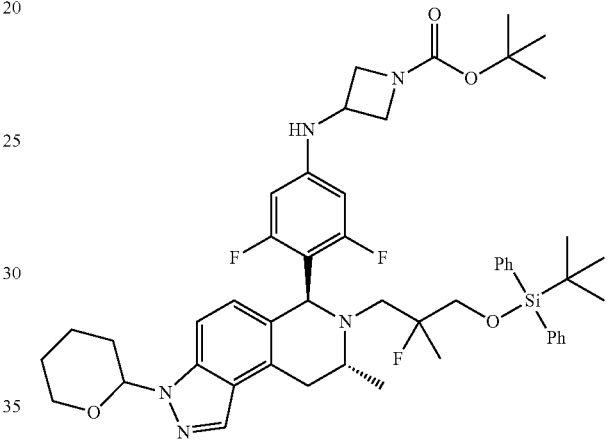

A vial was charged with a stirrer bar, (6S,8R)-6-(4-bromo-2,6-difluorophenyl)-7-(3-((tert-butyldiphenylsilyl)oxy)-2-fluoro-2-methylpropyl)-8-methyl-3-(tetrahydro-2H-pyran-2-yl)-6,7,8,9-tetrahydro-3H-pyrazolo[4,3-f]isoquinoline (126 mg, 0.16 mmol), tert-butyl 3-aminoazetidine-1-carboxylate (41 mg, 0.24 mmol), Pd₂dba₃ (9.3 mg, 0.01 mmol), 4,5-bis(diphenylphosphino)-9,9-dimethylxanthene (Xantphos) (16 mg, 0.02 mmol), and cesium carbonate (156 mg, 0.48 mmol). The vial was sealed, evacuated and backfilled with nitrogen (3×) prior to the addition of 1,4-dioxane (1 mL) via syringe. The mixture was stirred at ambient temperature for 2 minutes and then heated at 90° C. for 16 hours. The mixture was allowed to cool and then diluted with EtOAc, filtered through diatomaceous earth, and concentrated under reduced pressure. The resulting residue was purified by flash silica chromatography, elution gradient 0 to 40% EtOAc in hexanes, to afford tert-butyl 3-((4-((6S,8R)-7-(3-((tert-butyldiphenylsilyl)oxy)-2-fluoro-2-methylpropyl)-8-methyl-3-(tetrahydro-2H-pyran-2-yl)-6,7,8,9-tetrahydro-3H-pyrazolo[4,3-f]isoquinolin-6-yl)-3,5-difluorophenyl)amino)azetidine-1-carboxylate (95 mg, 68%) as a pale yellow solid. m/z: ES+ [M+H]+ 883.

Preparation of a diastereoisomeric mixture of N-(4-((6S,8R)-7-(3-((tert-butyldiphenylsilyl)oxy)-2-fluoro-2-methylpropyl)-8-methyl-6,7,8,9-tetrahydro-3H-pyrazolo[4,3-f]isoquinolin-6-yl)-3,5-difluorophenyl)azetidin-3-amine

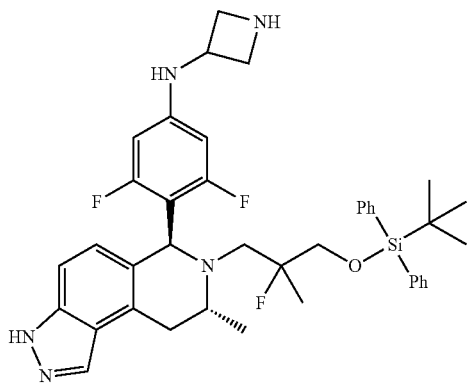 [SMILES: C[C@@H]1Cc2c(ccc3[nH]ncc23)[C@@H](c2c(F)cc(NC3CNC3)cc2F)N1CC(C)(F)CO[Si](c1ccccc1)(c1ccccc1)C(C)(C)C]

Formic acid (0.5 mL, 13.04 mmol) was added to tert-butyl 3-((4-((6S,8R)-7-(3-((tert-butyldiphenylsilyl)oxy)-2-fluoro-2-methylpropyl)-8-methyl-3-(tetrahydro-2H-pyran-2-yl)-6,7,8,9-tetrahydro-3H-pyrazolo[4,3-j]isoquinolin-6-yl)-3,5-difluorophenyl)amino)azetidine-1-carboxylate (53 mg, 0.06 mmol) and the resulting solution was stirred at ambient temperature for 18 hours. The reaction was concentrated under reduced pressure, and the resulting residue was dissolved in THF (0.5 mL) and treated with aqueous NaOH (5N; 0.081 mL, 2.40 mmol). The mixture was stirred at 30° C. for 20 hours and then maintained at 40° C. for 4 hours. Additional aqueous NaOH (5N; 0.081 mL, 2.40 mmol) was added, and the reaction stirred at 40° C. for 46 hours before being heated at 55° C. for 5 hours. The reaction mixture was allowed to cool to ambient temperature. Meanwhile, in a separate vial, HCl in dioxane (4N; 0.38 mL, 1.5 mmol) was added to a stirred solution of tert-butyl 3-((4-((6S,8R)-7-(3-((tert-butyldiphenylsilyl)oxy)-2-fluoro-2-methylpropyl)-8-methyl-3-(tetrahydro-2H-pyran-2-yl)-6,7,8,9-tetrahydro-3H-pyrazolo[4,3-f]isoquinolin-6-yl)-3,5-difluorophenyl)amino)azetidine-1-carboxylate (89 mg, 0.10 mmol) in MeOH (0.5 mL). The reaction was stirred at room temperature for 5 hours and then concentrated under reduced pressure. The resulting residue was combined with the previous reaction (as a mixture in aqueous NaOH (5N) and THF). The new mixture was diluted with DCM (5 mL), the phases were separated, and the aqueous phase was extracted with DCM (2×5 mL). The combined organic layers were dried over MgSO$_4$, filtered and concentrated under reduced pressure to afford N-(4-((6S,8R)-7-(3-((tert-butyldiphenylsilyl)oxy)-2-fluoro-2-methylpropyl)-8-methyl-6,7,8,9-tetrahydro-3H-pyrazolo[4,3-f]isoquinolin-6-yl)-3,5-difluorophenyl)azetidin-3-amine (177 mg) as a pale yellow solid, which was used in the next step without further purification. m/z: ES+ [M+H]+ 698.

Preparation of a diastereoisomeric mixture of N-(4-((6S,8R)-7-(3-((tert-butyldiphenylsilyl)oxy)-2-fluoro-2-methylpropyl)-8-methyl-6,7,8,9-tetrahydro-3H-pyrazolo[4,3-f]isoquinolin-6-yl)-3,5-difluorophenyl)-1-(3-fluoropropyl)azetidin-3-amine

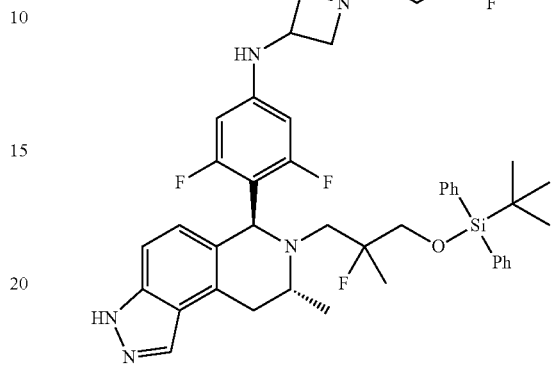

1-Fluoro-3-iodopropane (0.026 mL, 0.16 mmol) was added to a stirred solution of N-(4-((6S,8R)-7-(3-((tert-butyldiphenylsilyl)oxy)-2-fluoro-2-methylpropyl)-8-methyl-6,7,8,9-tetrahydro-3H-pyrazolo[4,3-f]isoquinolin-6-yl)-3,5-difluorophenyl)azetidin-3-amine (115 mg, 0.16 mmol) and diisopropylethylamine (0.058 mL, 0.33 mmol) in NMP (0.75 mL). The reaction was stirred for 16 hours at room temperature before being diluted with EtOAc and washed with saturated aqueous NaHCO$_3$. The layers were separated and the aqueous layer was extracted with EtOAc. The combined organic layers were washed with saturated aqueous NaCl (2×5 mL), dried over MgSO$_4$, filtered, and concentrated under reduced pressure. The resulting residue was purified by flash silica chromatography, elution gradient 1 to 20% MeOH in DCM to afford N-(4-((6S,8R)-7-(3-((tert-butyldiphenylsilyl)oxy)-2-fluoro-2-methylpropyl)-8-methyl-6,7,8,9-tetrahydro-3H-pyrazolo[4,3-f]isoquinolin-6-yl)-3,5-difluorophenyl)-1-(3-fluoropropyl)azetidin-3-amine (82 mg, 66%) as a pale yellow film. m/z: ES+ [M+H]+ 758.

Example 25

Preparation of 6-((6S,8R)-7-(2,2-difluoroethyl)-8-methyl-6,7,8,9-tetrahydro-3H-pyrazolo[4,3-f]isoquinolin-6-yl)-N-(1-(3-fluoropropyl)azetidin-3-yl)pyridin-3-amine

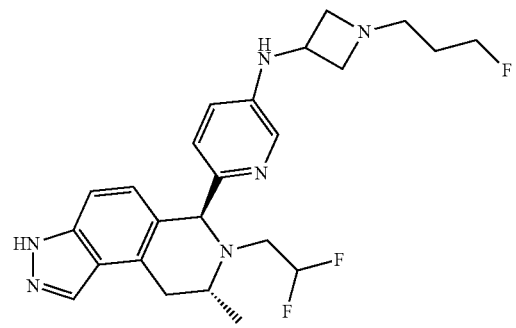 [SMILES: C[C@@H]1Cc2c(ccc3[nH]ncc23)[C@@H](c2ccc(NC3CN(CCCF)C3)cn2)N1CC(F)F]

HCl in dioxane (4N; 0.86 mL, 3.4 mmol) was added dropwise to a solution of tert-butyl 3-((6-((6S,8R)-7-(2,2-difluoroethyl)-8-methyl-3-(tetrahydro-2H-pyran-2-yl)-6,7,8,9-tetrahydro-3H-pyrazolo[4,3-f]isoquinolin-6-yl)pyridin-3-yl)amino)azetidine-1-carboxylate (0.20 g, 0.34 mmol) in MeOH (2.5 mL), and the reaction was stirred at room temperature for 2 hours. The reaction was concentrated under reduced pressure to afford N-(azetidin-3-yl)-6-((6S,8R)-7-(2,2-difluoroethyl)-8-methyl-6,7,8,9-tetrahydro-3H-pyrazolo[4,3-f]isoquinolin-6-yl)pyridin-3-amine hydrochloride (200 mg) as a solid. m/z: (ES+), [M+H]+ 399.

DMF (0.5 mL) and 1-fluoro-3-iodopropane (0.036 mL, 0.34 mmol) were added sequentially at ambient temperature. Then excess diisopropylethylamine (1.2 mL, 6.80 mmol) was added dropwise. The reaction was stirred at room temperature for 18 hours and then concentrated under reduced pressure. The resulting residue was purified by reverse phase flash C18 chromatography, elution gradient 20 to 75% acetonitrile in (water containing 0.2% NH$_4$OH), to afford 6-((6S,8R)-7-(2,2-difluoroethyl)-8-methyl-6,7,8,9-tetrahydro-3H-pyrazolo[4,3-f]isoquinolin-6-yl)-N-(1-(3-fluoropropyl)azetidin-3-yl)pyridin-3-amine (45 mg, 29%) as a solid. $^1$H NMR (500 MHz, DMSO-d$_6$, 27° C.) 1.04 (3H, d), 1.60-1.75 (2H, m), 2.51-2.70 (3H, m), 2.79-2.96 (3H, m), 3.03 (1H, dd), 3.13 (1H, br dd), 3.41-3.53 (1H, m), 3.74 (2H, br s), 3.98 (1H, br d), 4.45 (2H, dt), 4.86 (1H, s), 5.83 (1H, tt), 6.26 (1H, d), 6.74 (1H, d), 6.81 (1H, dd), 6.96 (1H, d), 7.18 (1H, d), 7.76 (1H, d), 8.04 (1H, s), 12.95 (1H, s). m/z: (ES+), [M+H]+ 459.

Procedures used to prepare the starting material tert-butyl 3-((6-((6S,8R)-7-(2,2-difluoroethyl)-8-methyl-3-(tetrahydro-2H-pyran-2-yl)-6,7,8,9-tetrahydro-3H-pyrazolo[4,3-f]isoquinolin-6-yl)pyridin-3-yl)amino)azetidine-1-carboxylate are described below.

Preparation of (1S,3R)-1-(5-bromopyridin-2-yl)-2-(2,2-difluoroethyl)-3,5-dimethyl-1,2,3,4-tetrahydroisoquinolin-6-amine

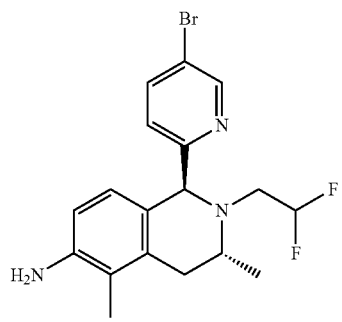 [SMILES: Cc1c(N)ccc2c1C[C@@H](C)N(CC(F)F)[C@@H]2c1ccc(Br)cn1]

5-Bromopicolinaldehyde (2.74 g, 14.7 mmol) was added to a solution of (R)-3-(2-((2,2-difluoroethyl)amino)propyl)-2-methylaniline (1.6 g, 7.0 mmol) in acetic acid (34.4 mL) and water (0.631 mL, 35.0 mmol). The reaction was heated at 80° C. for 3 hours and then concentrated under reduced pressure. The resulting residue was dissolved in MeOH (40 mL) and sodium acetate (1.15 g, 14.0 mmol) and hydroxylamine hydrochloride (0.730 g, 10.5 mmol) were added. The reaction was stirred at room temperature for 3 hours and then concentrated under reduced pressure. The residue was dissolved in water, neutralized with saturated aqueous NaHCO$_3$, and then extracted with EtOAc. The combined organic layers were concentrated under reduced pressure, and the resulting residue was purified by flash silica chromatography, elution gradient 0 to 90% EtOAc in hexanes. Product fractions were concentrated under reduced pressure, and the resulting residue was further purified by flash silica chromatography, elution gradient 0 to 90% EtOAc in hexanes, to afford (1S,3R)-1-(5-bromopyridin-2-yl)-2-(2,2-difluoroethyl)-3,5-dimethyl-1,2,3,4-tetrahydroisoquinolin-6-amine (1.40 g, 49%) as a gum. $^1$H NMR (300 MHz, DMSO-d$_6$, 27° C.) 0.99 (3H, d), 1.93 (3H, s), 2.38-2.47 (1H, m), 2.51-2.62 (1H, m), 2.72 (1H, dd), 2.92-3.14 (1H, m), 3.23-3.29 (1H, m), 4.65 (2H, s), 4.79 (1H, s), 5.98 (1H, tt), 6.39 (2H, s), 7.22 (1H, d), 7.91 (1H, dd), 8.55 (1H, d). m/z: ES+ [M+H]+ 396.

Preparation of (6S,8R)-6-(5-bromopyridin-2-yl)-7-(2,2-difluoroethyl)-8-methyl-6,7,8,9-tetrahydro-3H-pyrazolo[4,3-f]isoquinoline

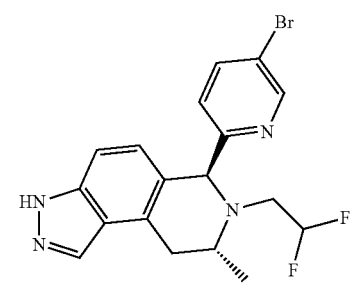 [SMILES: C[C@@H]1Cc2c(ccc3[nH]ncc23)[C@@H](c2ccc(Br)cn2)N1CC(F)F]

Acetic acid (541 mg, 9.01 mmol) was added to a stirred solution of (1S,3R)-1-(5-bromopyridin-2-yl)-2-(2,2-difluoroethyl)-3,5-dimethyl-1,2,3,4-tetrahydroisoquinolin-6-amine (714 mg, 1.80 mmol) in CHCl$_3$ (8 mL). The reaction was cooled to 0° C., and a solution of isopentyl nitrite (422 mg, 3.60 mmol) in CHCl$_3$ (1 mL) was added dropwise. The reaction was stirred at 0° C. for 2 hours and then quenched by the slow addition of a solution of NaHCO$_3$ (1.5 g, 18 mmol) in water (20 mL). The phases were separated, and the organic layer was concentrated under reduced pressure. The resulting residue was purified by flash silica chromatography, elution gradient 5 to 35% EtOAc in hexanes, to afford (6S,8R)-6-(5-bromopyridin-2-yl)-7-(2,2-difluoroethyl)-8-methyl-6,7,8,9-tetrahydro-3H-pyrazolo[4,3-f]isoquinoline (438 mg, 60%) as a light brown solid. $^1$H NMR (300 MHz, CDCl$_3$, 27° C.) 1.13 (3H, d), 2.68-2.85 (1H, m), 2.91 (1H, dd), 2.98-3.17 (1H, m), 3.34 (1H, dd), 3.47-3.63 (1H, m), 5.05 (1H, s), 5.63 (1H, tt), 6.87 (1H, d), 7.19 (1H, d), 7.28 (1H, d), 7.71 (1H, dd), 8.04 (1H, d), 8.57 (1H, dd). Indazole NH not observed. m/z: ES+ [M+H]+ 405.

Preparation of (6S,8R)-6-(5-bromopyridin-2-yl)-7-(2,2-difluoroethyl)-8-methyl-3-(tetrahydro-2H-pyran-2-yl)-6,7,8,9-tetrahydro-3H-pyrazolo[4,3-f]isoquinoline

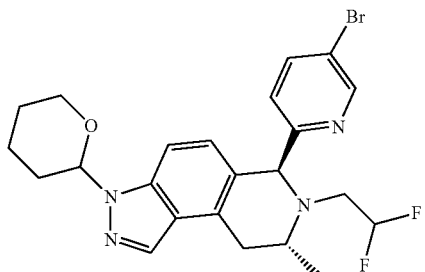

3,4-Dihydro-2H-pyran (0.294 mL, 3.23 mmol) was added to a solution of (6S,8R)-6-(5-bromopyridin-2-yl)-7-(2,2-difluoroethyl)-8-methyl-6,7,8,9-tetrahydro-3H-pyrazolo[4,3-f]isoquinoline (438 mg, 1.08 mmol) and para-toluenesulfonic acid monohydrate (21 mg, 0.11 mmol) in DCM (4 mL). The reaction was heated at 100° C. for 6 hours under microwave conditions (300 W). The reaction was then allowed to cool and then washed with saturated aqueous NaHCO₃, dried over Na₂SO₄, filtered, and concentrated under reduced pressure. The resulting residue was purified by flash silica chromatography, elution gradient 10 to 30% EtOAc in hexanes, to afford (6S,8R)-6-(5-bromopyridin-2-yl)-7-(2,2-difluoroethyl)-8-methyl-3-(tetrahydro-2H-pyran-2-yl)-6,7,8,9-tetrahydro-3H-pyrazolo[4,3-f]isoquinoline (441 mg, 83%) as a light brown gummy solid. m/z: ES+ [M+H]+ 491.

Preparation of tert-butyl 3-((6-(((6S,8R)-7-(2,2-difluoroethyl)-8-methyl-3-(tetrahydro-2H-pyran-2-yl)-6,7,8,9-tetrahydro-3H-pyrazolo[4,3-f]isoquinolin-6-yl)pyridin-3-yl)amino)azetidine-1-carboxylate

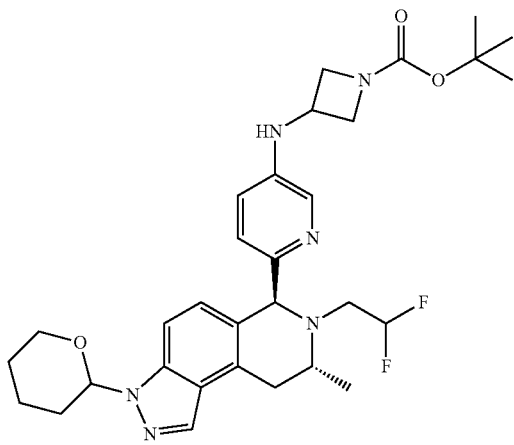 [SMILES: C[C@@H]1Cc2c(ccc3c2cnn3C2CCCCO2)[C@@H](c2ccc(NC3CN(C(=O)OC(C)(C)C)C3)cn2)N1CC(F)F]

A vial was charged with a stirrer bar, (6S,8R)-6-(5-bromopyridin-2-yl)-7-(2,2-difluoroethyl)-8-methyl-3-(tetrahydro-2H-pyran-2-yl)-6,7,8,9-tetrahydro-3H-pyrazolo[4,3-f]isoquinoline (0.22 g, 0.44 mmol), tert-butyl 3-aminoazetidine-1-carboxylate (0.151 g, 0.88 mmol), cesium carbonate (0.29 g, 0.88 mmol), and BrettPhos 3$^{rd}$ Generation Precatalyst (0.040 g, 0.040 mmol). The vial was sealed, evacuated, and filled with nitrogen. 1,4-Dioxane (4 mL) was added, and the vial was again evacuated and backfilled with nitrogen. The reaction was stirred at 110° C. for 13 hours and then concentrated under reduced pressure. The resulting residue was purified by flash silica chromatography, elution gradient 10 to 30% EtOAc in hexanes, to afford tert-butyl 3-((6-(((6S,8R)-7-(2,2-difluoroethyl)-8-methyl-3-(tetrahydro-2H-pyran-2-yl)-6,7,8,9-tetrahydro-3H-pyrazolo[4,3-f]isoquinolin-6-yl)pyridin-3-yl)amino)azetidine-1-carboxylate (0.20 g, 78%) as a beige solid. ¹H NMR (300 MHz, CD₃OD, 27° C.) 1.10 (3H, dd), 1.43 (9H, s), 1.56-1.72 (2H, m), 1.72-1.87 (1H, m), 1.92-1.99 (1H, m), 2.03-2.17 (1H, m), 2.38-2.53 (1H, m), 2.62-2.82 (1H, m), 2.88-3.14 (2H, m), 3.33-3.44 (1H, m), 3.49-3.60 (1H, m), 3.67-3.83 (3H, m), 3.92-4.02 (1H, m), 4.17-4.33 (3H, m), 4.91 (1H, s), 5.34-5.57 (1H, m), 5.69-5.77 (1H, m), 6.79 (1H, d), 6.89 (1H, dd), 7.05 (1H, dd), 7.34 (1H, d), 7.78-7.81 (1H, m), 8.07 (1H, s), aniline NH, not observed. m/z: ES+ [M+H]+ 583.

Example 26

Preparation of (6S,8R)-7-(2,2-difluoroethyl)-6-(5-O-(3-fluoropropyl)azetidin-3-yl)oxy)pyridin-2-yl)-8-methyl-6,7,8,9-tetrahydro-3H-pyrazolo[4,3-f]isoquinoline

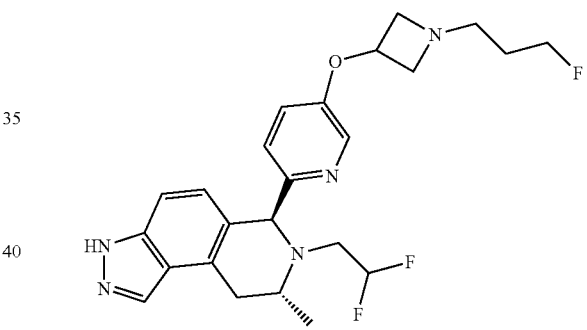

HCl in dioxane (4N; 0.97 mL, 3.9 mmol) was added dropwise to a solution of tert-butyl 3-((6-(((6S,8R)-7-(2,2-difluoroethyl)-8-methyl-3-(tetrahydro-2H-pyran-2-yl)-6,7,8,9-tetrahydro-3H-pyrazolo[4,3-f]isoquinolin-6-yl)pyridin-3-yl)oxy)azetidine-1-carboxylate (0.227 g, 0.39 mmol) in MeOH (3 mL), and the reaction was stirred at room temperature for 18 hours. The reaction was concentrated under reduced pressure to afford (6S,8R)-6-(5-(azetidin-3-yloxy)pyridin-2-yl)-7-(2,2-difluoroethyl)-8-methyl-6,7,8,9-tetrahydro-3H-pyrazolo[4,3-f]isoquinoline hydrochloride (0.235 g; number of equivalents of HCl not determined) as a solid, which was used without further purification. m/z: (ES+), [M+H]+ 400.

1-Fluoro-3-iodopropane (0.041 mL, 0.34 mmol) was added to a stirred solution of (6S,8R)-6-(5-(azetidin-3-yloxy)pyridin-2-yl)-7-(2,2-difluoroethyl)-8-methyl-6,7,8,9-tetrahydro-3H-pyrazolo[4,3-f]isoquinoline hydrochloride (235 mg) in DMF (0.6 mL) at ambient temperature. Excess diisopropylethylamine (1.36 mL, 7.80 mmol) was added dropwise. The reaction was stirred for 18 hours at room temperature and then concentrated under reduced pressure. The resulting residue was purified by reverse phase flash C18 chromatography, elution gradient 20 to 75% acetonitrile in (water containing 0.2% NH₄OH). Product fractions were combined and lyophilized to afford (6S,8R)-7-(2,2-difluoroethyl)-6-(5-((1-(3-fluoropropyl)azetidin-3-yl)oxy)pyridin-2-yl)-8-methyl-6,7,8,9-tetrahydro-3H-pyrazolo[4,3-f]isoquinoline (53 mg, 30%) as a solid. ¹H NMR (500 MHz, DMSO-d₆, 27° C.) 1.05 (3H, d), 1.60-1.77 (2H, m), 2.54-2.70 (3H, m), 2.85 (1H, dd), 2.97-3.22 (4H, m), 3.39-3.50 (1H, m), 3.87 (2H, br s), 4.45 (2H, dt), 4.80-4.92 (1H, m), 5.00 (1H, s), 5.93 (1H, tt), 6.78 (1H, d), 7.19-7.26 (3H, m), 8.05 (1H, s), 8.06 (1H, d), 12.97 (1H, s). m/z: ES+ [M+H]+ 460.

Procedures used to prepare the starting material tert-butyl 3-((6-((6S,8R)-7-(2,2-difluoroethyl)-8-methyl-3-(tetrahydro-2H-pyran-2-yl)-6,7,8,9-tetrahydro-3H-pyrazolo[4,3-f]isoquinolin-6-yl)pyridin-3-yl)oxy)azetidine-1-carboxylate are described below.

Preparation of tert-butyl 3-((6-((6S,8R)-7-(2,2-difluoroethyl)-8-methyl-3-(tetrahydro-2H-pyran-2-yl)-6,7,8,9-tetrahydro-3H-pyrazolo[4,3-f]isoquinolin-6-yl)pyridin-3-yl)oxy)azetidine-1-carboxylate

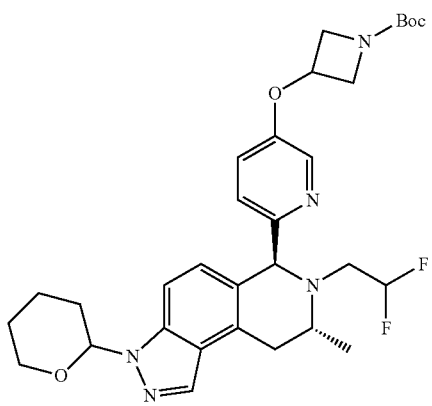 [SMILES: C[C@@H]1Cc2c(ccc3c2cnn3C2CCCCO2)[C@@H](c2ccc(OC3CN(C(=O)OC(C)(C)C)C3)cn2)N1CC(F)F]

Tert-butyl 3-hydroxyazetidine-1-carboxylate (227 mg, 1.31 mmol), (6S,8R)-6-(5-bromopyridin-2-yl)-7-(2,2-difluoroethyl)-8-methyl-3-(tetrahydro-2H-pyran-2-yl)-6,7,8,9-tetrahydro-3H-pyrazolo[4,3-f]isoquinoline (215 mg, 0.44 mmol), RockPhos 3rd Generation Precatalyst (37.1 mg, 0.04 mmol), and cesium carbonate (285 mg, 0.88 mmol) were suspended in toluene (4 mL) in a sealed microwave vial. The reaction was heated at 110° C. for 1 hour under microwave conditions (300 W). The reaction was concentrated under reduced pressure, and the resulting residue was purified by flash silica chromatography, elution gradient 20 to 60% EtOAc in hexanes, to afford tert-butyl 3-((6-((6S,8R)-7-(2, 2-difluoroethyl)-8-methyl-3-(tetrahydro-2H-pyran-2-yl)-6, 7,8,9-tetrahydro-3H-pyrazolo[4,3-f]isoquinolin-6-yl)pyridin-3-yl)oxy)azetidine-1-carboxylate (227 mg, 89%) as a solid. ¹H NMR (300 MHz, CD₃OD, 27° C.) 1.11 (3H, dd), 1.41-1.43 (9H, m), 1.61-1.66 (1H, m), 1.66-1.86 (2H, m), 2.04-2.17 (1H, m), 2.36-2.54 (1H, m), 2.59-2.79 (1H, m), 2.89-3.02 (1H, m), 3.03-3.17 (1H, m), 3.31-3.43 (1H, m), 3.48-3.60 (1H, m), 3.70 (2H, dd), 3.88-3.95 (2H, m), 4.09-4.13 (1H, m), 4.27-4.39 (2H, m), 4.99-5.08 (2H, m), 5.64 (1H, tt), 5.73 (1H, dt), 6.81 (1H, dd), 7.20 (1H, dd), 7.27 (1H, dd), 7.36 (1H, d), 8.04-8.10 (2H, m). m/z: ES+ [M+H]+ 584.

Example 27

1-(3-Fluoropropyl)-N-(4-((6R,8R)-8-methyl-7-(2,2, 2-trifluoroethyl)-6,7,8,9-tetrahydro-3H-pyrazolo[4,3-f]isoquinolin-6-yl)phenyl)azetidin-3-amine

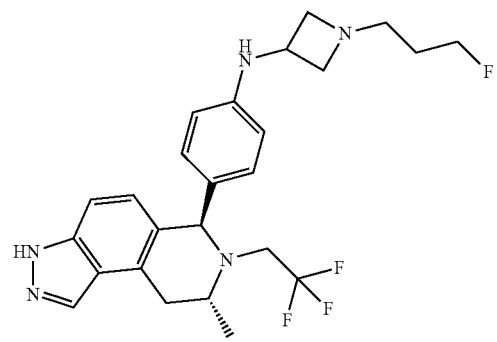 [SMILES: C[C@@H]1Cc2c(ccc3[nH]ncc23)[C@@H](c2ccc(NC3CN(CCCF)C3)cc2)N1CC(F)(F)F]

Sodium tert-butoxide (2.118 g, 22.06 mmol) and BrettPhos G3 (0.166 g, 0.18 mmol) were added to a degassed solution of 1-(3-fluoropropyl)azetidin-3-amine (0.632 g, 4.78 mmol) and (6R,8R)-6-(4-bromophenyl)-8-methyl-7-(2,2,2-trifluoroethyl)-6,7,8,9-tetrahydro-3H-pyrazolo[4,3-f]isoquinoline (1.56 g, 3.68 mmol) in 1,4-dioxane (18.4 ml) and the reaction was warmed to 90° C. and stirred overnight. After cooling, the reaction was diluted with EtOAc (20 mL) and water (20 mL), and the layers were separated. The aqueous was extracted with EtOAc (20 mL), then the combined organics were dried and evaporated. Purification was by HPLC (Waters CSH C18 OBD column, 5μ silica, 30 mm diameter, 100 mm length), using decreasingly polar mixtures of water (containing 0.1% NH₃ and MeCN as eluents) to give a gum. This was taken up in methanol (5 mL), then water (95 mL) was added and the mixture was slurried overnight at room temperature. The resulting solid was collected by filtration, washed with 5% methanol in water and dried in a vac oven at 50° C. overnight to give 1-(3-fluoropropyl)-N-(4-((6R,8R)-8-methyl-7-(2,2,2-trifluoroethyl)-6,7,8,9-tetrahydro-3H-pyrazolo[4,3-f]isoquinolin-6-yl)phenyl)azetidin-3-amine (0.935 g, 54%) as a colourless solid. ¹H NMR (500 MHz, CDCl₃, 27° C.) 1.13 (3H, d), 1.68-1.83 (2H, m), 2.59 (2H, t), 2.77 (1H, dd), 2.86 (2H, t), 2.89-2.99 (1H, m), 3.04 (1H, dd), 3.15-3.26 (1H, m), 3.37-3.48 (1H, m), 3.71-3.76 (2H, m), 3.93 (1H, d), 4.10 (1H, q), 4.43 (1H, t), 4.53 (1H, t), 4.99 (1H, s), 6.41-6.46 (2H, m), 6.97 (1H, d), 7.00 (2H, d), 7.26 (1H, s), 8.06 (1H, d), 10.10 (1H, s); m/z: ES+ [M+H]+ 476.

The (6R,8R)-6-(4-bromophenyl)-8-methyl-7-(2,2,2-trifluoroethyl)-6,7,8,9-tetrahydro-3H-pyrazolo[4,3-f]isoquinoline used as starting material was synthesised as follows:

(6R,8R)-6-(4-bromophenyl)-8-methyl-7-(2,2,2-trifluoroethyl)-6,7,8,9-tetrahydro-3H-pyrazolo[4,3-f]isoquinoline

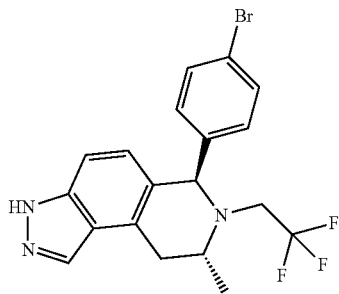 [SMILES: C[C@@H]1Cc2c(ccc3[nH]ncc23)[C@@H](c2ccc(Br)cc2)N1CC(F)(F)F]

Trifluoroacetic acid (1.85 mL) was added to a solution of (R)-1-(1H-indazol-4-yl)-N-(2,2,2-trifluoroethyl)propan-2-amine (2.0 g, 7.77 mmol) and 4-bromobenzaldehyde (7.19 g, 38.9 mmol) in toluene (37 mL) and the resulting mixture was stirred at 90° C. for 30 hours. The reaction was allowed to cool and partitioned between DCM (100 mL) and saturated aqueous sodium bicarbonate (50 mL). The layers were separated and the organic layer concentrated in vacuo. Purification was by silica gel column chromatography eluting with 0-50% ethyl acetate in heptane to give (6R,8R)-6-(4-bromophenyl)-8-methyl-7-(2,2,2-trifluoroethyl)-6,7,8,9-tetrahydro-3H-pyrazolo[4,3-f]isoquinoline (1.560 g, 47%) as a foam, and as a 6:1 ratio of isomers. $^1$H NMR (500 MHz, CDCl$_3$, 27° C.) 1.14 (3H, d), 2.80 (1H, dd), 2.94 (1H, dd), 3.05 (1H, dd), 3.25 (1H, dd), 3.33 (1H, ddd), 5.04 (1H, s), 6.95 (1H, d), 7.08-7.12 (2H, m), 7.28-7.33 (1H, m), 7.37-7.40 (2H, m), 8.08 (1H, d), 10.12 (1H, s); m/z: ES− [M−H]− 422.

Example 28

Preparation of 1-(3-fluoropropyl)-N-(3-methoxy-4-((6S,8R)-8-methyl-7-(2,2,2-trifluoroethyl)-6,7,8,9-tetrahydro-3H-pyrazolo[4,3-f]isoquinolin-6-yl)phenyl)azetidin-3-amine

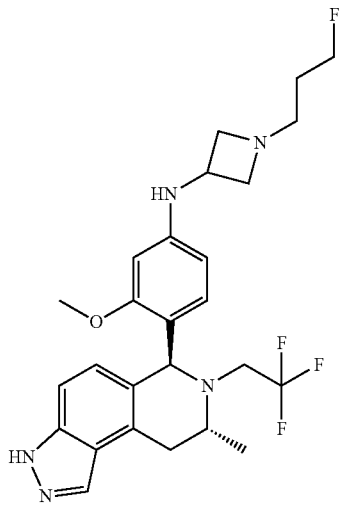 [SMILES: COc1cc(NC2CN(CCCF)C2)ccc1[C@@H]1c2ccc3[nH]ncc3c2C[C@@H](C)N1CC(F)(F)F]

BrettPhos 3rd Generation Precatalyst (10 mg, 0.01 mmol) and sodium tert-butoxide (0.127 g, 1.32 mmol) were added in one portion to a degassed solution of 1-(3-fluoropropyl)azetidin-3-amine (0.033 g, 0.25 mmol) and (6S,8R)-6-(4-bromo-2-methoxyphenyl)-8-methyl-7-(2,2,2-trifluoroethyl)-6,7,8,9-tetrahydro-3H-pyrazolo[4,3-f]isoquinoline (0.10 g, 0.22 mmol) in 1,4-dioxane (1.10 mL). The orange mixture was then immersed in an oil bath that had been preheated to 50° C. After 5 minutes, the reaction was cooled to room temperature. In a separate flask, sodium tert-butoxide (1.81 g, 18.8 mmol) and BrettPhos 3rd Generation Precatalyst (0.17 g, 0.19 mmol) were added in one portion to a degassed solution of (6S,8R)-6-(4-bromo-2-methoxyphenyl)-8-methyl-7-(2,2,2-trifluoroethyl)-6,7,8,9-tetrahydro-3H-pyrazolo[4,3-f]isoquinoline (1.71 g, 3.76 mmol) and 1-(3-fluoropropyl)azetidin-3-amine (0.597 g, 4.52 mmol) in 1,4-dioxane (18.8 mL). The light orange mixture was immersed in an oil bath that had been preheated to 50° C. After 5 minutes, the reaction was cooled to room temperature. Once cooled, both reactions were combined, diluted with ethyl acetate and washed sequentially with water (×2) and saturated aqueous sodium chloride. The organic layer was dried over sodium sulfate, filtered and concentrated under reduced pressure. The resulting orange oil was purified by flash silica chromatography, elution gradient 0 to 10% methanol in DCM, to afford 1-(3-fluoropropyl)-N-(3-methoxy-4-((6S,8R)-8-methyl-7-(2,2,2-trifluoroethyl)-6,7,8,9-tetrahydro-3H-pyrazolo[4,3-f]isoquinolin-6-yl)phenyl)azetidin-3-amine (1.84 g, 92%) as a solid and an ~84:16 trans:cis mixture based on UV HPLC profile. This material was resolved using preparative SFC (column: Chiralpak AD, 21.2×250 mm, 5 µm; 75 mL/min), eluting with 20% (methanol containing 0.2% NH$_4$OH) in CO$_2$, to afford 1-(3-fluoropropyl)-N-(3-methoxy-4-((6S,8R)-8-methyl-7-(2,2,2-trifluoroethyl)-6,7,8,9-tetrahydro-3H-pyrazolo[4,3-f]isoquinolin-6-yl)phenyl)azetidin-3-amine (1.01 g) as a light orange solid and a second eluting peak. This material was further purified by flash silica chromatography, elution gradient 0 to 30% methanol in ethyl acetate, to afford 1-(3-fluoropropyl)-N-(3-methoxy-4-46S,8R)-8-methyl-7-(2,2,2-trifluoroethyl)-6,7,8,9-tetrahydro-3H-pyrazolo[4,3-f]isoquinolin-6-yl)phenyl)azetidin-3-amine (0.954 g) as a white solid. This material was purified a final time by preparative HPLC (column: Xbridge C18, 30×100 mm, 5 µm, 40 mL/min), eluting with 40 to 70% acetonotrile in (water containing 0.2% NH$_4$OH). Product fractions were combined, washed with ethyl acetate (×3), and the combined organic layers were washed with saturated aqueous sodium chloride, dried over sodium sulfate, filtered, and concentrated under reduced pressure to afford 1-(3-fluoropropyl)-N-(3-methoxy-4-((6S,8R)-8-methyl-7-(2,2,2-trifluoroethyl)-6,7,8,9-tetrahydro-3H-pyrazolo[4,3-f]isoquinolin-6-yl)phenyl)azetidin-3-amine (551 mg, 27%) as an off-white foam solid. $^1$H NMR (500 MHz, DMSO-d$_6$, 27° C.) 1.04 (3H, d), 1.63 (2H, dtt), 2.44 (2H, t), 2.70 (2H, dd), 2.81 (1H, dd), 2.84-2.94 (1H, m), 3.09 (1H, dd), 3.34 (1H, br s), 3.44 (1H, dqd), 3.61 (2H, dd), 3.77 (3H, s), 3.90 (1H, m), 4.43 (2H, dt), 5.28 (1H, s), 5.87 (1H, dd), 6.02 (1H, d), 6.16 (1H, d), 6.32 (1H, d), 6.65 (1H, d), 7.18 (1H, d), 8.02 (1H, s), 12.95 (1H, s). m/z: ES+ [M+H]+ 506.

Procedures used to prepare the starting material (6S,8R)-6-(4-bromo-2-methoxyphenyl)-8-methyl-7-(2,2,2-trifluoroethyl)-6,7,8,9-tetrahydro-3H-pyrazolo[4,3-f]isoquinoline are described below.

Preparation of (R)-N-(1-(3-amino-2-methylphenyl) propan-2-0)-2,2,2-trifluoroacetamide

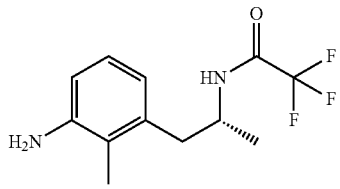 [SMILES: Cc1c(N)cccc1C[C@@H](C)NC(=O)C(F)(F)F]

Ethyl 2,2,2-trifluoroacetate (3.75 ml, 31.5 mmol) was added to a dark amber-red solution of (R)-3-(2-aminopropyl)-2-methylaniline (5.17 g, 31.5 mmol) and triethylamine (4.83 mL, 34.6 mmol) in MeOH (70.1 mL). After 15 min, the reaction was concentrated to a dark amber oil. The oil was dissolved in ethyl acetate, washed with water, and the aqueous layer extracted with ethyl acetate (×2). The combined organic layers were dried over sodium sulfate, filtered and concentrated under reduced pressure. The resulting oil was purified by flash silica chromatography, elution gradient 0 to 40% ethyl acetate in hexanes, to afford (R)-N-(1-(3-amino-2-methylphenyl)propan-2-yl)-2,2,2-trifluoroacetamide (6.47 g, 79%) as a yellow-orange oil that crystallized to a light orange solid on standing. $^1$H NMR (300 MHz, DMSO-$d_6$, 27° C.) 1.11 (3H, d), 2.01 (3H, s), 2.63 (1H, dd), 2.78 (1H, dd), 3.93-4.05 (1H, m), 4.71 (2H, s), 6.36 (1H, dd), 6.49 (1H, dd), 6.78 (1H, t), 9.25 (1H, br d). m/z: ES+ [M+H]+ 261.

Preparation of (R)-2-methyl-3-(2-((2,2,2-trifluoroethyl)amino)propyl)aniline

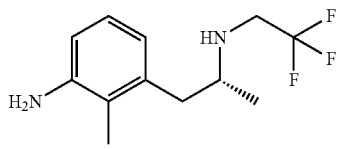 [SMILES: Cc1c(N)cccc1C[C@@H](C)NCC(F)(F)F]

Borane tetrahydrofuran complex in THF (1 M; 149 mL, 149 mmol) was added via syringe (6×25 mL) to a solution of (R)-N-(1-(3-amino-2-methylphenyl)propan-2-yl)-2,2,2-trifluoroacetamide (6.47 g, 24.9 mmol) in tetrahydrofuran (81 mL) at 0° C. The ice bath was removed, and, upon warming, gas evolution was observed. Once no further gas evolution was visible (~20 minutes), the reaction was warmed to 65° C. After 4 hours, the reaction was cooled and maintained at room temperature for 18 hours. The reaction was then cooled to 0° C. and quenched by dropwise addition of methanol (22 mL). The reaction was warmed to room temperature, and, after gas evolution ceased, the reaction was warmed to 65° C. After 14 hours, the reaction was then cooled to room temperature and stirred under these conditions for 3.5 days before being concentrated under reduced pressure. The resulting oil was purified by flash silica chromatography, elution gradient 0 to 70% ethyl acetate in hexanes, to afford (R)-2-methyl-3-(2-((2,2,2-trifluoroethyl)amino)propyl)aniline (5.62 g, 92%) as a light yellow oil. $^1$H NMR (300 MHz, DMSO-$d_6$, 27° C.) 0.90 (3H, d), 1.98 (3H, s), 2.09-2.20 (1H, m), 2.25-2.40 (1H, m), 2.72-2.84 (2H, m), 3.17-3.29 (2H, m), 4.69 (2H, s), 6.36 (1H, dd), 6.49 (1H, dd), 6.78 (1H, t). m/z: ES+ [M+H]+ 247

Preparation of (1S,3R)-1-(4-Bromo-2-methoxyphenyl)-3,5-dimethyl-2-(2,2,2-trifluoroethyl)-1,2,3,4-tetrahydroisoquinolin-6-amine

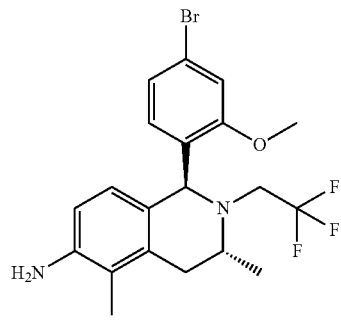 [SMILES: COc1cc(Br)ccc1[C@@H]1c2ccc(N)c(C)c2C[C@@H](C)N1CC(F)(F)F]

4-Bromo-2-methoxybenzaldehyde (1.83 g, 8.53 mmol) and (R)-2-methyl-3-(2-((2,2,2-trifluoroethyl)amino)propyl) aniline (2.00 g, 8.12 mmol) were added to a solution of water (0.7 mL, 41 mmol) and acetic acid (40 mL). The resulting light yellow solution was immersed in an oil bath that had been preheated to 65° C. and was maintained under these conditions for 18 hours. The resulting dark amber solution was then concentrated under reduced pressure (water bath: 55° C.). The resulting residue was diluted with ethyl acetate and washed with saturated aqueous sodium hydrogencarbonate until the aqueous layer was confirmed to be pH=8 using a pH strip. The organic layer was dried over sodium sulfate, filtered, and concentrated under reduced pressure. The resulting residue was dissolved in methanol (20 mL) and hydroxylamine hydrochloride (0.152 g, 2.19 mmol) and excess potassium carbonate were added. After 5 minutes, the mixture was diluted with ethyl acetate, filtered, and the filtrate was concentrated under reduced pressure. The resulting residue was purified by flash silica chromatgraphy, elution gradient 0 to 50% ethyl acetate in hexanes, to afford (1S,3R)-1-(4-bromo-2-methoxyphenyl)-3,5-dimethyl-2-(2, 2,2-trifluoroethyl)-1,2,3,4-tetrahydroisoquinolin-6-amine as a dark amber oil in an 83:17 trans:cis ratio based on NMR integration. The oil was reconcentrated from DCM and dried under vacuum to a light amber foam solid (2.55 g, 71%). A small amount of this material (150 mg) was resolved using preparative SFC (column: (S,S) Whelk-01, 21.2×250 mm, 5 μm; 75 mL/min), eluting with 15% (methanol containing 0.2% NH$_4$OH) in CO$_2$, to afford slower eluting (1S,3R)-1-(4-bromo-2-methoxyphenyl)-3,5-dimethyl-2-(2,2,2-trifluoroethyl)-1,2,3,4-tetrahydroisoquinolin-6-amine (101 mg) and faster eluting (1R,3R)-1-(4-bromo-2-methoxyphenyl)-3,5-dimethyl-2-(2,2,2-trifluoroethyl)-1,2,3,4-tetrahydroisoquinolin-6-amine (18 mg) as faint yellow foam solids.

(1S,3R): $^1$H NMR (300 MHz, DMSO-$d_6$, 27° C.) 1.00 (3H, d), 1.95 (3H, s), 2.43 (1H, dd), 2.64-2.85 (2H, m), 3.19-3.43 (2H, m), 3.86 (3H, s), 4.67 (2H, s), 5.18 (1H, s), 6.29 (1H, d), 6.41 (1H, d), 6.60 (1H, d), 6.96 (1H, dd), 7.18 (1H, d). m/z: ES+ [M+H]+ 443.

(1R,3R): $^1$H NMR (300 MHz, DMSO-$d_6$, 27° C.) 1.19 (3H, d), 1.94 (3H, s), 2.53-2.60 (1H, m), 2.78 (1H, br dd), 2.98-3.12 (1H, br m), 3.16-3.36 (2H, m), 3.84 (3H, s), 4.61 (2H, s), 5.31 (1H, s), 6.20 (1H, d), 6.33 (1H, d), 7.03-7.13 (2H, m), 7.19 (1H, d). m/z: ES+ [M+H]+443.

Preparation of (6S,8R)-6-(4-bromo-2-methoxyphenyl)-8-methyl-7-(2,2,2-trifluoroethyl)-6,7,8,9-tetrahydro-3H-pyrazolo[4,3-f]isoquinoline

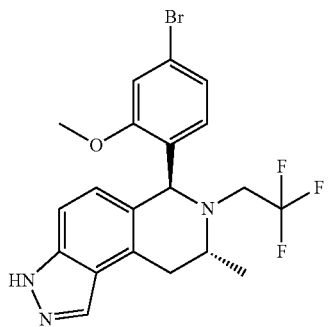 [SMILES: COc1cc(Br)ccc1[C@@H]1c2ccc3[nH]ncc3c2C[C@@H](C)N1CC(F)(F)F]

A solution of sodium nitrite (0.413 g, 5.98 mmol) in water (3.83 mL) was added dropwise over 5 minutes to a stirred solution of (1S,3R)-1-(4-bromo-2-methoxyphenyl)-3,5-dimethyl-2-(2,2,2-trifluoroethyl)-1,2,3,4-tetrahydroisoquinolin-6-amine (2.55 g, 5.75 mmol; 83:17 trans:cis) in propionic acid (19.2 mL) maintained at −15° C. using a cooling bath consisting ice, solid sodium chloride, and saturated aqueous sodium chloride. After 20 minutes the reaction was diluted with toluene (100 mL) that had been precooled to −70° C. The resulting light yellow mixture was stirred vigorously, and, after 5 minutes, the cooling bath was removed. Upon reaching room temperature, the red reaction mixture was maintained under these conditions for 1.5 hours and then washed with water (×2). The combined aqueous layers were extracted with ethyl acetate. The combined organic layers were dried over sodium sulfate, filtered, and concentrated under reduced pressure to approximately 20% of the starting volume. This mixture was diluted with EtOAc (20 mL) and washed with saturated aqueous sodium bicarbonate. Solid potassium carbonate was then added until gas evolution ceased and the mixture tested as being basic using a pH strip. The layers were separated and the organic layer was dried over sodium sulfate, filtered and concentrated under reduced pressure. The resulting oil was purified by flash silica chromatography, elution gradient 0 to 70% ethyl acetate in hexanes, to afford (6S,8R)-6-(4-bromo-2-methoxyphenyl)-8-methyl-7-(2,2,2-trifluoroethyl)-6,7,8,9-tetrahydro-3H-pyrazolo[4,3-f]isoquinoline (1.96 g, 75%) as a light orange foam solid and a ~9:1 trans:cis mixture based on NMR integration. $^1$H NMR (300 MHz, DMSO-$d_6$, 27° C.) 1.06 (3H, d), 2.80-2.98 (2H, m), 3.15 (1H, br dd), 3.33-3.53 (2H, m), 3.90 (3H, s), 5.40 (1H, s), 6.63 (1H, d), 6.67 (1H, d), 6.96 (1H, dd), 7.20-7.27 (2H, m), 8.08 (1H, s), 13.00 (1H, s). m/z: ES+ [M+H]+ 454.

Example 29

Preparation of 2-fluoro-N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine

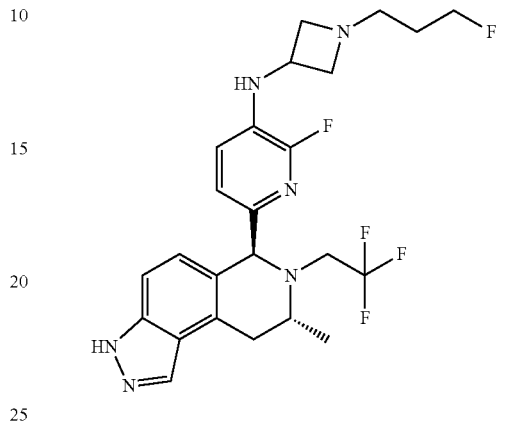

Sodium tert-butoxide (1.08 g, 11.3 mmol) and BrettPhos 3rd Generation Precatalyst (0.16 g, 0.18 mmol) were added to a degassed solution of (6S,8R)-6-(5-bromo-6-fluoropyridin-2-yl)-8-methyl-7-(2,2,2-trifluoroethyl)-6,7,8,9-tetrahydro-3H-pyrazolo[4,3-f]isoquinoline (2.00 g, 4.51 mmol) and 1-(3-fluoropropyl)azetidin-3-amine (0.90 g, 5.41 mmol) in 1,4-dioxane (22.6 mL) at room temperature. The red-orange mixture was immersed in an oil bath preheated to 44° C. After 22 minutes, the orange mixture was removed from the heat and poured into ethyl acetate and saturated aqueous sodium chloride and the layers were separated. The aqueous layer was extracted with ethyl acetate, and the combined organic layers were washed with saturated aqueous sodium chloride, dried over sodium sulfate, filtered and concentrated under reduced pressure. The resulting residue was purified by flash silica chormatography, elution gradient 0 to 30% methanol in ethyl acetate, to afford 2-fluoro-N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine (1.58 g) as a light yellow foam solid and an approximate 84:16 trans:cis mixture based on NMR integration. This material was resolved by preparative SFC (column: Lux Cellulose-4, 21.2×250 mm, 5 μm; 70 mL/min), eluting with 35% (methanol containing 0.2% NH$_4$OH) in CO$_2$, to afford a light orange foam solid. This solid was repurified by flash silica chormatography, elution gradient 0 to 30% methanol in ethyl acetate. Product fractions were concentrated under reduced pressure. The resulting residue was taken up in acetonitrile, filtered, and concentrated under reduced pressure to afford 2-fluoro-N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine (1.03 g, 46%) as a light yellow foam solid. $^1$H NMR (600 MHz, DMSO-$d_6$, 27° C.) 1.10 (3H, d), 1.64 (2H, dtt), 2.48 (2H, t), 2.83 (1H, dd), 2.86 (2H, br d), 2.97 (1H, br dq), 3.02 (1H, dd), 3.45 (1H, dqd), 3.54 (1H, dq), 3.63 (2H, br s), 3.96 (1H, dquin), 4.44 (2H, dt), 4.91 (1H, s), 6.13 (1H, br d), 6.87 (1H, d), 6.92-7.01 (2H, m), 7.25 (1H, d), 8.06 (1H, s), 13.00 (1H, s). m/z: ES+ [M+H]+ 495.

Procedures used to prepare the starting material (6S,8R)-6-(5-bromo-6-fluoropyridin-2-yl)-8-methyl-7-(2,2,2-trifluoroethyl)-6,7,8,9-tetrahydro-3H-pyrazolo[4,3-f]isoquinoline are described below.

Preparation of tert-butyl (R)-(1-(1H-indazol-4-yl)propan-2-yl)carbamate

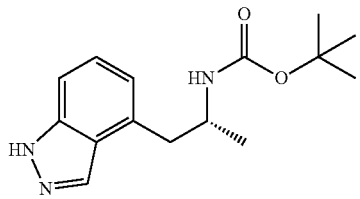 [SMILES: C[C@H](Cc1cccc2[nH]ncc12)NC(=O)OC(C)(C)C]

n-Butyllithium in hexane (2.5 M; 96 mL, 241 mmol) was added to a solution of 4-bromo-1H-indazole (24.8 g, 126 mmol) in THF (200 mL) at −78° C. over 20 minutes, and the mixture was stirred at −78° C. for 7 hours. Tert-butyl (R)-4-methyl-1,2,3-oxathiazolidine-3-carboxylate 2,2-dioxide (26 g, 110 mmol) was added, and the resultant mixture was stirred at −78° C. for 15 minutes. The cooling bath was removed, and the mixture was stirred under these conditions for 18 hours. Aqueous citric acid (1N; 130 mL) was added and stirring was continued for 30 minutes. The mixture was extracted with hexanes, and the organic layer was washed with saturated aqueous sodium carbonate, dried over sodium sulfate, filtered and concentrated under reduced pressure. The resulting residue was purified by flash silica chromatography, eluting with 0 to 60% EtOAc in hexanes, to give tert-butyl (R)-(1-(1H-indazol-4-yl)propan-2-yl)carbamate (17.3 g, 57%) as a white solid. $^1$H NMR (300 MHz, DMSO-$d_6$, 27° C.) 1.02 (3H, br d), 1.34 (9H, s), 2.82 (1H, br dd), 3.09 (1H, br dd), 3.82 (1H, dt), 6.82 (1H, br d), 6.88 (1H, d), 7.24 (1H, dd), 7.35 (1H, br d), 8.18 (1H, s), 12.97 (1H, s). m/z: ES+ [M+1]+276.

Preparation of (R)-1-(1H-indazol-4-yl)propan-2-amine dihydrochloride

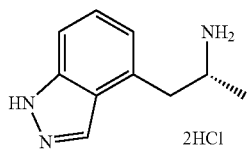

HCl dioxane (4 M, 100 mL, 400 mmol) was added to a suspension of tert-butyl (R)-(1-(1H-indazol-4-yl)propan-2-yl)carbamate (17.3 g, 62.7 mmol) in DCM (200 mL) at room temperature over 10 minutes. The resulting slurry was stirred overnight and then concentrated under reduced pressure to afford (R)-1-(1H-indazol-4-yl)propan-2-amine (15.9 g, 102%) as white solid. $^1$H NMR (300 MHz, DMSO-$d_6$, 27° C.) 1.14 (3H, d), 2.97 (1H, dd), 3.40 (1H, dd), 3.45-3.62 (1H, m), 6.96 (1H, d), 7.29 (1H, dd), 7.45 (1H, d), 7.97-8.27 (3H, br s), 8.29 (1H, d). m/z: ES+ [M+H]+ 176.

Preparation of (R)-1-(1H-indazol-4-yl)-N-(2,2,2-trifluoroethyl)propan-2-amine

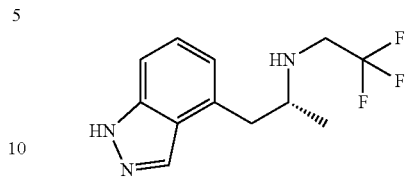

Potassium carbonate (4.75 g, 34.3 mmol) was added to a stirred suspension of (R)-1-(1H-indazol-4-yl)propan-2-amine dihydrochloride salt (2.13 g, 8.58 mmol) in acetonitrile (25 mL) then 2,2,2-trifluoroethyl trifluoromethanesulfonate (2.191 g, 9.44 mmol) in DCM (12.6 mL) was added dropwise. The mixture was stirred at room temperature for 1.5 days. Then additional 2,2,2-trifluoroethyl trifluoromethanesulfonate (398 mg) in DCM (0.3 mL) was added. The reaction was warmed to 60° C. and after 3 hours, the reaction was cooled to room temperature and a further portion of 2,2,2-trifluoroethyl trifluoromethanesulfonate (398 mg) was added as a solution in DCM (0.3 mL). After 18 hours, the reaction was concentrated under reduced pressure to reduced volume and then diluted with DCM. The mixture was washed with water, and the organic layer was dried over sodium sulfate, filtered and concentrated under reduced pressure. The resulting residue was purified by flash silica chromatography, elution gradient 0 to 60% ethyl acetate in hexanes, to afford (R)-1-(1H-indazol-4-yl)-N-(2,2,2-trifluoroethyl)propan-2-amine (2.06 g, 93%) as a gum. m/z: ES+ [M+H]+ 257.

Preparation of (6S,8R)-6-(5-bromo-6-fluoropyridin-2-yl)-8-methyl-7-(2,2,2-trifluoroethyl)-6,7,8,9-tetrahydro-3H-pyrazolo[4,3-f]isoquinoline

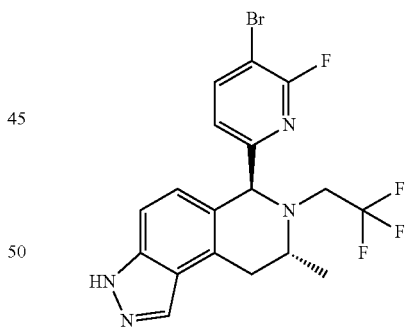

Trifluoroacetic acid (1.7 mL) was added to a solution of (R)-1-(1H-indazol-4-yl)-N-(2,2,2-trifluoroethyl)propan-2-amine (1.83 g, 7.11 mmol) and 5-bromo-6-fluoropicolinaldehyde (1.45 g, 7.11 mmol) in toluene (33.8 mL). The reaction was heated at 90° C. for 24 hours and then concentrated to reduced volume. The mixture was then diluted with dichloromethane and basified with saturated aqueous sodium hydrogencarbonate. The organic layer was dried over sodium sulfate, filtered and concentrated under reduced pressure. The resulting residue was purified by flash silica chromatography, elution gradient 0 to 50% ethyl acetate in hexanes, to afford (6S,8R)-6-(5-bromo-6-fluoropyridin-2-yl)-8-methyl-7-(2,2,2-trifluoroethyl)-6,7,8,9-tetrahydro-3H- pyrazolo[4,3-f]isoquinoline (2.01 g, 64%) as a white solid. ¹H NMR (300 MHz, DMSO-d₆, 27° C.) 1.11 (3H, d), 2.89 (1H, br dd), 2.94-3.09 (2H, m), 3.31-3.42 (1H, m), 3.52-3.71 (1H, m), 5.07 (1H, s), 6.96 (1H, d), 7.24-7.36 (2H, m), 8.06 (1H, d), 8.23 (1H, dd), 13.02 (1H, s). m/z: ES+ [M+H]+ 443.

Example 30

5-fluoro-N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine

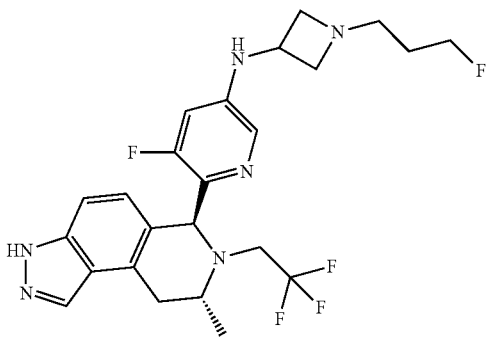 [SMILES: C[C@@H]1Cc2c(ccc3[nH]ncc23)[C@@H](c2ncc(NC3CN(CCCF)C3)cc2F)N1CC(F)(F)F]

1-(3-Fluoropropyl)azetidin-3-amine (435 mg, 3.29 mmol), (6S,8R)-6-(5-bromo-3-fluoropyridin-2-yl)-8-methyl-7-(2,2,2-trifluoroethyl)-6,7,8,9-tetrahydro-3H-pyrazolo[4,3-f]isoquinoline (730 mg, 1.65 mmol) and sodium tert-butoxide (950 mg, 9.88 mmol) were suspended in 1,4-dioxane (18.3 mL). The mixture was degassed and Brettphos 3G precatalyst (149 mg, 0.16 mmol) was added. The reaction was heated to 80° C. for 1 hour. The reaction mixture was cooled to room temperature and diluted with ethyl acetate (10 mL) and washed with water (10 mL). The organic layer was dried over magnesium sulfate, filtered and concentrated under vacuum. The crude product was purified by preparative LCMS (Waters XSelect CSH C18 column, 5µ silica, 50 mm diameter, 100 mm length), using decreasingly polar mixtures of water (containing 1% NH₃) and MeCN as eluents. The sample was dissolved in MeOH and separated by SFC using the following chromatographc conditions: Column: Phenomonex Lux C1, 30×250 mm, 5 micron, Mobile phase: 30% MeOH+0.1% NH₃/70% scCO₂ to afford 5-fluoro-N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine (396 mg, 49%) as a yellow solid. ¹H NMR (500 MHz, CDCl₃, 27° C.) 1.15 (3H, d), 1.69-1.81 (2H, m), 2.60 (2H, t), 2.77 (1H, dd), 2.92-3.03 (3H, m), 3.14-3.31 (2H, m), 3.65-3.79 (3H, m), 4.04 (1H, q), 4.43 (2H, t), 4.53 (1H, t), 5.35 (1H, s), 6.54 (1H, dd), 6.76 (1H, d), 7.00 (1H, d), 7.66 (1H, d), 7.93 (1H, d), 11.06 (1H, s); m/z: ES+ [M+H]+ 495.

The (6S,8R)-6-(5-bromo-3-fluoropyridin-2-yl)-8-methyl-7-(2,2,2-trifluoroethyl)-6,7,8,9-tetrahydro-3H-pyrazolo[4,3-f]isoquinoline used as starting material was synthesised as follows:

(6S,8R)-6-(5-bromo-3-fluoropyridin-2-yl)-8-methyl-7-(2,2,2-trifluoroethyl)-6,7,8,9-tetrahydro-3H-pyrazolo[4,3-f]isoquinoline

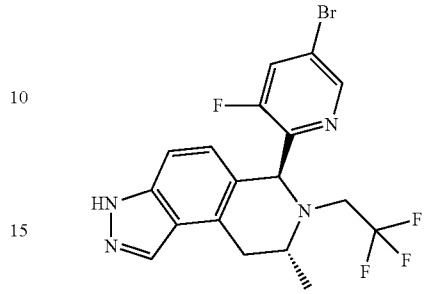

Trifluoroacetic acid (2.13 mL) was added to a solution of (R)-1-(1H-indazol-4-yl)-N-(2,2,2-trifluoroethyl)propan-2-amine (1.15 g, 4.47 mmol) and 5-bromo-3-fluoropicolinaldehyde (912 mg, 4.47 mmol) in toluene (42.6 mL) and the resulting mixture was stirred at 100° C. for 30 minutes. The reaction was evaporated and the residue partitioned between DCM (20 mL) and 2M NaOH (20 mL). The layers were separated and the organic phase was concentrated under reduced pressure. The crude product was purified by flash silica chromatography, elution gradient 0 to 40% EtOAc in heptane. Product containing fractions were evaporated to dryness to afford (6S,8R)-6-(5-bromo-3-fluoropyridin-2-yl)-8-methyl-7-(2,2,2-trifluoroethyl)-6,7,8,9-tetrahydro-3H-pyrazolo[4,3-f]isoquinoline (1.15 g, 58%) as a yellow solid. ¹H NMR (500 MHz, CDCl₃, 27° C.) 1.16 (3H, d), 2.86 (1H, dd), 3.01 (1H, dq), 3.19-3.35 (2H, m), 3.68-3.78 (1H, m), 5.42 (1H, s), 6.80 (1H, d), 7.20 (1H, d), 7.59 (1H, dd), 8.05 (1H, d), 8.27-8.5 (1H, m). m/z: ES+ [M+H]+ 443.

Example 31

2,2-Difluoro-3-((6S,8R)-6-(3-fluoro-5-((1-(3-fluoropropyl)azetidin-3-yl)amino)pyridin-2-yl)-8-methyl-3,6,8,9-tetrahydro-7H-pyrazolo[4,3-f]isoquinolin-7-yl)propan-1-ol

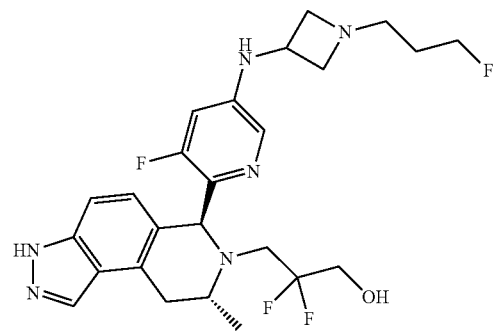 [SMILES: C[C@@H]1Cc2c(ccc3[nH]ncc23)[C@@H](c2ncc(NC3CN(CCCF)C3)cc2F)N1CC(F)(F)CO]

Tetrabutylammonium fluoride (1.0 M in THF, 0.65 mL, 0.65 mmol) was added to a solution of 6-((6S,8R)-7-(3-((tert-butyldiphenylsilyl)oxy)-2,2-difluoropropyl)-8-methyl-6,7,8,9-tetrahydro-3H-pyrazolo[4,3-f]isoquinolin-6-yl)-5-fluoro-N-(1-(3-fluoropropyl)azetidin-3-yl)pyridin-3-amine (320 mg, 0.43 mmol) in THF (2.66 mL) at room temperature and stirred for 64 hours. The reaction mixture was evaporated and then dissolved in DMSO and the crude product was purified by flash reverse phase (Puriflash, 220 g, C18, 30μ column), using decreasingly polar mixtures of water (containing 1% NH₃) and MeCN as eluents. Fractions containing the desired compound were evaporated to dryness to afford a crude product (143 mg). The crude product was purified by flash silica chromatography, elution gradient 0 to 20% MeOH in EtOAc. Product containing fractions were evaporated to dryness to afford 2,2-difluoro-3-((6S,8R)-6-(3-fluoro-5-((1-(3-fluoropropyl)azetidin-3-yl)amino)pyridin-2-yl)-8-methyl-3,6,8,9-tetrahydro-7H-pyrazolo[4,3-f]isoquinolin-7-yl)propan-1-ol (118 mg, 54%) as a mixture of isomers. The material was repurified by preparative HPLC (Waters XSelect CSH C18 column, 5μ silica, 30 mm diameter, 100 mm length), using decreasingly polar mixtures of water (containing 0.1% formic acid) and MeCN as eluents. Fractions containing the desired compound were combined and purified by ion exchange chromatography, using an SCX-2 column. The desired product was eluted from the column using 1M NH₃/MeOH and product containing fractions were evaporated to dryness to afford 2,2-difluoro-3-((6S,8R)-6-(3-fluoro-5-((1-(3-fluoropropyl)azetidin-3-yl)amino)pyridin-2-yl)-8-methyl-3,6,8,9-tetrahydro-7H-pyrazolo[4,3-f]isoquinolin-7-yl)propan-1-ol (62.1 mg, 29%) as a colourless solid. ¹H NMR (500 MHz, DMSO, 27° C.) 1.03 (3H, dd), 1.64 (2H, dq), 2.44 (2H, t), 2.60-2.66 (1H, m), 2.79 (3H, dd), 2.97 (1H, dd), 3.04-3.15 (1H, m), 3.50-3.73 (5H, m), 3.89-3.97 (1H, m), 4.39 (1H, t), 4.48 (1H, t), 5.21 (1H, s), 5.26 (1H, t), 6.58 (1H, d), 6.65-6.71 (2H, m), 7.19 (1H, d), 7.55 (1H, dd), 8.03 (1H, s), 12.94 (1H, s); m/z: ES+ [M+H]+ 507.

The 6-((6S,8R)-7-(3-((tert-butyldiphenylsilyl)oxy)-2,2-difluoropropyl)-8-methyl-6,7,8,9-tetrahydro-3H-pyrazolo[4,3-f]isoquinolin-6-yl)-5-fluoro-N-(1-(3-fluoropropyl)azetidin-3-yl)pyridin-3-amine used as starting material was synthesised as follows:

(R)-N-(1-(1H-indazol-4-yl)propan-2-yl)-3-((tert-butyldiphenylsilyl)oxy)-2,2-difluoropropan-1-amine

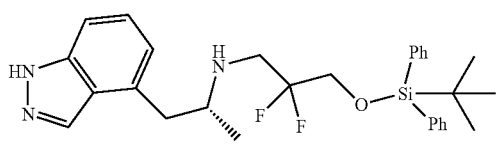 [SMILES: C[C@H](Cc1cccc2[nH]ncc12)NCC(F)(F)CO[Si](c1ccccc1)(c1ccccc1)C(C)(C)C]

3-((Tert-butyldiphenylsilyl)oxy)-2,2-difluoropropyl trifluoromethanesulfonate (2.59 g, 5.36 mmol) was added to a solution of (R)-1-(1H-indazol-4-yl)propan-2-amine (0.94 g, 5.36 mmol) and DIPEA (1.39 ml, 8.05 mmol) in 1,4-dioxane (38.9 mL) and the reaction was stirred at 50° C. for 18 hours. The reaction mixture was evaporated then the residue was diluted with EtOAc and washed with water and the aqueous layer was further extracted with EtOAc. The combined organic layers were washed with saturated brine, dried over magnesium sulfate, filtered and evaporated to dryness. The crude product was purified by flash silica chromatography, elution gradient 0 to 50% EtOAc in heptane. Pure fractions were evaporated to dryness to afford (R)-N-(1-(1H-indazol-4-yl)propan-2-yl)-3-((tert-butyldiphenylsilyl)oxy)-2,2-difluoropropan-1-amine (1.515 g, 52%) as a colourless gum. ¹H NMR (500 MHz, DMSO, 27° C.) 0.92 (3H, d), 0.97 (9H, s), 1.78-1.86 (1H, m), 2.73 (1H, dd), 2.98-3.14 (4H, m), 3.83 (2H, td), 6.85 (1H, d), 7.20 (1H, dd), 7.34 (1H, d), 7.41-7.50 (6H, m), 7.58-7.64 (4H, m), 8.08 (1H, s), 12.98 (1H, s); m/z: ES+ [M+H]+ 508.

(6S,8R)-6-(5-bromo-3-fluoropyridin-2-yl)-7-(3-((tert-butyldiphenylsilyl)oxy)-2,2-difluoropropyl)-8-methyl-6,7,8,9-tetrahydro-3H-pyrazolo[4,3-f]isoquinoline

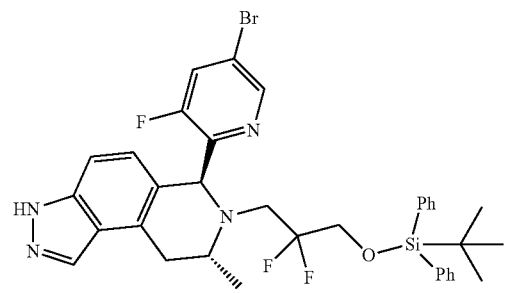 [SMILES: C[C@@H]1Cc2c(ccc3[nH]ncc23)[C@@H](c2ncc(Br)cc2F)N1CC(F)(F)CO[Si](c1ccccc1)(c1ccccc1)C(C)(C)C]

Trifluoroacetic acid (319 μL) was added to a solution of (R)-N-(1-(1H-indazol-4-yl)propan-2-yl)-3-((tert-butyldiphenylsilyl)oxy)-2,2-difluoropropan-1-amine (681 mg, 1.34 mmol) and 5-bromo-3-fluoropicolinaldehyde (287 mg, 1.41 mmol) in toluene (6.39 mL) and the resulting mixture was stirred at 110° C. for 1 hour. The reaction was allowed to cool to room temperature, evaporated to dryness and dissolved in DMSO. The crude product was purified byfFlash reverse phase chromatography (100 g Redisep Rf C18 column), using decreasingly polar mixtures of water (containing 0.1% formic acid) and MeCN (60-100%) as eluents. Fractions containing the desired compound were combined and was isolated by ion exchange chromatography, using an SCX-2 column. The desired product was eluted from the column using 1M NH₃/MeOH and pure fractions were evaporated to dryness to afford (6S,8R)-6-(5-bromo-3-fluoropyridin-2-yl)-7-(3-((tert-butyldiphenylsilyl)oxy)-2,2-difluoropropyl)-8-methyl-6,7,8,9-tetrahydro-3H-pyrazolo[4,3-f]isoquinoline (763 mg, 82%) as an off-white solid. ¹H NMR (500 MHz, DMSO, 27° C.) 0.99 (9H, s), 1.04 (3H, d), 2.74-2.89 (2H, m), 2.97-3.04 (1H, m), 3.31 (1H, s), 3.54-3.62 (1H, m), 3.78 (1H, q), 3.92-4.02 (1H, m), 5.36 (1H, s), 6.72 (1H, d), 7.23 (1H, d), 7.41-7.49 (6H, m), 7.57-7.61 (4H, m), 8.04 (1H, dd), 8.09 (1H, s), 8.38 (1H, d), 13.01 (1H, s); m/z: ES+ [M+H]+ 693.

6-((6S,8R)-7-(3-((tert-butyldiphenylsilyl)oxy)-2,2-difluoropropyl)-8-methyl-6,7,8,9-tetrahydro-3H-pyrazolo[4,3-f]isoquinolin-6-yl)-5-fluoro-N-(1-(3-fluoropropyl)azetidin-3-yl)pyridin-3-amine

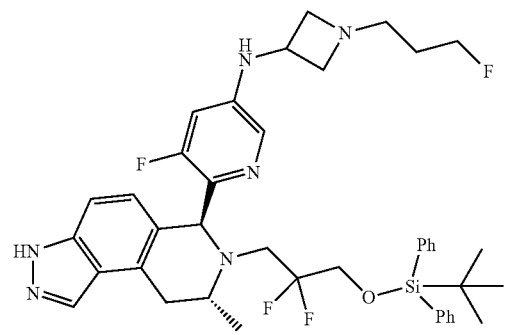 [SMILES: C[C@@H]1Cc2c(ccc3[nH]ncc23)[C@@H](c2ncc(NC3CN(CCCF)C3)cc2F)N1CC(F)(F)CO[Si](c1ccccc1)(c1ccccc1)C(C)(C)C]

1-(3-Fluoropropyl)azetidin-3-amine (114 mg, 0.86 mmol), (6S,8R)-6-(5-bromo-3-fluoropyridin-2-yl)-7-(3-((tert-butyldiphenylsilyl)oxy)-2,2-difluoropropyl)-8-methyl-6,7,8,9-tetrahydro-3H-pyrazolo[4,3-f]isoquinoline (300 mg, 0.43 mmol) and sodium tert-butoxide (249 mg, 2.59 mmol) were suspended in degassed 1,4-dioxane (4.81 mL). Brettphos 3G precatalyst (39.2 mg, 0.04 mmol) was added and the mixture was evacuated and purged with nitrogen (×2) and the reaction was then heated to 80° C. for 45 minutes. The reaction mixture was allowed to cool to room temperature and diluted with EtOAc and washed with water. The aqueous layer was further extracted with EtOAc and the combined organic layers were washed with saturated brine, dried over magnesium sulfate, filtered and evaporated to dryness and used directly without further purification. m/z: ES+ [M+H]+ 745.

Example 32

6-((6S,8R)-1-fluoro-8-methyl-7-(2,2,2-trifluoroethyl)-6,7,9,8-tetrahydro-3H-pyrazolo[4,3-f]isoquin-6-yl)-N-(3-fluoropropyl)azetidi-3-yl)pyridin-3-amine

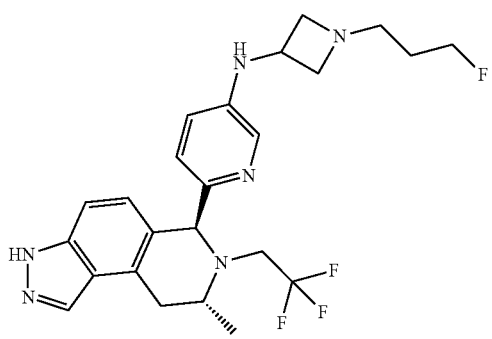 [SMILES: C[C@@H]1Cc2c(ccc3[nH]ncc23)[C@@H](c2ccc(NC3CN(CCCF)C3)cn2)N1CC(F)(F)F]

Sodium tert-butoxide (116 mg, 1.20 mmol) and BrettPhos G3 (9.09 mg, 10.04 µmol) were added to a degassed solution of (6S,8R)-6-(5-bromopyridin-2-yl)-1-fluoro-8-methyl-7-(2,2,2-trifluoroethyl)-6,7,8,9-tetrahydro-3H-pyrazolo[4,3-f]isoquinoline (89 mg, 0.20 mmol) and 1-(3-fluoropropyl)azetidin-3-amine (39.8 mg, 0.30 mmol) in 1,4-dioxane (1.00 mL) and reaction was warmed to 90° C. and stirred for 6 hours. After cooling, the reaction was diluted with EtOAc and water, and the layers were separated. The aqueous layer was extracted with EtOAc, then the combined organics were dried over sodium sulfate and evaporated. Purification was by HPLC (Waters CSH C18 OBD column, 5µ silica, 30 mm diameter, 100 mm length), using decreasingly polar mixtures of water (containing 0.1% NH₃ and MeCN as eluents) to give the product (42.0 mg, 42%) as a film. ¹H NMR (500 MHz, CDCl₃, 27° C.) 1.13 (3H, d), 1.69-1.84 (2H, m), 2.61 (2H, td), 2.76 (1H, dd), 2.94 (3H, ddd), 3.16-3.28 (2H, m), 3.45-3.54 (1H, m), 3.67-3.76 (2H, m), 4.09 (1H, dt), 4.24 (1H, d), 4.43 (1H, td), 4.53 (1H, td), 5.02 (1H, s), 6.76 (1H, dd), 6.81 (1H, d), 6.89 (1H, dd), 7.39 is (1H, d), 7.81 (1H, d), 11.10 (1H, s); m/z: ES+ [M+H]+ 495.

The (6S,8R)-6-(5-bromopyridin-2-yl)-1-fluoro-8-methyl-7-(2,2,2-trifluoroethyl)-6,7,8,9-tetrahydro-3H-pyrazolo[4,3-f]isoquinoline used as starting material was synthesised as follows:

4-Bromo-3-fluoro-1H-indazole

Selectfluor (49.40 g, 139.6 mmol) was added to a solution of 4-bromo-1H-indazole (25.0 g, 127 mmol) in DMF (254 mL) and the reaction was heated to 70° C. overnight. After cooling, the reaction mixture was poured onto water. The precipitated solid was filtered and dried, then the crude product was purified by flash silica chromatography, elution gradient 0 to 30% EtOAc in heptane. Product containing fractions were evaporated to dryness to afford 4-bromo-3-fluoro-1H-indazole (4.20 g, 15%) as a pale yellow solid. ¹H NMR (500 MHz, CDCl₃, 27° C.) 7.24-7.28 (1H, m), 7.32-7.36 (2H, m), 9.20 (1H, s); m/z: ES- [M-H]- 213.

Tert-butyl (R)-(1-(3-fluoro-1H-indazol-4-yl)propan-2-yl)carbamate

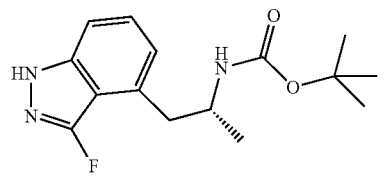 [SMILES: C[C@H](Cc1cccc2[nH]nc(F)c12)NC(=O)OC(C)(C)C]

n-Butyl lithium (1.6M, 51.9 ml, 83.01 mmol) was added to 4-bromo-3-fluoro-1H-indazole (8.50 g, 39.5 mmol) in THF (124 mL) at -78° C. and the reaction was stirred for 15 minutes, warmed to -50° C. for 15 minutes, then cooled back to -78° C. Tert-butyl (R)-4-methyl-1,2,3-oxathiazolidine-3-carboxylate 2,2-dioxide (10.32 g, 43.48 mmol) was added in THF (20 mL) and the reaction was stirred for 15 minutes before being allowed to warm to -10° C. over 30 minutes. 1N citric acid (200 mL) was added and the mixture was stirred for 15 minutes, before being extracted with EtOAc (×2). The combined organics were dried over magnesium sulfate and evaporated. The crude product was purified by flash silica chromatography, elution gradient 0 to 40% EtOAc in heptane. Product containing fractions were evaporated to dryness to afford tert-butyl (R)-(1-(3-fluoro-1H-indazol-4-yl)propan-2-yl)carbamate (5.93 g, 51%) as a colourless solid. ¹H NMR (500 MHz, CDCl₃, 2 7° C.) 1.17 (3H, d), 1.35 (9H, s), 3.09 (2H, d), 4.00-4.09 (1H, m), 4.41-4.49 (1H, m), 6.97 (1H, d), 7.22 (1H, dd), 7.33 (1H, dd), 9.36 (1H, s); m/z: ES- [M-H]- 292.

(R)-1-(3-Fluoro-1H-indazol-4-yl)propan-2-amine

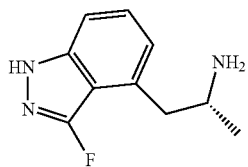

4N Hydrochloric acid in dioxane (23.86 ml, 95.45 mmol) was added to tert-butyl (R)-(1-(3-fluoro-1H-indazol-4-yl)propan-2-yl)carbamate (5.60 g, 19.1 mmol) in MeOH (23.9 mL) and the reaction was stirred at room temperature for 2 hours. The crude mixture was concentrated, then suspended in EtOAc (100 mL) and washed with saturated aqueous sodium bicarbonate (50 mL). The aqueous layer was extracted with EtOAc (×5), then the combined organics were dried over sodium sulfate and evaporated to afford (R)-1-(3-fluoro-1H-indazol-4-yl)propan-2-amine (3.10 g, 84%) as a yellow oil, which solidified on standing.

$^1$H NMR (500 MHz, CDCl$_3$, 27° C.) 1.19 (3H, d), 2.86 (1H, dd), 3.09 (1H, dd), 3.33 (1H, dddd), 6.96 (1H, d), 7.22 (1H, dd), 7.33 (1H, dd), 9.93 (1H, s); m/z: ES+ [M+H]+ 194.

(R)-1-(3-Fluoro-1H-indazol-4-yl)-N-(2,2,2-trifluoroethyl)propan-2-amine

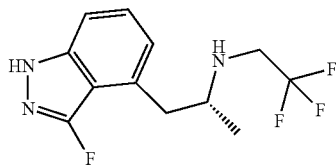 [SMILES: C[C@H](Cc1cccc2[nH]nc(F)c12)NCC(F)(F)F]

2,2,2-Trifluoroethyl trifluoromethanesulfonate 0.1M solution in DCM (25.9 mL, 2.59 mmol) was added to (R)-1-(3-fluoro-1H-indazol-4-yl)propan-2-amine (0.4 g, 2.07 mmol) and DIPEA (0.541 mL, 3.11 mmol) in 1,4-dioxane (20 mL) and the resulting mixture was stirred at 75° C. overnight. The reaction was concentrated in vacuo and partitioned between ethyl acetate (25 mL) and saturated aqueous sodium bicarbonate (25 mL). The layers were separated and the aqueous layer extracted with ethyl acetate (25 mL). The combined organics were washed with saturated aqueous sodium chloride (25 mL), dried over sodium sulphate, filtered and concentrated in vacuo. The resulting gum was taken up in methanol and applied to a pre-wetted (methanol) SCX-2 cartridge. The cartridge was washed with methanol and eluted with 1M ammonia in methanol. The eluent was concentrated in vacu to give (R)-1-(3-fluoro-1H-indazol-4-yl)-N-(2,2,2-trifluoroethyl)propan-2-amine (0.455 g, 80%) as a brown gum. $^1$H NMR (500 MHz, CDCl$_3$, 27° C.) 1.11 (3H, d), 2.92 (1H, dd), 3.07-3.22 (4H, m), 6.96 (1H, d), 7.25 (1H, dd), 7.34 (1H, dd), 9.50 (1H, s); m/z: ES+ [M+H]+276.

(6S,8R)-6-(5-bromopyridin-2-yl)-1-fluoro-8-methyl-7-(2,2,2-trifluoroethyl)-6,7,8,9-tetrahydro-3H-pyrazolo[4,3-f]isoquinoline

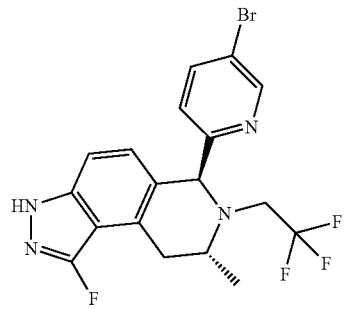 [SMILES: C[C@@H]1Cc2c(ccc3[nH]nc(F)c23)[C@@H](c2ccc(Br)cn2)N1CC(F)(F)F]

Trifluroacetic acid (87 µL) was added to a solution of (R)-1-(3-fluoro-1H-indazol-4-yl)-N-(2,2,2-trifluoroethyl)propan-2-amine (100 mg, 0.36 mmol) and 5-bromopicolinaldehyde (67.6 mg, 0.36 mmol) in toluene (0.87 mL) and the resulting mixture was stirred at 90° C. for 1 hour. The reaction was allowed to cool to room temperature and partitioned between DCM (5 mL) and saturated aqueous sodium bicarbonate (5 mL). The layers were separated and the organic layer was concentrated in vacuo. Purification was by silica gel column chromatography eluting with 0-50% ethyl acetate in heptane to give (6S,8R)-6-(5-bromopyridin-2-yl)-1-fluoro-8-methyl-7-(2,2,2-trifluoroethyl)-6,7,8,9-tetrahydro-3H-pyrazolo[4,3-f]isoquinoline (89 mg, 55%) as a white solid. $^1$H NMR (500 MHz, CDCl$_3$, 27° C.) 1.16 (3H, d), 2.92-3.00 (2H, m), 3.25-3.36 (2H, m), 3.46-3.52 (1H, m), 5.07 (1H, s), 6.98 (1H, d), 7.09 (1H, dd), 7.43 (1H, d), 7.77 (1H, dd), 8.55 (1H, dd), 9.09 (1H, s); m/z: ES+ [M+H]+ 443.

Example 33

5-Fluoro-6-(((6S,8R)-1-fluoro-8-methyl-7-(2,2,2-trifluoroethyl)-6,7,8,9-tetrahydro-3H-pyrazolo[4,3-f]isoquinolin-6-yl)-N-(1-(3-fluoropropyl)azetidin-3-yl)pyridin-3-amine

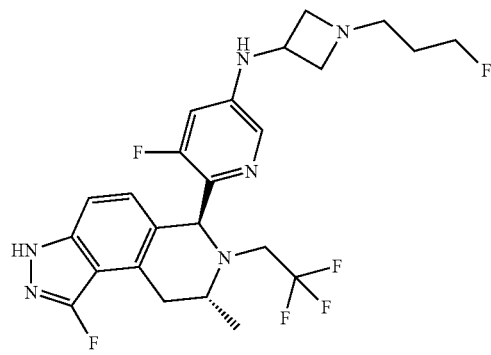 [SMILES: C[C@@H]1Cc2c(ccc3[nH]nc(F)c23)[C@@H](c2ncc(NC3CN(CCCF)C3)cc2F)N1CC(F)(F)F]

Sodium tert-butoxide (3.12 g, 32.52 mmol) and BrettPhos G3 (0.245 g, 0.27 mmol) were added to a degassed solution of (6S,8R)-6-(5-bromo-3-fluoropyridin-2-yl)-1-fluoro-8-methyl-7-(2,2,2-trifluoroethyl)-6,7,8,9-tetrahydro-3H-pyrazolo[4,3-f]isoquinoline (2.50 g, 5.42 mmol) and 1-(3-fluoropropyl)azetidin-3-amine (1.075 g, 8.13 mmol) in 1,4-dioxane (27.1 mL) and reaction was warmed to 60° C. and stirred for 2 hours. After cooling, the reaction was diluted with EtOAc and water, and the layers were separated. The aqueous layer was extracted with EtOAc, then the combined organics were dried over sodium sulfate and evaporated. Purification was first by silica gel column chromatography eluting with 0-100% (10% methanol in ethyl acetate) in heptane then by reverse phase Interchim (0.1% $NH_3$ and MeCN as eluents) to give the product as a mixture of isomers. The products were separated by SFC; the sample was dissolved in MeOH and separated using the following SFC conditions: Column: Phenomonex C4, 30×250 mm, 5 micron, mobile phase: 25% MeOH+0.1% $NH_3$, flow rate: 100 ml/min, BPR 120 bar, column temp: 40° C. to give 5-fluoro-6-((6S,8R)-1-fluoro-8-methyl-7-(2,2,2-trifluoroethyl)-6,7,8,9-tetrahydro-3H-pyrazolo[4,3-f]isoquinolin-6-yl)-N-(1-(3-fluoropropyl)azetidin-3-yl)pyridin-3-amine (1.780 g, 64%) as a foam. $^1$H NMR (500 MHz, $CDCl_3$, 27° C.) 1.15 (3H, d), 1.67-1.81 (2H, m), 2.59 (2H, t), 2.81-3.03 (4H, m), 3.17-3.34 (2H, m), 3.70 (3H, q), 4.01-4.08 (1H, m), 4.20 (1H, d), 4.43 (1H, t), 4.53 (1H, t), 5.32 (1H, s), 6.54 (1H, dd), 6.81 (1H, d), 6.95 (1H, d), 7.64-7.68 (1H, m), 9.46 (1H, s); m/z: ES+ [M+H]+ 513.

The (6S,8R)-6-(5-bromo-3-fluoropyridin-2-yl)-1-fluoro-8-methyl-7-(2,2,2-trifluoroethyl)-6,7,8,9-tetrahydro-3H-pyrazolo[4,3-f]isoquinoline used as starting material was synthesised as follows:

(6S,8R)-6-(5-bromo-3-fluoropyridin-2-yl)-1-fluoro-8-methyl-7-(2,2,2-trifluoroethyl)-6,7,8,9-tetrahydro-3H-pyrazolo[4,3-f]isoquinoline

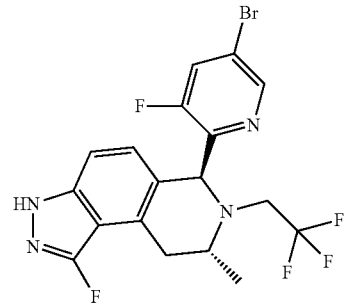 [SMILES: C[C@@H]1Cc2c(ccc3[nH]nc(F)c23)[C@@H](c2ncc(Br)cc2F)N1CC(F)(F)F]

Trifluoroacetic acid (2.16 mL) was added to a solution of (R)-1-(3-fluoro-1H-indazol-4-yl)-N-(2,2,2-trifluoroethyl) propan-2-amine (2.50 g, 9.08 mmol) and 5-bromo-3-fluoropicolinaldehyde (1.85 g, 9.08 mmol) in toluene (43.3 mL) and the resulting mixture was stirred at 90° C. for 90 minutes. The reaction was allowed to cool and partitioned between DCM (50 mL) and saturated aqueous sodium bicarbonate (50 mL). The layers were separated and the organic layer was concentrated in vacuo. Purification was by silica gel column chromatography eluting with 0-50% ethyl acetate in heptane to give (6S,8R)-6-(5-bromo-3-fluoropyridin-2-yl)-1-fluoro-8-methyl-7-(2,2,2-trifluoroethyl)-6,7,8,9-tetrahydro-3H-pyrazolo[4,3-f]isoquinoline (2.90 g, 69%) as a white solid. $^1$H NMR (500 MHz, $CDCl_3$, 27° C.) 1.15 (3H, d), 2.88-3.04 (2H, m), 3.24-3.35 (2H, m), 3.63-3.71 (1H, m), 5.39 (1H, s), 6.83 (1H, d), 7.08 (1H, dd), 7.60 (1H, dd), 8.36 (1H, dd), 9.13 (1H, s); m/z: ES+ [M+H]+ 461.

Examples 34 to 73 (table below) were prepared using synthetic methods analogous to those described above.

| Ex No | Structure | Name | 1H NMR | LCMS [M + H] |
|---|---|---|---|---|
| 34 | 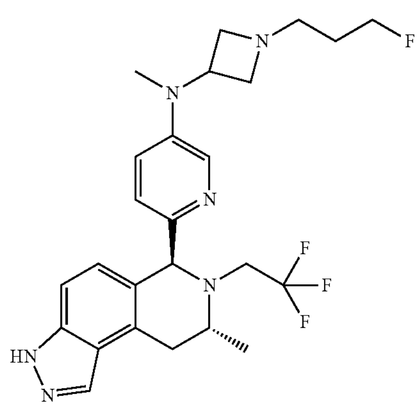 [SMILES: C[C@@H]1Cc2c(ccc3[nH]ncc23)[C@@H](c2ccc(N(C)C3CN(CCCF)C3)cn2)N1CC(F)(F)F] | N-(1-(3-fluoropropyl)azetidin-3-yl)-N-methyl-6-((6S,8R)-8-methyl-7-(2,2,2-trifluoroethyl)-6,7,8,9-tetrahydro-3H-pyrazolo[4,3-f]isoquinolin-6-yl)pyridin-3-amine | $^1$H NMR (500 MHz, $CDCl_3$, 27° C.) 1.15 (3H, d), 1.65-1.86 (2H, m), 2.59 (2H, t), 2.74-2.84 (1H, m), 2.85 (3H, s), 2.89-3.09 (3H, m), 3.16-3.41 (2H, m), 3.59 (1H, td), 3.64-3.80 (2H, m), 4.10 (1H, q), 4.44 (1H, t), 4.53 (1H, t), 5.06 (1H, s), 6.89 (1H, d), 6.99 (1H, dd), 7.11 (1H, d), 7.30 (1H, d), 7.96-7.98 (2H, m), 10.78 (1H, s). | 491 |

| Ex No | Structure | Name | 1H NMR | LCMS [M + H] |
|---|---|---|---|---|
| 35 | 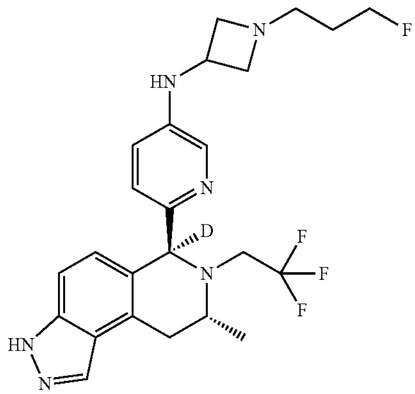 [SMILES: [2H][C@@]1(c2ccc(NC3CN(CCCF)C3)cn2)c2ccc3[nH]ncc3c2C[C@@H](C)N1CC(F)(F)F] | N-(1-(3-fluoropropyl)azetidin-3-yl)-6-((6S,8R)-6-deuterio-8-methyl-7-(2,2,2-trifluoroethyl)-6,7,8,9-tetrahydro-3H-pyrazolo[4,3-f]isoquinolin-6-yl)pyridin-3-amine | ¹H NMR (500 MHz, CDCl₃, 27° C.) 1.14 (3H, d), 1.76 (2H, dq), 2.62 (2H, t), 2.85 (1H, dd), 2.93-2.98 (2H, m), 2.99-3.04 (1H, m), 3.21-3.31 (2H, m), 3.55-3.63 (1H, m), 3.73 (2H, s), 4.11 (2H, s), 4.44 (1H, t), 4.53 (1H, t), 6.80 (1H, dd), 6.90 (1H, d), 7.16 (1H, d), 7.21 (1H, d), 7.84 (1H, d), 8.01 (1H, s) | 478 |
| 36 | 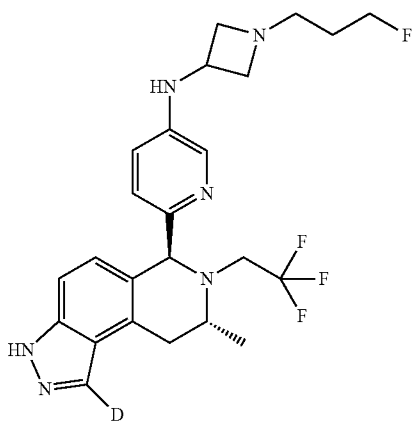 [SMILES: [2H]c1n[nH]c2ccc3c(c12)C[C@@H](C)N(CC(F)(F)F)[C@@H]3c1ccc(NC2CN(CCCF)C2)cn1] | N-(1-(3-fluoropropyl)azetidin-3-yl)-6-((6S,8R)-1-deuterio-8-methyl-7-(2,2,2-trifluoroethyl)-6,7,8,9-tetrahydro-3H-pyrazolo[4,3-f]isoquinolin-6-yl)pyridin-3-amine | ¹H NMR (500 MHz, CDCl₃, 27° C.) 1.14 (3H, d), 1.71-1.81 (2H, m), 2.62 (2H, t), 2.86 (1H, dd), 2.93-3.04 (3H, s), 3.20-3.32 (2H, m), 3.59 (1H, d), 3.73 (2H, s), 4.11 (2H, s), 4.43 (1H, t), 4.53 (1H, t), 5.03 (1H, s), 6.80 (1H, d), 6.90 (1H, d), 7.18 (2H, dd), 7.84 (1H, s) | 478 |
| 37 | 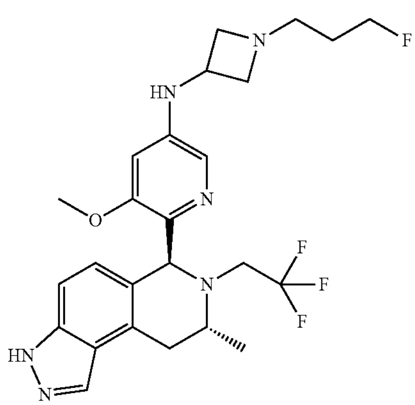 [SMILES: COc1cc(NC2CN(CCCF)C2)cnc1[C@@H]1c2ccc3[nH]ncc3c2C[C@@H](C)N1CC(F)(F)F] | N-(1-(3-fluoropropyl)azetidin-3-yl)-5-methoxy-6-((6S,8R)-8-methyl-7-(2,2,2-trifluoroethyl)-6,7,8,9-tetrahydro-3H-pyrazolo[4,3-f]isoquinolin-6-yl)pyridin-3-amine | ¹H NMR (300 MHz, DMSO-d₆, 27° C.) 1.08 (3H, d), 1.52-1.78 (2H, m), 2.46 (2H, t), 2.63-2.84 (3H, m), 2.87-3.07 (2H, m), 3.34-3.50 (1H, m), 3.58-3.69 (2H, m), 3.80 (3H, s), 3.83-4.07 (2H, m), 4.45 (2H, dt), 5.42 (1H, s), 6.24 (1H, d), 6.54 (1H, d), 6.66 (1H, d), 7.17 (1H, d), 7.26 (1H, d), 8.03 (1H, s), 12.90 (1H, s). | 507 |

| Ex No | Structure | Name | 1H NMR | LCMS [M + H] |
|---|---|---|---|---|
| 38 | 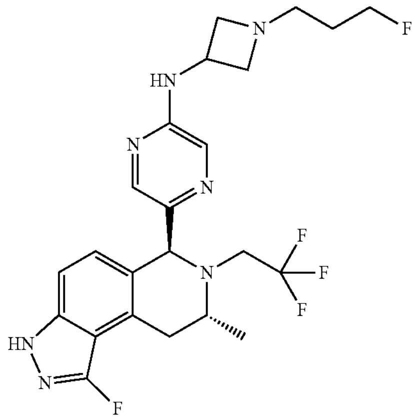 [SMILES: C[C@@H]1Cc2c(ccc3[nH]nc(F)c23)[C@@H](c2cnc(NC3CN(CCCF)C3)cn2)N1CC(F)(F)F] | 5-((6S,8R)-1-fluoro-8-methyl-7-(2,2,2-trifluoroethyl)-6,7,8,9-tetrahydro-3H-pyrazolo[4,3-f]isoquinolin-6-yl)-N-(1-(3-fluoropropyl)azetidin-3-yl)pyrazin-2-amine | ¹H NMR (500 MHz, CDCl₃, 27° C.) 1.16 (3H, d), 1.68-1.85 (2H, m), 2.63 (2H, t), 2.83 (1H, dd), 2.93-2.98 (1H, m), 2.99-3.07 (2H, m), 3.21 (1H, dd), 3.24-3.35 (1H, m), 3.49-3.54 (1H, m), 3.72 (2H, t), 4.44 (1H, t), 4.47 (1H, d), 4.53 (1H, t), 5.05 (1H, s), 5.37 (1H, d), 6.89 (1H, d), 6.96 (1H, dd), 7.75 (1H, d), 8.17 (1H, d), 10.63 (1H, s). | 496 |
| 39 | 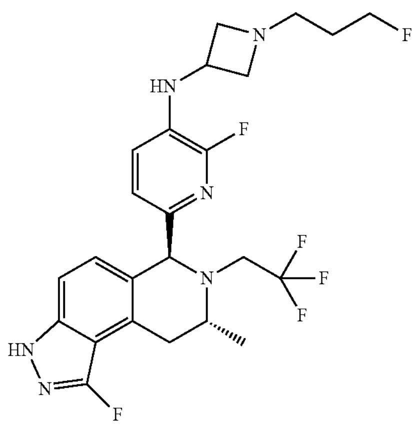 [SMILES: C[C@@H]1Cc2c(ccc3[nH]nc(F)c23)[C@@H](c2ccc(NC3CN(CCCF)C3)c(F)n2)N1CC(F)(F)F] | 2-fluoro-6-((6S,8R)-1-fluoro-8-methyl-7-(2,2,2-trifluoroethyl)-6,7,8,9-tetrahydro-3H-pyrazolo[4,3-f]isoquinolin-6-yl)-N-(1-(3-fluoropropyl)azetidin-3-yl)pyridin-3-amine | ¹H NMR (500 MHz, CDCl₃, 27° C.) 1.14 (3H, d), 1.69-1.86 (2H, m), 2.63 (2H, t), 2.83 (1H, dd), 2.91-3.08 (3H, m), 3.13-3.38 (2H, m), 3.52 (1H, ddd), 3.77 (2H, q), 4.11 (1H, q), 4.31-4.39 (1H, m), 4.44 (1H, t), 4.53 (1H, t), 4.95 (1H, s), 6.85 (1H, dd), 6.89-6.98 (2H, m), 7.23 (1H, d), 10.41 (1H, s) | 513 |
| 40 | 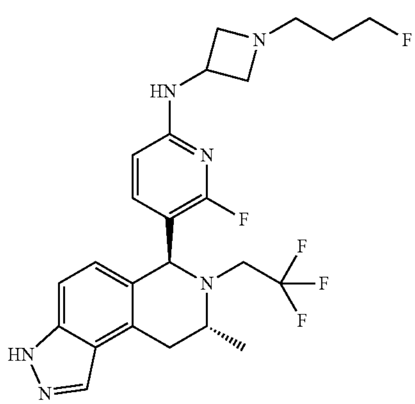 [SMILES: C[C@@H]1Cc2c(ccc3[nH]ncc23)[C@@H](c2ccc(NC3CN(CCCF)C3)nc2F)N1CC(F)(F)F] | 6-fluoro-N-(1-(3-fluoropropyl)azetidin-3-yl)-3-((6S,8R)-8-methyl-7-(2,2,2-trifluoroethyl)-6,7,8,9-tetrahydro-3H-pyrazolo[4,3-f]isoquinolin-6-yl)pyridin-2-amine | ¹H NMR (500 MHz, CDCl₃, 27° C.) 1.14 (3H, d), 1.83 (2H, dp), 2.76 (2H, s), 2.81-2.91 (1H, m), 2.90-3.03 (1H, m), 3.11-3.32 (4H, m), 3.53 (1H, dt), 3.84 (2H, d), 4.46 (2H, q), 4.55 (1H, t), 5.20 (1H, s), 5.98-6.10 (1H, m), 6.83 (1H, d), 6.99-7.08 (1H, m), 7.23 (1H, d), 8.06 (1H, d), 10.48 (1H, s). | 495 |

| Ex No | Structure | Name | 1H NMR | LCMS [M + H] |
|---|---|---|---|---|
| 41 | 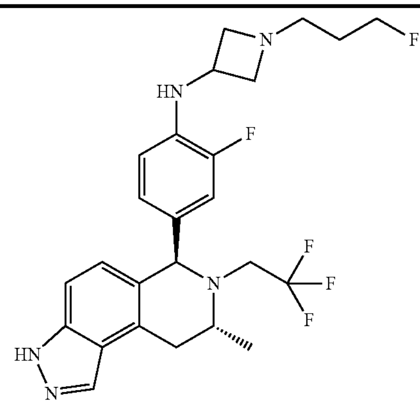 | N-(2-fluoro-4-((6R,8R)-8-methyl-7-(2,2,2-trifluoroethyl)-6,7,8,9-tetrahydro-3H-pyrazolo[4,3-f]isoquinolin-6-yl)phenyl)-1-(3-fluoropropyl)azetidin-3-amine | ¹H NMR (500 MHz, CDCl₃, 27° C.) 1.14 (3H, d), 1.69-1.83 (2H, m), 2.59 (2H, t), 2.77 (1H, dd), 2.84-2.89 (2H, m), 2.89-2.98 (1H, m), 3.03 (1H, dd), 3.21 (1H, dq), 3.38 (1H, ddd), 3.71-3.80 (2H, m), 4.04-4.16 (2H, m), 4.44 (1H, t), 4.53 (1H, t), 4.97 (1H, s), 6.41 (1H, t), 6.76 (1H, dd), 6.90 (1H, dd), 6.97 (1H, d), 7.28 (1H, d), 8.06 (1H, d), 10.20 (1H, s). | 494 |
| 42 | 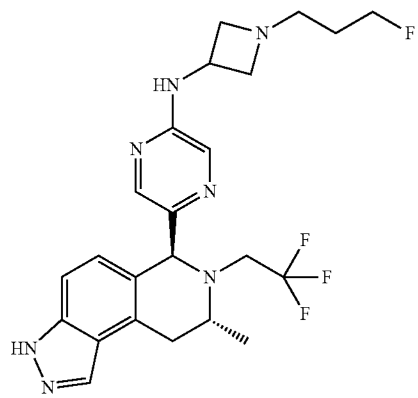 [SMILES: C[C@@H]1Cc2c(ccc3[nH]ncc23)[C@@H](c2cnc(NC3CN(CCCF)C3)cn2)N1CC(F)(F)F] | N-(1-(3-fluoropropyl)azetidin-3-yl)-5-((6S,8R)-8-methyl-7-(2,2,2-trifluoroethyl)-6,7,8,9-tetrahydro-3H-pyrazolo[4,3-f]isoquinolin-6-yl)pyrazin-2-amine | ¹H NMR (300 MHz, DMSO-d₆, 27° C.) 1.11 (3H, d), 1.49-1.80 (2H, m), 2.42-2.48 (2H, m), 2.76-2.93 (3H, m), 2.93-3.21 (2H, m), 3.42-3.69 (4H, m), 4.23-4.34 (1H, m), 4.45 (2H, dt), 4.99 (1H, s), 6.85 (1H, d), 7.25 (1H, d), 7.42 (1H, d), 7.78 (1H, d), 7.82 (1H, d), 8.06 (1H, s), 12.98 (1H, s). | 478 |
| 43 | 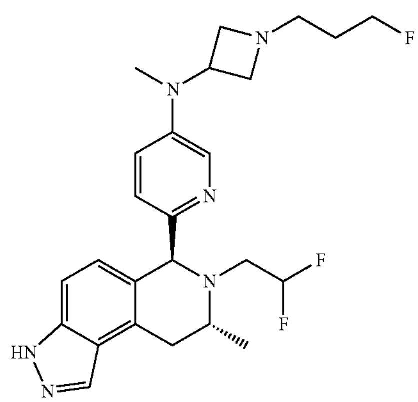 | 6-((6S,8R)-7-(2,2-difluoroethyl)-8-methyl-6,7,8,9-tetrahydro-3H-pyrazolo[4,3-f]isoquinolin-6-yl)-N-(1-(3-fluoropropyl)azetidin-3-yl)-N-methylpyridin-3-amine | ¹H NMR (300 MHz, DMSO-d₆, 27° C.) 1.06 (3H, d), 1.56-1.78 (2H, m), 2.42-2.48 (2H, m), 2.55-2.70 (1H, m), 2.81 (3H, s), 2.82-2.95 (3H, m), 2.96-3.23 (2H, m), 3.39-3.54 (1H, m), 3.57-3.69 (2H, m), 4.05 (1H, quin), 4.45 (2H, dt), 4.93 (1H, s), 5.88 (1H, tt), 6.77 (1H, d), 7.07 (2H, d), 7.21 (1H, d), 7.93 (1H, t), 8.05 (1H, s), 12.95 (1H, s). | 473 |
| 44 | 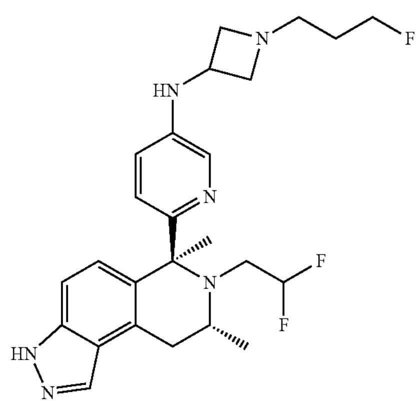 | 6-((6S,8R)-7-(2,2-difluoroethyl)-6,8-dimethyl-6,7,8,9-tetrahydro-3H-pyrazolo[4,3-f]isoquinolin-6-yl)-N-(1-(3-fluoropropyl)azetidin-3-yl)pyridin-3-amine | ¹H NMR (500 MHz, CDCl₃, 27° C.) 1.20 (3H, d), 1.68-1.81 (3H, m), 1.87 (3H, s), 2.59 (2H, t), 2.89 (2H, d), 3.01 (2H, dd), 3.32 (1H, dd), 3.54-3.62 (1H, m), 3.68-3.75 (2H, m), 3.93 (1H, d), 4.07 (1H, q), 4.43 (1H, t), 4.53 (1H, t), 5.25-5.62 (1H, m), 6.68 (1H, dd), 7.01 (1H, d), 7.08 (1H, d), 7.20 (1H, d), 7.83 (1H, d), 8.06 (1H, s), 10.01 (1H, s). | 473 |

| Ex No | Structure | Name | 1H NMR | LCMS [M + H] |
|---|---|---|---|---|
| 45 | 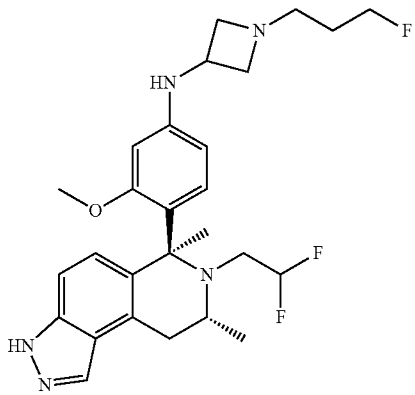 [SMILES: COc1cc(NC2CN(CCCF)C2)ccc1[C@]1(C)c2ccc3[nH]ncc3c2C[C@@H](C)N1CC(F)F] | N-(4-((6S,8R)-7-(2,2-difluoroethyl)-6,8-dimethyl-6,7,8,9-tetrahydro-3H-pyrazolo[4,3-f]isoquinolin-6-yl)-3-methoxyphenyl)-1-(3-fluoropropyl)azetidin-3-amine | ¹H NMR (500 MHz, CDCl₃, 27° C.) 1.14 (3H, d), 1.68-1.82 (2H, m), 1.85 (3H, s), 2.58 (2H, t), 2.78-2.99 (5H, m), 3.17 (1H, dd), 3.44 (3H, s), 3.49-3.60 (1H, m), 3.66-3.78 (2H, m), 3.89 (1H, d), 4.03-4.14 (1H, m), 4.48 (2H, dt), 5.26-5.54 (1H, m), 5.97 (1H, dd), 6.03 (1H, d), 6.82 (1H, d), 7.00 (1H, d), 7.17 (1H, d), 8.06 (1H, d), 9.95 (1H, s). | 502 |
| 46 | 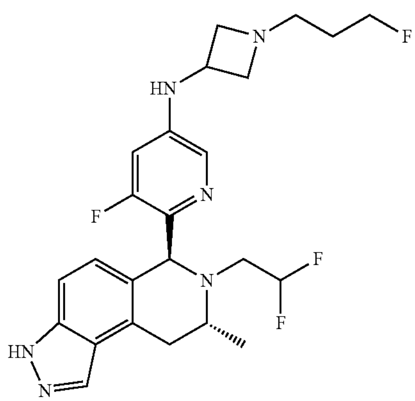 | 6-((6S,8R)-7-(2,2-difluoroethyl)-8-methyl-6,7,8,9-tetrahydro-3H-pyrazolo[4,3-f]isoquinolin-6-yl)-5-fluoro-N-(1-(3-fluoropropyl)azetidin-3-yl)pyridin-3-amine | ¹H NMR (500 MHz, CDCl₃, 27° C.) 1.14 (3H, d), 1.66-1.82 (2H, m), 2.59 (2H, t), 2.72-2.80 (1H, m), 2.85 (1H, dd), 2.90 (2H, d), 2.98-3.12 (1H, m), 3.24 (1H, dd), 3.49 (1H, d), 3.64-3.73 (2H, m), 3.98-4.08 (1H, m), 4.16 (1H, d), 4.43 (1H, t), 4.53 (1H, t), 5.28 (1H, s), 5.58-5.89 (1H, m), 6.52 (1H, dd), 6.82 (1H, d), 7.19 (1H, d), 7.64-7.69 (1H, m), 8.05 (1H, s), 10.04 (1H, s). | 477 |
| 47 | 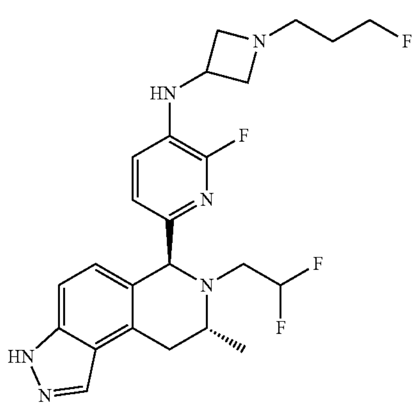 | 6-((6S,8R)-7-(2,2-difluoroethyl)-8-methyl-6,7,8,9-tetrahydro-3H-pyrazolo[4,3-f]isoquinolin-6-yl)-2-fluoro-N-(1-(3-fluoropropyl)azetidin-3-yl)pyridin-3-amine | ¹H NMR (500 MHz, CDCl₃, 27° C.) 1.12 (3H, d), 1.67-1.81 (2H, m), 2.59 (2H, t), 2.79 (1H, dddd), 2.86-2.93 (2H, m), 3.04 (1H, ddd), 3.33 (1H, dd), 3.53-3.62 (1H, m), 3.69-3.79 (2H, m), 4.06 (1H, q), 4.21 (1H, d), 4.44 (1H, t), 4.53 (1H, t), 4.89 (1H, s), 5.48-5.76 (1H, m), 6.75 (1H, dd), 6.93 (1H, d), 6.98 (1H, d), 7.19 (1H, d), 8.05 (1H, s), 9.99 (1H, s). | 477 |

| Ex No | Structure | Name | 1H NMR | LCMS [M + H] |
|---|---|---|---|---|
| 48 | 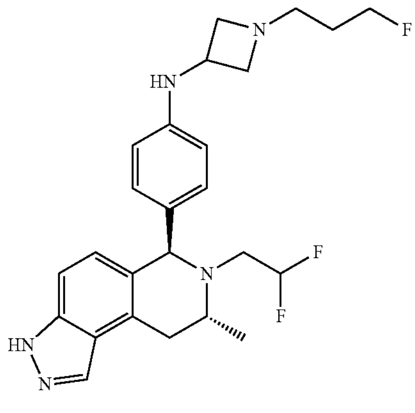 | N-(4-((6R,8R)-7-(2,2-difluoroethyl)-8-methyl-6,7,8,9-tetrahydro-3H-pyrazolo[4,3-f]isoquinolin-6-yl)phenyl)-1-(3-fluoropropyl)azetidin-3-amine | $^1$H NMR (500 MHz, DMSO-d$_6$, 27° C.) 0.96 (3H, d), 1.52-1.64 (2H, m), 2.49-2.61 (1H, m), 2.63-2.78 (3H, m), 2.88-3.02 (2H, m), 3.26-3.31 (1H, m), 3.53-3.64 (2H, m), 3.80-3.87 (1H, m), 4.38 (2H, dt), 4.74 (1H, s), 5.76 (1H, tt), 5.88-5.93 (1H, m), 6.33 (2H, d), 6.70 (1H, d), 6.80 (2H, d), 7.17 (1H, d), 7.98 (1H, s), 12.91 (1H, s). (Two hydrogens not observed). | 458 |
| 49 | 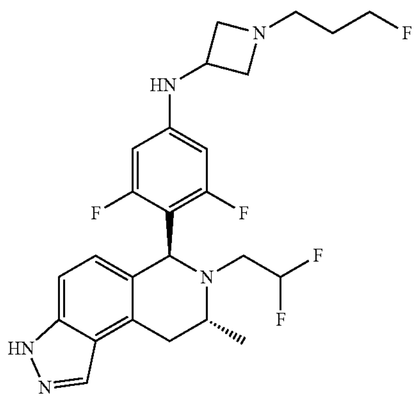 | N-(4-((6S,8R)-7-(2,2-difluoroethyl)-8-methyl-6,7,8,9-tetrahydro-3H-pyrazolo[4,3-f]isoquinolin-6-yl)-3,5-difluorophenyl)-1-(3-fluoropropyl)azetidin-3-amine | $^1$H NMR (500 MHz, DMSO-d$_6$, 27° C.) 0.95 (3H, d), 1.58-1.70 (2H, m), 2.50-2.70 (3H, m), 2.79 (1H, br dd), 2.86-2.97 (1H, m), 2.95-3.12 (2H, m), 3.09 (1H, br dd), 3.33-3.45 (1H, m), 3.71-3.88 (2H, m), 3.88-4.01 (1H, m), 4.38 (2H, dt), 5.03 (1H, s), 5.70 (1H, tt), 6.03 (2H, br d), 6.63 (1H, d), 6.69 (1H, br d), 7.13 (1H, d), 7.96 (1H, s), 12.89 (1H, s) | 494 |
| 50 | 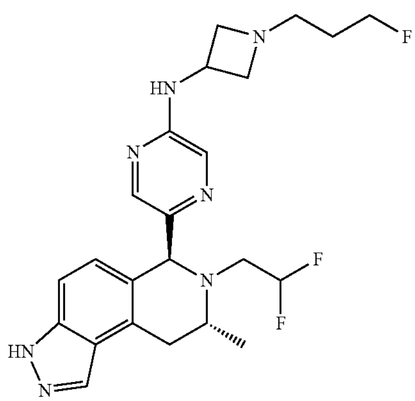 | 5-((6S,8R)-7-(2,2-difluoroethyl)-8-methyl-6,7,8,9-tetrahydro-3H-pyrazolo[4,3-f]isoquinolin-6-yl)-N-(1-(3-fluoropropyl)azetidin-3-yl)pyrazin-2-amine | $^1$H NMR (500 MHz, DMSO-d$_6$, 27° C.) 1.06 (3H, d), 1.56-1.70 (2H, m), 2.42-2.47 (2H, m), 2.57-2.69 (1H, m), 2.75-2.87 (3H, m), 2.99-3.13 (2H, m), 3.43-3.51 (1H, m), 3.54-3.62 (2H, m), 4.29 (1H, sxt), 4.43 (2H, dt), 4.94 (1H, s), 5.97 (1H, tt), 6.79 (1H, d), 7.22 (1H, d), 7.41 (1H, d), 7.77 (1H, d), 7.84 (1H, d), 8.04 (1H, s), 12.97 (1H, s) | 460 |
| 51 | 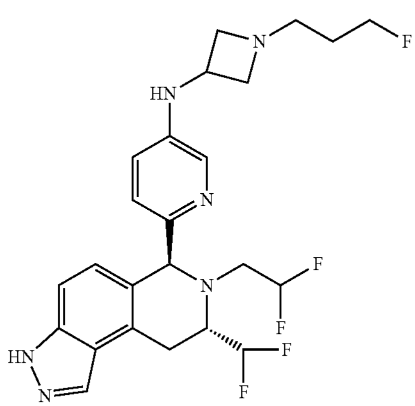 [SMILES: FCCCN1CC(Nc2ccc([C@@H]3c4ccc5[nH]ncc5c4C[C@@H](C(F)F)N3CC(F)F)nc2)C1] | 6-((6S,8S)-7-(2,2-difluoroethyl)-8-(difluoromethyl)-6,7,8,9-tetrahydro-3H-pyrazolo[4,3-f]isoquinolin-6-yl)-N-(1-(3-fluoropropyl)azetidin-3-yl)pyridin-3-amine | $^1$H NMR (500 MHz, CDCl$_3$, 27° C.) 1.68-1.86 (2H, m), 2.63 (2H, dd), 2.98 (2H, dd), 3.00-3.07 (1H, m), 3.20 (1H, dd), 3.28-3.44 (2H, m), 3.70 (3H, q), 4.10 (1H, dh), 4.43 (2H, t), 4.52 (1H, t), 5.19 (1H, s), 5.43 (1H, tdd), 5.81 (1H, td), 6.77 (1H, dd), 6.84 (1H, d), 7.09 (2H, t), 7.86 (1H, d), 8.00-8.02 (1H, m). | 495 |

| Ex No | Structure | Name | 1H NMR | LCMS [M + H] |
|---|---|---|---|---|
| 52 | 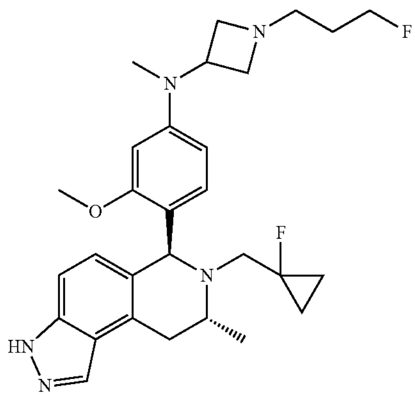 [SMILES: COc1cc(N(C)C2CN(CCCF)C2)ccc1[C@@H]1c2ccc3[nH]ncc3c2C[C@@H](C)N1CC1(F)CC1] | N-(4-((6S,8R)-7-((1-fluorocyclopropyl)methyl)-8-methyl-6,7,8,9-tetrahydro-3H-pyrazolo[4,3-f]isoquinolin-6-yl)-3-methoxyphenyl)-1-(3-fluoropropyl)-N-methylazetidin-3-amine | $^1$H NMR (500 MHz, CDCl$_3$, 27° C.) 0.46-0.62 (2H, m), 0.85-1.03 (2H, m), 1.10 (3H, d), 1.66-1.89 (2H, m), 2.56-2.62 (2H, m), 2.64 (1H, d), 2.80 (3H, s), 2.89 (1H, dd), 2.98 (2H, dt), 3.09 (1H, dd), 3.33 (1H, dd), 3.73 (2H, q), 3.80 (1H, q), 3.87 (3H, s), 4.08 (1H, p), 4.44 (1H, t), 4.53 (1H, t), 5.37 (1H, s), 6.13 (1H, dd), 6.26 (1H, d), 6.79 (2H, t), 7.07 (1H, d), 8.05 (1H, s), 10.53 (1H, s). | 510 |
| 53 | 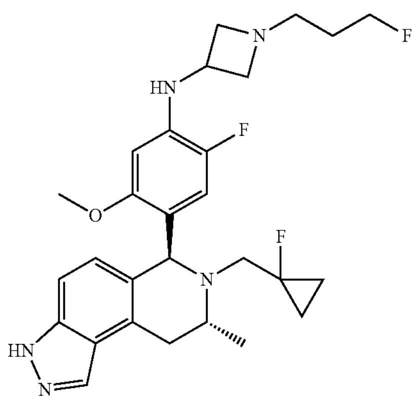 [SMILES: COc1cc(NC2CN(CCCF)C2)c(F)cc1[C@@H]1c2ccc3[nH]ncc3c2C[C@@H](C)N1CC1(F)CC1] | N-(2-fluoro-4-((6S,8R)-7-((1-fluorocyclopropyl)methyl)-8-methyl-6,7,8,9-tetrahydro-3H-pyrazolo[4,3-f]isoquinolin-6-yl)-5-methoxyphenyl)-1-(3-fluoropropyl)azetidin-3-amine | $^1$H NMR (500 MHz, CDCl$_3$, 27° C.) 0.46-0.52 (2H, m), 0.92-1.01 (2H, m), 1.08 (3H, d), 1.71-1.83 (2H, m), 2.55-2.64 (3H, m), 2.84-2.93 (3H, m), 3.02-3.11 (1H, m), 3.35-3.42 (1H, m), 3.77-3.89 (6H, m), 4.03-4.09 (1H, m), 4.12-4.18 (1H, m), 4.50 (2H, dt), 5.30 (1H, s), 6.13 (1H, d), 6.65 (1H, d), 6.80 (1H, d), 7.12 (1H, d), 8.05 (1H, s), 9.97 (1H, s). | 514 |
| 54 | 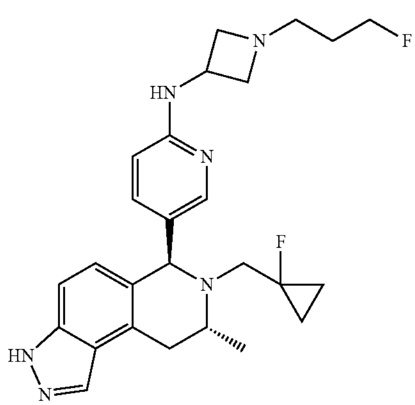 [SMILES: C[C@@H]1Cc2c(ccc3[nH]ncc23)[C@@H](c2ccc(NC3CN(CCCF)C3)nc2)N1CC1(F)CC1] | 5-((6S,8R)-7-((1-fluorocyclopropyl)methyl)-8-methyl-6,7,8,9-tetrahydro-3H-pyrazolo[4,3-f]isoquinolin-6-yl)-N-(1-(3-fluoropropyl)azetidin-3-yl)pyridin-2-amine | $^1$H NMR (500 MHz, CDCl$_3$, 27° C.) 0.47-0.61 (2H, m), 1.04 (2H, d), 1.09 (3H, d), 1.66-1.81 (2H, m), 2.59 (2H, t), 2.72 (1H, dd), 2.84 (1H, dd), 2.92 (2H, td), 3.01 (1H, dd), 3.14 (1H, dd), 3.51-3.61 (1H, m), 3.68-3.83 (2H, m), 4.39 (1H, q), 4.43 (1H, t), 4.52 (1H, t), 4.92 (1H, d), 4.96 (1H, s), 6.29 (1H, d), 6.88 (1H, d), 7.17 (1H, d), 7.40 (1H, dd), 7.82 (1H, d), 8.04 (1H, d), 11.07 (1H, s). | 467 |

| Ex No | Structure | Name | 1H NMR | LCMS [M + H] |
|---|---|---|---|---|
| 55 | 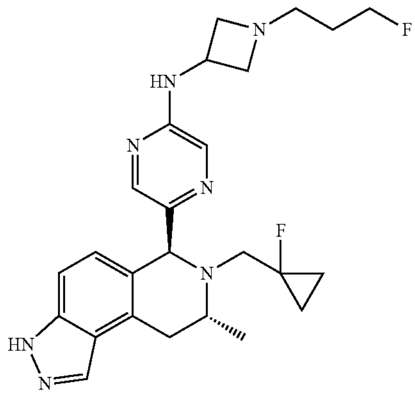 | 5-((6S,8R)-7-((1-fluorocyclopropyl)methyl)-8-methyl-6,7,8,9-tetrahydro-3H-pyrazolo[4,3-f]isoquinolin-6-yl)-N-(1-(3-fluoropropyl)azetidin-3-yl)pyrazin-2-amine | $^1$H NMR (300 MHz, DMSO-d$_6$, 27° C.) 0.47-0.63 (1H, m), 0.67-0.80 (1H, m), 0.81-1.01 (2H, m), 1.04 (3H, d), 1.49-1.78 (2H, m), 2.45 (2H, t), 2.57-2.94 (4H, m), 2.96-3.23 (2H, m), 3.47-3.71 (3H, m), 4.22-4.34 (1H, m), 4.44 (2H, dt), 4.92 (1H, s), 6.82 (1H, d), 7.22 (1H, d), 7.35 (1H, d), 7.78 (1H, d), 7.82 (1H, d), 8.05 (1H, d), 12.94 (1H, br d). | 468 |
| 56 | 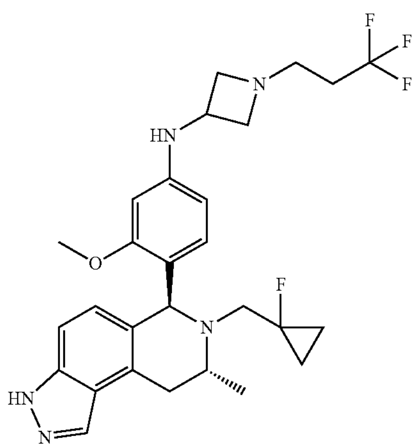 [SMILES: COc1cc(NC2CN(CCC(F)(F)F)C2)ccc1[C@@H]1c2ccc3[nH]ncc3c2C[C@@H](C)N1CC1(F)CC1] | N-(4-((6S,8R)-7-((1-fluorocyclopropyl)methyl)-8-methyl-6,7,8,9-tetrahydro-3H-pyrazolo[4,3-f]isoquinolin-6-yl)-3-methoxyphenyl)-1-(3,3,3-trifluoropropyl)azetidin-3-amine | $^1$H NMR (500 MHz, CDCl$_3$, 27° C.) 0.48-0.55 (2H, m), 0.90-0.98 (2H, m), 1.09 (3H, d), 2.10-2.21 (2H, m), 2.57-2.72 (3H, m), 2.85-2.92 (3H, m), 3.07 (1H, dd), 3.34 (1H, dd), 3.71-3.82 (3H, m), 3.86 (3H, s), 4.07-4.14 (1H, m), 5.33 (1H, s), 5.96 (1H, dd), 6.11 (1H, d), 6.75 (1H, d), 6.81 (1H, d), 7.11 (1H, d), 8.05 (1H, d), 10.00 (1H, s). | 532 |
| 57 | 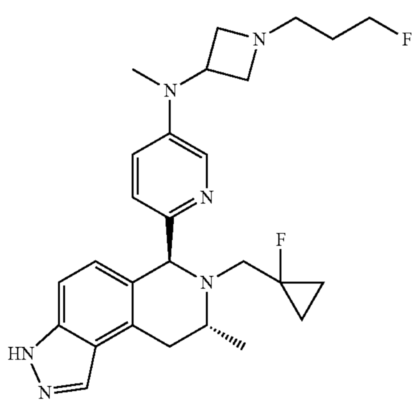 [SMILES: C[C@@H]1Cc2c(ccc3[nH]ncc23)[C@@H](c2ccc(N(C)C3CN(CCCF)C3)cn2)N1CC1(F)CC1] | 6-((6S,8R)-7-((1-fluorocyclopropyl)methyl)-8-methyl-6,7,8,9-tetrahydro-3H-pyrazolo[4,3-f]isoquinolin-6-yl)-N-(1-(3-fluoropropyl)azetidin-3-yl)-N-methylpyridin-3-amine | $^1$H NMR (300 MHz, DMSO-d$_6$, 27° C.) 0.40-0.57 (1H, m), 0.61-0.77 (1H, m), 0.78-1.00 (2H, m), 1.02 (3H, d), 1.57-1.75 (2H, m), 2.42-2.48 (2H, m), 2.66 (1H, dd), 2.80 (3H, s), 2.83-2.93 (3H, m), 3.00 (1H, dd), 3.19 (1H, br dd), 3.57-3.71 (3H, m), 4.04 (1H, quin), 4.45 (2H, dt), 4.88 (1H, s), 6.80 (1H, d), 7.01-7.10 (2H, m), 7.19 (1H, d), 7.93 (1H, d), 8.04 (1H, s), 12.93 (1H, s). | 481 |

| Ex No | Name | 1H NMR | LCMS [M + H] |
|---|---|---|---|
| 58 | 2,2-difluoro-3-((6S,8R)-6-(5-((1-(3-fluoropropyl)azetidin-3-yl)oxy)pyridin-2-yl)-8-methyl-3,6,8,9-tetrahydro-7H-pyrazolo[4,3-f]isoquinolin-7-yl)propan-1-ol | $^1$H NMR (500 MHz, DMSO, 27° C.) 1.06 (3H, d), 1.65 (2H, dq), 2.61-2.71 (1H, m), 2.82 (1H, dd), 2.94 (2H, dd), 3.00 (1H, dd), 3.11-3.21 (1H, m), 3.36-3.42 (1H, m), 3.64-3.74 (4H, m), 4.39 (1H, t), 4.48 (1H, t), 4.80 (1H, p), 5.04 (1H, s), 5.39 (1H, t), 6.84 (1H, d), 7.17-7.26 (3H, m), 8.02-8.07 (2H, m), 12.97 (1H, s). | 490 |
| 59 | 2,2-difluoro-3-((6S,8R)-6-(3-fluoro-5-((1-(3-fluoropropyl)azetidin-3-yl)oxy)pyridin-2-yl)-8-methyl-3,6,8,9-tetrahydro-7H-pyrazolo[4,3-f]isoquinolin-7-yl)propan-1-ol | $^1$H NMR (500 MHz, CDCl$_3$, 27° C.) 1.17 (3H, d), 1.71-1.82 (2H, m), 2.65 (2H, t), 2.79-2.95 (3H, m), 3.11-3.18 (2H, m), 3.19-3.28 (1H, m), 3.33 (1H, dd), 3.68 (1H, td), 3.84 (4H, ddt), 4.44 (1H, t), 4.53 (1H, t), 4.79 (1H, p), 5.39 (1H, s), 6.75 (1H, d), 6.86 (1H, dd), 7.20 (1H, d), 7.94 (1H, d), 8.06 (1H, d). | 508 |
| 60 | 2,2-difluoro-3-((6S,8R)-6-(4-((1-(3-fluoropropyl)azetidin-3-yl)amino)-2-methoxyphenyl)-8-methyl-3,6,8,9-tetrahydro-7H-pyrazolo[4,3-f]isoquinolin-7-yl)propan-1-ol | $^1$H NMR (500 MHz, CDCl$_3$, 27° C.) 1.13 (3H, d), 1.39 (1H, h), 1.68-1.83 (2H, m), 2.59 (2H, t), 2.82-2.99 (4H, m), 3.13 (1H, dt), 3.24 (1H, dd), 3.30-3.39 (1H, m), 3.56-3.86 (8H, m), 4.09 (1H, p), 4.44 (1H, t), 4.53 (1H, t), 5.28 (1H, s), 5.98 (1H, dd), 6.11 (1H, d), 6.59 (1H, d), 6.76 (1H, d), 7.16 (1H, d), 8.04 (1H, d). | 518 |

| Ex No | Structure | Name | 1H NMR | LCMS [M + H] |
|---|---|---|---|---|
| 61 | 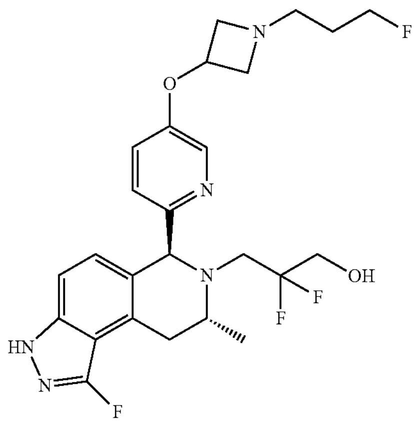 [SMILES: C[C@@H]1Cc2c(ccc3[nH]nc(F)c23)[C@@H](c2ccc(OC3CN(CCCF)C3)cn2)N1CC(F)(F)CO] | 2,2-difluoro-3-((6S,8R)-1-fluoro-6-(5-((1-(3-fluoropropyl)azetidin-3-yl)amino)pyridin-2-yl)-8-methyl-3,6,8,9-tetrahydro-7H-pyrazolo[4,3-f]isoquinolin-7-yl)propan-1-ol | 1H NMR (500 MHz, CDCl$_3$, 27° C.) 1.15 (3H, d), 1.66-1.88 (2H, m), 2.62 (2H, t), 2.88 (1H, dd), 2.92-3.02 (3H, m), 3.14 (1H, dd), 3.22 (1H, td), 3.37 (1H, ddd), 3.67-3.73 (2H, m), 3.76 (1H, td), 3.97-4.15 (2H, m), 4.31 (1H, d), 4.44 (1H, t), 4.53 (1H, t), 5.11 (1H, s), 6.72 (1H, dd), 6.79 (1H, d), 6.87 (1H, d), 7.01 (1H, d), 7.93 (1H, d), 10.19 (1H, s). | 507 |
| 62 | 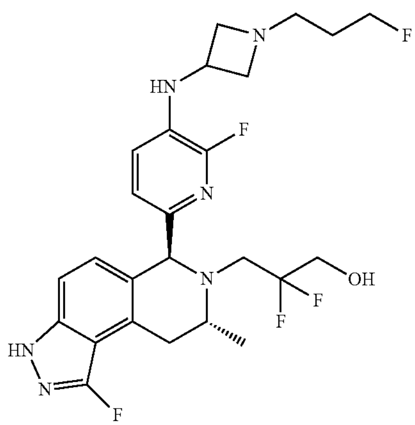 [SMILES: C[C@@H]1Cc2c(ccc3[nH]nc(F)c23)[C@@H](c2ccc(NC3CN(CCCF)C3)c(F)n2)N1CC(F)(F)CO] | 2,2-difluoro-3-((6S,8R)-1-fluoro-6-(6-fluoro-5-((1-(3-fluoropropyl)azetidin-3-yl)amino)pyridin-2-yl)-8-methyl-3,6,8,9-tetrahydro-7H-pyrazolo[4,3-f]isoquinolin-7-yl)propan-1-ol | $^1$H NMR (500 MHz, CDCl$_3$, 27° C.) 1.17 (3H, d), 1.68-1.84 (2H, m), 2.62 (2H, t), 2.88 (1H, dd), 2.92-2.97 (3H, m), 3.08-3.16 (1H, m), 3.16-3.27 (1H, m), 3.35-3.44 (1H, m), 3.71-3.78 (2H, m), 3.83 (1H, td), 3.93-4.14 (2H, m), 4.38 (1H, d), 4.44 (1H, t), 4.53 (1H, t), 5.03 (1H, s), 6.59-6.79 (2H, m), 6.92 (1H, d), 7.09 (1H, dd), 10.06 (1H, s). | 525 |
| 63 | 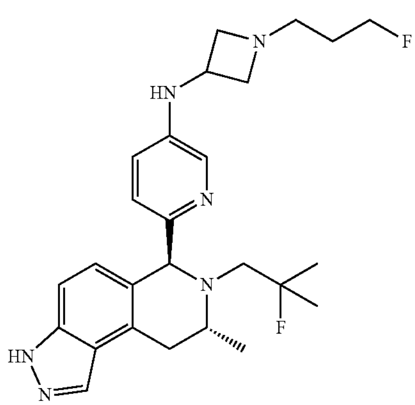 | 6-((6S,8R)-7-(2-fluoro-2-methylpropyl)-8-methyl-6,7,8,9-tetrahydro-3H-pyrazolo[4,3-f]isoquinolin-6-yl)-N-(1-(3-fluoropropyl)azetidin-3-yl)pyridin-3-amine | $^1$H NMR (500 MHz, DMSO-d$_6$, 27° C.) 0.94 (3H, d), 1.13-1.27 (6H, m), 1.51-1.67 (2H, m), 2.23-2.34 (1H, m), 2.61-2.77 (4H, m), 2.97 (1H, br dd), 3.40-3.48 (1H, m), 3.50-3.65 (2H, m), 3.81-3.93 (1H, m), 4.38 (2H, dt), 4.80 (1H, s), 6.11 (1H, br d), 6.69-6.78 (2H, m), 6.95 (1H, d), 7.12 (1H, d), 7.66 (1H, d), 7.96 (1H, s), 12.86 (1H, s). (Two hydrogens not observed). | 469 |

| Ex No | Structure | Name | 1H NMR | LCMS [M + H] |
| --- | --- | --- | --- | --- |
| 64 | 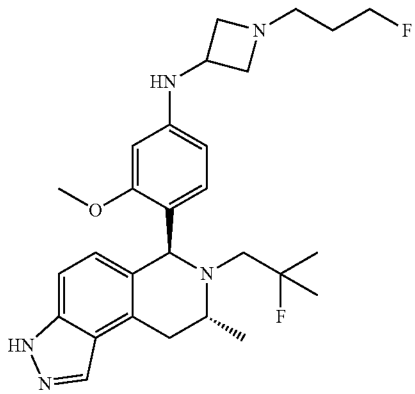 [SMILES: COc1cc(NC2CN(CCCF)C2)ccc1[C@@H]1c2ccc3[nH]ncc3c2C[C@@H](C)N1CC(C)(C)F] | N-(4-((6S,8R)-7-(2-fluoro-2-methylpropyl)-8-methyl-6,7,8,9-tetrahydro-3H-pyrazolo[4,3-f]isoquinolin-6-yl)-3-methoxyphenyl)-1-(3-fluoropropyl)azetidin-3-amine | ¹H NMR (500 MHz, CDCl₃, 27° C.) 1.05 (3H, d), 1.26 (6H, dd), 1.74 (2H, ddd), 2.37 (1H, dd), 2.54-2.64 (2H, m), 2.71-2.9 (4H, m), 3.26 (1H, d), 3.73 (3H, d), 3.84 (3H, s), 3.93 (1H, s), 4.10 (1H, s), 4.43 (1H, t), 4.53 (1H, t), 5.30 (1H, s), 5.94 (1H, dd), 6.11 (1H, d), 6.67 (1H, d), 6.80 (1H, d), 7.11 (1H, d), 8.04 (1H, d), 10.06 (1H, s). | 498 |
| 65 | Isomer A | 6-((6S,8R)-7-(2-fluoropropyl)-8-methyl-6,7,8,9-tetrahydro-3H-pyrazolo[4,3-f]isoquinolin-6-yl)-N-(1-(3-fluoropropyl)azetidin-3-yl)pyridin-3-amine | ¹H NMR (500 MHz, DMSO-d₆, 27° C.) 1.00 (3H, d), 1.22 (3H, dd), 1.59-1.70 (2H, m), 2.65-2.86 (4H, m), 3.14 (1H, br dd), 3.48 (1H, sxt), 3.59-3.73 (2H, br m), 3.94 (1H, sxt), 4.44 (2H, dt), 4.60 (1H, br dsxt), 4.79 (1H, s), 6.19 (1H, br d), 6.74 (1H, d), 6.78 (1H, dd), 6.93 (1H, d), 7.16 (1H, d), 7.74 (1H, d), 8.03 (1H, s), 12.93 (1H, s). (Three hydrogen multiplet obscured by DMSO). | 455 |
| 66 | Isomer B | 6-((6S,8R)-7-(2-fluoropropyl)-8-methyl-6,7,8,9-tetrahydro-3H-pyrazolo[4,3-f]isoquinolin-6-yl)-N-(1-(3-fluoropropyl)azetidin-3-yl)pyridin-3-amine | ¹H NMR (500 MHz, DMSO-d₆, 27° C.) 1.00 (3H, d), 1.13 (3H, dd), 1.56-1.70 (2H, m), 2.28-2.41 (1H, m), 2.45 (2H, t), 2.72 (2H, q), 2.77-2.87 (2H, m), 3.13 (1H, br dd), 3.46 (1H, sxt), 3.56-3.66 (2H, m), 3.92 (1H, sxt), 4.44 (2H, dt), 4.55-4.72 (1H, m), 4.77 (1H, s), 6.18 (1H, d), 6.73 (1H, d), 6.79 (1H, dd), 6.93 (1H, d), 7.16 (1H, d), 7.75 (1H, d), 8.02 (1H, s), 12.92 (1H, s) | 455 |

| Ex No | Structure | Name | 1H NMR | LCMS [M + H] |
|---|---|---|---|---|
| 67 | 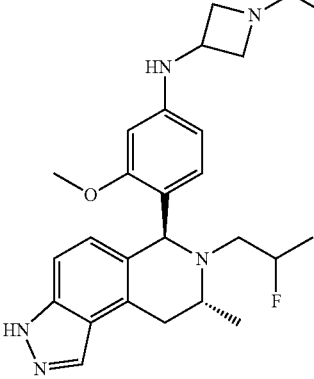 Isomer A | 1-(3-fluoropropyl)-N-(4-((6S,8R)-7-(2-fluoropropyl)-8-methyl-6,7,8,9-tetrahydro-3H-pyrazolo[4,3-f]isoquinolin-6-yl)-3-methoxyphenyl)azetidin-3-amine | ¹H NMR (400 MHz, DMSO-d₆, 27° C.) 1.01 (3H, d), 1.29 (3H, dd), 1.56-1.76 (2H, m), 2.43-2.49 (1H, m), 2.57-2.66 (1H, m), 2.69-2.89 (3H, m), 3.06 (1H, br dd), 3.35-3.42 (1H, m), 3.63-3.74 (2H, m), 3.81 (3H, s), 3.89-3.99 (1H, m), 4.45 (2H, dt), 4.70-4.91 (1H, m), 5.17 (1H, s), 5.88 (1H, dd), 6.00 (1H, br d), 6.18 (1H, d), 6.32 (1H, d), 6.69 (1H, d), 7.19 (1H, d), 8.03 (1H, s), 12.93 (1H, s). (Two hydrogen multiplet obscured by DMSO). | 484 |
| 68 | 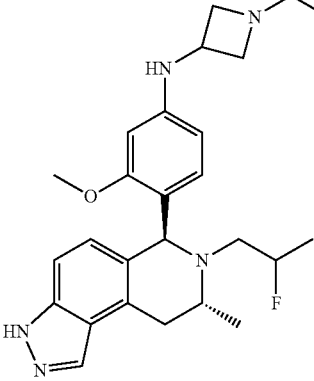 Isomer B | 1-(3-fluoropropyl)-N-(4-((6S,8R)-7-(2-fluoropropyl)-8-methyl-6,7,8,9-tetrahydro-3H-pyrazolo[4,3-f]isoquinolin-6-yl)-3-methoxyphenyl)azetidin-3-amine | ¹H NMR (400 MHz, DMSO-d₆, 27° C.) 1.00 (3H, d), 1.14 (3H, dd), 1.57-1.73 (2H, m), 2.20-2.33 (1H, m), 2.42-2.48 (2H, m), 2.68-2.83 (4H, m), 3.11 (1H, br dd), 3.37-3.47 (1H, m), 3.59-3.66 (2H, m), 3.81 (3H, s), 3.92 (1H, sxt), 4.45 (2H, dt), 4.63-4.84 (1H, m), 5.14 (1H, s), 5.91 (1H, dd), 5.98 (1H, d), 6.18 (1H, d), 6.42 (1H, d), 6.65 (1H, d), 7.16 (1H, d), 8.02 (1H, s), 12.93 (1H, s) | 484 |
| 69 | 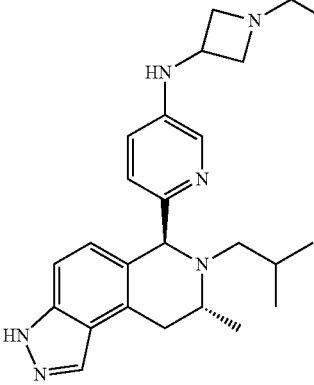 | N-(1-(3-fluoropropyl)azetidin-3-yl)-6-((6S,8R)-7-isobutyl-8-methyl-6,7,8,9-tetrahydro-3H-pyrazolo[4,3-f]isoquinolin-6-yl)pyridin-3-amine | ¹H NMR (300 MHz, DMSO-d₆, 27° C.) 0.73 (3H, d), 0.81 (3H, d), 0.97 (3H, d), 1.51-1.81 (3H, m), 1.99 (1H, dd), 2.34 (1H, dd), 2.42-2.48 (2H, m), 2.74 (2H, td), 2.85 (1H, dd), 3.09-3.22 (1H, m), 3.37-3.54 (1H, m), 3.56-3.71 (2H, m), 3.93 (1H, sxt), 4.45 (2H, dt), 4.69 (1H, s), 6.12 (1H, d), 6.72-6.84 (2H, m), 6.94 (1H, d), 7.16 (1H, d), 7.75 (1H, d), 8.03 (1H, s), 12.90 (1H, s). | 451 |

-continued

| Ex No | Structure | Name | 1H NMR | LCMS [M + H] |
|---|---|---|---|---|
| 70 | 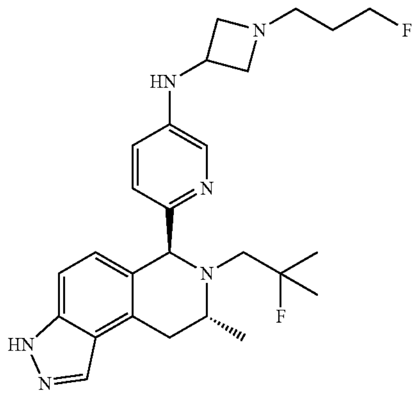 [SMILES: CC(C)CN1[C@H](c2ccc(NC3CN(CCCF)C3)cn2)c2ccc3[nH]ncc3c2C[C@H]1C] | 6-((6S,8R)-7-(2,2-difluoropropyl)-8-methyl-6,7,8,9-tetrahydro-3H-pyrazolo[4,3-f]isoquinolin-6-yl)-N-(1-(3-fluoropropyl)azetidin-3-yl)pyridin-3-amine | $^{1}$H NMR (300 MHz, DMSO-d$_6$, 27° C.) 1.07 (3H, d), 1.58 (3H, br t), 1.80-2.05 (2H, m), 2.53-2.72 (1H, m), 2.86 (1H, br dd), 2.98-3.27 (3H, m), 3.43-3.54 (1H, m), 3.87 (1H, br s), 4.06 (1H, br d), 4.22-4.50 (3H, m), 4.52-4.65 (2H, m), 4.99 (1H, br s), 6.56 (1H, br s), 6.80 (1H, d), 6.86-7.20 (2H, m), 7.24 (1H, brd), 7.73-7.88 (1H, m), 8.08 (1H, s), 9.54-10.04 (1H, m), 12.99 (1H, br s) | 473 |
| 71 | 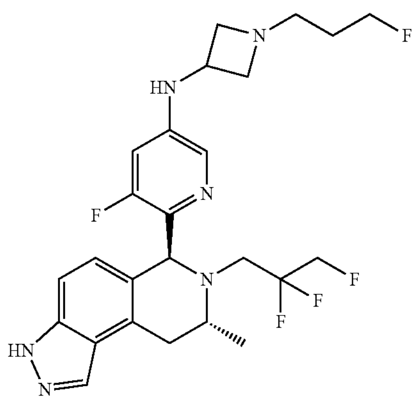 [SMILES: C[C@@H]1Cc2c(ccc3[nH]ncc23)[C@@H](c2ncc(NC3CN(CCCF)C3)cc2F)N1CC(F)(F)CF] | 5-fluoro-N-(1-(3-fluoropropyl)azetidin-3-yl)-6-((6S,8R)-8-methyl-7-(2,2,3-trifluoropropyl)-6,7,8,9-tetrahydro-3H-pyrazolo[4,3-f]isoquinolin-6-yl)pyridin-3-amine | $^{1}$H NMR (500 MHz, DMSO, 27° C.) 1.04 (3H, d), 1.64 (2H, dq), 2.44 (2H, t), 2.66-2.84 (4H, m), 2.97 (1H, dd), 3.15-3.26 (1H, m), 3.56-3.64 (3H, m), 3.94 (1H, h), 4.39 (1H, t), 4.48 (1H, t), 4.56-4.82 (2H, m), 5.19 (1H, s), 6.61 (1H, d), 6.66-6.73 (2H, m), 7.20 (1H, d), 7.55 (1H, dd), 8.04 (1H, s), 12.95 (1H, s). | 509 |
| 72 | 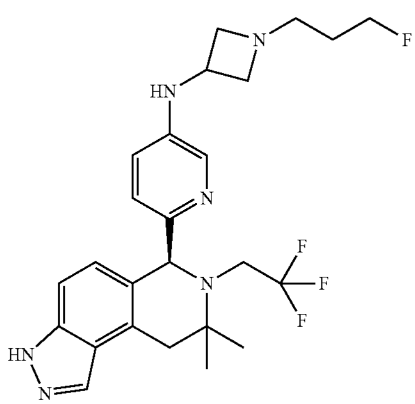 [SMILES: CC1(C)Cc2c(ccc3[nH]ncc23)[C@@H](c2ccc(NC3CN(CCCF)C3)cn2)N1CC(F)(F)F] | (S)-6-(8,8-dimethyl-7-(2,2,2-trifluoroethyl)-6,7,8,9-tetrahydro-3H-pyrazolo[4,3-f]isoquinolin-6-yl)-N-(1-(3-fluoropropyl)azetidin-3-yl)pyridin-3-amine | $^{1}$H NMR (500 MHz, CDCl$_3$, 27° C.) 1.06 (3H, s), 1.41 (3H, s), 1.66-1.83 (2H, m), 2.61 (2H, t), 2.93 (3H, dt), 3.13-3.36 (2H, m), 3.36-3.56 (1H, m), 3.71 (2H, q), 4.10 (2H, d), 4.44 (1H, t), 4.53 (1H, t), 4.98 (1H, s), 6.72 (1H, dd), 6.77 (1H, d), 6.98 (1H, d), 7.11 (1H, d), 7.83 (1H, d), 8.04 (1H, d), 10.72 (1H, s). | 491 |

-continued

| Ex No | Structure | Name | 1H NMR | LCMS [M + H] |
|---|---|---|---|---|
| 73 | 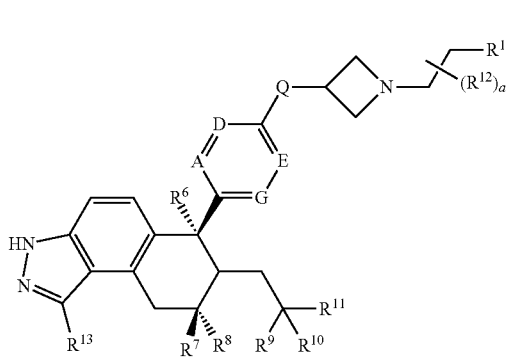 | (S)-6-(7-(2,2-difluoroethyl)-8,8-dimethyl-6,7,8,9-tetrahydro-3H-pyrazolo[4,3-f]isoquinolin-6-yl)-N-(1-(3-fluoropropyl)azetidin-3-yl)pyridin-3-amine | $^1$H NMR (500 MHz, CDCl$_3$, 27° C.) 1.04 (3H, s), 1.41 (3H, s), 2.85-2.95 (6H, m), 3.21 (2H, t), 3.21-3.35 (2H, m), 3.52 (2H, t), 4.01 (2H, q), 4.44 (1H, t), 4.55 (1H, t), 4.82 (1H, dt), 4.96 (1H, s), 6.72 (1H, dd), 7.07 (1H, dd), 7.09-7.13 (2H, m), 8.04 (1H, s), 8.20 (1H, s), 10.65 (1H, s). | 473 |

The above description of illustrative embodiments is intended only to acquaint others skilled in the art with the Applicant's specification, its principles, and its practical application so that others skilled in the art may readily adapt and apply the specification in its numerous forms, as they may be best suited to the requirements of a particular use. This description and its specific examples, while indicating embodiments of this specification, are intended for purposes of illustration only. This specification, therefore, is not limited to the illustrative embodiments described in this specification, and may be variously modified. In addition, it is to be appreciated that various features of the specification that are, for clarity reasons, described in the context of separate embodiments, also may be combined to form a single embodiment. Conversely, various features of the specification that are, for brevity reasons, described in the context of a single embodiment, also may be combined to form sub-combinations thereof.

What is claimed is:

1. A compound of Formula (I):

(I)

wherein:
A is CR$^2$ or N;
G is CR$^3$ or N;
D is CR$^4$ or N;
E is CR$^5$ or N;
Q is O, NH or NMe;
R$^1$ is CH$_2$F, CHF$_2$ or CF$_3$;
R$^2$ is H, F, Cl, Me, CN, OMe or OEt;
R$^3$ is H or F;
R$^4$ is H, F, CN or OMe;
R$^5$ is H or F;
R$^6$ is H, Me, CH$_2$F, CHF$_2$ or CF$_3$;
R$^7$ is H or Me;
R$^8$ is C$_{1-3}$ alkyl, CH$_2$F, CHF$_2$, CF$_3$ or C$_{3-4}$ cycloalkyl;
R$^9$ is Me, F or CH$_2$F;
R$^{10}$ is Me, F, CH$_2$F, CHF$_2$, CF$_3$, CH$_2$OMe or CH$_2$OH;
R$^{11}$ is H or F; or
R$^{10}$ and R$^{11}$ taken together with the carbon atom to which they are attached form a cyclopropyl ring or an oxetane ring;
R$^{12}$ is independently selected from F or Me;
R$^{13}$ is H or F; and
a is 0, 1 or 2;
or a pharmaceutically acceptable salt thereof.

2. A compound of Formula (I) or a pharmaceutically acceptable salt thereof, as claimed in claim 1, wherein Q is NH.

3. A compound of Formula (I) or a pharmaceutically acceptable salt thereof, as claimed in claim 1, wherein Q is O.

4. A compound of Formula (I) or a pharmaceutically acceptable salt thereof, as claimed in claim 1, wherein R$^6$ is H.

5. A compound of Formula (I) or a pharmaceutically acceptable salt thereof, as claimed in claim 1, wherein R$^7$ is H.

6. A compound of Formula (I) or a pharmaceutically acceptable salt thereof, as claimed in claim 1, wherein the group —CH$_2$—C(R$^9$)(R$^{10}$)(R$^{11}$) in the compound of Formula (I) is selected from the group consisting of:

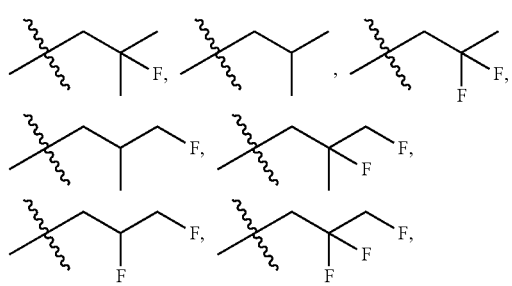

-continued

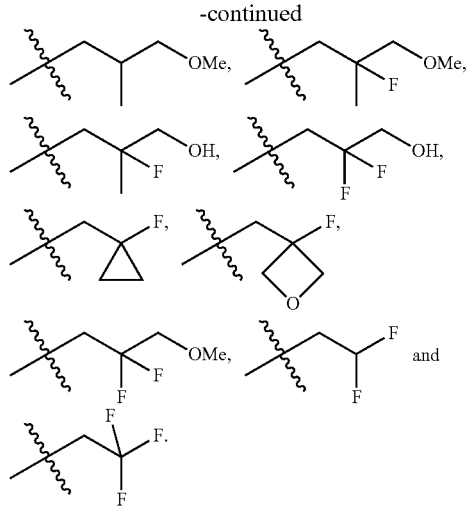

7. A compound of Formula (IA) as claimed in claim 1

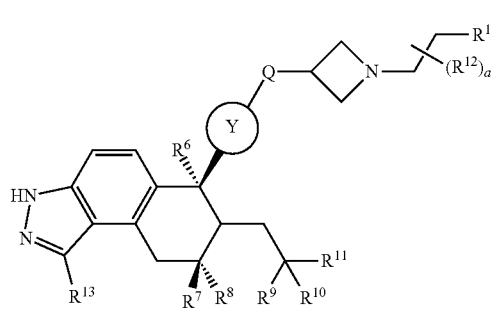
(IA)

wherein:
Q is O, NH or NMe;
R$^1$ is CH$_2$F, CHF$_2$ or CF$_3$;
R$^6$ is H or Me;
R$^7$ is H or Me;
R$^8$ is Me, CHF$_2$ or cyclopropyl;
R$^9$ is Me or F;
R$^{19}$ is Me, F, CH$_2$F, CH$_2$OMe or CH$_2$OH;
R$^{11}$ is H or F; or
R$^{10}$ and R$^{11}$ taken together with the carbon atom to which they are attached form a cyclopropyl ring or an oxetane ring;
R$^{12}$ is independently selected from H or Me;
R$^{13}$ is H or F;
a is 0, 1 or 2; and
Ring Y is selected from the group consisting of:

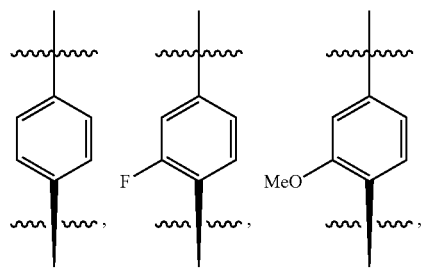

-continued

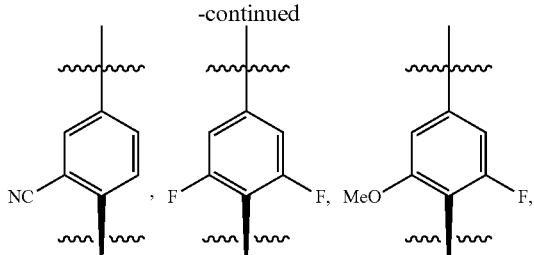

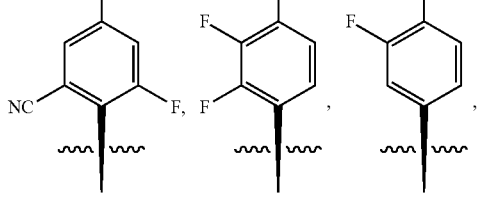

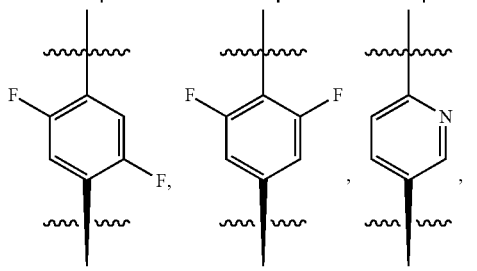

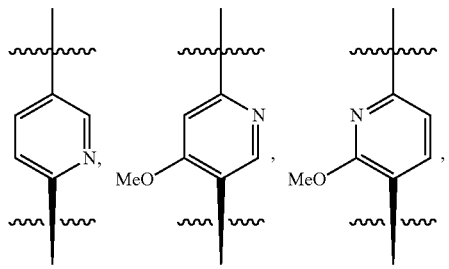

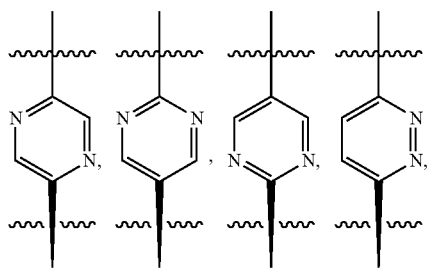

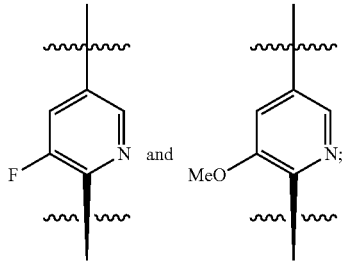

or a pharmaceutically acceptable salt thereof.

8. A compound of Formula (I) as claimed in claim 1, wherein the compound is selected from the group consisting of:

N-(4-((6S,8R)-7-(2,2-difluoro-3-methoxypropyl)-8-methyl-6,7,8,9-tetrahydro-3H-pyrazolo[4,3-f]isoquinolin-6-yl)-3-methoxyphenyl)-1-(3-fluoropropyl)azetidin-3-amine;

6-((6S,8R)-7-(2,2-difluoro-3-methoxypropyl)-8-methyl-6,7,8,9-tetrahydro-3H-pyrazolo[4,3-f]isoquinolin-6-yl)-N-(1-(3-fluoropropyl)azetidin-3-yl)pyridin-3-amine;

6-((6S,8R)-7-((1-fluorocyclopropyl)methyl)-8-methyl-6,7,8,9-tetrahydro-3H-pyrazolo[4,3-f]isoquinolin-6-yl)-N-(1-(3-fluoropropyl)azetidin-3-yl)pyridin-3-amine;

N-(4-((6S,8R)-7-(2-fluoro-3-methoxy-2-methylpropyl)-8-methyl-6,7,8,9-tetrahydro-3H-pyrazolo[4,3-f]isoquinolin-6-yl)-3-methoxyphenyl)-1-(3-fluoropropyl)azetidin-3-amine;

3-((6S,8R)-6-(2,6-difluoro-4-((1-(3-fluoropropyl)azetidin-3-yl)amino)phenyl)-8-methyl-3,6,8,9-tetrahydro-7H-pyrazolo[4,3-f]isoquinolin-7-yl)-2,2-difluoropropan-1-ol;

N-(4-((6S,8R)-7-((1-fluorocyclopropyl)methyl)-8-methyl-6,7,8,9-tetrahydro-3H-pyrazolo[4,3-f]isoquinolin-6-yl)-3-methoxyphenyl)-1-(3-fluoropropyl)azetidin-3-amine;

(6S,8R)-7-((1-fluorocyclopropyl)methyl)-6-(4-((1-(3-fluoropropyl)azetidin-3-yl)oxy)-2-methoxyphenyl)-8-methyl-6,7,8,9-tetrahydro-3H-pyrazolo[4,3-f]isoquinoline;

N-(3,5-difluoro-4-((6S,8R)-8-methyl-7-(2,2,2-trifluoroethyl)-6,7,8,9-tetrahydro-3H-pyrazolo[4,3-f]isoquinolin-6-yl)phenyl)-1-(3-fluoropropyl)azetidin-3-amine;

5-((6S,8R)-7-((1-fluorocyclopropyl)methyl)-8-methyl-6,7,8,9-tetrahydro-3H-pyrazolo[4,3-f]isoquinolin-6-yl)-N-(1-(3-fluoropropyl)azetidin-3-yl)-4-methoxypyridin-2-amine;

N-(4-((6S,8R)-7-((3-(fluoromethyl)oxetan-3-yl)methyl)-8-methyl-6,7,8,9-tetrahydro-3H-pyrazolo[4,3-f]isoquinolin-6-yl)-3-methoxyphenyl)-1-(3-fluoropropyl)azetidin-3-amine;

N-(3,5-difluoro-4-((6S,8R)-7-((1-fluorocyclopropyl)methyl)-8-methyl-6,7,8,9-tetrahydro-3H-pyrazolo[4,3-f]isoquinolin-6-yl)phenyl)-1-(3-fluoropropyl)azetidin-3-amine;

(6S,8R)-7-(2-fluoro-3-methoxy-2-methylpropyl)-6-(4-(1-(3-fluoropropyl)azetidin-3-yloxy)-2-methoxyphenyl)-8-methyl-6,7,8,9-tetrahydro-3H-pyrazolo[4,3-f]isoquinoline;

N-(4-((6S,8R)-7-(2-fluoro-3-methoxy-2-methylpropyl)-8-methyl-6,7,8,9-tetrahydro-3H-pyrazolo[4,3-f]isoquinolin-6-yl)-3-methoxyphenyl)-1-(3-fluoropropyl)azetidin-3-amine;

2,2-difluoro-3-((6S,8R)-6-(5-((1-(3-fluoropropyl)azetidin-3-yl)amino)pyridin-2-yl)-8-methyl-3,6,8,9-tetrahydro-7H-pyrazolo[4,3-f]isoquinolin-7-yl)propan-1-ol;

5-fluoro-6-((6S,8R)-7-((1-fluorocyclopropyl)methyl)-8-methyl-6,7,8,9-tetrahydro-3H-pyrazolo[4,3-f]isoquinolin-6-yl)-N-(1-(3-fluoropropyl)azetidin-3-yl)pyridin-3-amine;

N-(4-((6S,8R)-7-(2,2-difluoropropyl)-8-methyl-6,7,8,9-tetrahydro-3H-pyrazolo[4,3-f]isoquinolin-6-yl)-3-methoxyphenyl)-1-(3-fluoropropyl)azetidin-3-amine;

N-(3-ethoxy-4-((6S,8R)-7-((1-fluorocyclopropyl)methyl)-8-methyl-6,7,8,9-tetrahydro-3H-pyrazolo[4,3-f]isoquinolin-6-yl)phenyl)-1-(3-fluoropropyl)azetidin-3-amine;

N-(4-((6S,8R)-7-(2,2-difluoroethyl)-8-methyl-6,7,8,9-tetrahydro-3H-pyrazolo[4,3-f]isoquinolin-6-yl)-3-methoxyphenyl)-1-(3-fluoropropyl)azetidin-3-amine;

(6S,8R)-7-(2,2-difluoroethyl)-6-(4-((1-(3-fluoropropyl)azetidin-3-yl)oxy)-2-methoxyphenyl)-8-methyl-6,7,8,9-tetrahydro-3H-pyrazolo[4,3-f]isoquinoline;

3-((6S,8R)-6-(2,6-difluoro-4-(1-(3-fluoropropyl)azetidin-3-ylamino)phenyl)-8-methyl-8,9-dihydro-3H-pyrazolo[4,3-f]isoquinolin-7(6H)-yl)-2-fluoro-2-methylpropan-1-ol;

6-((6S,8R)-7-(2,2-difluoroethyl)-8-methyl-6,7,8,9-tetrahydro-3H-pyrazolo[4,3-]isoquinolin-6-yl)-N-(1-(3-fluoropropyl)azetidin-3-yl)pyridin-3-amine;

(6S,8R)-7-(2,2-difluoroethyl)-6-(5-((1-(3-fluoropropyl)azetidin-3-yl)oxy)pyridin-2-yl)-8-methyl-6,7,8,9-tetrahydro-3H-pyrazolo[4,3-f]isoquinoline;

1-(3-fluoropropyl)-N-(4-((6R,8R)-8-methyl-7-(2,2,2-trifluoroethyl)-6,7,8,9-tetrahydro-3H-pyrazolo[4,3-f]isoquinolin-6-yl)phenyl)azetidin-3-amine;

1-(3-fluoropropyl)-N-(3-methoxy-4-((6S,8R)-8-methyl-7-(2,2,2-trifluoroethyl)-6,7,8,9-tetrahydro-3H-pyrazolo[4,3-f]isoquinolin-6-yl)phenyl)azetidin-3-amine;

2-fluoro-N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine;

5-fluoro-N-(1-(3-fluoropropyl)azetidin-3-yl)-6-((6S,8R)-8-methyl-7-(2,2,2-trifluoroethyl)-6,7,8,9-tetrahydro-3H-pyrazolo[4,3-f]isoquinolin-6-yl)pyridin-3-amine;

2,2-difluoro-3-((6S,8R)-6-(3-fluoro-5-((1-(3-fluoropropyl)azetidin-3-yl)amino)pyridin-2-yl)-8-methyl-3,6,8,9-tetrahydro-7H-pyrazolo[4,3-f]isoquinolin-7-yl)propan-1-ol;

6-((6S,8R)-1-fluoro-8-methyl-7-(2,2,2-trifluoroethyl)-6,7,9,8-tetrahydro-3H-pyrazolo[4,3-f]isoquin-6-yl)-N-(3-fluoropropyl)azetidi-3-yl)pyridin-3-amine;

5-fluoro-6-((6S,8R)-1-fluoro-8-methyl-7-(2,2,2-trifluoroethyl)-6,7,8,9-tetrahydro-3H-pyrazolo[4,3-f]isoquinolin-6-yl)-N-(1-(3-fluoropropyl)azetidin-3-yl)pyridin-3-amine;

N-(1-(3-fluoropropyl)azetidin-3-yl)-N-methyl-6-((6S,8R)-8-methyl-7-(2,2,2-trifluoroethyl)-6,7,8,9-tetrahydro-3H-pyrazolo[4,3-f]isoquinolin-6-yl)pyridin-3-amine;

N-(1-(3-fluoropropyl)azetidin-3-yl)-5-methoxy-6-((6S,8R)-8-methyl-7-(2,2,2-trifluoroethyl)-6,7,8,9-tetrahydro-3H-pyrazolo[4,3-f]isoquinolin-6-yl)pyridin-3-amine;

5-((6S,8R)-1-fluoro-8-methyl-7-(2,2,2-trifluoroethyl)-6,7,8,9-tetrahydro-3H-pyrazolo[4,3-f]isoquinolin-6-yl)-N-(1-(3-fluoropropyl)azetidin-3-yl)pyrazin-2-amine;

2-fluoro-6-((6S,8R)-1-fluoro-8-methyl-7-(2,2,2-trifluoroethyl)-6,7,8,9-tetrahydro-3H-pyrazolo[4,3-f]isoquinolin-6-yl)-N-(1-(3-fluoropropyl)azetidin-3-yl)pyridin-3-amine;

6-fluoro-N-(1-(3-fluoropropyl)azetidin-3-yl)-5-((6S,8R)-8-methyl-7-(2,2,2-trifluoroethyl)-6,7,8,9-tetrahydro-3H-pyrazolo[4,3-f]isoquinolin-6-yl)pyridin-2-amine;

N-(2-fluoro-4-((6R,8R)-8-methyl-7-(2,2,2-trifluoroethyl)-6,7,8,9-tetrahydro-3H-pyrazolo[4,3-f]isoquinolin-6-yl)phenyl)-1-(3-fluoropropyl)azetidin-3-amine;

N-(1-(3-fluoropropyl)azetidin-3-yl)-5-((6S,8R)-8-methyl-7-(2,2,2-trifluoroethyl)-6,7,8,9-tetrahydro-3H-pyrazolo[4,3-f]isoquinolin-6-yl)pyrazin-2-amine;

6-((6S,8R)-7-(2,2-difluoroethyl)-8-methyl-6,7,8,9-tetrahydro-3H-pyrazolo[4,3-f]isoquinolin-6-yl)-N-(1-(3-fluoropropyl)azetidin-3-yl)-N-methylpyridin-3-amine;

6-((6S,8R)-7-(2,2-difluoroethyl)-6,8-dimethyl-6,7,8,9-tetrahydro-3H-pyrazolo[4,3-f]isoquinolin-6-yl)-N-(1-(3-fluoropropyl)azetidin-3-yl)pyridin-3-amine;

N-(4-((6S,8R)-7-(2,2-difluoroethyl)-6,8-dimethyl-6,7,8,9-tetrahydro-3H-pyrazolo[4,3-f]isoquinolin-6-yl)-3-methoxyphenyl)-1-(3-fluoropropyl)azetidin-3-amine;

6-((6S,8R)-7-(2,2-difluoroethyl)-8-methyl-6,7,8,9-tetrahydro-3H-pyrazolo[4,3-f]isoquinolin-6-yl)-5-fluoro-N-(1-(3-fluoropropyl)azetidin-3-yl)pyridin-3-amine;

6-((6S,8R)-7-(2,2-difluoroethyl)-8-methyl-6,7,8,9-tetrahydro-3H-pyrazolo[4,3-f]isoquinolin-6-yl)-2-fluoro-N-(1-(3-fluoropropyl)azetidin-3-yl)pyridin-3-amine;

N-(4-((6R,8R)-7-(2,2-difluoroethyl)-8-methyl-6,7,8,9-tetrahydro-3H-pyrazolo[4,3-f]isoquinolin-6-yl)phenyl)-1-(3-fluoropropyl)azetidin-3-amine;

N-(4-((6S,8R)-7-(2,2-difluoroethyl)-8-methyl-6,7,8,9-tetrahydro-3H-pyrazolo[4,3-f]isoquinolin-6-yl)-3,5-difluorophenyl)-1-(3-fluoropropyl)azetidin-3-amine;

5-((6S,8R)-7-(2,2-difluoroethyl)-8-methyl-6,7,8,9-tetrahydro-3H-pyrazolo[4,3-f]isoquinolin-6-yl)-N-(1-(3-fluoropropyl)azetidin-3-yl)pyrazin-2-amine;

6-((6S,8S)-7-(2,2-difluoroethyl)-8-(difluoromethyl)-6,7,8,9-tetrahydro-3H-pyrazolo[4,3-f]isoquinolin-6-yl)-N-(1-(3-fluoropropyl)azetidin-3-yl)pyridin-3-amine;

N-(4-((6S,8R)-7-((1-fluorocyclopropyl)methyl)-8-methyl-6,7,8,9-tetrahydro-3H-pyrazolo[4,3-f]isoquinolin-6-yl)-3-methoxyphenyl)-1-(3-fluoropropyl)-N-methylazetidin-3-amine;

N-(2-fluoro-4-((6S,8R)-7-((1-fluorocyclopropyl)methyl)-8-methyl-6,7,8,9-tetrahydro-3H-pyrazolo[4,3-f]isoquinolin-6-yl)-5-methoxyphenyl)-1-(3-fluoropropyl)azetidin-3-amine;

5-((6S,8R)-7-((1-fluorocyclopropyl)methyl)-8-methyl-6,7,8,9-tetrahydro-3H-pyrazolo[4,3-f]isoquinolin-6-yl)-N-(1-(3-fluoropropyl)azetidin-3-yl)pyridin-2-amine;

5-((6S,8R)-7-((1-fluorocyclopropyl)methyl)-8-methyl-6,7,8,9-tetrahydro-3H-pyrazolo[4,3-f]isoquinolin-6-yl)-N-(1-(3-fluoropropyl)azetidin-3-yl)pyrazin-2-amine;

N-(4-((6S,8R)-7-((1-fluorocyclopropyl)methyl)-8-methyl-6,7,8,9-tetrahydro-3H-pyrazolo[4,3-f]isoquinolin-6-yl)-3-methoxyphenyl)-1-(3,3,3-trifluoropropyl)azetidin-3-amine;

6-((6S,8R)-7-((1-fluorocyclopropyl)methyl)-8-methyl-6,7,8,9-tetrahydro-3H-pyrazolo[4,3-f]isoquinolin-6-yl)-N-(1-(3-fluoropropyl)azetidin-3-yl)-N-methylpyridin-3-amine;

2,2-difluoro-3-((6S,8R)-6-(5-((1-(3-fluoropropyl)azetidin-3-yl)oxy)pyridin-2-yl)-8-methyl-3,6,8,9-tetrahydro-7H-pyrazolo[4,3-f]isoquinolin-7-yl)propan-1-ol;

2,2-difluoro-3-((6S,8R)-6-(3-fluoro-5-((1-(3-fluoropropyl)azetidin-3-yl)oxy)pyridin-2-yl)-8-methyl-3,6,8,9-tetrahydro-7H-pyrazolo[4,3-f]isoquinolin-7-yl)propan-1-ol;

2,2-difluoro-3-((6S,8R)-6-(4-((1-(3-fluoropropyl)azetidin-3-yl)amino)-2-methoxyphenyl)-8-methyl-3,6,8,9-tetrahydro-7H-pyrazolo[4,3-f]isoquinolin-7-yl)propan-1-ol;

2,2-difluoro-3-((6S,8R)-1-fluoro-6-(5-((1-(3-fluoropropyl)azetidin-3-yl)amino)pyridin-2-yl)-8-methyl-3,6,8,9-tetrahydro-7H-pyrazolo[4,3-f]isoquinolin-7-yl)propan-1-ol;

2,2-difluoro-3-((6S,8R)-1-fluoro-6-(6-fluoro-5-((1-(3-fluoropropyl)azetidin-3-yl)amino)pyridin-2-yl)-8-methyl-3,6,8,9-tetrahydro-7H-pyrazolo[4,3-f]isoquinolin-7-yl)propan-1-ol;

6-((6S,8R)-7-(2-fluoro-2-methylpropyl)-8-methyl-6,7,8,9-tetrahydro-3H-pyrazolo[4,3-f]isoquinolin-6-yl)-N-(1-(3-fluoropropyl)azetidin-3-yl)pyridin-3-amine;

N-(4-((6S,8R)-7-(2-fluoro-2-methylpropyl)-8-methyl-6,7,8,9-tetrahydro-3H-pyrazolo[4,3-f]isoquinolin-6-yl)-3-methoxyphenyl)-1-(3-fluoropropyl)azetidin-3-amine;

6-((6S,8R)-7-(2-fluoropropyl)-8-methyl-6,7,8,9-tetrahydro-3H-pyrazolo[4,3-f]isoquinolin-6-yl)-N-(1-(3-fluoropropyl)azetidin-3-yl)pyridin-3-amine;

6-((6S,8R)-7-(2-fluoropropyl)-8-methyl-6,7,8,9-tetrahydro-3H-pyrazolo[4,3-f]isoquinolin-6-yl)-N-(1-(3-fluoropropyl)azetidin-3-yl)pyridin-3-amine;

1-(3-fluoropropyl)-N-(4-((6S,8R)-7-(2-fluoropropyl)-8-methyl-6,7,8,9-tetrahydro-3H-pyrazolo[4,3-f]isoquinolin-6-yl)-3-methoxyphenyl)azetidin-3-amine;

1-(3-fluoropropyl)-N-(4-((6S,8R)-7-(2-fluoropropyl)-8-methyl-6,7,8,9-tetrahydro-3H-pyrazolo[4,3-f]isoquinolin-6-yl)-3-methoxyphenyl)azetidin-3-amine;

N-(1-(3-fluoropropyl)azetidin-3-yl)-6-((6S,8R)-7-isobutyl-8-methyl-6,7,8,9-tetrahydro-3H-pyrazolo[4,3-f]isoquinolin-6-yl)pyridin-3-amine;

6-((6S,8R)-7-(2,2-difluoropropyl)-8-methyl-6,7,8,9-tetrahydro-3H-pyrazolo[4,3-f]isoquinolin-6-yl)-N-(1-(3-fluoropropyl)azetidin-3-yl)pyridin-3-amine;

5-fluoro-N-(1-(3-fluoropropyl)azetidin-3-yl)-6-((6S,8R)-8-methyl-7-(2,2,3-trifluoropropyl)-6,7,8,9-tetrahydro-3H-pyrazolo[4,3-f]isoquinolin-6-yl)pyridin-3-amine;

(S)-6-(8,8-dimethyl-7-(2,2,2-trifluoroethyl)-6,7,8,9-tetrahydro-3H-pyrazolo[4,3-f]isoquinolin-6-yl)-N-(1-(3-fluoropropyl)azetidin-3-yl)pyridin-3-amine; and (S)-6-(7-(2,2-difluoroethyl)-8,8-dimethyl-6,7,8,9-tetrahydro-3H-pyrazolo[4,3-f]isoquinolin-6-yl)-N-(1-(3-fluoropropyl)azetidin-3-yl)pyridin-3-amine, or a pharmaceutically acceptable salt thereof.

9. A pharmaceutical composition comprising a compound of Formula (I) or a pharmaceutically acceptable salt thereof, as claimed in claim 1, and a pharmaceutically acceptable excipient.

* * * * *

UNITED STATES PATENT AND TRADEMARK OFFICE
CERTIFICATE OF CORRECTION

PATENT NO. : 10,590,130 B2
APPLICATION NO. : 16/155041
DATED : March 17, 2020
INVENTOR(S) : Bernard Christophe Barlaam et al.

Page 1 of 1

It is certified that error appears in the above-identified patent and that said Letters Patent is hereby corrected as shown below:

In the Claims

In Claim 1, Column 243, Lines 45-60, please replace the structure of Formula (I) as follows:

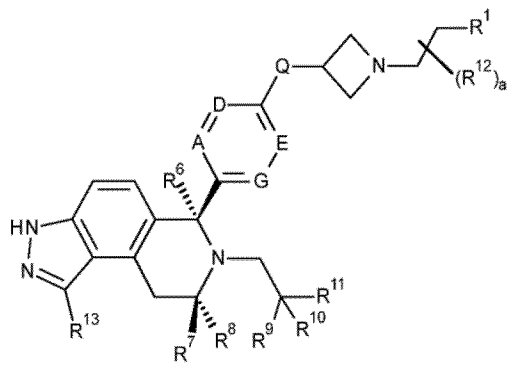

In Claim 7, Column 245, Lines 25-38, please replace the structure of Formula (IA) as follows:

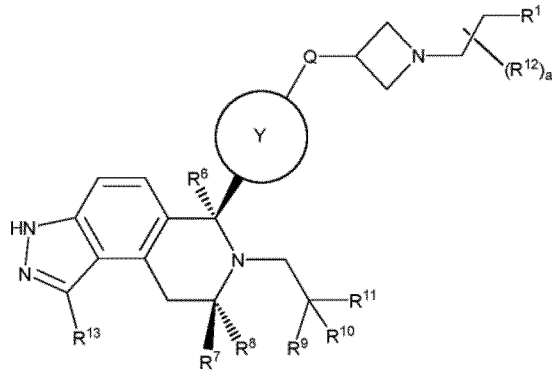

Signed and Sealed this
Twelfth Day of May, 2020

Andrei Iancu
*Director of the United States Patent and Trademark Office*